United States Patent
Allred et al.

(10) Patent No.: US 12,024,533 B2
(45) Date of Patent: Jul. 2, 2024

(54) ANTIMICROBIAL ORGANOSILANES

(71) Applicant: Topikos Scientific, Inc., Fort Wayne, IN (US)

(72) Inventors: Gary Allred, Wake Forest, NC (US); Lanny Liebeskind, Atlanta, GA (US); William R. Cast, Fort Wayne, IN (US); Carl Hilliard, Henderson, NV (US)

(73) Assignee: Topikos Scientific, Inc., Fort Wayne, IN (US)

( * ) Notice: Subject to any disclaimer, the term of this patent is extended or adjusted under 35 U.S.C. 154(b) by 0 days.

(21) Appl. No.: 18/087,587

(22) Filed: Dec. 22, 2022

(65) Prior Publication Data

US 2023/0143708 A1    May 11, 2023

Related U.S. Application Data

(63) Continuation of application No. 17/723,168, filed on Apr. 18, 2022, which is a continuation of application No. PCT/US2020/056392, filed on Oct. 19, 2020.

(60) Provisional application No. 63/014,535, filed on Apr. 23, 2020, provisional application No. 62/923,372, filed on Oct. 18, 2019.

(51) Int. Cl.
*C07F 7/18*    (2006.01)

(52) U.S. Cl.
CPC .................. *C07F 7/1896* (2013.01)

(58) Field of Classification Search
CPC .... C08L 83/04; A61L 15/26; A61L 2300/404; A61L 27/34; A61K 45/06
See application file for complete search history.

(56) References Cited

U.S. PATENT DOCUMENTS

| | | |
|---|---|---|
| 3,551,554 A | 12/1970 | Herschler |
| 3,560,385 A | 2/1971 | Roth |
| 3,730,701 A | 5/1973 | Isquith et al. |
| 3,743,727 A | 7/1973 | Herschler |
| 3,786,615 A | 1/1974 | Bauer |
| 3,794,736 A | 2/1974 | Abbott et al. |
| 3,860,709 A | 1/1975 | Abbott et al. |
| 4,005,028 A | 1/1977 | Heckert et al. |
| 4,005,030 A | 1/1977 | Heckert et al. |
| 4,024,871 A | 5/1977 | Stephenson |
| 4,282,366 A | 8/1981 | Eudy |
| 4,394,378 A | 7/1983 | Klein |
| 4,408,996 A | 10/1983 | Baldwin |
| 4,414,268 A | 11/1983 | Baldwin |
| 4,504,541 A | 3/1985 | Yasuda et al. |
| 4,615,937 A | 10/1986 | Bouchette |
| 4,631,273 A | 12/1986 | Blehm et al. |
| 4,692,374 A | 9/1987 | Bouchette |
| 4,772,593 A | 9/1988 | Whalen et al. |
| 4,842,766 A | 6/1989 | Blehm et al. |
| 4,856,504 A | 8/1989 | Yamamoto et al. |
| 4,865,844 A | 9/1989 | Blank et al. |
| 4,908,355 A | 3/1990 | Gettings et al. |
| 4,921,691 A | 5/1990 | Stockel et al. |
| 4,927,687 A | 5/1990 | Nuwayser |
| 5,064,613 A | 11/1991 | Higgs et al. |
| 5,358,688 A | 10/1994 | Robertson |
| 5,359,104 A | 10/1994 | Higgs et al. |
| 5,883,026 A | 3/1999 | Reader et al. |
| 5,954,869 A | 9/1999 | Elfersey et al. |
| 5,959,014 A | 9/1999 | Liebeskind et al. |
| 6,033,676 A | 3/2000 | Cortright |
| 6,120,587 A | 9/2000 | Elfersey et al. |
| 6,146,688 A | 11/2000 | Morgan et al. |
| 6,160,196 A | 12/2000 | Knieler et al. |
| 6,221,944 B1 | 4/2001 | Liebeskind et al. |
| 6,451,755 B1 | 9/2002 | Norman |
| 6,613,755 B2 | 9/2003 | Peterson et al. |
| 6,613,756 B2 | 9/2003 | Duncan et al. |
| 6,632,805 B1 | 10/2003 | Liebeskind et al. |
| 6,801,477 B2 | 10/2004 | Braunberger |
| 7,241,456 B2 | 7/2007 | Vromen |
| 7,553,983 B2 * | 6/2009 | Ranka .................. C07F 7/1804 556/419 |
| 7,589,054 B2 | 9/2009 | Ohlhausen et al. |
| 8,598,053 B2 | 12/2013 | Whitten et al. |
| 8,663,705 B2 | 3/2014 | Norton et al. |
| 8,691,874 B2 | 4/2014 | Karageozian et al. |
| 8,865,605 B2 | 10/2014 | Bender et al. |
| 8,906,115 B2 | 12/2014 | Bender |
| 9,314,407 B2 | 4/2016 | Blizzard et al. |
| 9,364,572 B2 | 6/2016 | Peterson, II et al. |
| 9,764,264 B2 | 9/2017 | Peterson, II et al. |
| 2002/0037260 A1 | 3/2002 | Budny et al. |

(Continued)

FOREIGN PATENT DOCUMENTS

| | | |
|---|---|---|
| CN | 104403161 A | 3/2015 |
| CN | 105646563 A | 6/2016 |

(Continued)

OTHER PUBLICATIONS

International Search Report and Written Opinion for PCT/2023/31069 dated Jan. 9, 2024, 12 pages.
National Center for Biotechnology Information) "N,N-Dimelhyl-N-(3-(trihydroxysilyl)propyl)ocladecan-1-aminium: Pubchem CID 21365909" Pubchem entry (online), pp. 1-14, Dec. 5, 2007; Retrieved on Aug. 7, 2023 from the Internet: [URL:https://pubchem.ncbi.nlm.nlh.gov/compound/21365909].
National Center for Biotechnology Information) "N-Tris(hydroxymelhyl)methyl-2-aminoethanesulfonlc acid: Pubchem CID 81831" Pubchem entry (online), pp. 1-12, Jun. 24, 2005; Retrieved on Aug. 9, 2023 from the Internet: [URL: https://pubchem.ncbi.nlm.nih.gov/compound/81831].

(Continued)

*Primary Examiner* — Pancham Bakshi
(74) *Attorney, Agent, or Firm* — Knowles Intellectual Property Strategies, LLC

(57) ABSTRACT

Organosilicon quaternary ammonium compounds, their formulations, including powdered and solid formulations, and methods of use to treat infections in humans and animals.

30 Claims, 2 Drawing Sheets

(56) References Cited

U.S. PATENT DOCUMENTS

| | | |
|---|---|---|
| 2003/0175232 A1 | 9/2003 | Elliott et al. |
| 2003/0215417 A1 | 11/2003 | Uchiyama et al. |
| 2003/0225003 A1 | 12/2003 | Ninkov |
| 2004/0101506 A1 | 5/2004 | Fust |
| 2005/0004098 A1 | 1/2005 | Britten et al. |
| 2005/0063997 A1 | 3/2005 | Peyman |
| 2006/0051385 A1 | 3/2006 | Scholz |
| 2006/0110348 A1 | 5/2006 | Ohlhausen et al. |
| 2006/0222675 A1 | 10/2006 | Sabnis et al. |
| 2007/0042198 A1 | 2/2007 | Schonemyr et al. |
| 2007/0184130 A1 | 8/2007 | Carrigan |
| 2007/0196329 A1 | 8/2007 | Xia et al. |
| 2007/0212343 A1 | 9/2007 | Owen |
| 2008/0009643 A1 | 1/2008 | Mehta et al. |
| 2008/0009644 A1 | 1/2008 | Ranka et al. |
| 2008/0026156 A1 | 1/2008 | Mehta et al. |
| 2008/0092909 A1 | 4/2008 | Hahne |
| 2008/0161219 A1 | 7/2008 | Ohlhausen et al. |
| 2009/0005339 A1 | 1/2009 | Scholz et al. |
| 2009/0223411 A1 | 9/2009 | Higgins et al. |
| 2009/0252647 A1 | 10/2009 | Orofino |
| 2010/0093666 A1 | 4/2010 | Moses et al. |
| 2010/0211034 A1 | 8/2010 | Toreki et al. |
| 2010/0211035 A1 | 8/2010 | Toreki et al. |
| 2011/0293681 A1 | 12/2011 | Berlin et al. |
| 2012/0052106 A1 | 3/2012 | Eddy |
| 2012/0196953 A1 | 8/2012 | Ziolkowski et al. |
| 2013/0017242 A1 | 1/2013 | Richardson et al. |
| 2013/0231599 A1 | 9/2013 | Eddy |
| 2014/0011766 A1 | 1/2014 | Krafft |
| 2014/0100504 A1 | 4/2014 | Eddy |
| 2014/0302146 A1 | 10/2014 | Kurose et al. |
| 2015/0024019 A1 | 1/2015 | Ali et al. |
| 2015/0296790 A1 | 10/2015 | Nagai et al. |
| 2015/0328241 A1 | 11/2015 | Hilliard et al. |
| 2016/0039949 A1 | 2/2016 | Zhao et al. |
| 2016/0287717 A1 | 10/2016 | Brinker et al. |
| 2016/0346193 A1 | 12/2016 | Neigel |
| 2016/0354307 A1 | 12/2016 | Hilliard et al. |
| 2017/0042916 A1 | 2/2017 | Hilliard et al. |
| 2017/0094974 A1 | 4/2017 | Smyth et al. |
| 2018/0027804 A1 | 2/2018 | Moudgil et al. |
| 2018/0071326 A1 | 3/2018 | Hilliard et al. |
| 2018/0280201 A1 | 10/2018 | Grossman et al. |
| 2018/0360861 A1 | 12/2018 | Hilliard et al. |

FOREIGN PATENT DOCUMENTS

| | | |
|---|---|---|
| CN | 106478711 A | 3/2017 |
| CN | 107130461 A | 9/2017 |
| CN | 107199745 A | 9/2017 |
| EP | 0108853 B1 | 5/1984 |
| EP | 0408017 A2 | 7/1990 |
| EP | 0408017 A2 | 1/1991 |
| EP | 1787650 A2 | 5/2006 |
| EP | 1787650 A2 | 5/2007 |
| EP | 2119363 A3 | 11/2011 |
| MX | 2012002853 A | 9/2013 |
| WO | WO 1992/14810 A1 | 9/1992 |
| WO | WO 1997/32957 A1 | 9/1997 |
| WO | WO 1998/26807 A1 | 6/1998 |
| WO | WO 2000/54587 A1 | 9/2000 |
| WO | WO 2002030455 A2 | 4/2002 |
| WO | WO 2004/004793 A1 | 1/2004 |
| WO | WO 2004/105687 A2 | 12/2004 |
| WO | WO 2006/049478 A1 | 5/2006 |
| WO | WO 2006/086271 A2 | 8/2006 |
| WO | WO 2007/092452 A2 | 8/2007 |
| WO | WO 2008/071680 A2 | 8/2007 |
| WO | WO 2008/071680 A1 | 6/2008 |
| WO | WO 2008/071681 A1 | 6/2008 |
| WO | WO 2009/003199 A1 | 12/2008 |
| WO | WO 2009/129470 A2 | 10/2009 |
| WO | WO 2010/013250 A2 | 2/2010 |
| WO | WO 2011/088347 A1 | 7/2011 |
| WO | WO 2011/107781 A1 | 9/2011 |
| WO | WO 2011/123623 A2 | 10/2011 |
| WO | WO 2012/088377 A2 | 6/2012 |
| WO | WO 2012/108850 A1 | 8/2012 |
| WO | WO 2013/106216 A1 | 7/2013 |
| WO | WO 2013/121222 A1 | 8/2013 |
| WO | WO 2015/042268 A1 | 3/2015 |
| WO | WO 2015/124945 A1 | 8/2015 |
| WO | WO 2016/073634 A1 | 5/2016 |
| WO | WO 2016/187391 A1 | 11/2016 |
| WO | WO 2018/183388 A1 | 10/2018 |
| WO | WO 2018/237077 A1 | 12/2018 |
| WO | WO 2020/082026 A1 | 4/2020 |
| WO | WO 2023/215521 | 11/2023 |

OTHER PUBLICATIONS

National Center for Biotechnology Information) "N-Tris(hydroxymelhyl)methyl-2-aminoethanesulfonlc acid: Pubchem CID 81831" Pubchem entry (online), pp. 1-12, Jun. 24, 2005; Retrieved on Jan. 23, 2024 from the Internet: [URL: https://pubchem.ncbi.nlm.nih.gov/compound/81831].

National Center for Biotechnology Information) "Tromelhamlne: Pubchem CID 6503" Pubchem entry (online), pp. 1-10, Mar. 26, 2005; Retrieved on Aug. 9, 2023 from the Internet: [URL: https://pubchem.ncbi.nlm.nih.govlcompound/6503].

National Center for Biotechnology Information) "Tromelhamlne: Pubchem CID 6503" Pubchem entry (online), pp. 1-10, Mar. 26, 2005; Retrieved on Jan. 23, 2024 from the Internet: [URL: https://pubchem.ncbi.nlm.nih.govlcompound/6503].

National Center for Biotechnology Information) "4-Hydroxy-3,3-bis(hydroxymethyl)butan"-1-sulfonic acid: Pubchem CID 296494" Pubchem entry (online), pp. 1-13, Mar. 26, 2005; Retrieved on Aug. 9, 2023 from the Internet: [URL:https://pubchem.ncbi.nlm.nih.gov/compound/296494].

National Center for Biotechnology Information) "2-[Bis(hydroxymethyl)amino) ethanesulfonic acid: Pubchem CID 57925512" Pubchem entry (online), pp. 1-11, Aug. 19, 2012; Retrieved on Aug. 9, 2023 from the internet: [URL: https://pubchem.ncbi.nlm.nih.gov/compound/57925512].

National Center for Biotechnology Information) "Dimethyl-octadecyl-octadecyl-[3-[tris(oxlran-2-ylmethoxy)silyl]propyl)azanium: Pubchem CID 156729836" Pubchem entry (online), pp. 1-9, Nov. 10, 2021; Retrieved on Aug. 9, 2023 from the Internet: [URL:https://pubchem.ncbi.nlm.nih.gov/compound/156729836].

US, 2023/0079298, A1, U.S. Appl. No. 17/723,168, Allred et al., Mar. 16, 2023.

US, 2023/0295195, A1, U.S. Appl. No. 18/087,555, Allred et al., Sep. 21, 2023.

Email to CAS customer center, Re U.S. Pat. No. 4,005,028 (2023).

CAS Abstract and indexed compounds D. Heckert et al. U.S. Pat. No. 4,005,028 (1977).

CAS Abstract and indexed compounds J. Brinker et al. US20160287717 (2016).

US, 2021/0253607, A1, U.S. Appl. No. 17/232,012, Allred et al., Aug. 19, 2021.

U.S. Appl. No. 18/087,555, Allred et al., filed Dec. 22, 2022.

U.S. Appl. No. 17/723,168, Allred et al., filed Apr. 18, 2022.

AEGIS Environments, "AEM 5700 Antimicrobial"; A Silane Quaternary Ammonium Salt EPA Reg. No. 64881-1 EPA Est. 34292-MI-01; product label, directions for use; [undated]; 1 page, 2006.

The National Institute for Occupational Safety and Health: Emergency Response Safety and Health Database: Methanol: Systemic Agent: CAS#67-56-1: RTECS#PC14000000; UN# 1230(Guide131), available at https://www.cdc.gov/niosh/ershdb/emergencyresponsecard_29750029.html, retrieved Aug. 2, 2017.

Dror, Naama, et al.; "Advances in Microbial biofilm prevention on indwelling medical devices with emphasis on usage of acoustic energy"; Sensors; Apr. 14, 2009; vol. 9, pp. 2539-2554; p. 2542, para. 3.

Gupta et al., "Microbial Keratinases and Their Prospective Applications: An Overview," Appl Microbial Biotechnology, Jan. 4, 2006, 70: 21-33.

(56) References Cited

OTHER PUBLICATIONS

International Search Report and Written Opinion, Oct. 17, 2016, PCT Application No. PCT/US16/33208, filed on May 19, 2016.
Unknown author; "Coeus Technology Material Safety Data Sheet; MonoFoil Antimicrobial (Typical Application Strength)"; Jul. 29, 2009, Revision No. 2; 6 pages.
International search report and written opinion for PCT/US2019/057069 mailed Feb. 6, 2020.
Hamel, Michelle; "NMT-LMT Certified Aroma Therapist Neuromuscular Pain Relief Center Orlando Massage Therapy", Infection-Biofilm Treatment Essential Oils Orlando; 2016.
Jenkins, Ben H.; "Treatment of Otitis Externa and Swimmer's Ear" The JAMA Network; Feb. 4, 1961;175(5):402-404; 2 pages.
Monticello, Robert A.; "The use of reactive silane chemistries to provide durable, non-leaching antimicrobial surfaces"; EGIS Environments; 2017; 77 pages.
MonoFoilUSA Redefining Clean; MonoFoil MSDS 2017; one page.
Saif, et al. "An eco-friendly, permanent, and non-leaching antimicrobial coating on cotton fabrics" 2014 pp. 1-6.
Sander, Robert; "Otitis Externa: A practical guide to treatment and prevention; Practical Therapeutics", Medical College of Wisconsin, Milwaukee, Wisconsin; American Family Physician; vol. 63, No. 5; Mar. 1, 2001; p. 927-936.
Song, Jooyoung, et al. "Bacterial adhesion inhibition of the quaternary ammonium functionalized silica nanoparticles," Colliods and Surfaces B: Biointerfaces 82 (2011) 651-656.
Internet Archive Wayback Machine, CFA Coatings for America, Bioshield '75 Bigstatic Surface Protectant Presentation 2013; 27 pages.
Wang, et al. "Specificity and Enzyme Kinetics of the Quorum-Quenching N-Acyl Homoserine Lactone Lactonase (AHL-lactonase)", The Journal of Biological Chemistry; 2004; vol. 279, No. 14. Issue of Apr. 2, pp. 13645-13651.
International Search Report and Written Opinion for PCT/2023/21069 dated Jan. 9, 2024, 12 pages.
National Center for Biotechnology Information) "N,N-Dimethyl-N-(3-(trihydroxysilyl)propyl)octadecan-1-aminium: Pubchem CID 21365909" Pubchem entry (online), pp. 1-14, Dec. 5, 2007; Retrieved on Aug. 7, 2023 from the Internet: [URL: https://pubchem.ncbi.nlm.nih.gov/compound/21365909].
National Center for Biotechnology Information) "N-Tris(hydroxymethyl)methyl-2-aminoethanesulfonic acid: Pubchem CID 81831" Pubchem entry (online), pp. 1-12, Jun. 24, 2005; Retrieved on Aug. 9, 2023 from the Internet: [URL: https://pubchem.ncbi.nlm.nih.gov/compound/81831].
National Center for Biotechnology Information) "N-Tris(hydroxymethyl)methyl-2-aminoethanesulfonic acid: Pubchem CID 81831" Pubchem entry (online), pp. 1-12, Jun. 24, 2005; Retrieved on Jan. 23, 2024 from the Internet: [URL: https://pubchem.ncbi.nlm.nih.gov/compound/81831].
National Center for Biotechnology Information) "Tromethamine: Pubchem CID 6503" Pubchem entry (online), pp. 1-10, Mar. 26, 2005; Retrieved on Aug. 9, 2023 from the Internet: [URL: https://pubchem.ncbi.nlm.nih.gov/compound/6503].
National Center for Biotechnology Information) "Tromethamine: Pubchem CID 6503" Pubchem entry (online), pp. 1-10, Mar. 26, 2005; Retrieved on Jan. 23, 2024 from the Internet: [URL: https://pubchem.ncbi.nlm.nih.gov/compound/6503].
National Center for Biotechnology Information) "Dimethyl-octadecyl-[3-[tris(oxiran-2-ylmethoxy)silyl]propyl]azanium: Pubchem CID 156729836" Pubchem entry (online), pp. 1-9, Nov. 10, 2021; Retrieved on Aug. 9, 2023 from the Internet: [URL: https://pubchem.ncbi.nlm.nih.gov/compound/156729836].

\* cited by examiner

ANTIMICROBIAL ORGANOSILANES

CROSS-REFERENCE TO RELATED APPLICATIONS

This application is a continuation of U.S. patent application Ser. No. 17/723,168, filed on Apr. 18, 2022, which is a of International Patent Application No. PCT/US2020/056392, filed in the U.S. Receiving Office on Oct. 19, 2020, which claims the benefit of provisional U.S. Application 62/923,372, filed Oct. 18, 2019, and U.S. Application 63/014,535, filed Apr. 23, 2020. The entirety of each of these applications is hereby incorporated by reference for all purposes.

FIELD OF THE INVENTION

This disclosure provides organosilicon quaternary ammonium compounds and compositions thereof and their uses for topical medical therapy in humans and animals as well as to disinfect surfaces including but not limited work, industrial, transportation and home applications.

BACKGROUND OF THE INVENTION

There is an urgent global need to provide new antimicrobials, including antifungals and antibiotics to treat infections in humans and animals, including difficult to treat infections that are not or are insufficiently responsive to current therapies.

In September 2018, The PEW Charitable Trusts reported on the critical need for new antibiotics. At that time, there were only 42 antibiotics in clinical development, with a predicted rate of not more than 20% approval. Of these, only 15 were likely to treat infections caused by resistant Gram-negative pathogens. Only 11 antibiotics in development have the potential to treat pathogens considered a critical threat by The World Health Organization.

One of the ways microorganisms evade current therapies is by the formation of a biofilm consisting of a group of microorganisms that adhere to each other and, in many cases, surrounding surfaces. These microorganisms may be fungi, bacteria, yeasts, algae, or commonly, mixtures thereof. The microbial communities are encased in extracellular polymeric substances (EPS) (see Karatan E., Watnick P. "Signals, regulatory networks, and materials that build and break bacterial biofilms" Microbiol. Mol. Biol Rev. 2009, 73:310-347), a mixture of polysaccharides, extracellular DNA (eDNA), and proteins that function as a matrix holding the microbial cells together. The biofilm matrix contributes to the overall architecture and the resistant phenotype of biofilms (See Sutherland I. W. "The biofilm matrix—An immobilized but dynamic microbial environment" Trends Microbiol. 2001, 9:222-227; and Branda S. S., Vik S., Friedman L., Kolter R. "Biofilms: The matrix revisited" Trends Microbiol. 2005, 13:20-26). This matrix also "confers a spatial organization on biofilms, from which they derive steep gradients, high biodiversity, and complex, dynamic and synergistic interactions, including cell-to-cell communication and enhanced horizontal gene transfer." (see Flemming H.-C., Wingender J., Szewzyk U. Steinberg, P., Rice S. A., Kjelleberg, S. "Biofilms: An emergent form of bacterial life" Nature Reviews Microbiology 2016, 14:563-575). This protective mode of growth allows microorganisms to survive in hostile environments and disperse seeding cells to colonize new niches under desirable conditions.

The increasing microbial resistance to present treatment regimens is at least in part due to the escalating effectiveness of the primary intrinsic defense mechanisms of microorganisms, particularly in biofilms. These defenses include decreased drug uptake, efflux, enzymatic inactivation, and target alterations by mutations. Microbes can also acquire resistance by sharing genetic material, called horizontal gene transfer (HGT), which can be a more rapid process than genetic selection involved in the development of intrinsic resistance. Simultaneous or sequential polymicrobial infection can occur with similar organisms of a different species or a mixture of bacteria and fungi. The available antimicrobials used for treatment often do not have significant activity overlap across multiple groups of potential pathogens (Tuft, S. "Polymicrobial infection and the eye" Br J Ophthalmol. 2006, 90(3):257-258).

Negative consequences of these biofilm interactions can result in large health care burdens such as nonhealing or chronic wounds. The management of a chronic wound—defined as a barrier defect that has not healed in 3 months—has become a major therapeutic challenge throughout the Western world, and it is a problem that will only escalate with the increasing incidence of conditions that impede wound healing, such as diabetes, obesity, and vascular disorders. These ulcers last on average 12 to 13 months, recur in up to 60% to 70% of patients, can lead to loss of function and decreased quality of life, and are a significant cause of morbidity (Richmond N A, Maderal A D, Vivas A C. Evidence-based management of common chronic lower extremity ulcers. Dermatol Ther 2013; 26:187-196). Despite being clinically and molecularly heterogeneous, all chronic wounds are generally assigned to one of three major clinical categories: leg ulcers, diabetic foot ulcers, or pressure ulcers. In the United States alone, these wounds affect an estimated 2.4-4.5 million people (Evidence-based management of PAD & the diabetic foot. Brownrigg J R et al., Eur J Vasc Endovasc Surg. 2013 June; 45(6):673-81). Chronic leg and foot ulcers occur in many adults with vascular disease or diabetes and are attributed to chronic venous insufficiency, arterial disease, prolonged pressure, or neuropathy (Richmond N A, Maderal A D, Vivas A C. Evidence-based management of common chronic lower extremity ulcers. Dermatol Ther 2013; 26:187-196). Diabetic-foot ulcers (DFUs) contribute to 80% of nontraumatic lower-extremity amputations and are associated with 5-year mortality rates of 43 to 55%.

These chronic wounds are largely believed to be critically colonized by polymicrobial communities that contribute to persistent inflammation and stalled healing processes, significantly reducing the quality of life for those afflicted. In tissue injury, microbes enter the wound where the physical environment differs from the skin surface in temperature, pH, nutrient availability, and host immune effectors. Here, microbial metabolism can shift, providing opportunities for commensal microbes to become virulent and community composition to fluctuate in response to host clinical factors. Once colonization occurs, these communities form a biofilm within the wound, disrupting the coordinated tissue regeneration process.

Current treatments for wounds with suspected biofilm are primarily focused on targeting bacteria, however, skin is also host to resident fungi, and our environment is rich with fungal diversity (Percival S L, McCarty S M, Lipsky B. 2015. Biofilms and wounds: an overview of the evidence. Adv Wound Care (New Rochelle) 4: 373-381). Chronic wound patients receive significantly more antibiotic prescriptions (both systemic and topical) than other age and gender matched patients. Many human commensal fungi or yeasts are also opportunistic pathogens, and many species are known to be prolific biofilm formers. There is now sufficient evidence to conclude that increased species diversity of biofilms is correlated to increased resistance to antimicrobials (Desai J V, Mitchell A P, Andes D R. 2014. Fungal biofilms, drug resistance, and recurrent infection. Cold Spring Harb Perspect Med 4: doi:10.1101/cshperspect.a019729). Moreover, use of antibiotics targeting bacteria in mixed communities have been shown to increase fungal diversity in wound tissue and provide a niche for fungal expansion in mixed bacterial-fungal biofilms.

Biofilms exist in a number of additional conditions, which can evolve into chronic or recurring infections. For example, ear infections can be the result of a biofilm, in humans as well as in animals such as dogs, cats, rabbits, and horses. In both animals and humans, if not treated properly, the infection can cause hearing loss and lead to other health problems.

Corneal vision impairment is a general term for conditions that result from a variety of infections that scar the cornea. The effective treatment of ocular infections with an affordable medication is clearly a global health priority. Fungi alone cause over a million eye infections every year, many of which result in blindness. The eye is particularly vulnerable to fungal infections when anatomical barriers are breached. The host's immune system is often unable to combat fungal infections and prevent loss of vision (see Klotz, S., Penn, C., Negvesky, G. and Butrus, S. "Fungal and Parasitic Infections of the Eye" Clin Microbiol Rev 2000, 13(4):662-685). The lack of potent fungicidal agents and poor ocular penetration of existing antifungal agents result in significant ocular morbidity. Bacteria are also a major contributor of ocular infections worldwide. If not treated properly, they can damage the structure of the eye, leading to visual impairment or possible blindness. Bacteria, and in particular gram-positive bacteria, are associated with conjunctivitis, keratitis, endophthalmitis, blepharitis, and orbital cellulitis.

An additional skin disorder that has proven difficult to treat includes acne vulgaris. Acne vulgaris is a common skin disease caused in part by excessive outgrowth of *Propionibacterium acnes* bacteria and inflammation induced in response to the *P. acnes* bacteria; and/or occurs when hair follicles become clogged with dead skin cells and oil from the skin. It has been suggested that *P. acnes* cells residing within the follicles grow as a biofilm, making treatment particularly difficult (see, e.g., Coenve et al., Biofilms in skin infections: *Propionibacterium acnes* and acne vulgaris. Infect Disorder Drug Targets. 2008 September; 8(3): 156-9).

Biofilm formation also occurs on abiotic (i.e., inanimate) surfaces such as in homes, workplaces, industrial areas including manufacturing plants, public areas, bathrooms, kitchens, furniture transportation sites and surfaces, and other surfaces that contacts humans or animals.

As nonlimiting examples, food and medical sectors constitutes a great public health concern. Biofilms present a persistent source for pathogens, such as *Pseudomonas aeruginosa* and *Staphylococcus aureus*, which lead to severe infections such as foodborne and nosocomial infections. Such biofilms are also a source of material deterioration and failure. The environmental conditions, commonly met in food and medical area, seem also to enhance the biofilm formation and their resistance to disinfectant agents.

Contamination caused by biofilms may occur at any stage of food processing via food handlers, contaminated equipment and food preparation surfaces (Verraes et al. 2013).

The Center for Disease Control and prevention (CDC) stated that 48 million episodes of foodborne illness occur in the USA each year, leading to 128,000 hospitalizations and up to 3,000 deaths (CDC 2013). In the European Union, 5,609 foodborne outbreaks have been reported in 2007, involving about 39,727 human cases (11,283 in France), with 3,291 hospitalizations and 19 deaths (7 in France) (EFSA 2009). Otherwise, healthcare-associated infections (HAIs), also known as nosocomial infections, commonly occur via the hands of healthcare personnel, contaminated surfaces and devices (surgical instruments, catheters, breathing system, endoscopes, needles, etc.) (Weber et al. 2013). The National Hospital Discharge Survey (NHDS) estimated the number of HAIs occurring in US hospitals, between 1990 and 2002, was up to 1.7 million cases in which 98,987 cases were fatal (Klevens et al. 2007). In Europe, the number of HAIs is estimated to be 3.2 million cases per year (Suetens et al.).

The world has also recently experienced, and continues to be plagued by, a global pandemic via the spread of the SARS-CoV virus. This pandemic has increased the awareness of the general population globally to the importance of disinfecting surfaces.

The problem of antimicrobial resistance has been growing for decades, and with fewer and fewer antibiotics and other antimicrobials being developed, many previously treatable infections are now much more difficult to treat with the current stable of medications, and may soon become untreatable.

Accordingly, there remains a strong need for new antimicrobials. New, safe, and effective topical medicines to treat a range of microbial infections are required to treat topical infections including those comprising biofilms of mixed pathogens, in humans and other animals. New effective antimicrobials are also needed to disinfect surfaces in a wide range of environments, including homes, workplaces, industrial areas, transportation locations and food production and services.

SUMMARY OF THE INVENTION

In one embodiment, new organosilane quaternary ammonium compounds are provided that can be administered in an effective amount in a pharmaceutical topical formulation to treat a range of infections, including fungal infections as well as Gram positive bacterial, Gram negative bacterial and viral infections, in a host in need thereof. The fungi can occur as a yeast, a mold or a combination of both forms. The new quaternary ammonium compounds and formulations described herein can treat microorganisms in a biofilm, including mixed organisms.

As shown in the Examples, several nonlimiting illustrative compounds described herein (for example Compound 1, Compound 2, and Compound 23), have potent anti-microbial activity and inhibition against a range of difficult to treat microbes present in persistent infections, including several *Candida* species, *Cladosporium herbarum*, *Aspergillus niger*, *Mycoplasma pneumoniae*, *Fusarium oxysporum*, *Staphylococcus aureus*, and *Enterococcus faecalis*. Such microbes are especially prevalent in microbial biofilms present in chronic wounds (see, e.g., Omar et al., Microbial Biofilms and Chronic Wounds. Microorganisms 2017, March; 5(1): 9).

Accordingly, in one aspect, the organosilane quaternary ammonium compounds described herein can be used in an effective amount in a topical formulation for direct application to an infection or incorporated into, for example, a dressing, bandage, surgical packing, gauze, wrap, conformable foam, or film for application to a wound, for example, a chronic wound or burn. When incorporated into an article, the organosilane quaternary ammonium compounds described herein may be incorporated in a manner such that the article provides controlled release of the compound or its pharmaceutically acceptable salt or composition into the surrounding area to provide extended inhibition of microbial growth. In some embodiments, an effective amount of a selected compound described herein is used to treat a chronic wound, for example, a pressure ulcer, venous ulcer, arterial wounds, neuropathic ulcer, diabetic ulcer, for example a lower limbic ulcer or foot ulcer, skin tear, or moisture-associated skin damage (MASD), for example incontinence-associated dermatitis. In some embodiments, the compounds described herein are used to treat a wound caused by a burn.

In additional aspects, the quaternary ammonium compounds described herein can be used in an effective amount to treat, for example, ocular infections (including bacterial or fungal infections and dry eye caused by Blepharitis), ear infections, skin infections including nail bed infections, acne vulgaris, eczema, medical implant infections, mouth and periodontal infections, nasal infections, vaginal infections, anal infections, and other infections accessible with a topical or suppository formulation. Furthermore, the quaternary ammonium compounds described herein can be incorporated into a medical implant in order to reduce the risk of infection associated with the use of such devices.

Importantly, in some embodiments, a new organosilane quaternary ammonium compound described herein can be provided as a stable powder or lyophilized material that can be formulated before administration using a pharmaceutically acceptable topical carrier. In an alternative embodiment, a new organosilane quaternary ammonium compound described herein can be incorporated into a dressing, conformable foam, or polymer for use in dressings, bandages, or films for use in medical applications, for example in a wound dressing or in surgical packings to reduce the risk of infection. In yet another alternative embodiment, a new organosilane quaternary ammonium compound described herein can be incorporated into a medical implant, for example but not limited to an orthopedic or dental implant.

In some embodiments, a topical infection in a human or animal that can be treated with the selected organosilane quaternary ammonium compound can be used to treat a microbe such as, for example, *Acinetobacter* (Gram-negative), *Pseudomonas* (Gram-negative), *Proteus* (genus of Gram-negative Proteobacteria), *Staphylococcus* (Gram-positive), *Streptococcus* (Gram-positive), MRSA (methicillin resistant *S. aureus*), *Escherichia coli* (Gram-negative), *Propionibacterium* (Gram-positive), *Klebsiella* (Gram-negative), *Enterococcus* (Gram-positive), *Haemophilus influenzae*, and fungi such as *Fusarium, Aspergillus, Cladosporium, Curvularia* and *Candida*, and dermatophytes such as *Trichophyton, Microsporum*, and *Epidermophyton*, or combinations or biofilms comprising combinations thereof.

In particular embodiments, the topical infection comprises a *Candida* fungal infection, for example, but not limited to, *C. albicans, C. auris*, or *C. glabrata*, or a combination thereof.

The present invention provides new organosilicon quaternary amine compounds which have a balancing pharmaceutically acceptable anion or anions (whether explicitly shown in the formula or not). In certain embodiments, the balancing anion is selected from chloride, fluoride, iodide, bromide, hydroxide, chlorite, chlorate, hydroxide, formate, acetate, lactate, benzoate, or salicylate anion. In a typical embodiment, the balancing anion is chloride or hydroxide.

In some embodiments, the quaternary ammonium compound includes a substituent that has a negative charge. The substituent with the negative charge may be neutralized with a pharmaceutically acceptable cation such as sodium or potassium.

In some embodiments, the quaternary ammonium compound is provided as a zwitterion, in which the positive charge of the internal quaternary amine is neutralized with an anion from a substituent in the molecule, as described further below.

The invention also provides a method of topical administration of an effective amount of one or more new organosilicon quaternary amine compounds described herein, which may optionally also include a pharmaceutically acceptable salt, and optionally in a composition thereof to treat, prevent, inhibit, or eliminate an infectious disease in a host in need thereof.

The invention also includes pharmaceutically acceptable compositions thereof in the form of a powder, lyophilized powder, or otherwise solid stable storage form.

A selected compound of the present invention can also be used in an effective amount optionally in a liquid, gel or solid carrier to disinfect a microbial growth or a biofilm formation that occurs on an abiotic (i.e., inanimate) surface such as in a home, workplace, industrial area including manufacturing plant, public area, bathroom, kitchen, furniture, transportation site or surface, or other surface that contacts or is in the environment of a human or animal. In one embodiment, an environmental surface, commonly met in food and medical area, seem also to enhance the biofilm formation and their resistance to disinfectant agents.

In one aspect, the present invention provides a quaternary ammonium compound having a Formula:

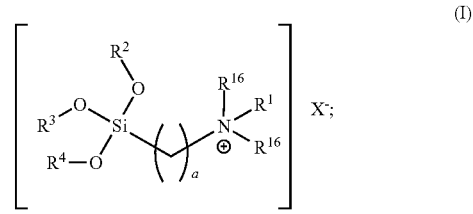

(I)

wherein a is 1, 2, 3, 4, 5, 6, 7 or 8 (and wherein a methylene can have a branching alkyl such as a $C_1$-$C_4$ alkyl including methyl);

$R^1$ is independently at each occurrence selected from $C_6$-$C_{22}$alkyl (and can be $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), $C_6$-$C_{22}$alkenyl (and can be $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), and $C_6$-$C_{22}$alkanoyl (and can be $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$) (and wherein any of these methylenes or aliphatic carbons can have a branching alkyl such as a $C_1$-$C_4$ alkyl including methyl);

$R^2$, $R^3$, and $R^4$ are independently at each occurrence selected from:

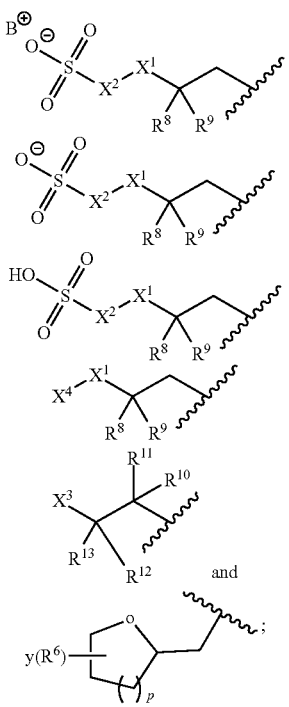

or a $C_2$-$C_{10}$ alkanoic acid (which can be $C_2$, $C_3$, $C_4$, $C_5$, $C_6$, $C_7$, $C_8$, $C_9$ or $C_{10}$) or salt thereof, and in some embodiments all of $R^2$, $R^3$, and $R^4$ are alkanoic acids (and wherein any of these methylenes or aliphatic carbons can have a branching alkyl such as a $C_1$-$C_4$ alkyl including methyl);

y is 0, 1, 2, 3, or 4;

p is independently at each occurrence selected from 1, 2, 3, and 4;

$R^6$ is independently selected from hydrogen, alkyl, aryl, cycloalkyl and heterocyclyl; wherein each of said alkyl, aryl, cycloalkyl and heterocyclyl, optionally includes a substituent group selected from $C_1$-$C_6$alkyl, hydroxyl, chloro, bromo, iodo, fluoro, $N(R^7)_2$, $COOR^7$, $C(O)R^7$, $CH_2OR^7$, $CON(R^7)_2$, and $NO_2$;

$R^8$, $R^9$, $R^{10}$, $R^{11}$, $R^{12}$, and $R^{13}$ are independently at each occurrence selected from hydrogen, halogen, hydroxyl, $N(R^7)_2$, $CH_2OR^7$, $CON(R^7)_2$, $COOR^7$, $C(O)R^7$, $C_1$-$C_8$alkyl, $C_1$-$C_8$hydroxyalkyl, $C_2$-$C_8$alkenyl, $C_2$-$C_8$ alkynyl, $C_1$-$C_8$ haloalkyl, $C_1$-$C_8$alkanoyl, heterocyclyl, heteroaryl, and aryl;

$R^7$ is independently at each occurrence selected from hydrogen, $C_1$-$C_8$ alkyl, $C_1$-$C_8$ hydroxyalkyl, $C_2$-$C_8$ alkenyl, $C_2$-$C_8$ alkynyl, $C_1$-$C_8$ haloalkyl, $C_1$-$C_8$ alkanoyl, heterocyclyl, heteroaryl, heterocycloalkyl, and aryl;

$X^1$ is independently at each occurrence selected from $NR^{17}$, $CH_2$, $CHOH$, and $C(O)$;

$X^2$ is independently at each occurrence selected from $C_1$-$C_3$alkyl and $C_1$-$C_3$hydroxyalkyl;

$X^3$ is independently at each occurrence selected from hydroxyl, $NO_2$, $N(R^7)_2$, $CH_2OR^7$, $CON(R^7)_2$, $COOR^7$, $C(O)R^7$, $C_1$-$C_{12}$alkanoic acid, $C_1$-$C_8$alkyl, $C_1$-$C_8$hydroxyalkyl, $C_2$-$C_8$alkenyl, $C_2$-$C_8$ alkynyl, $C_1$-$C_8$ haloalkyl, $C_1$-$C_8$alkanoyl, heterocyclyl, heteroaryl, and aryl;

$X^4$ is independently at each occurrence selected from $X^3$;

$R^{16}$ is independently at each occurrence selected from $C_1$-$C_4$alkyl, $C_2$-$C_4$alkenyl, $C_2$-$C_4$alkynyl, and $C_1$-$C_4$haloalkyl;

$R^{17}$ is independently at each occurrence selected from hydrogen, $C_1$-$C_8$ hydroxyalkyl, $C_2$-$C_8$ alkenyl, $C_2$-$C_8$ alkynyl, $C_1$-$C_8$ haloalkyl, $C_1$-$C_8$ alkanoyl, heterocyclyl, heteroaryl, heterocycloalkyl, and aryl;

$X^-$ is an anion, for example, chloride, fluoride, iodide, bromide, hydroxide, chlorite, chlorate, formate, acetate, lactate, benzoate, or salicylate, anion. When $X^-$ is an anion with a negative charge of more than one the charge stoichiometry should be balanced by other cations; and $B^+$ is a cation, for example, an ammonium, potassium or sodium. If it is useful to use a $B^+$ that has a charge of greater than one, for example, calcium, then the stoichiometry should be balanced as appropriate, for example:

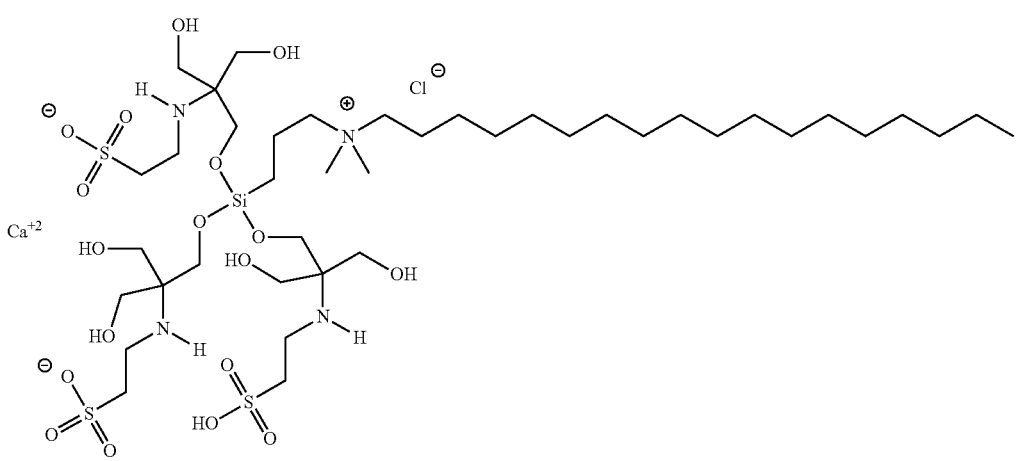

In some embodiments B+ is K+ or Na+. In another embodiment B+ is Ca+2 or Mg+2.

In certain embodiments, B+ is ammonium ion comprising NH$_4^+$, RNH$_3^+$, R$_2$NH$_2^+$, R$_3$NH$^+$, or R$_4$N$^+$; wherein R is independently at each occurrence selected from the group consisting of C$_1$-C$_8$ alkyl, C$_1$-C$_8$ hydroxyalkyl, C$_2$-C$_8$ alkenyl, C$_2$-C$_8$ alkynyl, C$_1$-C$_8$ haloalkyl, heterocyclyl, heteroaryl, heterocycloalkyl, and aryl.

In any of the formulas provided herein, wherein there is a length of alkyl or aliphatic chain, any of these methylenes or aliphatic carbons can have a branching alkyl such as a C$_1$-C$_4$ alkyl including methyl), and it is deemed specifically disclosed for each combination.

In another aspect, the present invention provides a quaternary ammonium compound having Formula

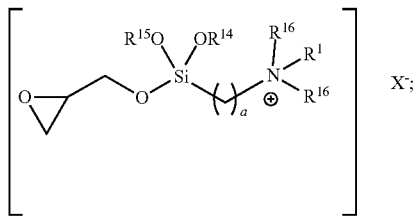

(II)

wherein
- a is 1, 2; 3, 4, 5, 6, 7, or 8 (and wherein any of these methylenes can have a branching alkyl such as a C$_1$-C$_4$ alkyl including methyl);
- X$^-$ is an anion, for example, chloride, fluoride, iodide, bromide, chlorite, chlorate, hydroxide, formate, acetate, lactate, benzoate, or salicylate, anion and when X$^-$ is an anion with a negative charge of more than one, the charge stoichiometry should be balanced as appropriate;
- R$^{14}$ and R$^{15}$ are independently at each occurrence selected from

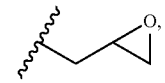

R$^2$, and R$^{17}$; and wherein all other variables are as defined herein.

In another aspect, the present invention provides a quaternary ammonium compound of Formula

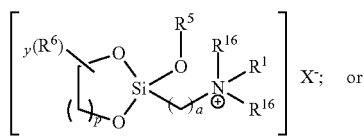

(III)

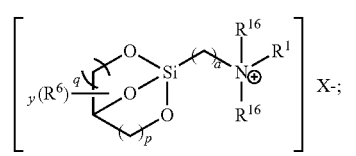

(IV)

wherein
- p and q are independently at each occurrence selected from 1, 2, 3, and 4;
- R$^5$ is independently at each occurrence selected from R$^2$, R$^{17}$, and C$_2$-C$_{10}$ alkanoic acid (which can be C$_2$, C$_3$, C$_4$, C$_5$, C$_6$, C$_7$, C$_8$, C$_9$ or C$_{10}$); and wherein the acid is optionally a diacid or a salt thereof; (and wherein any of these methylenes can have a branching alkyl such as a C$_1$-C$_4$ alkyl including methyl)
- R$^2$ is independently at each occurrence selected from

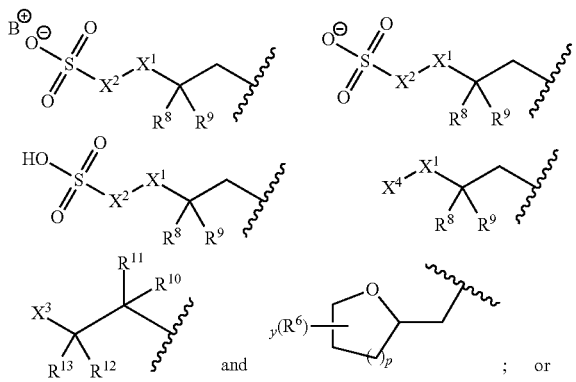

; or or
- R$^2$ is independently at each occurrence selected from a C$_1$-C$_8$alkanoic acid or salt thereof;
- R$^8$, R$^9$, R$^{10}$, R$^{11}$, R$^{12}$, and R$^{13}$ are independently at each occurrence selected from hydrogen, halogen, hydroxyl, N(R$^7$)$_2$, CH$_2$OR$^7$, CON(R$^7$)$_2$, COOR$^7$, C(O)R$^7$, C$_1$-C$_8$alkyl, C$_1$-C$_8$hydroxyalkyl, C$_2$-C$_8$alkenyl, C$_2$-C$_8$ alkynyl, C$_1$-C$_8$ haloalkyl, C$_1$-C$_8$alkanoyl, heterocyclyl, heteroaryl, and aryl;
- R$^7$ is independently at each occurrence selected from hydrogen, C$_1$-C$_8$ alkyl, C$_1$-C$_8$ hydroxyalkyl, C$_2$-C$_8$ alkenyl, C$_2$-C$_8$ alkynyl, C$_1$-C$_8$ haloalkyl, C$_1$-C$_8$ alkanoyl, heterocyclyl, heteroaryl, heterocycloalkyl, and aryl;
- X$^1$ is independently at each occurrence selected from NR$^{17}$, CH$_2$, CHOH, and C(O);
- X$^2$ is independently at each occurrence selected from C$_1$-C$_3$alkyl and C$_1$-C$_3$hydroxyalkyl;
- X$^3$ is independently at each occurrence selected from hydroxyl, NO$_2$, N(R$^7$)$_2$, CH$_2$OR$^7$, CON(R$^7$)$_2$, COOR$^7$, C(O)R$^7$, C$_1$-C$_{12}$alkanoic acid, C$_1$-C$_8$alkyl, C$_1$-C$_8$hydroxyalkyl, C$_2$-C$_8$alkenyl, C$_2$-C$_8$ alkynyl, C$_1$-C$_8$ haloalkyl, C$_1$-C$_8$alkanoyl, heterocyclyl, heteroaryl, and aryl;
- X$^4$ is independently at each occurrence selected from X$^3$; and
- R$^{17}$ is independently at each occurrence selected from hydrogen, C$_1$-C$_8$ hydroxyalkyl, C$_2$-C$_8$ alkenyl, C$_2$-C$_8$ alkynyl, C$_1$-C$_8$ haloalkyl, C$_1$-C$_8$ alkanoyl, heterocyclyl, heteroaryl, heterocycloalkyl, and aryl;
- X$^-$ is an anion, for example, chloride, fluoride, iodide, bromide, chlorite, chlorate, hydroxide, formate, acetate, lactate, benzoate, or salicylate, anion, when X$^-$ is an anion with a negative charge of more than 1 the charge stoichiometry is still balanced by other cations; and
- B$^+$ is a cation, for example, a sodium, potassium, magnesium, calcium, or lithium cation, and when B$^+$ is a cation with a positive charge of more than 1 the charge stoichiometry is appropriately balanced by other anions.

In certain embodiments, the quaternary ammonium compound has a negatively charged moiety that can form a pharmaceutically acceptable salt, wherein the cation is selected from sodium, potassium, magnesium, calcium, cesium, barium and lithium.

In one aspect, an oligomer or polymer product of Formula I', Formula II', Formula III', Formula IV' is formed by reacting one or more quaternary ammonium compounds of Formula I, Formula II, Formula III or Formula IV with a polyhydroxyl compound, for example, a compound selected from glycerin or a glycol selected from one or more of a glycidol, glycerol, glycerol-propylene oxide copolymer, ethylene glycol, propylene glycol, polyethylene glycol, polypropylene glycol, and polyvinyl alcohol.

In one aspect, an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL' is formed by reacting one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with a polyhydroxyl compound, for example, a compound selected from glycerin or a glycol selected from one or more of a glycidol, glycerol, glycerol-propylene oxide copolymer, ethylene glycol, propylene glycol, polyethylene glycol, polypropylene glycol, and polyvinyl alcohol.

In one aspect, the present invention provides a powder formulation comprising at least one quaternary ammonium compound as described herein, or a combination thereof. In some embodiments, the powder is a lyophilized powder.

In some embodiments, a pharmaceutical composition is provided with a quaternary ammonium compound as described herein, wherein the pharmaceutical composition contains less than about 5%, about 4%, about 3%, about 2%, about 1%, about 0.5%, or about 0.1% of methanol by weight, or no methanol is present.

In some embodiments, a quaternary ammonium compound as described herein, a pharmaceutically acceptable composition thereof, or a combination thereof, is administered as an aqueous or glycerin solution that has been formed by reconstituting a powder or solid formulation.

In some embodiments, any mixture of quaternary ammonium compounds as described herein, or a pharmaceutically acceptable composition thereof, is appropriate as long as the desired stability is achieved.

In some embodiments the compounds of the present invention exist as a mixture of related structures. As one non-limiting example, a composition that is primarily composed of molecule

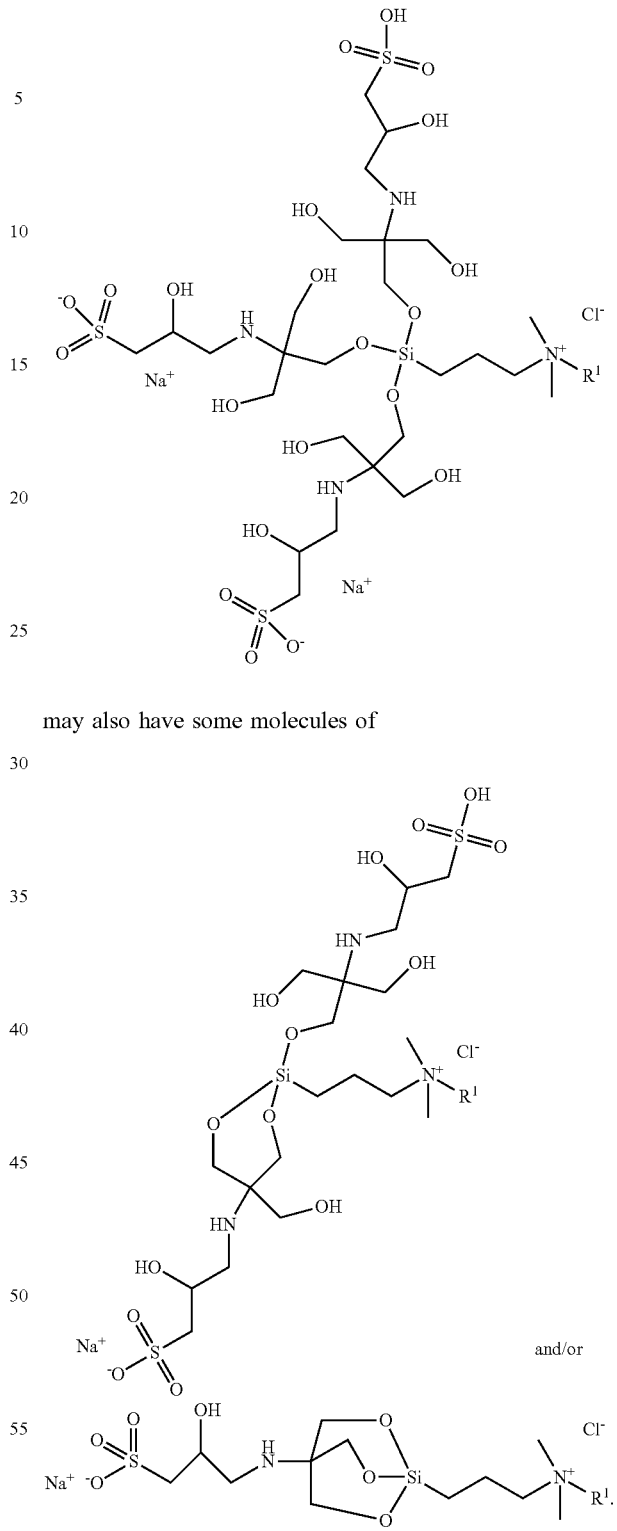

may also have some molecules of

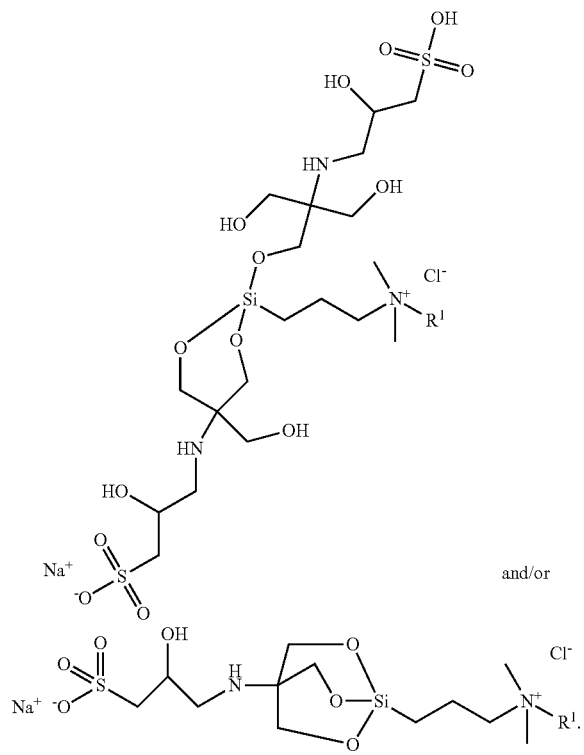

and/or

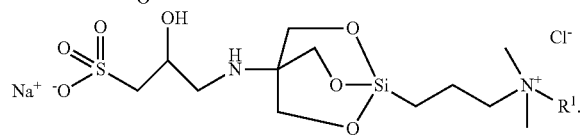

These related structures may interconvert in solution.

In certain embodiments the composition of any of the aspects of the present invention is independently a mixture of any of the molecules herein, but the drawn structure comprises at least 10%, 20%, 30%, 40%, 50%, 51%, at least 60%, at least 70%, at least 80%, at least 90%, or at least 95% of the mixture by mole, or alternatively, by weight.

The skilled artisan will also recognize that the compounds of the present invention may exist in various forms in solution while still accomplishing their intended goal. Thus, in certain embodiments the invention is a solution of the drawn compound, wherein that solution can include various related structures but the total ratio of silicon sidechain groups to silicone is the same as what is drawn. For example, in some embodiments the invention is a solution of

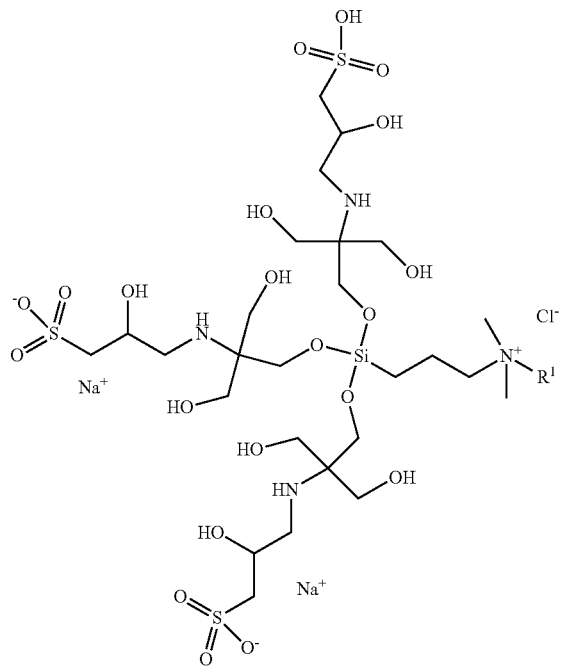

wherein that solution comprises various related molecules but the total number of

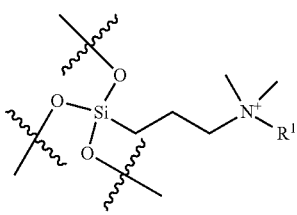

moieties to

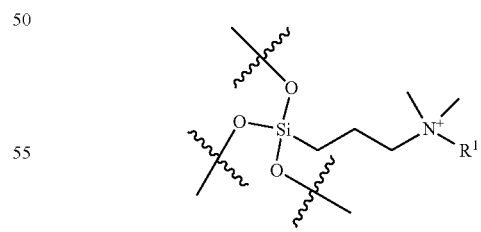

moieties is approximately 3 to 1 by ratio (i.e., by mole). In certain embodiments approximately 3 to 1 includes any ratio between 2.6:1 and 3.4:1. In other embodiments approximately 3 to 1 includes any ratio between 2.8:1 and 3.2:1. In certain embodiments, the sodium chloride (NaCl) salt can be replaced with another salt described herein. And, in another embodiment the invention is a solution of

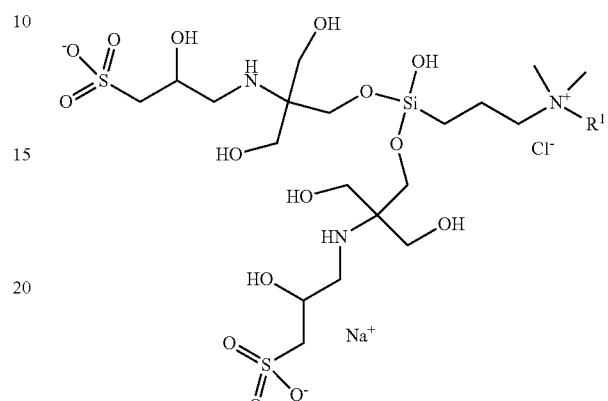

wherein that solution comprises various related molecules but the total number of

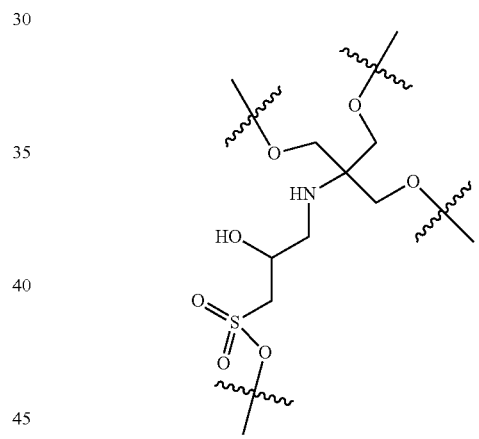

moieties to

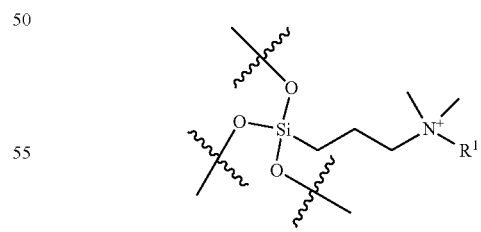

moieties is approximately 2 to 1 by ratio (i.e., by mole). In certain embodiments approximately 2 to 1 includes any ratio between 1.6 to 1 and 2.4 to 1. In other embodiments approximately 2 to 1 includes any ratio between 1.8 to 1 and 2.2 to 1. In certain embodiments, the sodium chloride (NaCl) salt can be replaced with another salt described herein.

In one aspect, the present invention provides a quaternary ammonium compound selected from Formula V, Formula VI, Formula VII, Formula VIII, Formula IX, Formula X, Formula XI, and Formula XII;

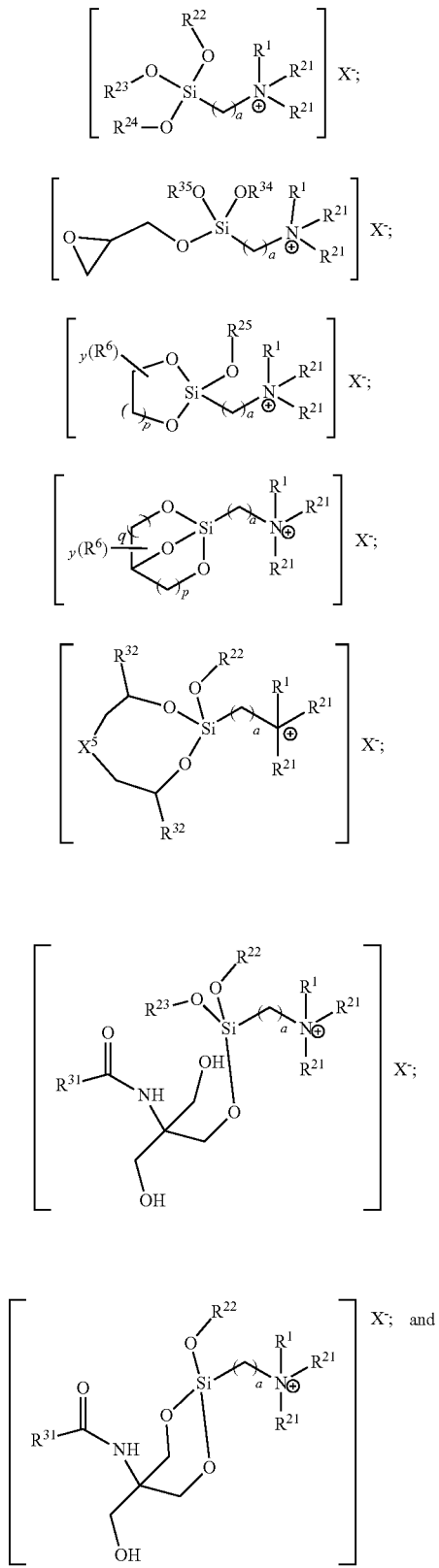

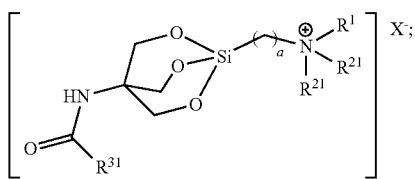

wherein:

each $R^{21}$ is independently selected from $C_1$-$C_{22}$alkyl (and can be $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), $C_2$-$C_{22}$alkenyl (and can be $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), $C_2$-$C_{22}$alkanoyl (and can be $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), and -alkyl-aryl; each of which $R^{21}$ is optionally substituted with 1, 2, or 3, substituents independently selected from $C_1$-$C_6$alkyl, halogen, and

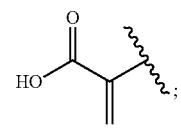

$R^{22}$, $R^{23}$, and $R^{24}$ are independently at each occurrence selected from:

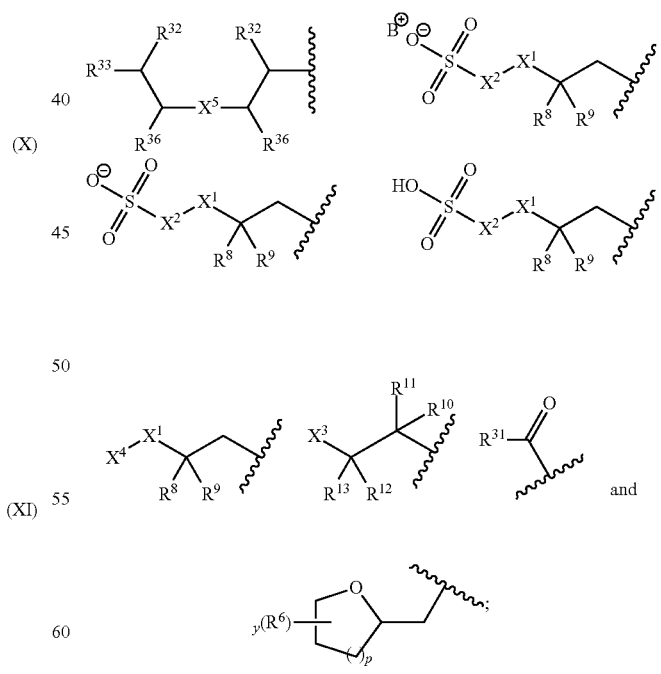

$R^{25}$ is independently at each occurrence selected from $R^{22}$, $R^{17}$, and $C_2$-$C_{10}$ alkanoic acid (which can be $C_2$, $C_3$, $C_4$, $C_5$, $C_6$, $C_7$, $C_8$, $C_9$ or $C_{10}$); and wherein the acid is optionally a diacid or a salt thereof;

$R^{31}$ is selected from $C_6$-$C_{22}$alkyl (and can be $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), $C_6$-$C_{22}$alkenyl (and can be $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), $C_6$-$C_{22}$alkynyl (and can be $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$), and $C_6$-$C_{22}$alkenylalkynyl (and can be $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$);

each $R^{32}$ is independently selected from hydrogen,

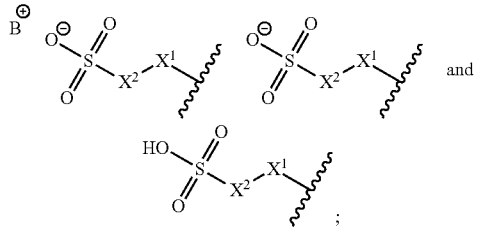

;

In certain embodiments, each $R^{32}$ is independently selected from hydrogen,

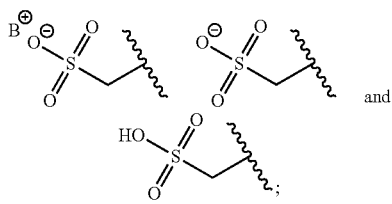

;

$R^{33}$ is independently at each occurrence selected from hydroxyl, hydrogen, $C_1$-$C_6$alkyl, and halogen;

$R^{34}$ and $R^{35}$ are independently at each occurrence selected from

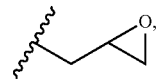

$R^{22}$, and $R^{17}$;

each $R^{36}$ is independently selected from hydrogen,

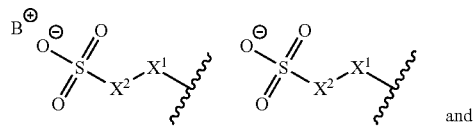

and

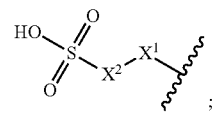

;

$X^5$ is selected from heterocycle, cycloalkyl, alkyl, aryl, heteroaryl, alkenyl, haloalkyl, and alkynyl; and wherein the remaining variables are as defined herein.

In certain embodiments the compound of the present invention is:

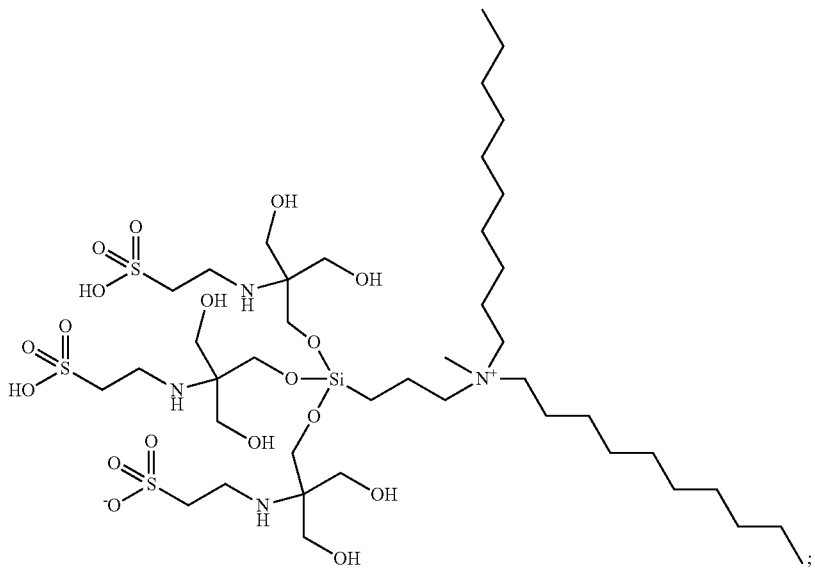

or a pharmaceutically acceptable salt thereof.

In certain embodiments $R^{22}$, $R^{23}$, and $R^{24}$ are independently at each occurrence selected from:

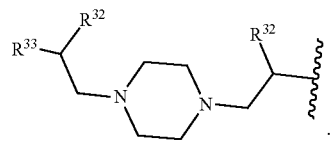

In certain embodiments $R^{22}$, $R^{23}$, and $R^{24}$ are independently at each occurrence selected from:

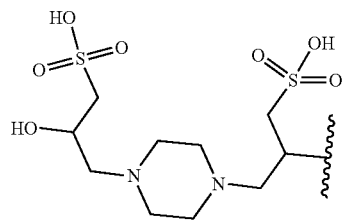

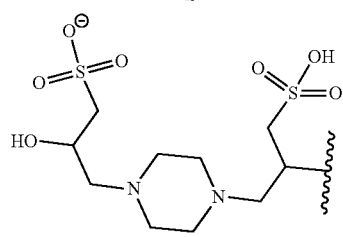

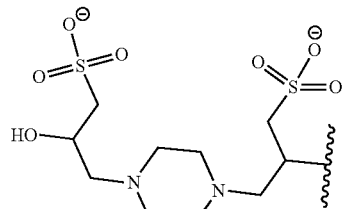

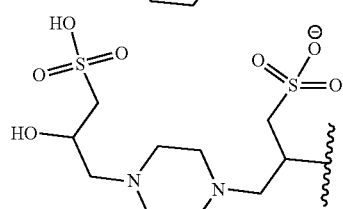

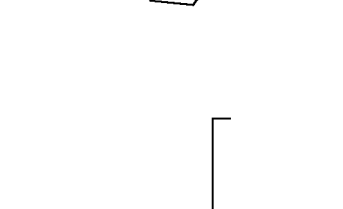

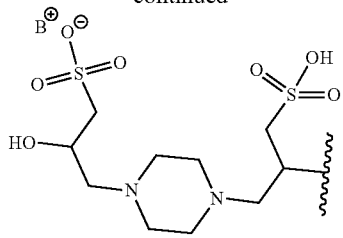

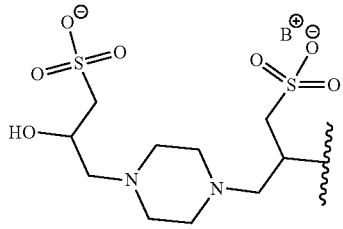

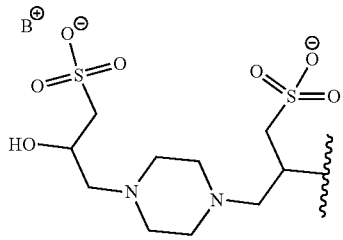

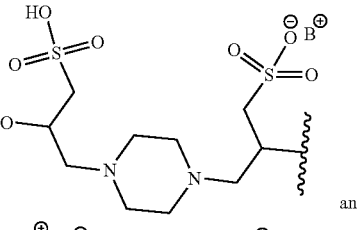

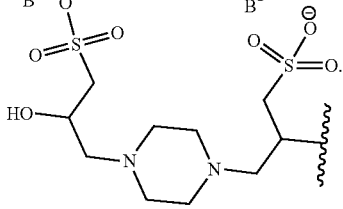

and

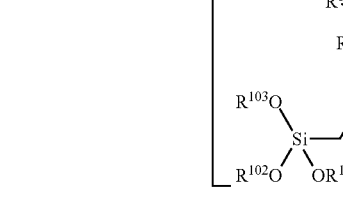

In certain embodiments each $R^{36}$ is hydrogen.
In certain embodiments each $R^{32}$ is —CH$_2$—SO$_3$H.
In one aspect of the present invention, a compound of Formula XIII, XIV, XV, XVI, XVII, XVIII, XIX, XX, or XXI is provided,

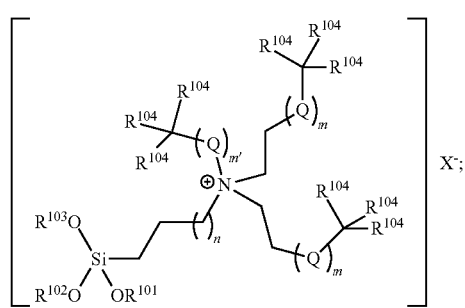

(XIII)

-continued
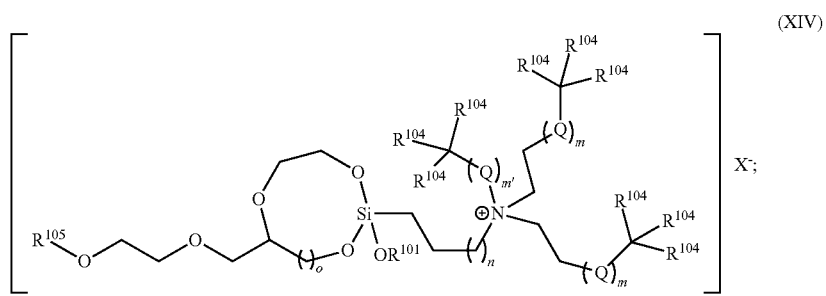
(XIV)
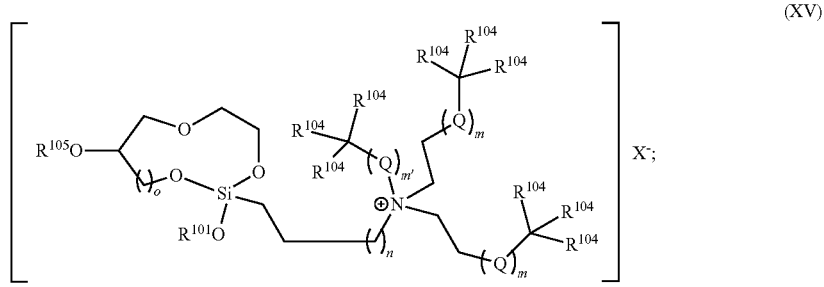
(XV)
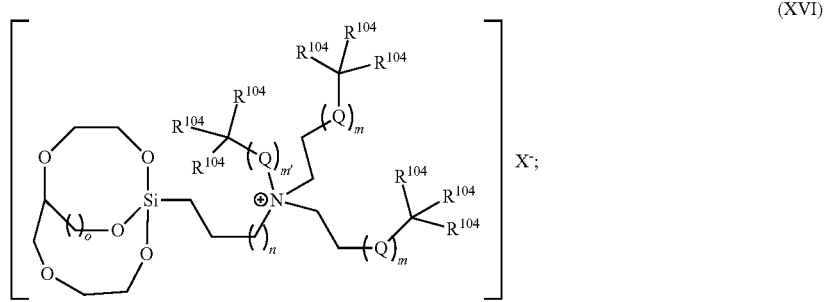
(XVI)
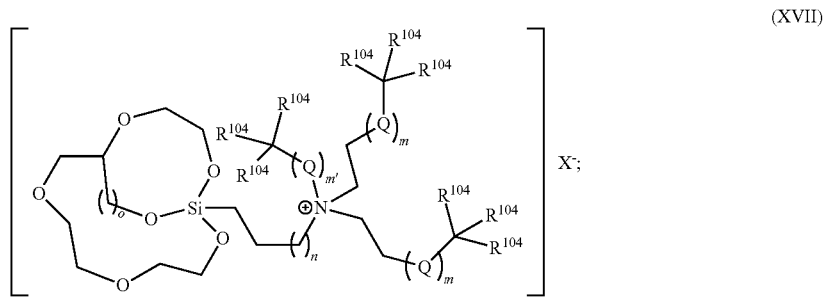
(XVII)
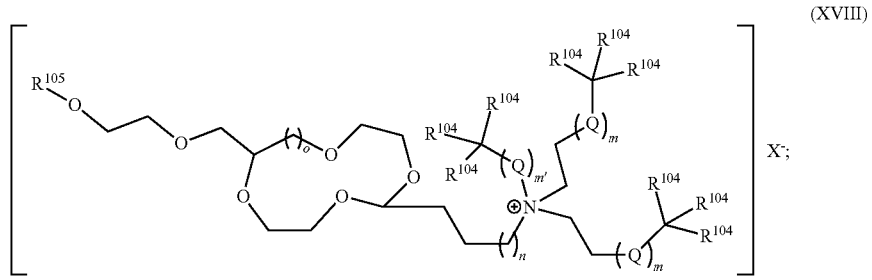
(XVIII)

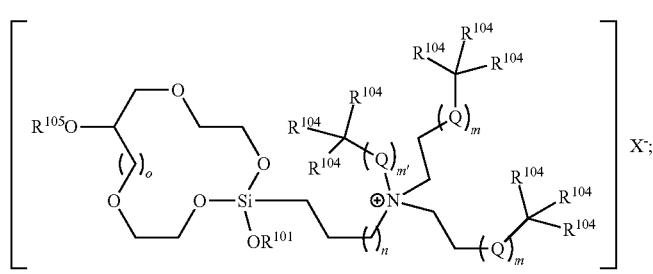

(XIX)

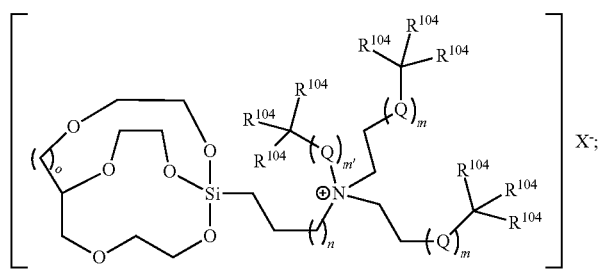

(XX)

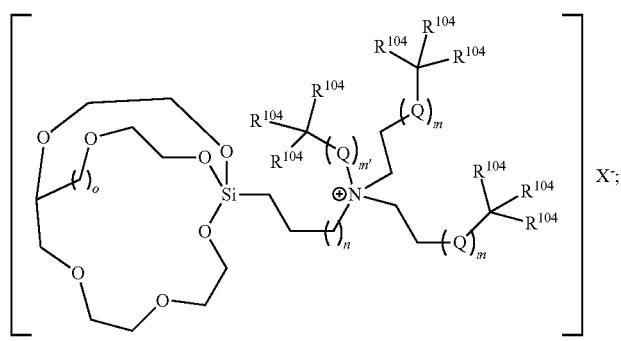

(XXI)

wherein:
  is 1 or 2;
  n is independently at each occurrence selected from 0, 1, and 2;
  m is independently at each occurrence selected from 0, 1, 2, 3, 4, 5, 6, 7, 8, 9, 10, 11, 12, 13, 14, 15, 16, 17, 18, 19, and 20;
  m' is 0, 1, 2, 3, 4, 5, 6, 7, 8, 9, 10, 11, 12, 13, 14, 15, 16, 17, 18, 19, 20, 21, or 22;
  Q is —$CR^{104}R^{104}$—;
  $R^{101}$ and $R^{102}$ are both hydrogen; or
  in an alternative embodiment, $R^{101}$ and $R^{102}$ are independently at each occurrence selected from hydrogen and ethyl;
  $R^{103}$ is independently at each occurrence selected from:

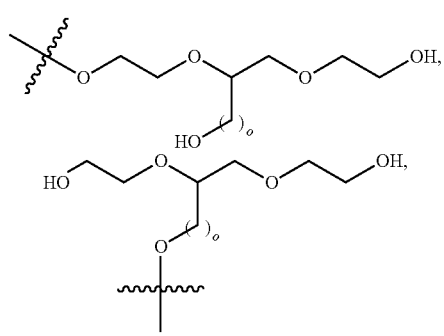

-continued

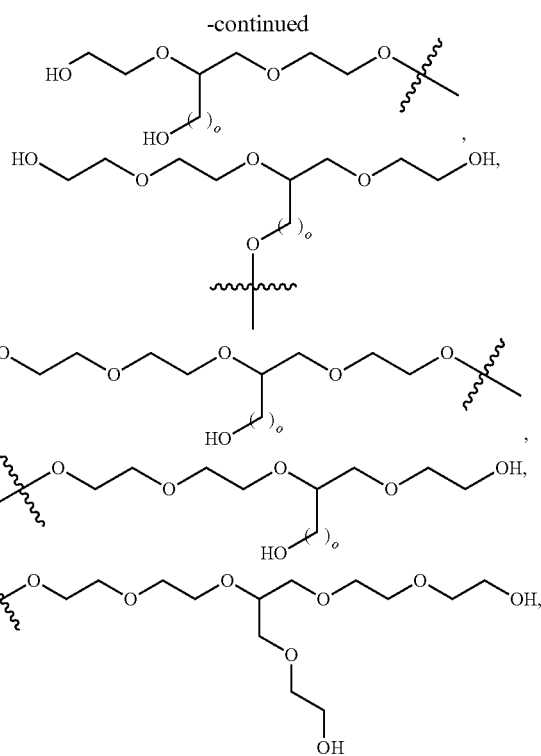

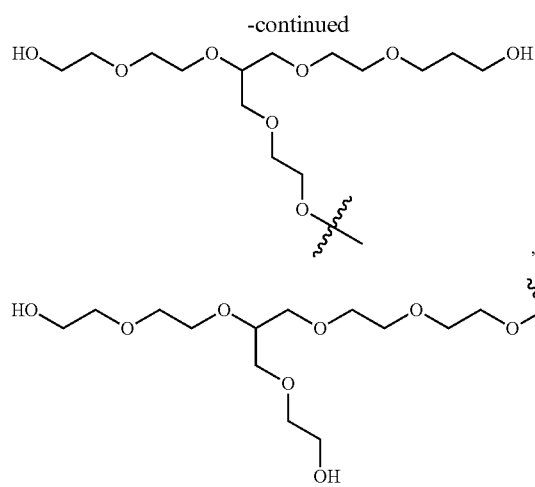

, and

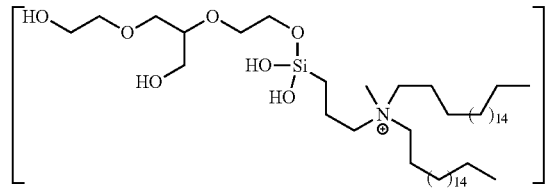

each $R^{104}$ is independently at each occurrence selected from hydrogen, alkyl, alkenyl, alkynyl, halogen, and haloalkyl; and $R^{105}$ is hydrogen or —CH$_2$CH$_2$OH.

In certain embodiments of the quaternary ammonium compounds of Formula XIII through Formula XXI, Formula XXIII through Formula XXXIII and Formula XXXV through Formula XL, variable m is independently at each occurrence selected from 6, 7, 8, 9, 10, 11, 12, 13, 14, 15 and 16. In certain embodiments of the quaternary ammonium compounds of Formula XIII through Formula XXI, m is 14. In certain embodiments of the quaternary ammonium compounds of Formula I through Formula XXI, m is independently selected from 12-16.

In certain embodiments ammonium compound of Formula XIII, XIV, XV, XVI, or XVII in solution is in equilibrium with other quaternary ammonium compounds of Formula XIII, XIV, XV, XVI, or XVII. In another embodiment, quaternary ammonium compounds of Formula XIII, XVIII, XIX, XX, and XXI are in equilibrium. For example, in one embodiment the below compounds may be in equilibrium:

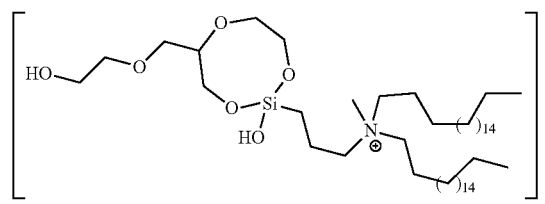

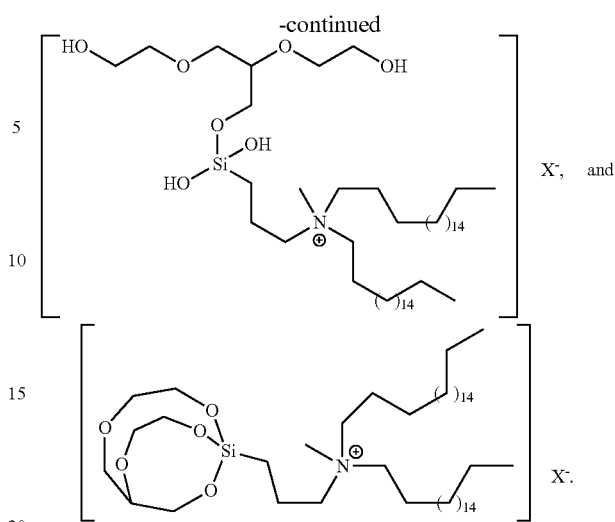

Due to the lability of silicon-oxygen bonds, these structures may interconvert via bond breakage and formation such that a mixture of Formula XIII, XIV, XV, XVI, and XVII or a mixture of a mixture of Formula XIII, XVIII, XIX, XX, or XXI may be present.

In another aspect of the present invention, a quaternary ammonium compound of Formula XXII, XXIII, XXIV, XXV, XXVI, or XXVII is provided:

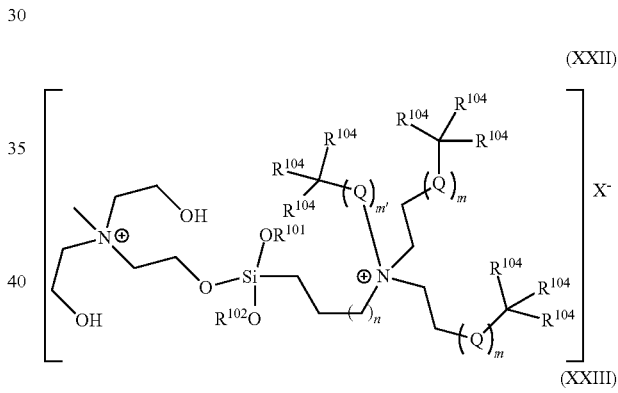

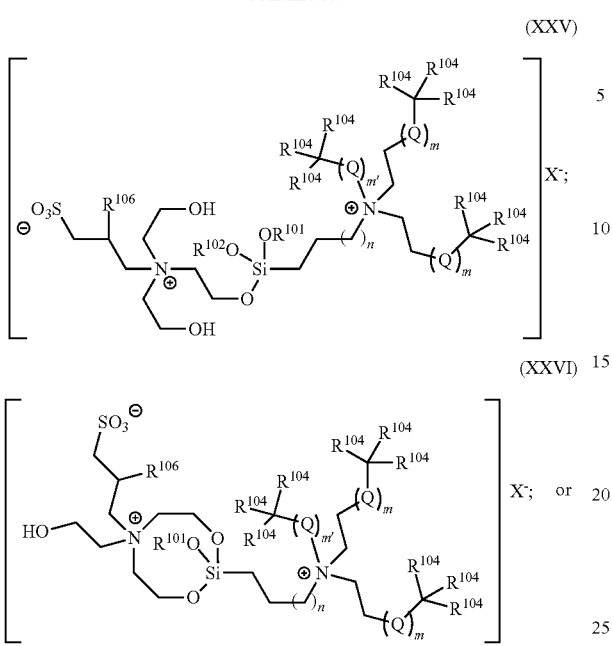

(XXV)

(XXVI)

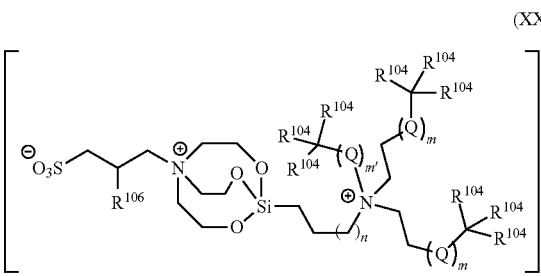

(XXVII)

wherein $R^{106}$ is independently at each occurrence selected from hydrogen, hydroxy, and $C_1$-$C_6$alkoxy and all other variables are as defined herein.

In one embodiment the quaternary ammonium compound of Formula XXII, XXIII, or XXIV in solution is in equilibrium with other quaternary ammonium compounds of Formula XXII, XXIII, or XXIV. For example, in one embodiment the below compounds may be in equilibrium:

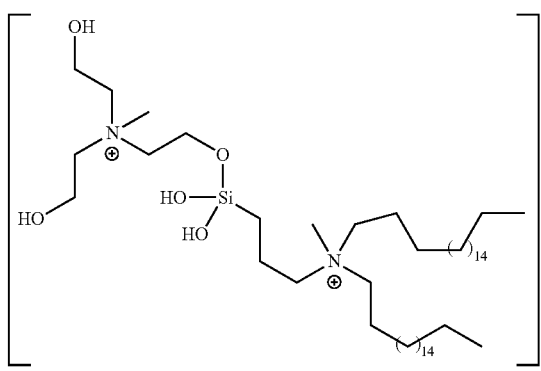

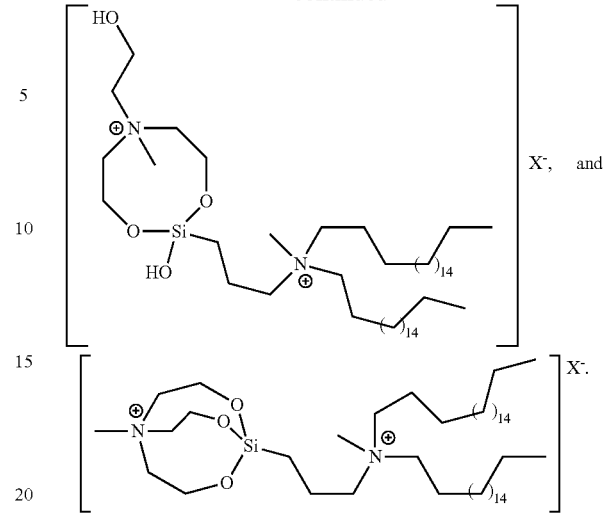

In one embodiment the quaternary ammonium compound of Formula XXV, XXVI, or XXVII is in equilibrium with other quaternary ammonium compounds of Formula XXV, XXVI, or XXVII. In one non-limiting illustrated example, the below compounds may be in equilibrium:

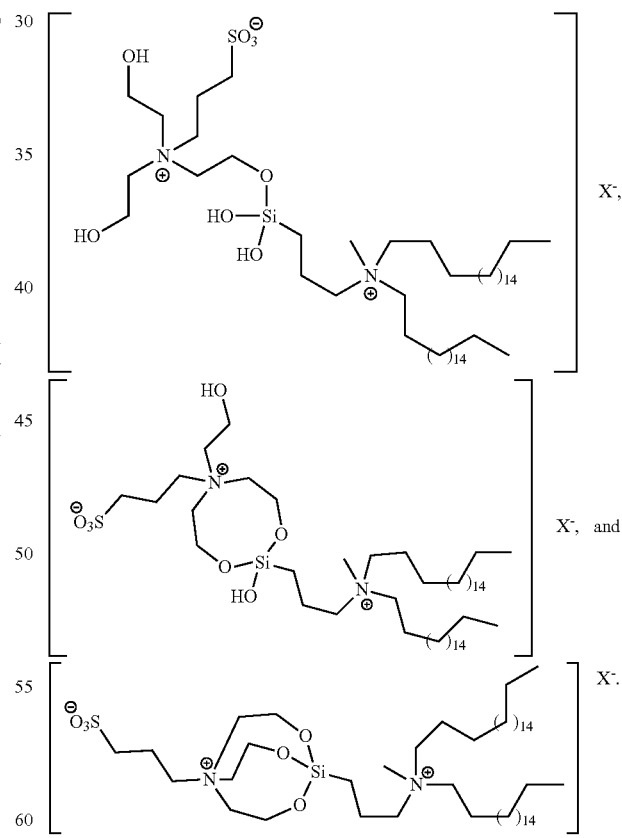

Due to the lability of silicon oxygen bonds, these structures may interconvert via bond breakage and formation such that a mixture of Formula XXII, XXIII, or XXIV may be present; or a mixture of Formula XXV, Formula XXVI, or Formula XXVII may be present.

In another aspect of the present invention, a quaternary ammonium compound of Formula XXVIII, XXIX, or XXX is provided:

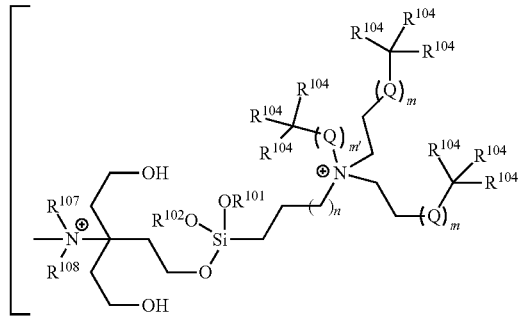

(XXVIII)

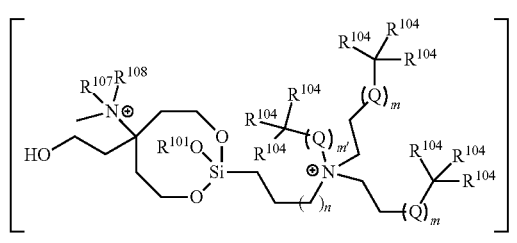

(XXIX)


(XXX)

wherein $R^{107}$ and $R^{108}$ are independently at each occurrence selected from $C_1$-$C_6$alkyl and all other variables are as defined herein.

In one embodiment the compound of Formula XXVIII, XXIX, or XXX is in equilibrium with other compounds of Formula XXVIII, XXIX, or XXX. For example, in one embodiment the below compounds may be in equilibrium:

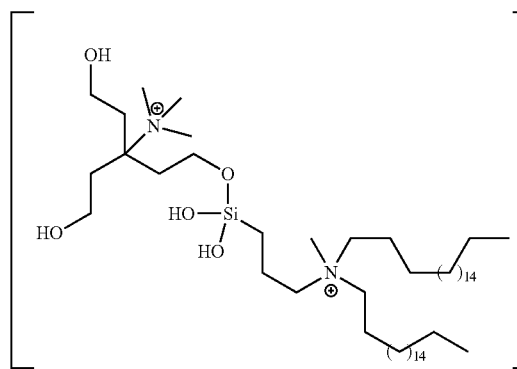

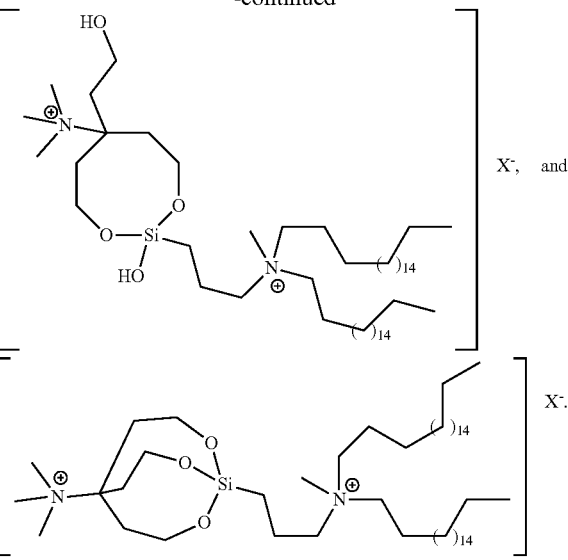

Due to the lability of silicon oxygen bonds, these structures may interconvert via bond breakage and formation such that a mixture of Formula XXVIII, Formula XXIX, or Formula XXX may be present.

In another aspect of the present invention, a quaternary ammonium compound of Formula XXXI or XXXII is provided:

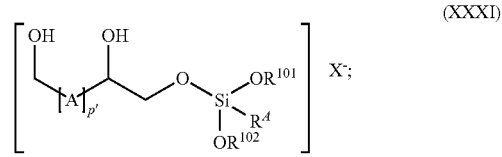

(XXXI)

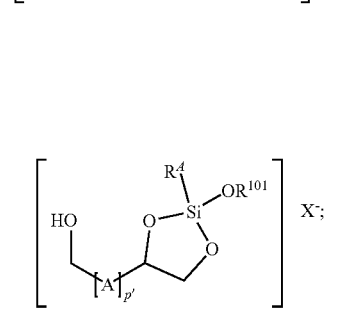

(XXXII)

wherein $R^A$ is

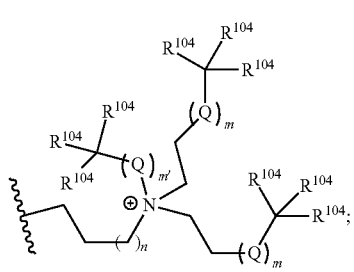

A is independently selected at each occurrence from:

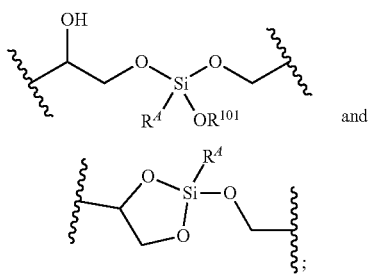

and p' is 0, 1, 2, 3, 4, 5, 6, 7, 8, 9, or 10; and all other variables are as defined herein.

Due to the lability of silicon oxygen bonds, these structures may interconvert via bond breakage and formation such that a mixture of Formula XXXI or Formula XXXII may be present.

In another embodiment the invention provides, is a quaternary ammonium compound of Formula XXXIII:

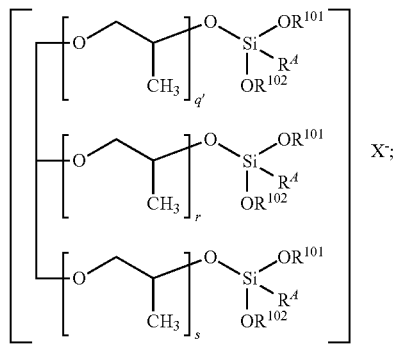

wherein all other variables are as defined herein; and q', r, and s are independently at each occurrence selected from 0, 1, 2, 3, 4, 5, 6, 7, 8, 9, or 10.

In one embodiment, q', r, and s are the same.

In another aspect of the present invention, a quaternary ammonium compound of Formula XXXIV, XXXV, or XXXVI is provided:

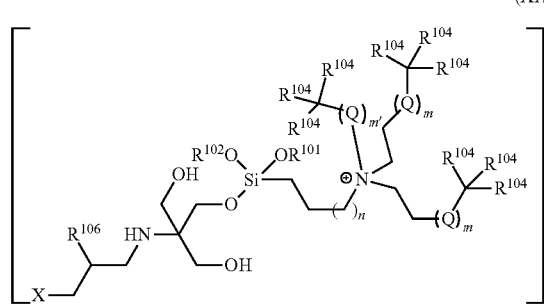

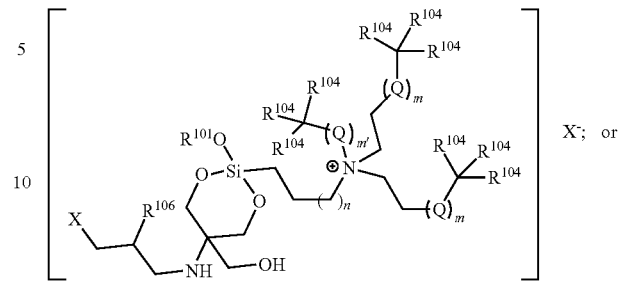

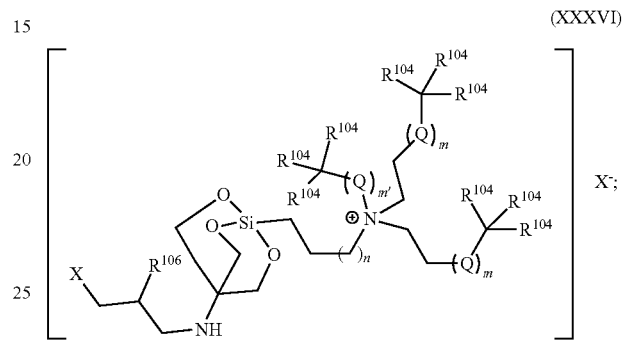

wherein:

X is selected from

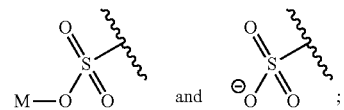

M is selected from hydrogen, sodium, potassium, cesium or lithium; and all other variables are as defined herein.

In one embodiment the compound of Formula XXXIV, XXXV, or XXXVI is in equilibrium with other compounds of Formula XXXIV, XXXV, or XXXVI. For example, in one embodiment the below compounds may be in equilibrium:

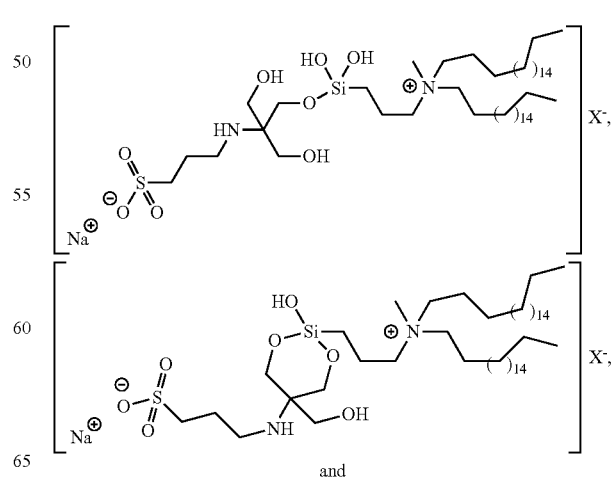

and

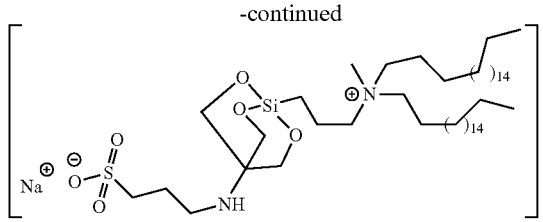

Due to the lability of silicon oxygen bonds, these structures may interconvert via bond breakage and formation such that a mixture of Formula XXXIV, XXXV, or XXXVI may be present.

In another aspect of the present invention, a quaternary ammonium compound of Formula XXXVII, XXXVIII, or XXXIX is provided:

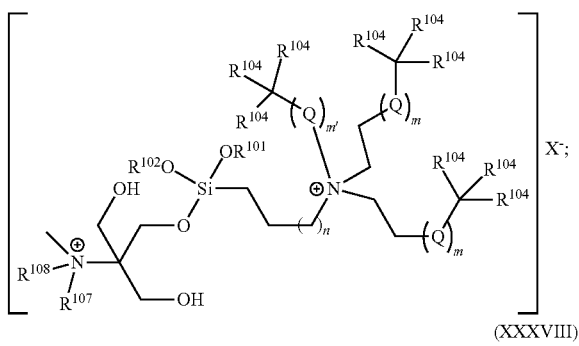
(XXXVII)

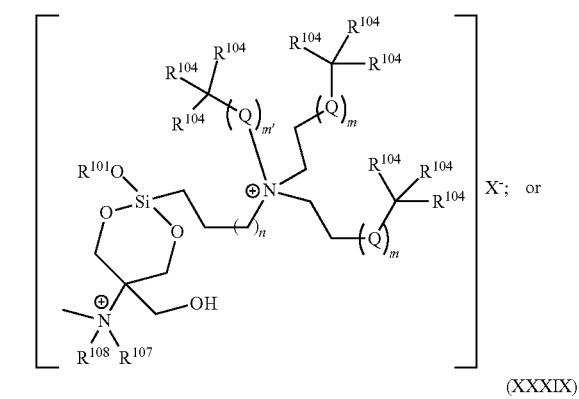
(XXXVIII)

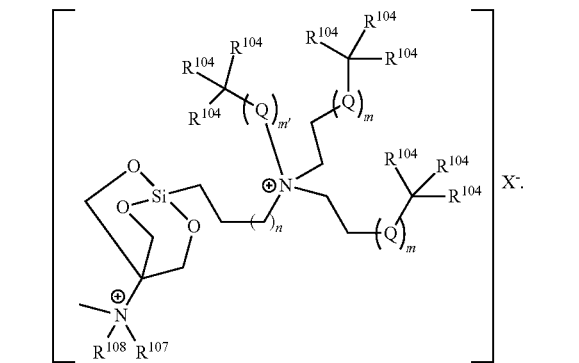
(XXXIX)

In one embodiment the quaternary ammonium compound of Formula XXXVII, XXXVIII, or XXXIX is in equilibrium with other quaternary ammonium compounds of Formula XXXVII, XXXVIII, or XXXIX. For example, in one embodiment the below compounds may be in equilibrium:

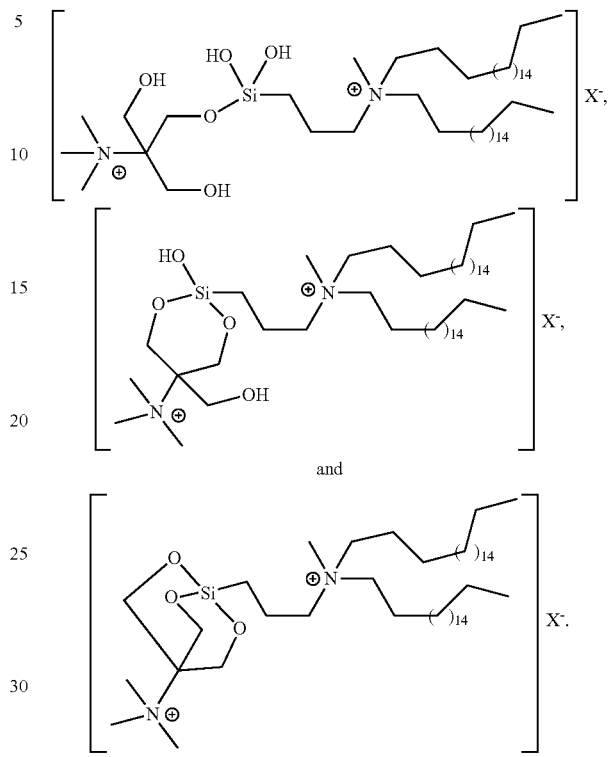

and

Due to the lability of silicon oxygen bonds, these structures may interconvert via bond breakage and formation such that a mixture of Formula XXXVII, XXXVIII, or XXXIX may be present.

The present invention, among other things, contemplates an antimicrobial composition containing one or more compounds of Formula XXXVII, XXXVIII, or XXXIX and an appropriate carrier.

The invention also includes a method of treating an infection, in a host in need thereof, with an effective amount of a quaternary ammonium compound of Formula XXXVII, XXXVIII, or XXXIX In another alternative aspect an oligomeric or polymeric quaternary ammonium compound of Formula XL is provided:

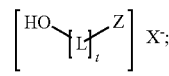
(XL)

wherein: $R^A$ is as defined above
t is 1, 2, 3, 4, 5, 6, 7, 8, 9, or 10;
Z is independently at each occurrence selected from:

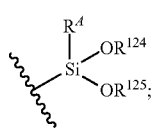 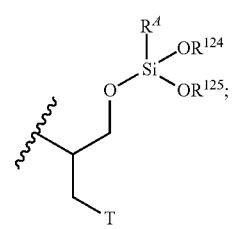

-continued

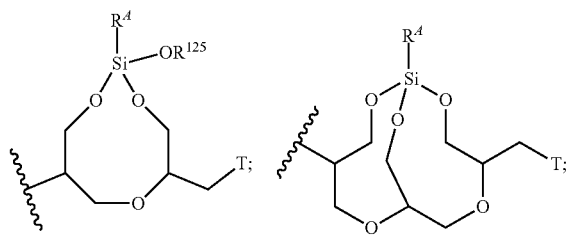

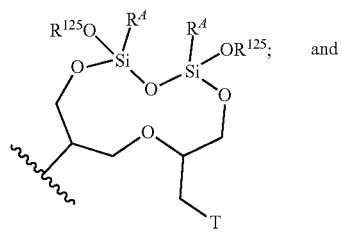

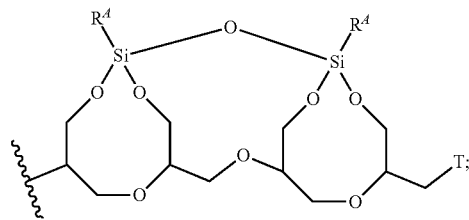

L is independently at each occurrence selected from:

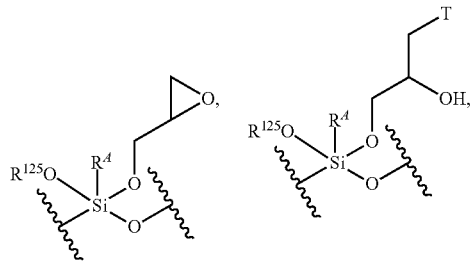

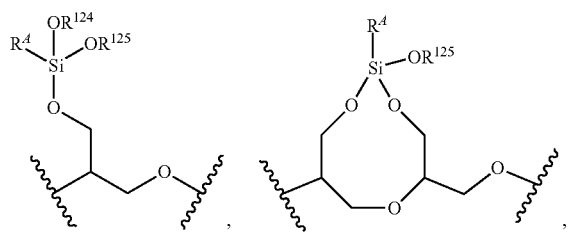

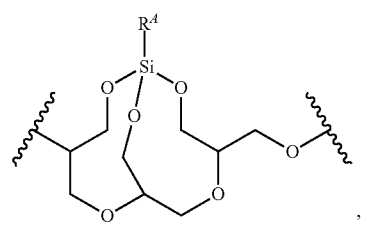

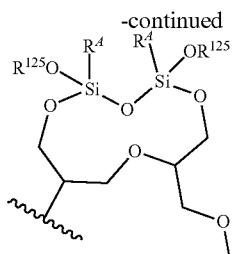

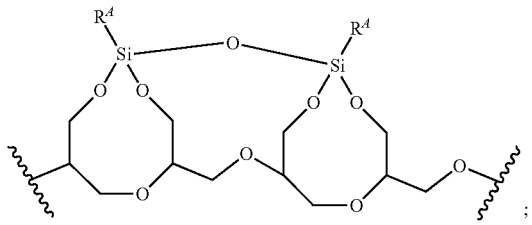

$R^{124}$ and $R^{125}$ are independently selected at each occurrence from hydrogen, ethyl,

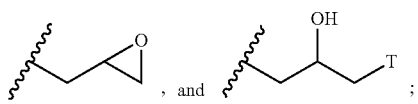

T is a monovalent capping group, that may optionally be derived from a curing agent, wherein all other variables are as defined herein.

The curing agent in Formula XL may be any compound that is pharmaceutically acceptable.

In certain embodiments, the curing agent of an oligomer or polymer as described herein comprises a diethylenetriamine (DTA), triethylenetetramine (TTA), tetraethylenepentamine (TEPA), dipropenediamine (DPDA), diethylaminopropylamine (DEAPA), Amine 248, N-aminoethylpiperazine (N-AEP), Lamiron C-260, Araldit HY-964, menthane diamine (MDA), isophoronediamine (IPDA), S Cure 211, S Cure 212, Wandamin HM, 1,3 BAC, m-xylenediamine (m-XDA), Sho-amine X, Amine black, Sho-amine black, Sho-amine N, Sho-amine 1001, Sho-amine 1010, metaphenylene diamine (MPDA), diaminodiphenylmethane (DDM), diaminodiphenylsulfone (DDS), piperidine, N,N-dimethylpiperidine, triethylenediamine, 2,4,6-tris(dimethylaminomethyl)phenol (DMP-30), benzyldimethylamine (BDMA), and 2-(dimethylaminomethyl)phenol (DMP-10); an imidazole such as 2-methylimidazole, 2-ethyl-4-methylimidazole, 1-cyanoethyl-2-undecylimidazolium trimellitate, and an epoxy-imidazole adduct; a liquid polymercaptan or a polysulfide resin; or an acid anhydride such as phthalic anhydride, trimellitic anhydride, pyromellitic anhydride, benzophenone tricarboxylic anhydride, ethylene glycol bistrimellitate, glycerol tritrimellitate, maleic anhydride, tetrahydrophthalic anhydride, methyltetrahydrophthalic anhydride, endomethylene tetrahydrophthalic anyhydride, methylendomethylene tetrahydrophthalic anhydride, methylbutenyl tetrahydrophthalic anhydride, dodecenyl succinic anhydride, hexahydrophthalic anhydride, hexahydro-4-methylphthalic anhydride, succinic anhydride, methylcyclohexene dicarboxylic anhydride, alkylstyrene-maleic anhydride copolymer, chlorendic anhydride, and polyazelaic polyanhydride.

In another aspect of the present invention, a product is provided that is formed by reacting a quaternary ammonium compound of Formula A:

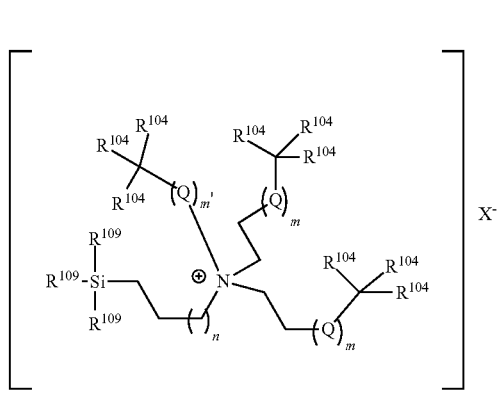

(A)

wherein
each $R^{109}$ is independently at each occurrence selected from halo, hydroxyl, and alkoxy and all other variables are as defined herein;
with one or more compounds of Formulas B, C, D, E, F, G, H or J;

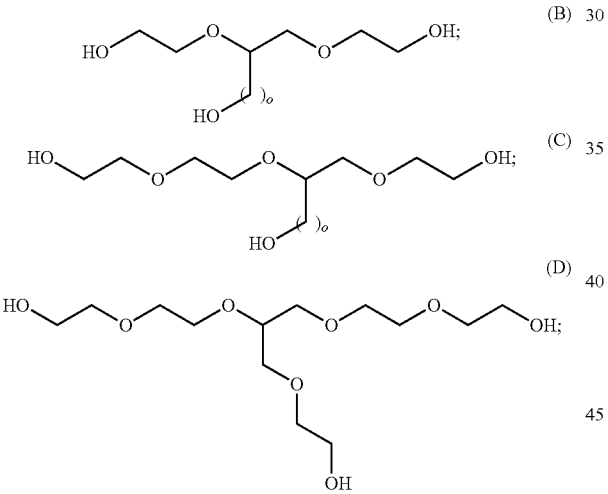

(B)

(C)

(D)

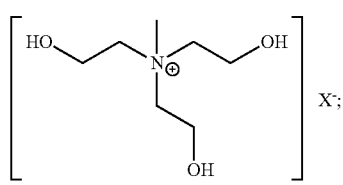

(E)

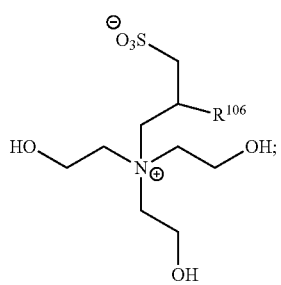

(F)

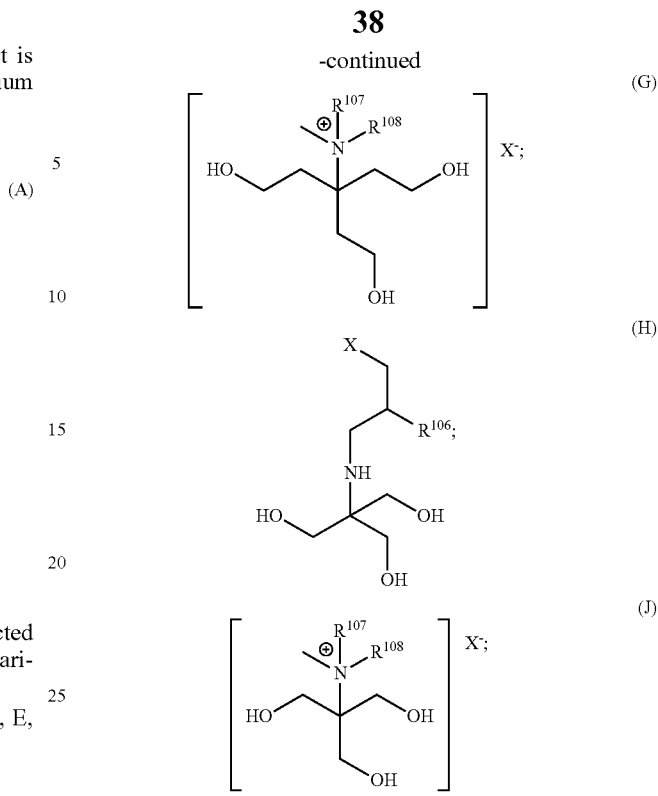

(G)

(H)

(J)

(K)

(L)

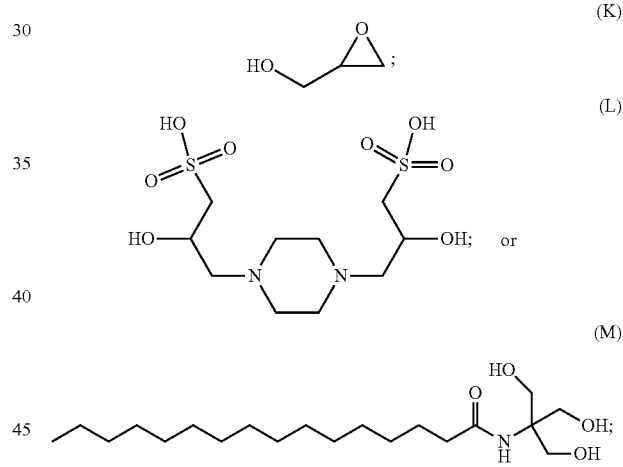

(M)

wherein all other variables are as defined herein.

In another aspect of the invention, compound B' is provided wherein compound B' is formed by the reaction of one or more compounds of Formula A with one or more compounds of Formula B. In one embodiment, compound B' is an oligomeric or polymeric compound with one or more Formula B units and one or more Formula A units.

In another aspect of the invention, compound C' is provided wherein compound C' is formed by the reaction of one or more compounds of Formula A with one or more compounds of Formula C. In one embodiment, compound C' is an oligomeric or polymeric compound with one or more Formula C units and one or more Formula A units.

In another aspect of the invention, compound D' is provided wherein compound D' is formed by the reaction of one or more compounds of Formula A with one or more compounds of Formula D. In one embodiment, compound D' is an oligomeric or polymeric compound with one or more Formula D units and one or more Formula A units.

In another aspect of the invention, compound E' is provided wherein compound E' is formed by the reaction of one or more compounds of Formula A with one or more compounds of Formula E. In one embodiment, compound E' is an oligomeric or polymeric compound with one or more Formula E units and one or more Formula A units.

In another aspect of the invention, compound F' is provided wherein compound F' is formed by the reaction of one or more compounds of Formula A with one or more compounds of Formula F. In one embodiment, compound F' is an oligomeric or polymeric compound with one or more Formula F units and one or more Formula A units.

In another aspect of the invention, compound G' is provided wherein compound G' is formed by the reaction of one or more compounds of Formula A with one or more compounds of Formula G. In one embodiment, compound G' is an oligomeric or polymeric compound with one or more Formula G units and one or more Formula A units.

In another aspect of the invention, compound H' is provided wherein compound H' is formed by the reaction of one or more compounds of Formula A with one or more compounds of Formula H. In one embodiment, compound H' is an oligomeric or polymeric compound with one or more Formula H units and one or more Formula A units.

In another aspect of the invention, compound J' is provided wherein compound J' is formed by the reaction of one or more compounds of Formula A with one or more compounds of Formula J. In one embodiment, compound J' is an oligomeric or polymeric compound with one or more Formula J units and one or more Formula A units.

In another aspect of the invention, compound K' is provided wherein compound K' is formed by the reaction of one or more compounds of Formula A with one or more compounds of Formula K. In one embodiment, compound K' is an oligomeric or polymeric compound with one or more Formula K units and one or more Formula A units.

In another aspect of the invention, compound L' is provided wherein compound L' is formed by the reaction of one or more compounds of Formula A with one or more compounds of Formula L. In one embodiment, compound L' is an oligomeric or polymeric compound with one or more Formula L units and one or more Formula A units.

In another aspect of the invention, compound M' is provided wherein compound M' is formed by the reaction of one or more compounds of Formula A with one or more compounds of Formula M. In one embodiment, compound M' is an oligomeric or polymeric compound with one or more Formula M units and one or more Formula A units.

In another aspect the compound of the present invention is an oil which can be administered topically as a neat compound. The oil is optionally mixed with an excipient, carrier, or diluent described herein to maintain a prolonged shelf life without solidification. For example, the oil of the present invention can be mixed with an ionic liquid, organic solvent, or aqueous solution to maintain the form of an oil. Non-limiting examples of oils that can be mixed with the compound of the present invention include palm oil, rice bran oil, and vegetable oil. In certain embodiments the mixture of the compound of the present invention and an additional oil forms a shelf stable oil composition that can be administered topically to a patient in need thereof.

In certain embodiments a compound of the present invention (optionally as an oil) is administered directly to a wound. Non-limiting examples of how the compound may be administered include dropping, pouring, dabbing, or otherwise applying to an open wound, a covered wound, or as part of a negative pressure wound treatment strategy. For example, the compound of the present invention can be administered on a sponge and inserted into the wound after which the surrounding skin is sealed with a membrane and pierced by a small suction tube that creates a sub-atmospheric vacuum that also pulls off exudate.

In another aspect, an anti-infective composition is provided, comprising one or more quaternary ammonium compounds of as described herein, or a pharmaceutically acceptable composition thereof; and an appropriate carrier in an effective amount to treat, prevent or eliminate an infection.

In certain embodiments, the pharmaceutically acceptable carrier comprises an aqueous or glycerin solution, for example, water, saline, or phosphate buffered saline.

In certain embodiments, the glycerin solution is selected from glycerol, glycidol, glycerol-propylene oxide copolymer, ethylene glycol, propylene glycol, polyethylene glycol, or polypropylene glycol, or combinations thereof.

In another aspect, a kit is provided comprising a vial which contains a sterile aqueous solution and a vial comprising a quaternary ammonium compound as described herein and an application device.

In another aspect, a kit is provided comprising a powder formulation comprising: a quaternary ammonium compound as described herein or a pharmaceutically acceptable salt thereof, with a sterile aqueous solution; and an application device. In some embodiments, the powder is a lyophilized powder.

In some embodiments, the application device is a syringe.

In another aspect, a kit is provided comprising a sterile aqueous solution and a quaternary ammonium compound as described herein, with one or more compounds selected from solketal, epichlorohydrin, and polyvinyl alcohol.

In another aspect, a kit is provided comprising a sterile aqueous or glycerin solution and a quaternary ammonium compound as described herein, with one or more compounds selected from glycerol, glycidol, glycerol-propylene oxide copolymer, ethylene glycol, propylene glycol, polyethylene glycol, and polypropylene glycol.

In some embodiments, the present invention provides a compound as described herein, or a pharmaceutically acceptable composition thereof; useful in an effective amount for the treatment, prevention, inhibition or elimination of an infectious disease in a host in need thereof.

In one aspect, a method is provided for the treatment, prevention, inhibition or elimination of an infection as further described herein, comprising administering, to a host in need thereof, an effective amount of one or more of the quaternary ammonium compounds as described herein, or a pharmaceutically acceptable composition thereof.

In some embodiments, the host is a human.

In another embodiment, the host is a mammal, for example a dog, cat, horse, cow, or pig.

In another aspect, the present invention provides a method of administering an effective amount of one or more compounds of the present invention, or a pharmaceutically acceptable composition thereof, useful to treat, inhibit, eliminate, or prevent said infection.

In some embodiments, the infection is a mixed infection that includes bacterial species, fungal species, and viral species.

In some embodiments, one or more quaternary ammonium compounds of the present invention, or compositions thereof, are used in an effective amount to treat or prevent infection in a chronic wound in a host in need thereof.

In some embodiments, the chronic wound is a diabetic ulcer, for example a diabetic ulcer such as a diabetic lower limb ulcer or diabetic foot ulcer.

In another embodiment, the chronic wound is a decubitus ulcer.

In some embodiments, the chronic wound is a pressure ulcer.

In some embodiments, the chronic wound is a venous ulcer.

In some embodiments, the chronic wound is an arterial ulcer.

In some embodiments, the chronic wound is a neuropathic ulcer.

In some embodiments, the chronic wound is a skin tear.

In some embodiments, the chronic wound is moisture-associated skin damage (MASD), for example incontinence-associated dermatitis.

In some embodiments, the compounds described herein are used to treat a wound caused by a burn.

In another embodiment, the infection in the chronic wound is caused by a biofilm.

In some embodiments, one or more quaternary ammonium compounds of the present invention, or compositions thereof, are used in an effective amount to treat, prevent or eliminate an ocular infection in a host in need thereof.

In some embodiments, the ocular infection is corneal keratitis.

In another embodiment, the ocular infection is bacterial keratitis, for example keratitis caused by *Staphylococcus aureus* or *Pseudomonas aeruginosa*.

In another embodiment, the ocular infection is fungal keratitis, for example keratitis caused by *Fusarium* spp., *Aspergillus* spp., *Candida* spp., or *Curvularia* spp. In some embodiments, the ocular infection is Acanthamoebic keratitis.

In another embodiment, the ocular infection is viral keratitis, for example Herpes simplex virus (HSV) keratitis.

In another embodiment, the ocular infection is bacterial conjunctivitis, for example conjunctivitis caused by *Staphylococcus aureus, Haemophilus influenzae, Streptococcus pneumoniae* or *Pseudomonas aeruginosa*.

In another embodiment, the ocular infection is viral conjunctivitis, for example conjunctivitis caused by adenovirus or enterovirus.

In another embodiment, the ocular infection is polymicrobial, which is more difficult to diagnose and treat. For example, when Acanthamoebic keratitis is associated with bacteria there is an increased risk of vascularization and prolonged healing.

In another embodiment, the ocular infection is sequential with one or more opportunistic organisms that can also cause infection. For example, a herpetic corneal ulcer can provide a niche for establishment of bacterial or fungal pathogens.

In another aspect, an ocular composition is providing comprising affective amount of one or more quaternary ammonium compounds of the present invention, and an acceptable carrier for the eye.

In some embodiments, the ocular composition does not contain any byproducts or additives, for example an alcohol.

In some embodiments, the ocular composition is substantially free of methanol. In some embodiments, the infection to be treated is an infection of the eye.

In another embodiment, the infection to be treated is infection of the ear, for example, an inner, an outer, or middle ear infection.

In some embodiments, the infection to be treated is an infection of the skin.

In some embodiments, the infection to be treated is an infection of the nails, for example a fungal infection of the nails.

In some embodiments, the infection to be treated is an infection of vaginal mucosal tissue, for example vulvovaginal candidiasis.

In some embodiments, the infection is within a chronic wound or ulcer, for example, but not limited to, a lower limb ulcer or diabetic ulcer such as a diabetic lower limb ulcer or diabetic foot ulcer.

In another aspect, a method is provided for the treatment of an ear infection in a host in need thereof comprising administering an effective amount of one or more quaternary ammonium compounds of the present invention, or compositions thereof.

In some embodiments, one or more quaternary ammonium compounds of the present invention, or compositions thereof, are used in an effective amount to treat, prevent or eliminate an ear infection in a host in need thereof.

In some embodiments, the ear infection is an inner ear infection (otitis interna).

In some embodiments, the ear infection is an outer ear infection (otitis externa).

In another embodiment, the ear infection is a middle ear infection (otitis media).

In some embodiments, the ear infection is caused by a bacterium or a fungi.

In another embodiment, the ear infection is caused by both a bacterium and a fungi.

In another embodiment, the infection is caused by a biofilm which may contain a combination of bacterial and fungal cells. In another embodiment, the infection is caused by a biofilm which may contain a combination of bacterial and fungal cells, and one or more viruses.

In another aspect, a method is provided for the treatment of an ocular infection in a host in need thereof comprising administering an effective amount of one or more quaternary ammonium compounds described herein, or compositions thereof.

In another aspect, a method is provided for the treatment of onychomycosis, i.e. a nail fungal infection, in a host in need thereof comprising administering an effective amount of one or more quaternary ammonium compounds described herein, or compositions thereof.

In some embodiments, one or more quaternary ammonium compounds of the present invention, or compositions thereof, are used in an effective amount to treat, prevent or eliminate onychomycosis in a host in need thereof.

In another aspect, a formulation for the treatment of onychomycosis in a host in need thereof is provided comprising administering an effective amount of one or more quaternary ammonium compounds described herein, in a carrier suitable for delivery to the nail bed. In some embodiments, the carrier is dimethylsulfoxide.

In some embodiments, one or more quaternary ammonium compounds described herein are administered as an aqueous, glycerin, or dimethyl sulfoxide solution that has been formed by reconstituting a powder formulation of one or more quaternary ammonium compounds. In some embodiments, the powder is a lyophilized powder.

In another embodiment, a method is provided for the treatment or prevention of an infection in a chronic wound, in a host in need thereof, comprising administering an effective amount of one or more quaternary ammonium compounds described herein, or compositions thereof.

In another embodiment, a method is provided for the treatment or prevention of a vaginal infection in a host in need thereof, comprising administering an effective amount of one or more quaternary ammonium compounds described herein, or compositions thereof.

In some embodiments, one or more quaternary ammonium compounds of the present invention, or compositions thereof, are used in an effective amount to treat or prevent a vaginal infection in a host in need thereof.

In some embodiments, the vaginal infection is vulvovaginal candidiasis.

In some embodiments, the vaginal infection, for example vulvovaginal candidiasis is a fungal infection caused by *Candida* spp.

In some embodiments, the vaginal infection is bacterial vaginosis.

In some embodiments, the vaginal infection, for example vulvovaginal candidiasis is a bacterial infection caused by Lactobacilli, *Bacteroides, Peptostreptococcus, Fusobacterium*, and/or *Eubacterium* In another aspect, a method is provided for the treatment of a dermatological disorder in a host in need thereof comprising administering an effective amount of one or more quaternary ammonium compounds described herein, or compositions thereof.

In an alternate embodiment, the infection to be treated is a dermatological disorder.

In certain embodiments, the dermatological disorder is for example, acne vulgaris, cystic acne, eczema, folliculitis and skin infections.

In certain embodiments, the dermatological disorder, for example, acne vulgaris is caused by gram positive bacterium *Propionibacterium acnes*, and/or *Staphylococcus epidermidis*.

In certain embodiments, the dermatological disorder, for example, eczema (atopic dermatitis), eczema herpeticum, eczema vaccinatum, or eczema coxsackium is caused by bacterial and viral infections.

In certain embodiments, the dermatological disorder, for example, eczema (atopic dermatitis) is caused by bacteria, for example, staphylococcal bacteria such as *Staphylococcus aureus* or streptococcal bacteria.

In certain embodiments, the dermatological disorder, for example, eczema (atopic dermatitis) is caused by virus, for example herpes simplex virus, and/or *Molluscum contagiosum*.

In certain embodiments, the dermatological disorder, for example, skin infection caused by *Staphylococcus aureus* (*S. aureus*).

In some embodiments, the effective amount of one or more quaternary ammonium compounds of the present invention, or compositions thereof, is an amount needed to treat, prevent or eliminate said infections described herein.

In another aspect, a method is provided for the treatment of a biofilm or microbial contamination on an abiotic (i.e., inanimate) surface comprising administering an effective amount of one of more quaternary ammonium compounds described herein, or mixtures thereof.

In some embodiments, the abiotic (i.e., inanimate) surface is treated directly with a solution containing one or more quaternary ammonium compounds described herein, or mixtures thereof to remove and/or prevent the recurrence of a bacterial biofilm or bacterial contamination.

In some embodiments, the bacterial biofilm or bacterial contamination is caused by *Staphylococcus aureus*.

In some embodiments, the bacterial biofilm or bacterial contamination is caused by methicillin-resistant *Staphylococcus aureus* (MRSA).

In some embodiments, the bacterial biofilm or bacterial contamination is caused by *Pseudomonas aeruginosa*.

In some embodiments, the abiotic (i.e., inanimate) surface is treated directly with a solution containing one or more quaternary ammonium compounds described herein, or mixtures thereof to remove and/or prevent the recurrence of a fungal biofilm or fungal contamination.

In some embodiments, the fungal biofilm or fungal contamination comprises a *Candida* fungal infection, for example, but not limited to, *C. albicans, C. auris*, or *C. glabrata*, or a combination thereof.

In some embodiments, the abiotic (i.e., inanimate) surface is treated directly with a solution containing one or more quaternary ammonium compounds described herein, or mixtures thereof to remove and/or prevent the recurrence of a viral biofilm or viral contamination.

In some embodiments, the viral biofilm or viral contamination is caused by SARS Coronavirus 2 (COVID-19).

In some embodiments, the abiotic (i.e., inanimate) surface is treated directly with a solution containing one or more quaternary ammonium compounds described herein, or mixtures thereof to remove and/or prevent the recurrence of a polymicrobial biofilm or polymicrobial contamination.

In some embodiments, the polymicrobial biofilm or polymicrobial contamination includes bacterial, fungal, and viral species.

In some embodiments, the one or more quaternary ammonium compounds described herein, or mixtures thereof may be formulated in an effective amount as an antimicrobial hand sanitizer, or a surface disinfecting spray, foam, liquid, gel or solid.

In some embodiments, a method is provided comprising administering an effective amount of a quaternary ammonium compound, or composition thereof described herein to provide enhanced antimicrobial activity to the surface of the skin.

In some embodiments, the antimicrobial activity is bacterial.

In some embodiments, the antimicrobial activity is fungal.

In some embodiments, the antimicrobial activity is viral.

In some embodiments, the antimicrobial activity is polymicrobial and includes a combination of bacterial, fungal, and/or viral microbes.

In some embodiments, the antimicrobial hand sanitizer is optionally combined with a thickener.

In some embodiments, the antimicrobial hand sanitizer is optionally combined with alcohol.

In other embodiments, the quaternary ammonium compound is provided in a carrier that does not include any alcohol.

In some embodiments, the antimicrobial hand sanitizer is optionally combined with a skin conditioner.

In some embodiments, the antimicrobial hand sanitizer is optionally combined with a fragrance.

In some embodiments, a quaternary ammonium compound is provided wherein at least one hydrogen has been replaced by deuterium.

Thus, the present invention includes at least the following features:

(a) a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL;

(b) a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL for use in the treatment of a bacterial, fungal and/or viral infection;

(c) use of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL in the manufacture of a medicament for the treatment of a bacterial, fungal and/or viral infection;

(d) a method for manufacturing a medicament intended for the therapeutic use of treating a bacterial, fungal and/or viral infection, characterized in that an effective amount of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL is used in the manufacture;

(e) a method for treating a bacterial, fungal and/or viral infection, comprising administering an effective amount of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, to a host in need thereof;

(f) a method for treating a bacterial, fungal and/or viral infection, comprising administering an effective amount of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, to a host in need thereof;

(g) an antimicrobial composition comprising an effective amount of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, and a pharmaceutically acceptable excipient;

(h) a powder or solidified formulation, including a lyophilized powder formulation, comprising one or more quaternary ammonium compounds Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL;

i) a kit comprising a powder or solid formulation, including a lyophilized powder, of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, a sterile aqueous solution, and an application device;

(j) a kit comprising a sterile aqueous solution comprising one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, and an application device;

(k) a process to synthesize a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL;

(l) a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, as a mixture of enantiomers or diastereomers (as relevant), including as a racemate;

(m) a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, in an enantiomerically or diastereomerically (as relevant) enriched form, including as an isolated enantiomer or diastereomer (i.e., greater than 85, 90, 95, 97 or 99% pure);

(n) a process for the preparation of therapeutic products that contain an effective amount of one or more quaternary ammonium compounds Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL;

(o) a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, glycerol-propylene oxide copolymer, solketal, glycidol, or epichlorohydrin;

(p) a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of a glycerol-propylene oxide copolymer, solketal, glycidol, or epichlorohydrin for use in the treatment of a bacterial, fungal and/or viral infection;

(q) use of a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL, one or more compounds of glycerol, glycerol-propylene oxide copolymer, solketal, glycidol, or epichlorohydrin in the manufacture of a medicament for the treatment of a bacterial, fungal and/or viral infection;

(r) a method for manufacturing a medicament intended for the therapeutic use of treating a bacterial, fungal and/or viral infection, characterized in that an effective amount of a product formed by reacting a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, a glycerol-propylene oxide copolymer, solketal, glycidol, or epichlorohydrin, is used for the manufacture;

(s) a method for treating a bacterial, fungal and/or viral infection, comprising administering an effective amount of a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, a glycerol-propylene oxide copolymer, solketal, glycidol, or epichlorohydrin to a patient in need thereof;

(t) a method for treating a bacterial, fungal and/or viral infection, comprising administering an effective amount of a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, a glycerol-propylene oxide copolymer, solketal, glycidol, or epichlorohydrin to a patient in need thereof;

(u) an antimicrobial composition comprising an effective amount of a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, a glycerol-propylene oxide copolymer, solketal, glycidol, or epichlorohydrin and a pharmaceutically acceptable excipient;

(v) a powder formulation or solid formulation, including a lyophilized powder, comprising a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, glycidol, glycerol-propylene oxide copolymer, ethylene glycol, propylene glycol, polyethylene glycol, polypropylene glycol, solketal, glycidol, or epichlorohydrin;

(w) a kit comprising a powder or solid formulation, including a lyophilized powder, of a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, a glycerol-propylene oxide copolymer, solketal, glycidol, or epichlorohydrin, a sterile aqueous solution, and an application device;

(x) a kit comprising a sterile aqueous or glycerin solution comprising a product formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, a glycerol-propylene oxide copolymer, solketal, glycidol, or epichlorohydrin; and an application device;

(y) a process for the preparation of therapeutic products formed by reacting a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with one or more compounds of glycerol, glycidol, glycerol-propylene oxide copolymer, ethylene glycol, propylene glycol, polyethylene glycol, polypropylene glycol, solketal, glycidol, or epichlorohydrin;

(z) a dressing, bandage, surgical packing, film, wrap, comfortable foam, or other type material incorporating a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL;

(aa) use of a dressing, bandage, surgical packing, film, wrap, comfortable foam, or other type material incorporating a compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL for treating a skin infection, wound, or ulcer, for example, but not limited to, a lower limb ulcer or a diabetic ulcer such as a diabetic lower limb ulcer or diabetic foot ulcer;

(bb) an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL';

(cc) an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL' for use in the treatment of a bacterial, fungal and/or viral infection;

(dd) use of an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL' in an effective amount, in the manufacture of a medicament for the treatment of a bacterial, fungal and/or viral infection;

(ee) a method for manufacturing a medicament intended for the therapeutic use of treating a bacterial, fungal and/or viral infection, characterized in that an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL' is used in the manufacture;

(ff) a method for treating a bacterial, fungal and/or viral infection, comprising administering an effective amount of an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL', to a host in need thereof;

(gg) an antimicrobial composition comprising an effective amount of a oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL', and a pharmaceutically acceptable excipient;

(hh) a powder or solid formulation, including a lyophilized powder, comprising an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL' or combinations thereof;

(ii) a kit comprising a powder or solid formulation, including a lyophilized powder, of an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL', a sterile aqueous solution, and an application device;

(jj) a kit comprising a sterile aqueous or glycerin solution comprising an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL'; and an application device;

(kk) a process for the preparation of therapeutic products that contain an oligomer or polymer product of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL';

(ll) a dressing, bandage, surgical packing, film, wrap, comfortable foam, or other type material incorporating a compound of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL';

(mm) use of a dressing, bandage, surgical packing, film, wrap, comfortable foam, or other type material incorporating a compound of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL' for treating a skin infection, wound, or ulcer, for example, but not limited to, a lower limb ulcer or a diabetic ulcer such as a diabetic lower limb ulcer or diabetic foot ulcer; and, (nn) a medical or dental implant incorporating a compound of Formula I', II', III', IV', V', VI', VII', VIII', IX', X', XI', XII', XIII', XIV', XV', XVI', XVII', XVIII', XIX', XX', XXI', XXII', XXIII', XXIV', XXV', XXVI', XXVII', XXVIII', XXIX', XXX', XXXI', XXXII', XXXIII', XXXIV', XXXV', XXXVI', XXXVII', XXXVIII', XXXIX', or XL';

(oo) a method for the treatment of a biofilm or microbial contamination by administering an effective amount of one or more quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL to an abiotic (i.e., inanimate) surface; and (pp) an antimicrobial quaternary compound of the present invention for use as a disinfectant on an inanimate surface, including but not limited to a home surface, workspace, industrial area, transportation area or carrier, kitchen, bathroom, furniture, etc., optionally in a suitable carrier for appropriate application.

DETAILED DESCRIPTION OF THE INVENTION

Figure 1:
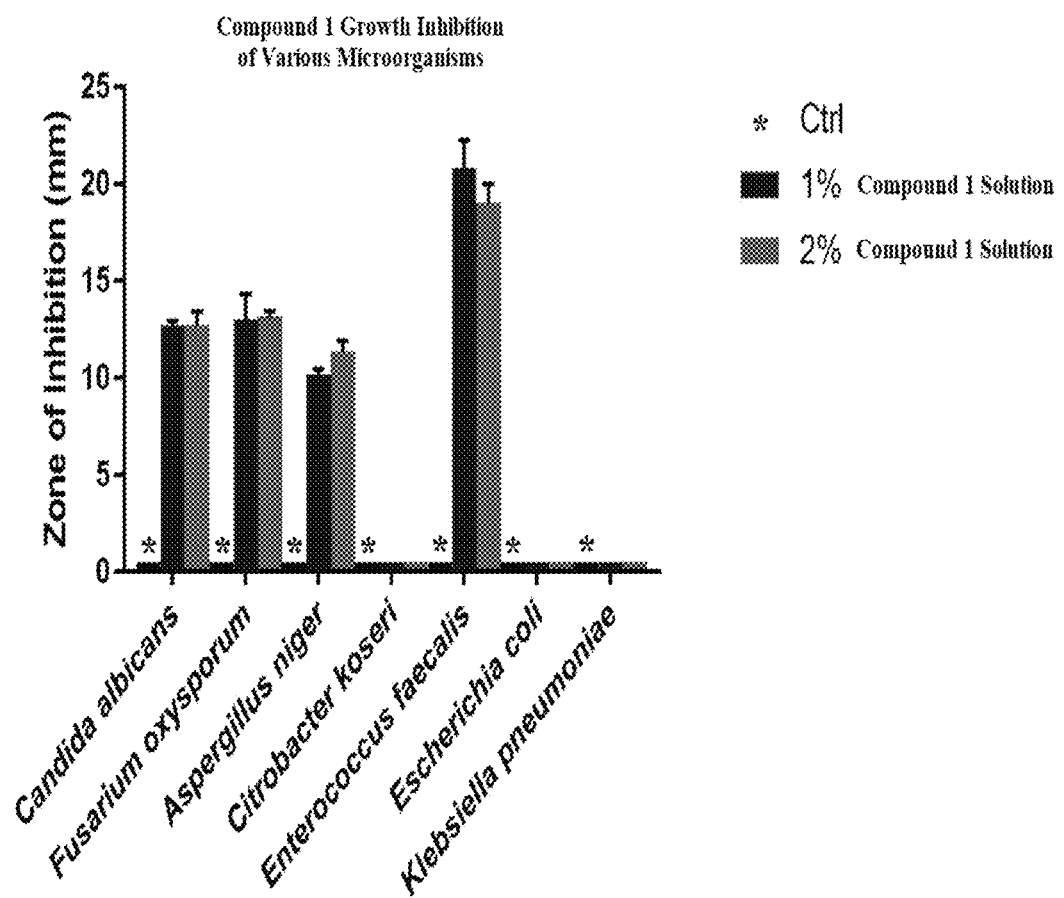
FIG. 1 is a bar graph showing the results of a disk diffusion susceptibility test of two solutions of Compound 1 against a range of microorganisms. The x-axis shows the strains being tested under three reaction conditions, which include two concentrations of Compound 1 and a control. The y-axis is the zone of inhibition, which is measured in millimeters.

In one embodiment, new organosilane quaternary ammonium compounds are provided that can be administered in an effective amount in a pharmaceutical topical formulation to treat a range of infections, including fungal infections as well as Gram positive bacterial, Gram negative bacterial and viral infections, in a host in need thereof. The fungi can occur as a yeast, a mold or a combination of both forms. The new quaternary ammonium compounds and formulations described herein can treat microorganisms in a biofilm, including mixed organisms.

Accordingly, in one aspect, the organosilane quaternary ammonium compounds described herein can be used in an effective amount in a topical formulation for direct application to an infection or incorporated into, for example, a dressing, bandage, surgical packing, gauze, wrap, conformable foam, or film for application to a wound, for example, a chronic wound or burn. When incorporated into an article, the organosilane quaternary ammonium compounds described herein may be incorporated in a manner such that the article provides controlled release of the compound or its pharmaceutically acceptable salt or composition into the surrounding area to provide extended inhibition of microbial growth. In some embodiments, an effective amount of a selected compound described herein is used to treat a chronic wound, for example, a pressure ulcer, venous ulcer, arterial wounds, neuropathic ulcer, diabetic ulcer, for example a lower limbic ulcer or foot ulcer, skin tear, or moisture-associated skin damage (MASD), for example incontinence-associated dermatitis. In some embodiments, the compounds described herein are used to treat a wound caused by a burn.

Importantly, in some embodiments, a new organosilane quaternary ammonium compound described herein can be provided as a stable powder or lyophilized material that can be formulated before administration using a pharmaceutically acceptable topical carrier. In an alternative embodiment, a new organosilane quaternary ammonium compound described herein can be incorporated into a dressing, conformable foam, or polymer for use in dressings, bandages, or films for use in medical applications, for example in a wound dressing or in surgical packings to reduce the risk of infection. In yet another alternative embodiment, a new organosilane quaternary ammonium compound described herein can be incorporated into a medical implant, for example but not limited to an orthopedic or dental implant.

In some embodiments, a topical infection in a human or animal that can be treated with the selected organosilane quaternary ammonium compound can be used to treat a microbe such as, for example, *Acinetobacter* (Gram-negative), *Pseudomonas* (Gram-negative), *Proteus* (genus of Gram-negative Proteobacteria), *Staphylococcus* (Gram-positive), *Streptococcus* (Gram-positive), MRSA (methicillin resistant *S. aureus*), *Escherichia coli* (Gram-negative), *Propionibacterium* (Gram-positive), *Klebsiella* (Gram-negative), *Enterococcus* (Gram-positive), *Haemophilus influenzae*, and fungi such as *Fusarium, Aspergillus, Cladosporium, Curvularia* and *Candida*, and dermatophytes such as *Trichophyton, Microsporum*, and *Epidermophyton*, or combinations or biofilms comprising combinations thereof.

A selected compound of the present invention can also be used in an effective amount optionally in a liquid, gel or solid carrier to disinfect a microbial growth or a biofilm formation that occurs on an abiotic (i.e., inanimate) surface such as in a home, workplace, industrial area including manufacturing plant, public area, bathroom, kitchen, furniture, transportation site or surface, or other surface that contacts or is in the environment of a human or animal. In one embodiment, an environmental surface, commonly met in food and medical area, seem also to enhance the biofilm formation and their resistance to disinfectant agents.

Definitions

Compounds are described using standard nomenclature. Unless defined otherwise, all technical and scientific terms used herein have the same meaning as is commonly understood by one of skill in the art to which this invention belongs.

The quaternary ammonium compounds in any of the Formulas described herein include racemates, enantiomers, mixtures of enantiomers, diastereomers, mixtures of diastereomers, tautomers, isomers; such as rotamers, as if each is specifically described.

The terms "a" and "an" do not denote a limitation of quantity, but rather denote the presence of at least one of the referenced items. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes quaternary ammonium compounds of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into quaternary ammonium compounds of the invention include isotopes of hydrogen, carbon, nitrogen, oxygen, fluorine, chlorine and iodine such as $^2H$, $^3H$, $^{11}C$, $^{13}C$, $^{14}C$, $^{15}N$, $^{17}O$, $^{18}O$, $^{18}F$, $^{36}Cl$, and $^{125}I$ respectively. In one non-limiting embodiment, isotopically labelled quaternary ammonium compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled quaternary ammonium compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is at least about 90, 95 or 99% or more enriched in an isotope at any location of interest. In one non-limiting embodiment, deuterium is at least about 90, 95 or 99% enriched at a desired location.

In one non-limiting embodiment, the substitution of one or more hydrogen atoms for a deuterium atoms can be provided in any of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XL. In one non-limiting embodiment, the substitution of a hydrogen atom for a deuterium atom occurs within a group selected from any of $R^1$, $R^2$, $R^3$, $R^4$, $R^5$, $R^6$, $R^7$, $R^8$, $R^9$, $R^{10}$, $R^{11}$, $R^{12}$, $R^{13}$ $R^{14}$, $R^{15}$, $R^{16}$, $R^{17}$, $X^1$, $X^2$, $X^3$, $X^4$, or any other variable defined herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The quaternary ammonium compound of the present invention can be provided in any suitable form, for example, liquid, gel, aerosol, or solid form or adsorbed onto a carrier.

The quaternary ammonium compound of the present invention may or may not form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, saline, dimethyl sulfoxide (DMSO), glycols (including propylene glycol), acetone and other common organic solvents. The term "hydrate" refers to a molecular complex comprising a quaternary ammonium compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the keto (C=O) group.

The term "Group I" herein refers to Group I alkali metals, specifically lithium (Li), sodium (Na), potassium (K), rubidium (Rb), cesium (Cs), and francium (Fr). "Group II" herein refers to Group II alkali earth metals, specifically beryllium (Be), magnesium (Mg), calcium (Ca), strontium (Sr), barium (Ba), and radium (Ra). "Group III" herein refers to aluminum. "Transition metals" herein refers to any element in the d-block, f-block lanthanide and actinide of the periodic table. Also included are post-transition metals, specifically, gallium, indium, tin, thallium, and lead.

"Aryl" indicates an aromatic group containing only carbon in the aromatic ring or rings. In some embodiments, the aryl group contains 1 to 3 separate or fused rings and is 6 to about 14 or 18 ring atoms, without heteroatoms as ring members. When indicated, such aryl group may be further substituted with carbon or non-carbon atoms or groups. Such substitution may include fusion to a 3 to 7-membered saturated cyclic group that optionally contains 1 or 2 heteroatoms independently chosen from N, O, and S, to form, for example, a 3,4-methylenedioxyphenyl group. Aryl groups include, for example, phenyl and naphthyl, including 1-naphthyl and 2-naphthyl. In some embodiments, aryl groups are pendant. An example of a pendant ring is a phenyl group substituted with a phenyl group. In some embodiments, the aryl group is optionally substituted as described above.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, haloalkyl, etc. can all be considered to include the cyclic forms of alkyl, unless unambiguously excluded by context.

"Hydroxyalkyl" herein refers to any alkyl group as previously described, substituted with at least one hydroxyl substituent.

"Alkanoic acid" herein, refers to any carboxylic acid where the R is an alkyl; wherein an alkyl is as defined herein. Additionally, the acid can be a diacid; and/or contain one or more substituent group selected from a halogen such as a chloride, bromide, fluoride, iodide; hydroxyl, $N(R^7)_2$, $NO_2$, alkyl, alkenyl, and the like.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation.

"Halo" and "Halogen" is fluorine, chlorine, bromine or iodine.

"Haloalkyl" is a branched or straight-chain alkyl groups substituted with 1 or more halogen atoms, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

The term "heterocyclyl," or "heterocyclic ring" as used herein refers to a saturated or a partially unsaturated (i.e., having one or more double and/or triple bonds within the ring without aromaticity) carbocyclic radical of 3 to about 12, and more typically 3, 5, 6, 7 to 10 ring atoms in which at least one ring atom is a heteroatom selected from nitrogen, oxygen, phosphorus and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 6 to 10 ring members (4 to 9 carbon atoms and 1 to 6 heteroatoms selected from N, O, P, and S), for example: a bicyclo [4,5], [5,5], [5,6], or [6,6] system. In some embodiments, the only heteroatom is nitrogen. In some embodiments, the only heteroatom is oxygen. In some embodiments, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocyclyl groups herein are optionally substituted independently with one or more substituents described herein.

Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "carrier" applied to compositions/combinations of the invention refers to a diluent, excipient, or vehicle with which an active compound is provided.

A "patient" or "host" or "subject" is a human or non-human animal in need of treatment or prevention of any of an infection as described herein. In some embodiments, the host is a human. A "patient" or "host" or "subject" also refers to for example, a mammal, primate (e.g., human), cows, sheep, goat, horse, dog, cat, rabbit, rat, mice, fish, bird and the like.

A "therapeutically effective amount" of a composition/combination of this invention means an amount effective, when administered to a host, to provide a therapeutic benefit such as an amelioration of symptoms or reduction or diminution of the disease itself. In some embodiments, a therapeutically effective amount is an amount sufficient to inhibit progression, cause a regression, cause a cure, or inhibit, eliminate, or prevent an infection in a host in need thereof.

As used herein, "salt" is a derivative of the disclosed compound in which the parent compound is modified by making inorganic or organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reactive free base forms of these compounds with a stoichiometric amount of the appropriate acid. Such reactions are typically carrier out in water or in an organic solvent, or in a mixture of the two. Generally, non-aqueous media like ether, ethyl acetate, ethanol, isopropanol, or acetonitrile are typical, where practical. Salts of the present compounds further include solvates of the compound and the compound salts.

Examples of salts include, but are not limited to, mineral or organic acid salts of basic residues such as amines; alkali or organic salts of acidic residues such as carboxylic acids; and the like. The salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_{n'}$—COOH where n' is 0-4, and the like, or using a different acid that produces the same counterion. Lists of additional suitable salts may be found, e.g., in Remington's Pharmaceutical Sciences, 17$^{th}$ 20 ed., Mack Publishing Company, Easton, Pa., p. 1418 (1985).

In a typical embodiment, the positive charges in the formulas described herein are paired with one or more negatively charged ions, such as chloride.

Chemistry
Embodiments of "Alkyl"

In some embodiments, "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In some embodiments, "alkyl" has one carbon.
In some embodiments, "alkyl" has two carbons.
In some embodiments, "alkyl" has three carbons.
In some embodiments, "alkyl" has four carbons.
In some embodiments, "alkyl" has five carbons.
In some embodiments, "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neo-pentyl, 3-pentyl, and active pentyl.

In some embodiments, "alkyl" is "substituted alkyl"
In some embodiments, "alkenyl" is "substituted alkenyl"
In some embodiments, "alkynyl" is "substituted alkynyl"

Embodiments of "Haloalkyl"

In some embodiments, "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In some embodiments, "haloalkyl" has one carbon.
In some embodiments, "haloalkyl" has one carbon and one halogen.
In some embodiments, "haloalkyl" has one carbon and two halogens.
In some embodiments, "haloalkyl" has one carbon and three halogens.
In some embodiments, "haloalkyl" has two carbons.
In some embodiments, "haloalkyl" has three carbons.
In some embodiments, "haloalkyl" has four carbons.
In some embodiments, "haloalkyl" has five carbons.
In some embodiments, "haloalkyl" has six carbons.

Non-limiting examples of "haloalkyl" include:

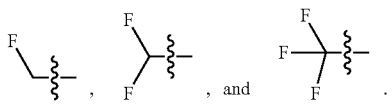

Additional non-limiting examples of "haloalkyl" include:

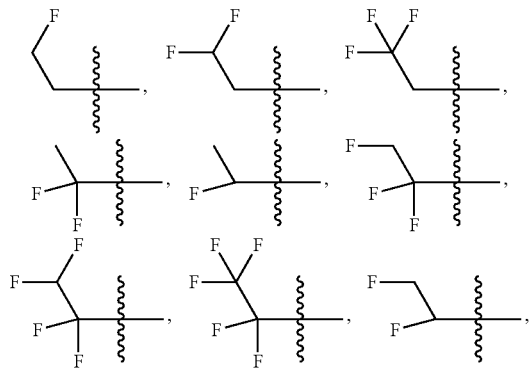

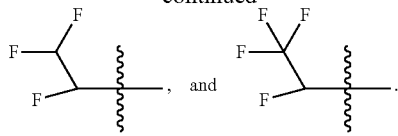

Additional non-limiting examples of "haloalkyl" include:

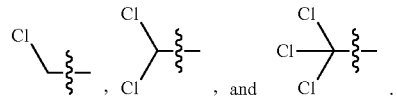

Additional non-limiting examples of "haloalkyl" include:

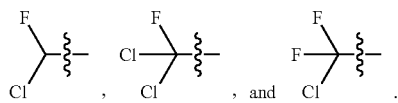

Silane quaternary amine compounds has been previously described for biocidal applications, however, their usage has been limited to industrial, agricultural applications such as fabric and textiles, apparel, construction materials, food packaging and containers, adhesives, roof shingles, fiberglass, plastics, agricultural products, paints, coatings and surface treatments, carpets, wood, water purification systems, and laundry additives, among others; and medical applications such as medical articles and surgical gloves. Additionally, many of these silane quaternary amine compounds are typically marketed in methanol which can be toxic for pharmaceutical and other medical applications. (U.S. Pat. Nos. 3,560,385; 3,794,736; 5,954,869 and 8,999,357).

These quaternary ammonium compounds do not break down to form components that are unduly toxic to the host. They can be used in remote areas to treat people and animals currently not served by adequate antimicrobial healthcare approaches.

The quaternary ammonium compounds described herein have increased stability in comparison to other organosilane, for example, 3-(trihydroxysilyl)-N-propyl-N,N-dimethyloctadecyl ammonium chloride, and also provide improved shelf life due to decreased levels of polymerization to subsequently insoluble polysilsequioxane materials in both solid form and in solution. Additionally, formulations of the present invention are substantially free alcohols such as methanol, ethanol and/or other unwanted small volatile organic.

The quaternary ammonium compounds of the present invention do not produce byproducts such as methanol upon hydrolysis. Powder or other solid formulations, for example lyophilized powder, of the present invention are substantially free of methanol, ethanol and/or other unwanted small volatile organic compounds due to either (i) not using such compounds in the manufacture or (ii) the use of vacuum drying during processing, a significant improvement over commercially available aqueous solutions of other organosilane antimicrobials, such as 3-(trihydroxysilyl)-N-propyl-N, N-dimethyloctadecyl ammonium chloride, which often contain significant quantities of methanol as a byproduct of its synthesis.

The molecules are of small enough of a size to allow ready perfusion with a biofilm and can do so even as an oligomeric species; and are also stabile in aqueous or glycerin solution to traverse the small channels of a biofilm, providing increased penetration into the biofilm with efficacy to eliminate the entire biofilm, including persister cells.

Potency is retained after interacting with and killing microbes since the organosilane molecule is not consumed by such interactions and can continue to be lethal to active microbes. Furthermore, the killing mechanism for these compounds diminishes the possibility of resistance development in targeted organisms compared to other topical infection treatments that use antibiotics and antifungals.

Organosilane quats with sulfonate salts have also been previously described, however applications have been specific for industrial and agricultural applications, and not medical applications as described above. Such molecules would be toxic for medical applications such as eye and ear care. These organosilanes have an organosulfate esters, which is both hazardous and toxic for the eye and ears (U.S. Pat. No. 5,954,869).

Other organosilane quaternary compounds such as 3-(trimethoxysilyl)-N-propyl-N,N-dimethyloctadecyl ammonium chloride and related trialkoxysilane, have been used for the treatment of infections including wounds (see U.S. Pat. Nos. 4,865,844; 4,908,355; U.S. Patent Appl. Pub. Nos. 2011/0293681; 2012/0052106; 2013/0231599; 2014/0100504; 2016/0346193; 2017/0094974; and International Patent Appl. Pub. Nos. WO2000/54587; WO2004/004793). However, such compounds hydrolyze, both in the aqueous environment of living systems and when formed into aqueous compositions releasing methanol, which can be toxic to living organisms, being just as toxic by absorption in tissue as by ingestion (see Ind. Eng. Chem. 1931, 23, 931-936). The production of toxic methanol as a byproduct significantly limits or largely excludes their use in pharmaceutical and medical applications. Additionally, no stable form of silane quaternary ammonium compounds are known, that does not use additives that would be inappropriate for medical applications.

In some embodiments, the quaternary ammonium compound of the present invention is a solid compound that readily dissolves in water to form a stable aqueous solution. For example, the quaternary ammonium compound can be dissolved in saline solution, deionized water, or a buffer to form a visibly clear aqueous solution. In some embodiments, the aqueous solution can be stored at room temperature without clouding for at least 1, 2, 3, 4, 5, 6, 8, 12, 16, or more days. In another embodiment, the quaternary ammonium compound can be made more soluble by first applying a lyophilizer to make a powder.

In another embodiment, the quaternary ammonium compound of the present invention forms a solution that is or is nearly neutral when dissolved in water. For example, the aqueous solution can have a pH of approximately 6.4, 6.8, 7.0, 7.2, 7.4, 7.6, 7.8 or 8.0.

In some embodiments, the solutions described above have at least 0.2%, 0.4%, 0.6%, 0.8% 1%, 1.2%, 1.4%, 1.6%, 1.8%, or 2.0% concentration of the quaternary ammonium compound of the present invention.

Zwitterions of the Present Invention

In certain alternative embodiments, the quaternary ammonium compound of the present invention is a zwitterion. In these embodiments $X^-$ may be absent and the quaternary amine is balanced with an internal anion. One non-limiting example is the following compound of Formula I:

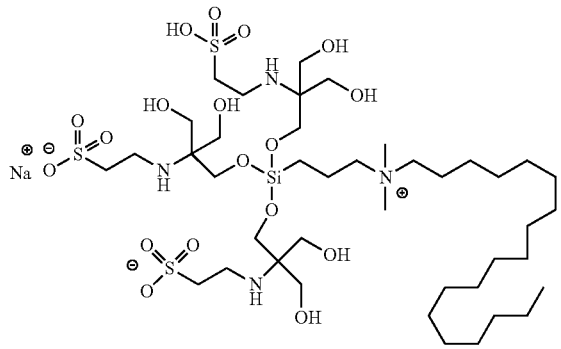

In other embodiments, the quaternary ammonium compound of the present invention is not a zwitterion. In this embodiment the quaternary amine is balanced with $X^-$. For example, the compound of Formula I can be:

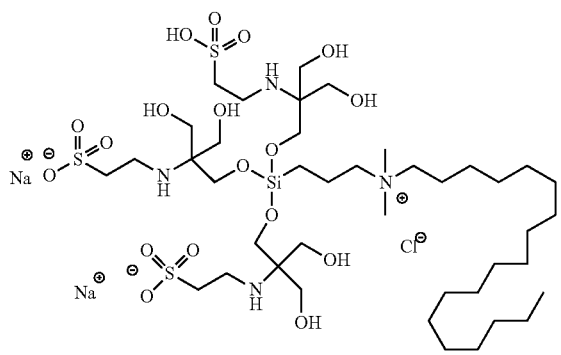

In some embodiments, the zwitterionic quaternary ammonium compound is more soluble in aqueous media than its non-zwitterionic form. In yet another embodiment, the zwitterionic compound is more stable in an aqueous solution than its non-zwitterionic form. In some embodiments, the zwitterionic compound is more soluble in aqueous media than its non-zwitterionic form. In yet another embodiment, the zwitterionic compound is more stable in an aqueous solution than its non-zwitterionic form. In certain embodiments, the sodium chloride (NaCl) salt can be replaced with another salt described herein.

In alternative embodiments, the quaternary ammonium compound of Formula I is zwitterionic and the X− ion is not present. For example, in some embodiments, Formula I is:

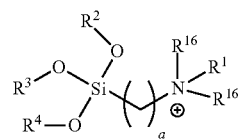

and a representative compound of Formula I is

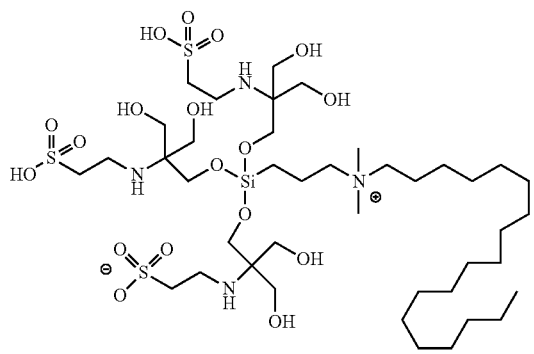

In alternative embodiments, the quaternary ammonium compound of Formula III is zwitterionic and the X– ion is not present. For example, in some embodiments, Formula III is:

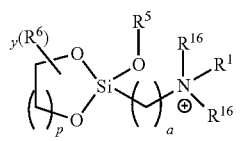

p and a representative compound of Formula III is

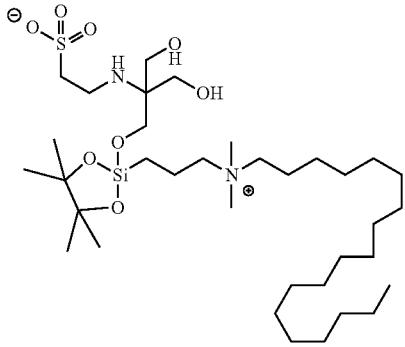

In alternative embodiments, the quaternary ammonium compound of Formula IV is zwitterionic and the X– ion is not present. For example, in some embodiments, Formula IV is:

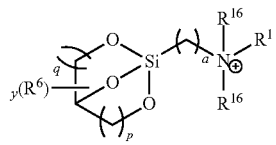

p and a representative compound of Formula IV is

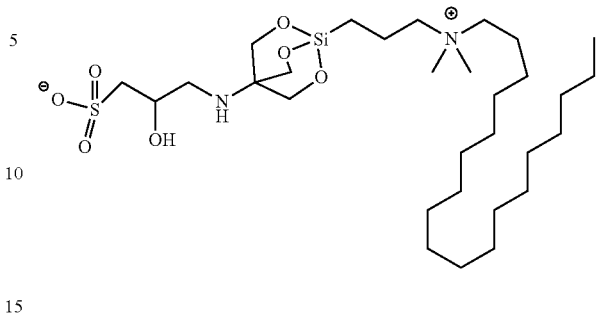

Representative Compounds of the Present Invention

In some embodiments, the quaternary ammonium compound of the present invention is:

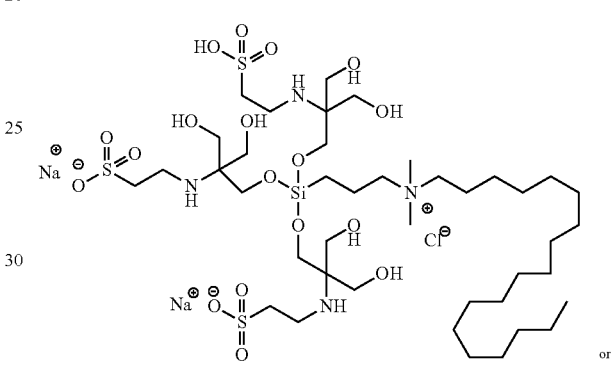

or

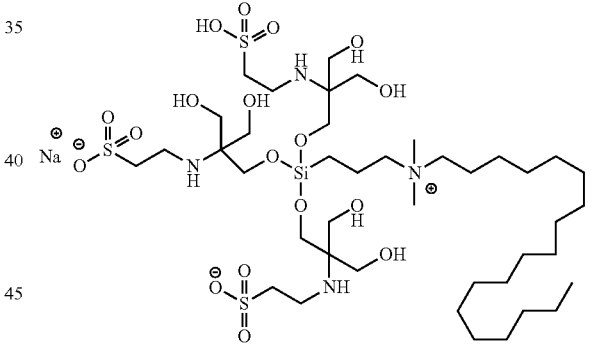

In some embodiments, the quaternary ammonium compound of the present invention is:

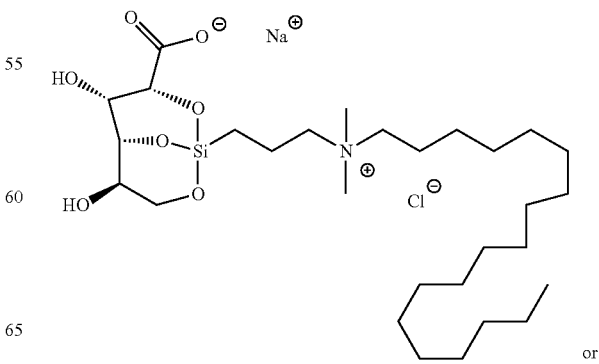

or

63
-continued
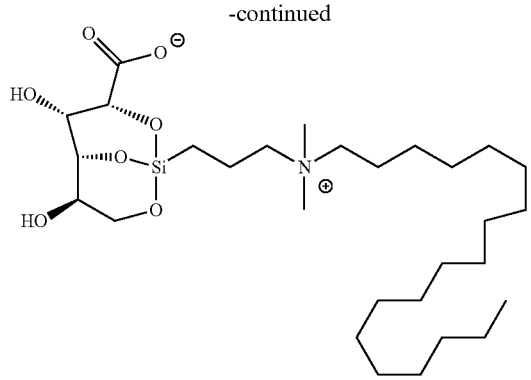
In some embodiments, the quaternary ammonium compound of the present invention is:
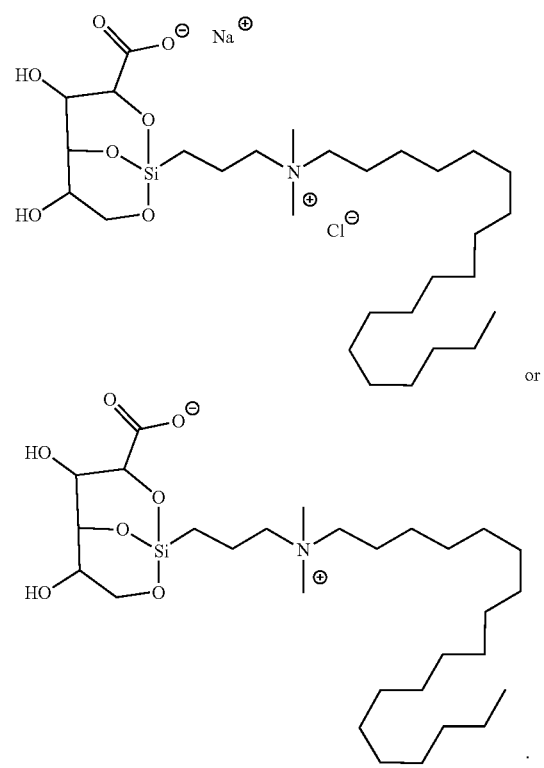
or
In some embodiments, the quaternary ammonium compound of the present invention is:
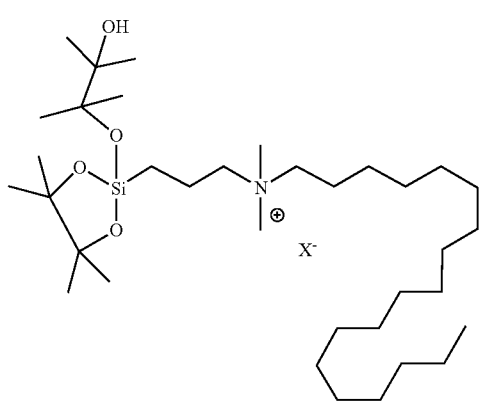
64
-continued
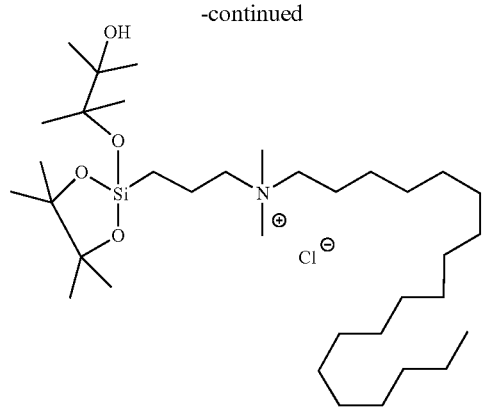
In some embodiments, the quaternary ammonium compound of the present invention is:
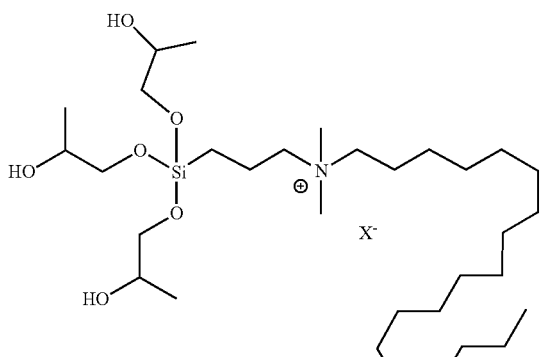
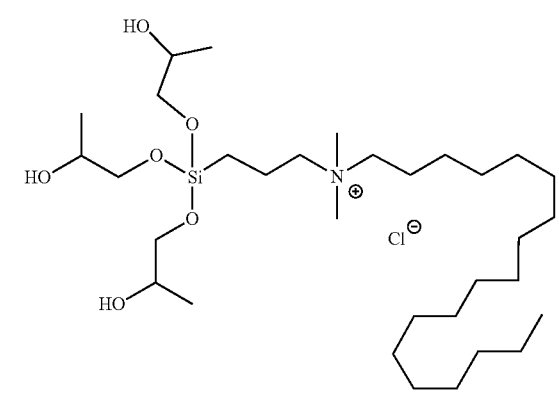
In some embodiments, the quaternary ammonium compound of the present invention is:

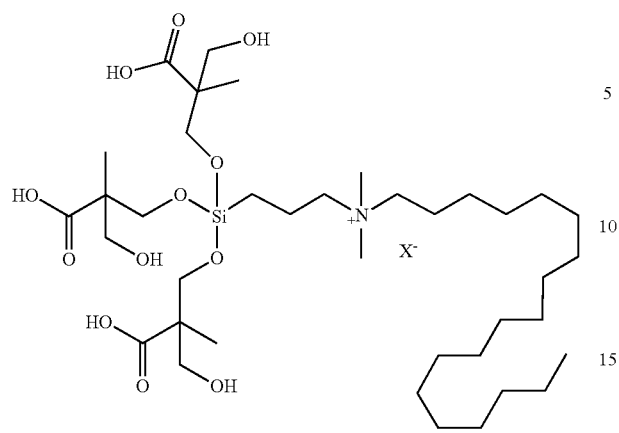
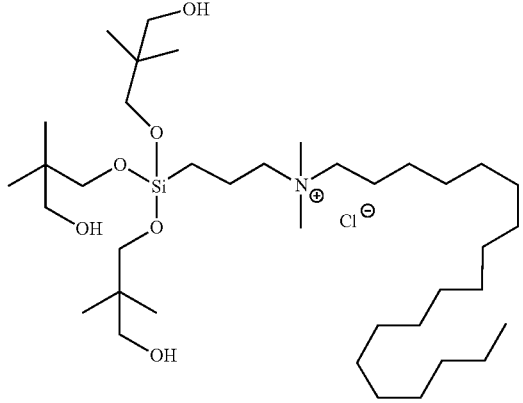
In some embodiments, the quaternary ammonium compound of the present invention is:
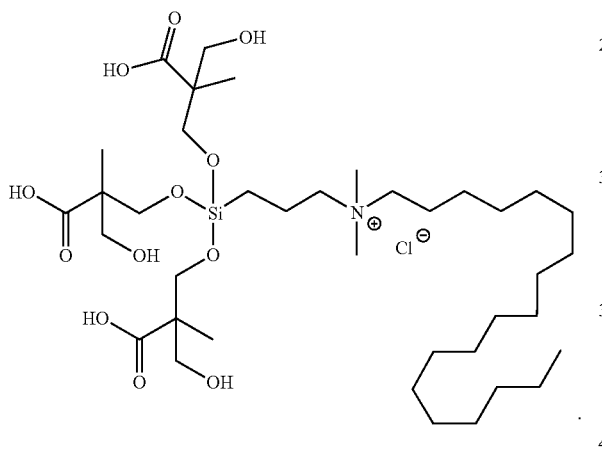
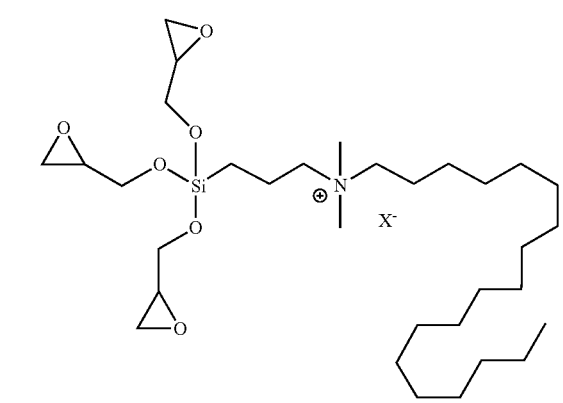
In some embodiments, the quaternary ammonium compound of the present invention is:
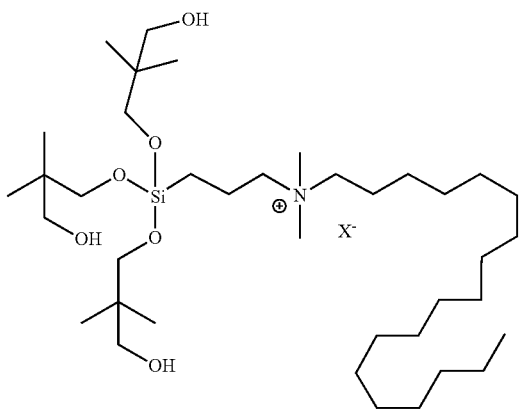
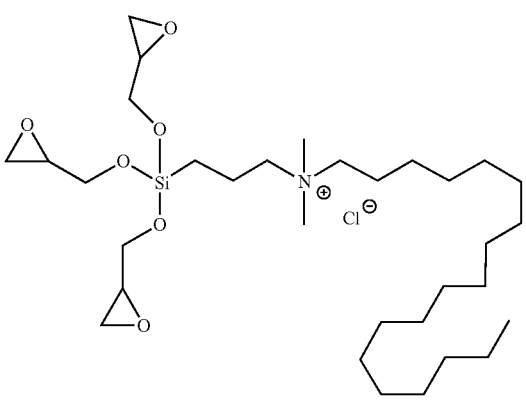
In some embodiments, the quaternary ammonium compound of the present invention is:

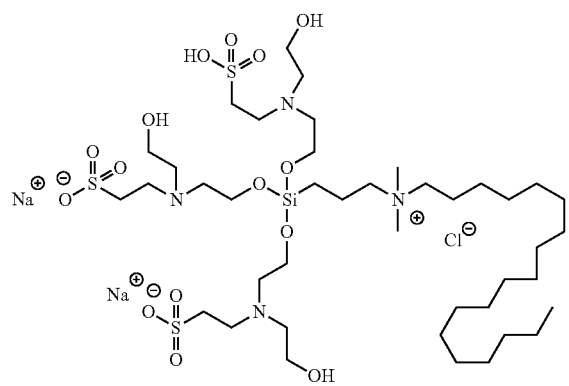
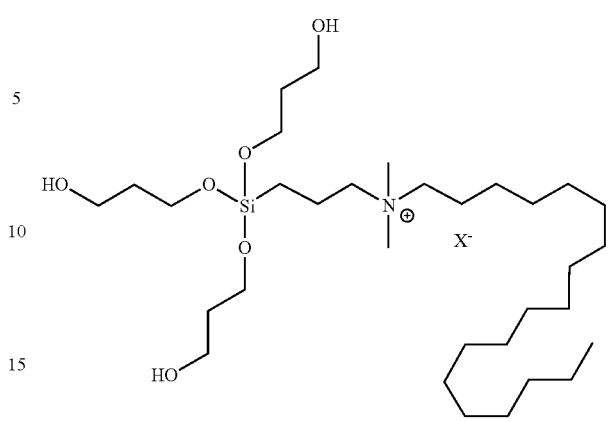
In some embodiments, the quaternary ammonium compound of the present invention is:
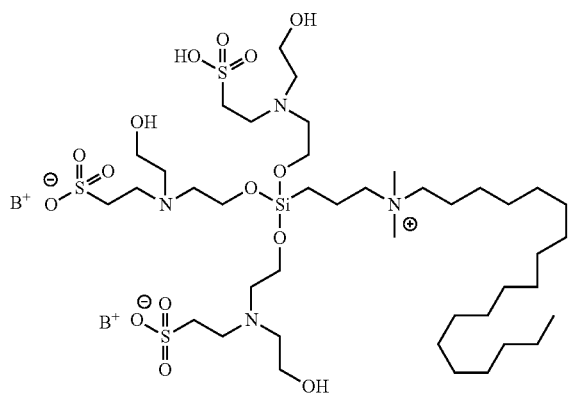
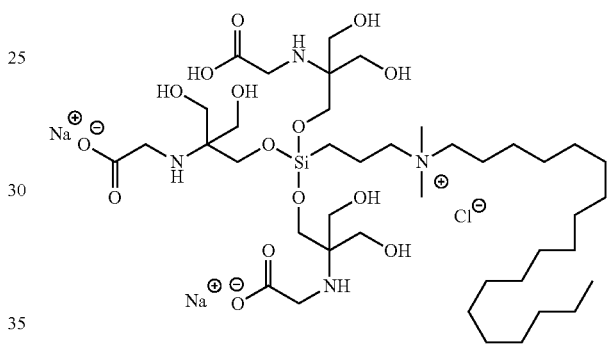
or
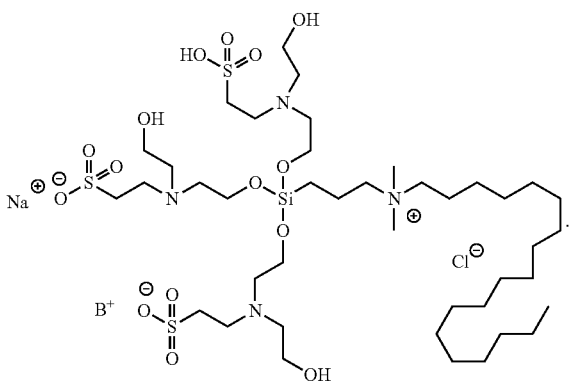
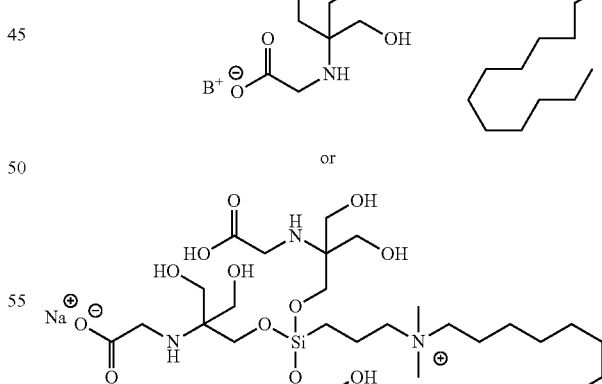
In some embodiments, the quaternary ammonium compound of the present invention is:
In some embodiments, the quaternary ammonium compound of the present invention is:

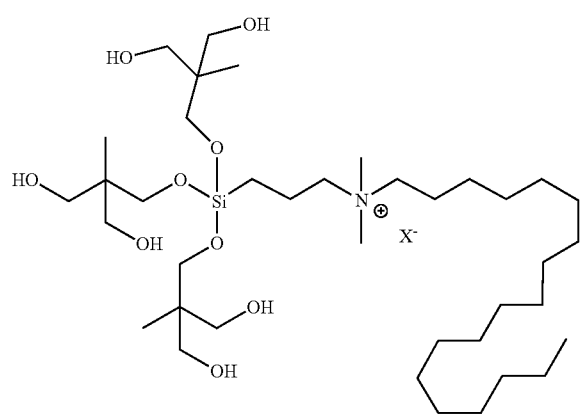
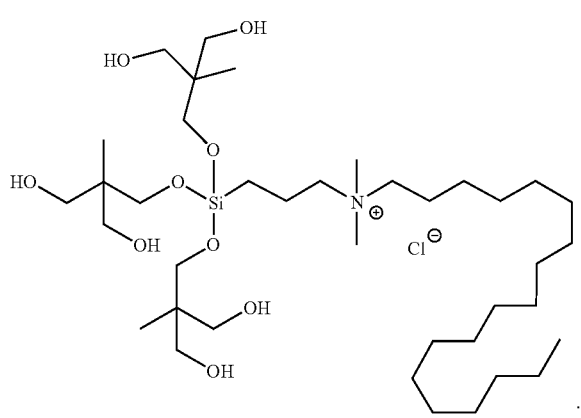
In some embodiments, the quaternary ammonium compound of the present invention is:
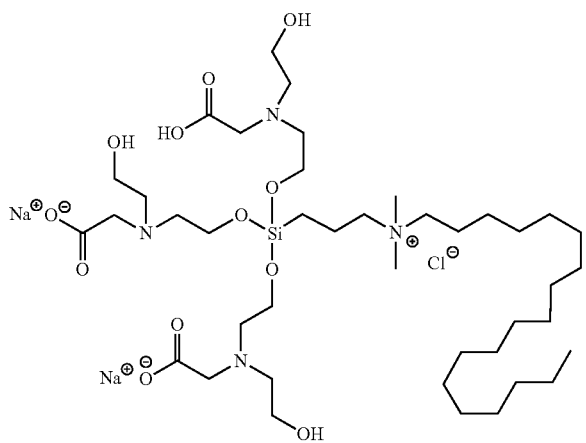
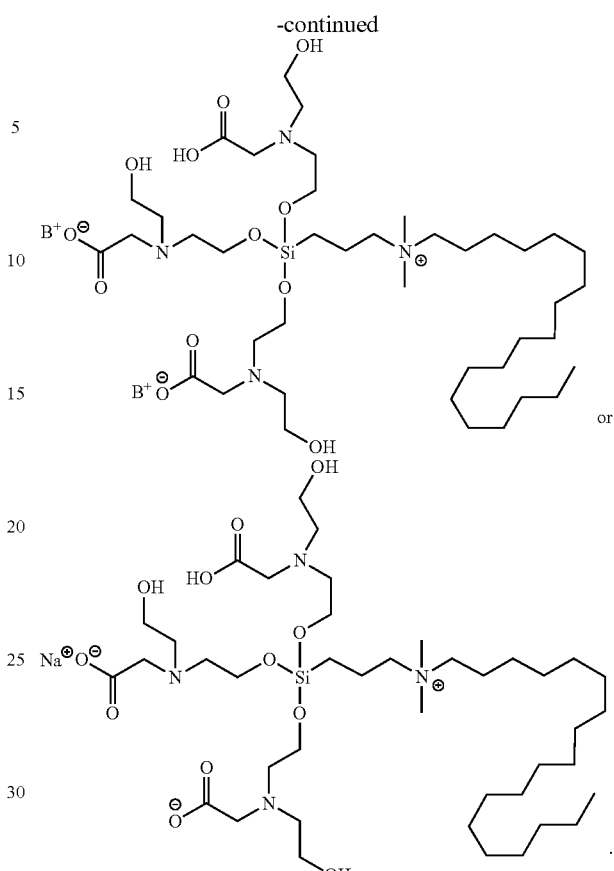
In some embodiments, the quaternary ammonium compound of the present invention is:
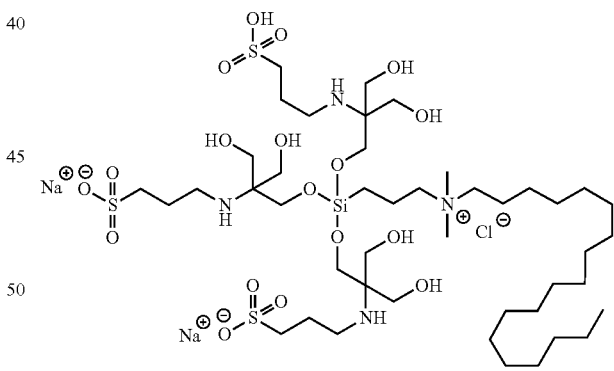
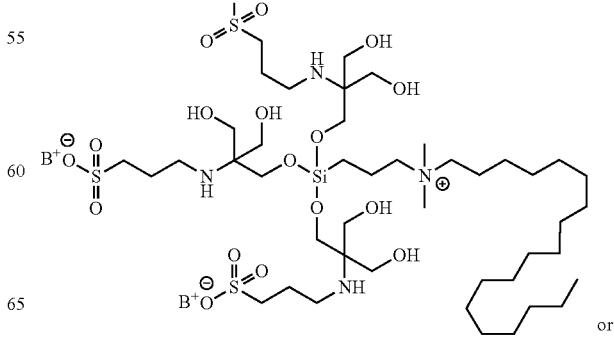
or

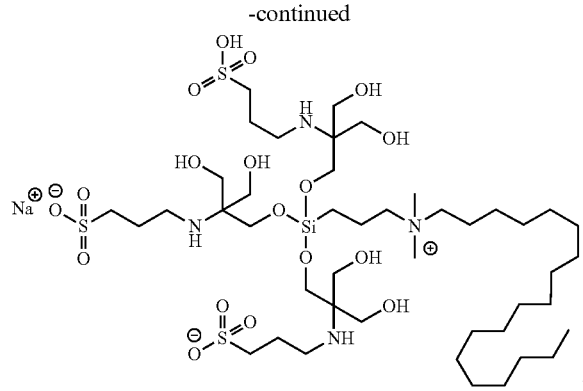
In some embodiments, the quaternary ammonium compound of the present invention is:
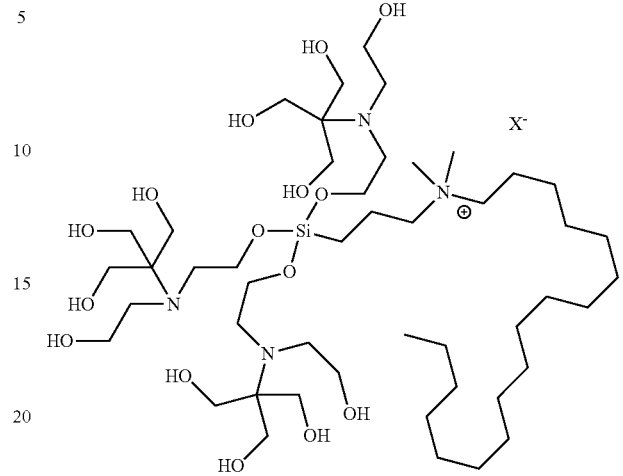
In some embodiments, the quaternary ammonium compound of the present invention is:
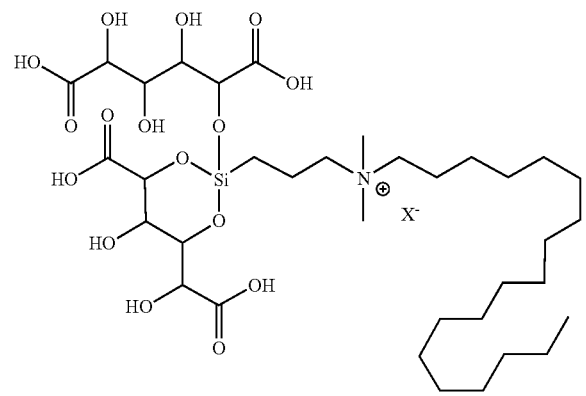
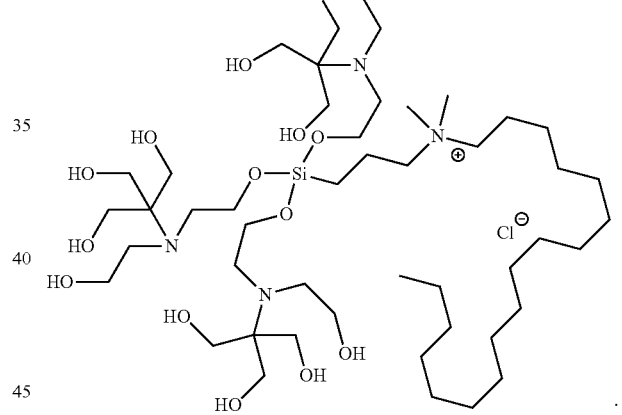
In some embodiments, the quaternary ammonium compound of the present invention is:
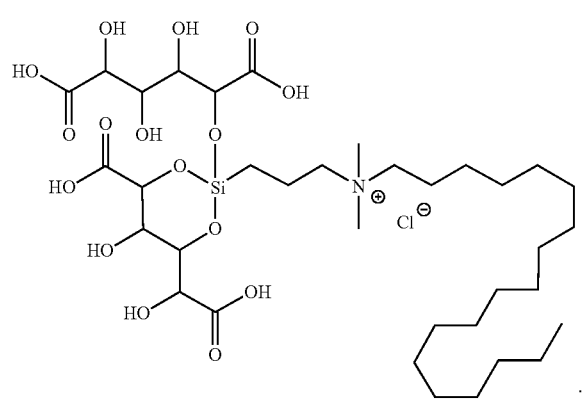
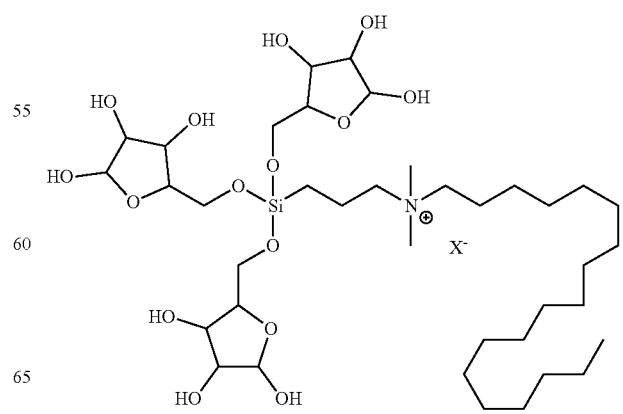

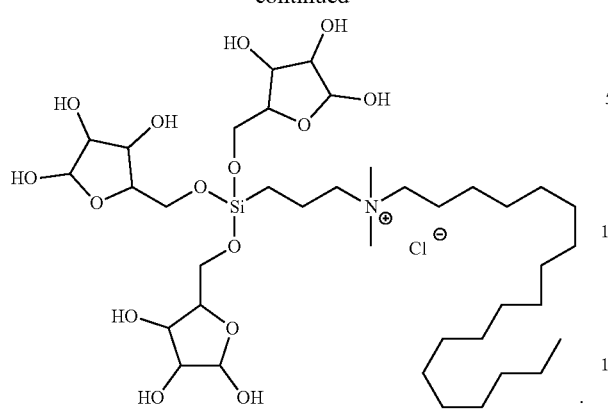
In some embodiments, the quaternary ammonium compound of the present invention is:
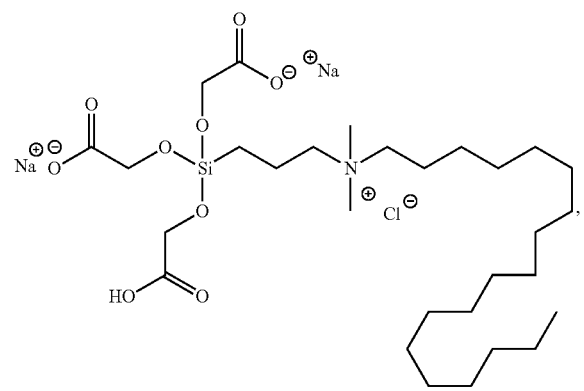
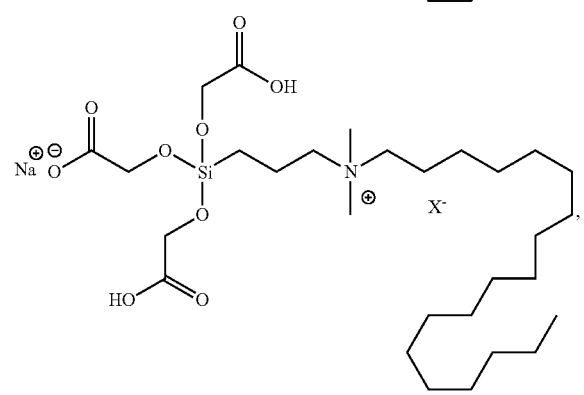
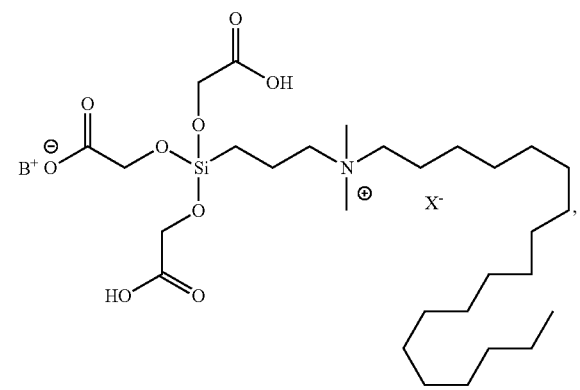
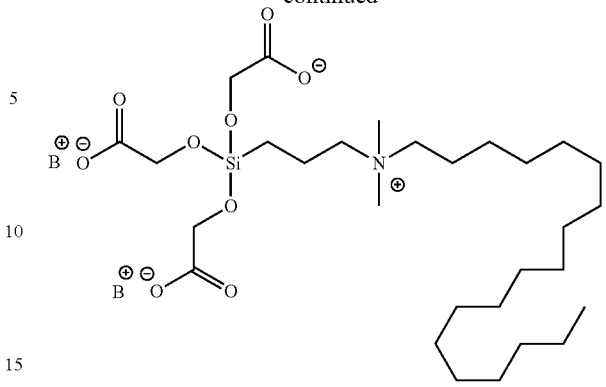
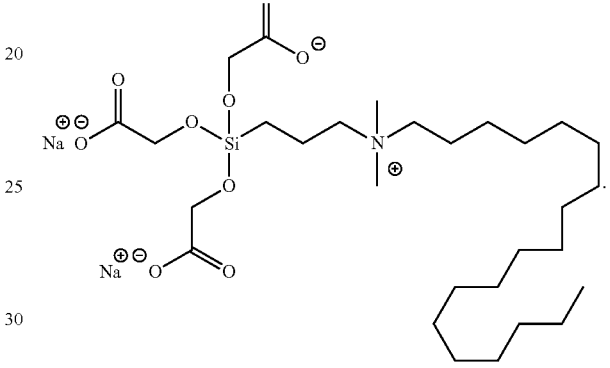
In some embodiments, the quaternary ammonium compound of the present invention is:
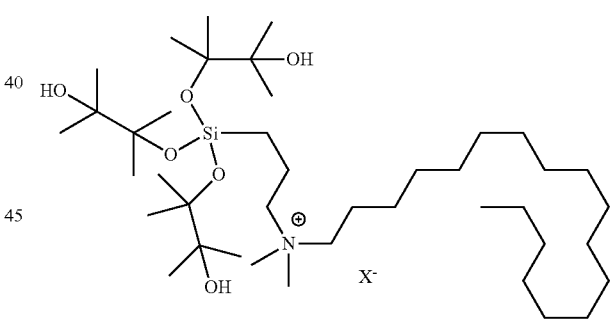
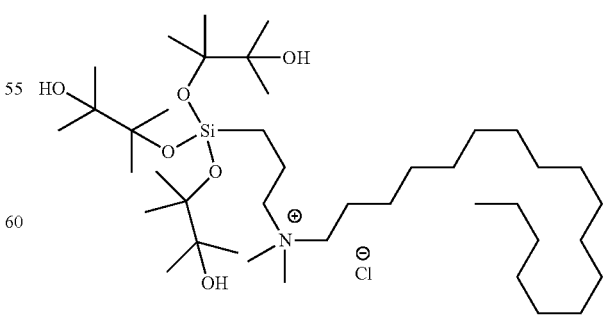
In some embodiments, the quaternary ammonium compound of the present invention is:

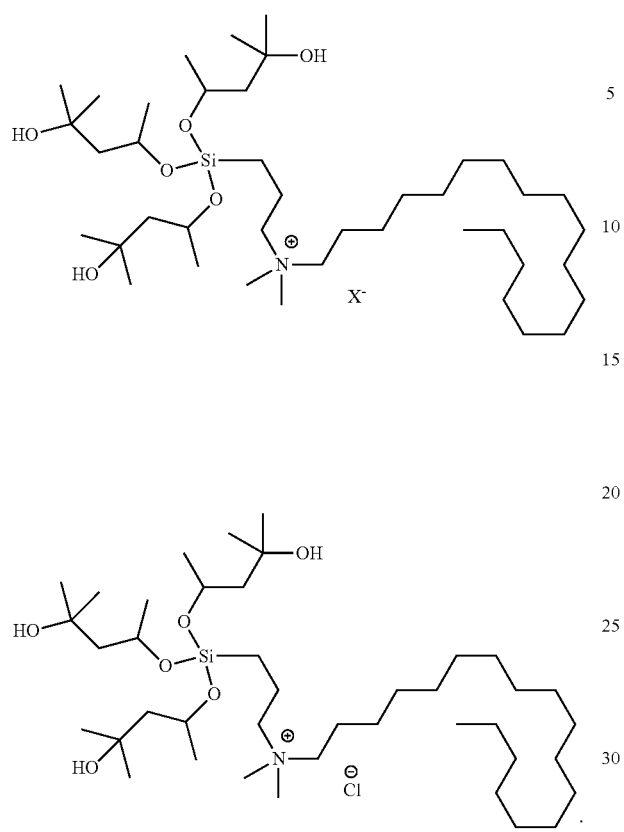
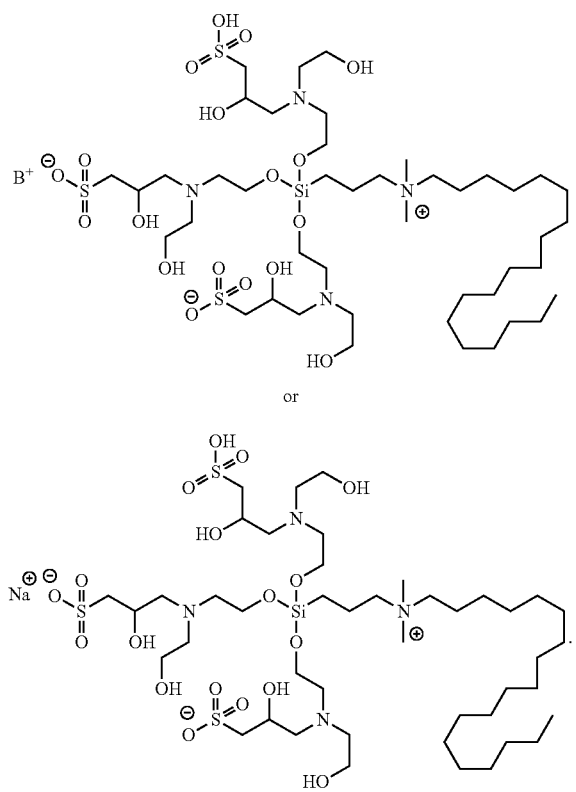
In some embodiments, the quaternary ammonium compound of the present invention is:
In some embodiments, the quaternary ammonium compound of the present invention is:
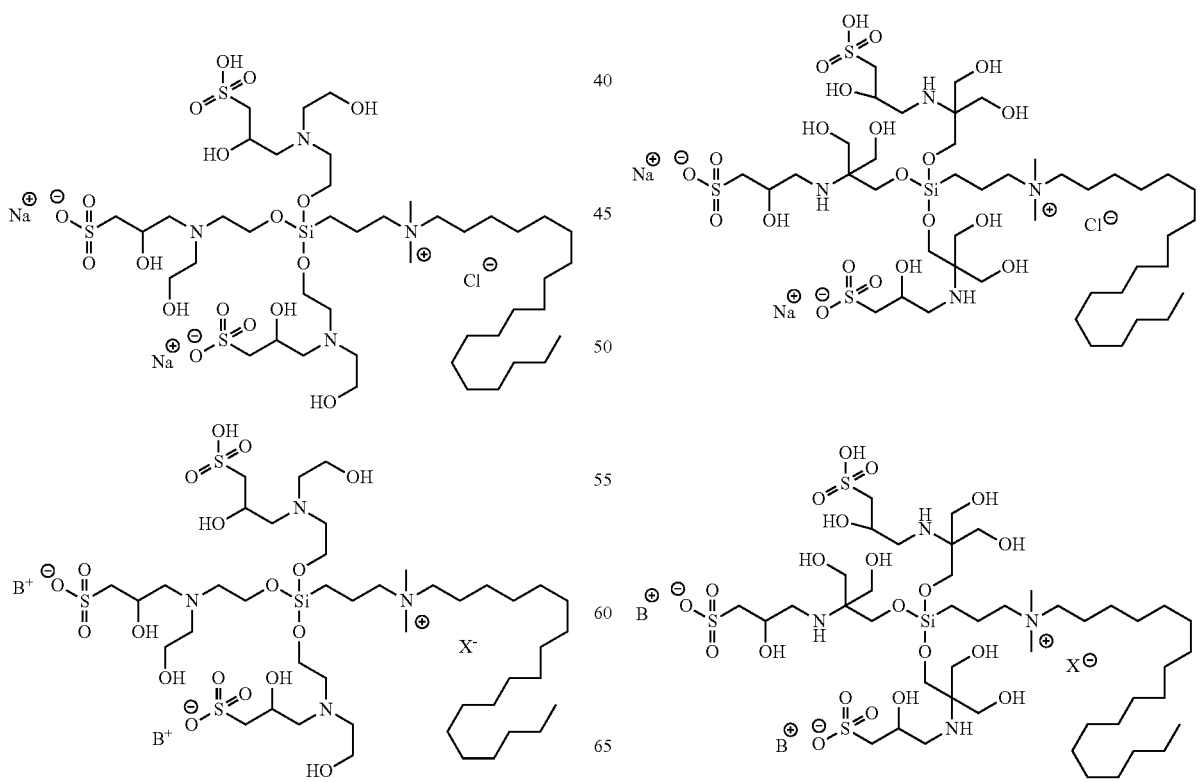

77
-continued
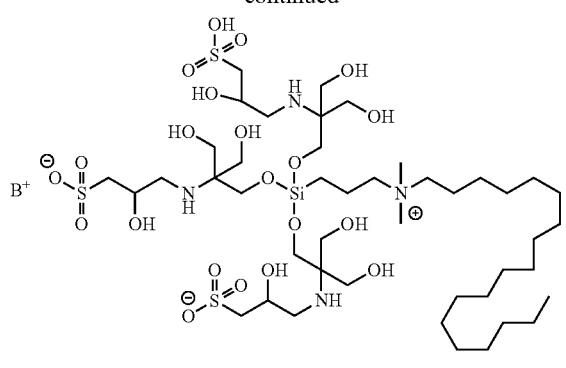
78
-continued
or
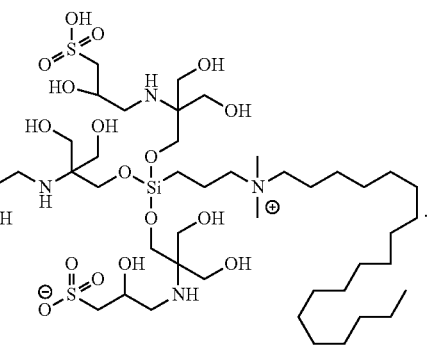
Representative Compounds of the Present Invention
In certain embodiments, the quaternary ammonium compound of the present invention is:
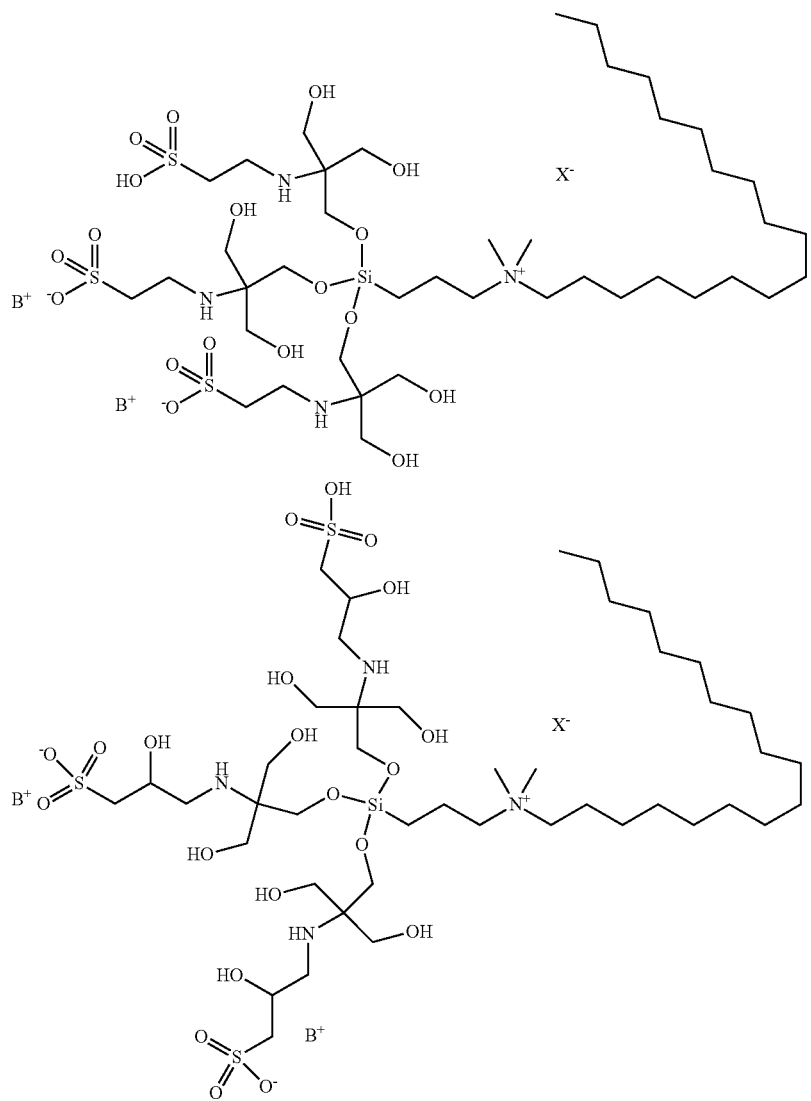

-continued
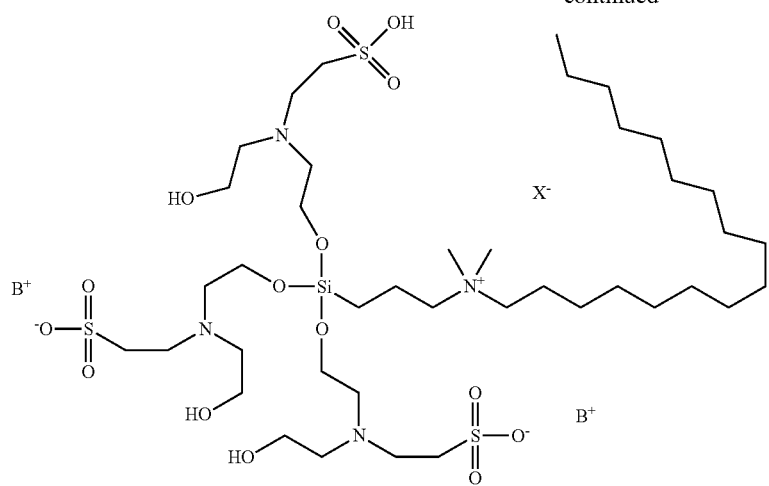
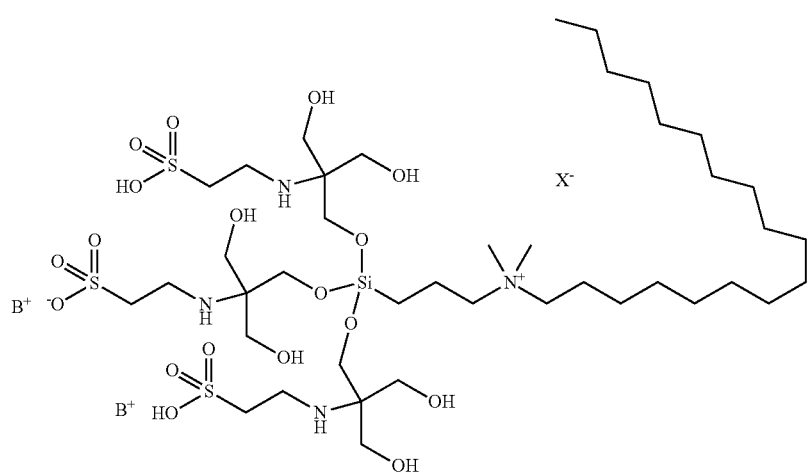
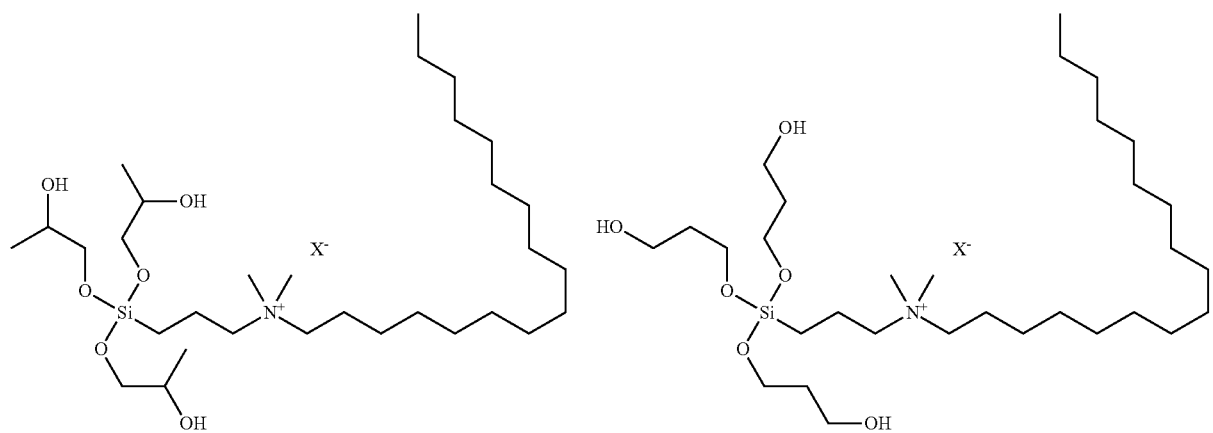

-continued
81
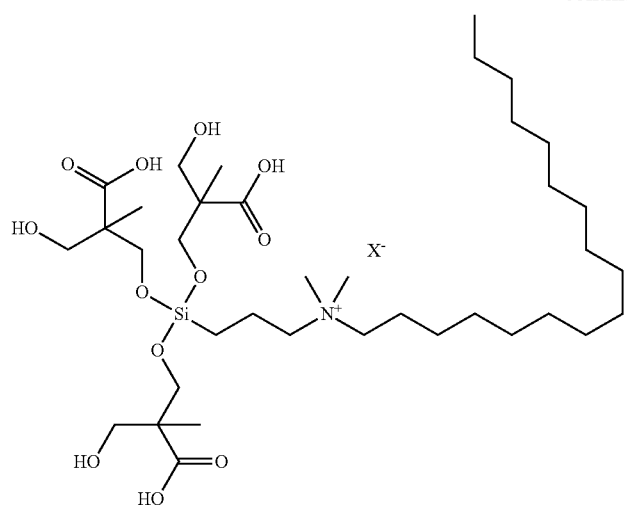
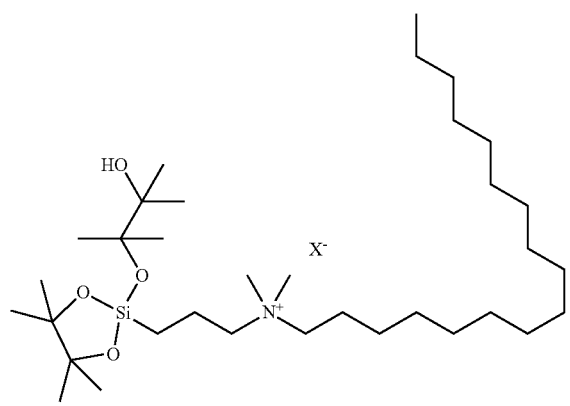
82
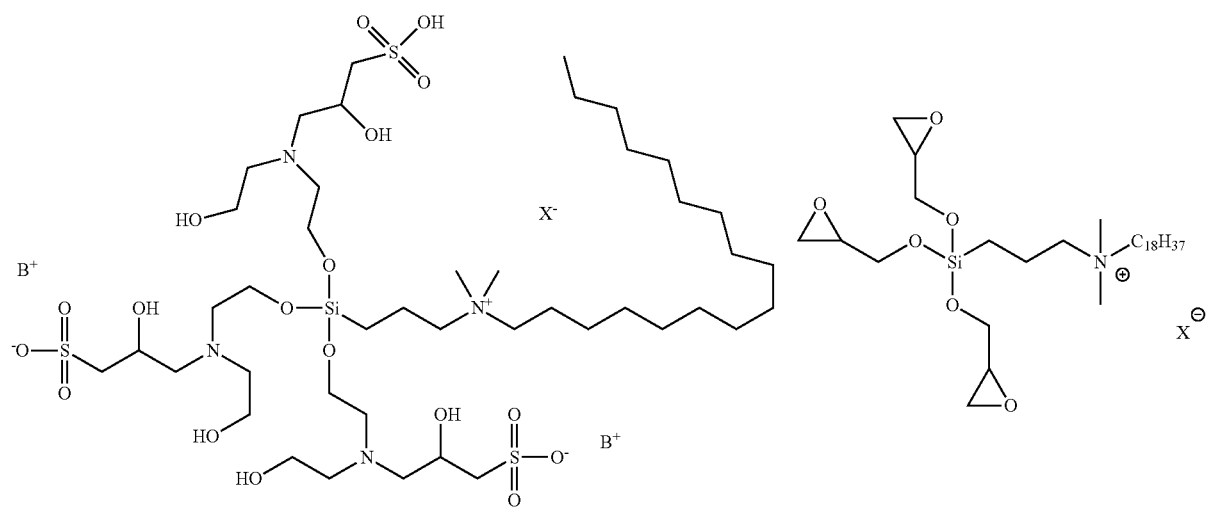

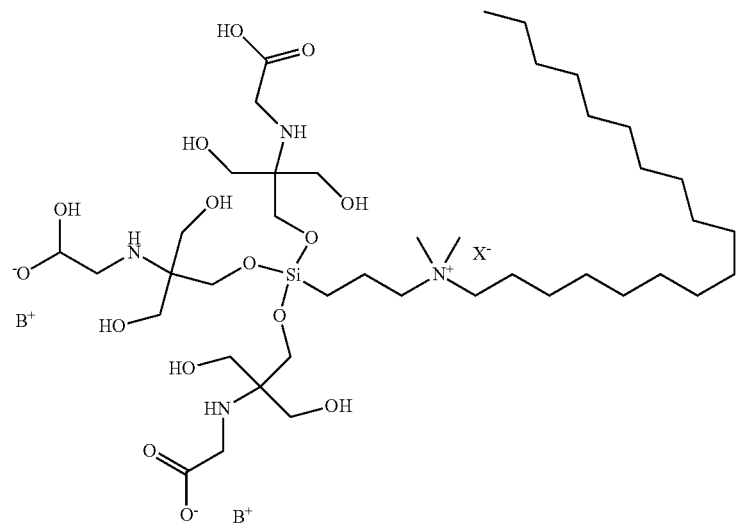
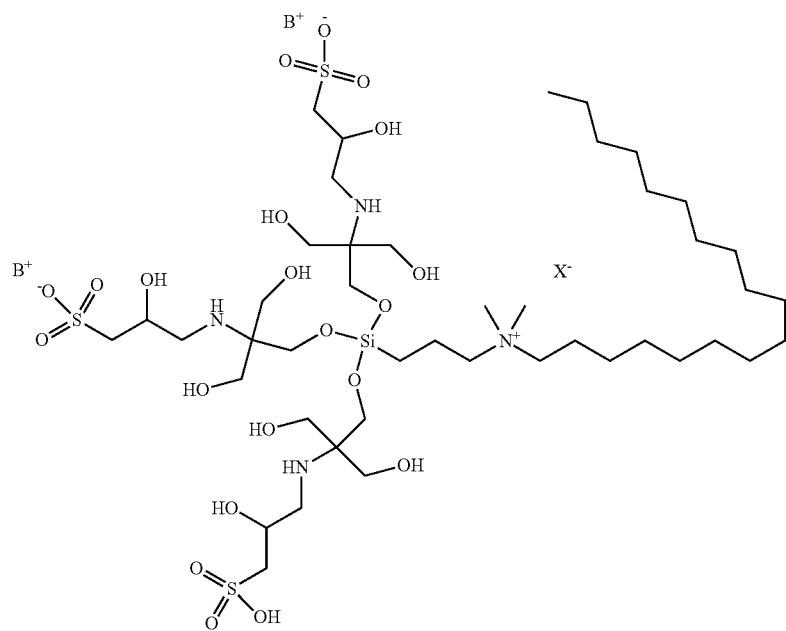
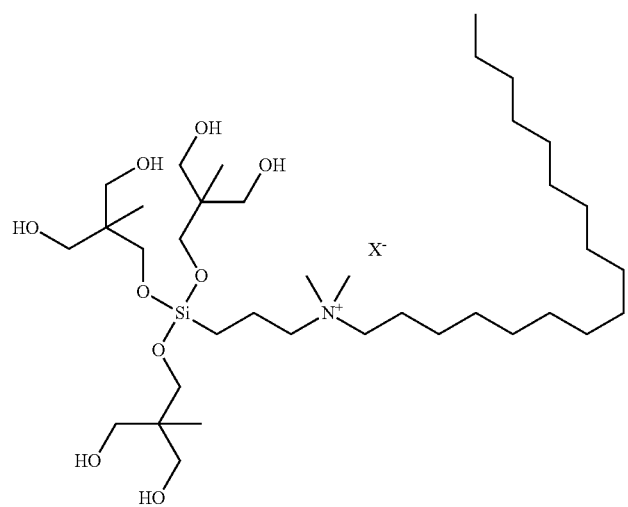

-continued
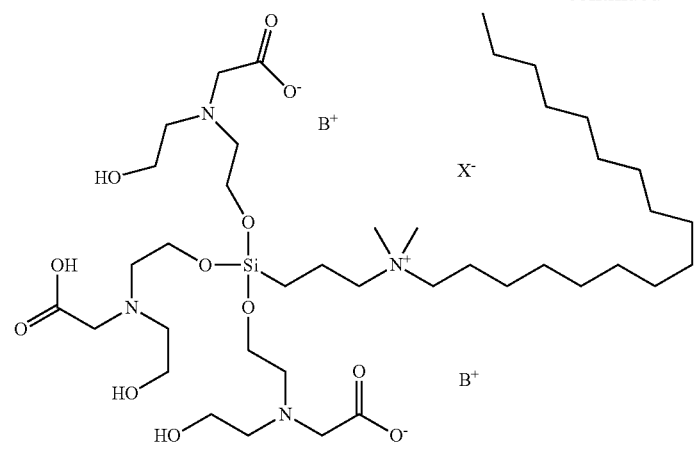
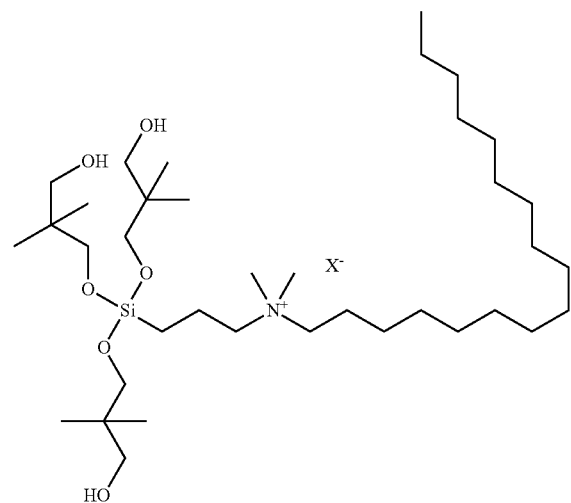
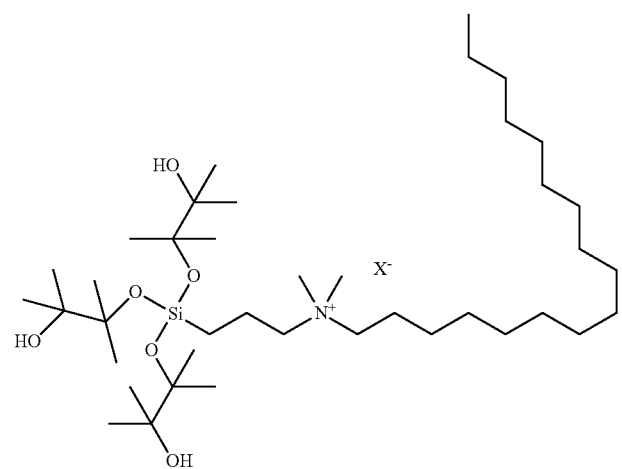
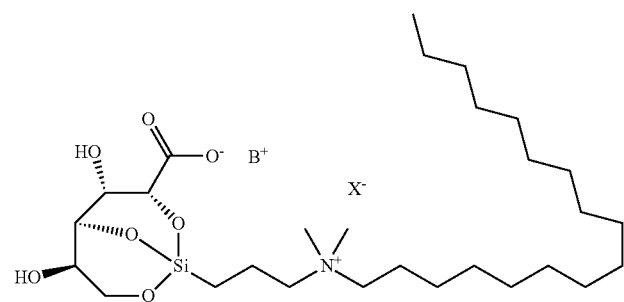

-continued
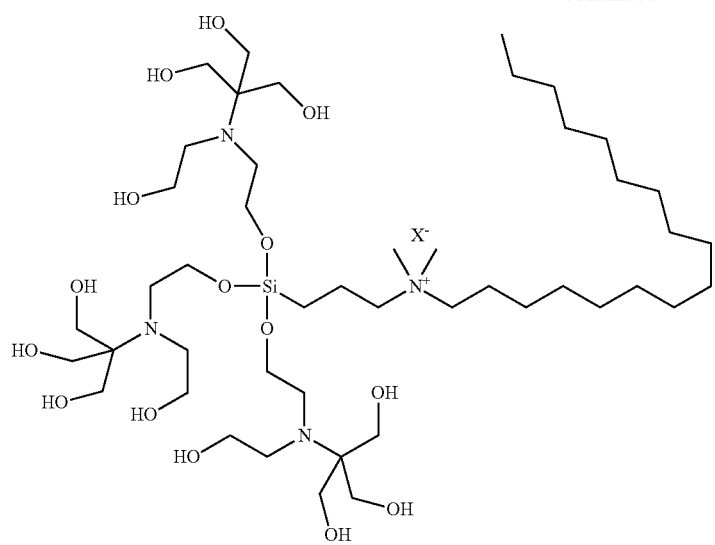
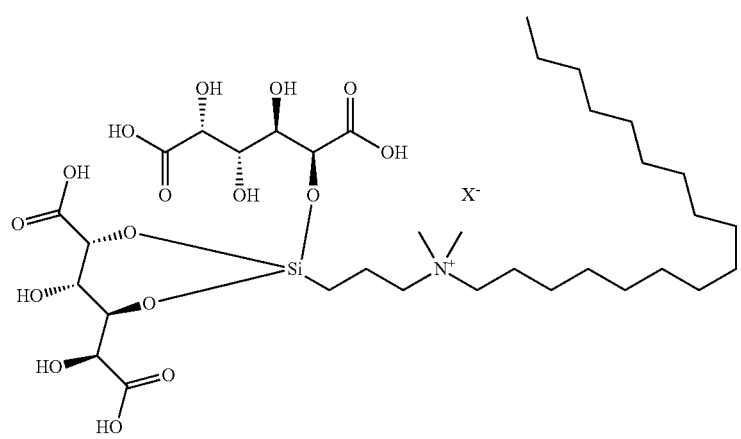
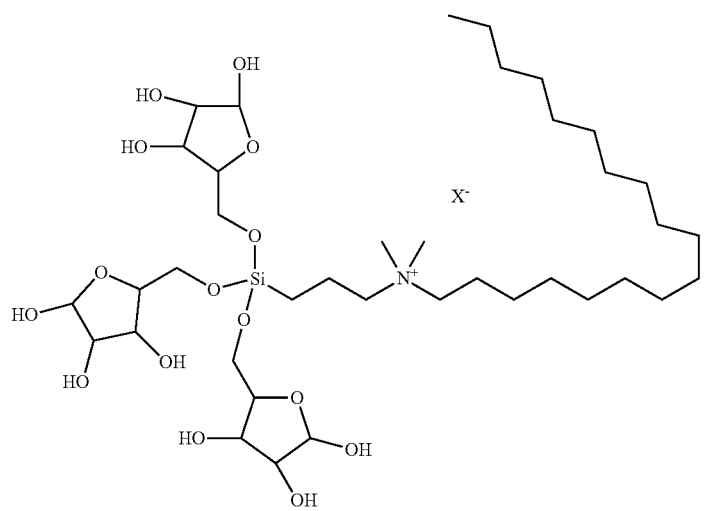

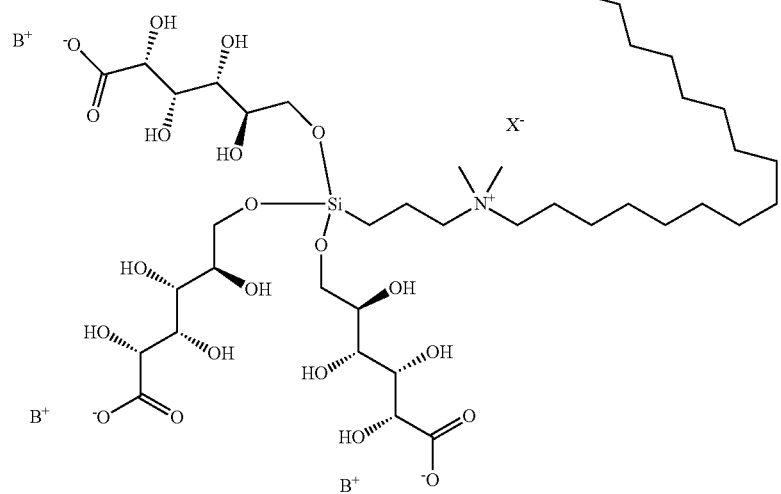
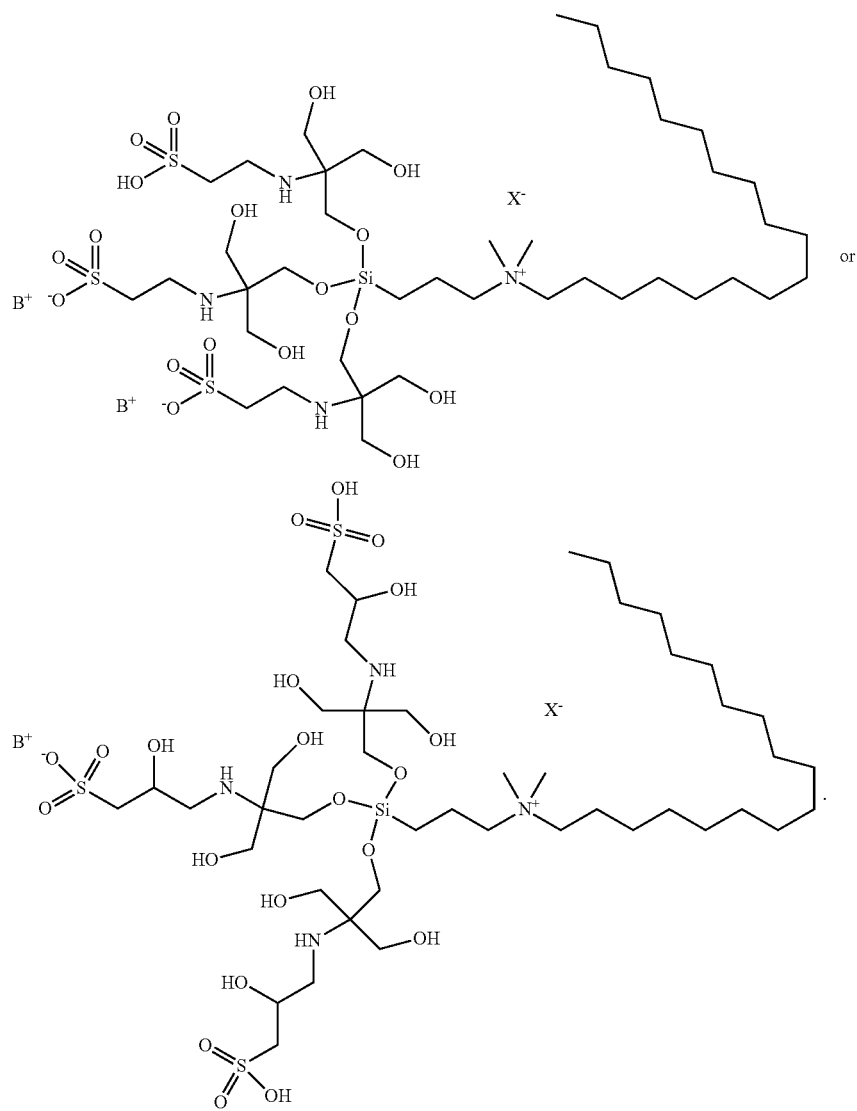

In certain embodiments, the compound of the present invention is selected from:
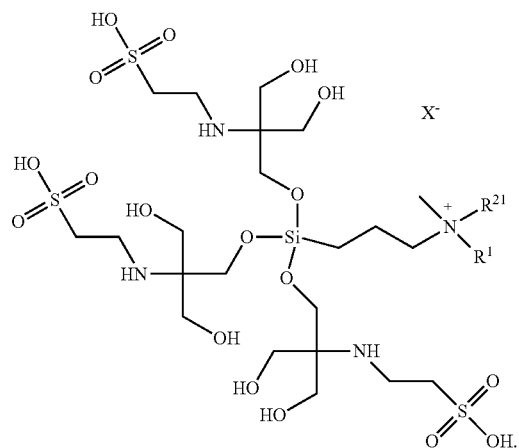
In certain embodiments, the compound of the present invention is selected from:
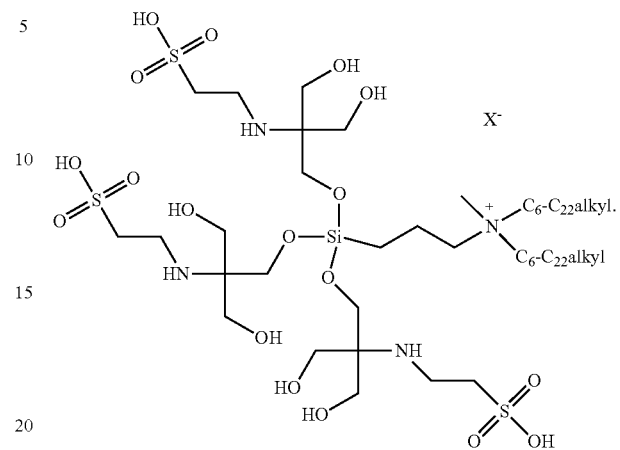
In certain embodiments, the compound of the present invention is selected from:
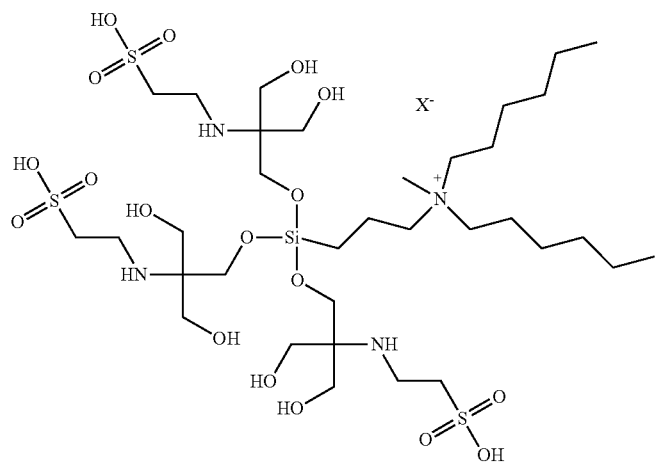
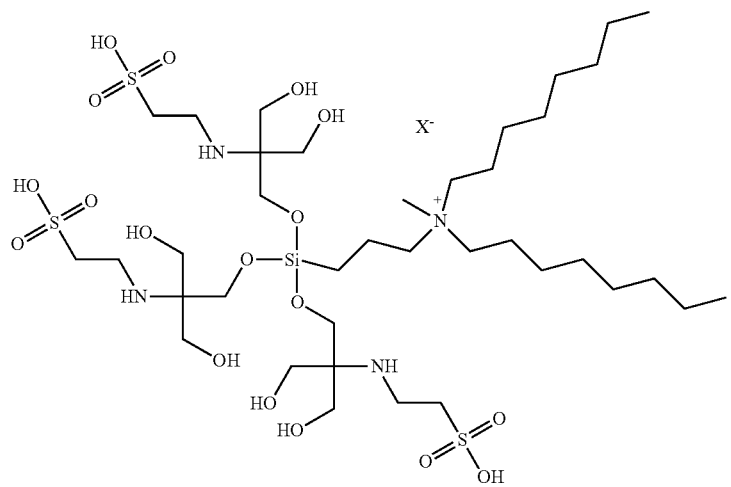

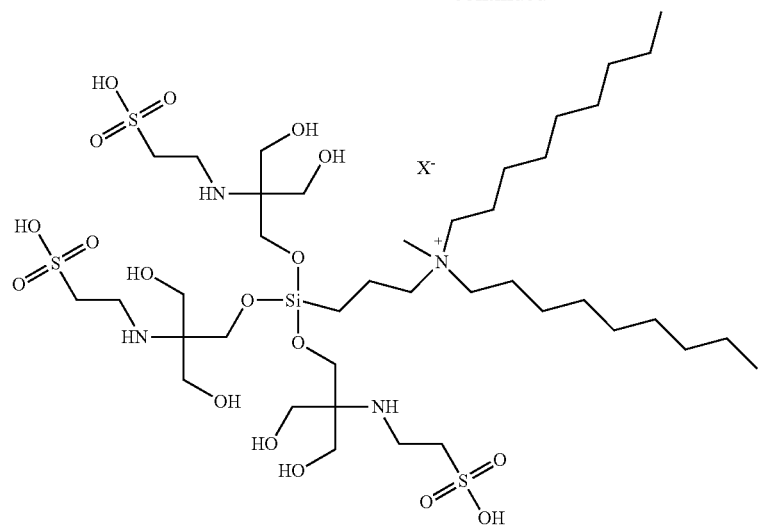
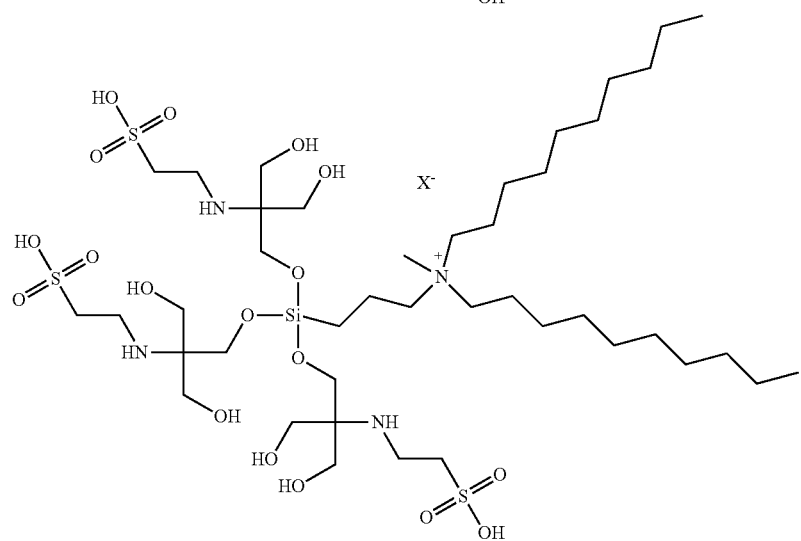
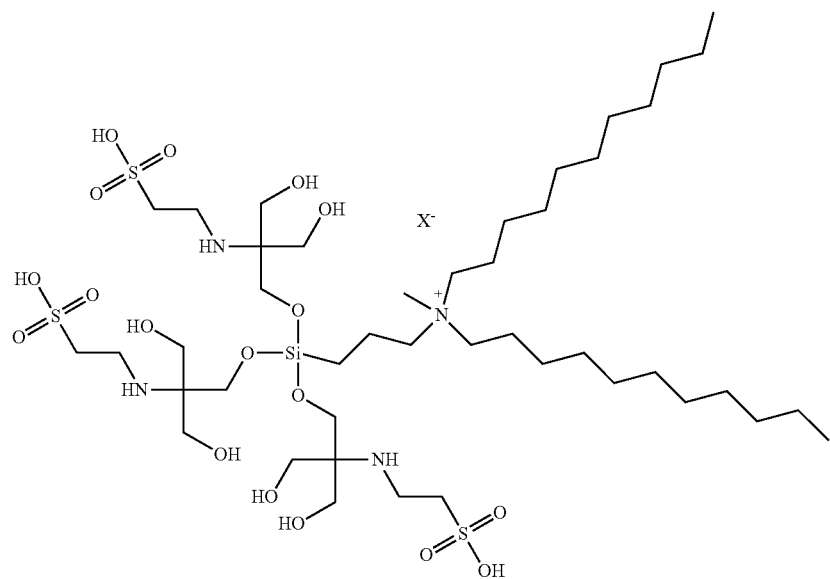

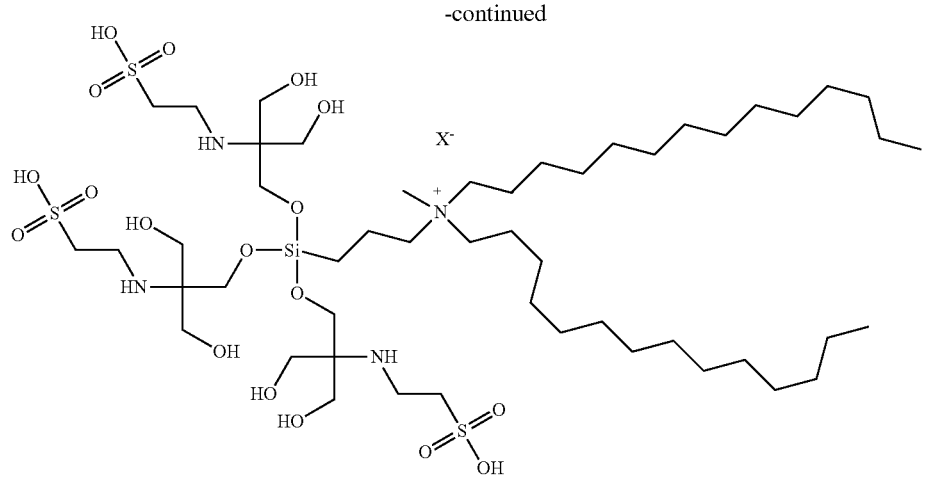
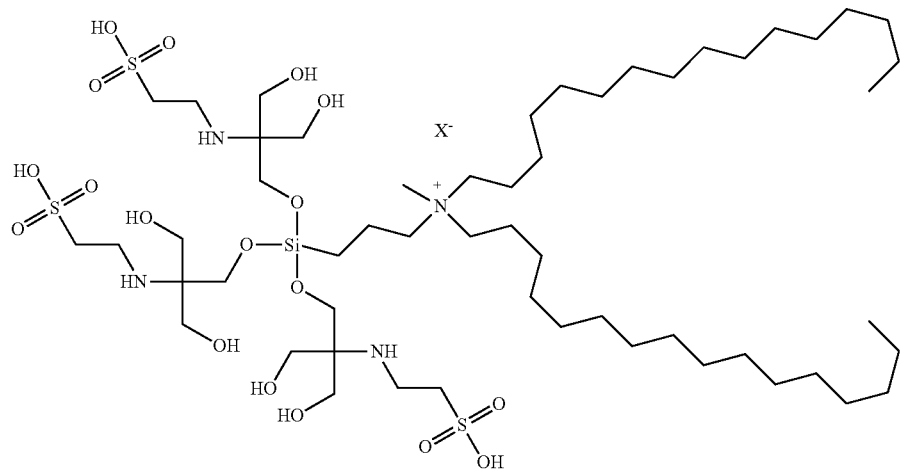
and
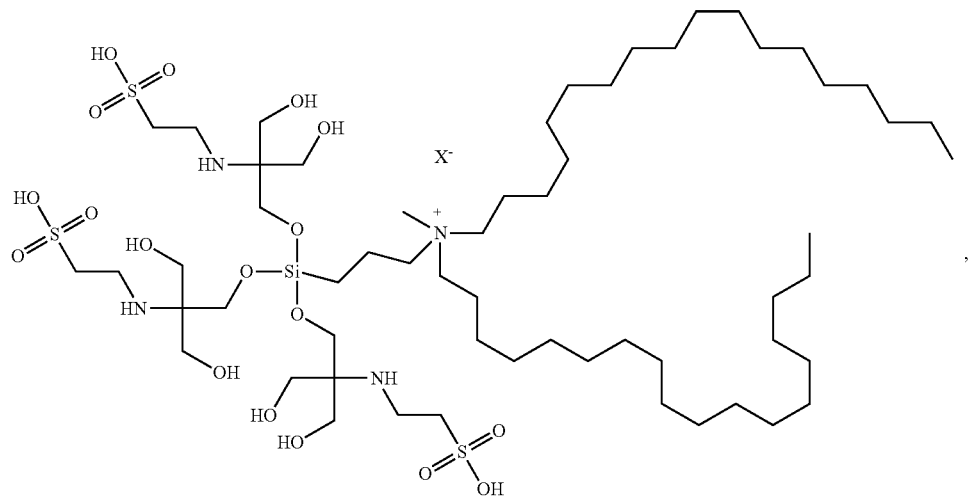
,
or any alternative protonation state thereof, as is available at a pH of 6-8, with additional $B^+$ or $X^-$ counterions as appropriate to reach charge balance.

In certain embodiments, the compound of the present invention is selected from:
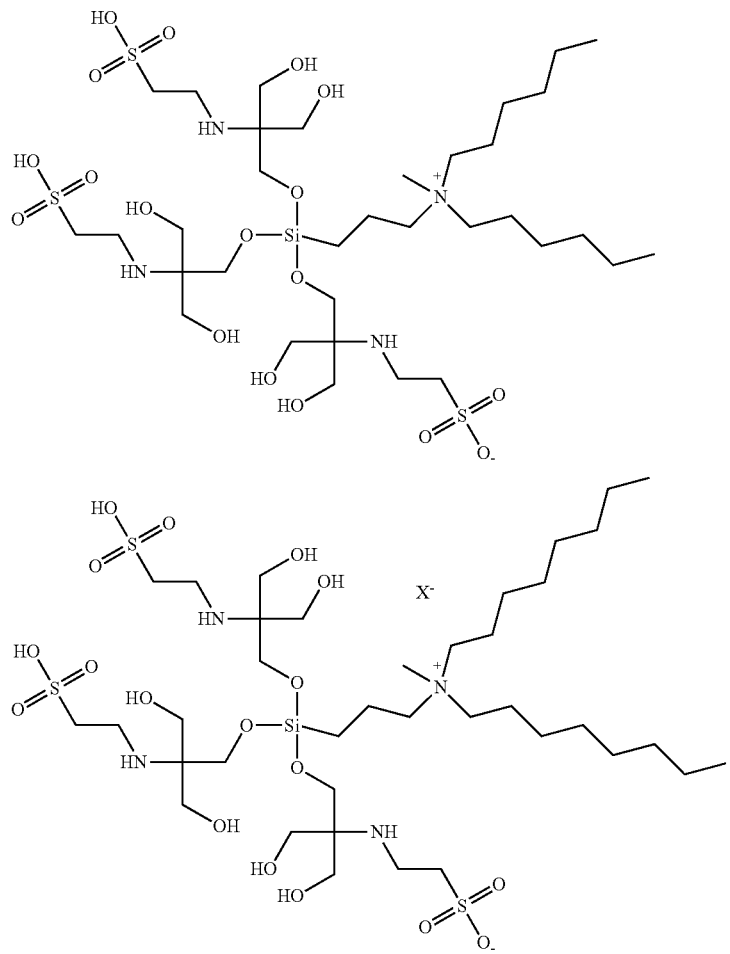
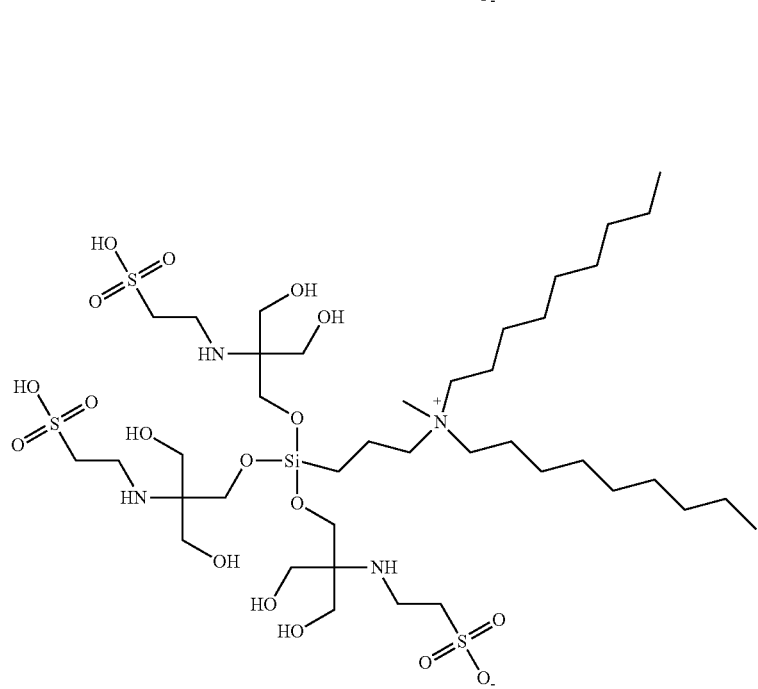

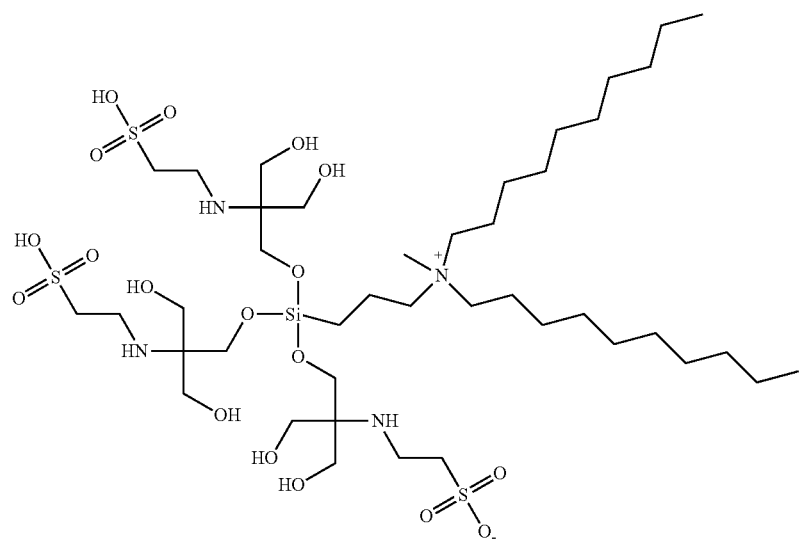
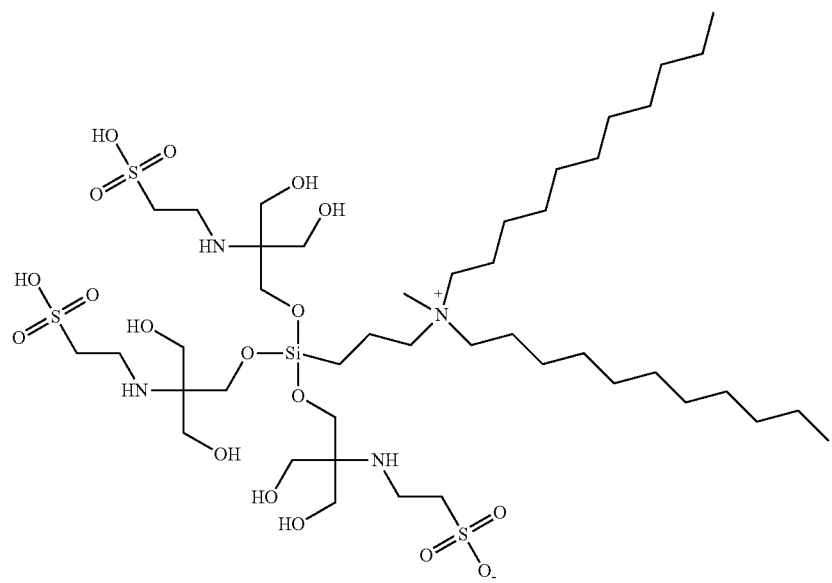
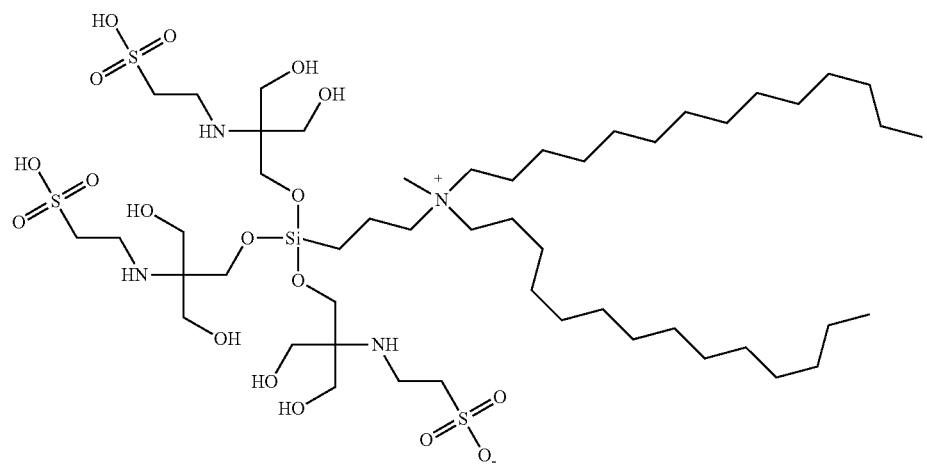

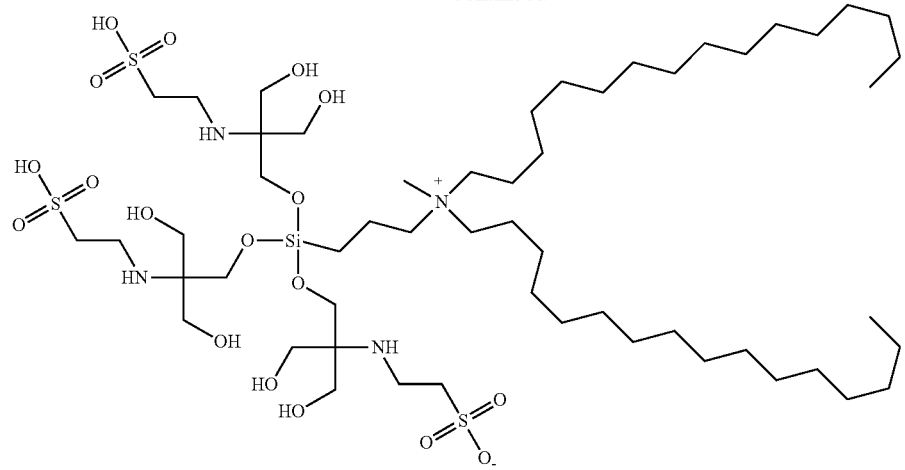
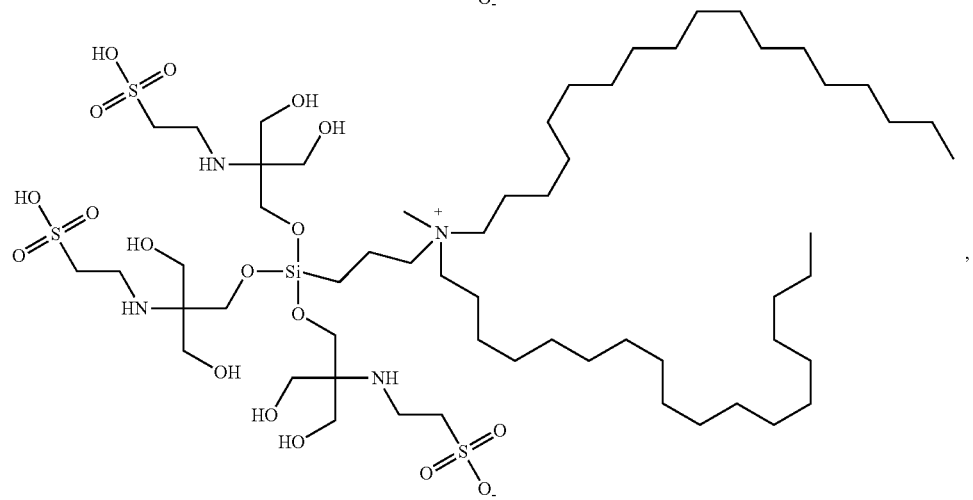
or any alternative protonation state thereof, as is available at a pH of 6-8, with additional $B^+$ or $X^-$ counterions as appropriate to reach charge balance.
In certain embodiments, the compound of the present invention is selected from:
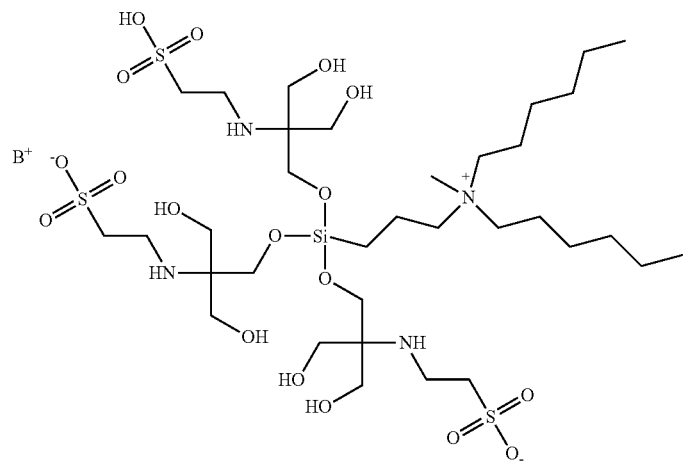

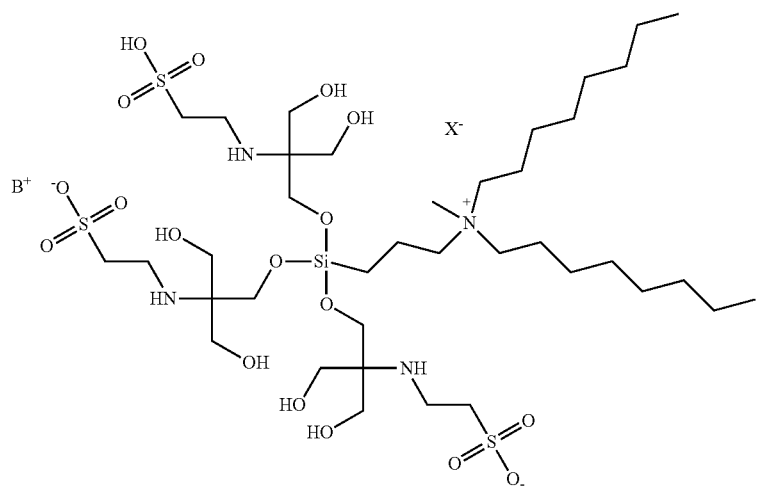
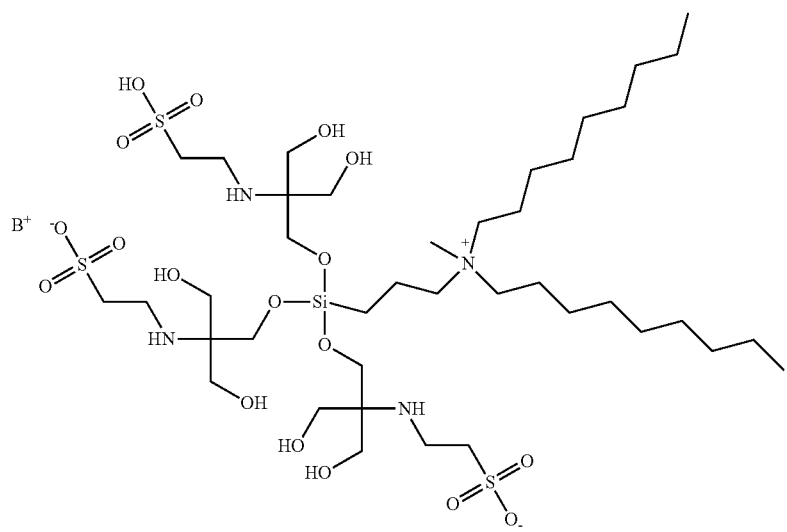
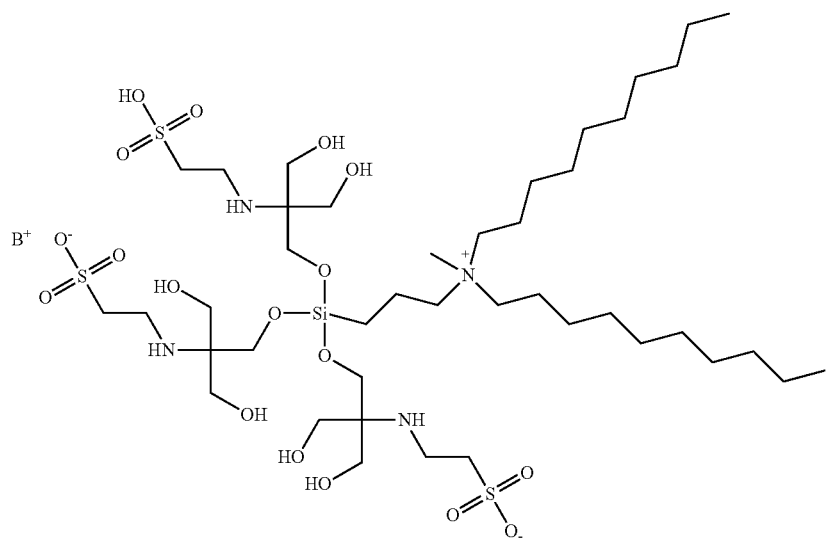

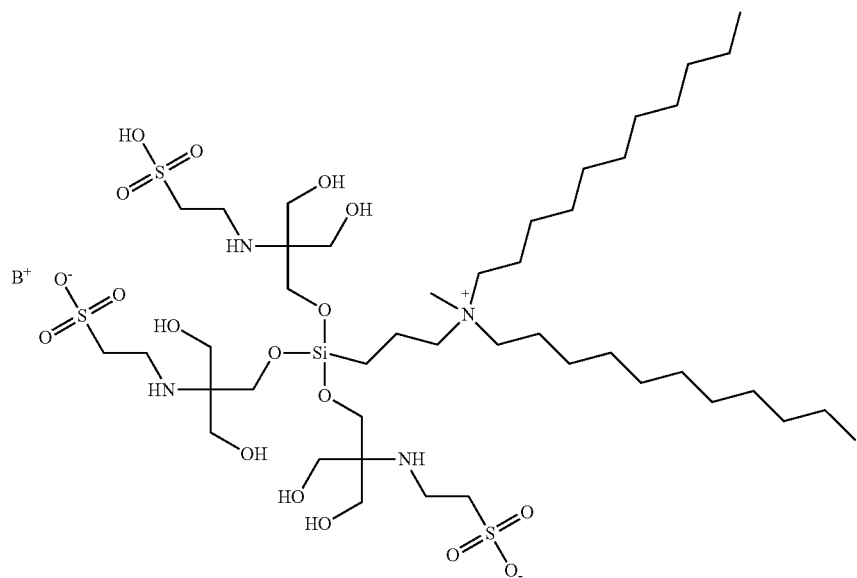
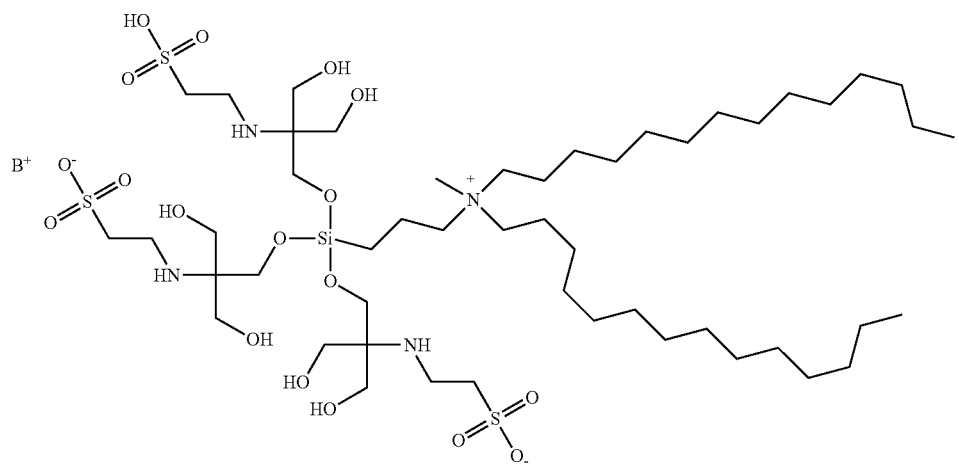
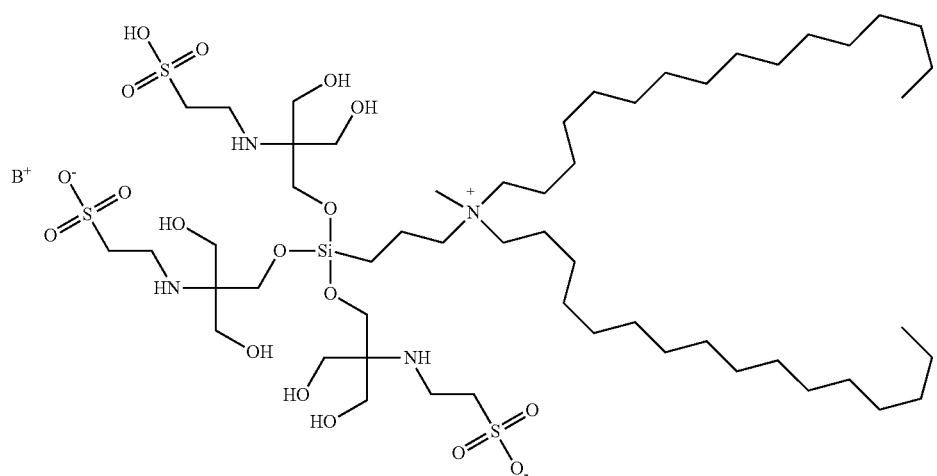
and

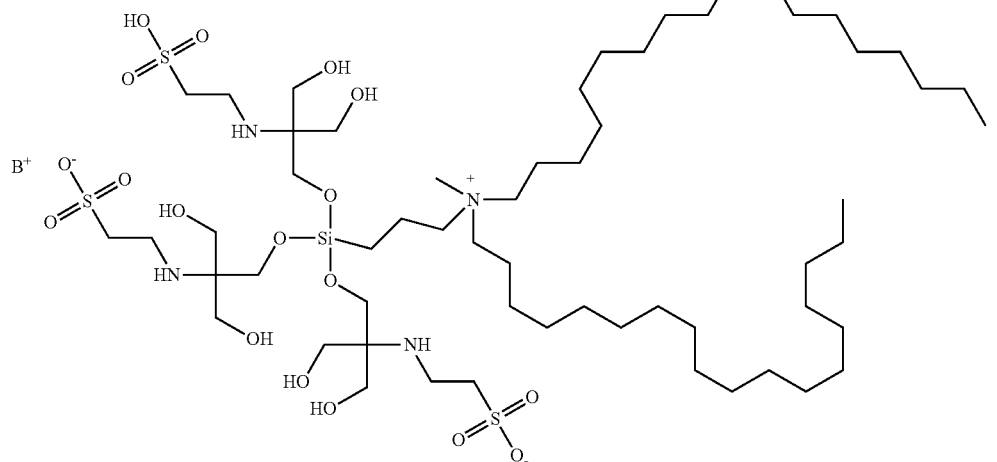

or any alternative protonation state thereof, as is available at a pH of 6-8, with additional $B^+$ or $X^-$ counterions as appropriate to reach charge balance.

In certain embodiments, the compound of the present invention is selected from:

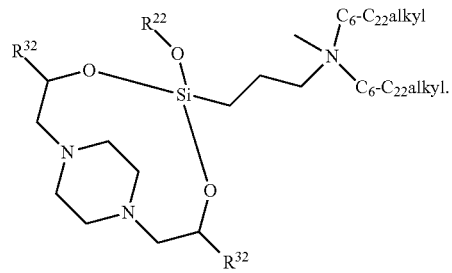

In certain embodiments, the compound of the present invention is selected from:

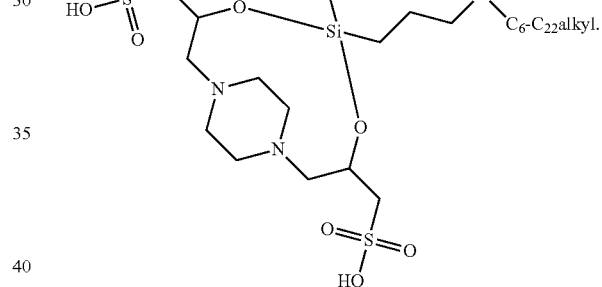

In certain embodiments, the compound of the present invention is selected from:

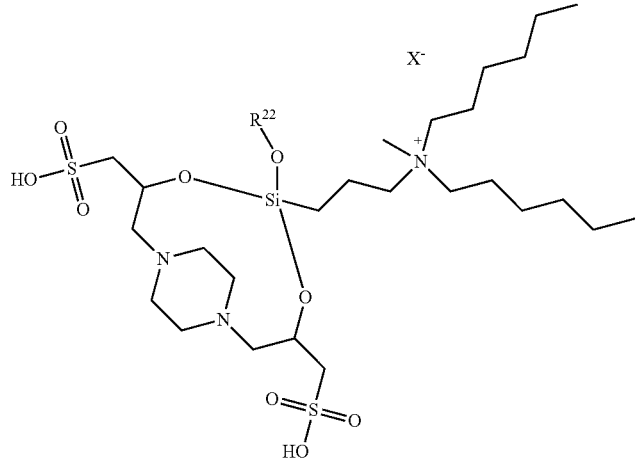

-continued
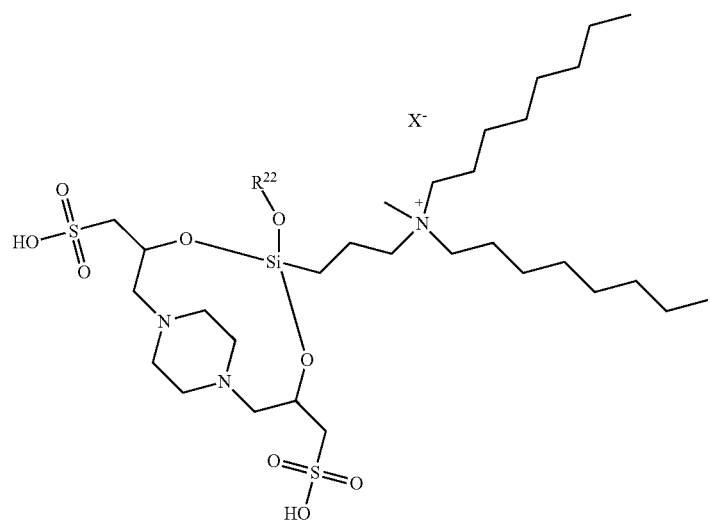
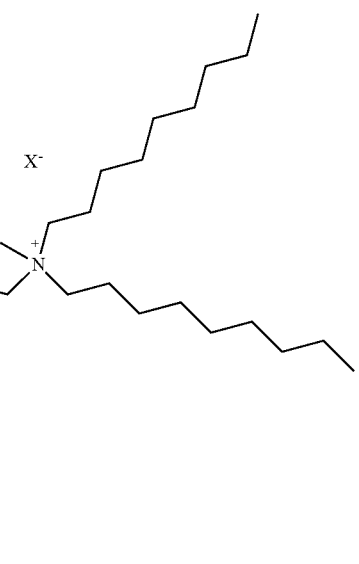
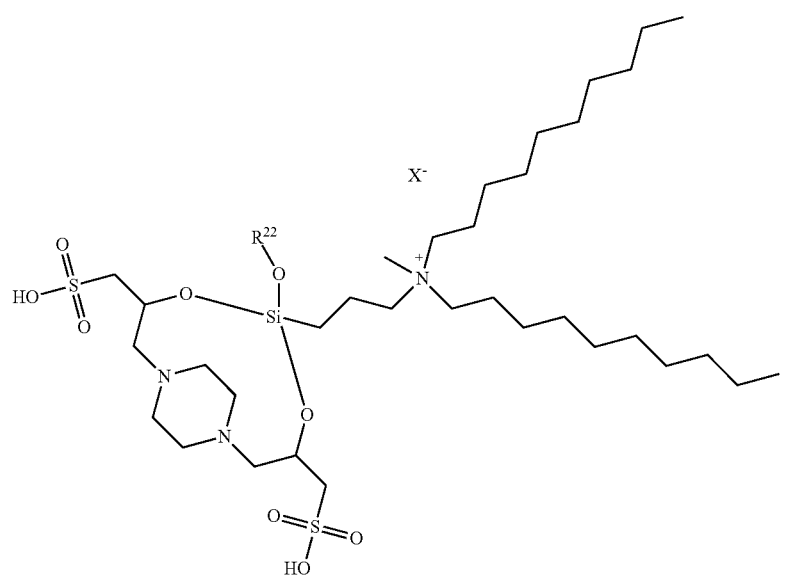

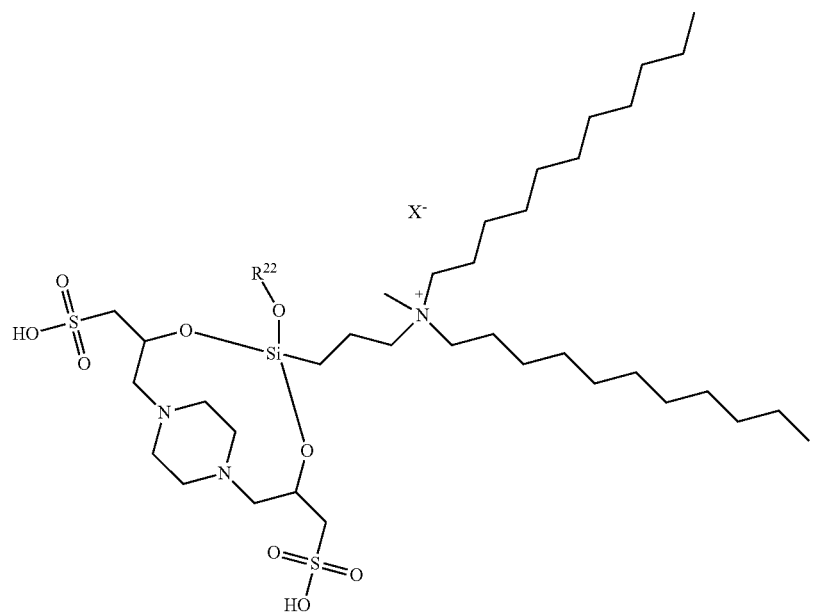
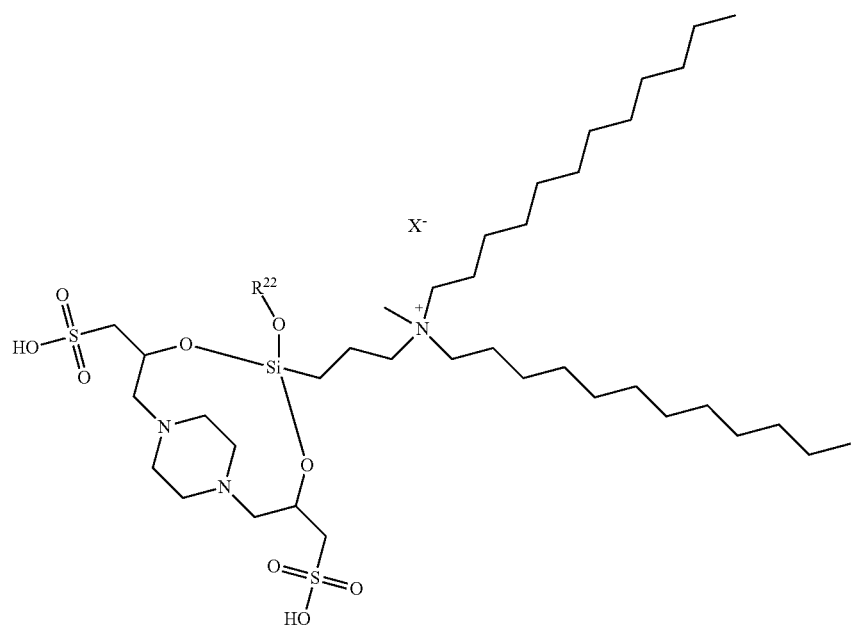
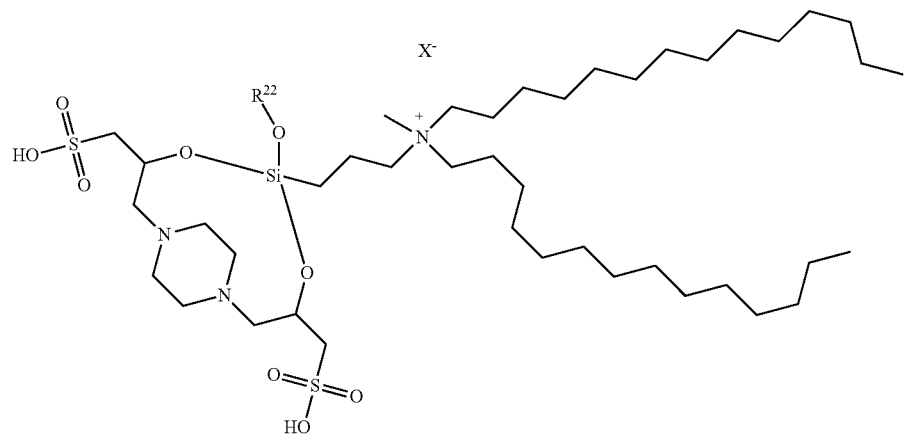

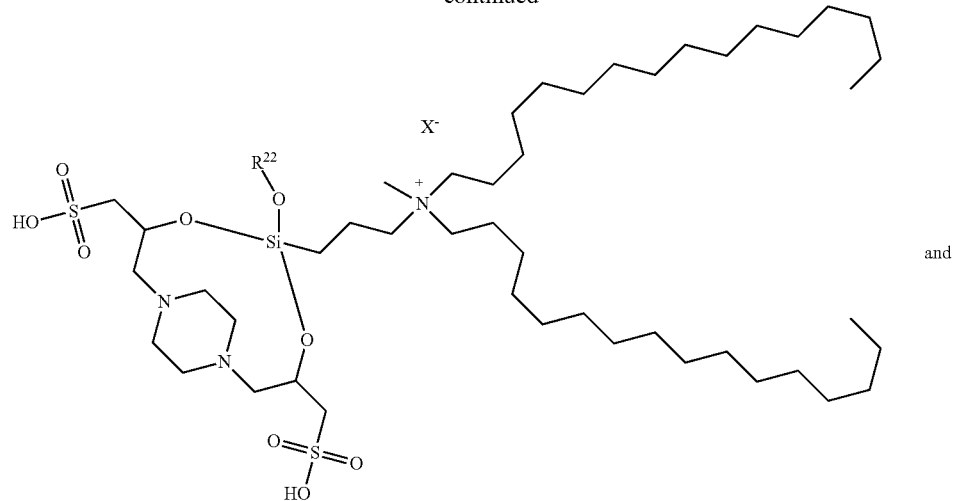
and
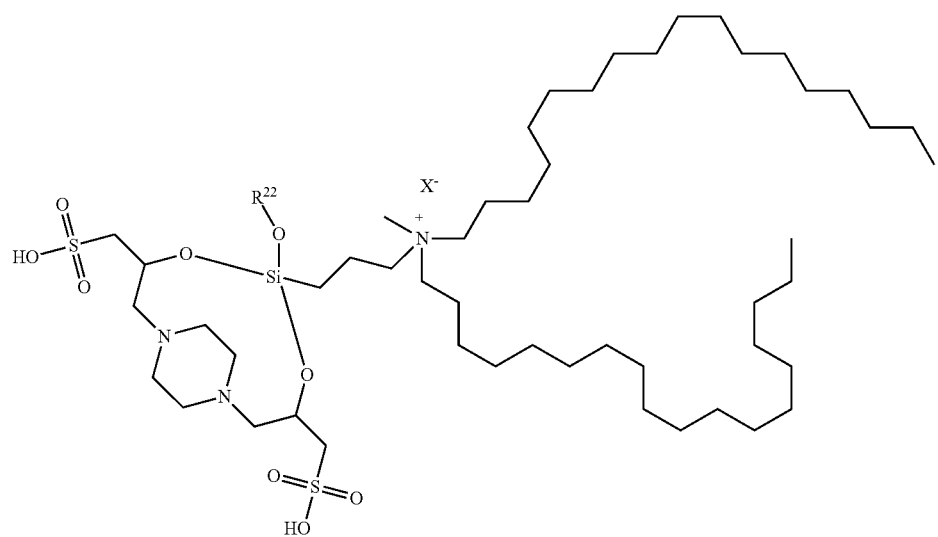
,
or any alternative protonation state thereof, as is available at a pH of 6-8, with additional $B^+$ or $X^-$ counterions as appropriate to reach charge balance.
In certain embodiments, the compound of the present invention is selected from:
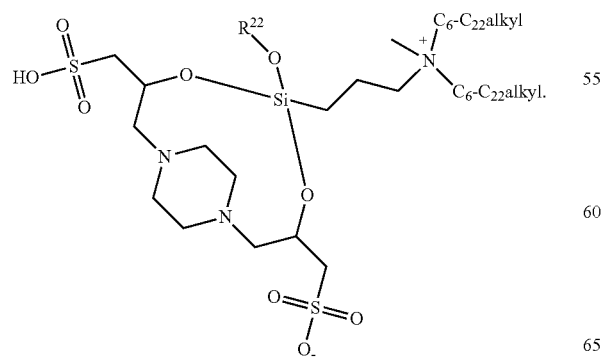

In certain embodiments, the compound of the present invention is selected from:
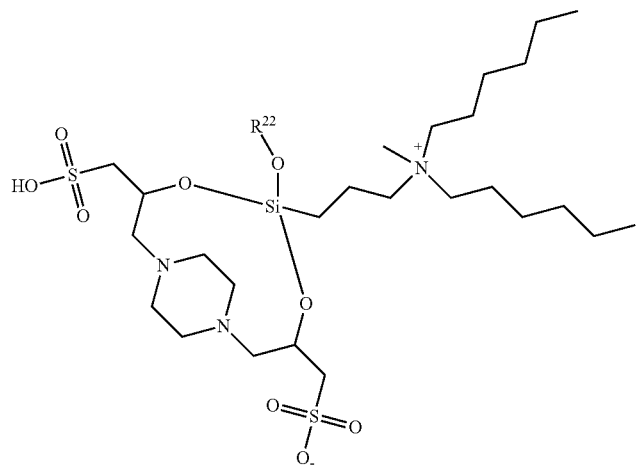
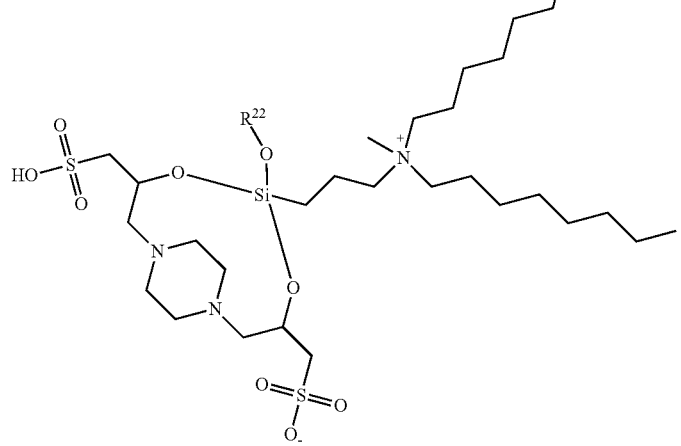
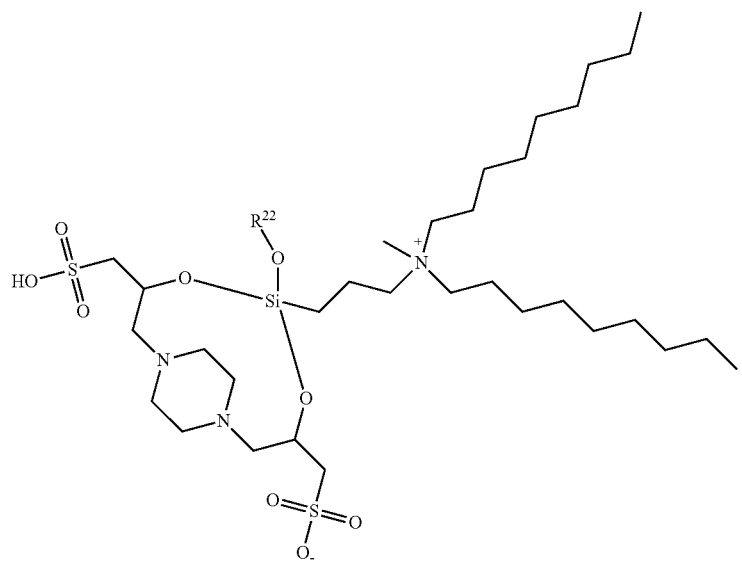

-continued
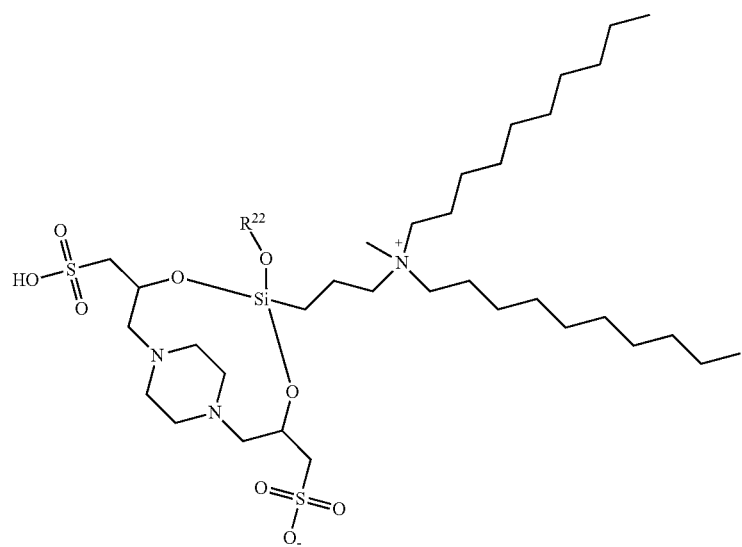
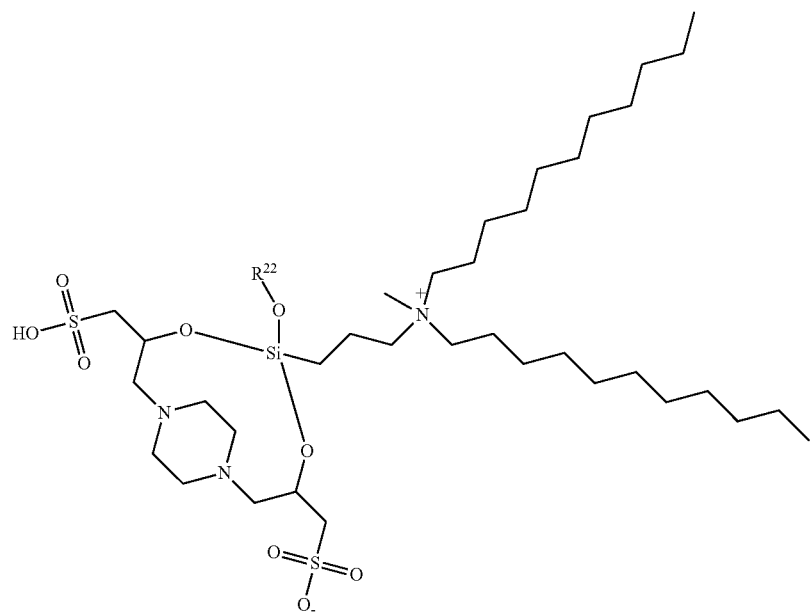

-continued
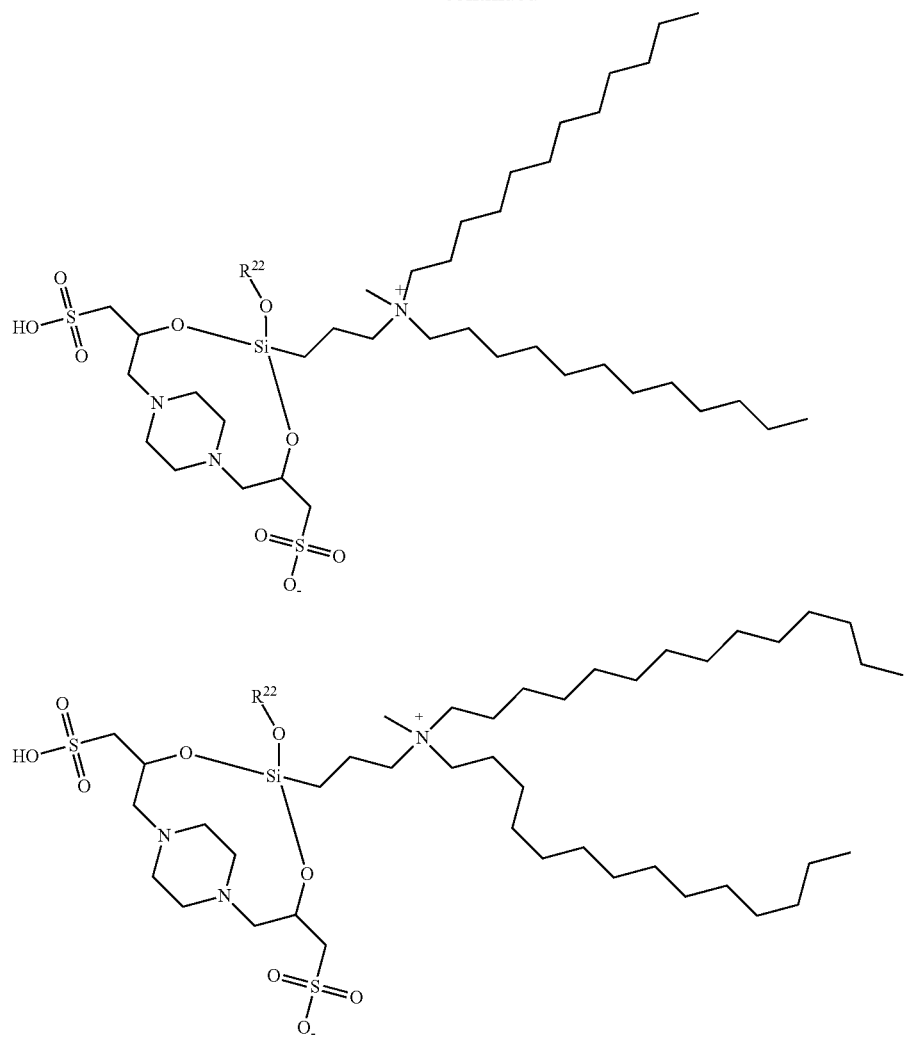
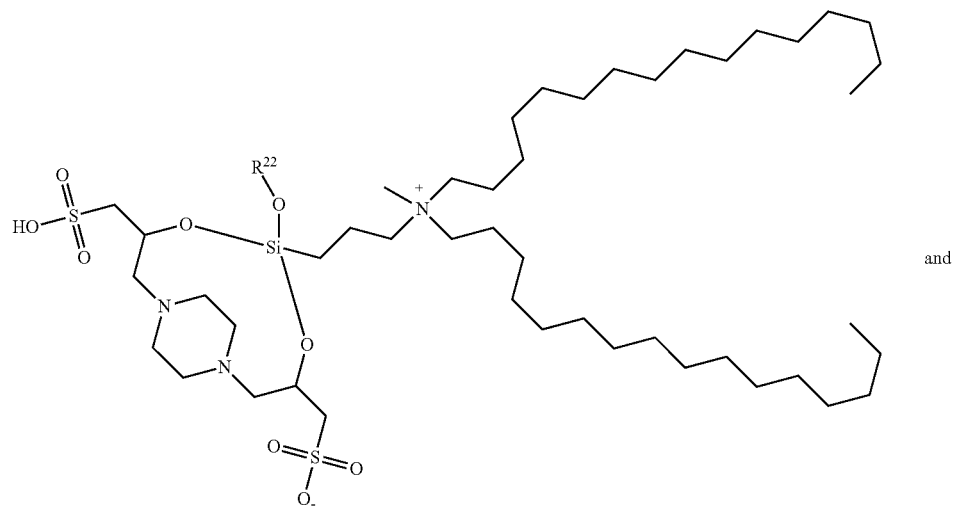
and

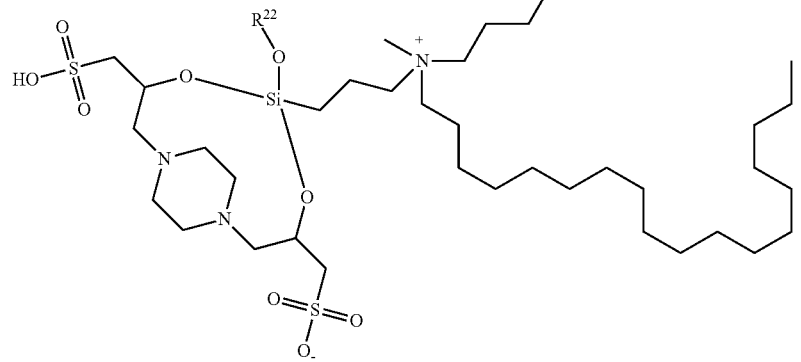
or any alternative protonation state thereof, as is available at a pH of 6-8, with additional B⁺ or X⁻ counterions as appropriate to reach charge balance.
In certain embodiments, the compound of the present invention is selected from:
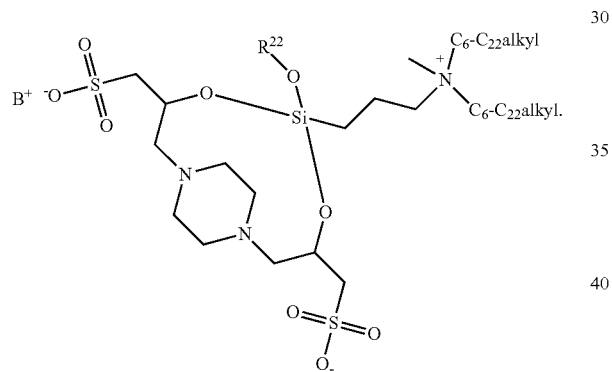
In certain embodiments, the compound of the present invention is selected from:
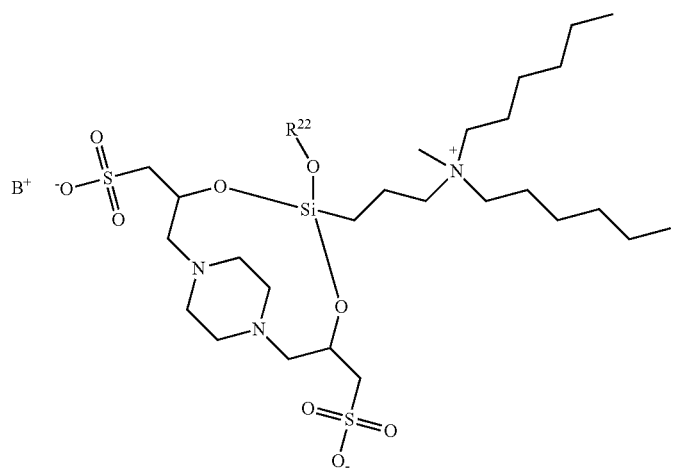

-continued
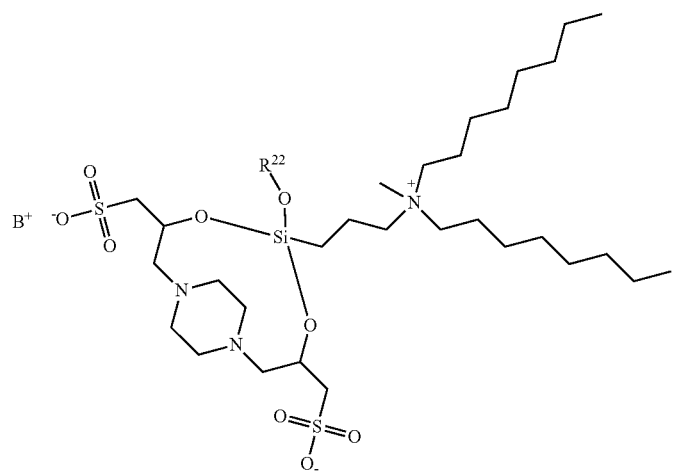
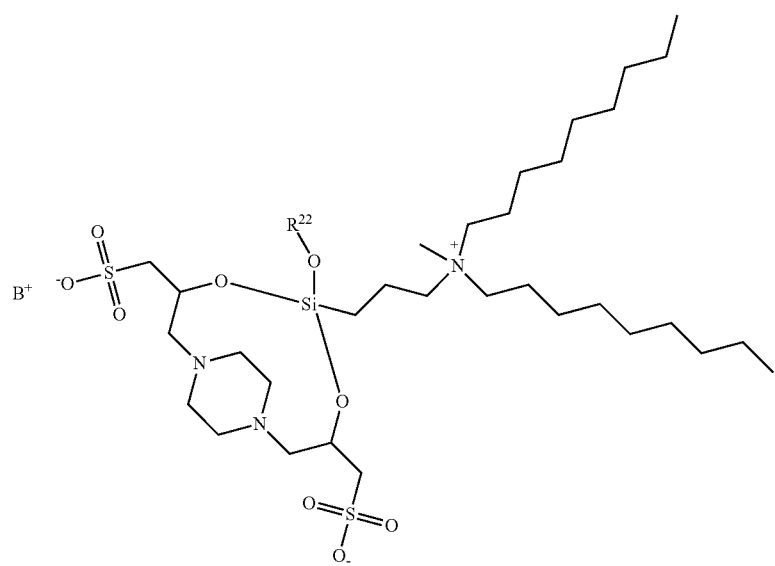
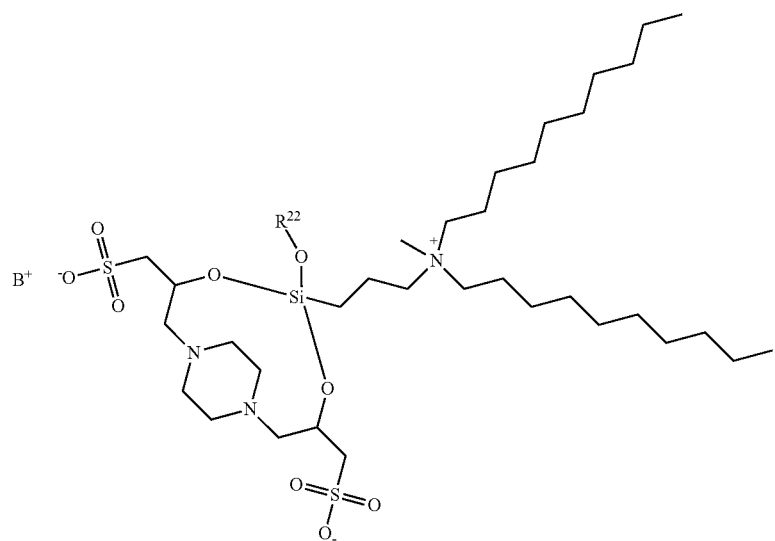

-continued
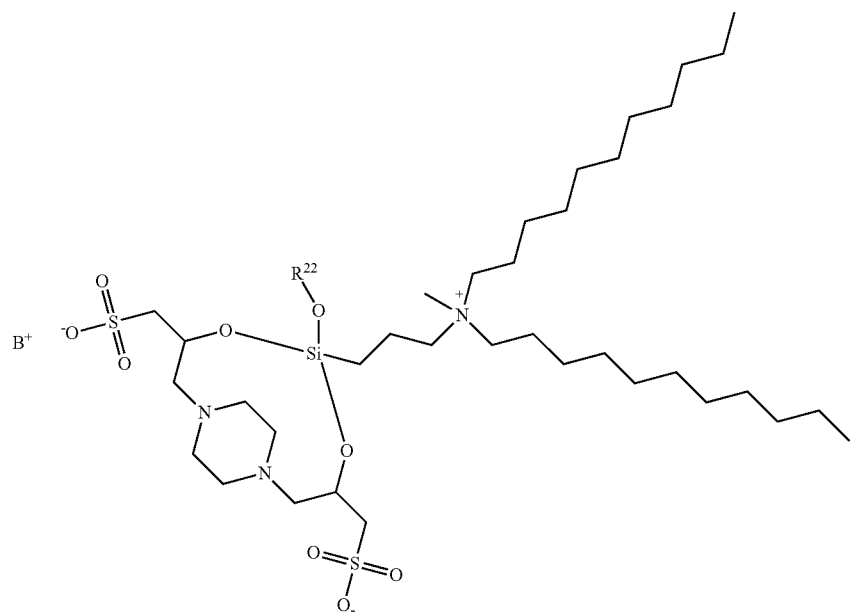
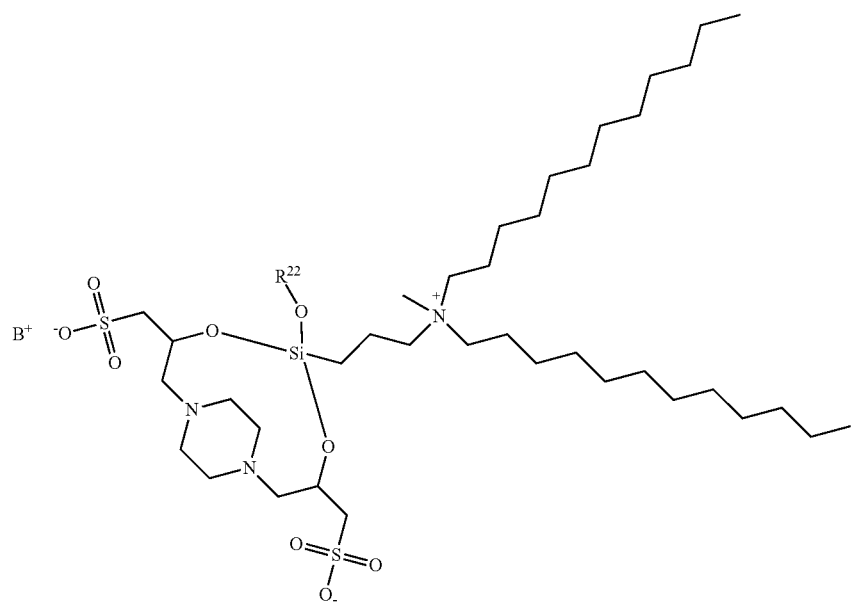
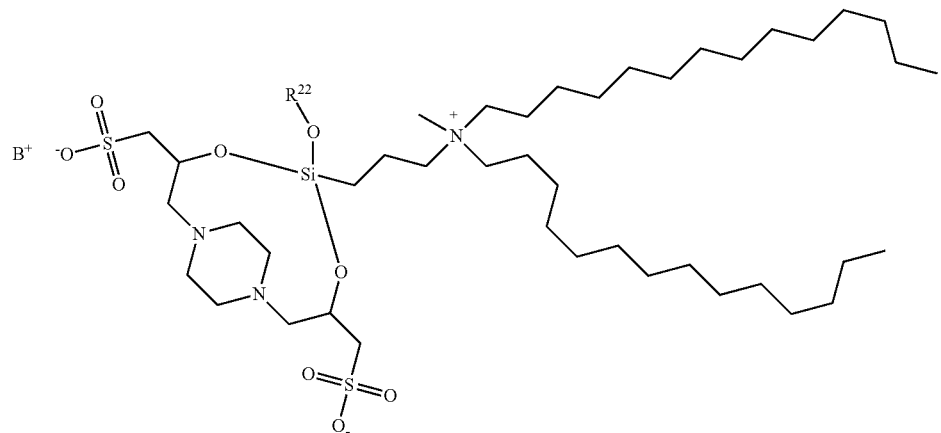

-continued
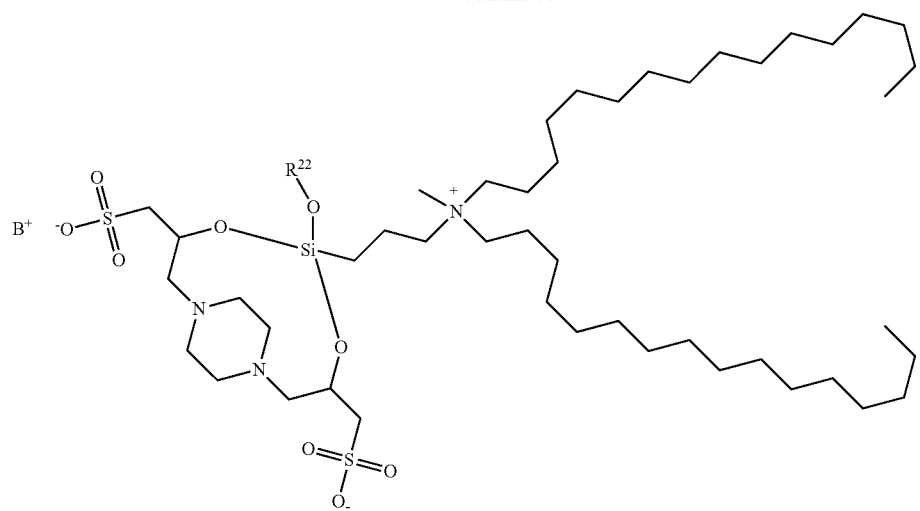
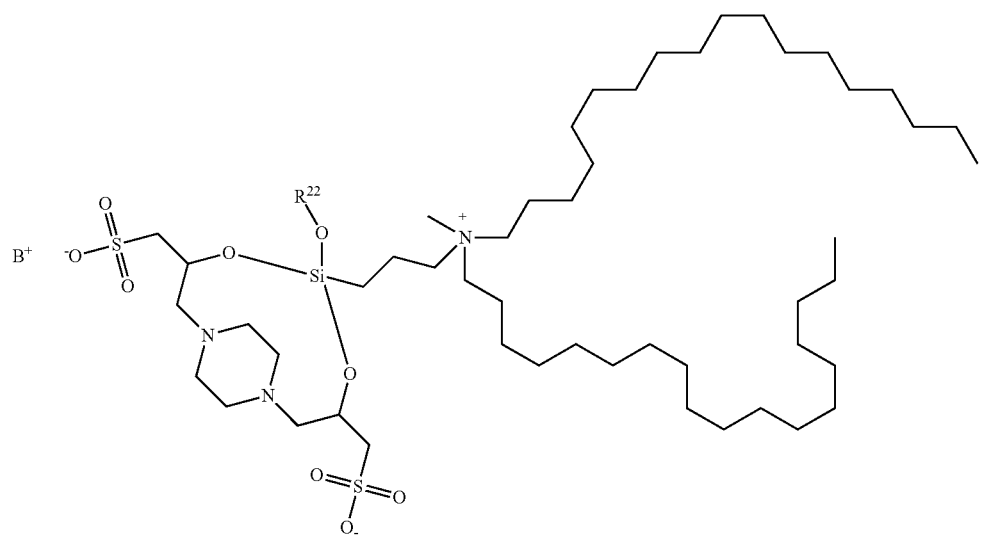

or any alternative protonation state thereof, as is available at a pH of 6-8, with additional B⁺ or X⁻ counterions as appropriate to reach charge balance.

In certain embodiments, the compound of the present invention is selected from.

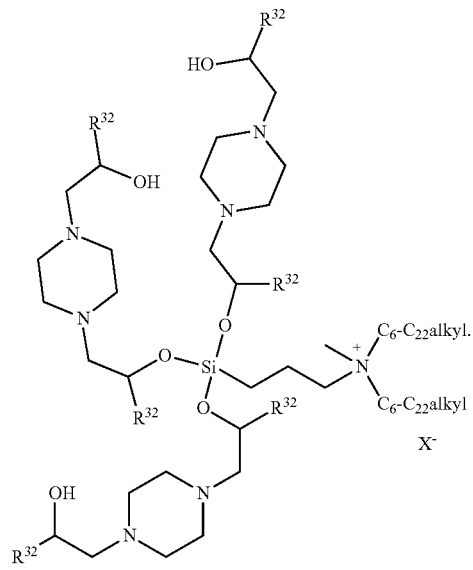

In certain embodiments, the compound of the present invention is selected from:

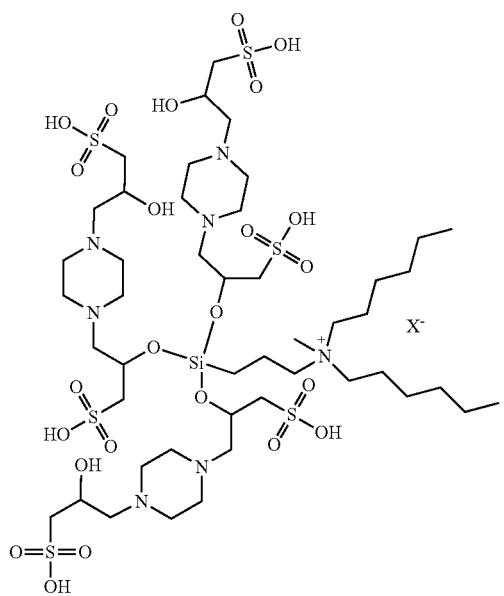

In certain embodiments, the compound of the present invention is selected from:

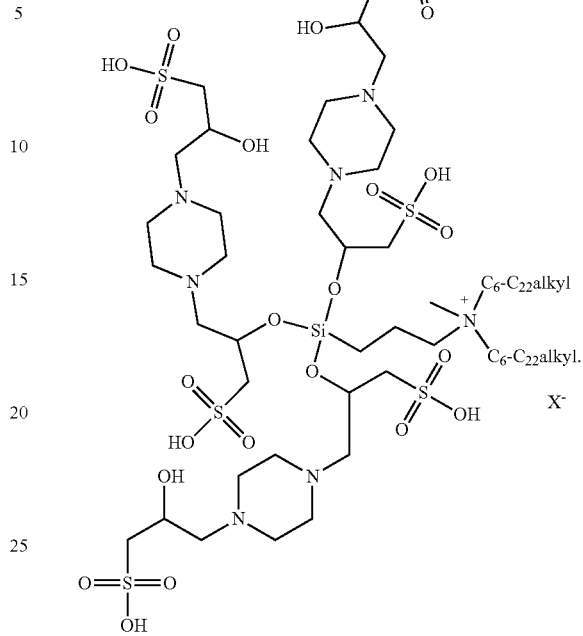

In certain embodiments, the compound of the present invention is selected from:

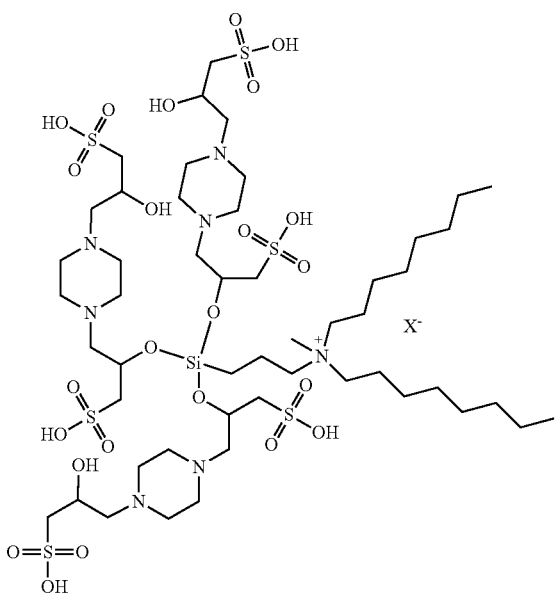

-continued
131
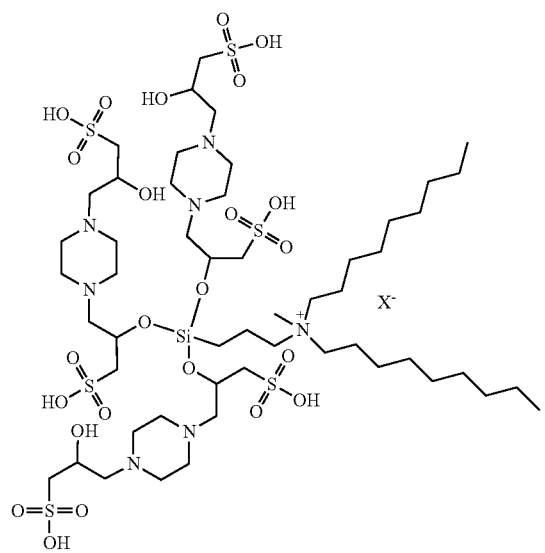
132
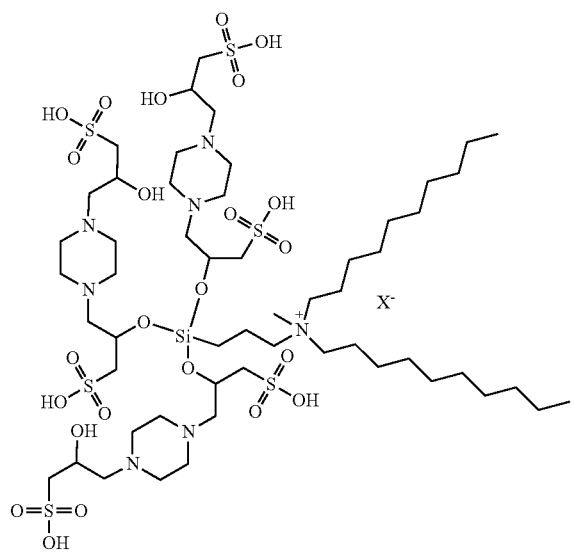
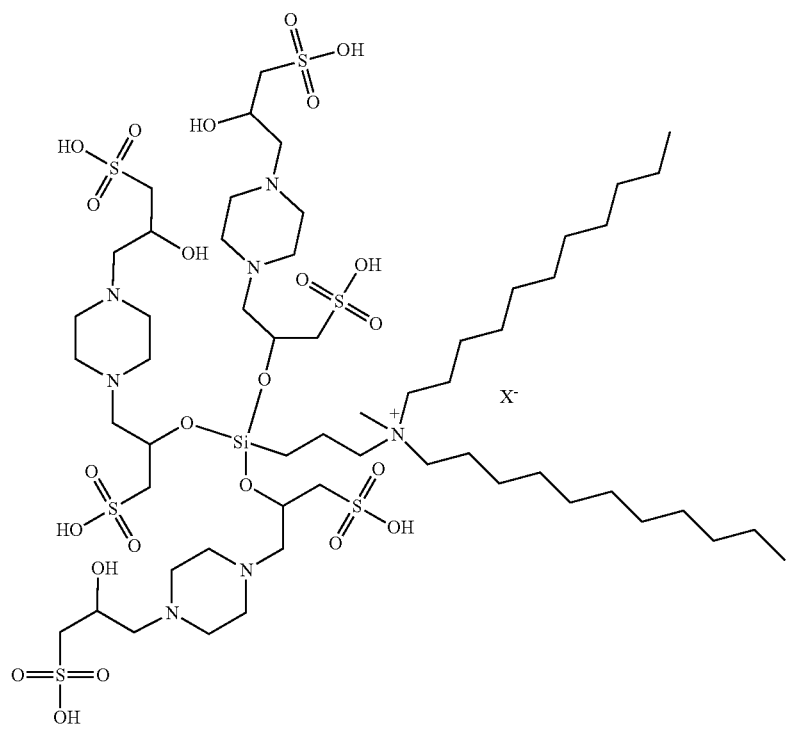

-continued
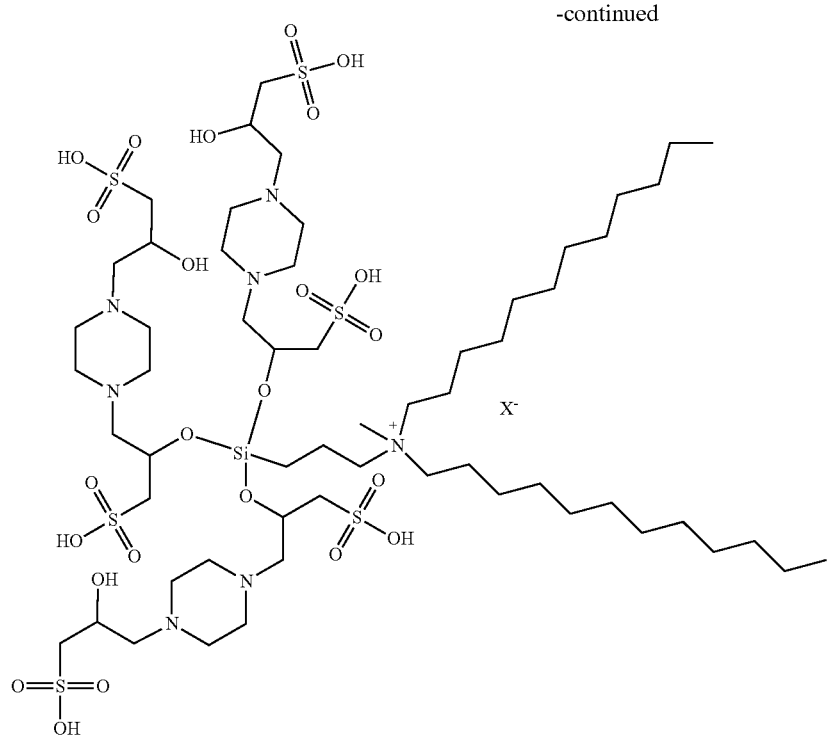
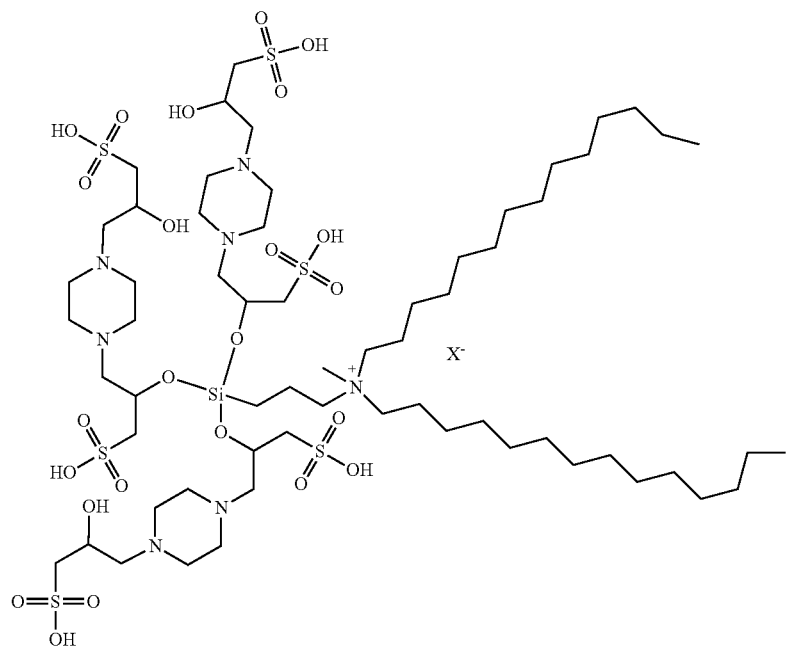

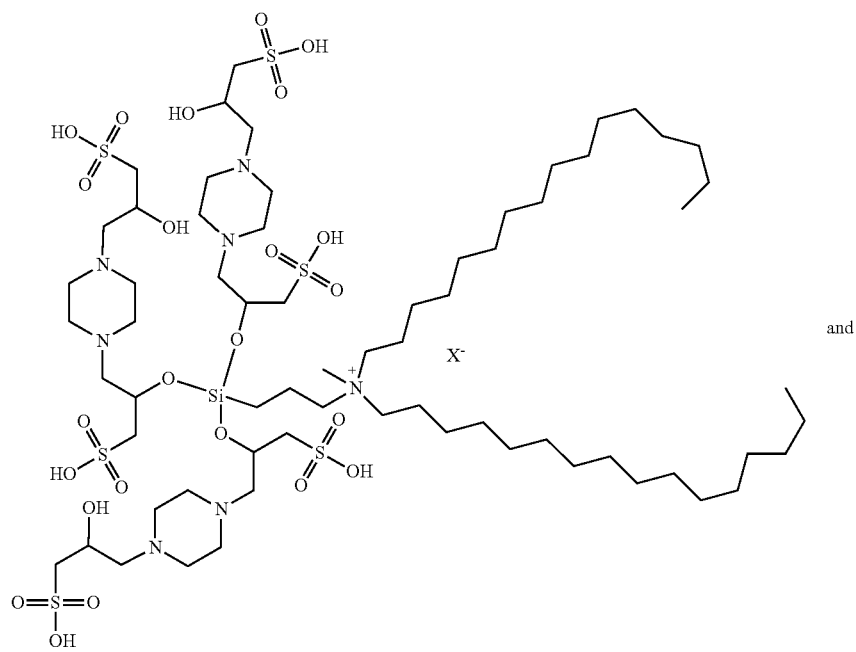
and
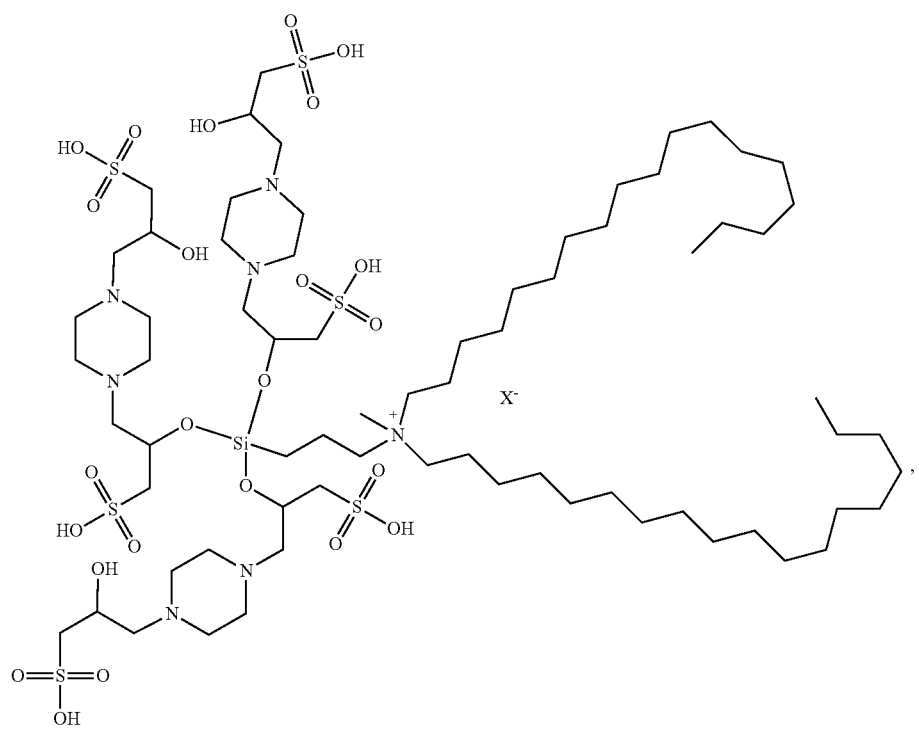

or any alternative protonation state thereof, as is available at a pH of 6-8, with additional B⁺ or X⁻ counterions as appropriate to reach charge balance.
In certain embodiments, the compound of the present invention is selected from:
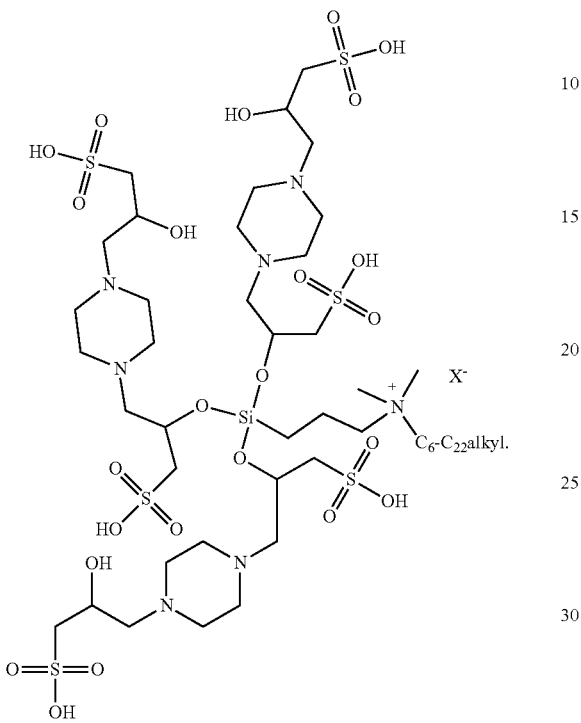
In certain embodiments, the compound of the present invention is selected from:
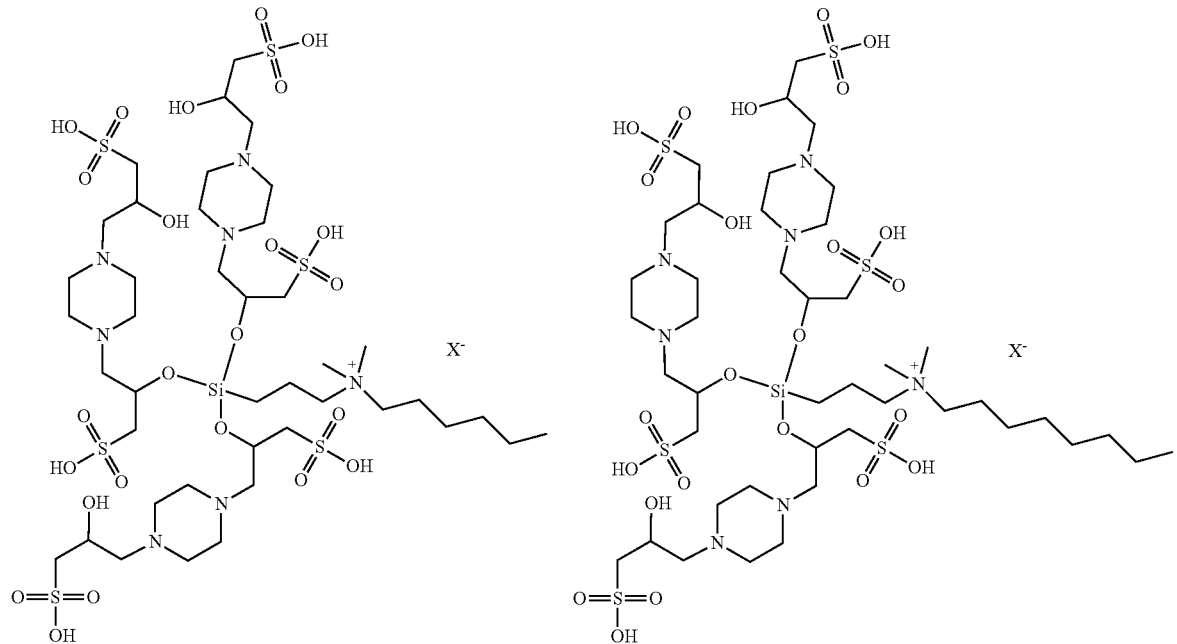

-continued
139
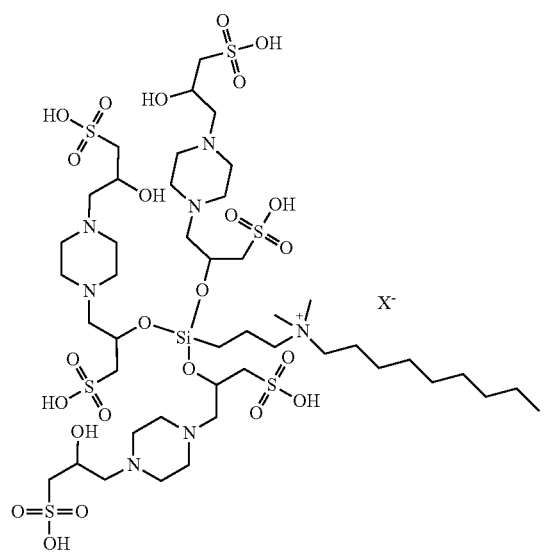
140
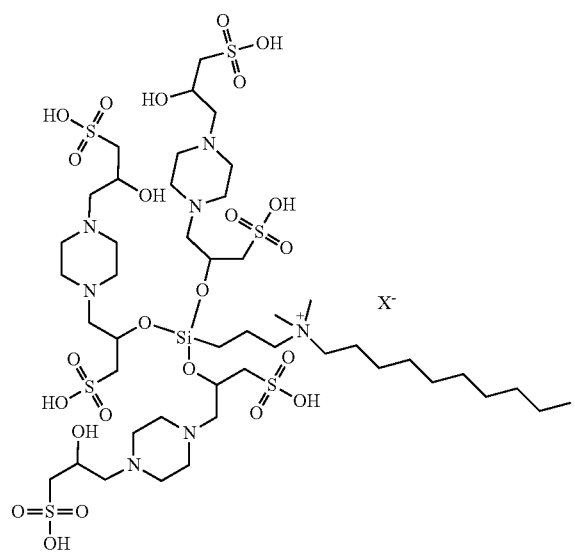
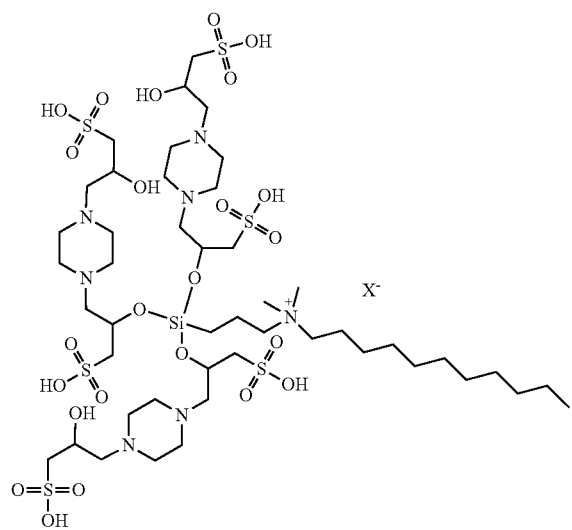
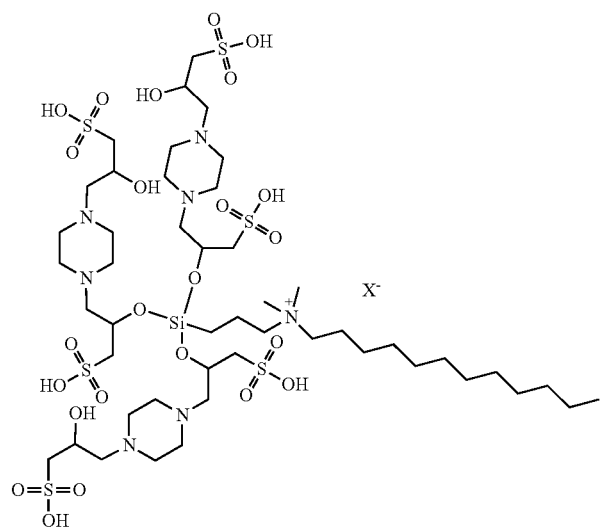

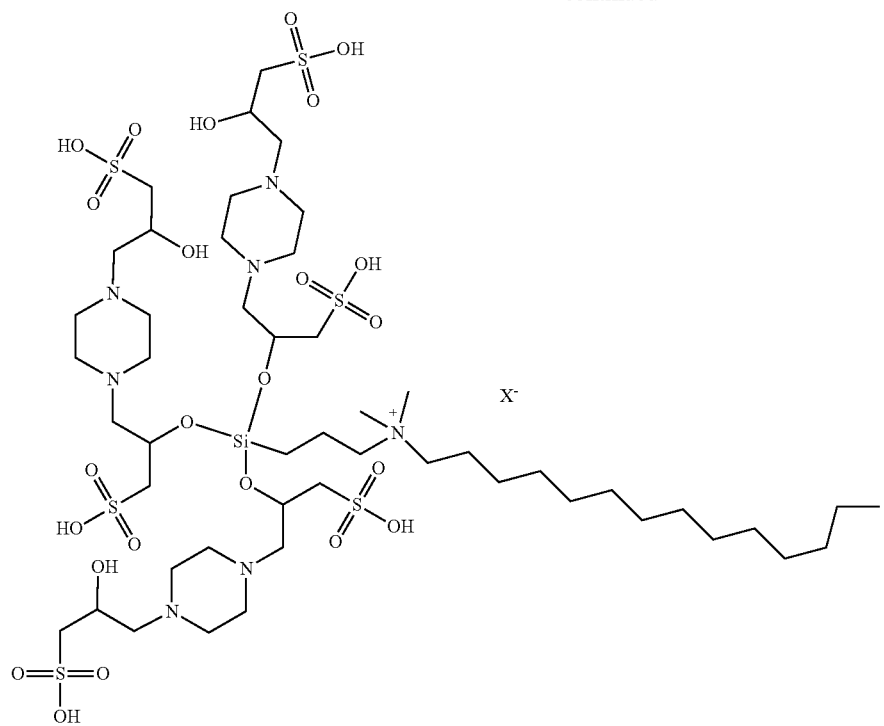
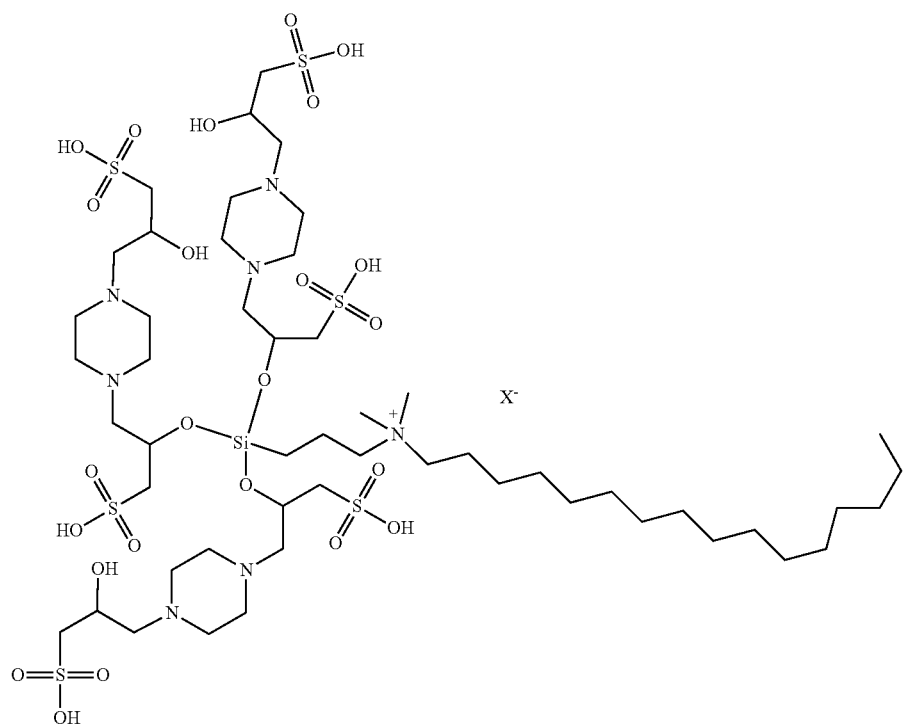

-continued
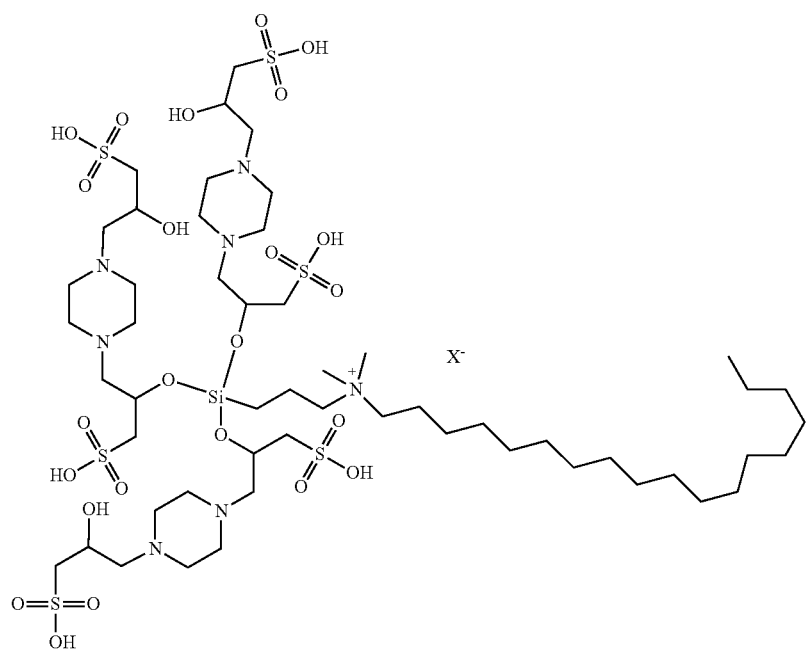
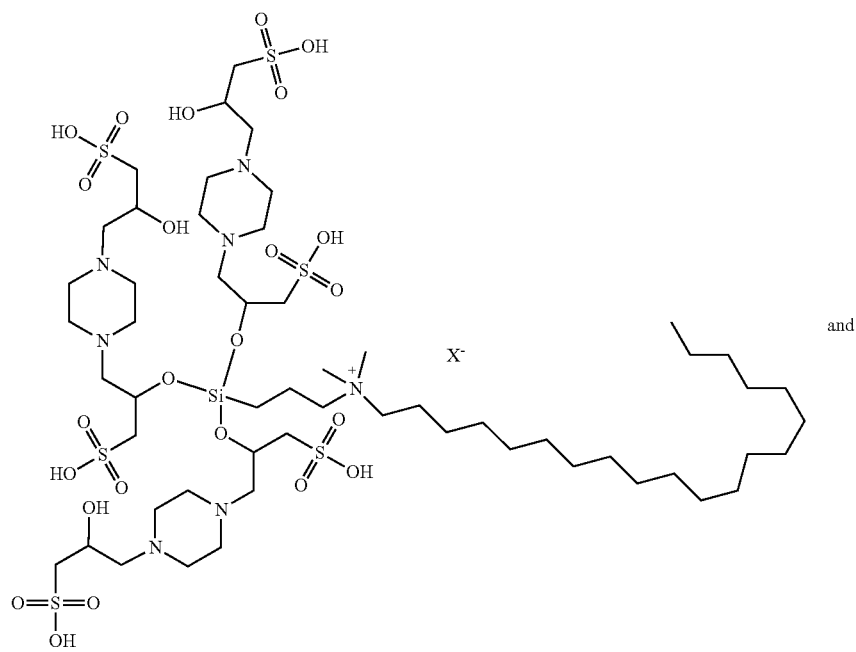
and

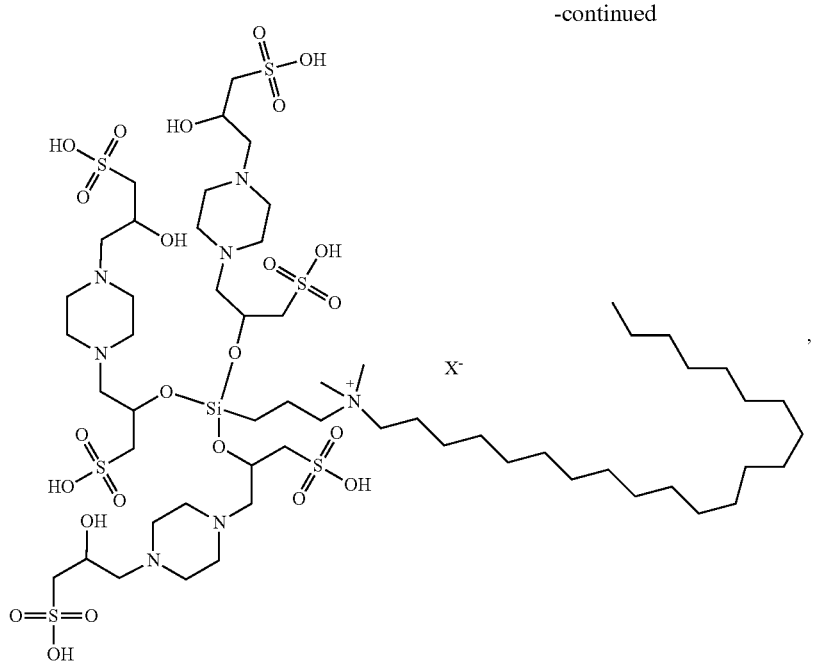
or any alternative protonation state thereof, as is available at a pH of 6-8, with additional $B^+$ or $X^-$ counterions as appropriate to reach charge balance.
In certain embodiments, the compound of the present invention is selected from:
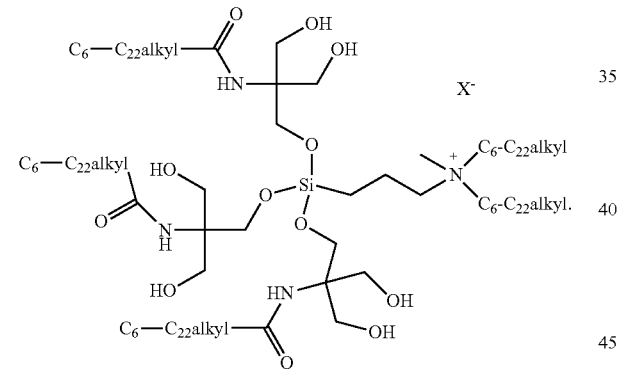
In certain embodiments, the compound of the present invention is selected from:
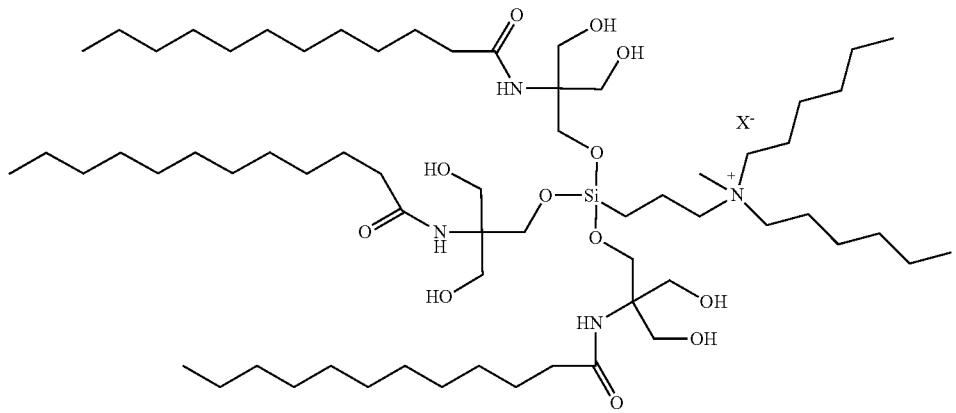

-continued
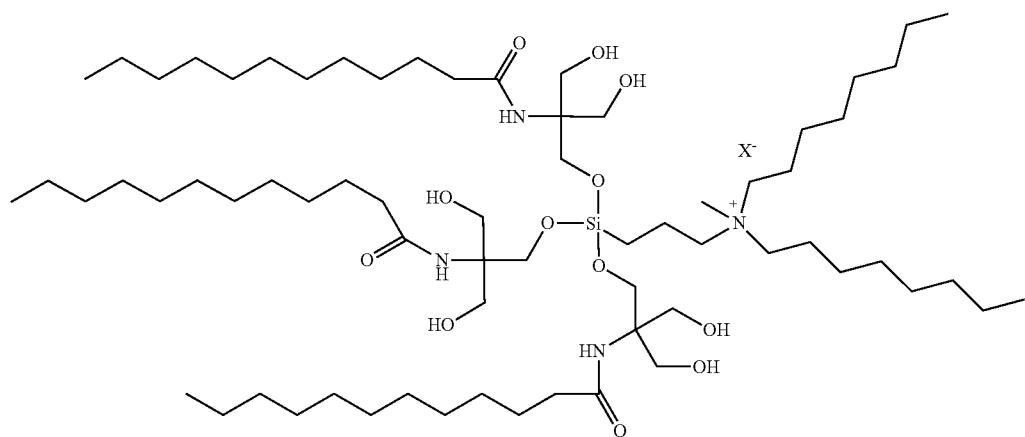
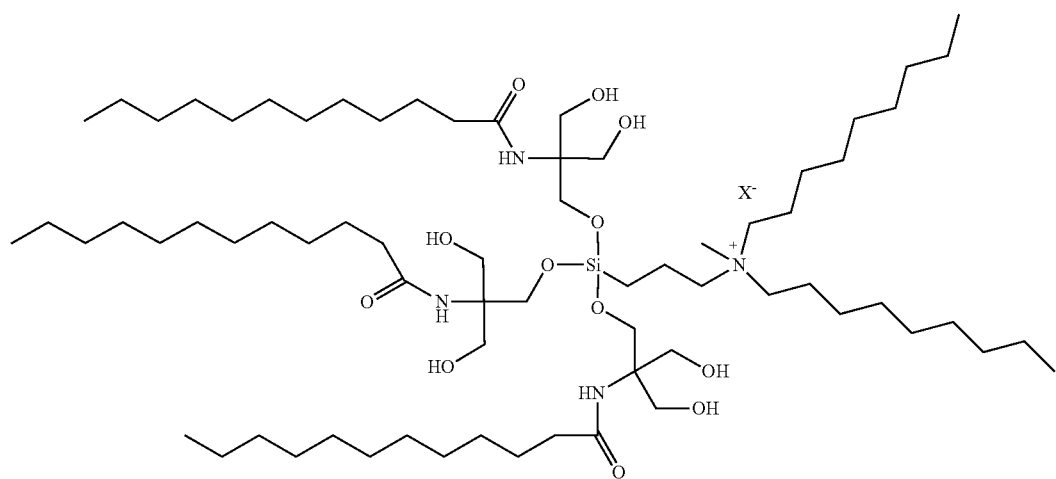
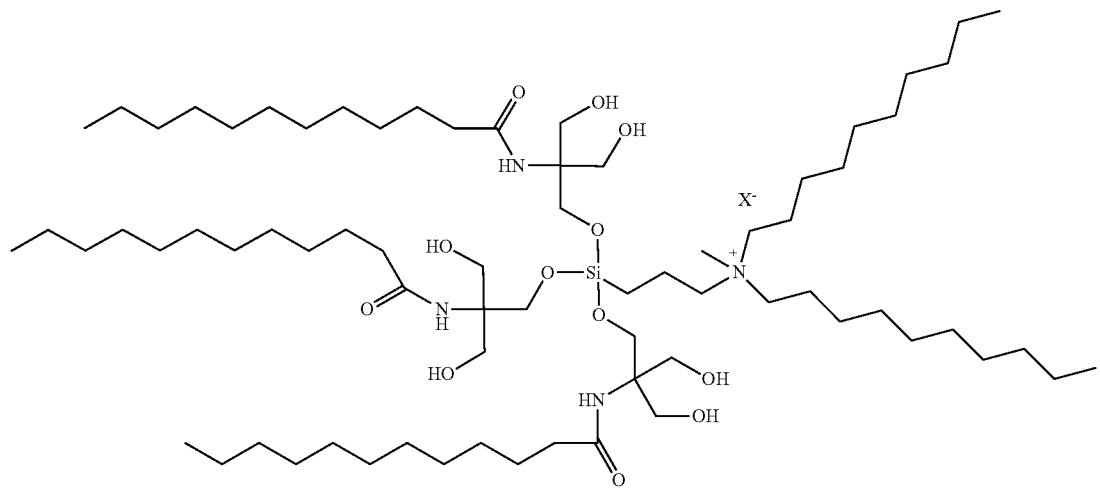

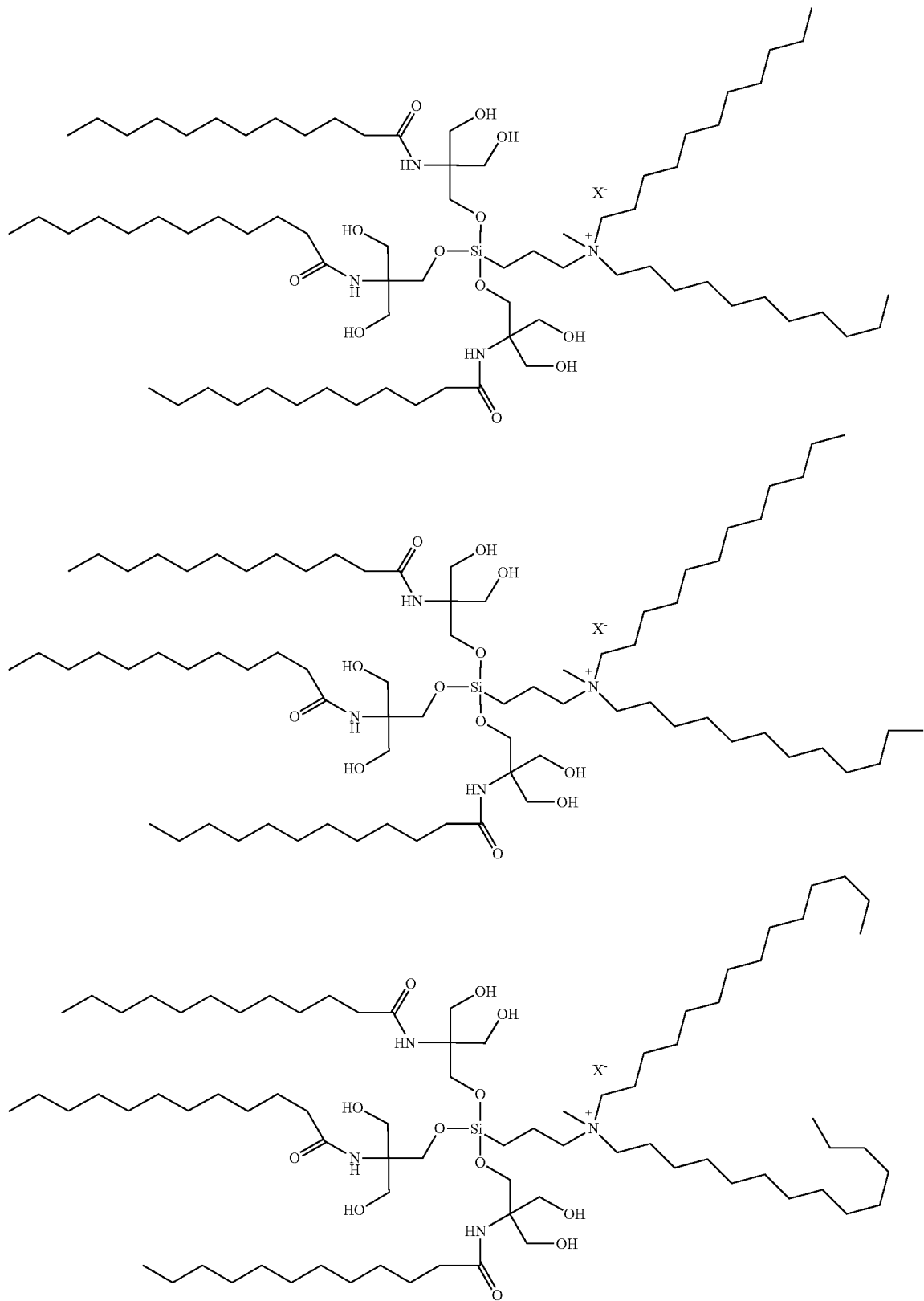

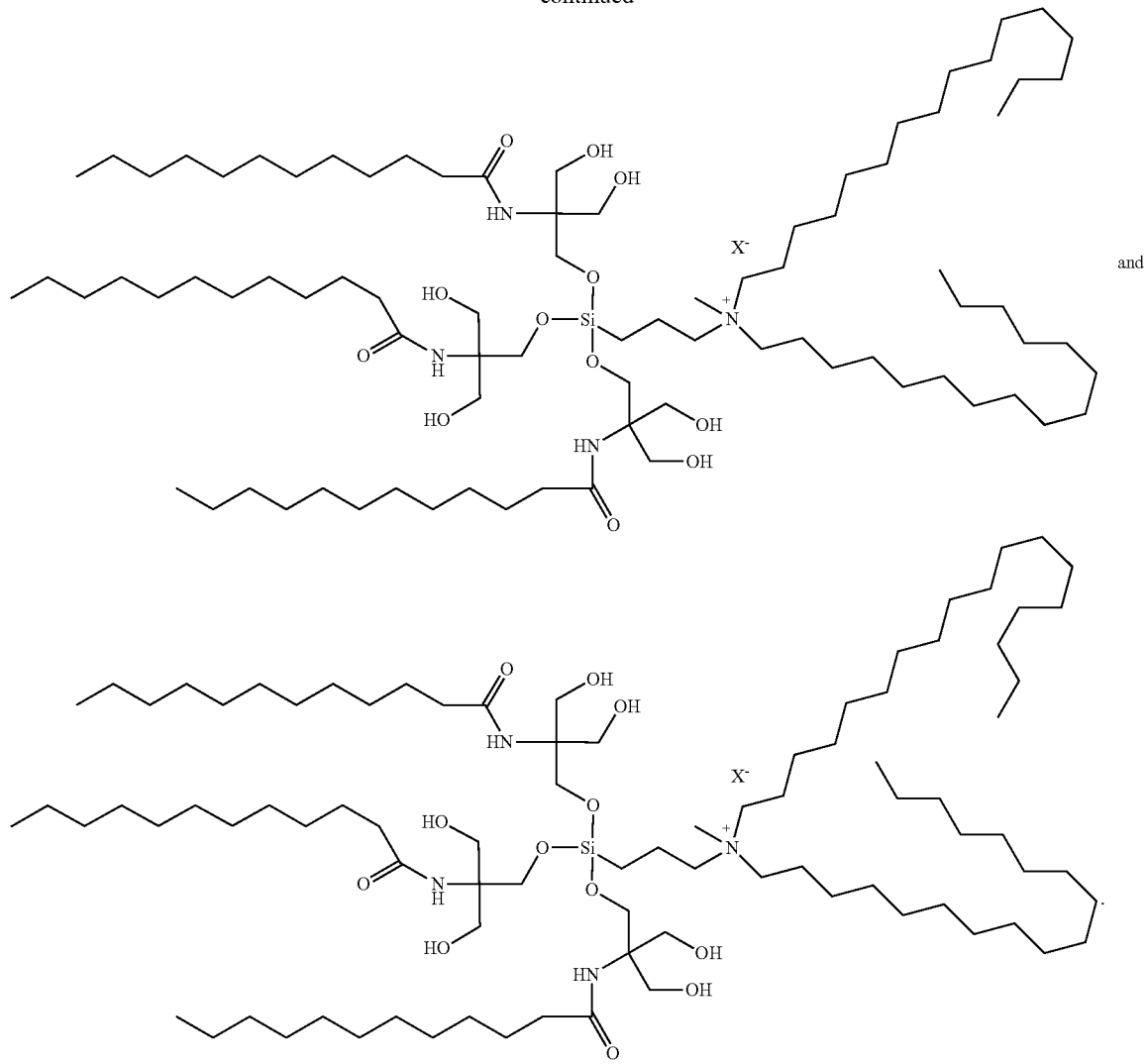
In certain embodiments, the compound of the present invention is selected from:
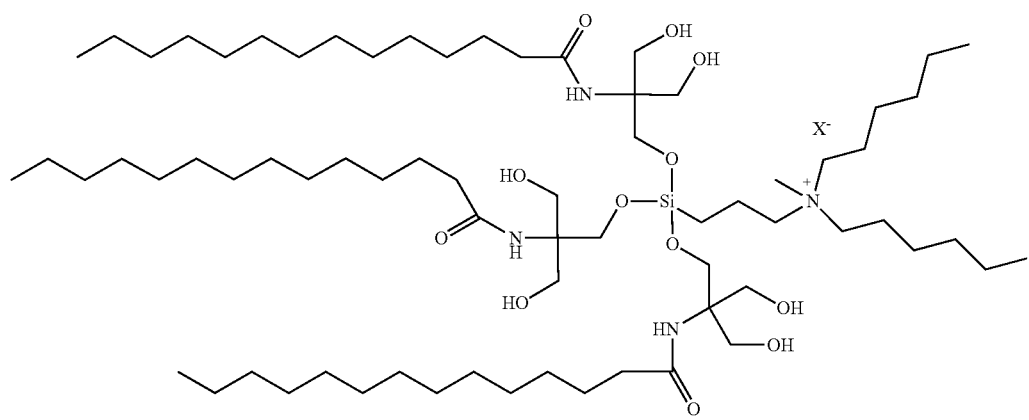

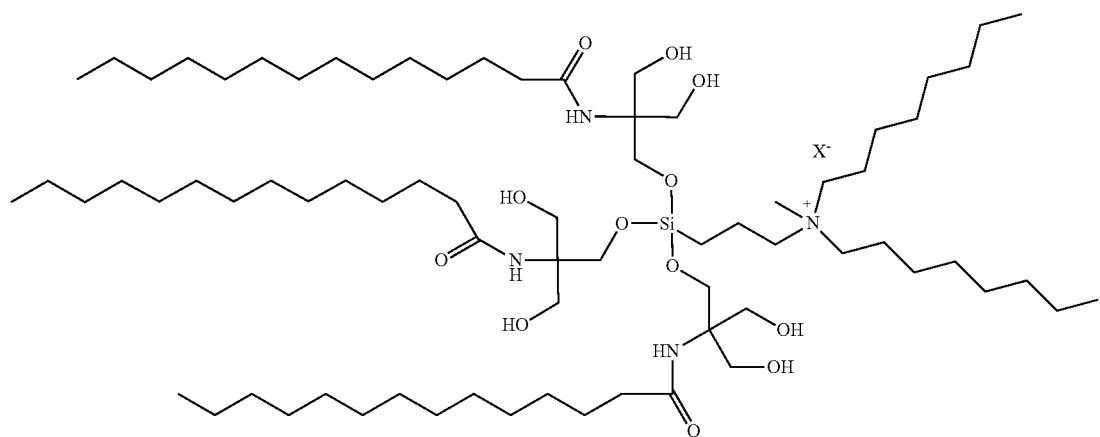
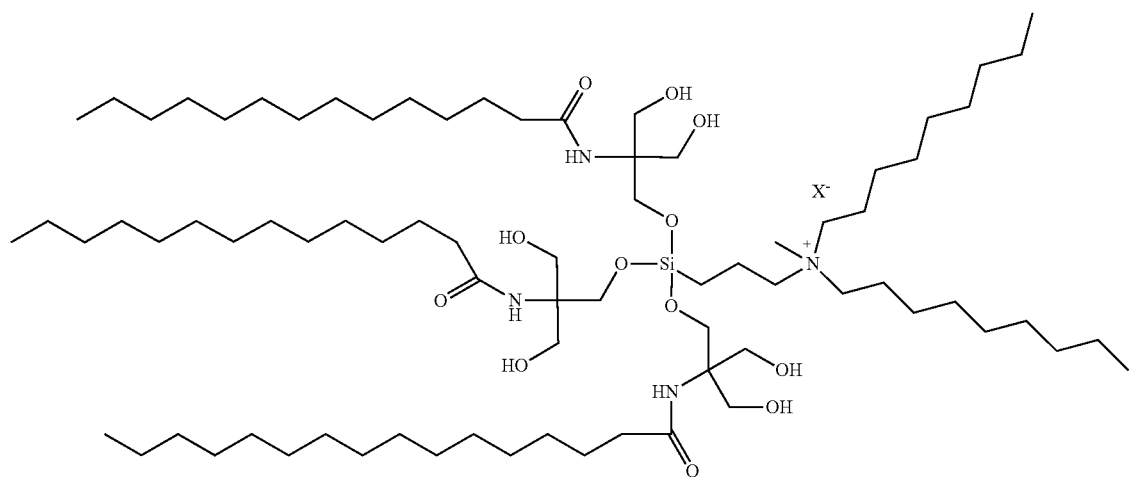
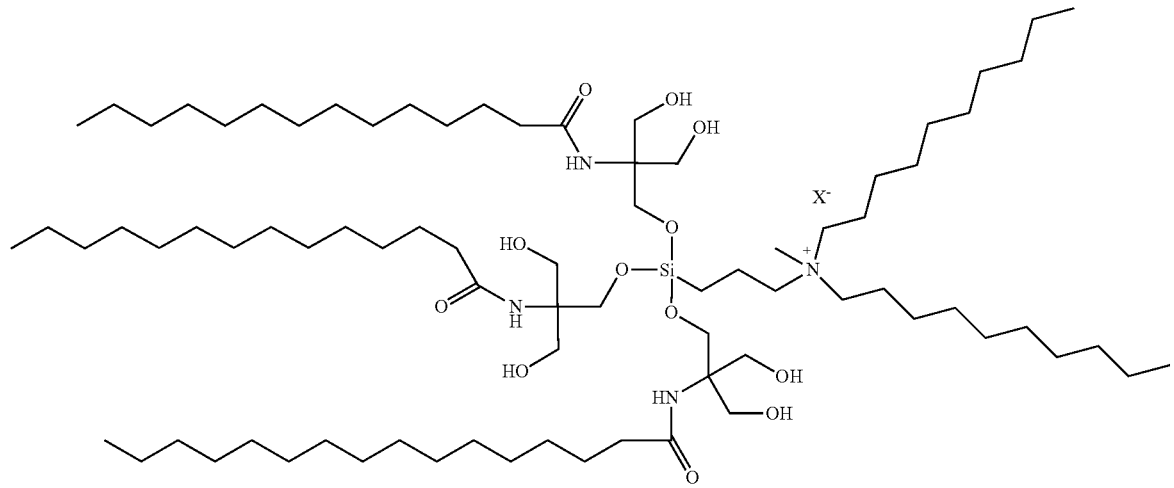

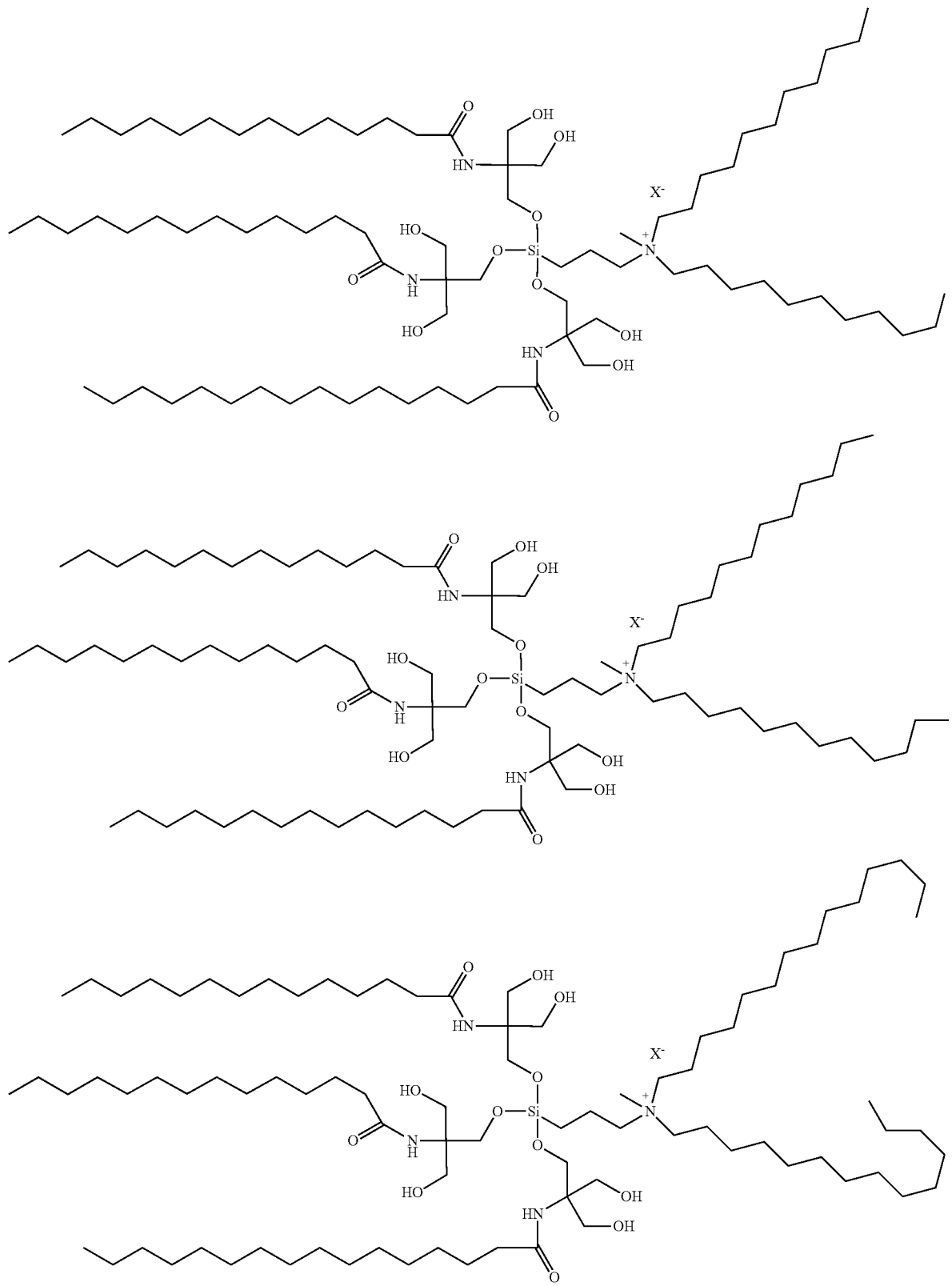

-continued
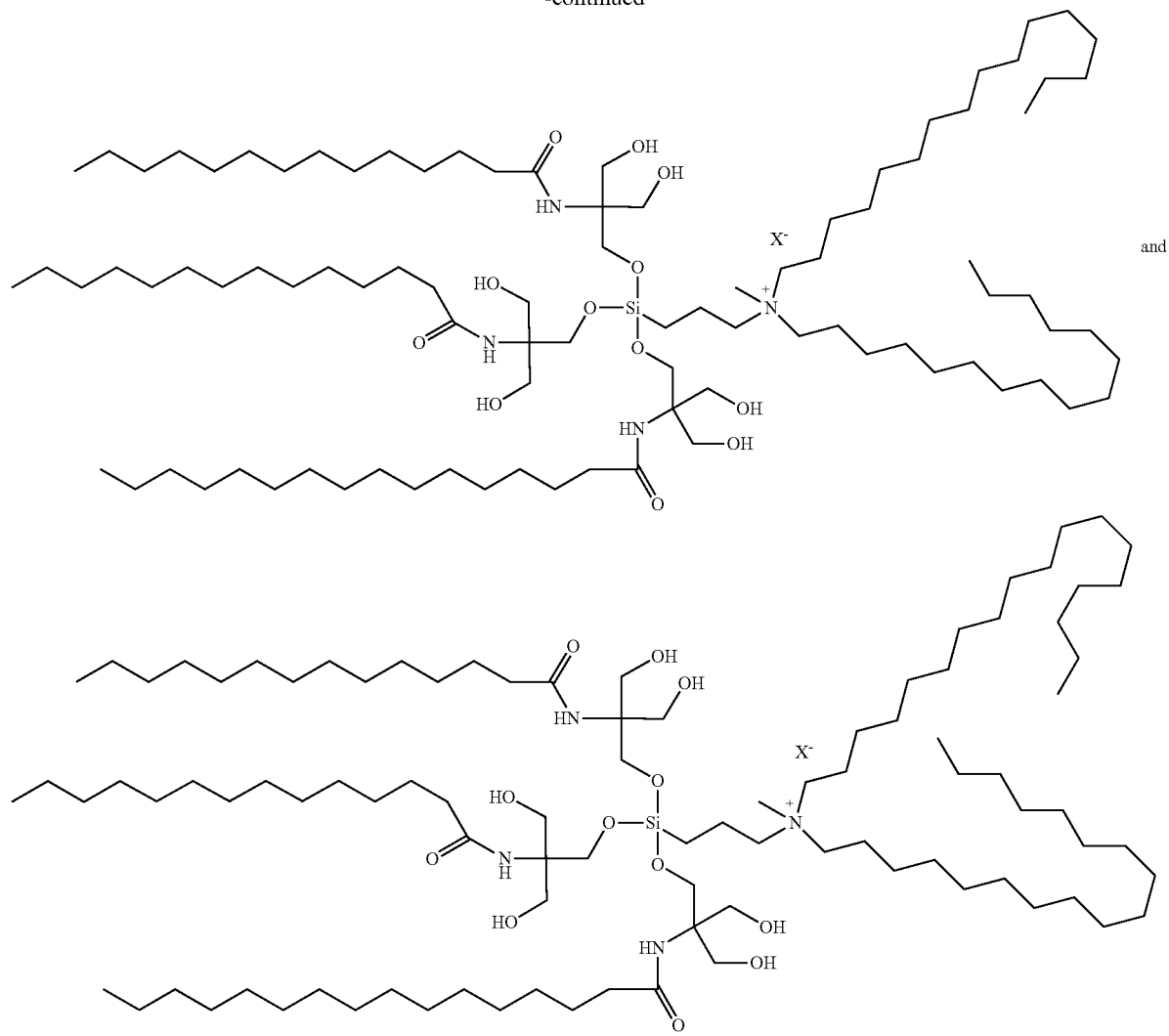
and
In certain embodiments, the compound of the present invention is selected from.
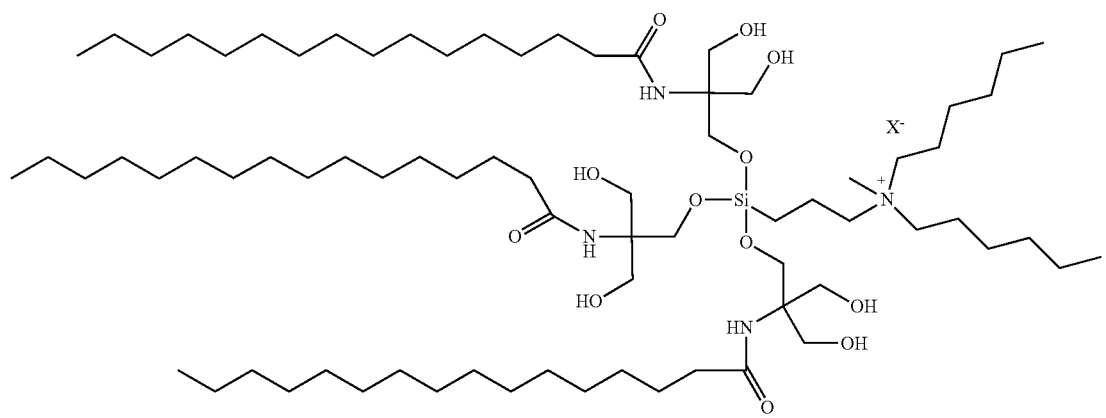

-continued
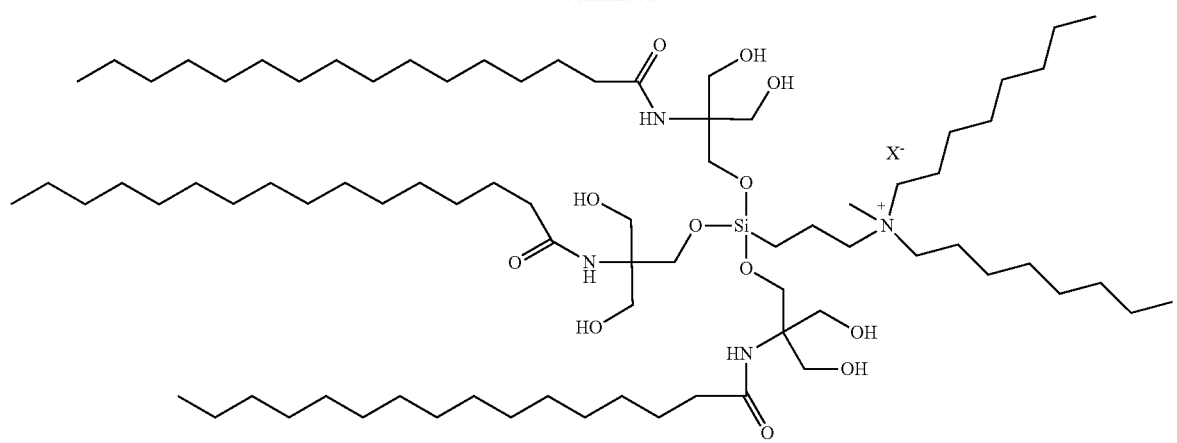
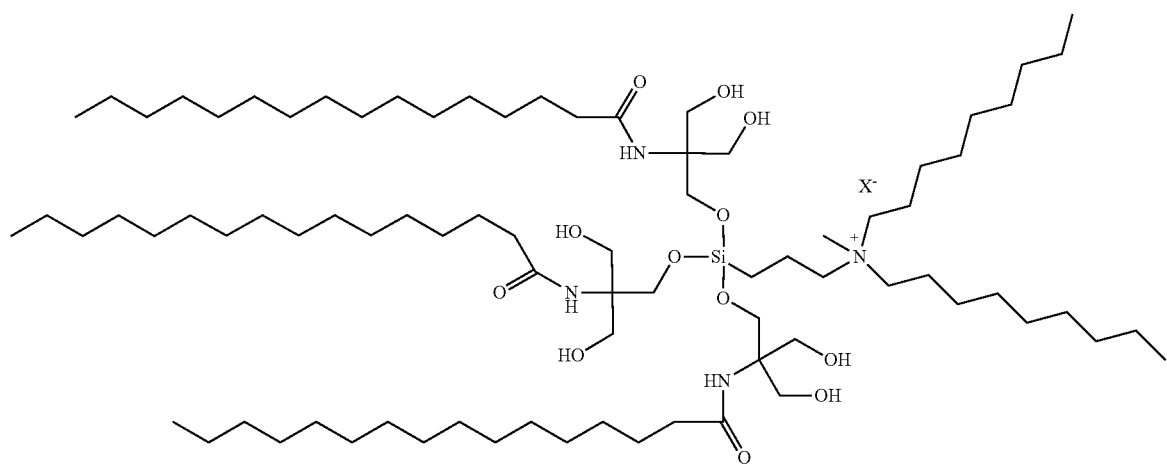
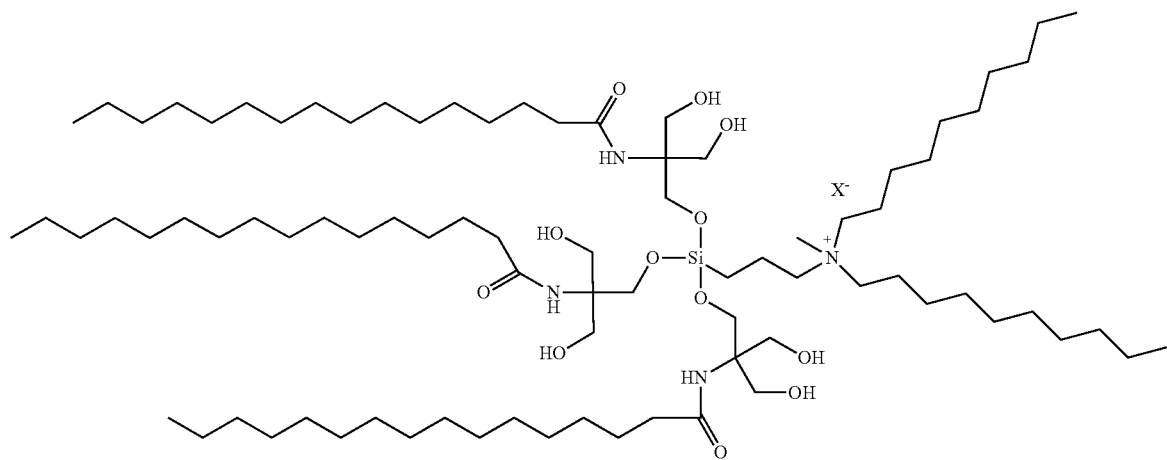

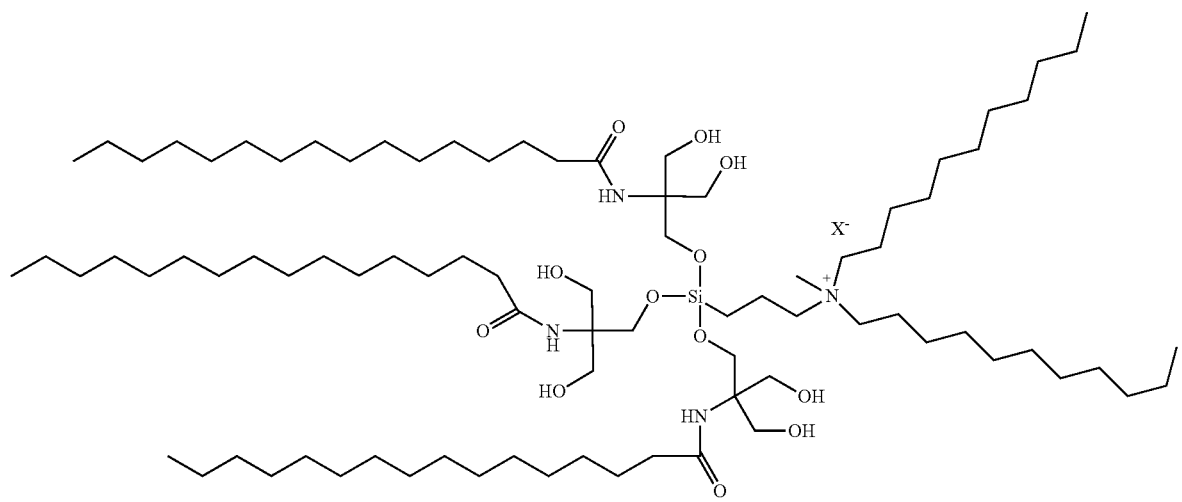
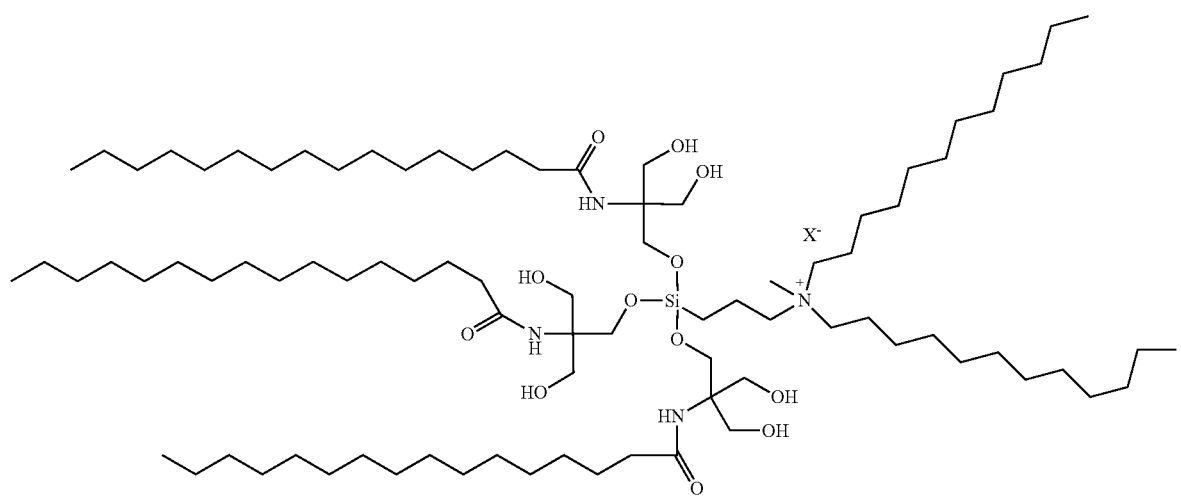
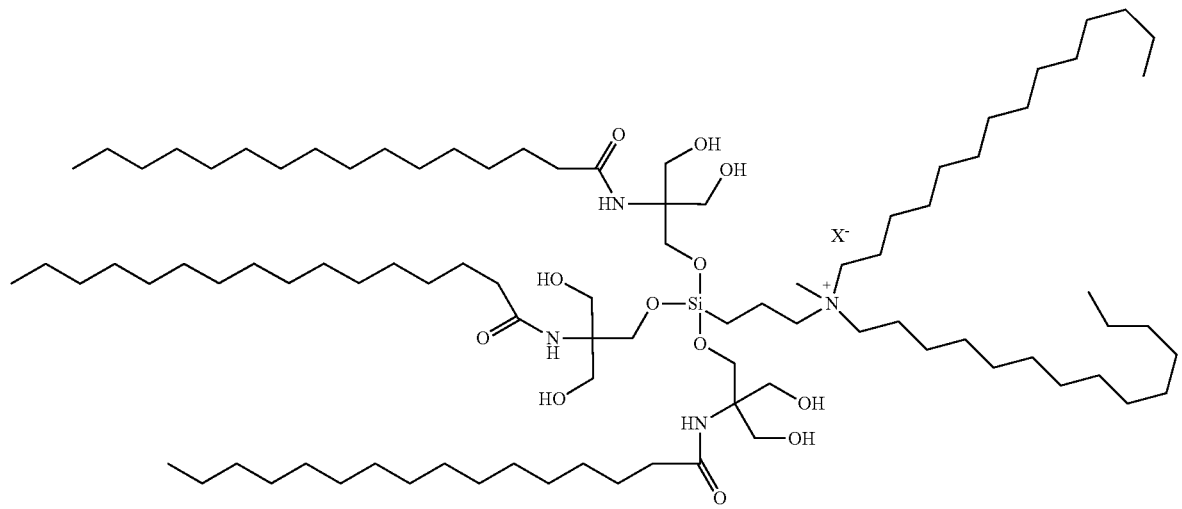

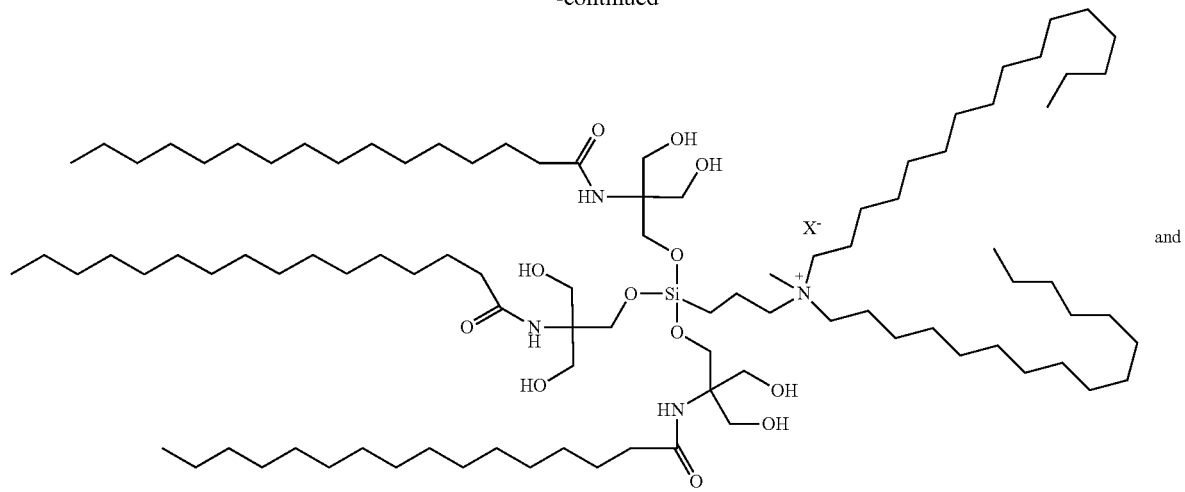
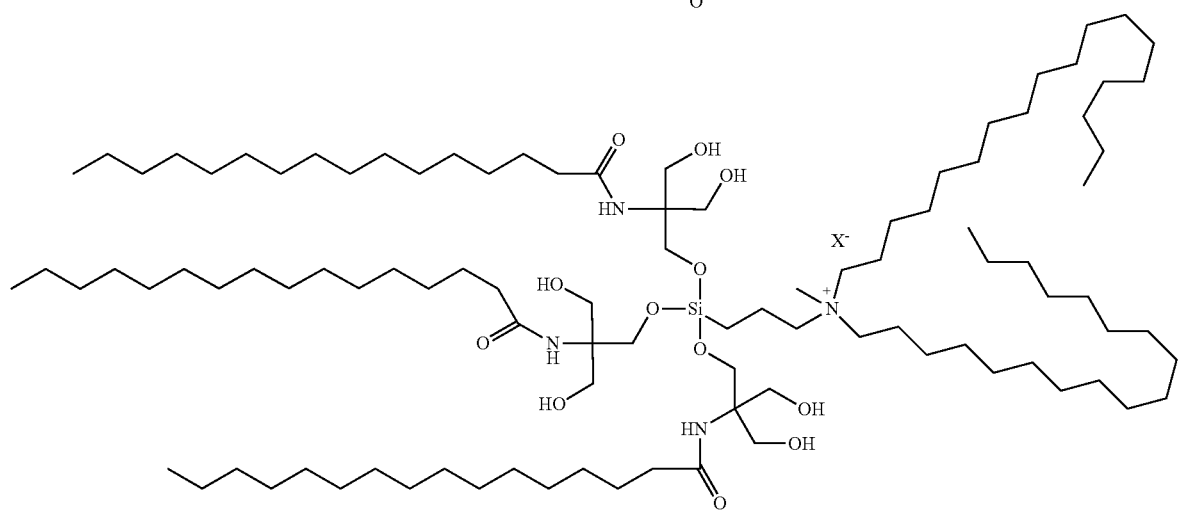
In certain embodiments, the compound of the present invention is selected from:
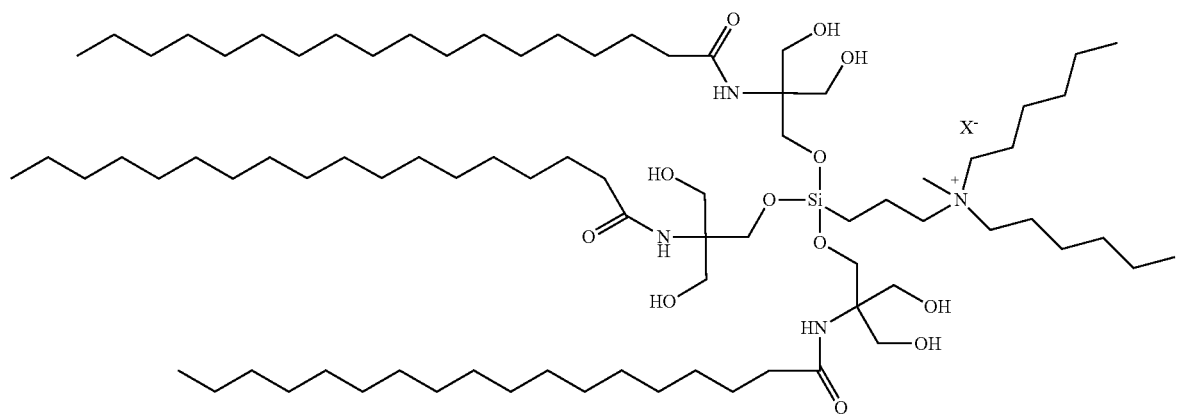

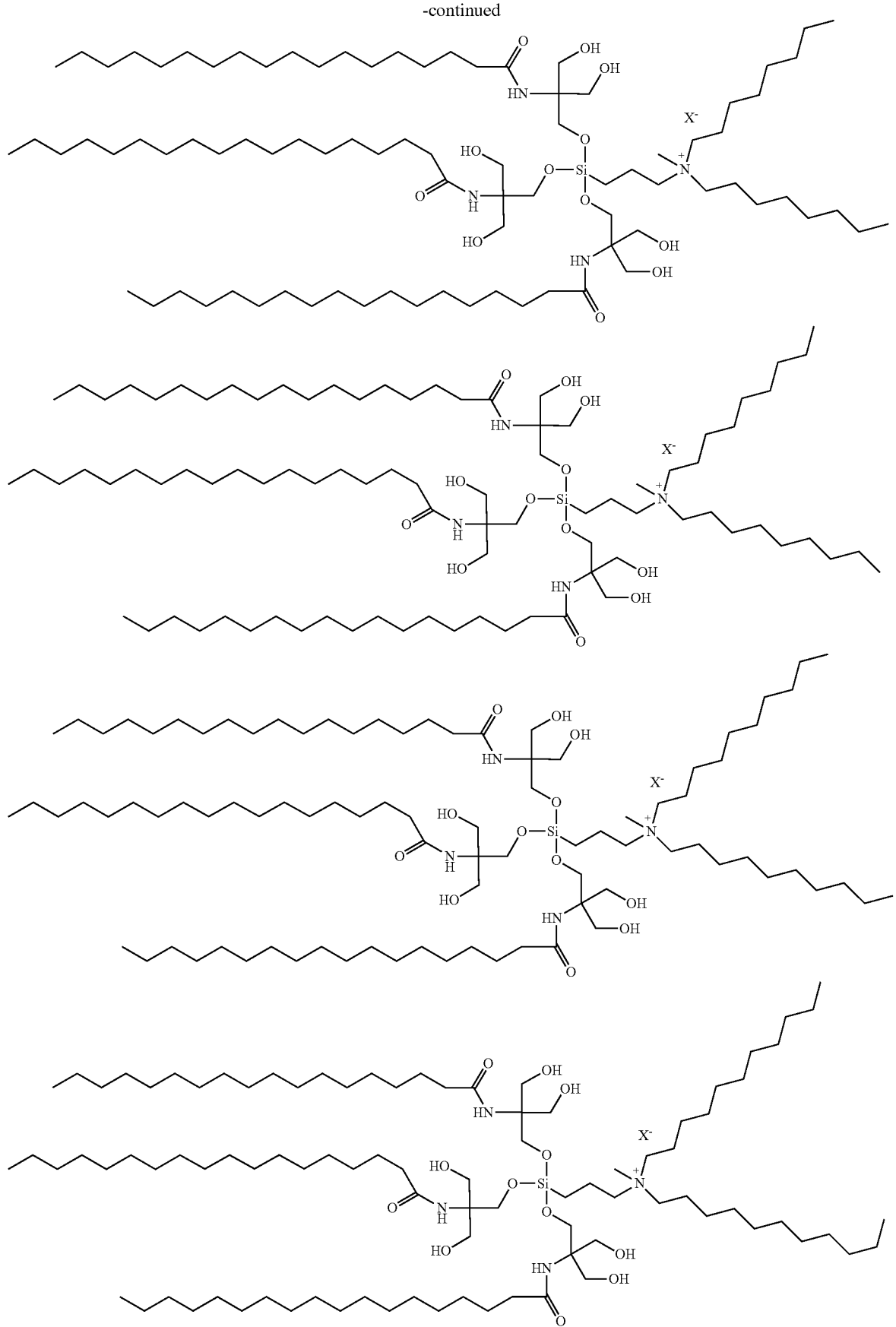

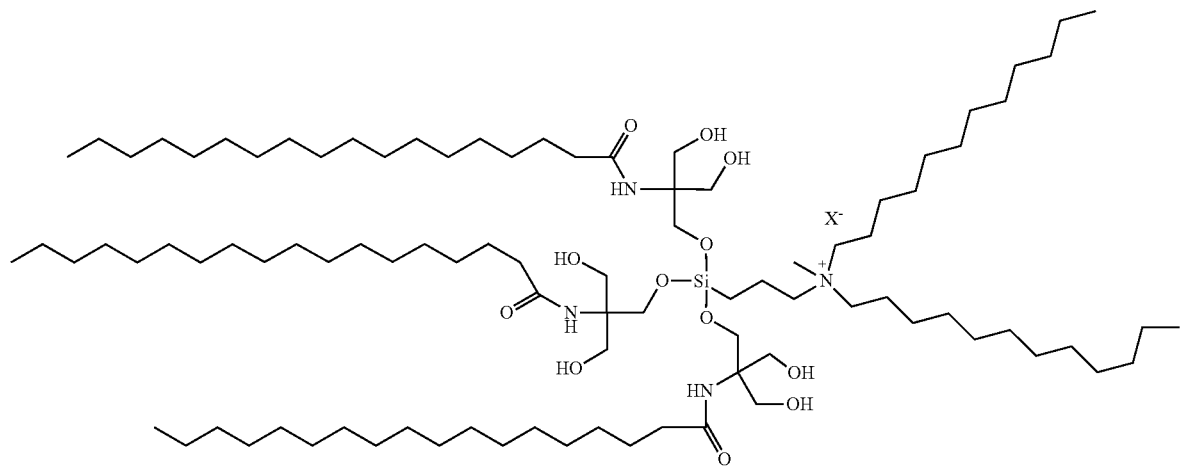
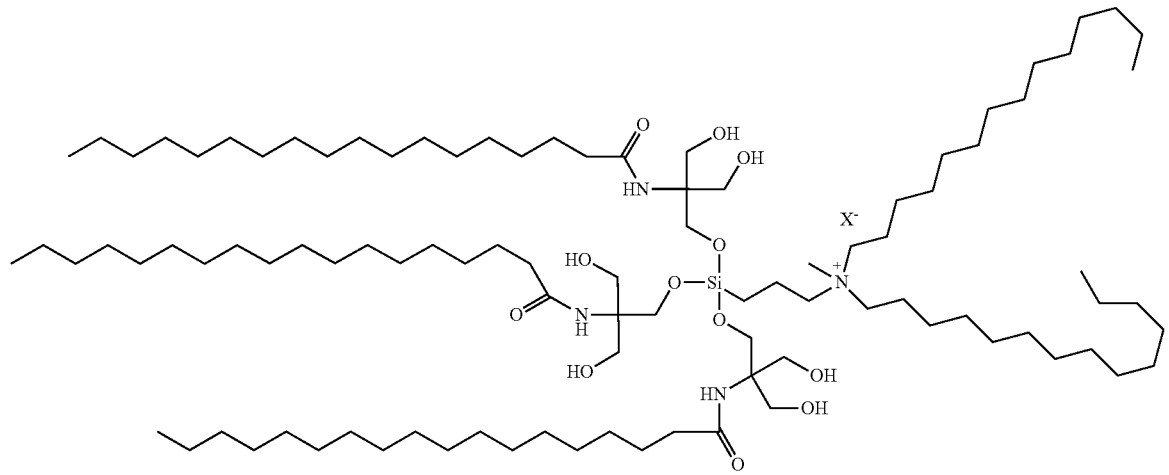
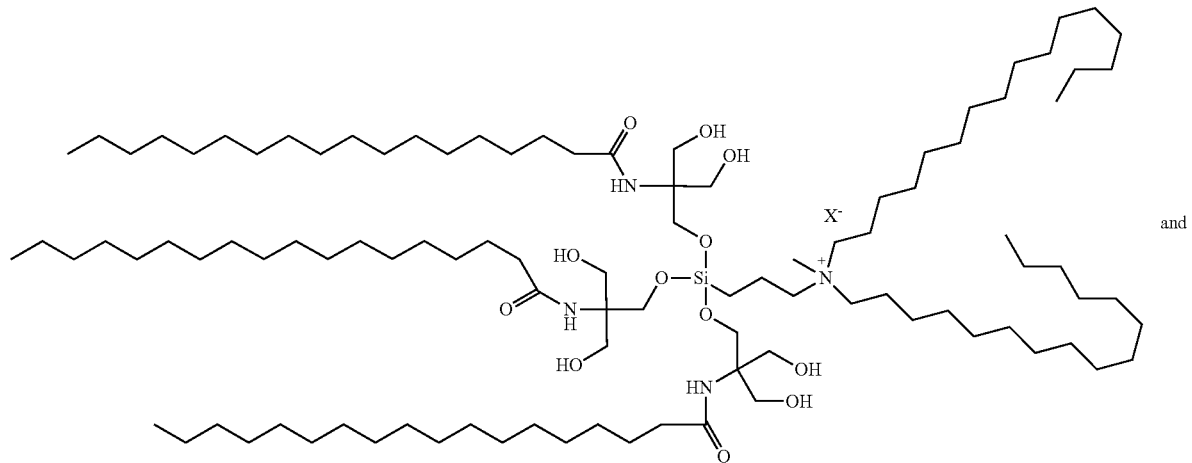
and

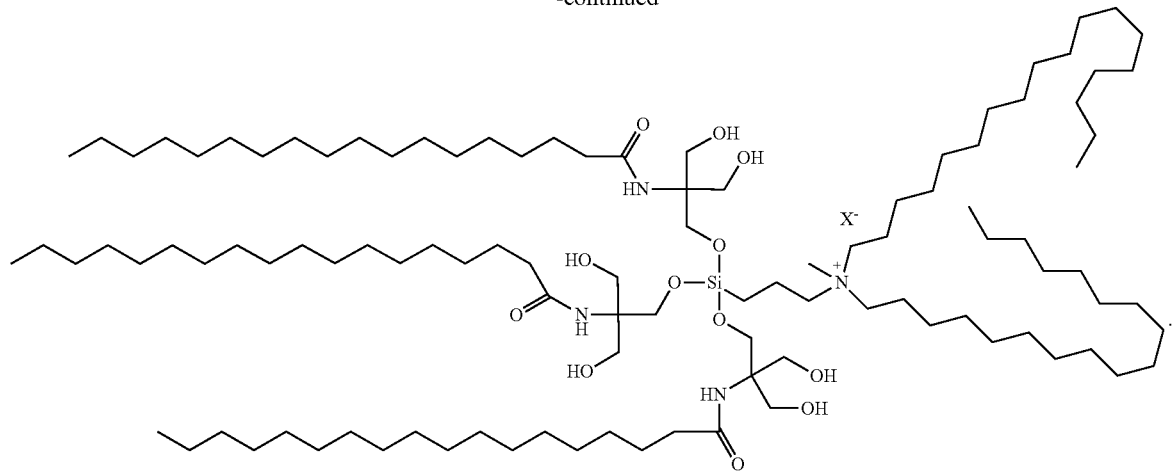
In certain embodiments, the compound of the present invention is selected from:
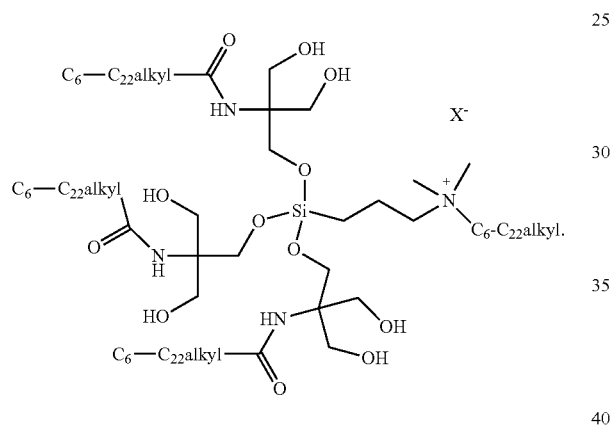
In certain embodiments, the compound of the present invention is selected from:
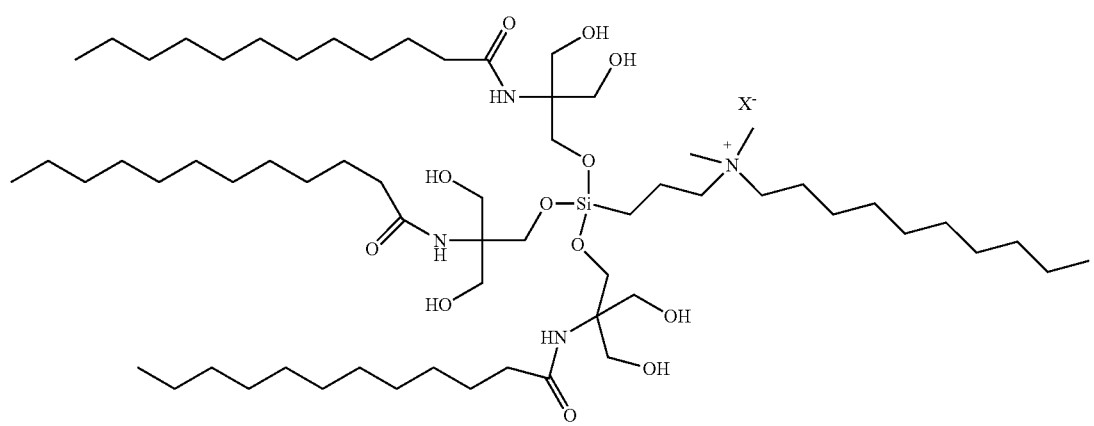

-continued
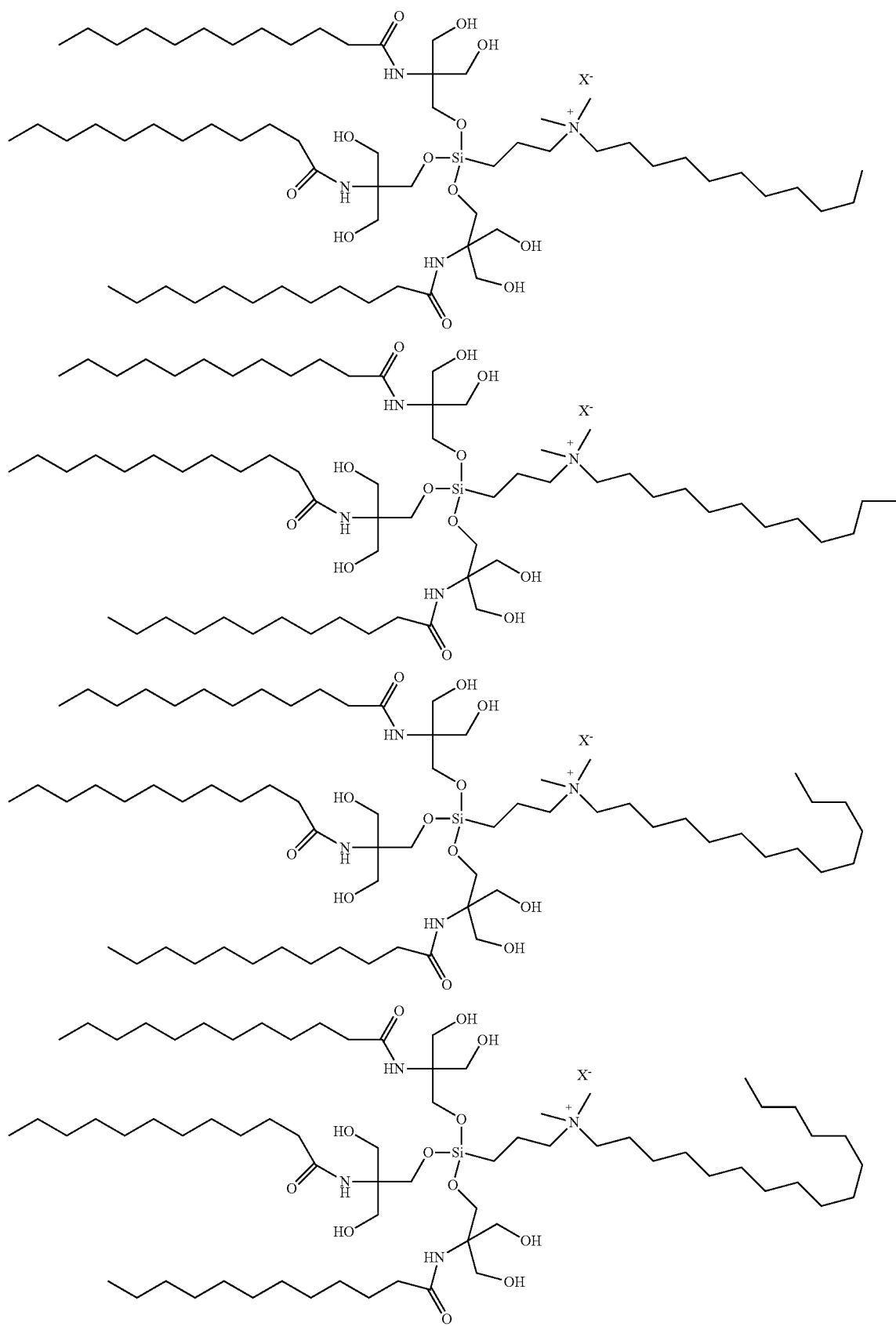

-continued
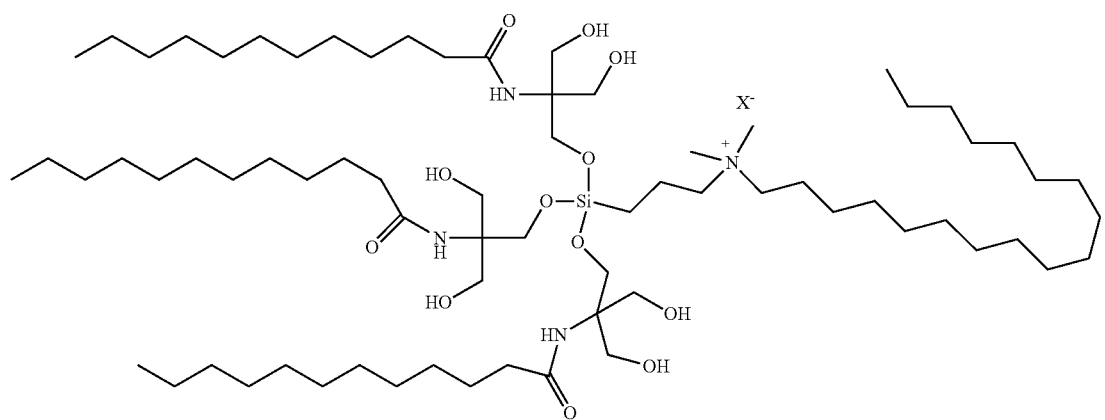
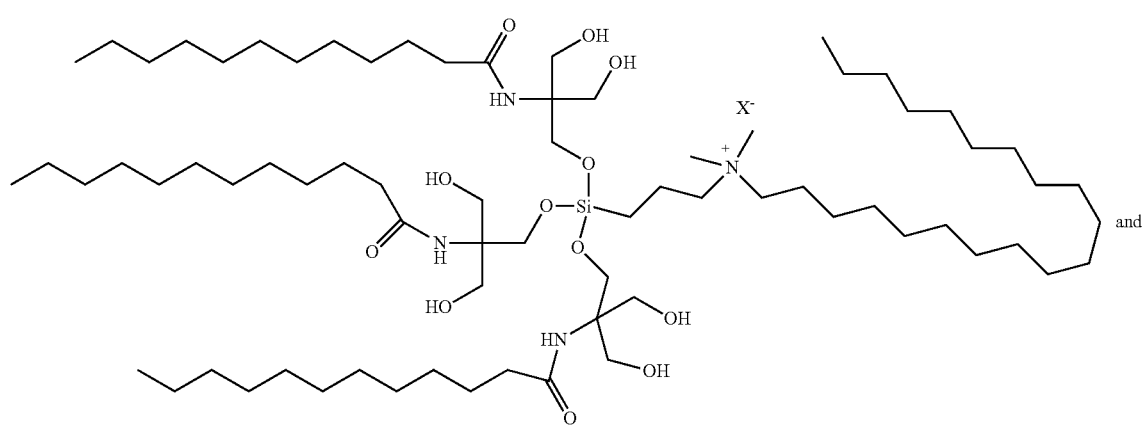
and
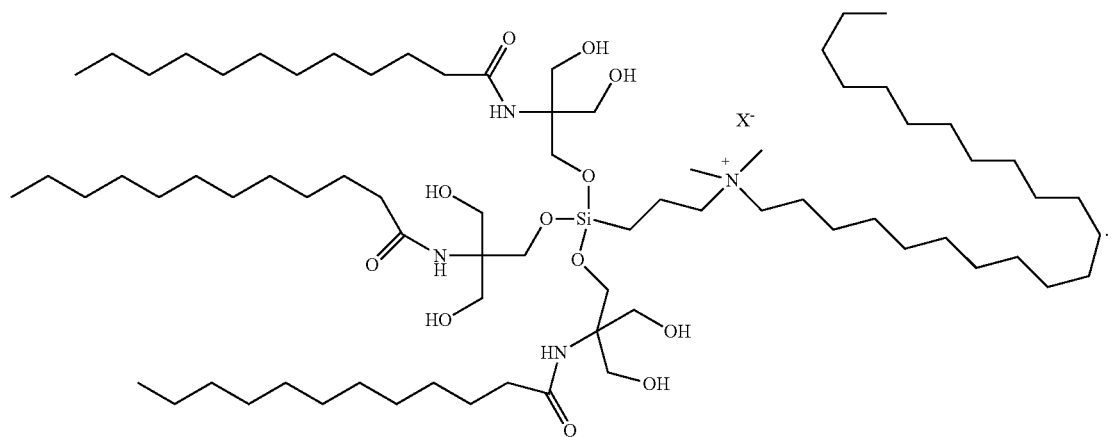

In certain embodiments, the compound of the present invention is selected from:
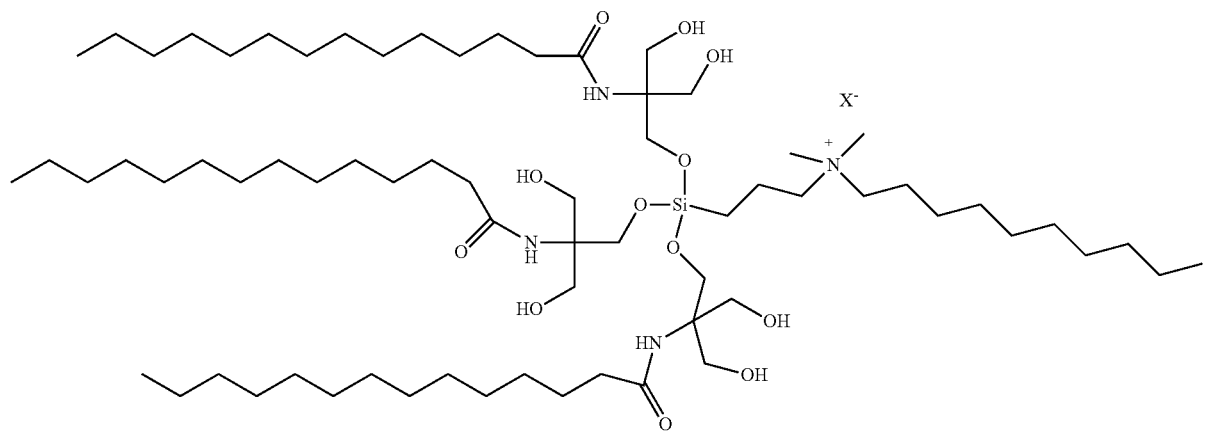
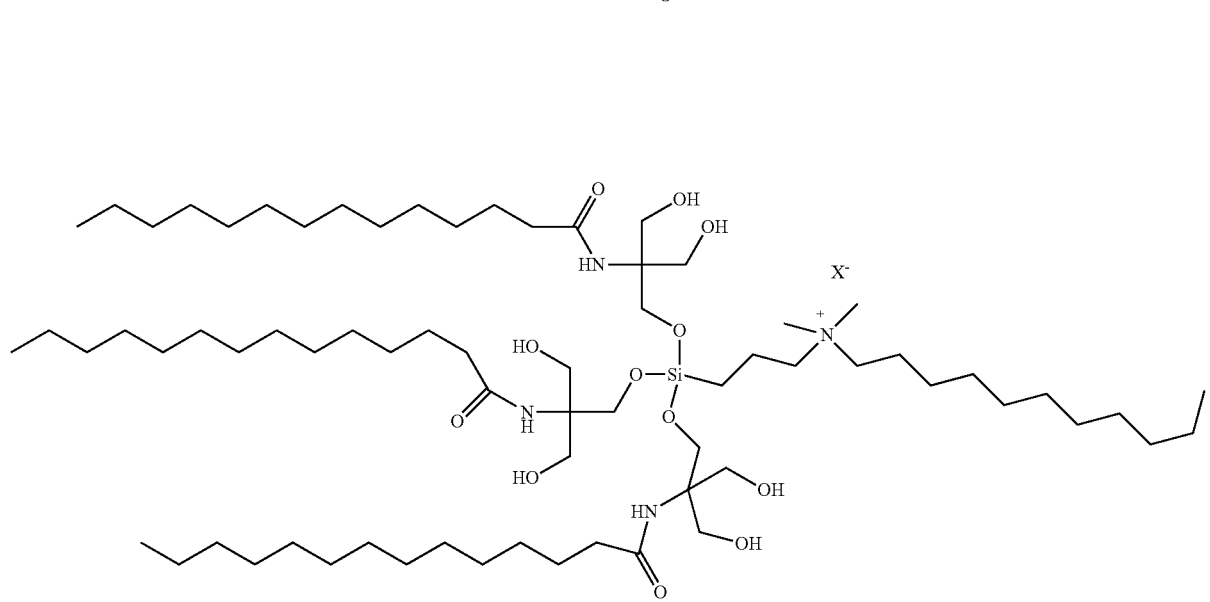
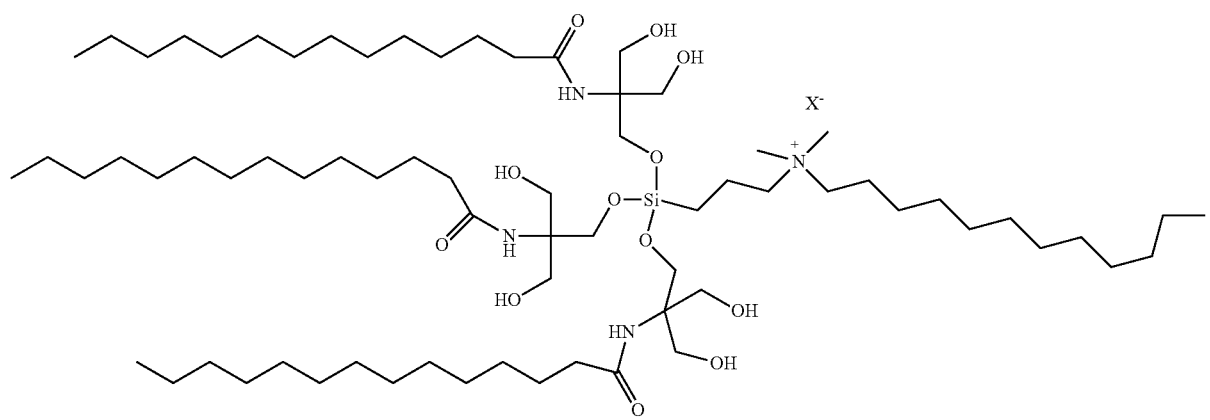

-continued
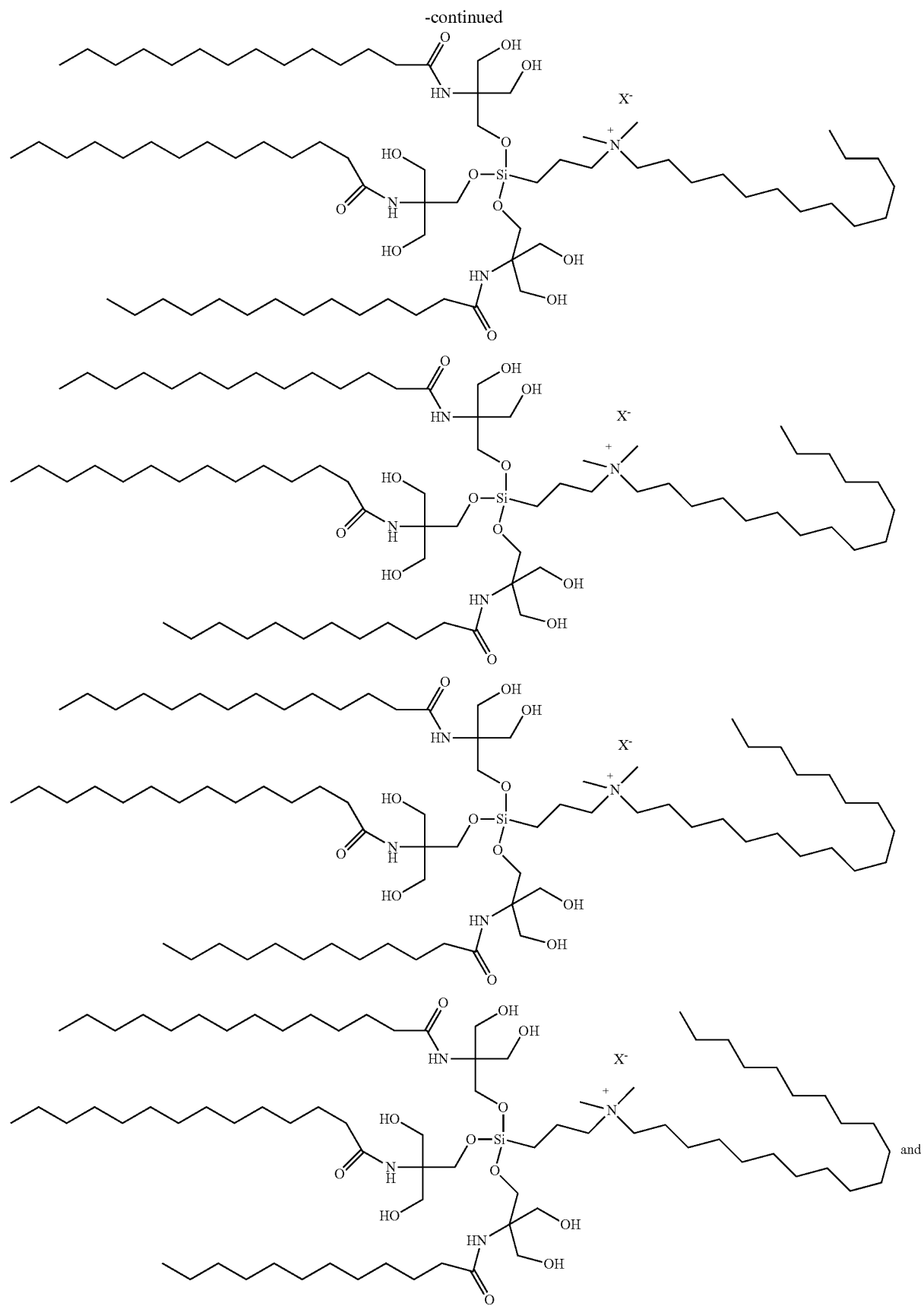
and

-continued
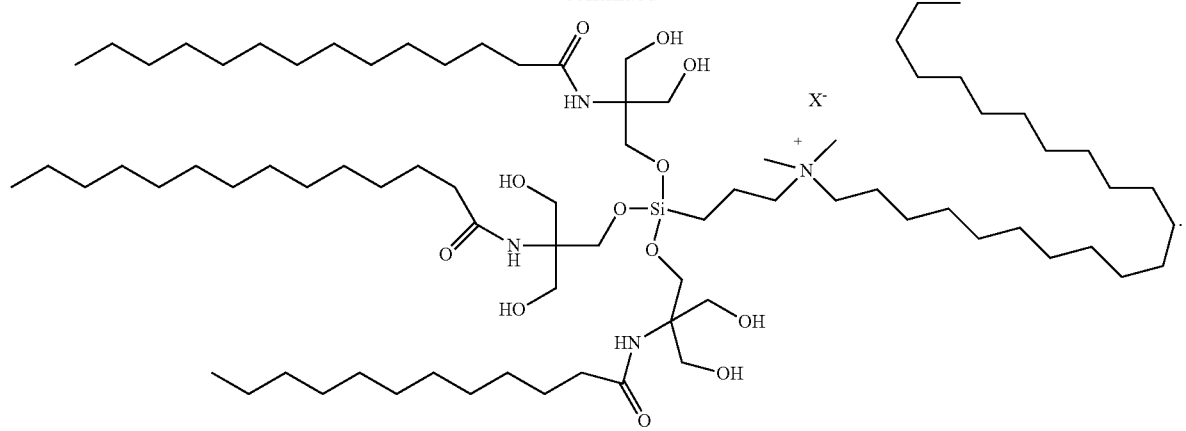
In certain embodiments, the compound of the present invention is selected from:
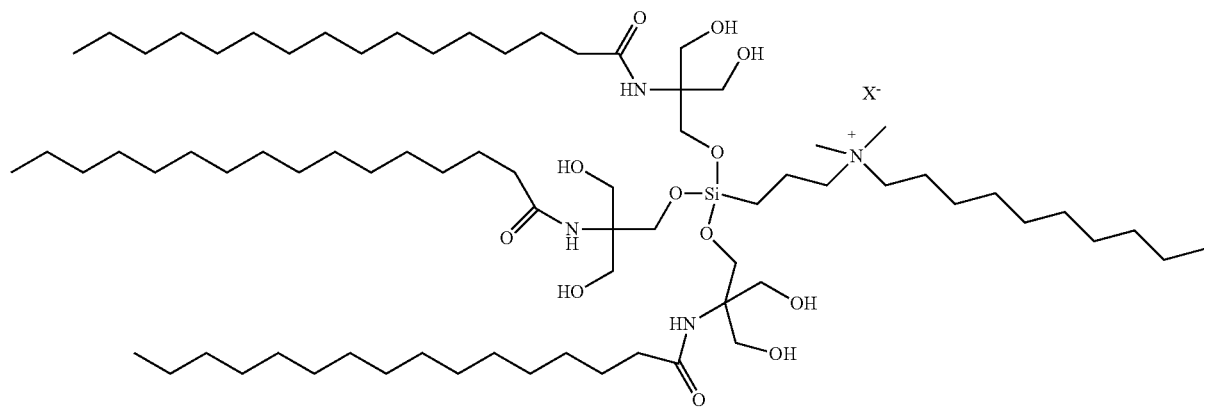
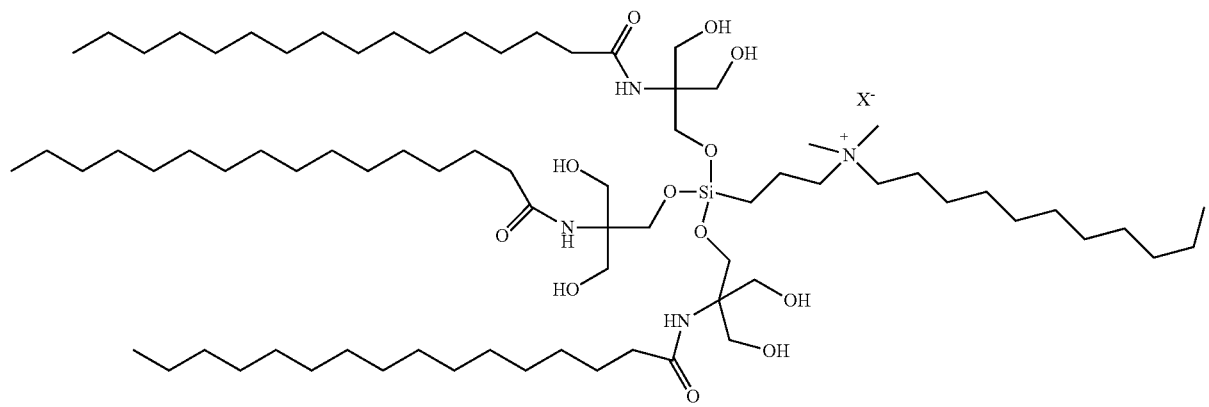

-continued
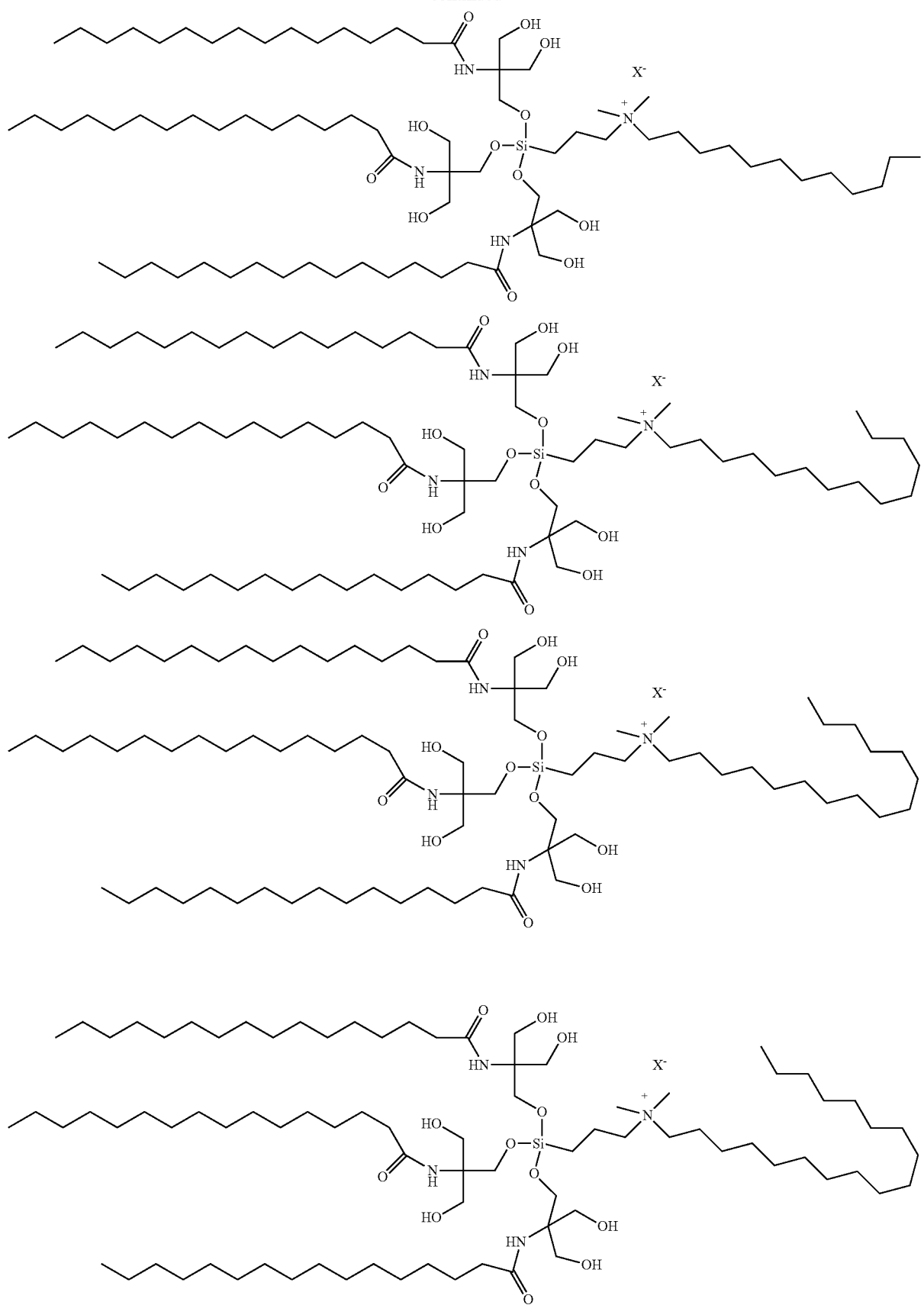

-continued
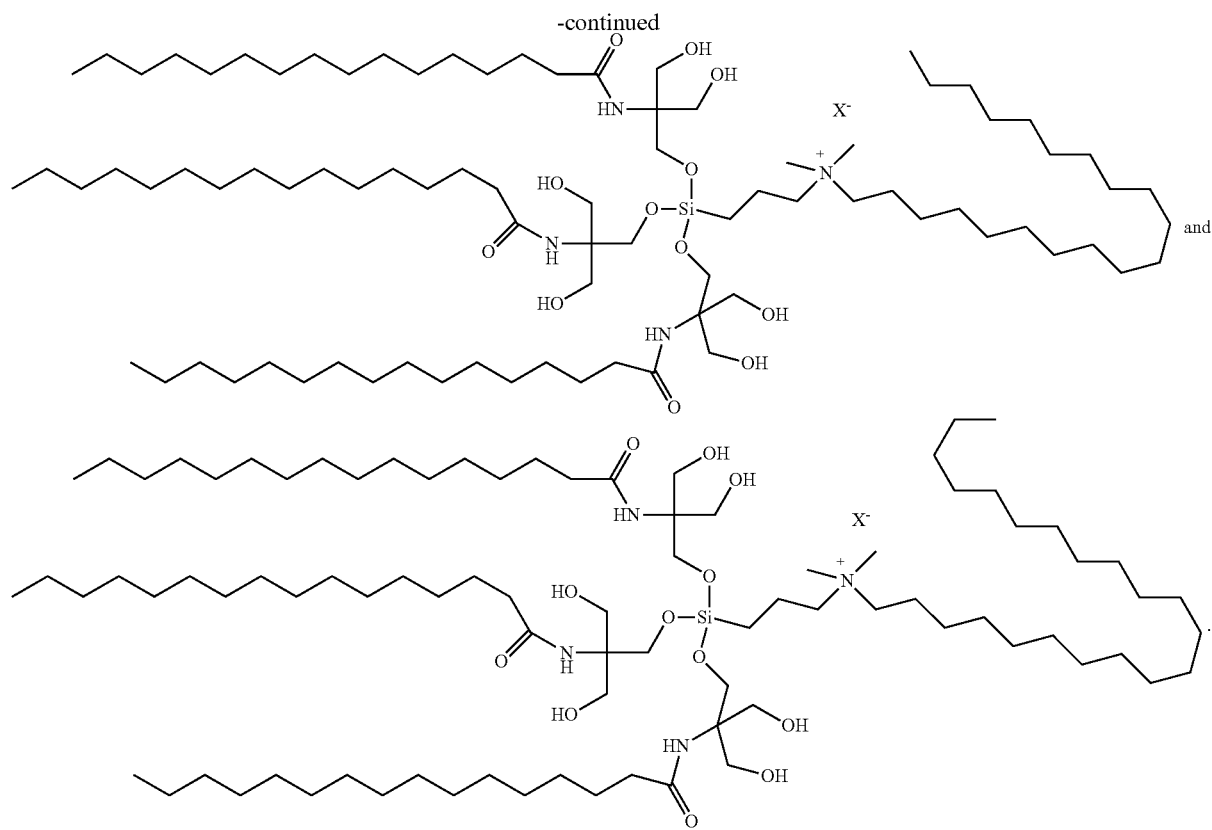
In certain embodiments, the compound of the present invention is selected from:
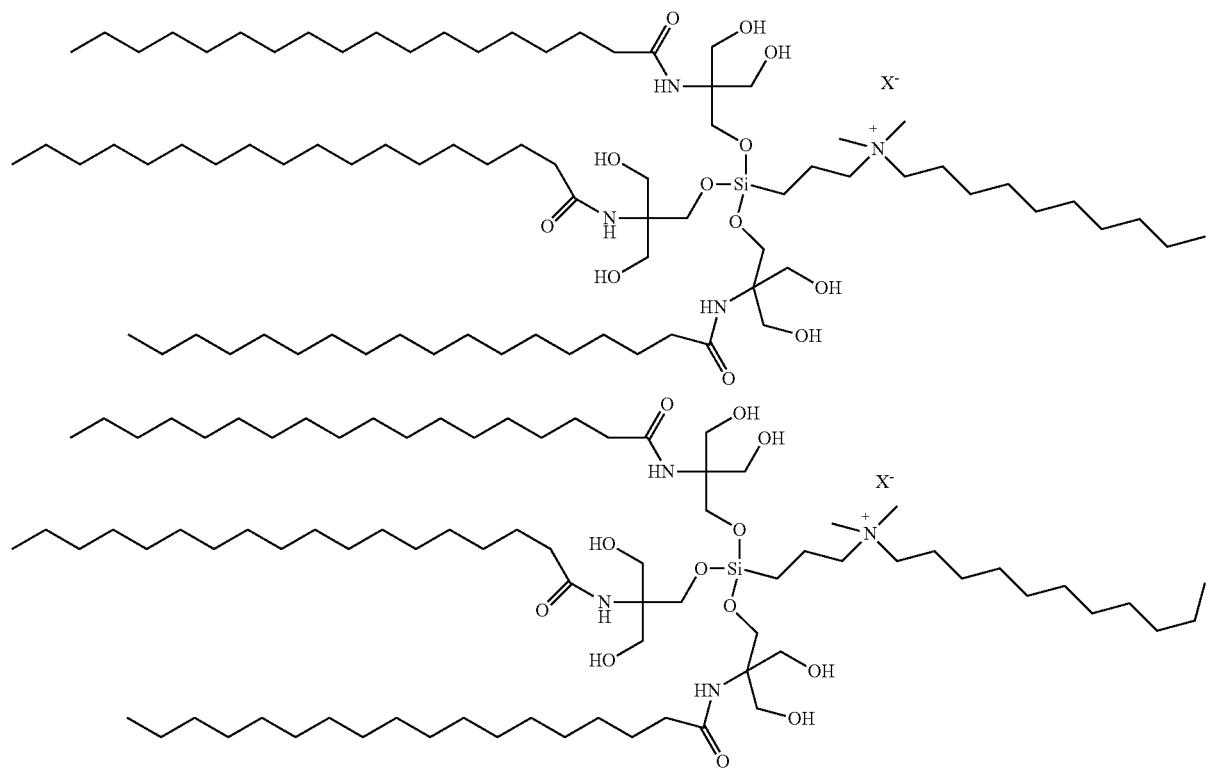

-continued
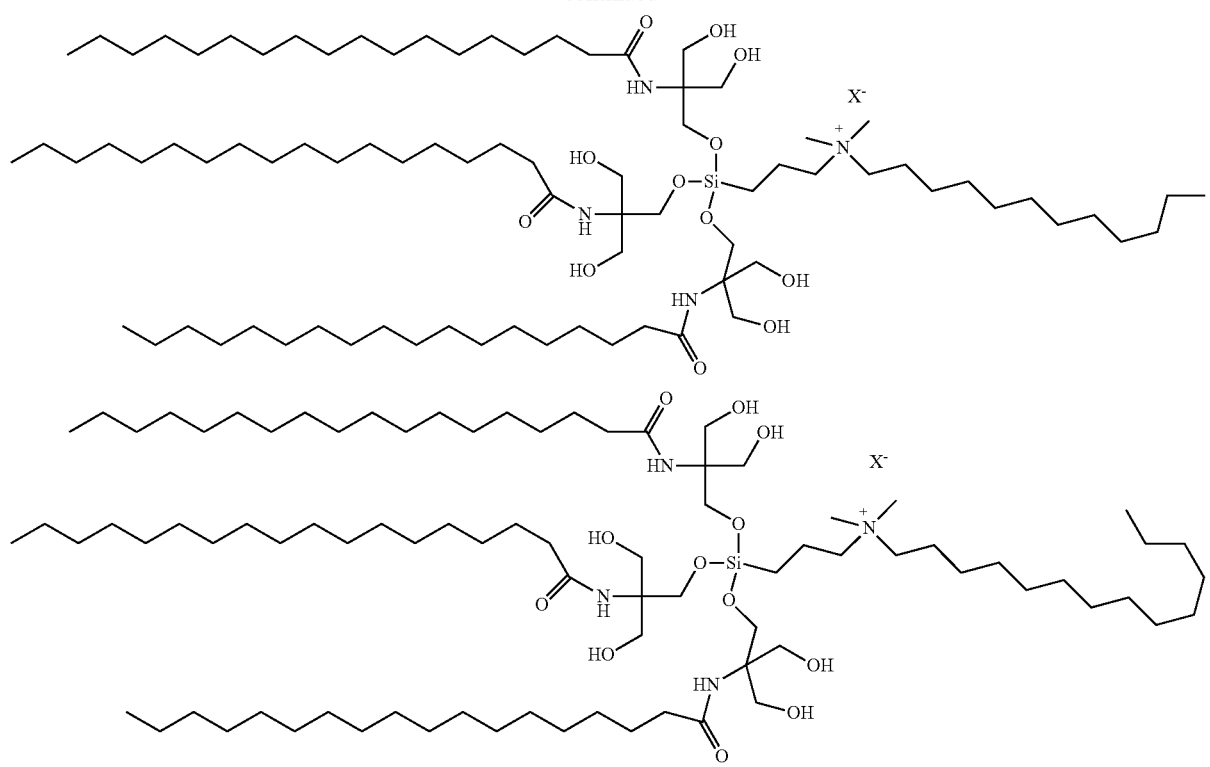
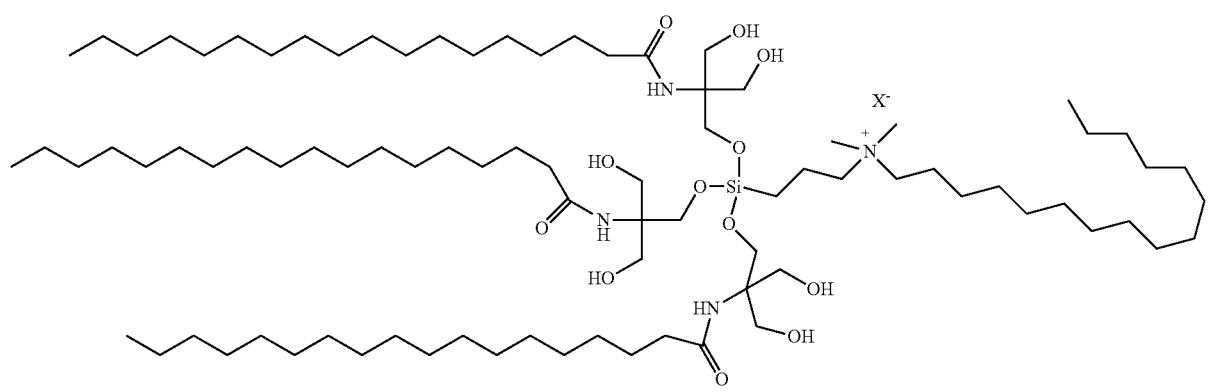
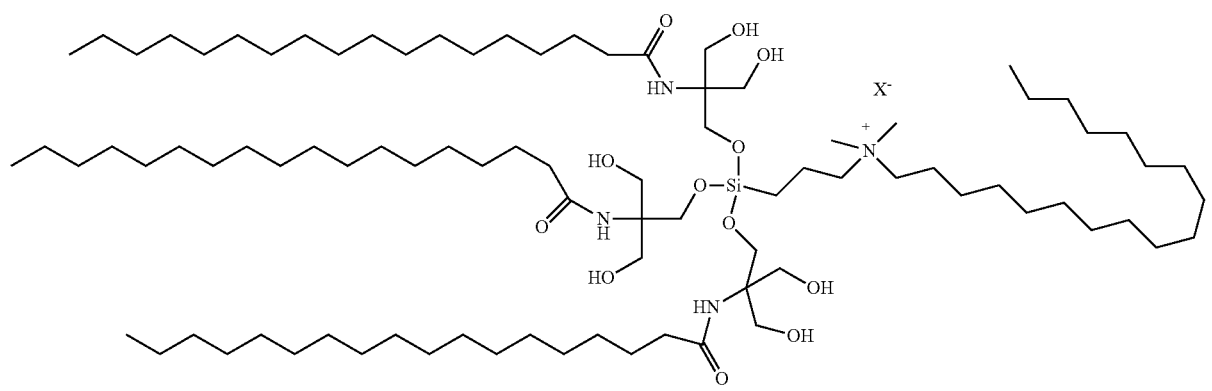

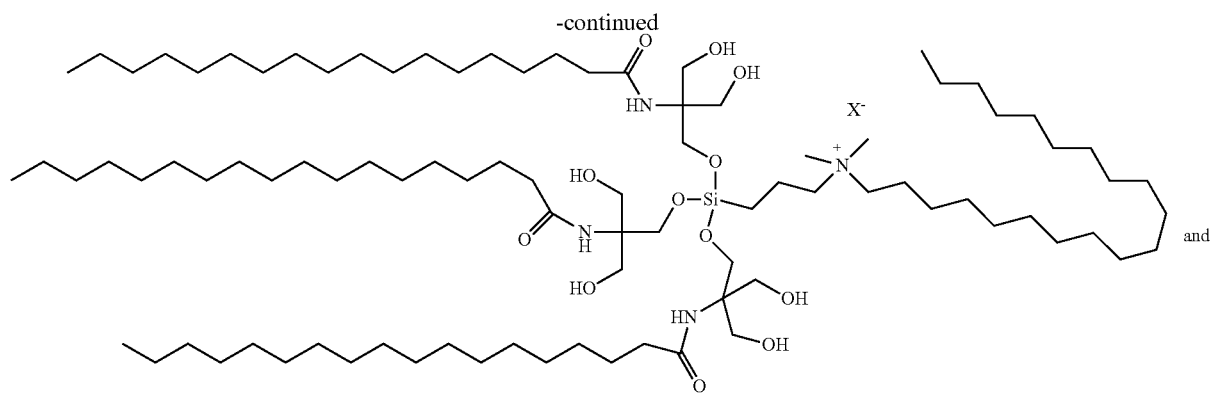
and
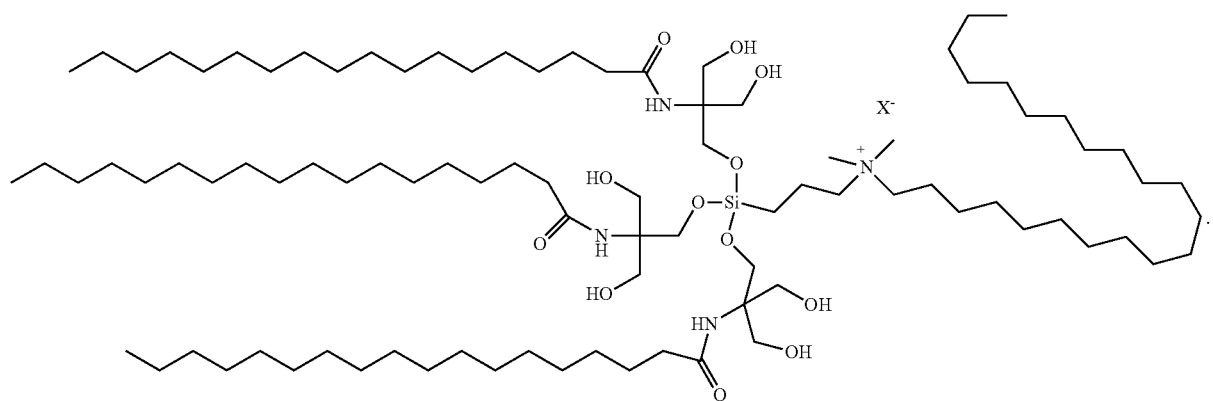
In certain embodiments, the compound of the present invention is selected from:
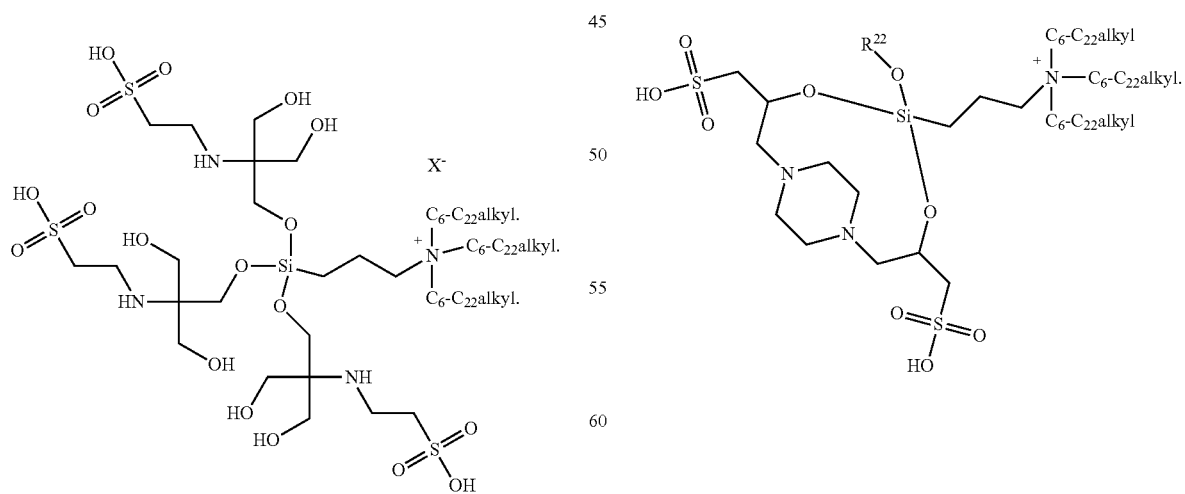
In certain embodiments, the compound of the present invention is selected from:
In certain embodiments, the compound of the present invention is selected from:

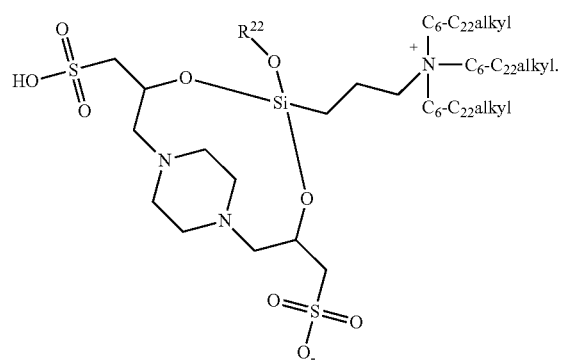
In certain embodiments, the compound of the present invention is selected from:
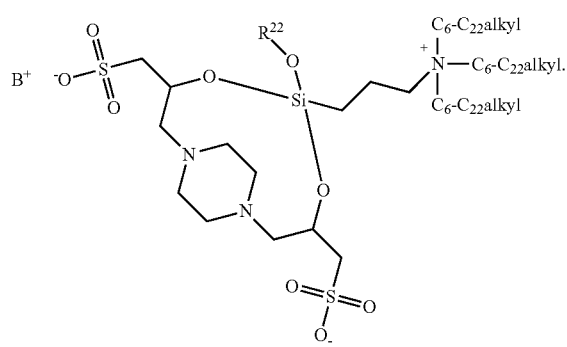
In certain embodiments, the compound of the present invention is selected from:
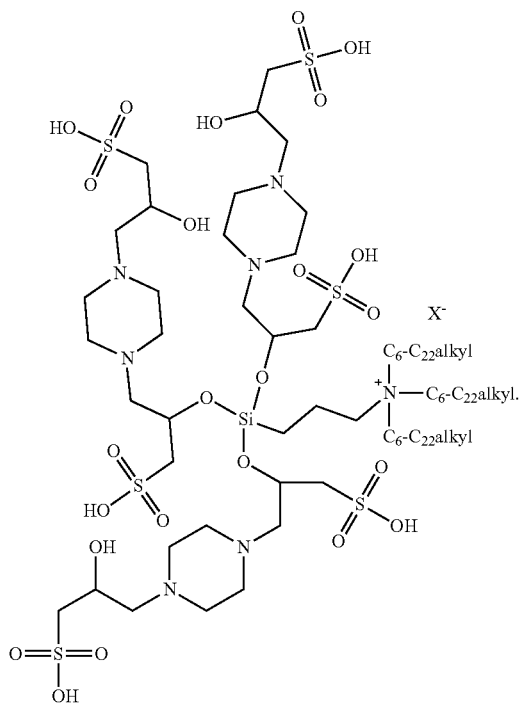
In certain embodiments, the compound of the present invention is selected from:
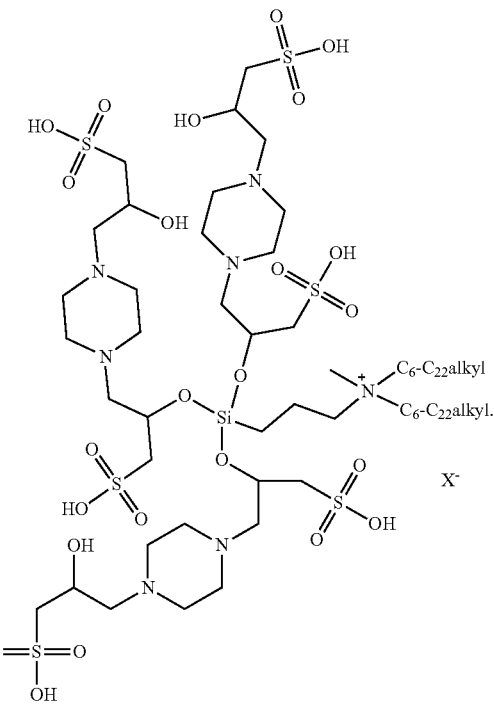
In certain embodiments, the compound of the present invention is selected from:
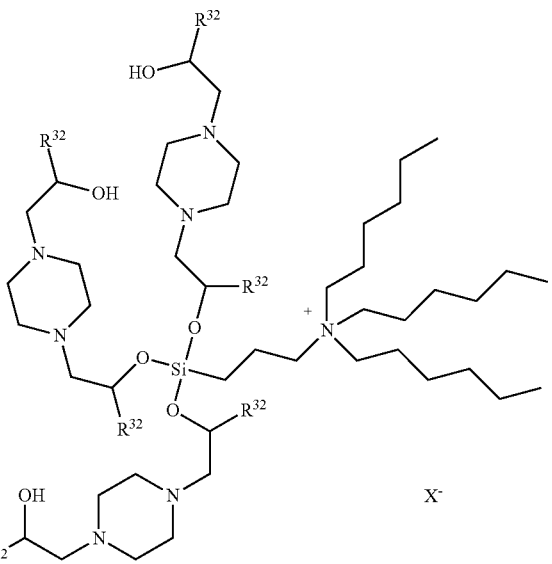

191
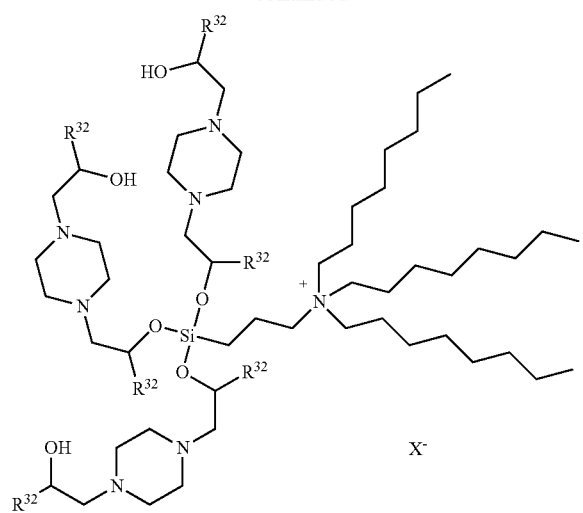
192
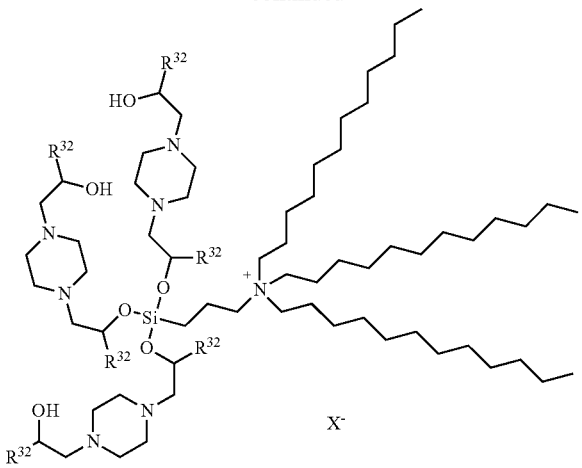
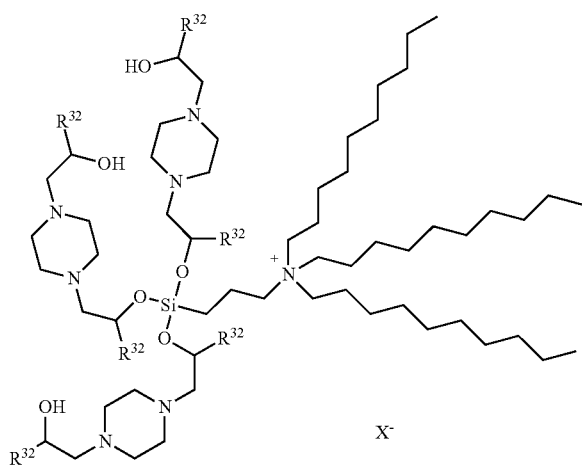
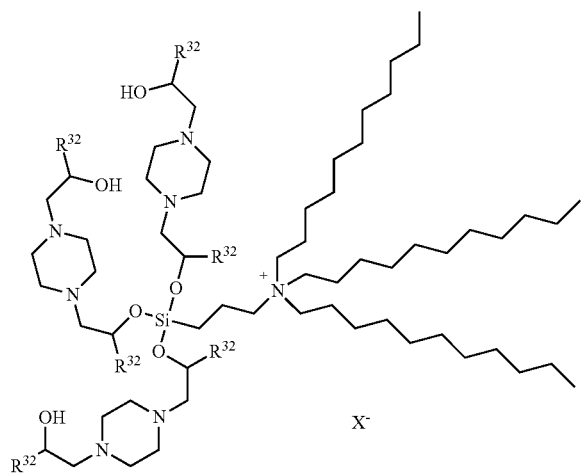
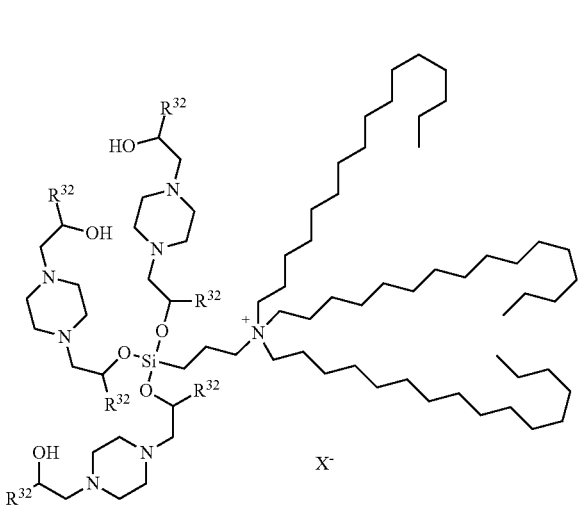

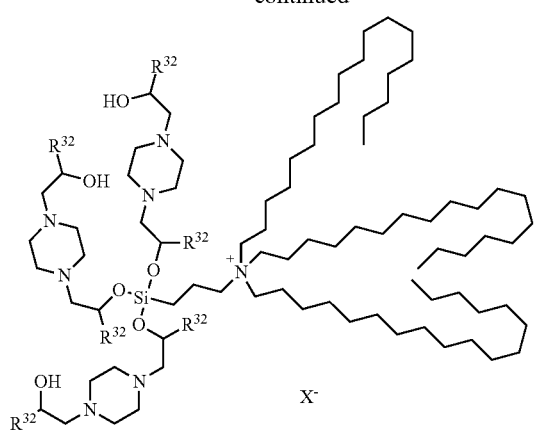 and 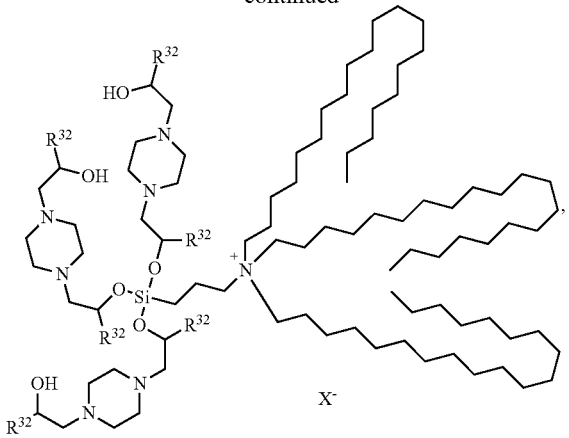
or any alternative protonation state thereof, as is available at a pH of 6-8, with additional $B^+$ or $X^-$ counterions as appropriate to reach charge balance.
In certain embodiments, the compound of the present invention is selected from:
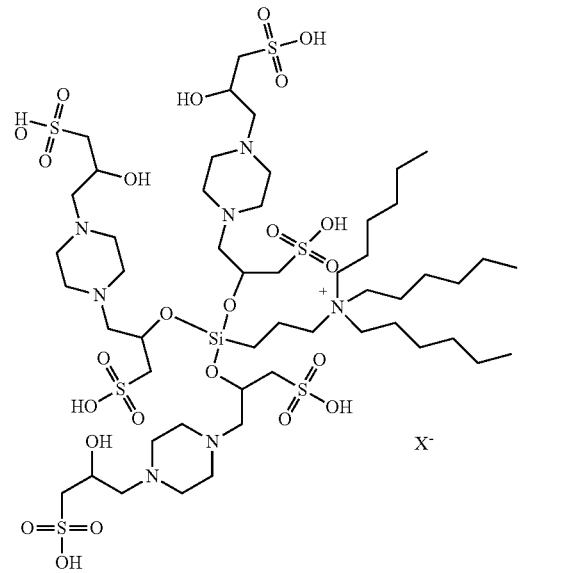
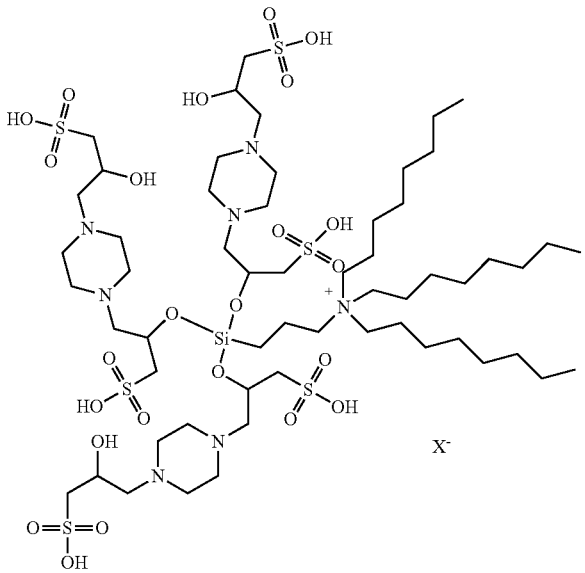
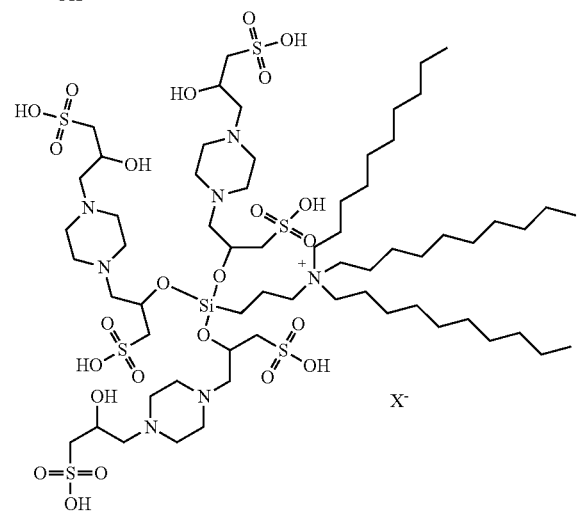
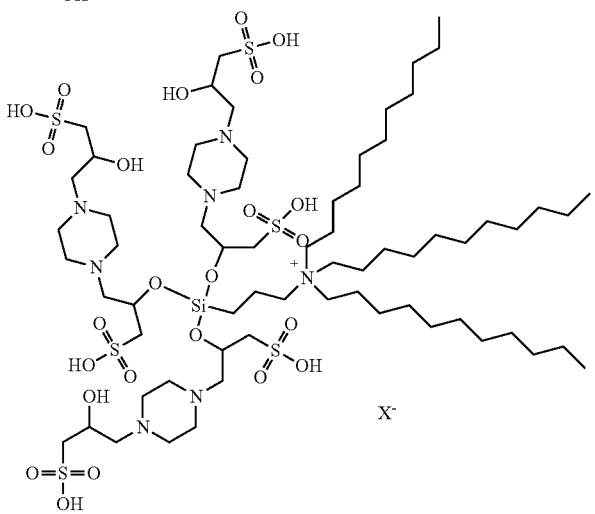

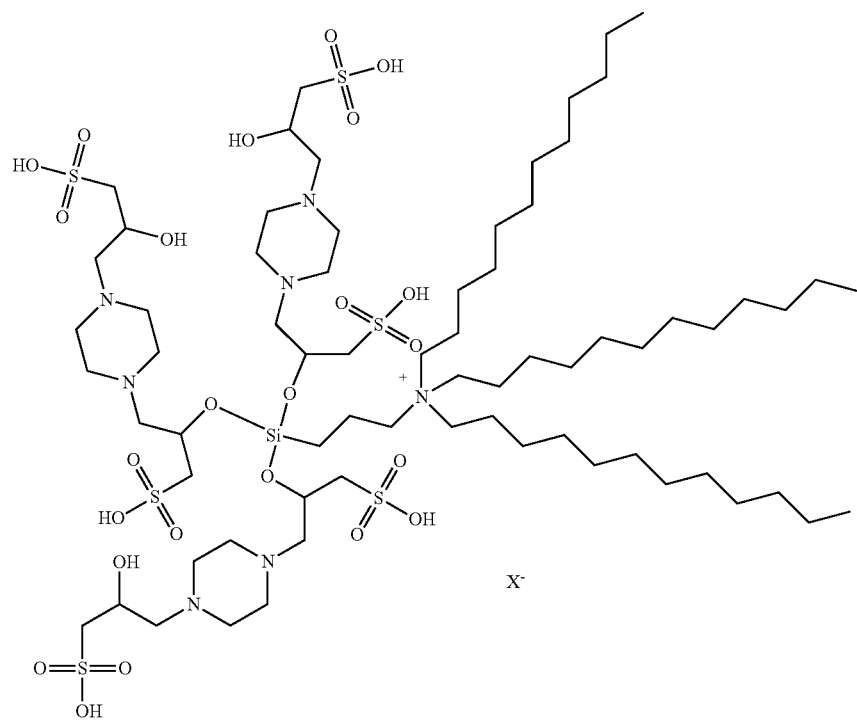
-continued
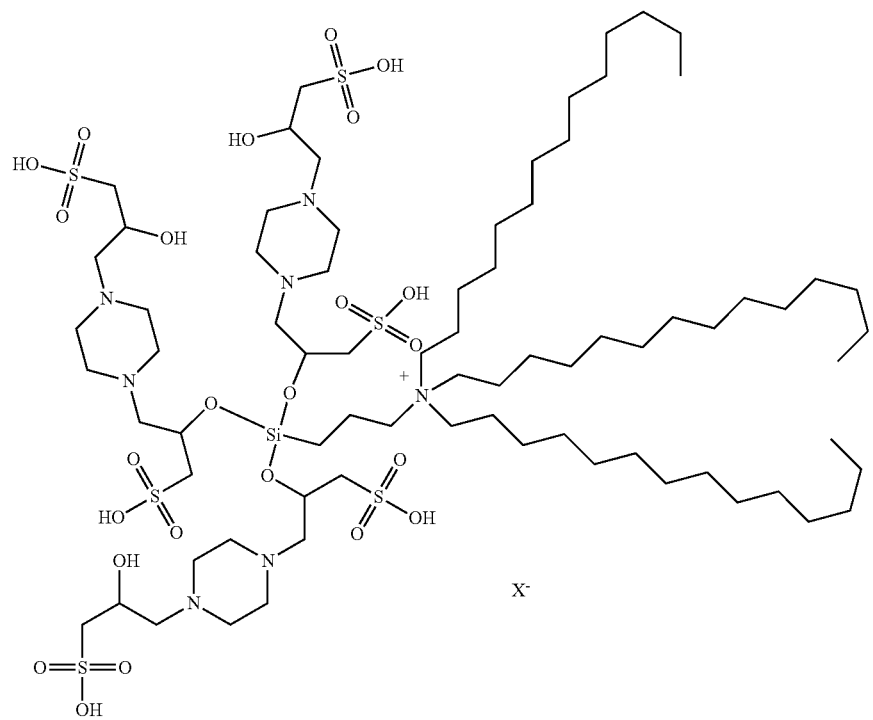

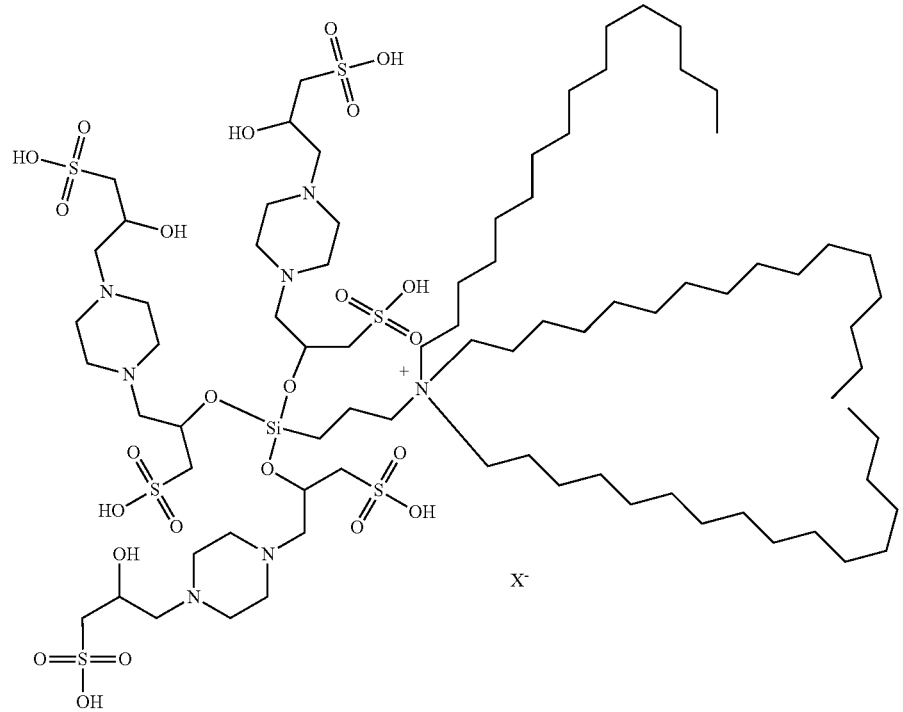
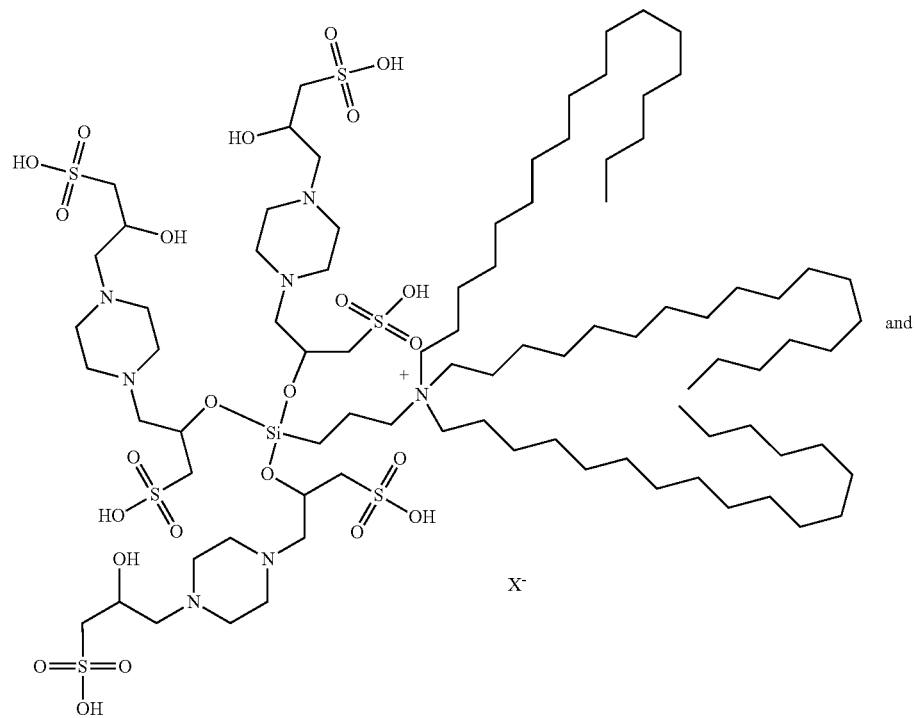

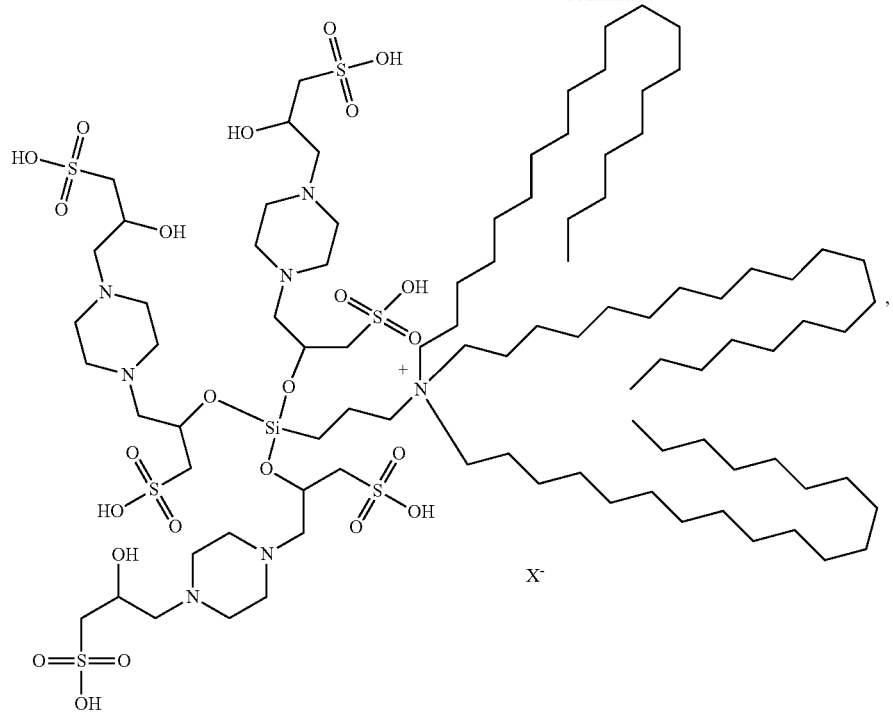
or any alternative protonation state thereof, as is available at a pH of 6-8, with additional B⁺ or X⁻ counterions as appropriate to reach charge balance.
In certain embodiments, the compound of the present invention is selected from:
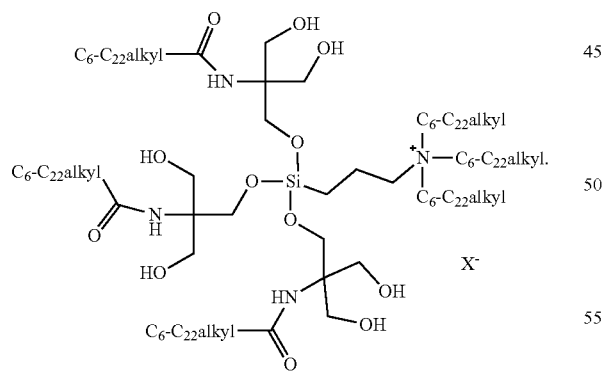
In certain embodiments the compound of the present invention is selected from:

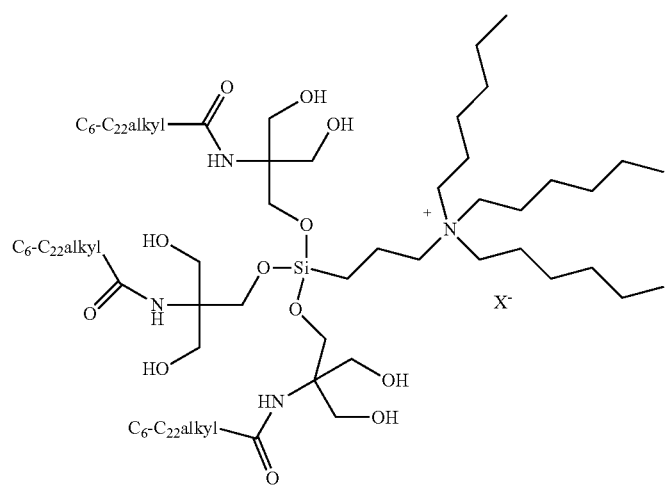
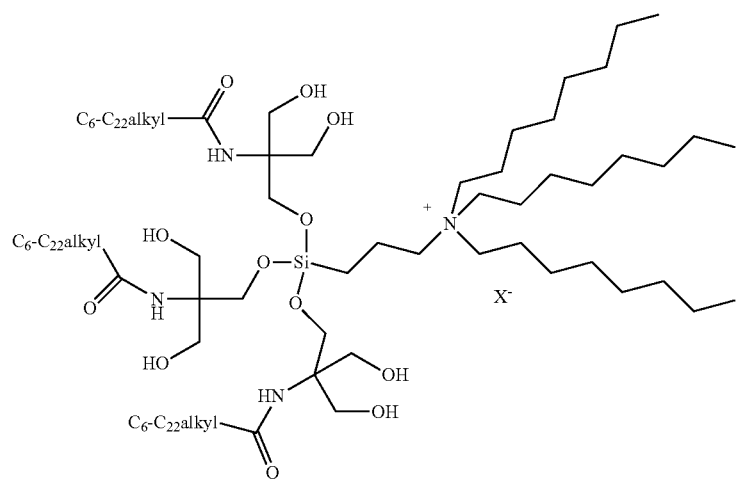
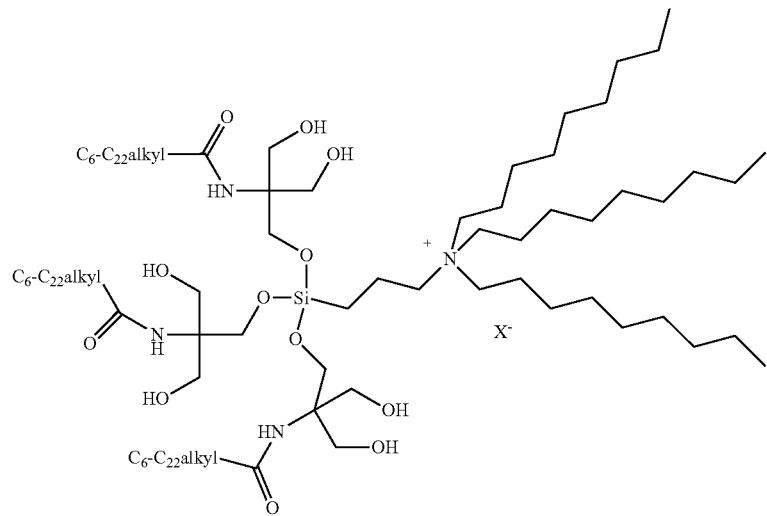

-continued
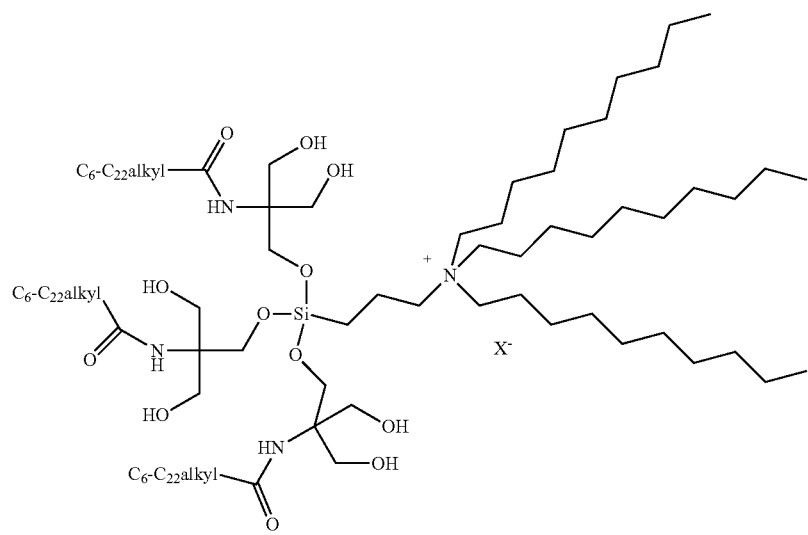
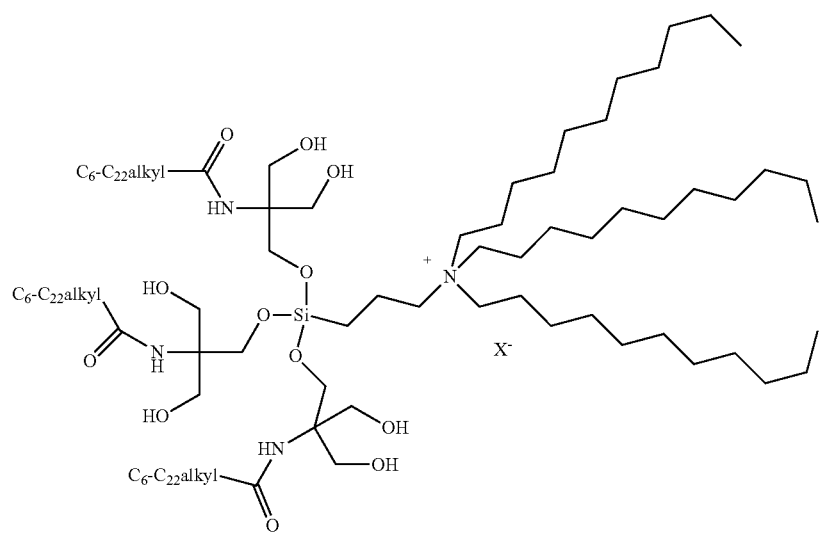
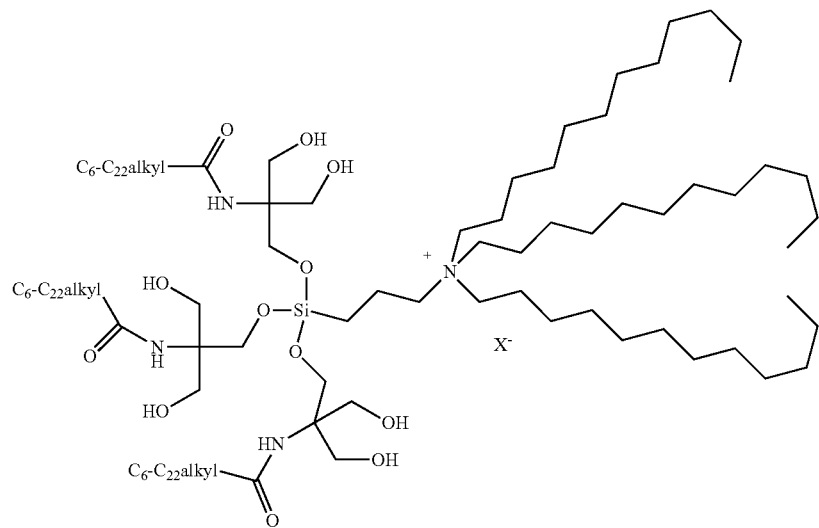

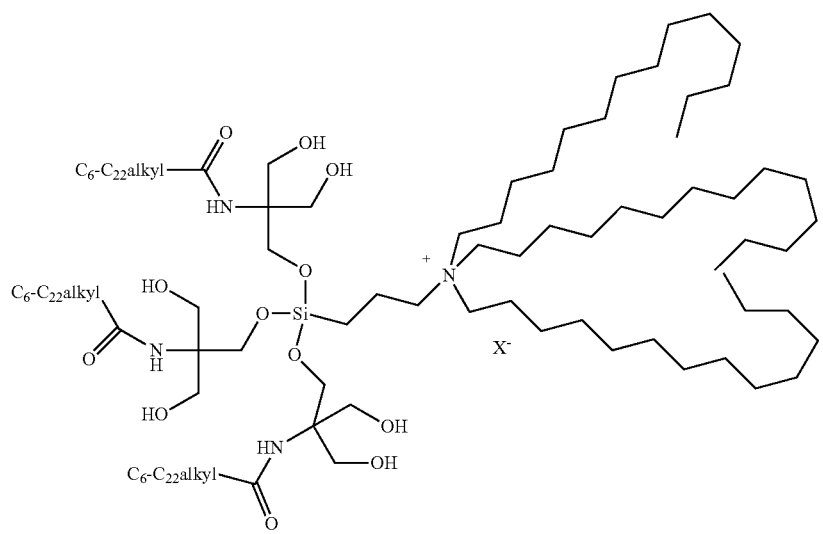
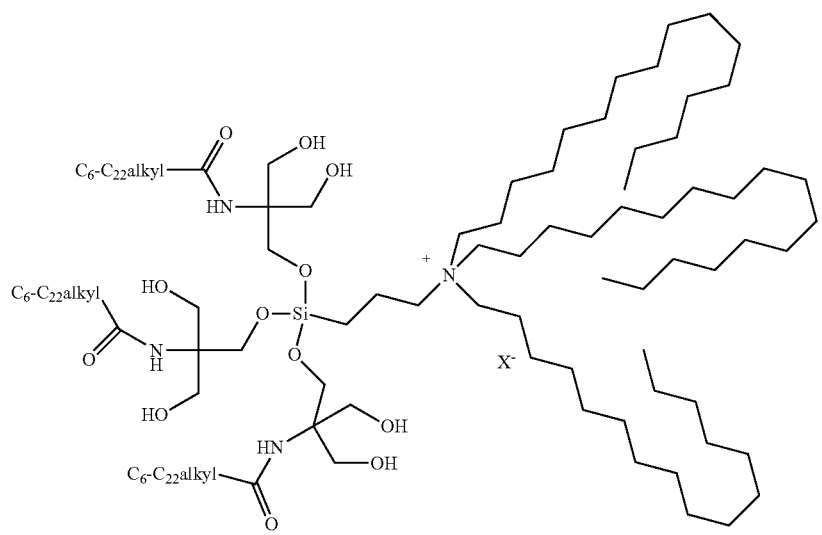
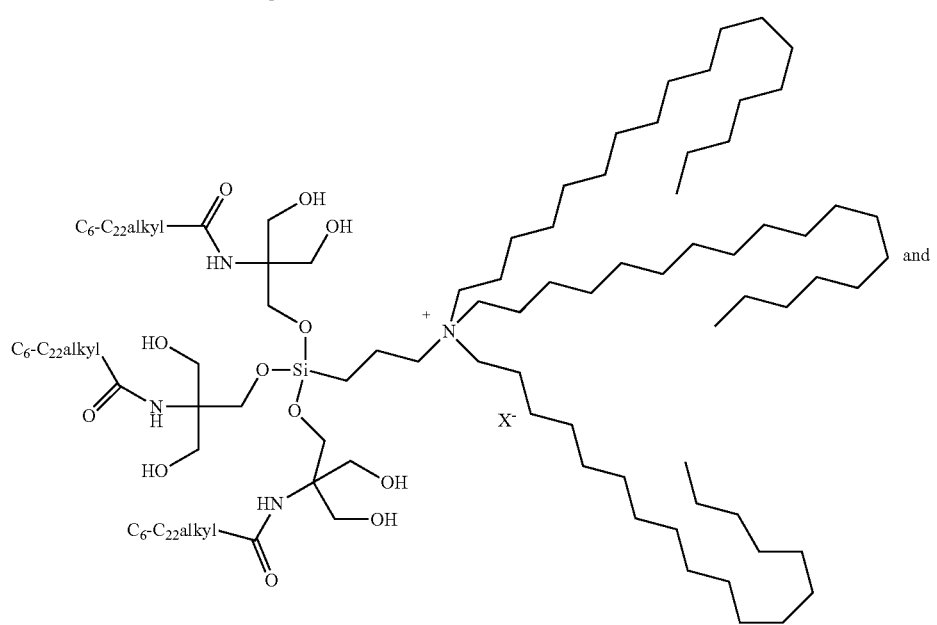

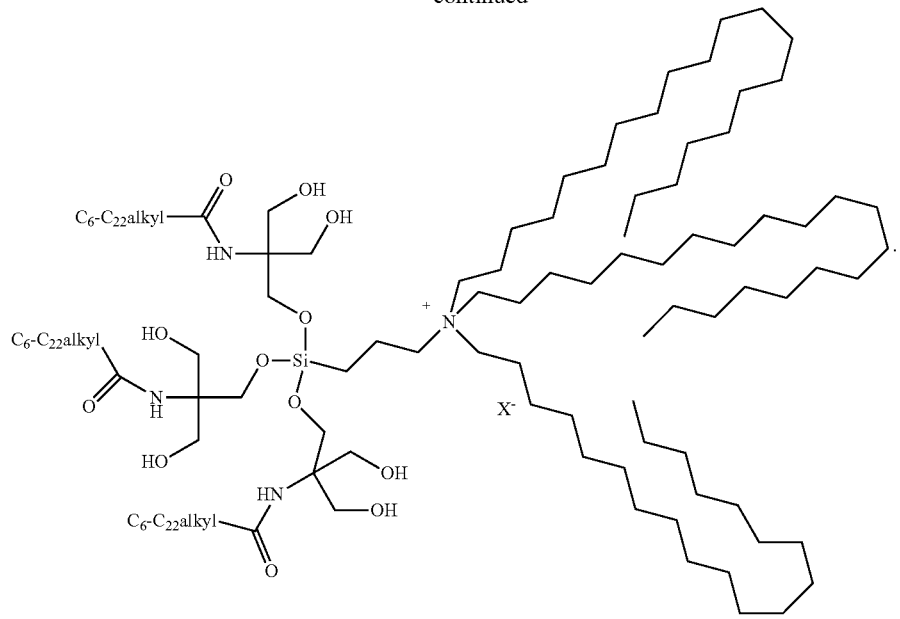

In some embodiments, the present invention provides a quaternary ammonium compound having a Formula:

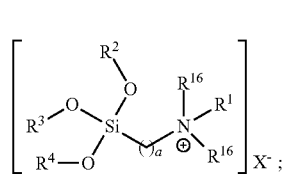

Wherein all variables are as defined herein.

In certain embodiments of Formula I, $R^2$, $R^3$ and $R^4$ are independently selected from:

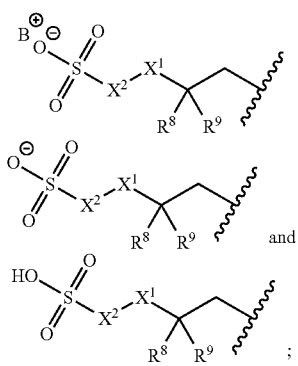

wherein $R^8$, $R^9$, $X^1$, $X^2$, and $B^+$ are as defined herein.

In certain embodiment, $R^8$ and $R^9$ are independently selected from hydrogen, hydroxyl, $C_1$-$C_8$alkyl, and $C_1$-$C_8$hydroxyalkyl.

In certain embodiments, $X^1$ is NH.
In certain embodiments, $X^1$ is $NR^{17}$; wherein $R^{17}$ is a $C_1$-$C_8$ hydroxyalkyl.
In certain embodiments, $X^1$ is $CH_2$.
In certain embodiments, $X^2$ is a $C_1$-$C_3$alkyl.
In certain embodiments, $X^2$ is a $C_1$-$C_3$hydroxyalkyl.

In certain embodiments of Formula I,

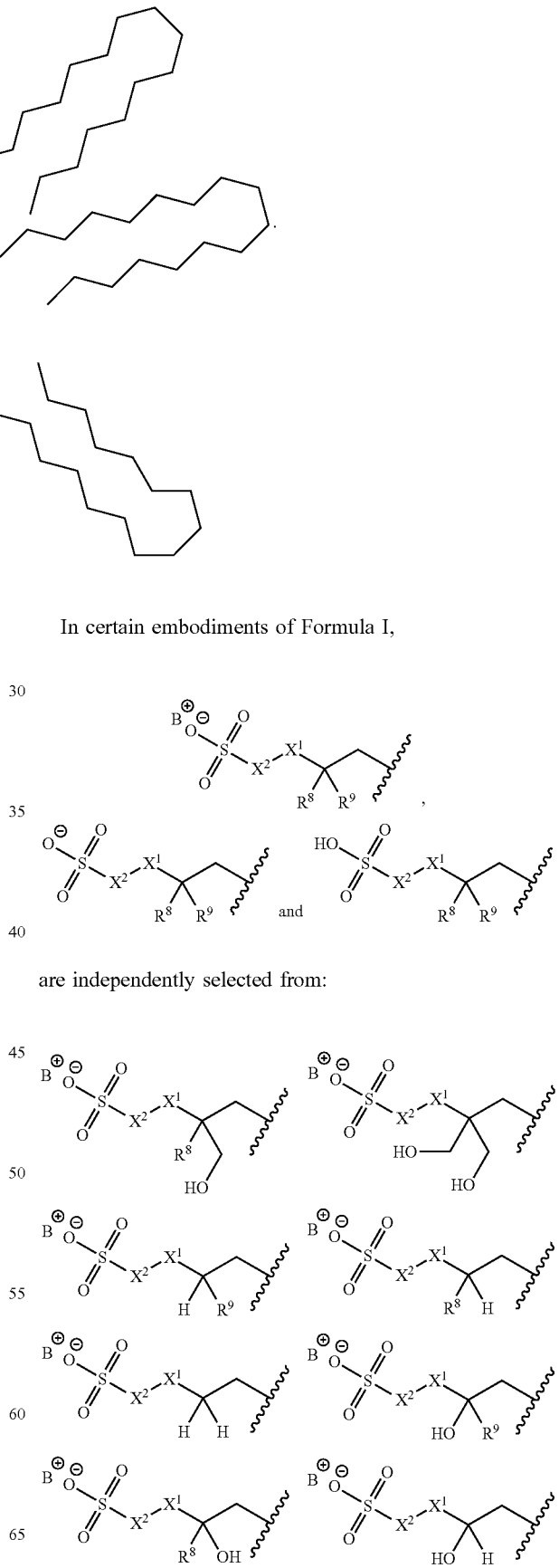

are independently selected from:

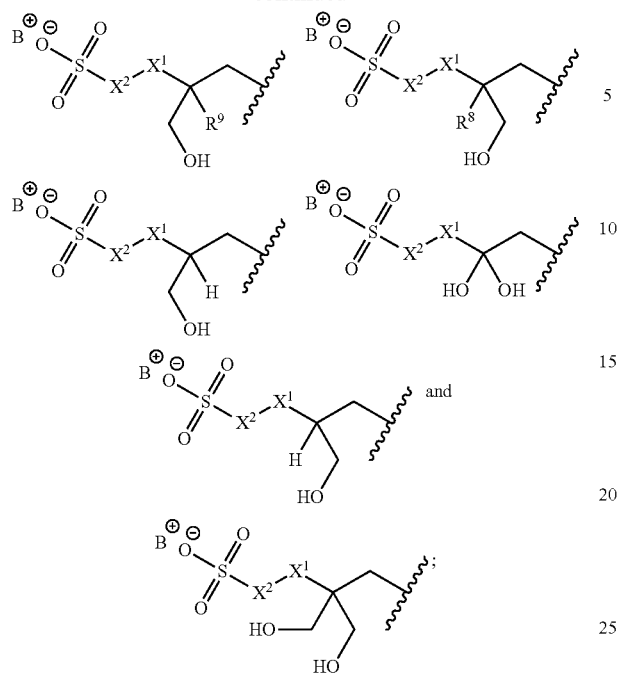
and wherein B⁺ can optionally be replaced with a H⁺ or B⁺ is absent and the moiety is anionic.
In certain embodiments of Formula I,
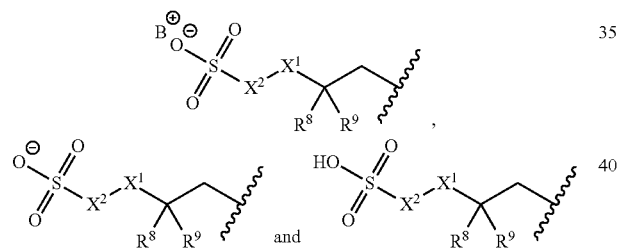
are independently selected from:
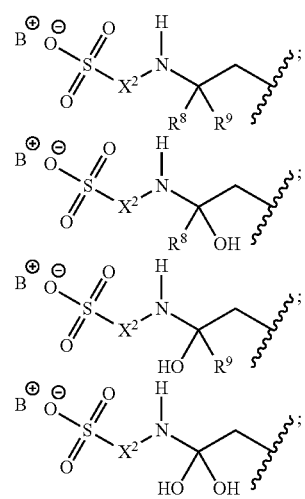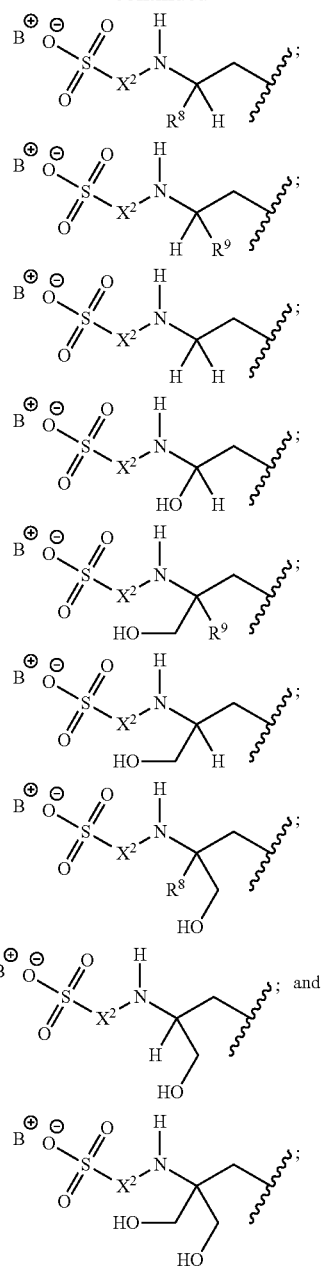
and wherein B⁺ can optionally be replaced with a H⁺ or B⁺ is absent and the moiety is anionic.
In certain embodiments of Formula I,
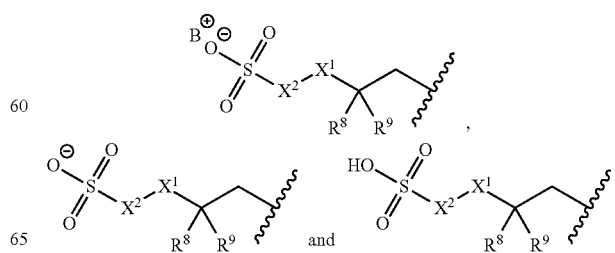

are independently selected from:
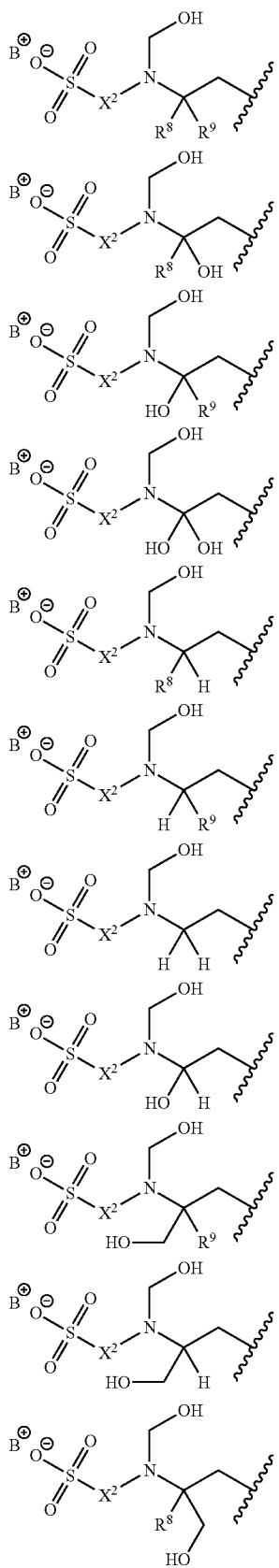
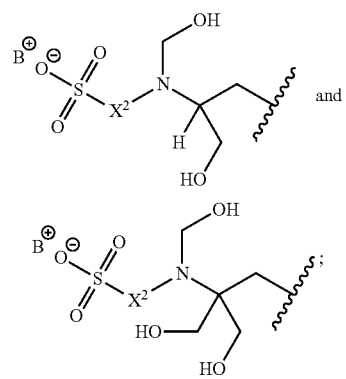
and wherein B⁺ can optionally be replaced with a H⁺ or B⁺ is absent and the moiety is anionic.
In certain embodiments of Formula I,
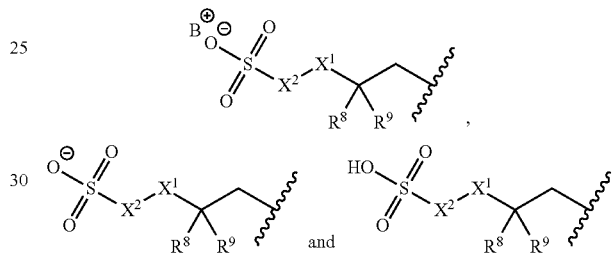
are independently selected from:
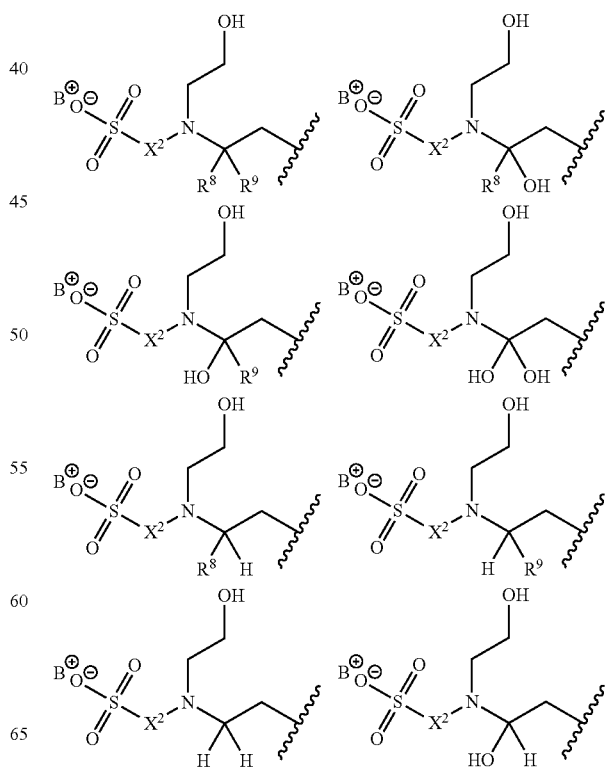

-continued
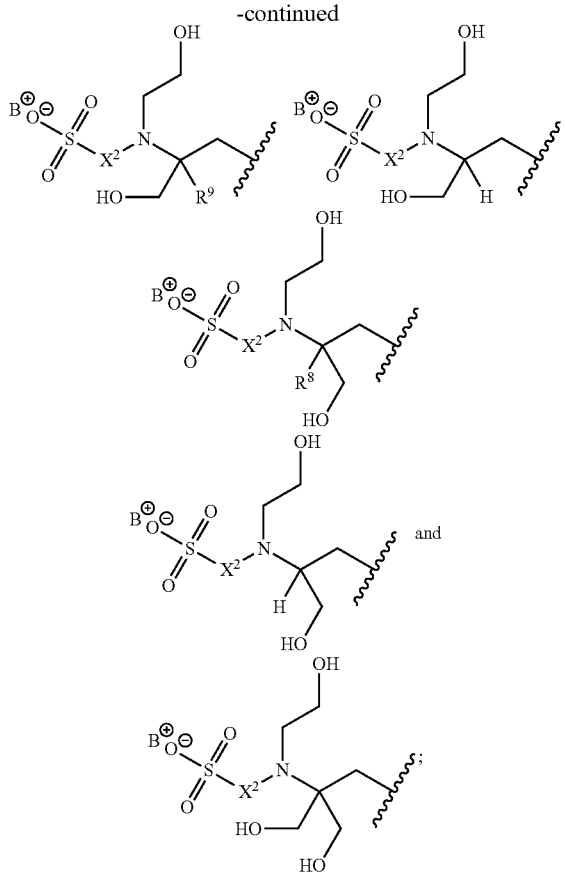
and wherein B⁺ can optionally be replaced with a H⁺ or B⁺ is absent and the moiety is anionic.
In certain embodiments of Formula I,
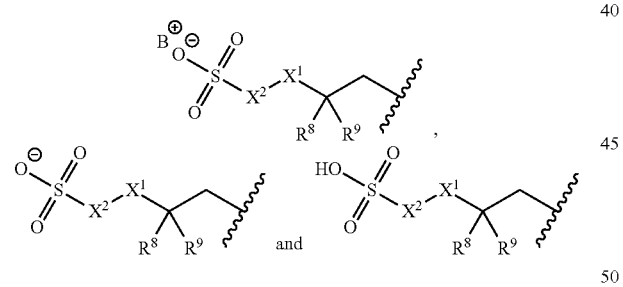
are independently selected from:
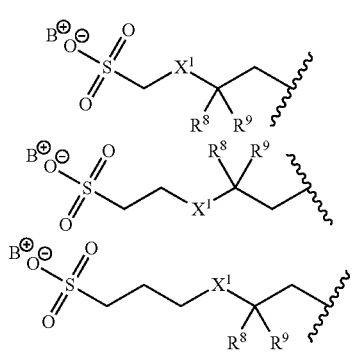
-continued
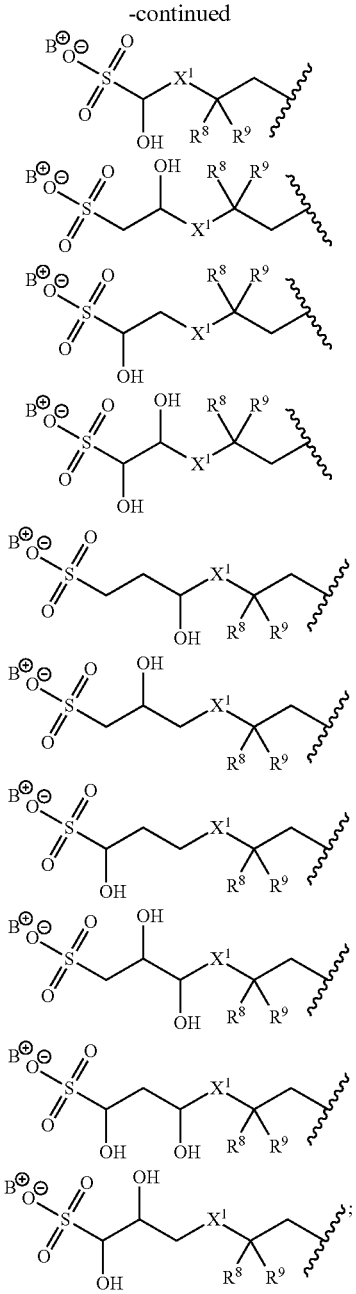
and wherein B⁺ can optionally be replaced with a H⁺ or B⁺ is absent and the moiety is anionic.
In certain embodiments of Formula I,
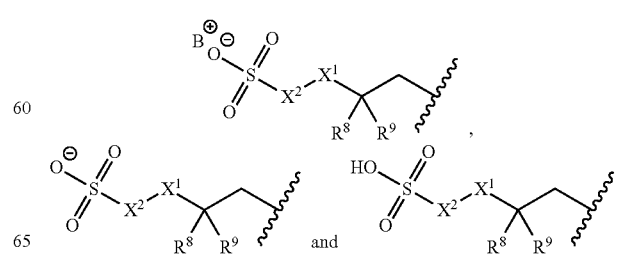

are independently selected from:
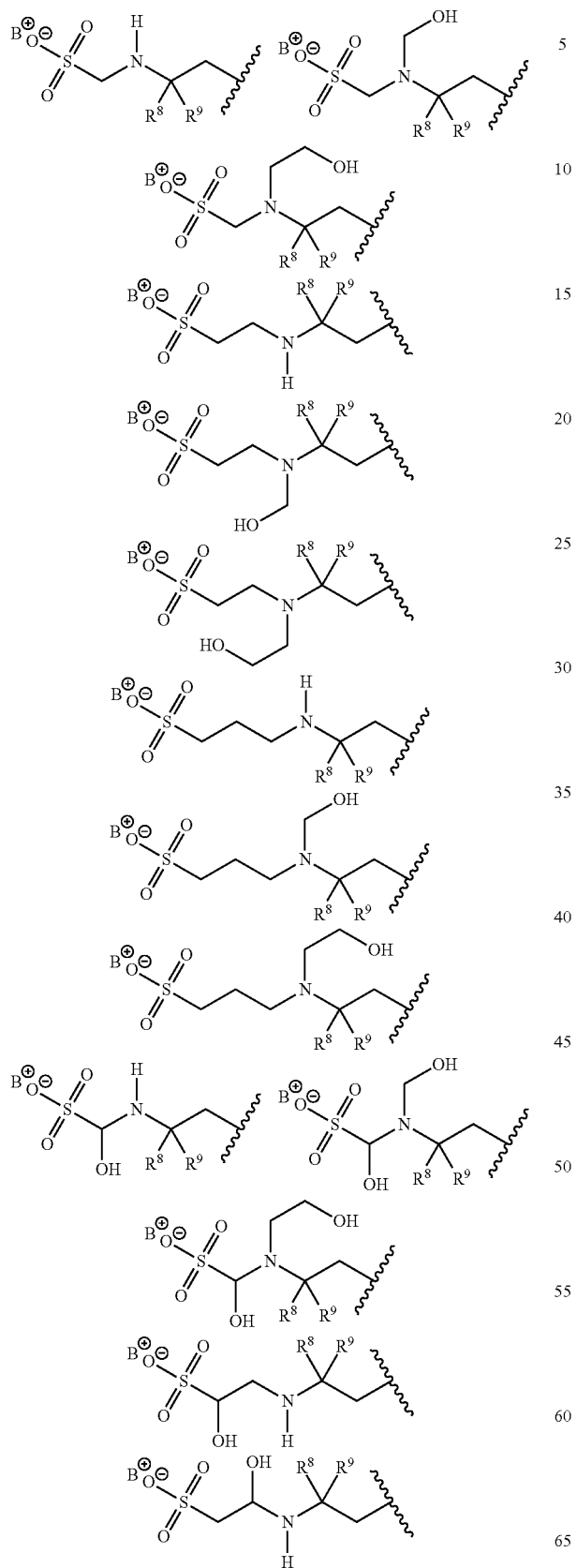
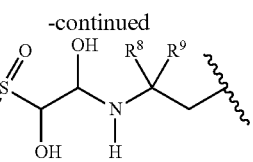
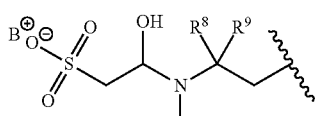
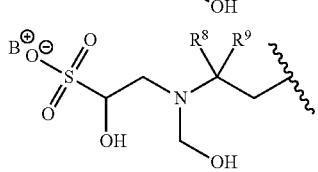
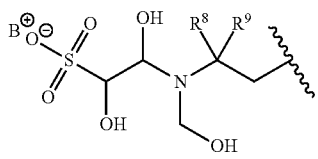
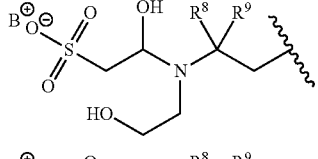
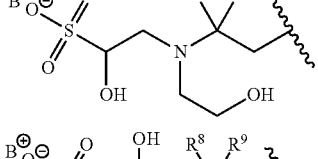
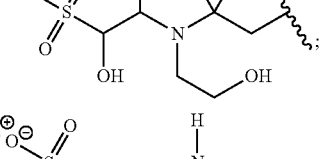
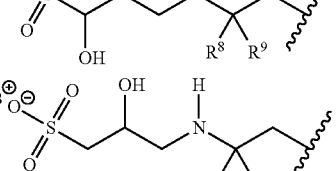
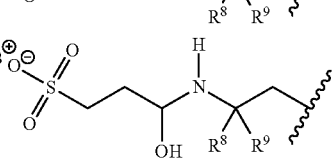
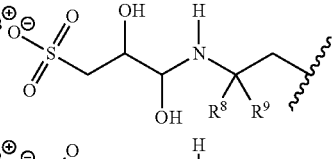
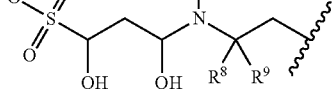

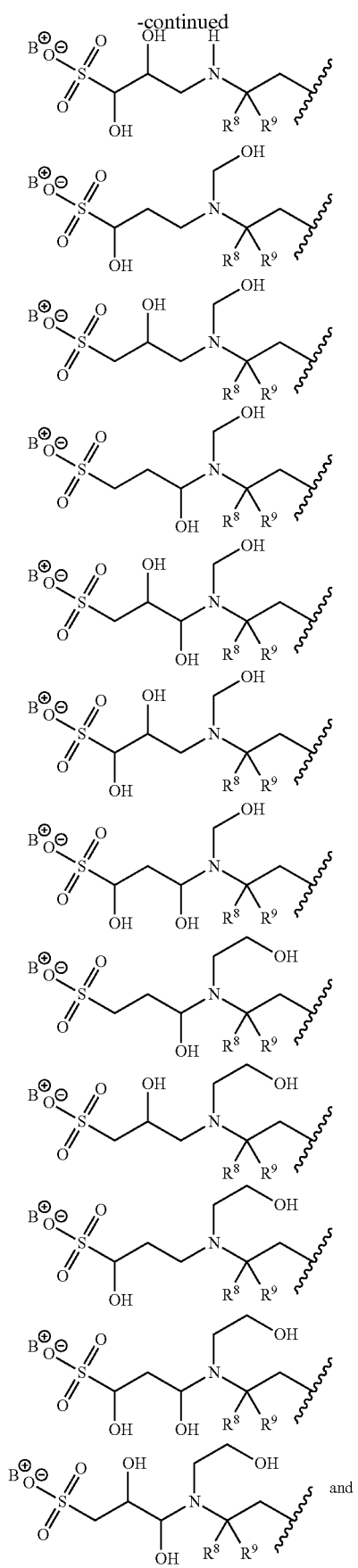
and
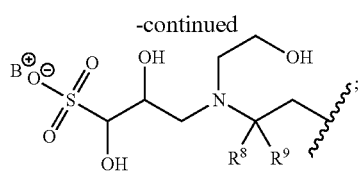
and wherein B⁺ can optionally be replaced with a H⁺ or B⁺ is absent and the moiety is anionic.
In certain embodiments of Formula I,
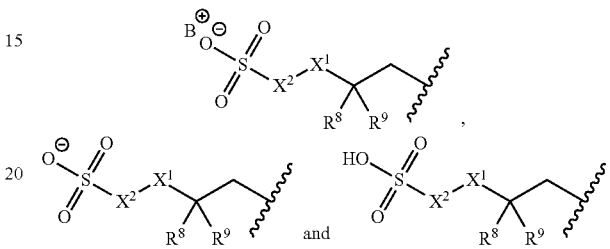
are independently selected from:
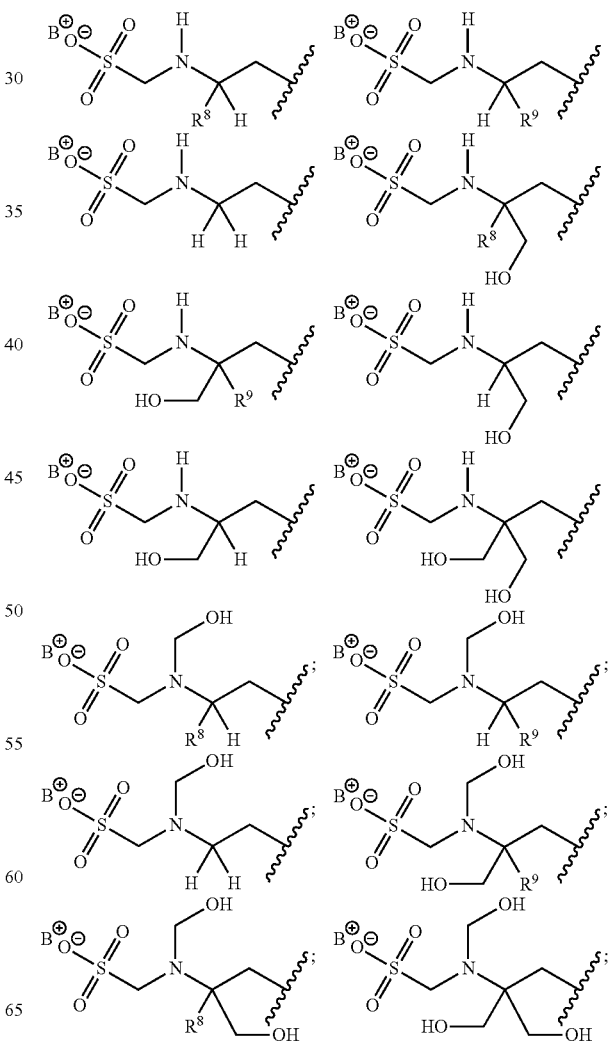

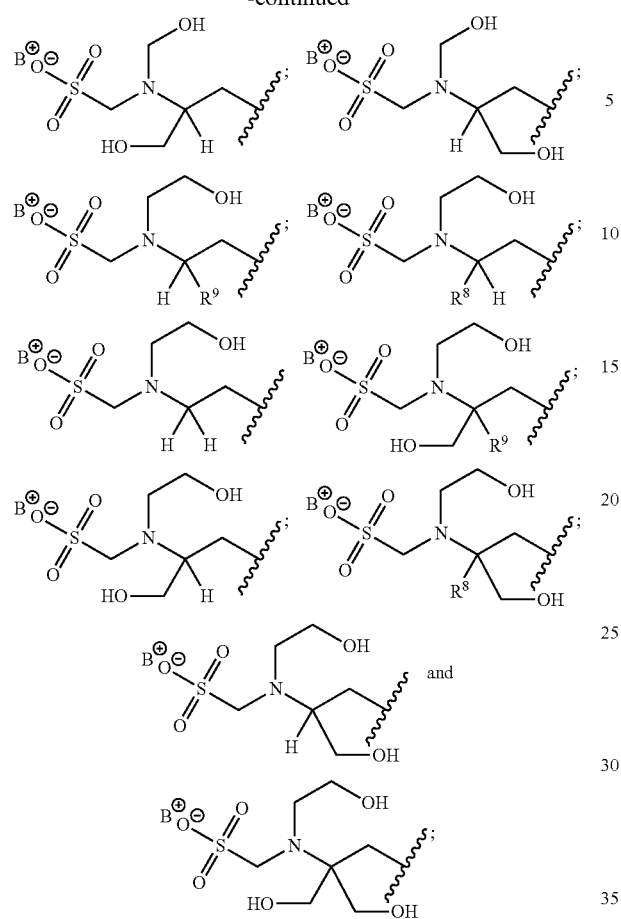
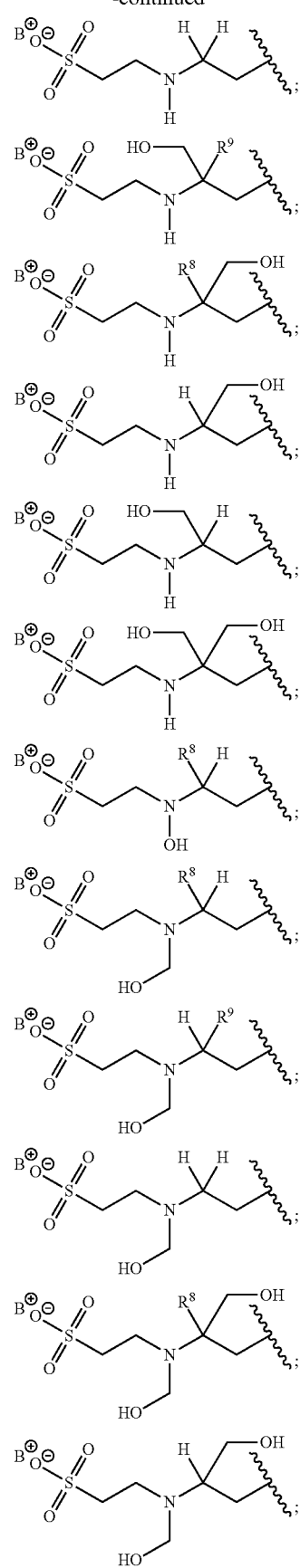
and wherein B⁺ can optionally be replaced with a H⁺ or B⁺ is absent and the moiety is anionic.
In certain embodiments of Formula I,
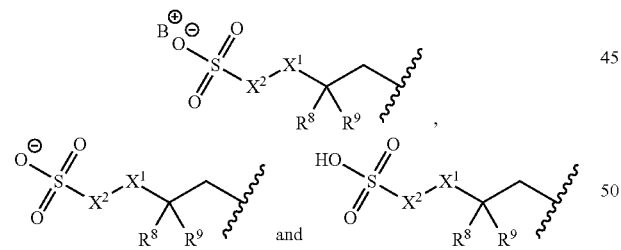
are independently selected from:
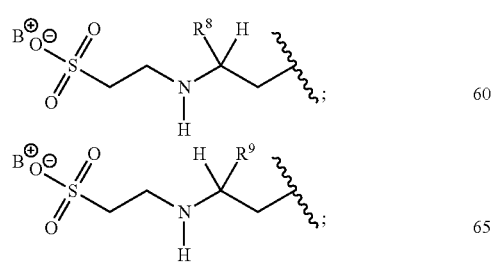

-continued
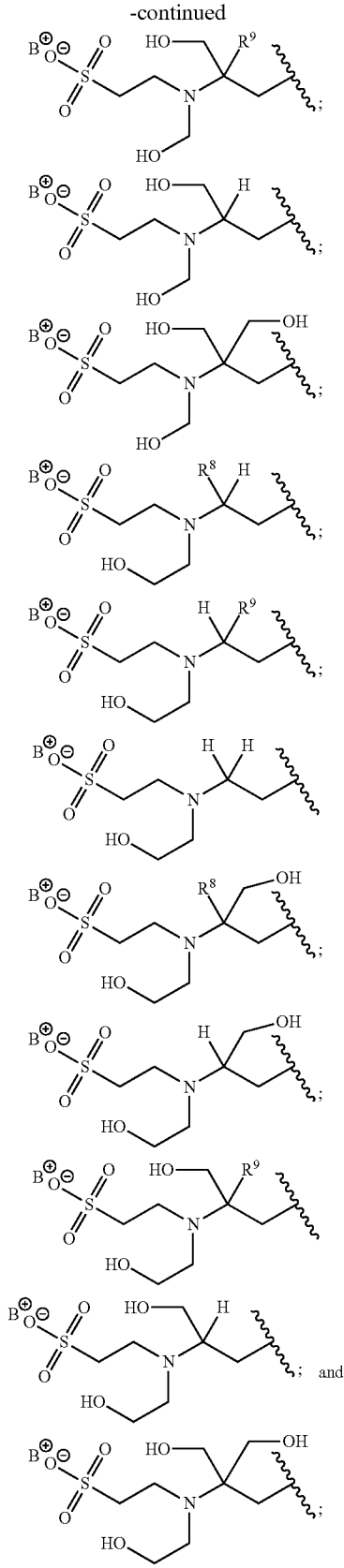
and wherein B⁺ can optionally be replaced with a H⁺ or B⁺ is absent and the moiety is anionic.
In certain embodiments of Formula I,
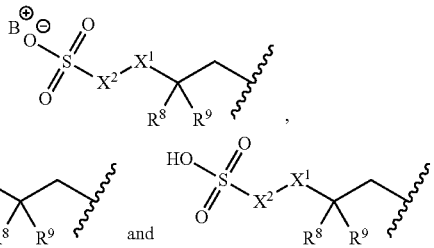
are independently selected from:
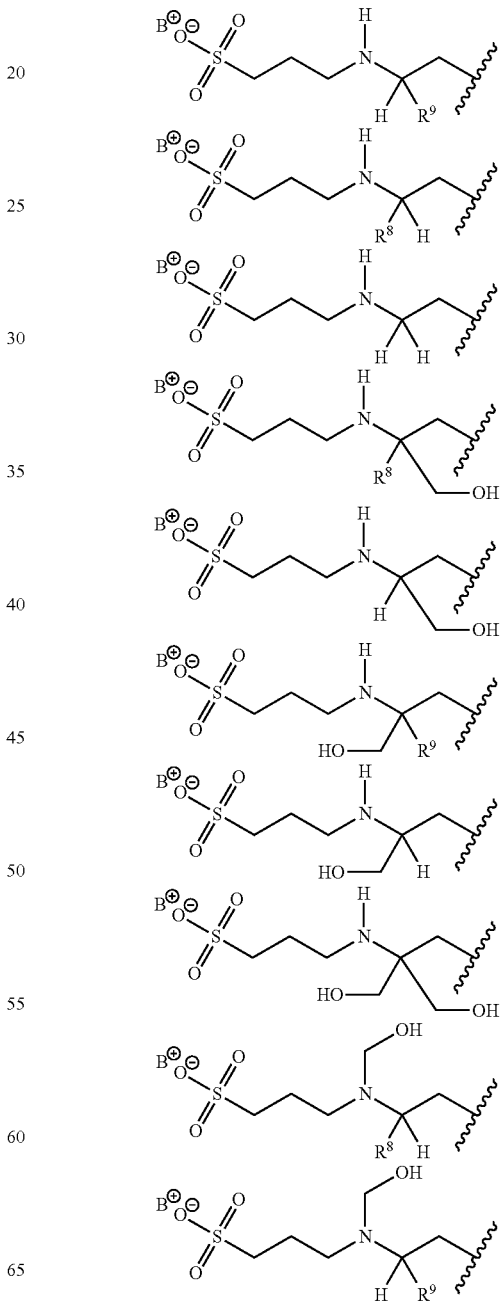

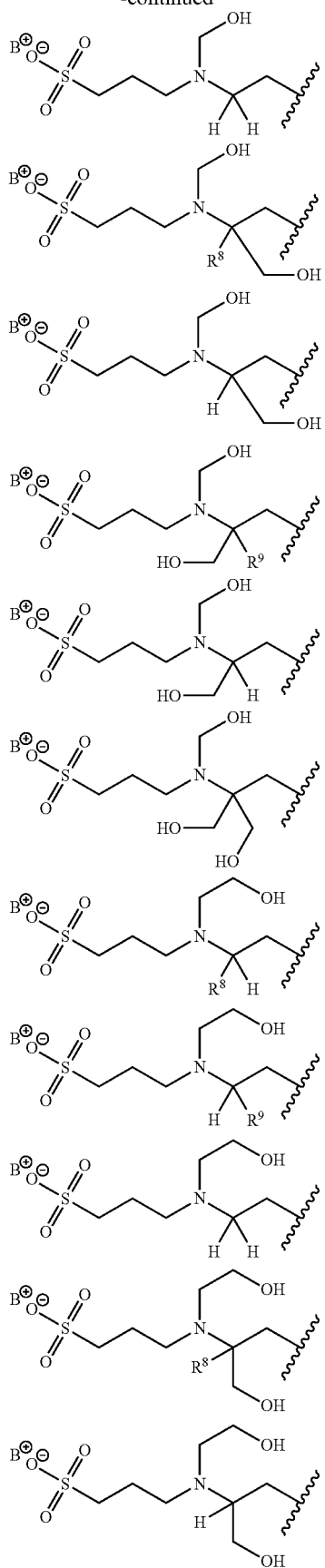
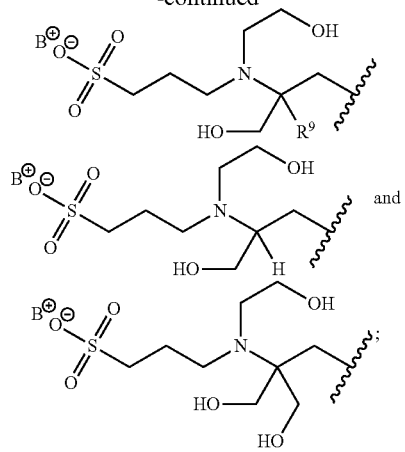
and wherein B⁺ can optionally be replaced with a H⁺ or B⁺ is absent and the moiety is anionic.
In certain embodiments of Formula I,
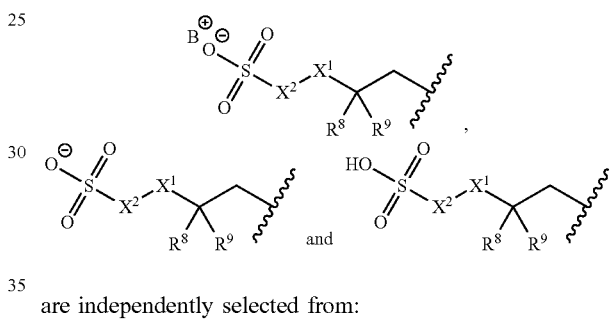
are independently selected from:
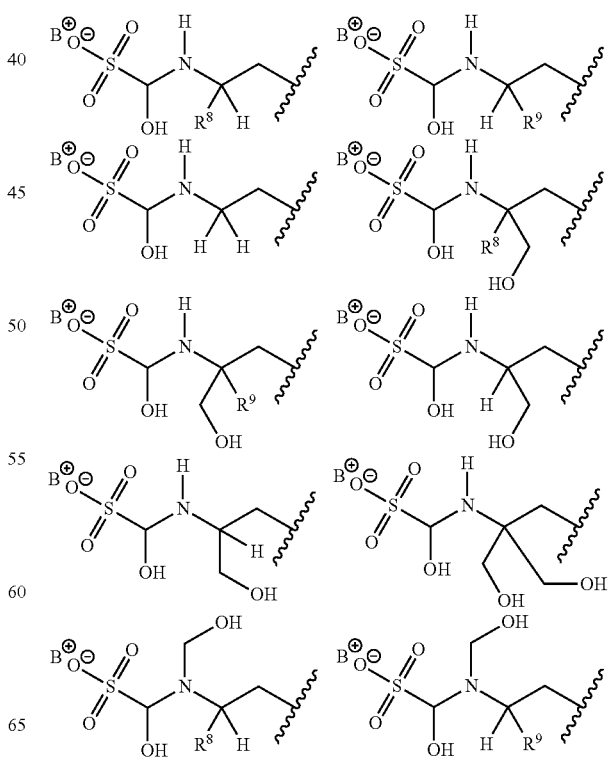

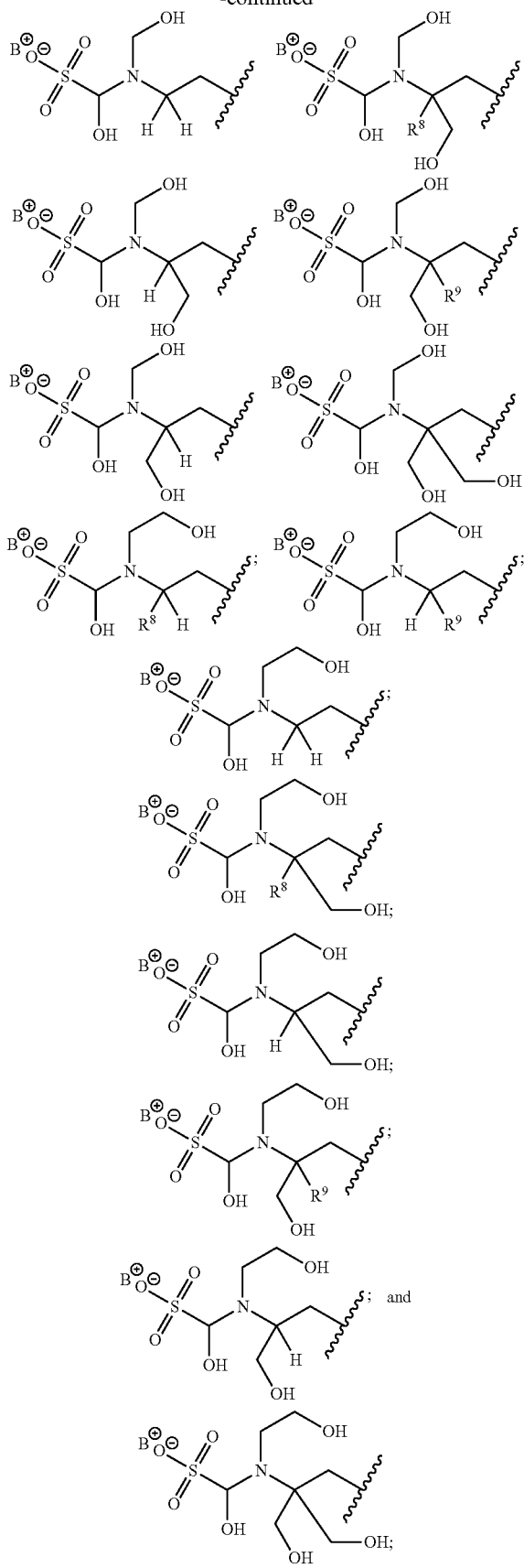
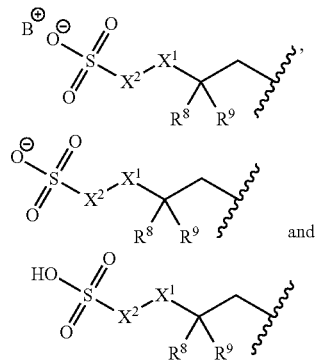
and wherein $B^+$ can optionally be replaced with a $H^+$ or $B^+$ is absent and the moiety is anionic.
In certain embodiments of Formula I,
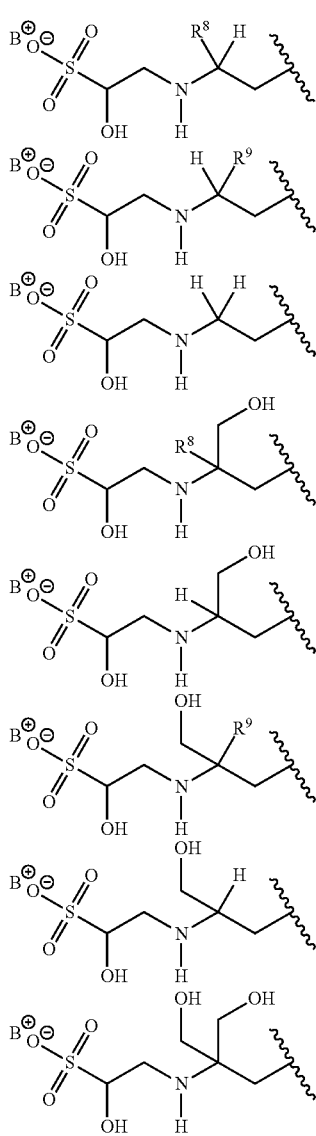
are independently selected from:

227
-continued
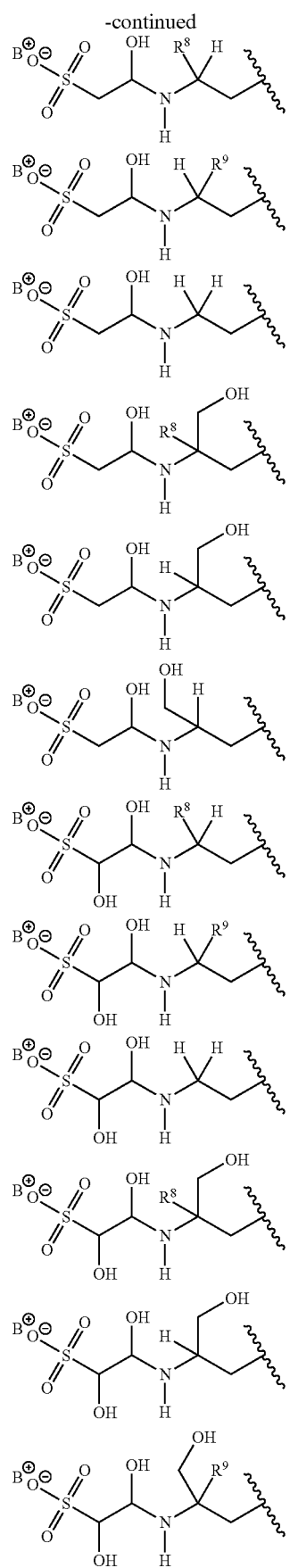
228
-continued
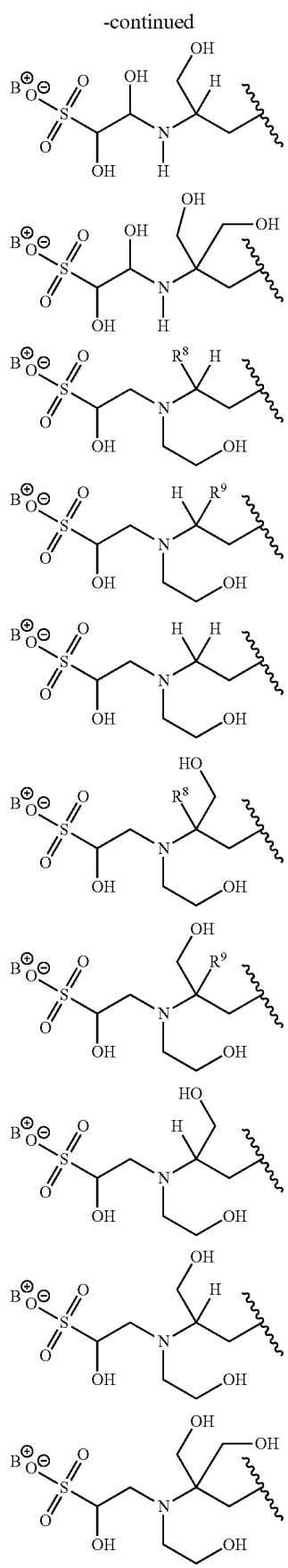

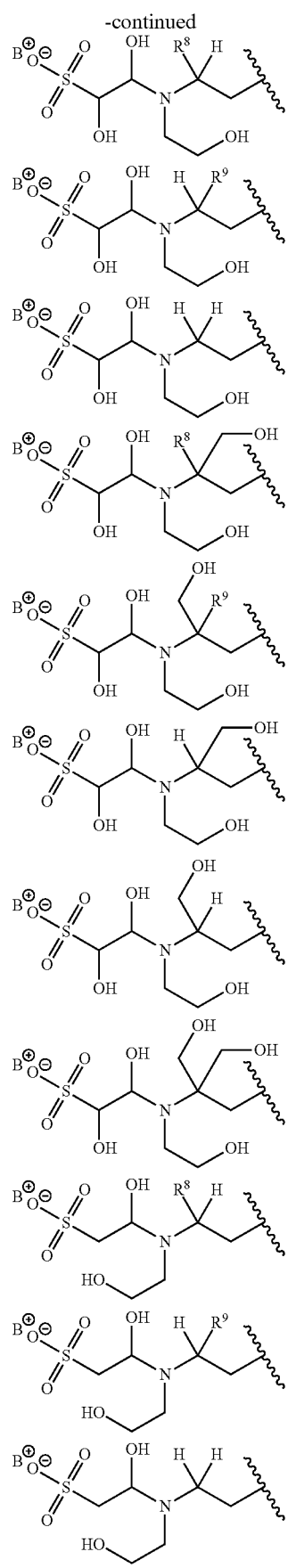
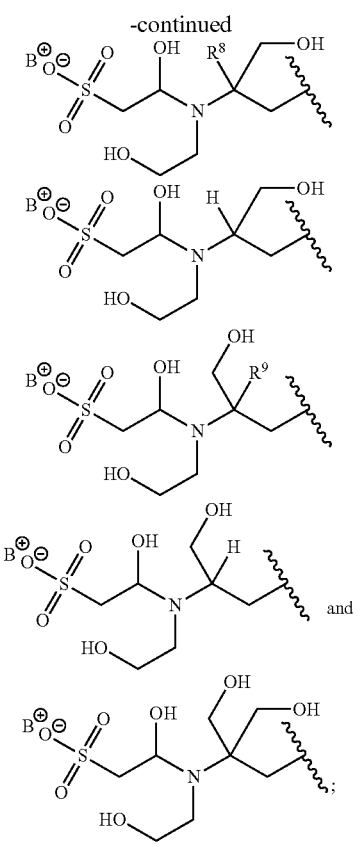
and wherein B⁺ can optionally be replaced with a H⁺ or B⁺ is absent and the moiety is anionic.
In certain embodiments of Formula I,
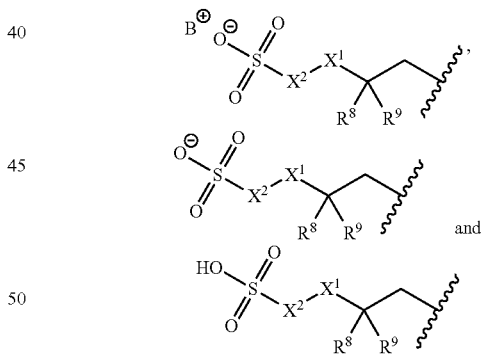
are independently selected from:
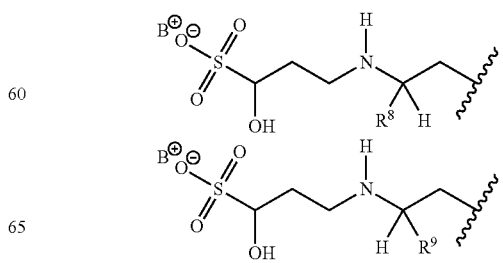

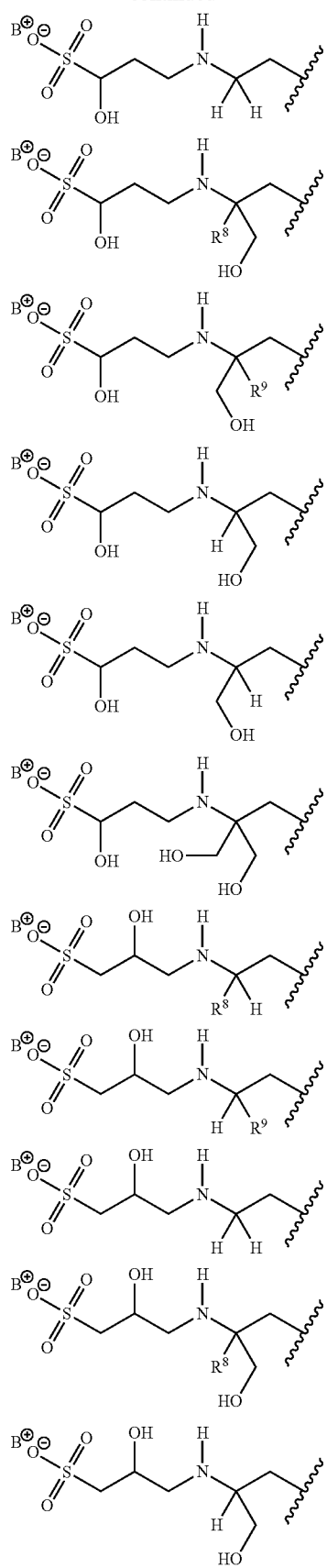
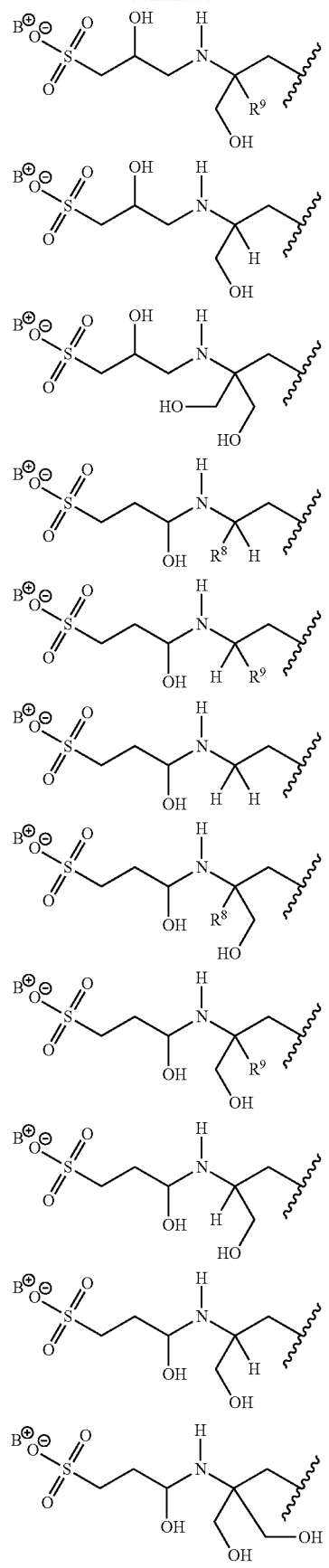

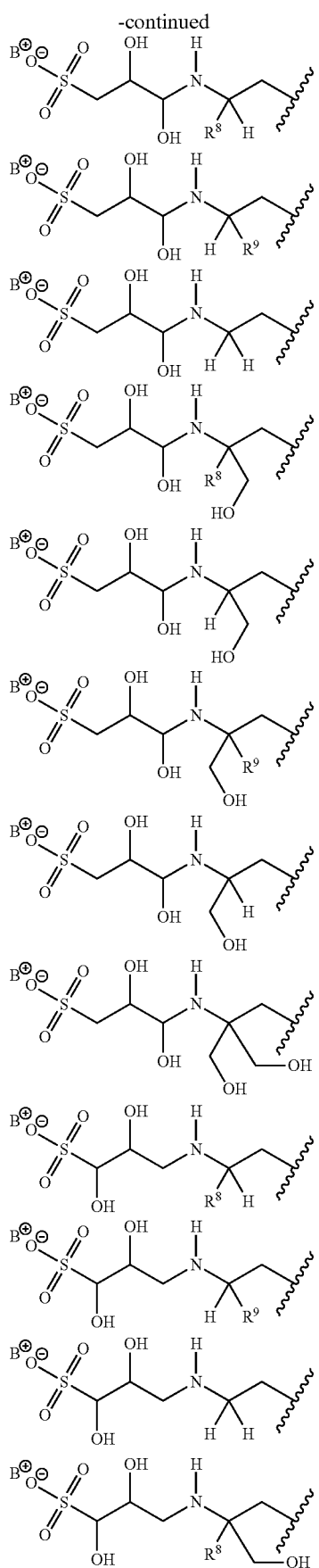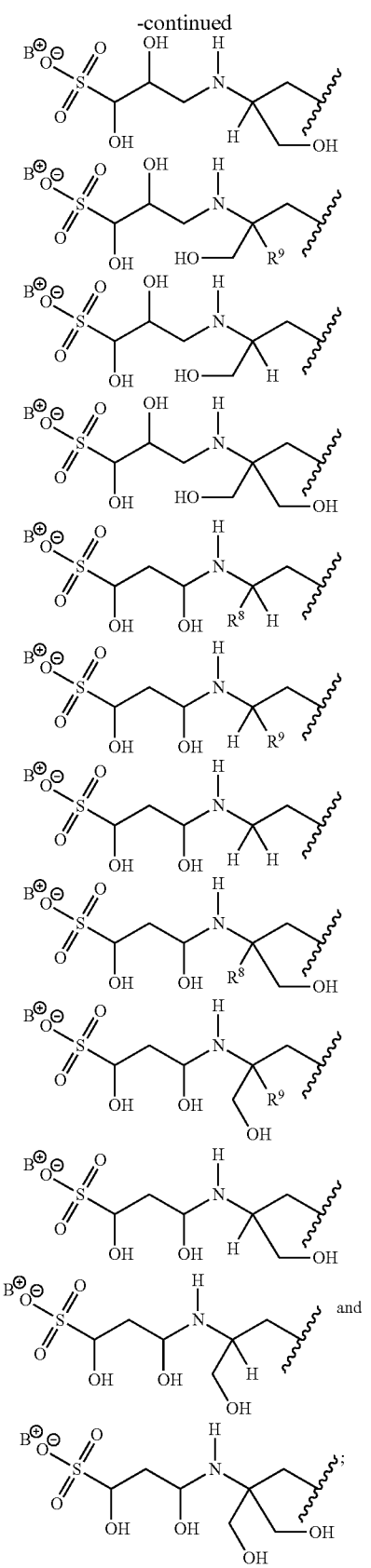
and wherein B⁺ can optionally be replaced with a H⁺ or B⁺ is absent and the moiety is anionic.

In certain embodiments of Formula I,
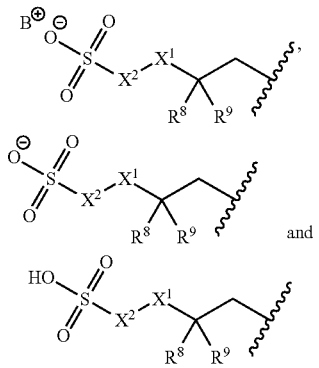
are independently selected from:
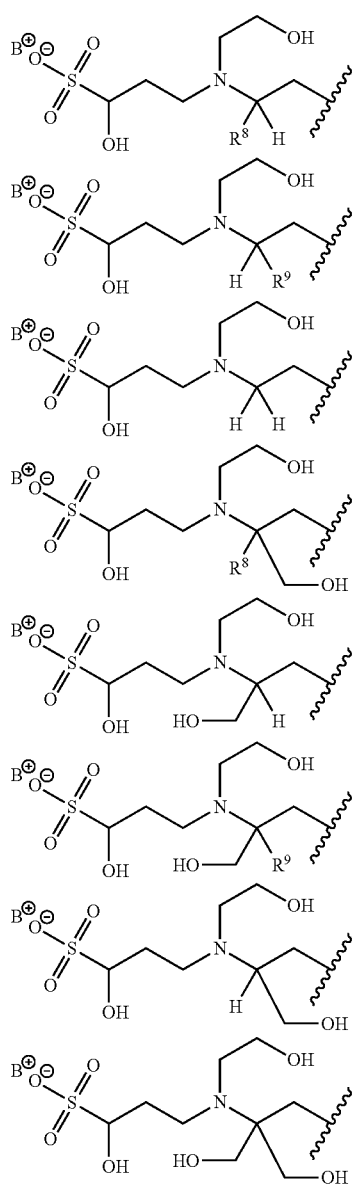
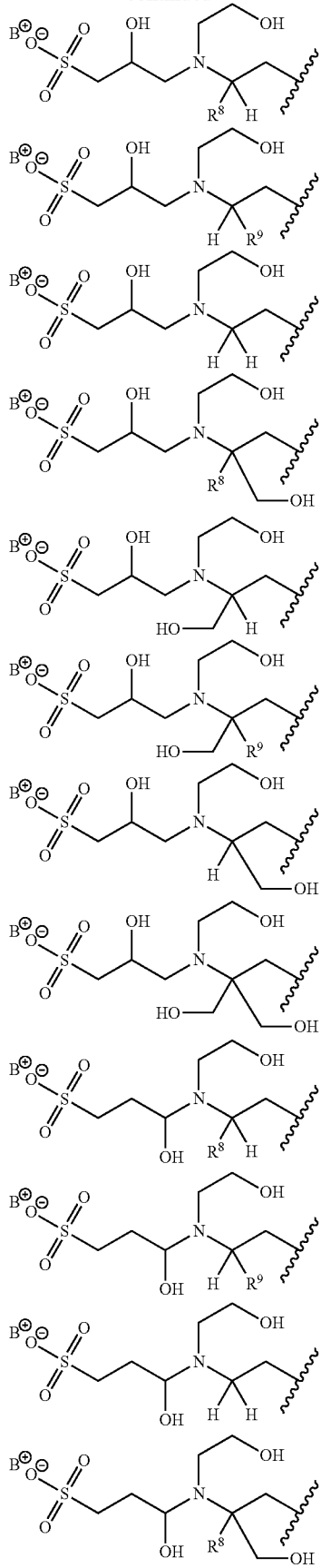

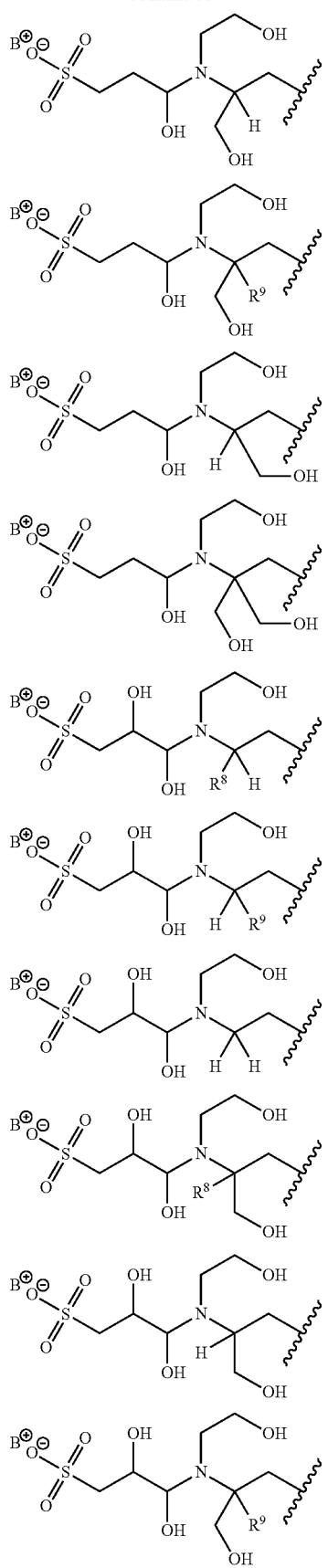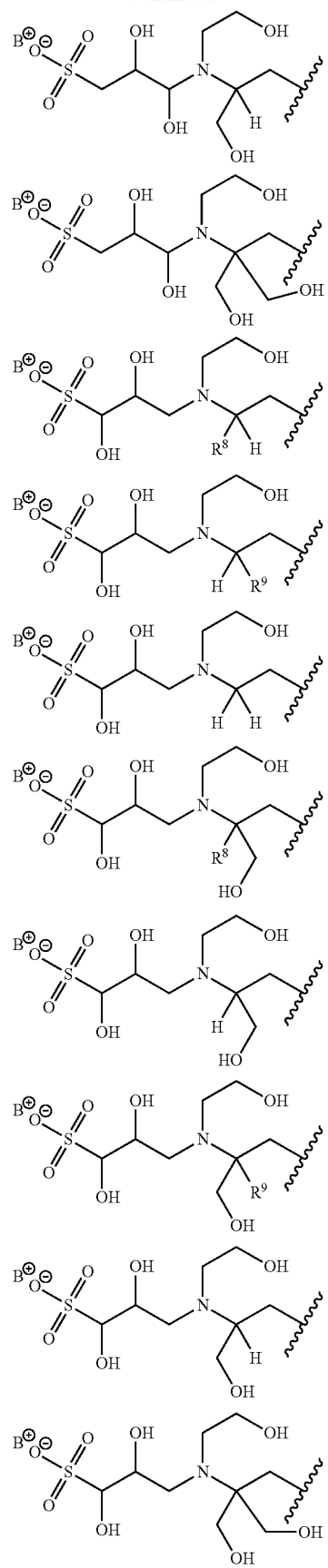

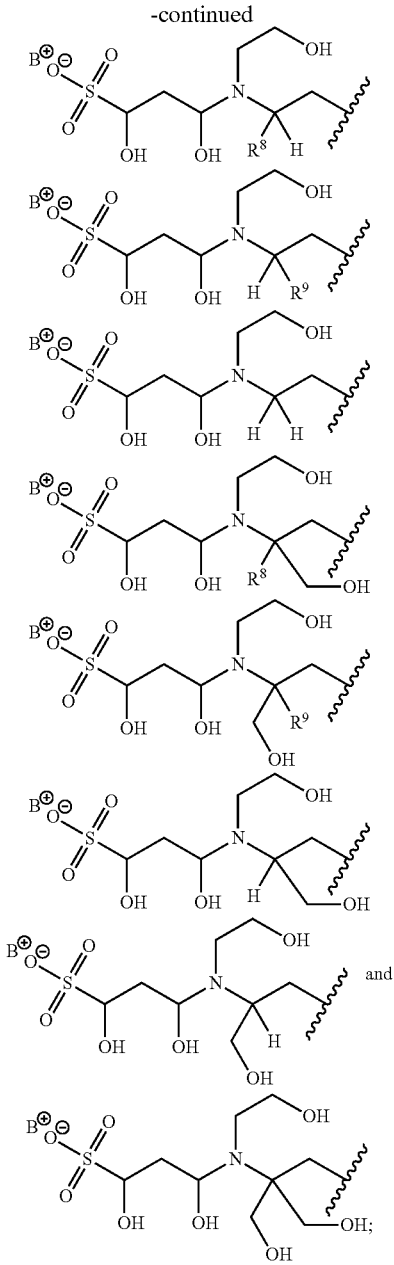

and wherein B⁺ can optionally be replaced with a H or B⁺ is absent and the moiety is anionic.

In certain embodiments of Formula I, $R^2$, $R^3$ and $R^4$ are independently selected from:

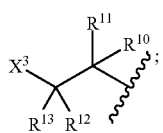

wherein $R^{10}$, $R^{11}$, $R^{12}$, $R^1$, and $X^3$ are as defined herein.

In certain embodiment, $R^{10}$ and $R^{11}$ are independently selected from hydrogen, and $C_1$-$C_8$alkyl.

In certain embodiments, $R^{12}$ and $R^{13}$ are independently selected from hydrogen, hydroxyl, $C_1$-$C_8$alkyl, COOH, and $C_1$-$C_8$hydroxyalkyl.

In certain embodiments, $X^3$ is independently selected from hydroxyl, $C_1$-$C_8$alkyl, and $C_1$-$C_8$hydroxyalkyl.

In certain embodiments of Formula I,

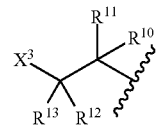

is selected from:

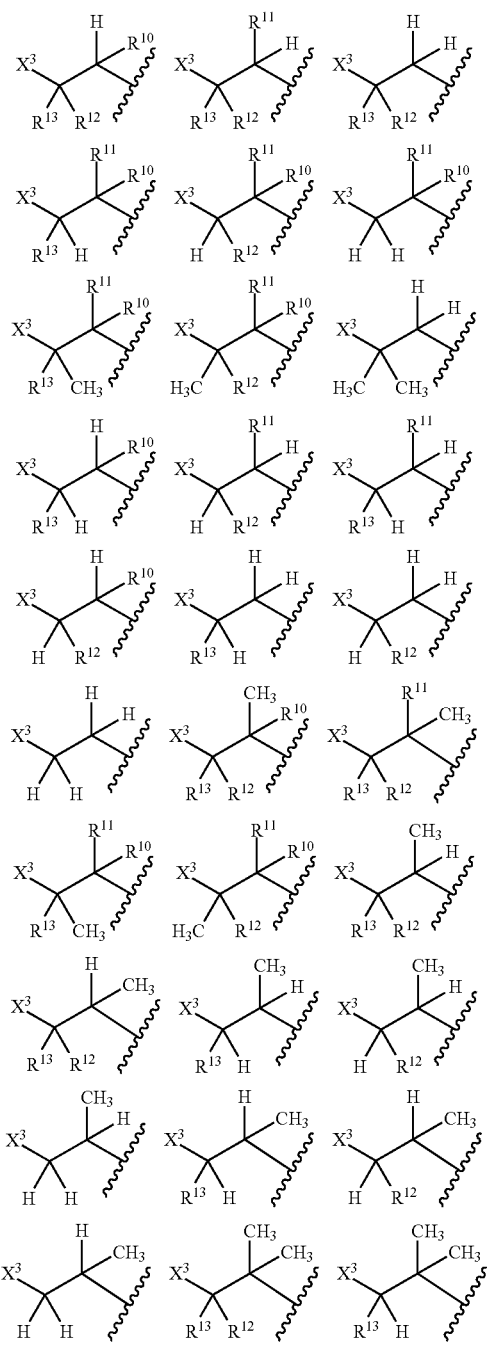

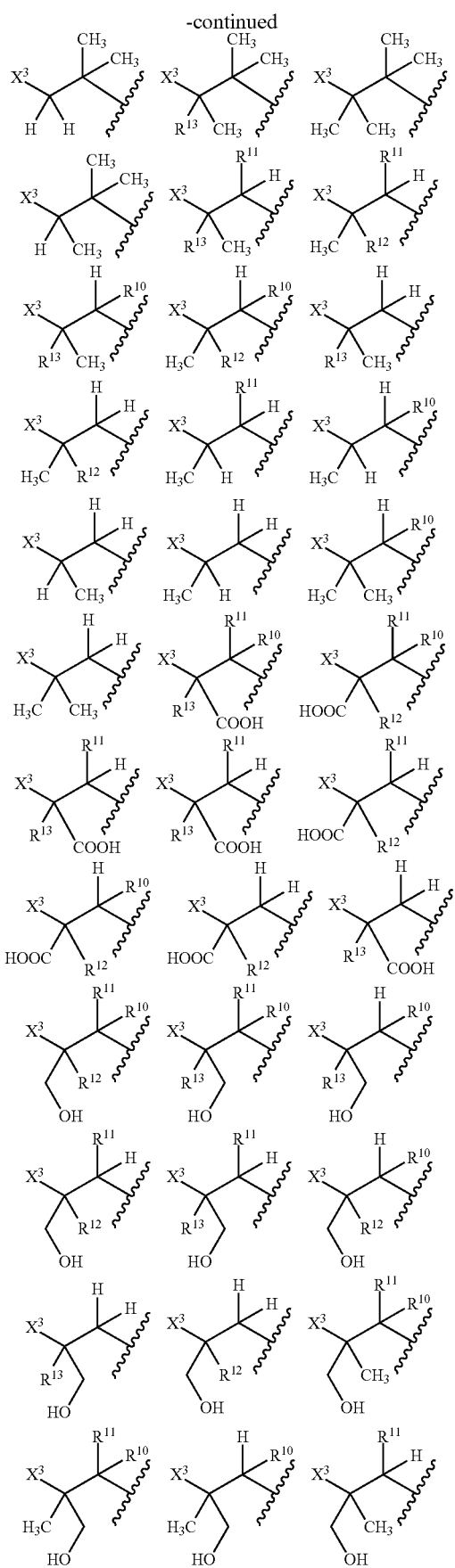
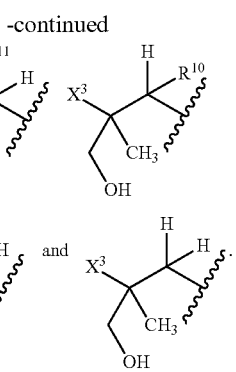
and
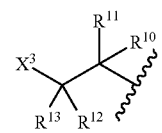
In certain embodiments of Formula I,
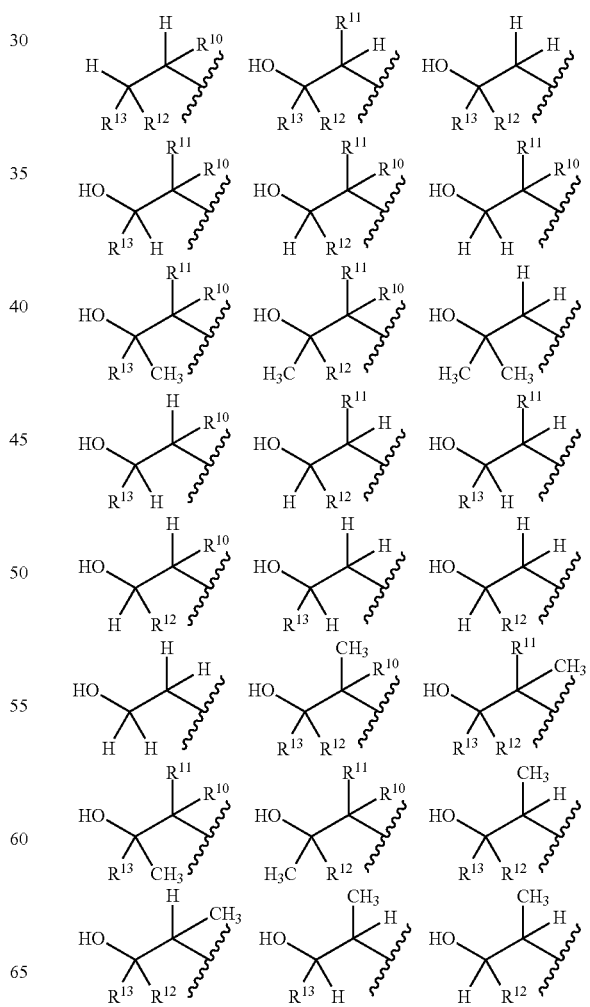
is selected from:

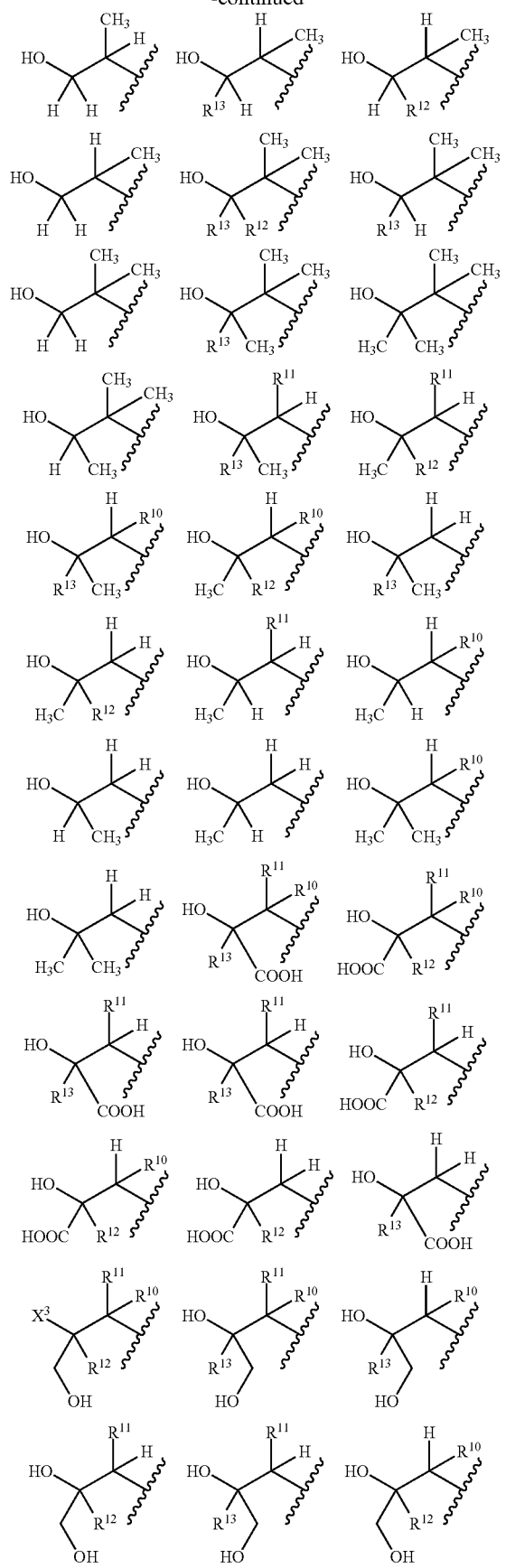
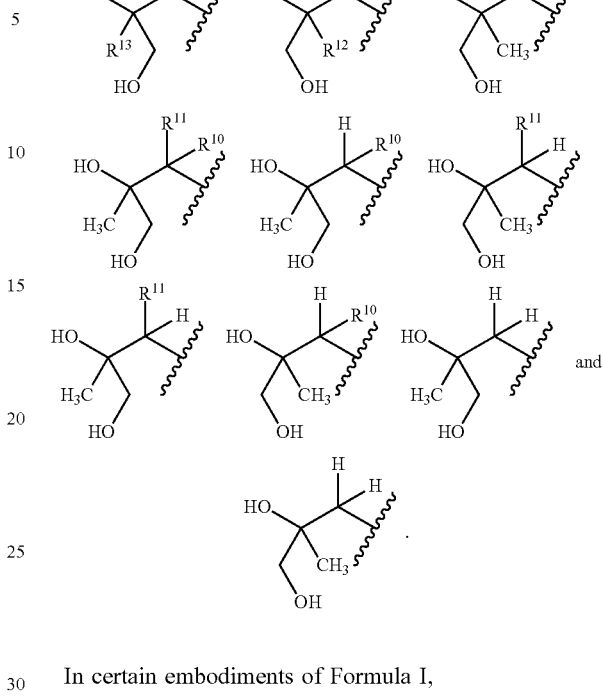
In certain embodiments of Formula I,
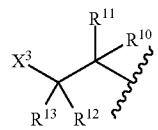
is selected from:
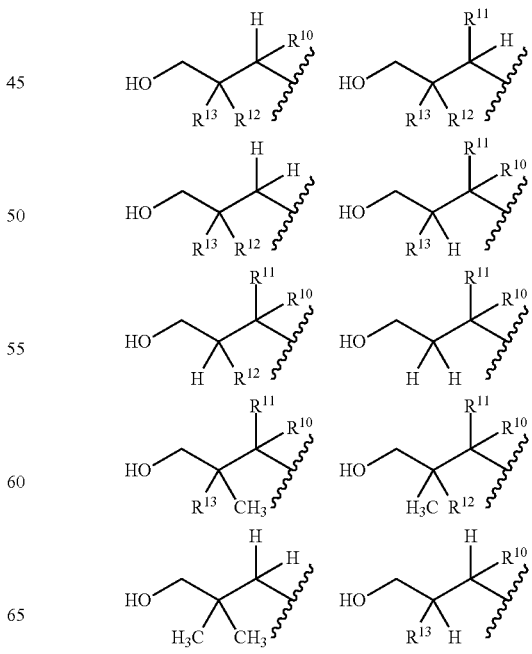
and

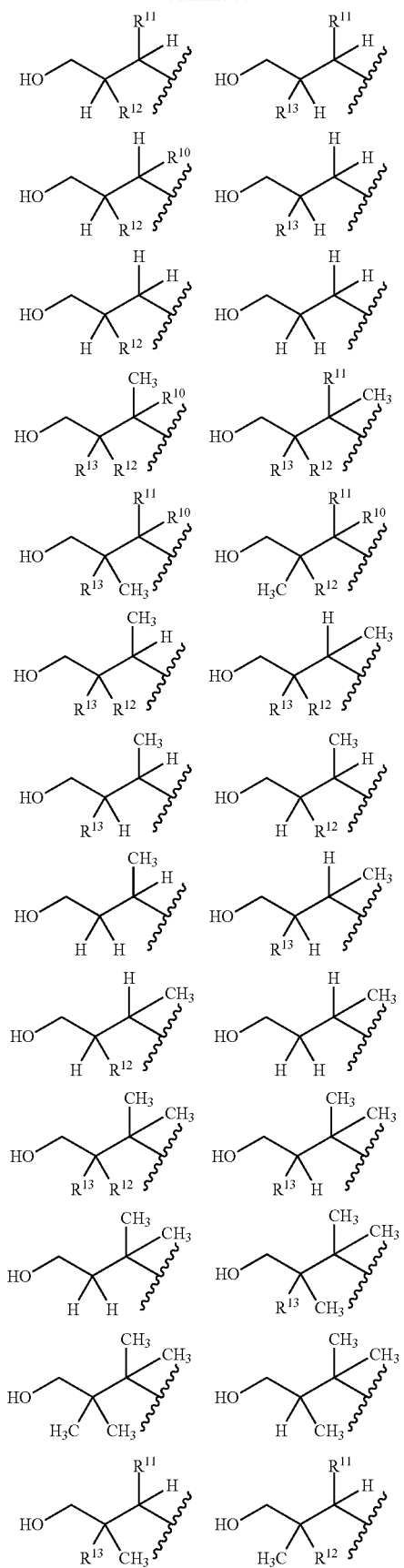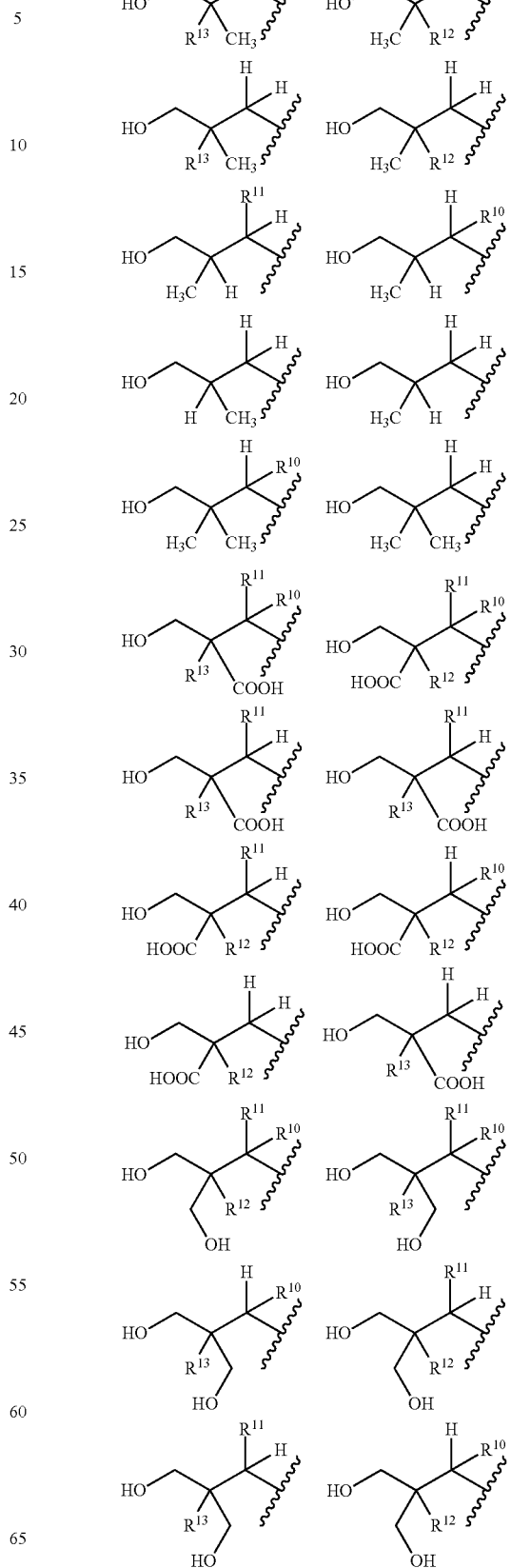

-continued
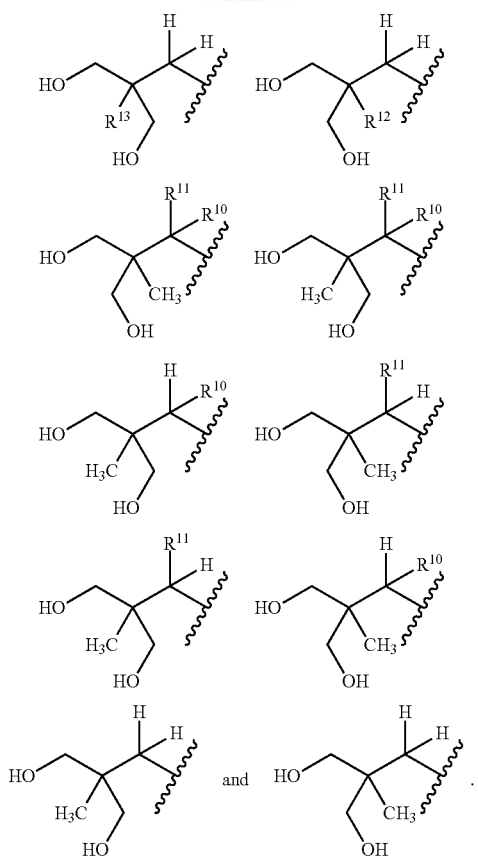
In certain embodiments of Formula I,
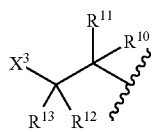
is selected from:
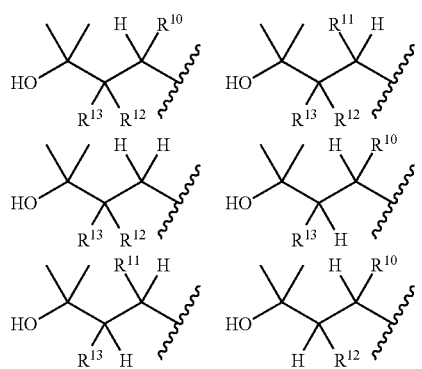
-continued
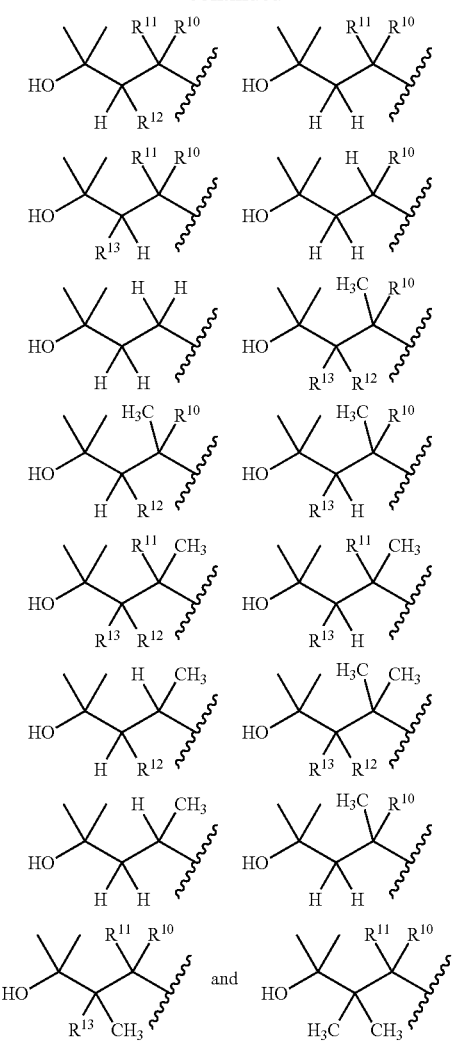
In certain embodiments of Formula I, $R^2$, $R^3$ and $R^4$ are independently selected from:
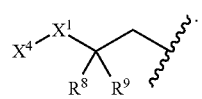
wherein $R^8$, $R^9$, $X^1$ and $X^4$ are as defined herein.
In certain embodiments
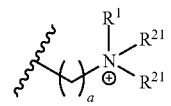

is selected from:
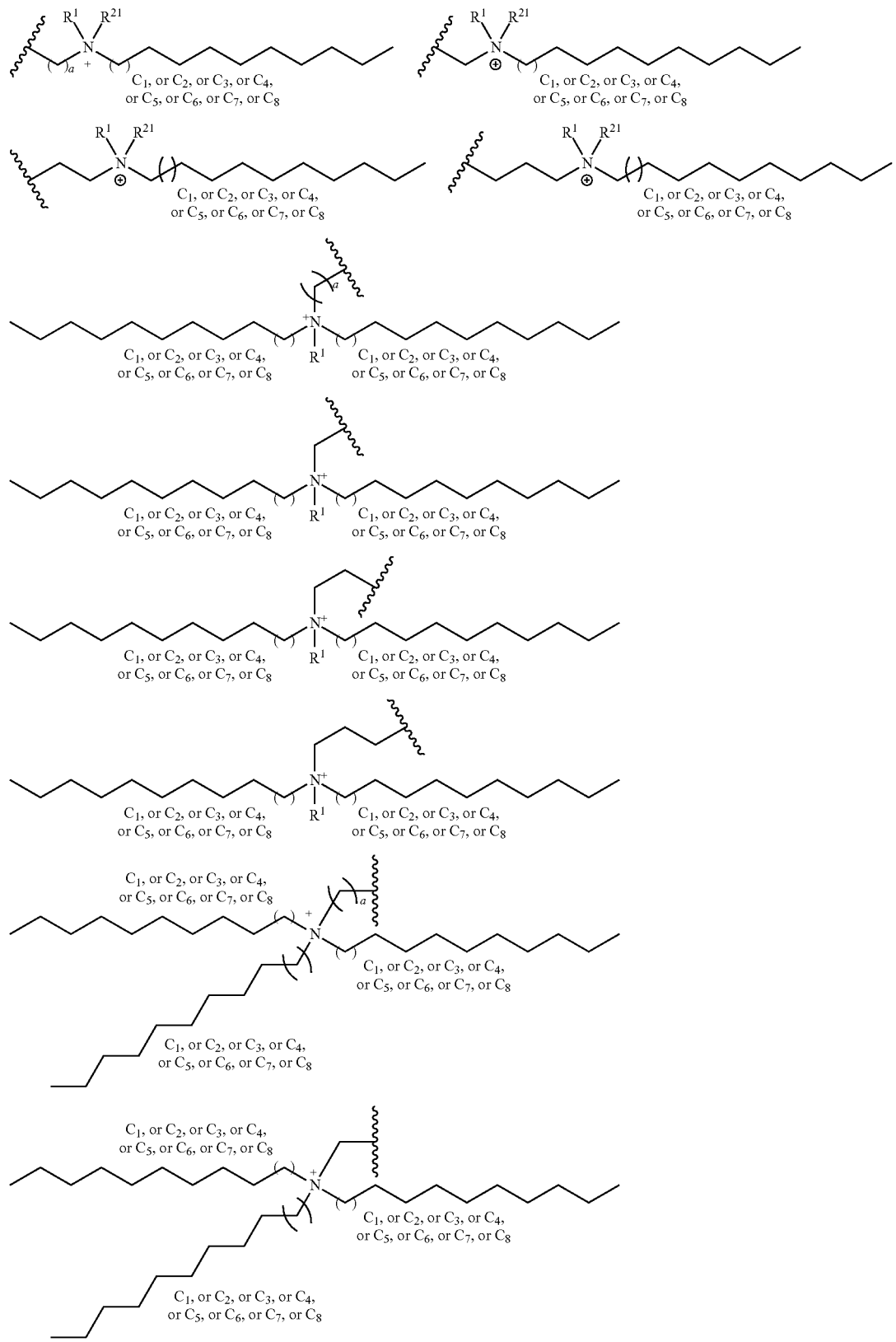

-continued
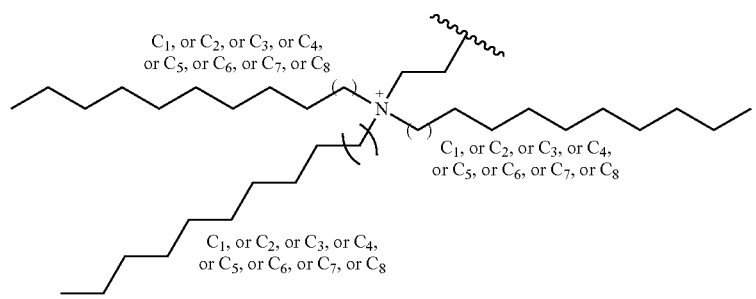
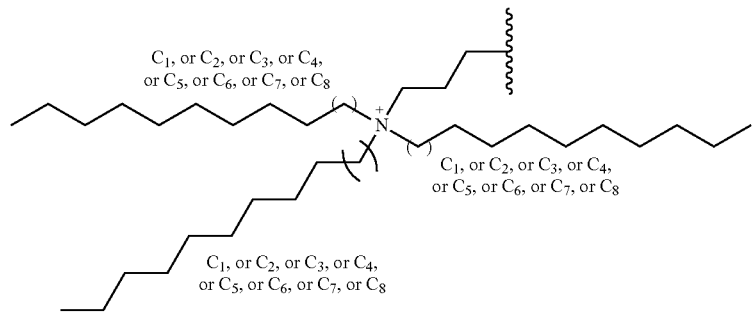
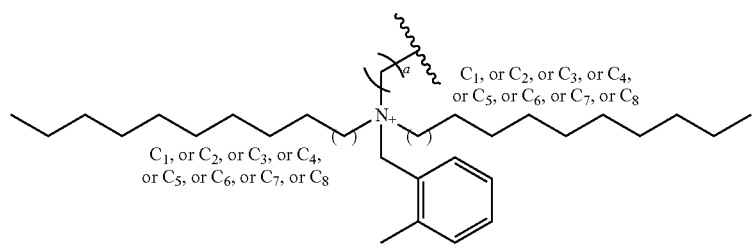
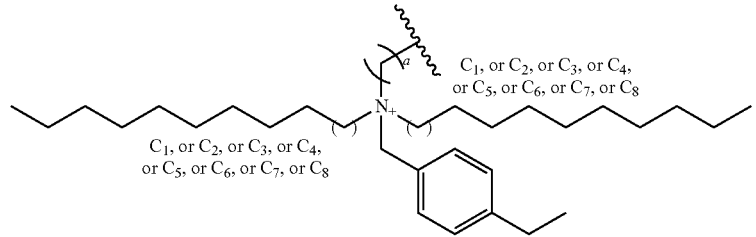
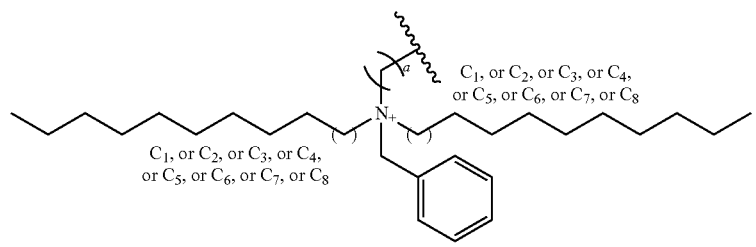
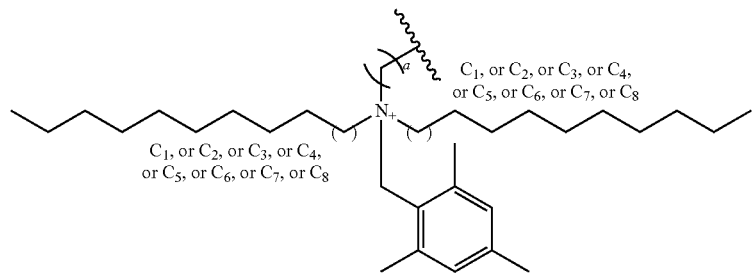
and

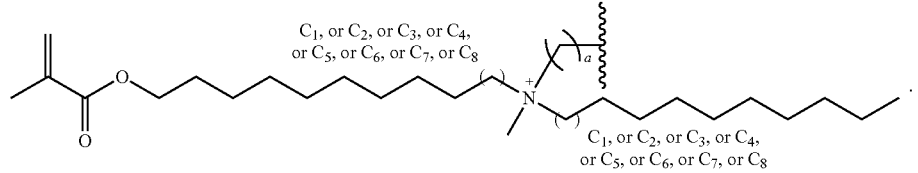
In certain embodiments,
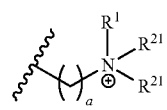
is selected from:
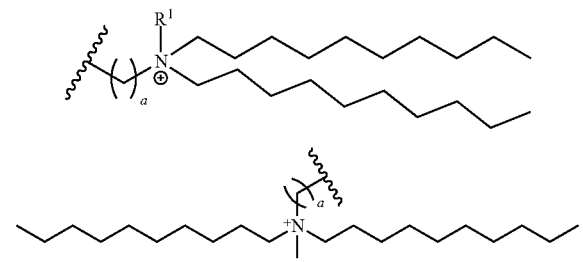
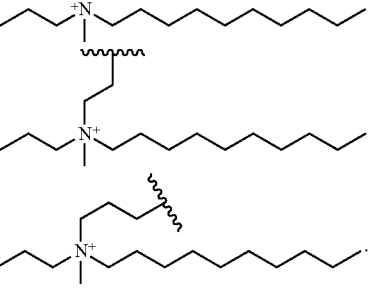
In certain embodiments,
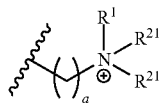
is selected from:
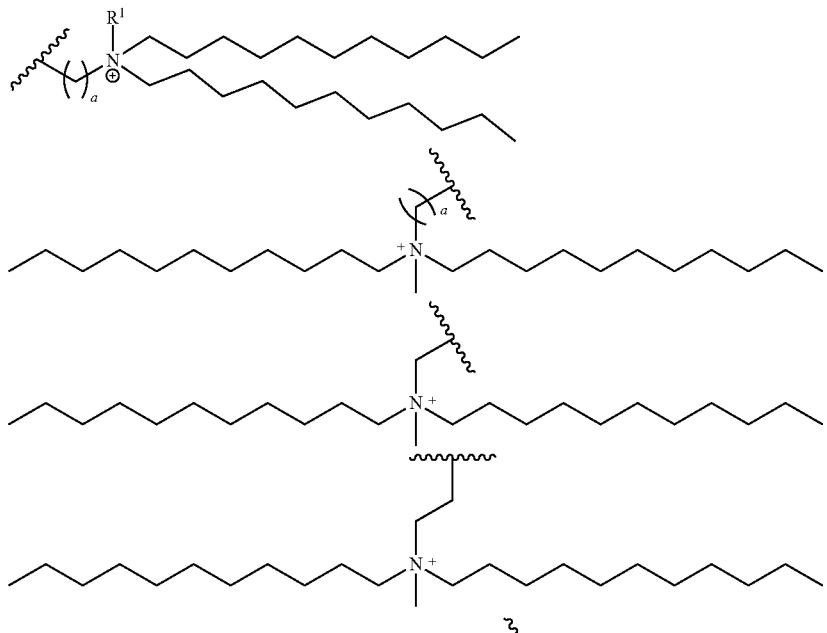
and
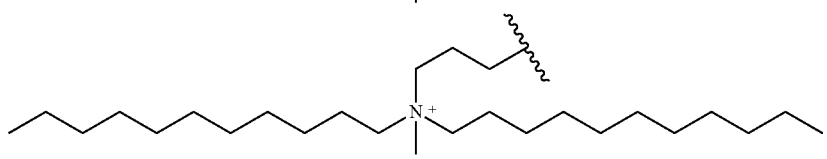

In certain embodiments,
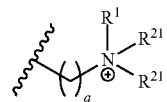
is selected from:
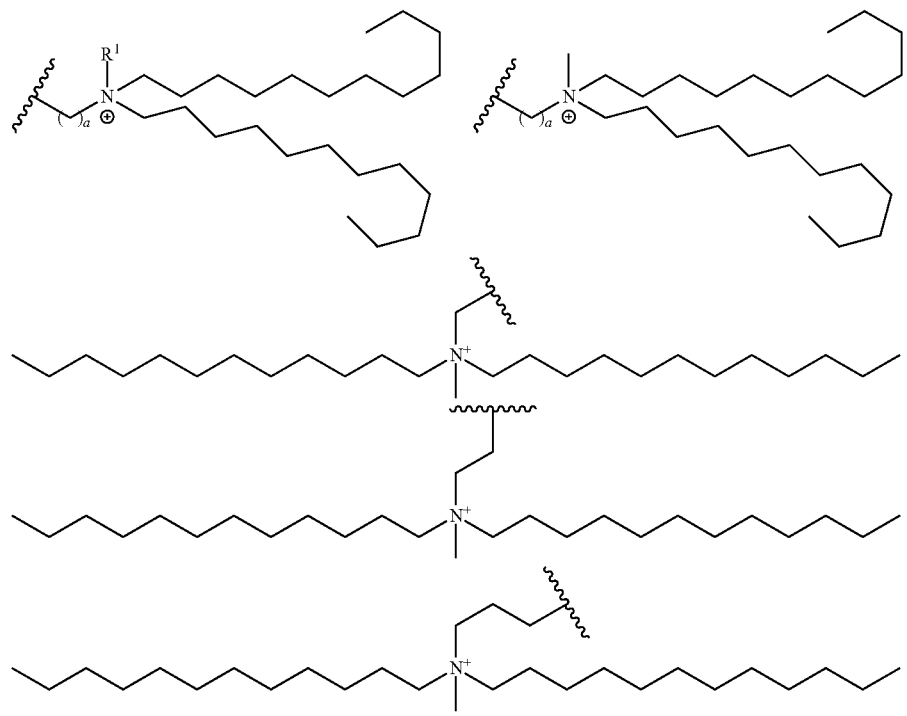
and
In certain embodiments,
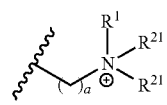
is selected from:
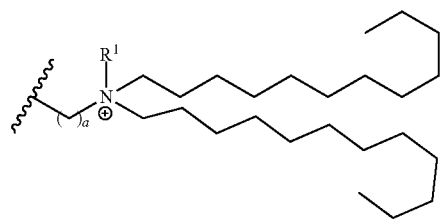

-continued
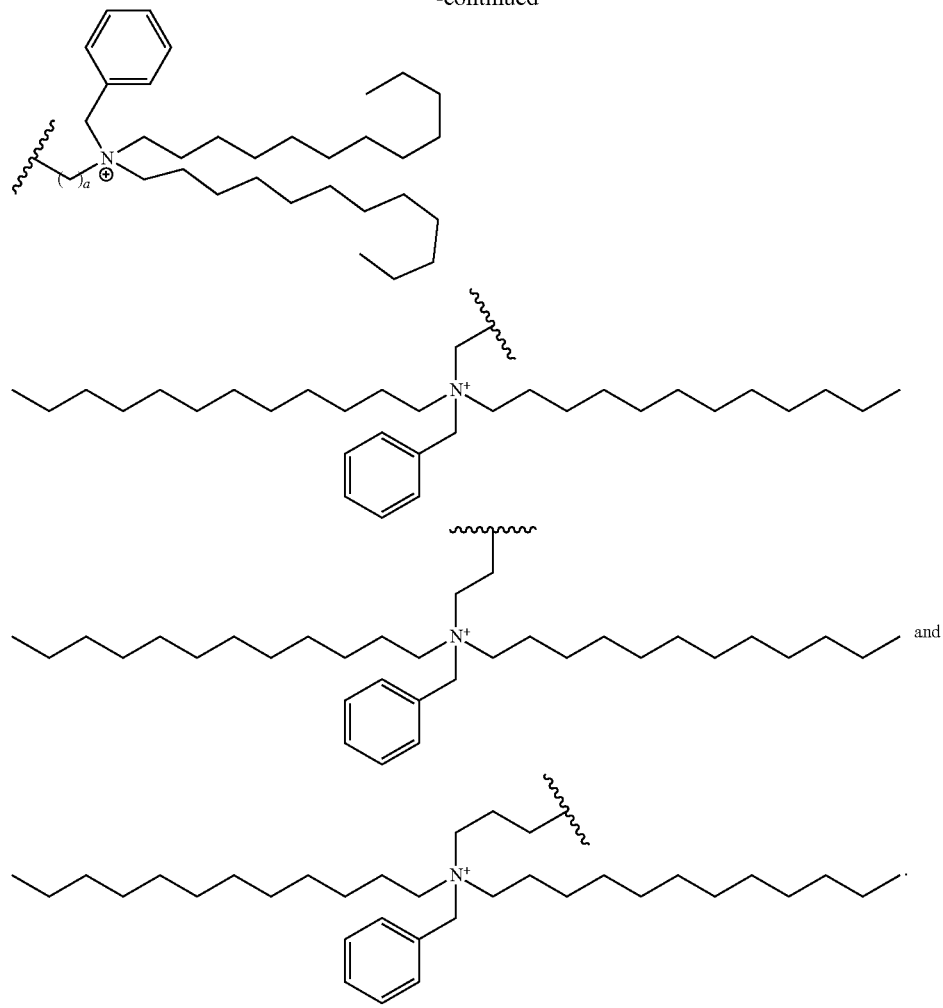
In certain embodiments,
is selected from:
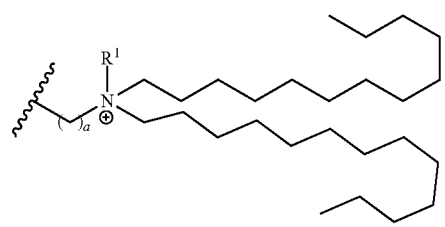

-continued
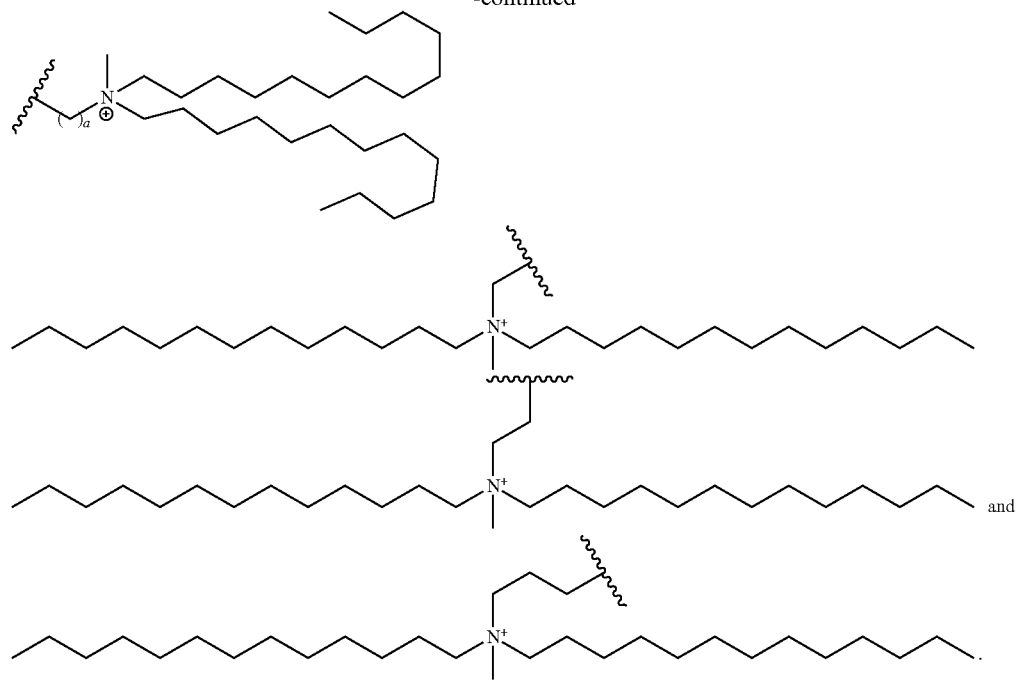
In certain embodiments,
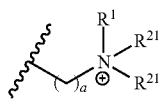
is selected from:
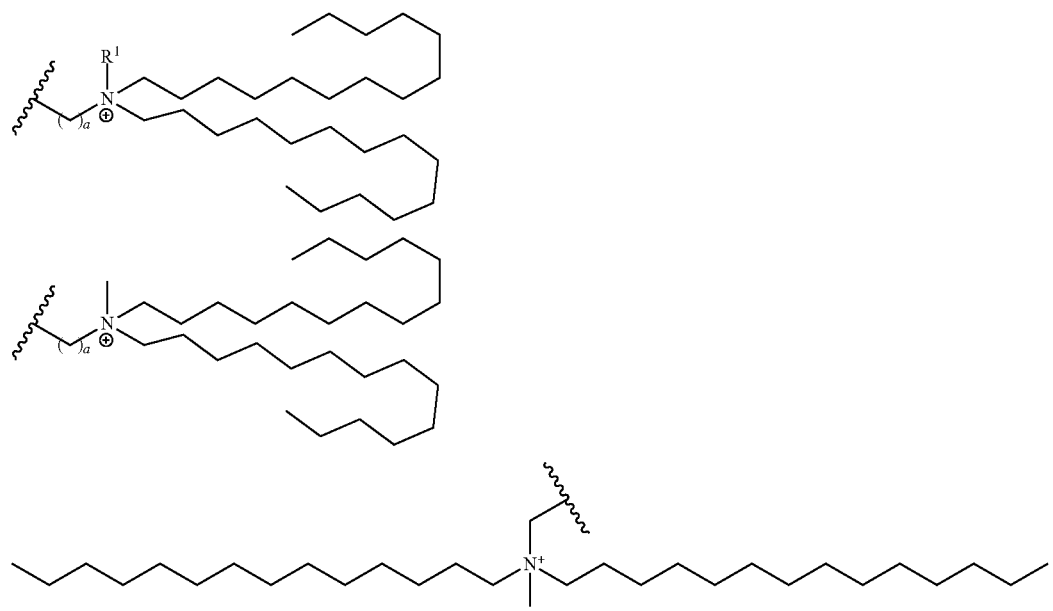

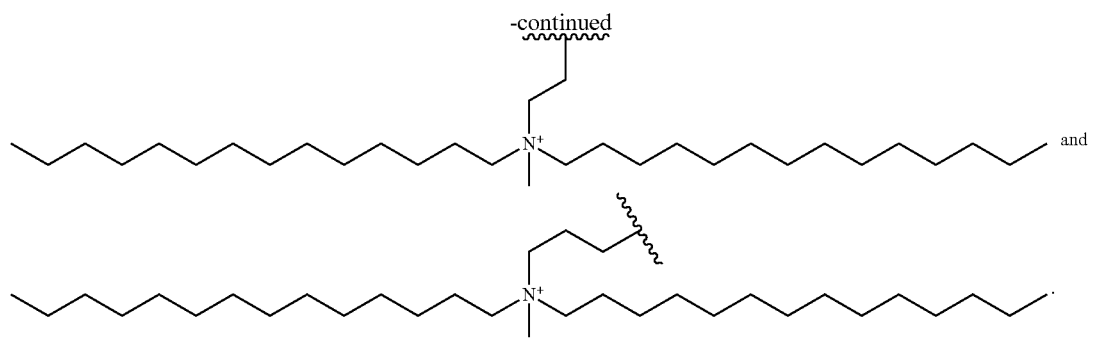
In certain embodiments,
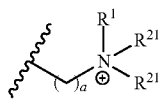
is selected from:
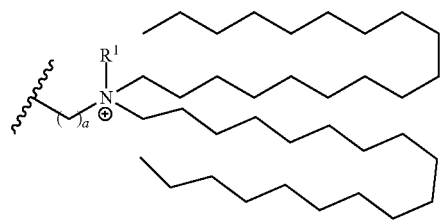
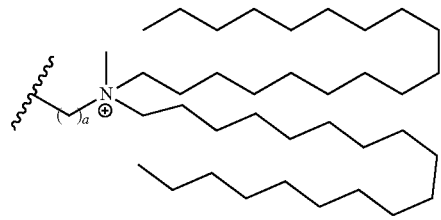
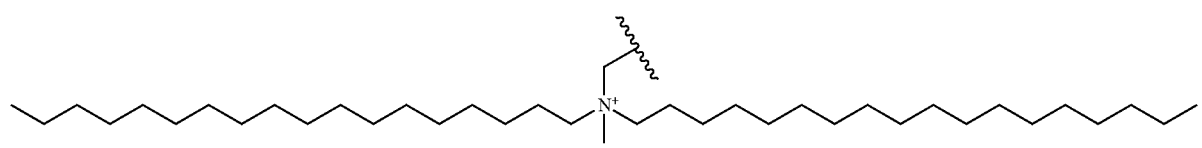
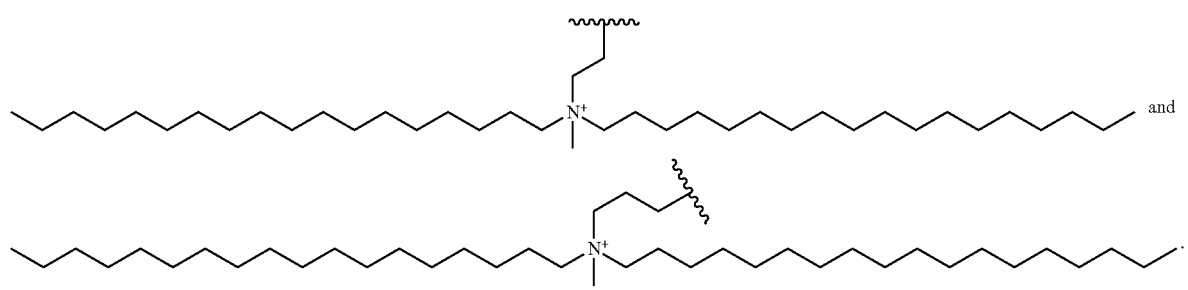
In certain embodiments,
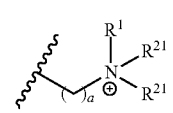

is selected from:
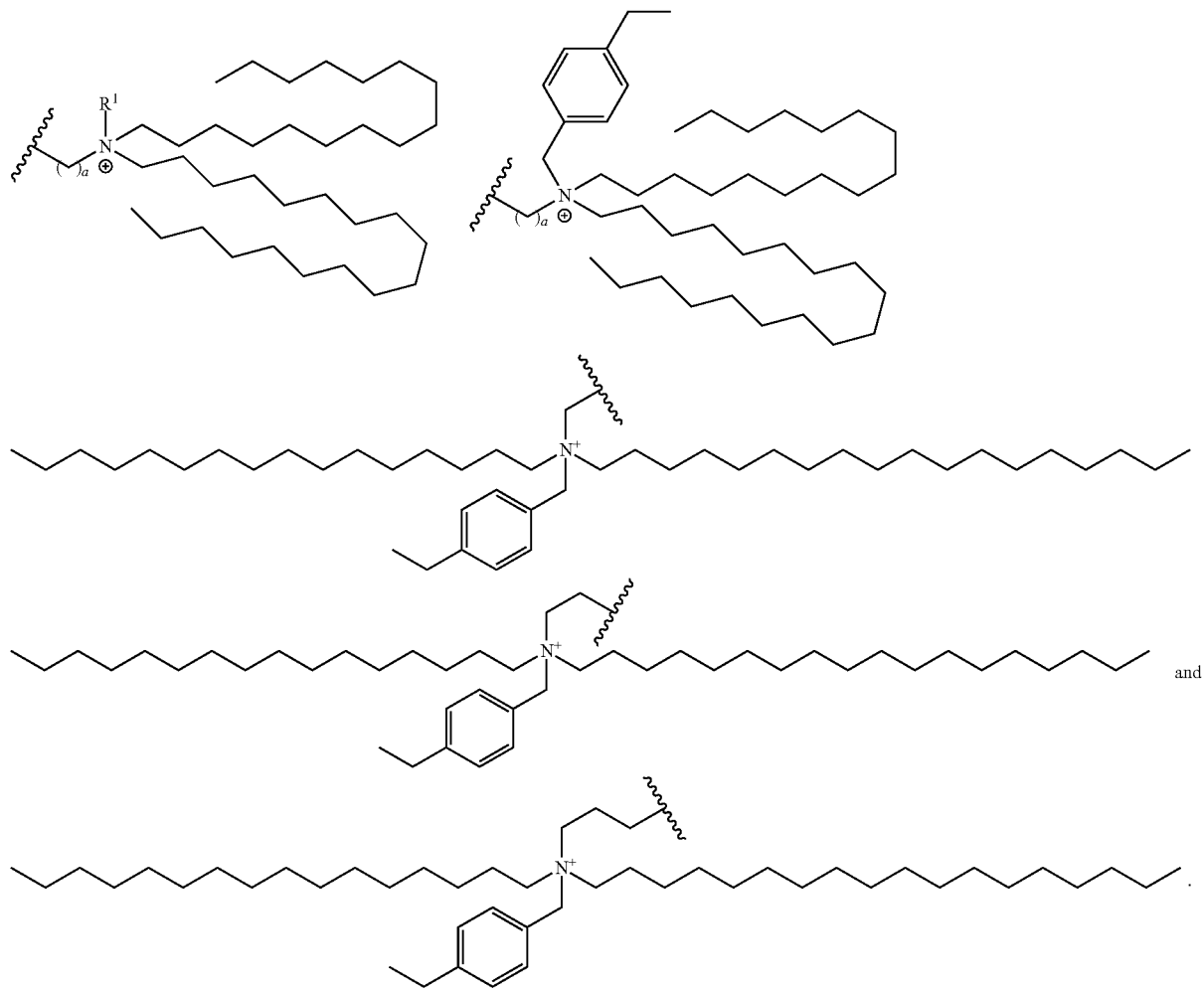
and
In certain embodiments,
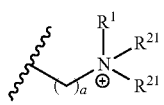
is selected from:
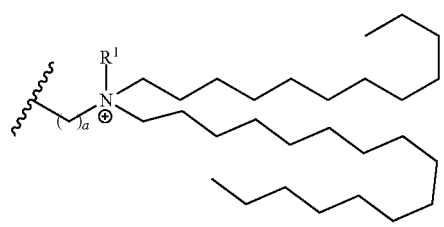

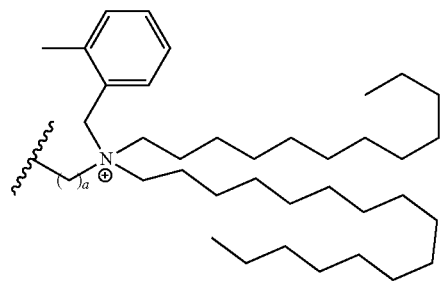
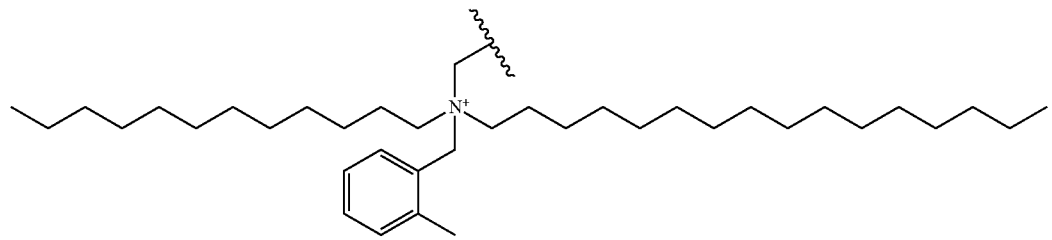
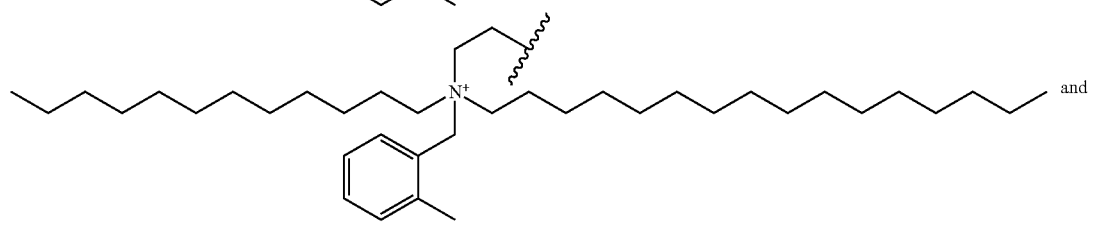
and
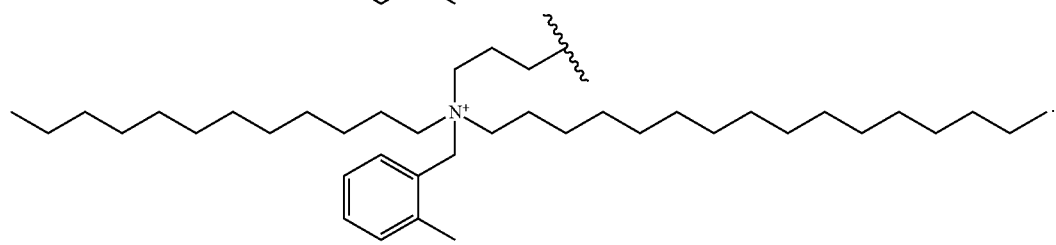
In certain embodiments,
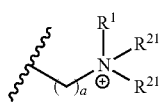
is selected from:
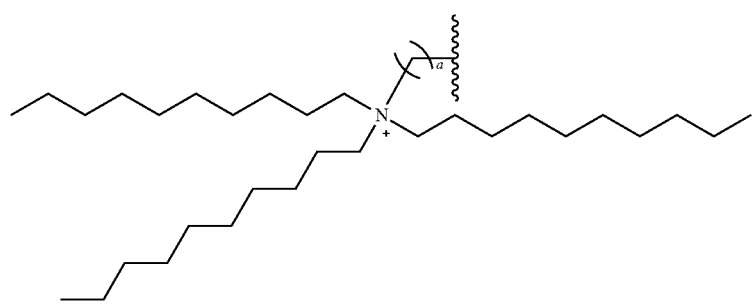

-continued
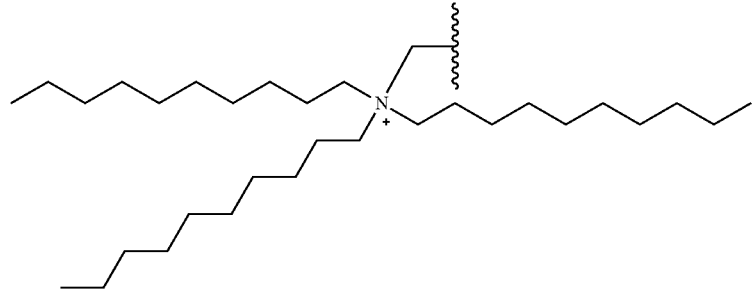
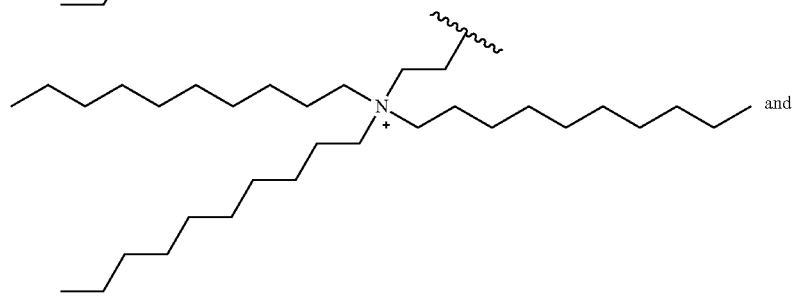 and
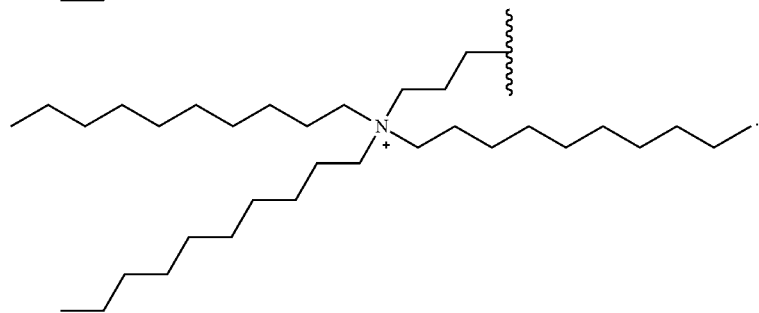.
In certain embodiments,
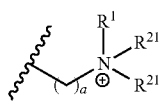
is selected from:
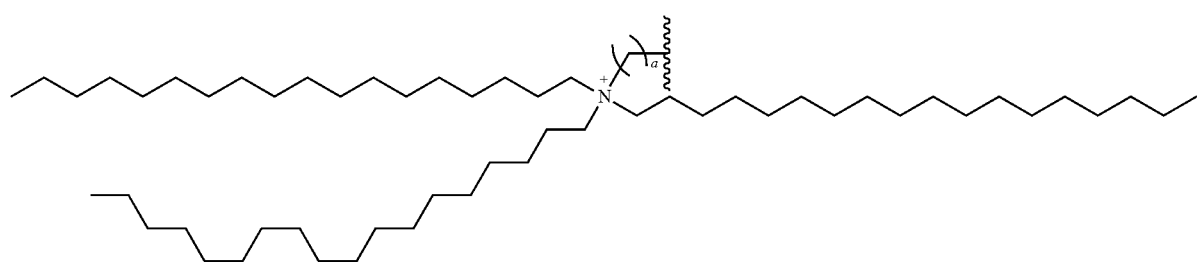

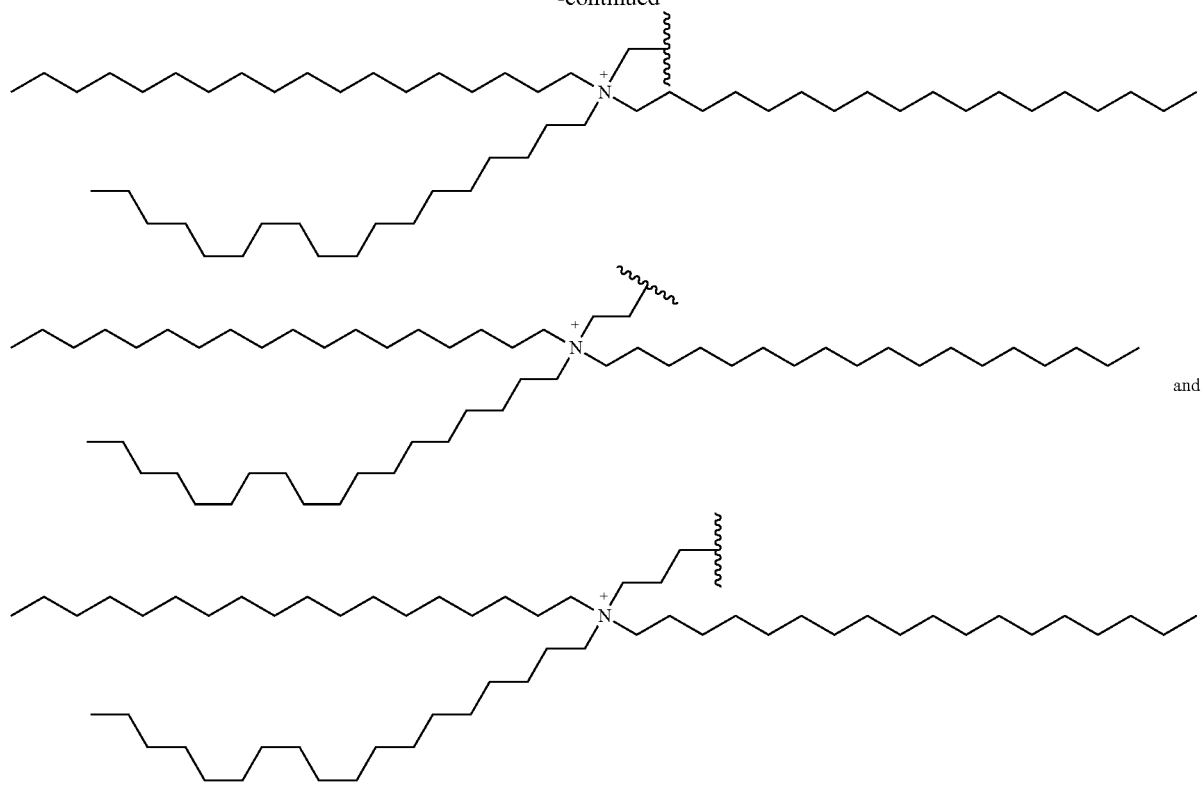
In certain embodiments,
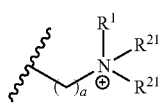
is selected from:
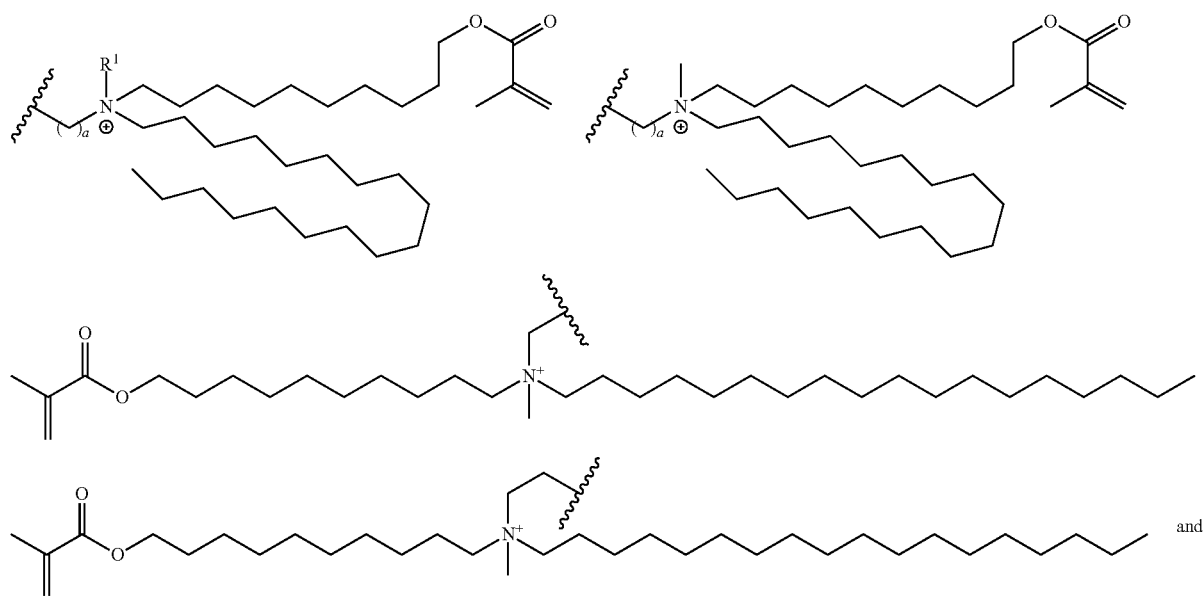

-continued
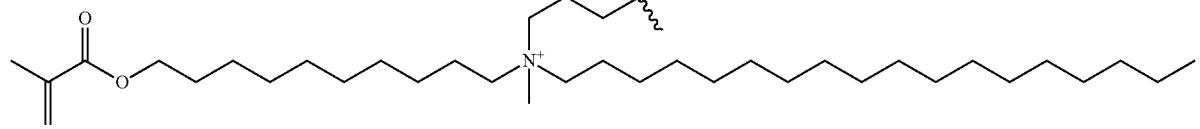
In certain embodiments,
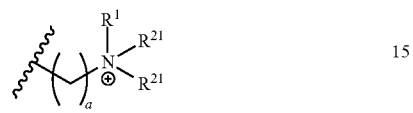
is selected from:
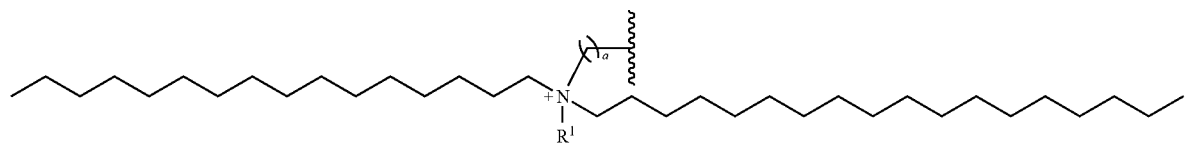
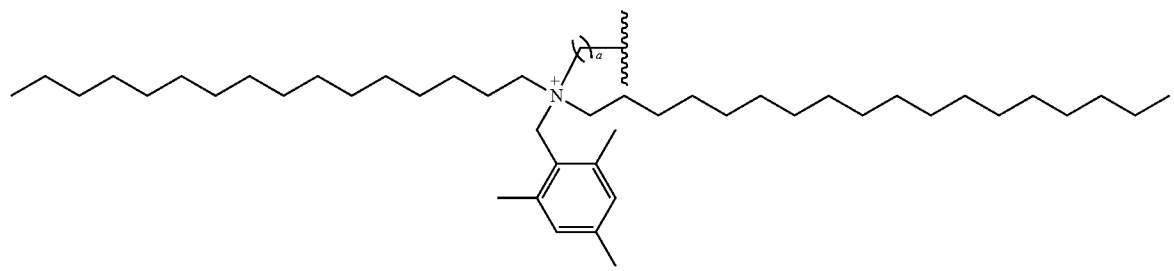
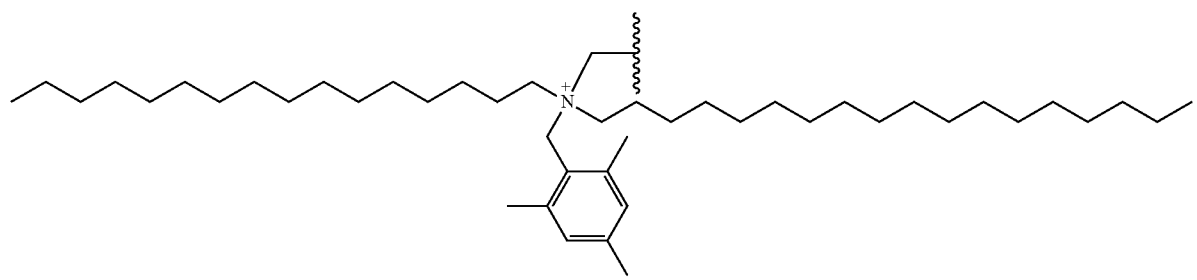
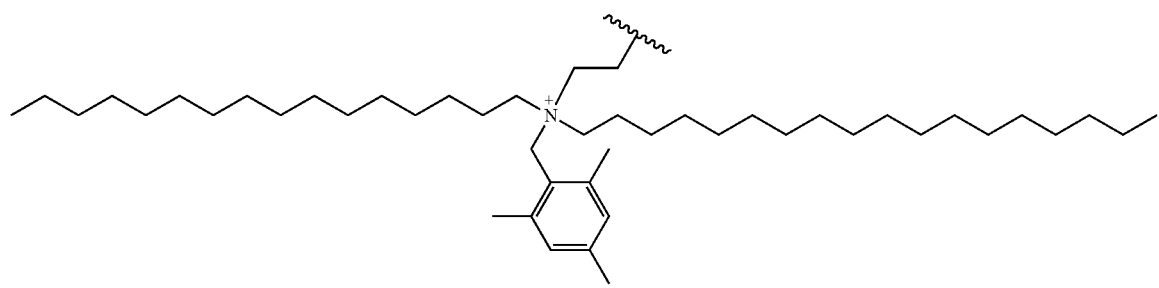
and -continued

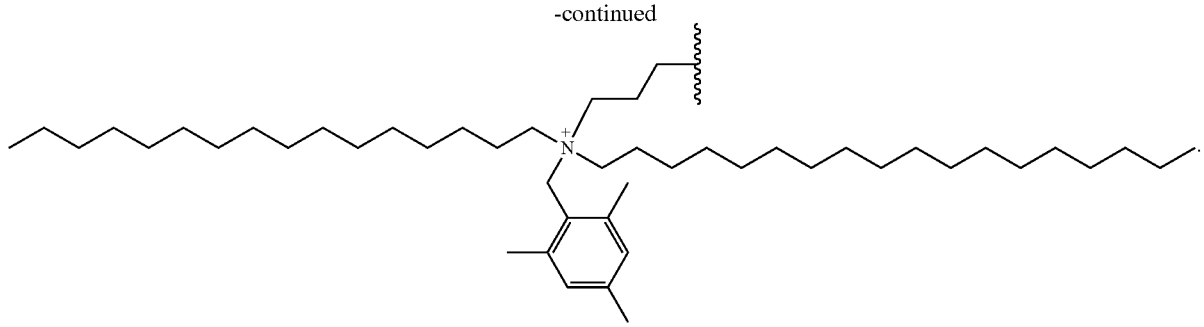

In certain embodiment, $R^8$ and $R^9$ are independently selected from hydrogen, hydroxyl, $C_1$-$C_8$alkyl, and $C_1$-$C_8$hydroxyalkyl.

In certain embodiments, $X^1$ is NH.

In certain embodiments, $X^1$ is $NR^{17}$; wherein $R^{17}$ is independently at each occurrence selected from hydrogen, $C_1$-$C_8$ hydroxyalkyl, $C_2$-$C_8$ alkenyl, $C_2$-$C_8$ alkynyl, $C_1$-$C_8$ haloalkyl, $C_1$-$C_8$ alkanoyl, heterocyclyl, heteroaryl, heterocycloalkyl, and aryl.

In certain embodiments, $X^1$ is $CH_2$.

In certain embodiments, $X^4$ is $NH_2$.

In certain embodiments, $X^4$ is $N(R^7)_2$; wherein $R^7$ is independently at each occurrence selected from hydrogen, $C_1$-$C_8$ alkyl, $C_1$-$C_8$ hydroxyalkyl, $C_2$-$C_8$ alkenyl, $C_2$-$C_8$ alkynyl, $C_1$-$C_8$ haloalkyl, $C_1$-$C_8$ alkanoyl, heterocyclyl, heteroaryl, heterocycloalkyl, and aryl.

In certain embodiments, $X^4$ is $C_1$-$C_{12}$alkanoic acid.

In some embodiments of Formula I,

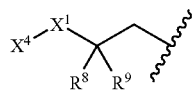

is selected from

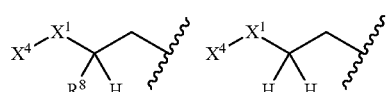
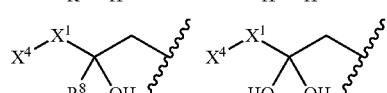
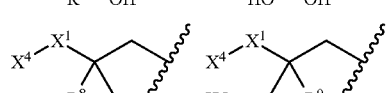
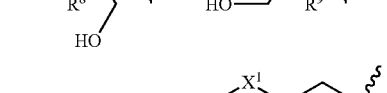
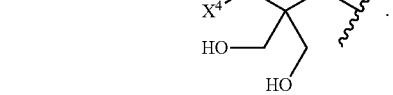

In some embodiments of Formula I,

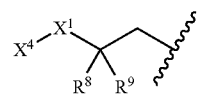

is selected from

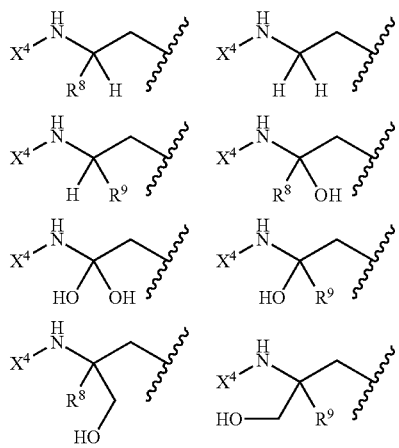
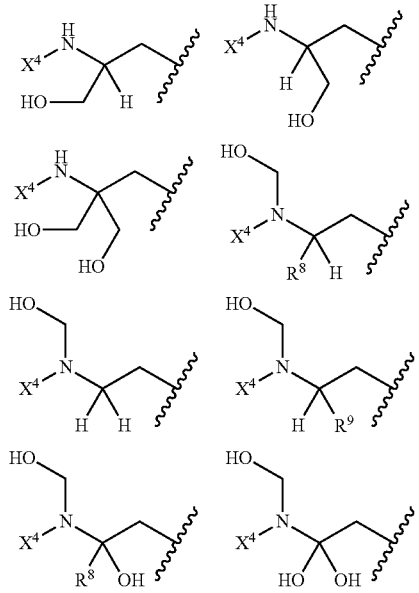

-continued
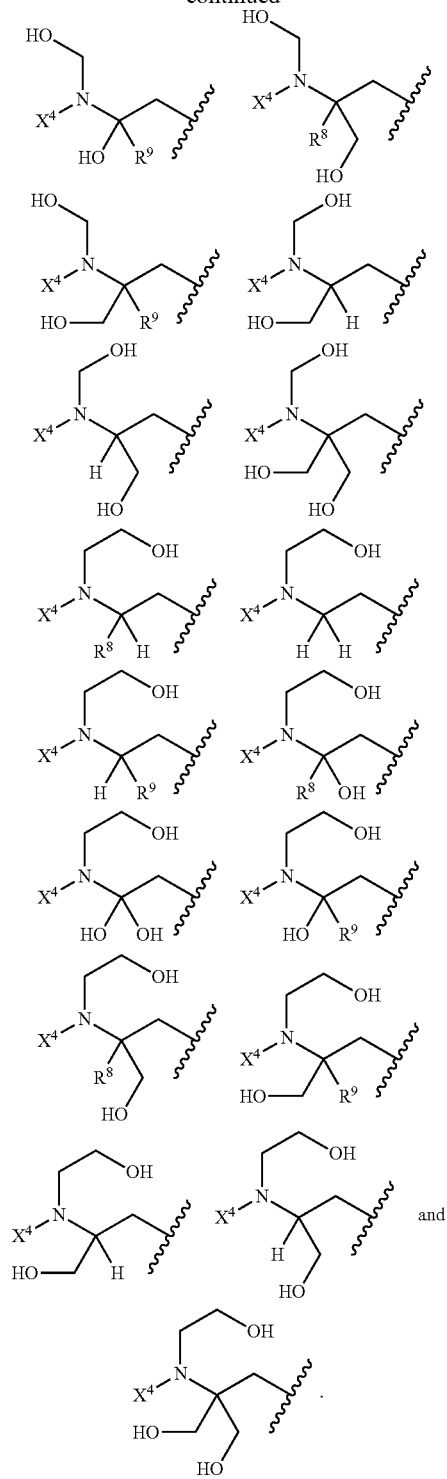
In some embodiments of Formula I,
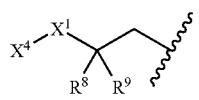
is selected from
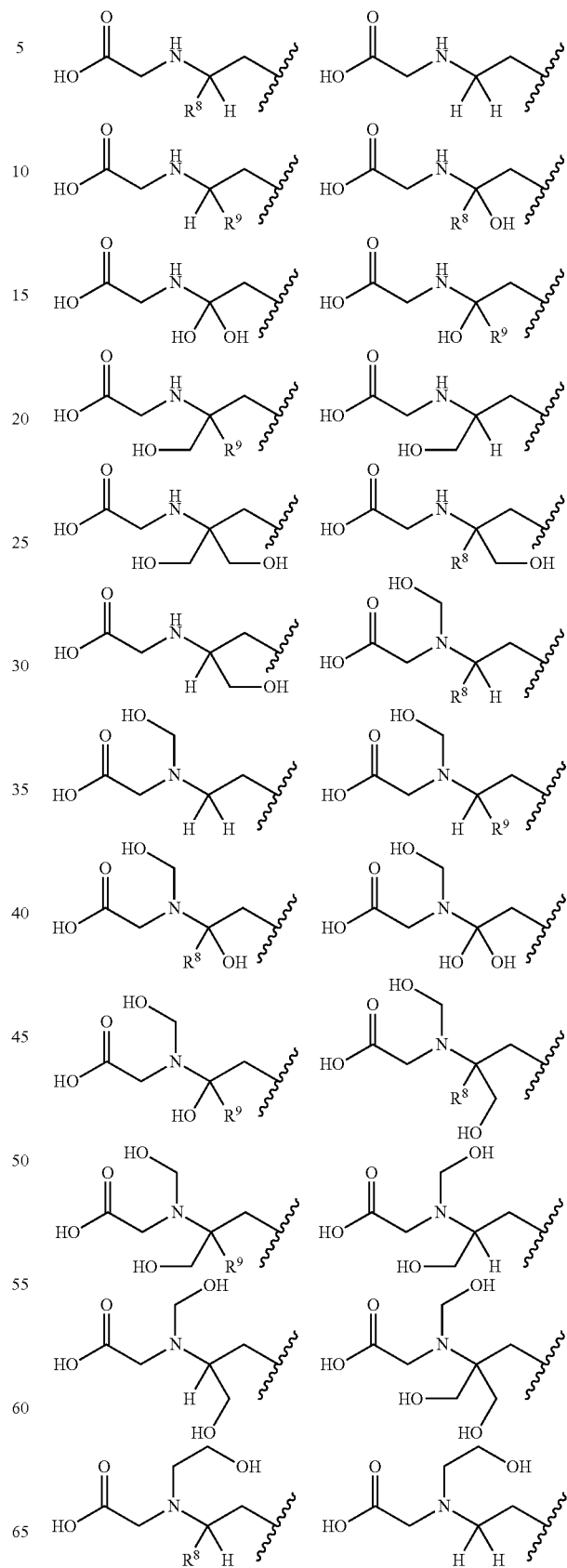

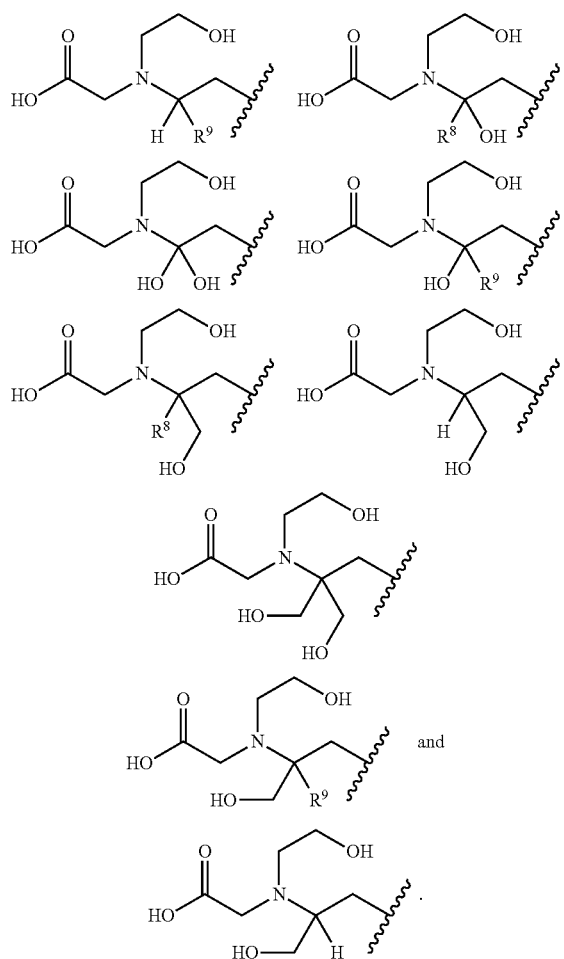
In some embodiments of Formula I,
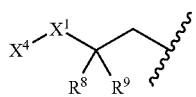
is selected from
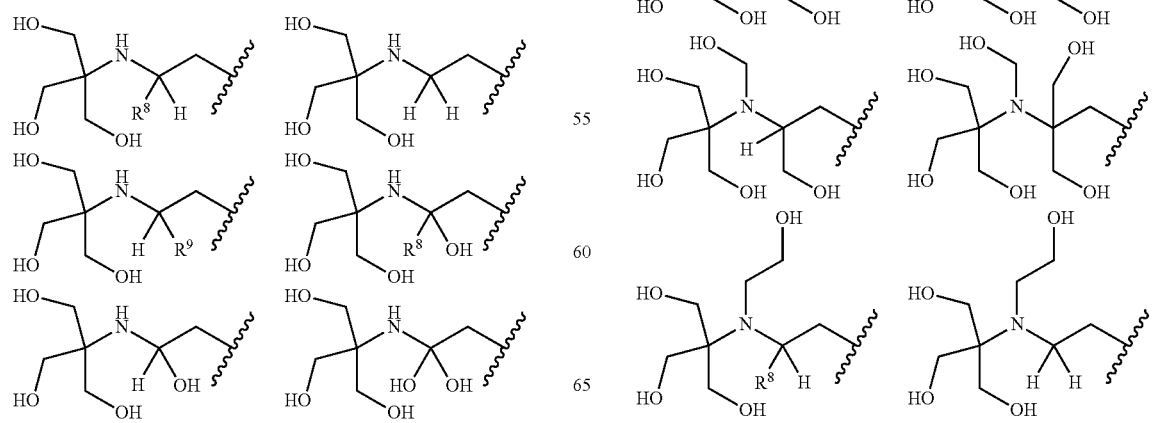

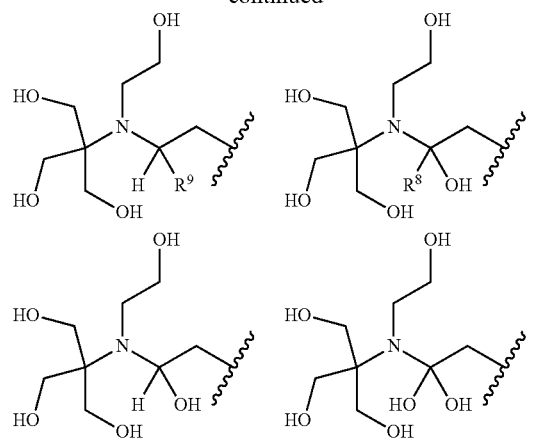
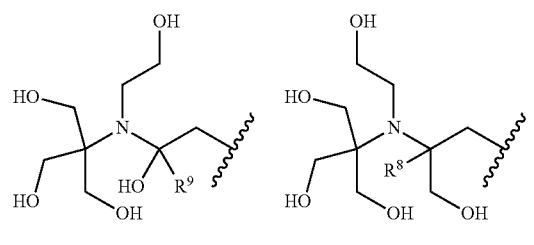
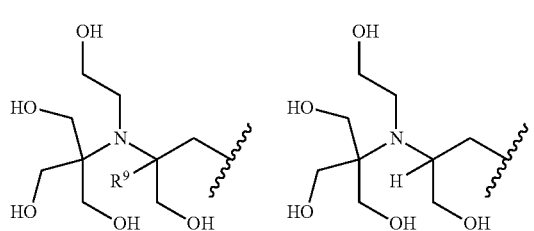
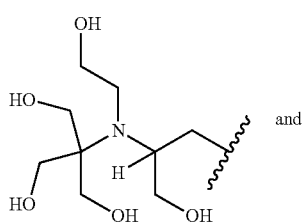
and
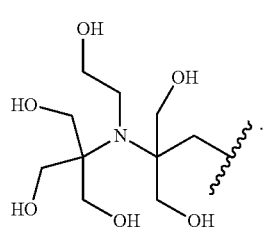
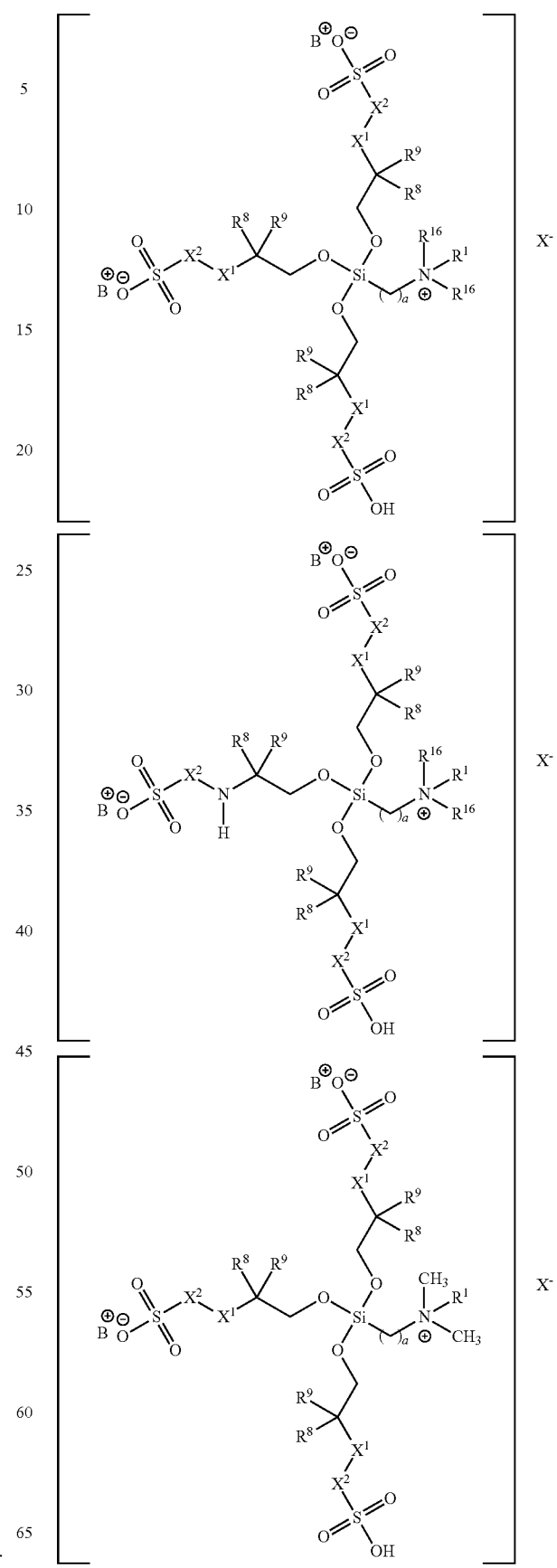
In certain embodiments, a quaternary ammonium compound of Formula I is selected from 281
-continued
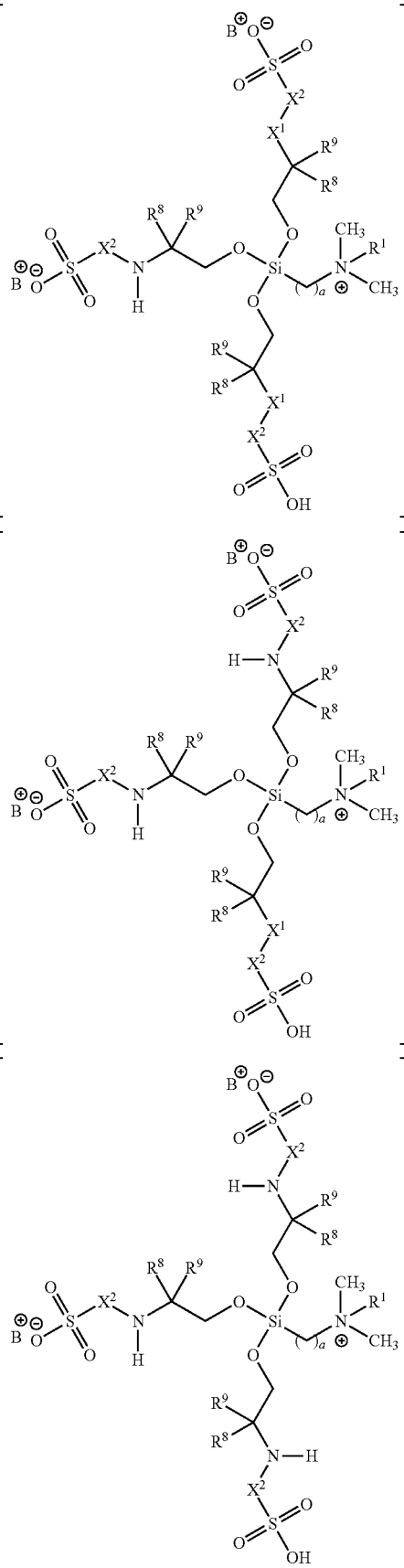
282
-continued
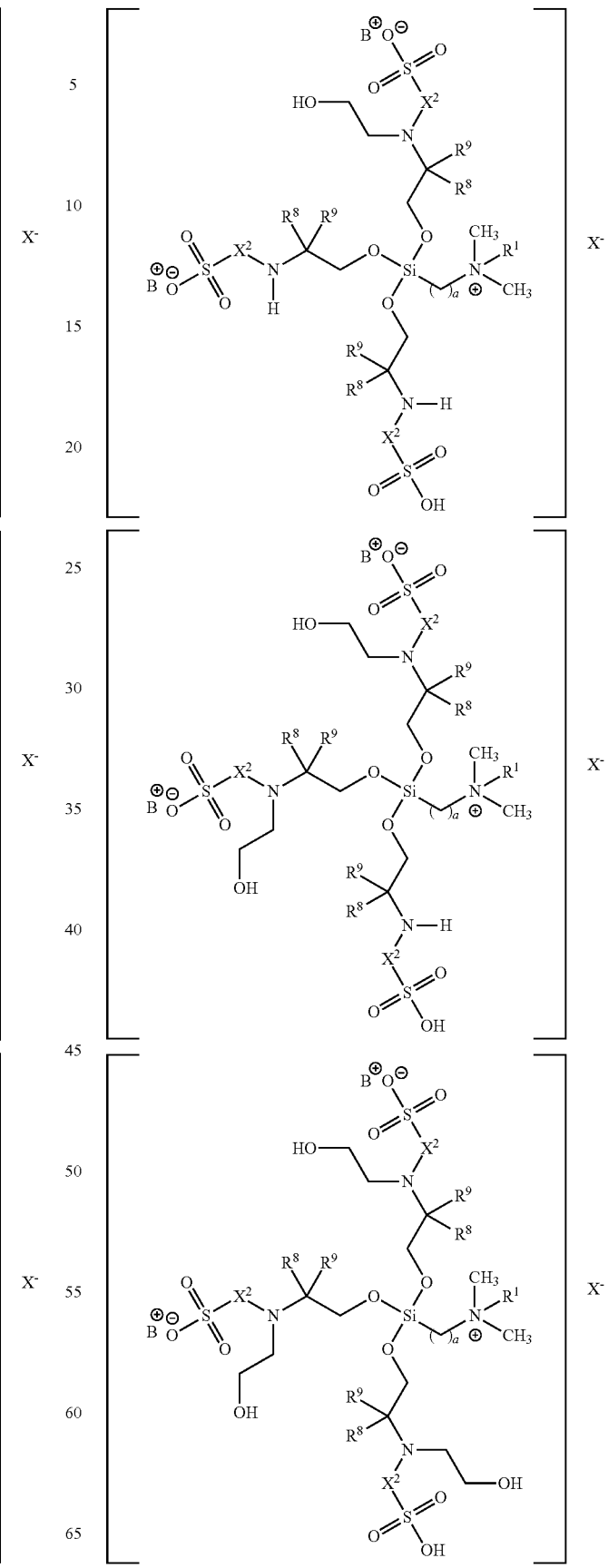

283
-continued
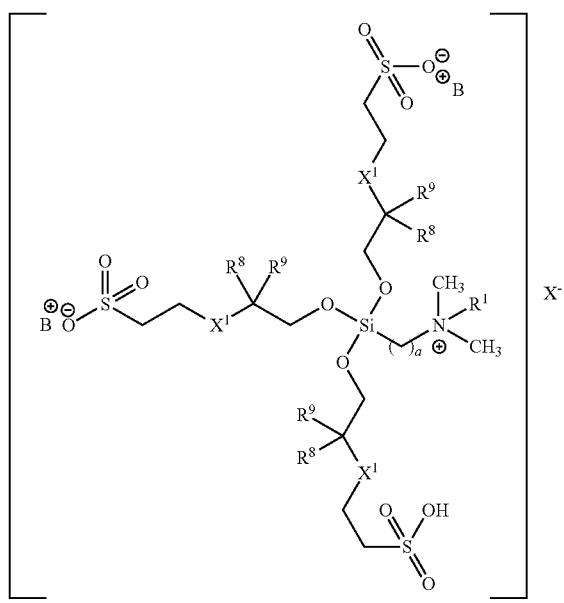
284
-continued
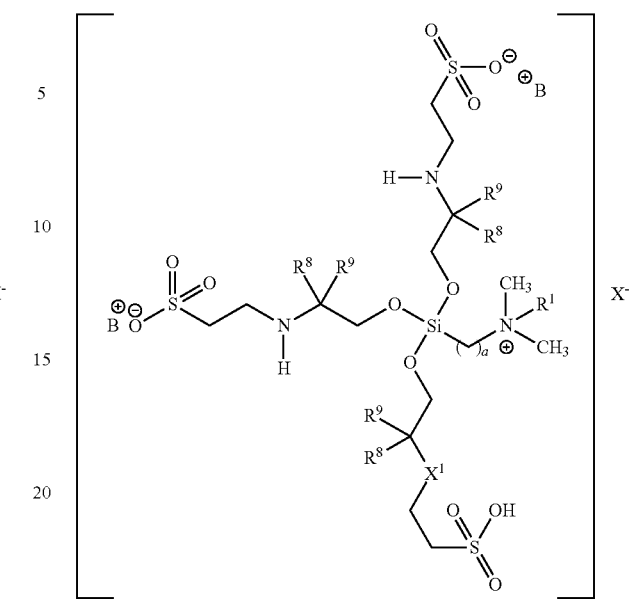
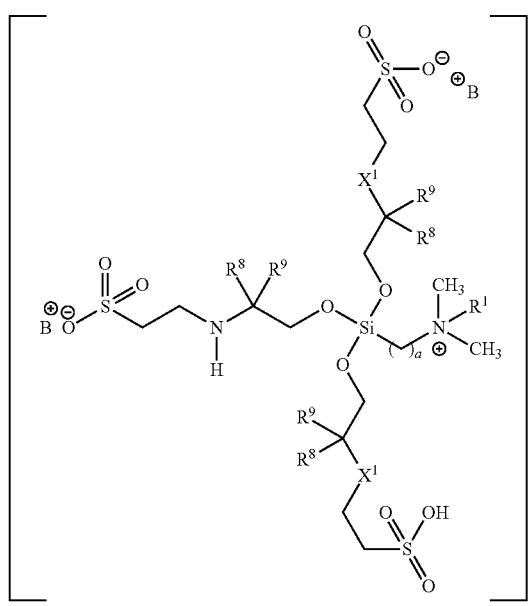
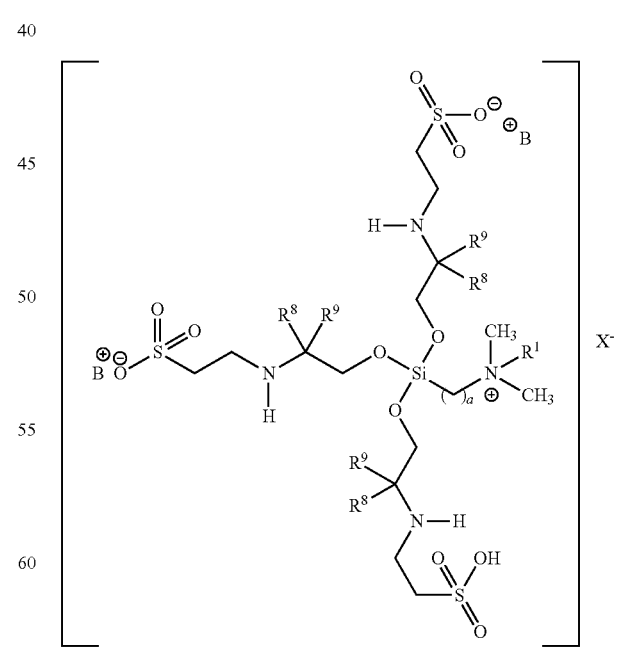

285
-continued
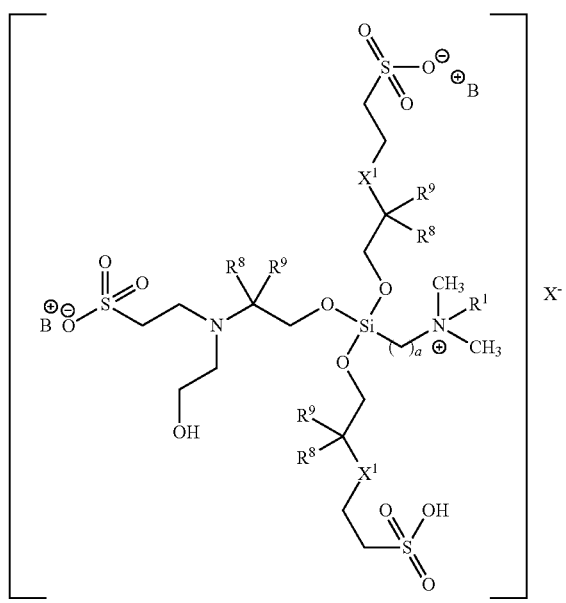
286
-continued
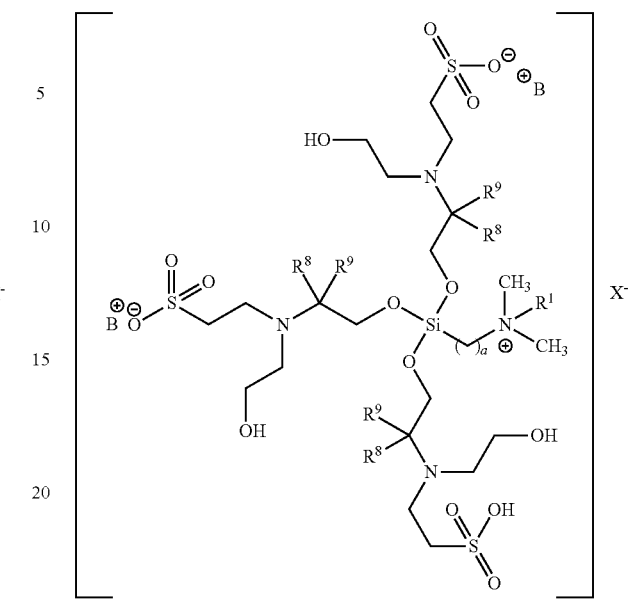
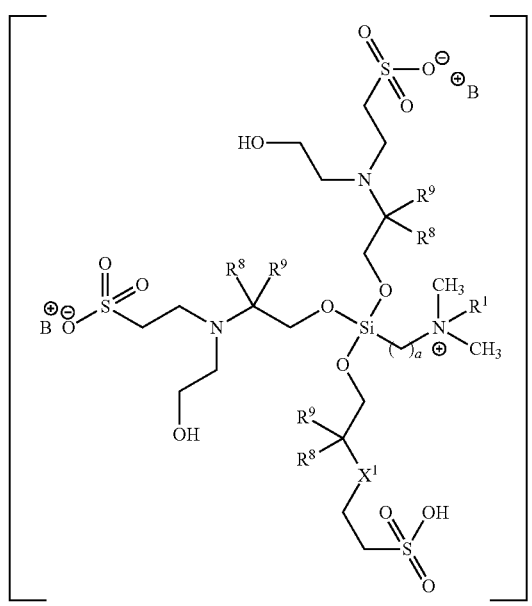
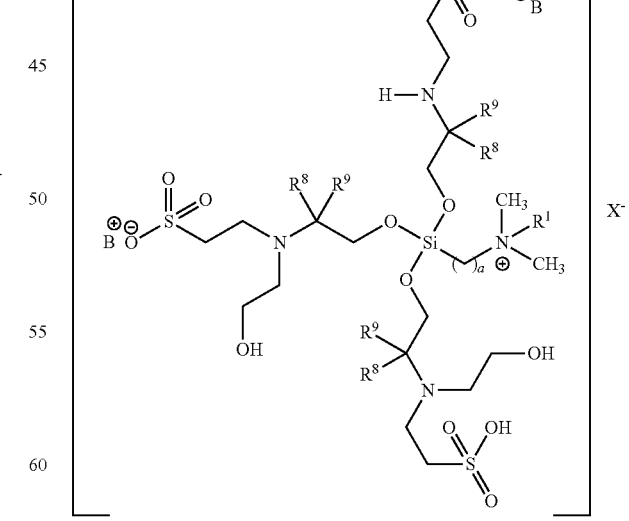

287
-continued
288
-continued
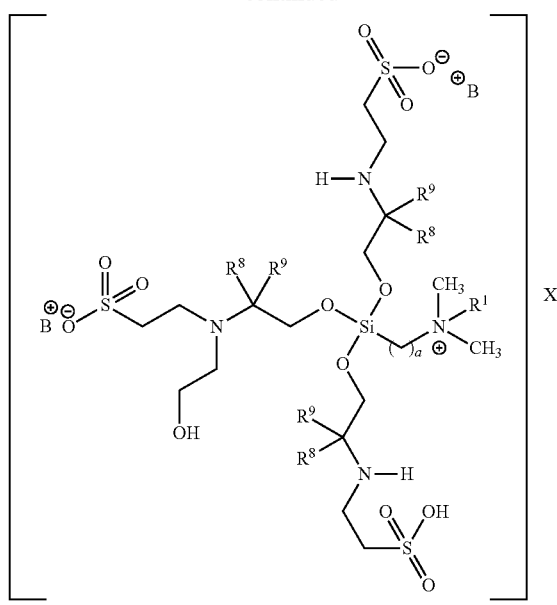
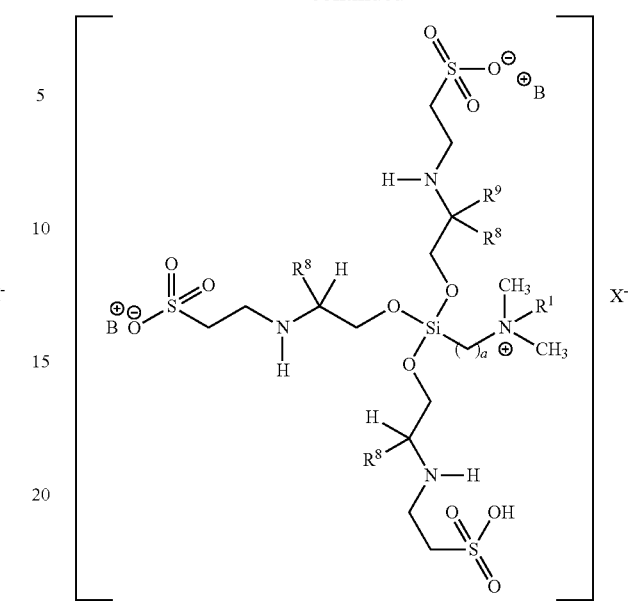
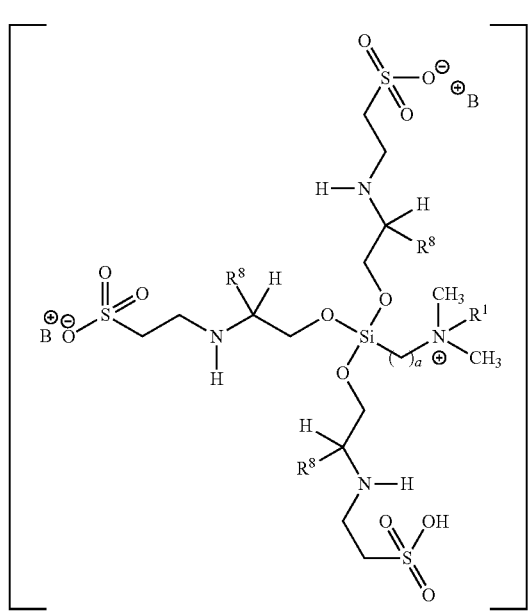
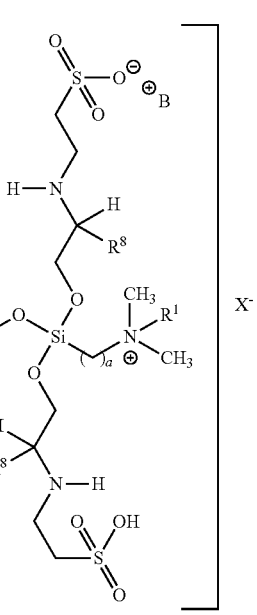

289
-continued
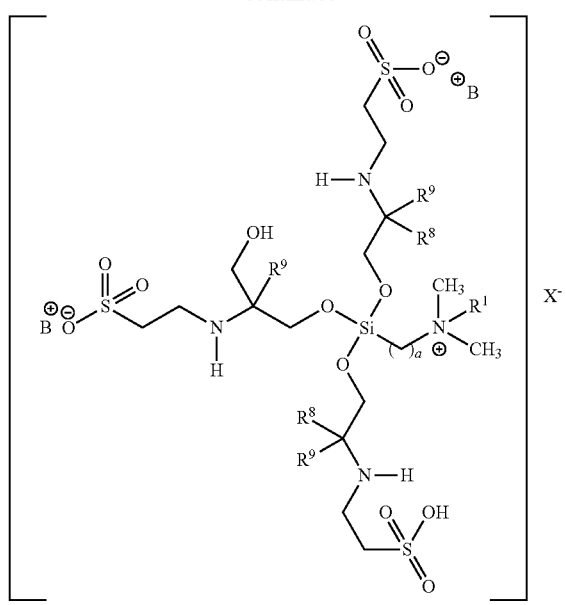
290
-continued
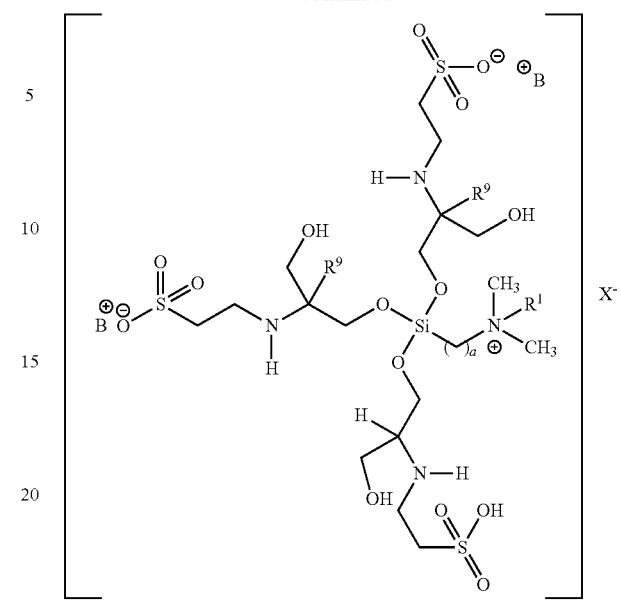
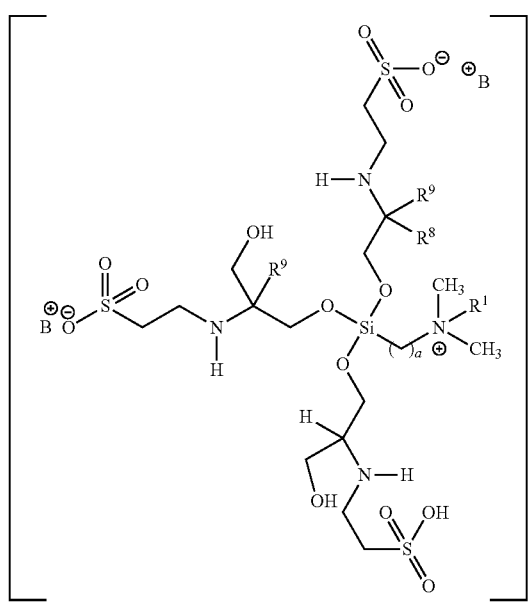

291
-continued
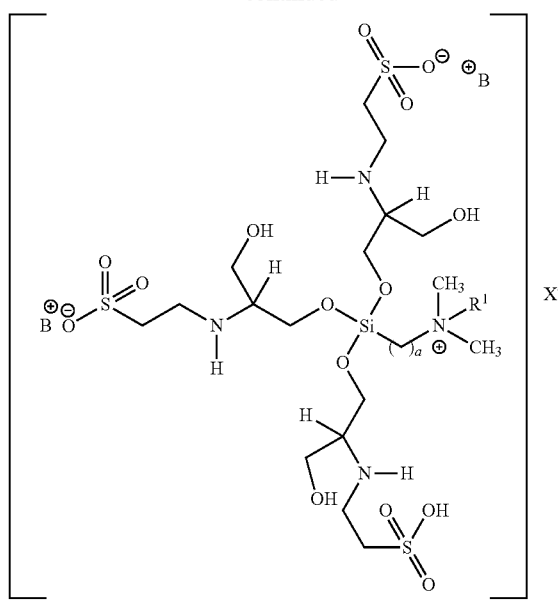
292
-continued
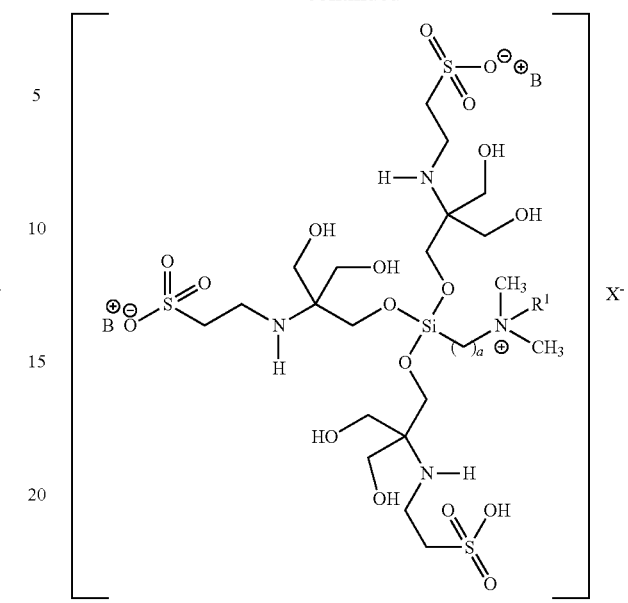
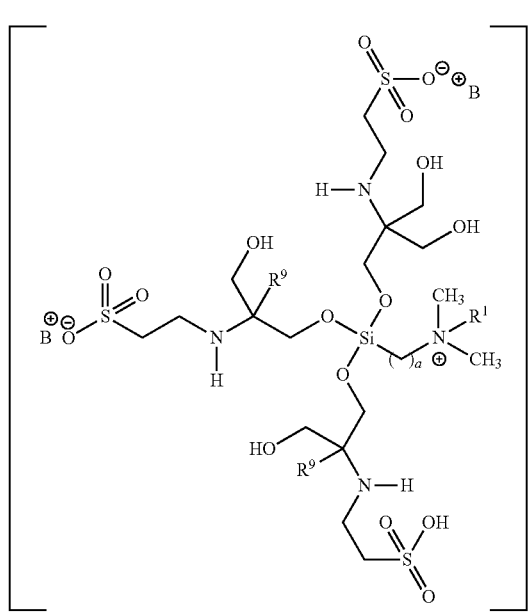
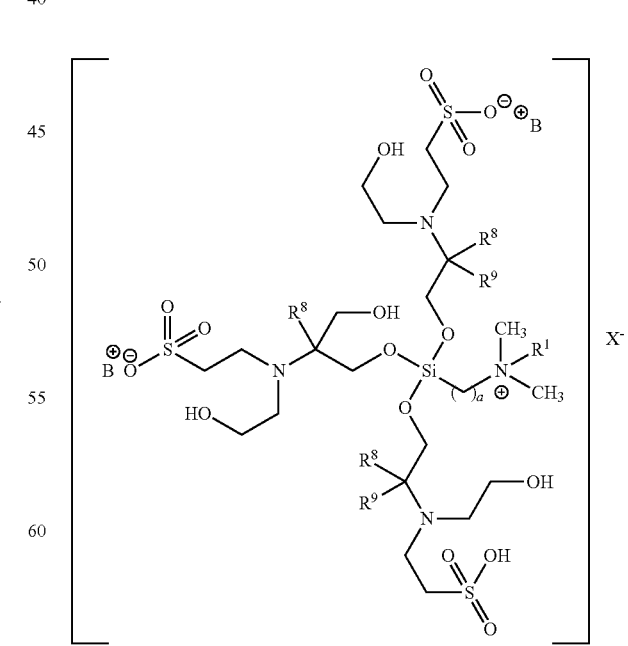

293
-continued
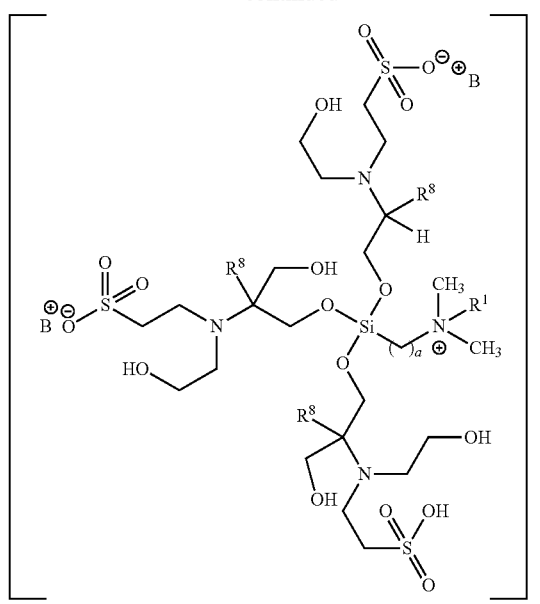
294
-continued
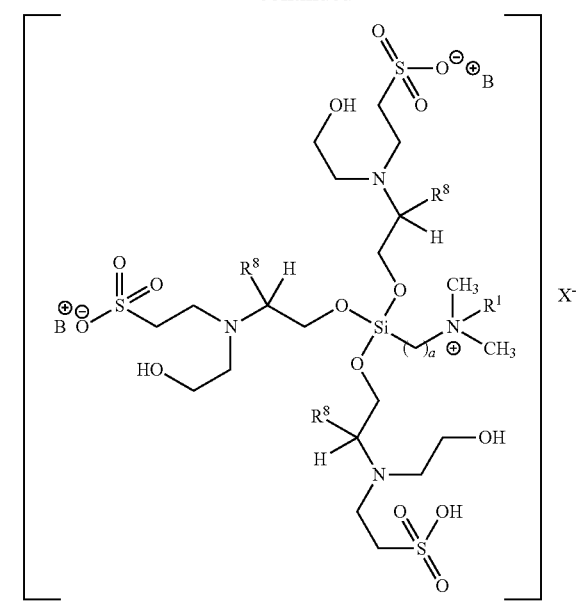
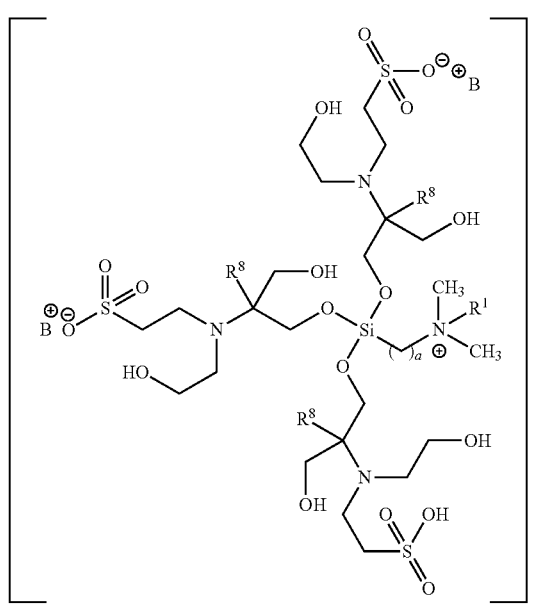
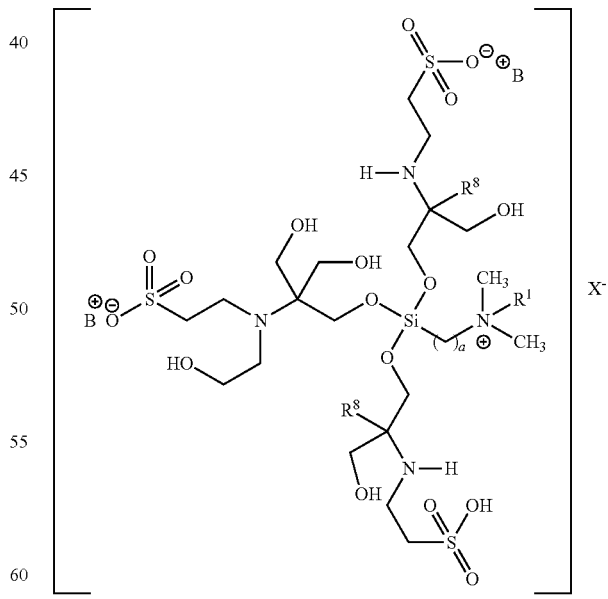

295
-continued
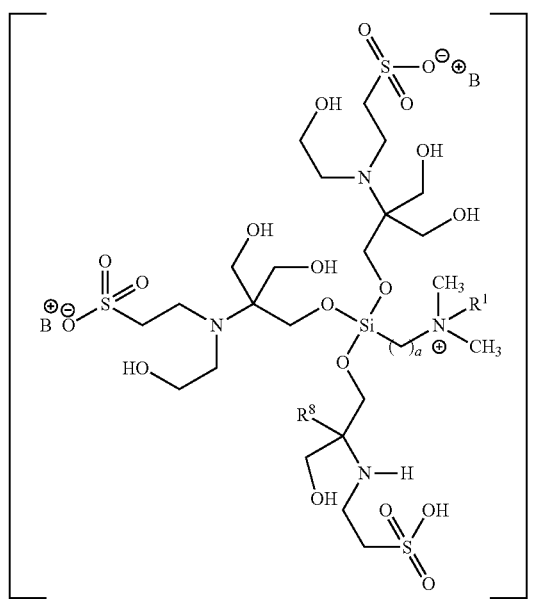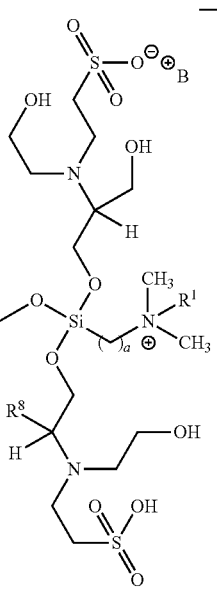
296
-continued
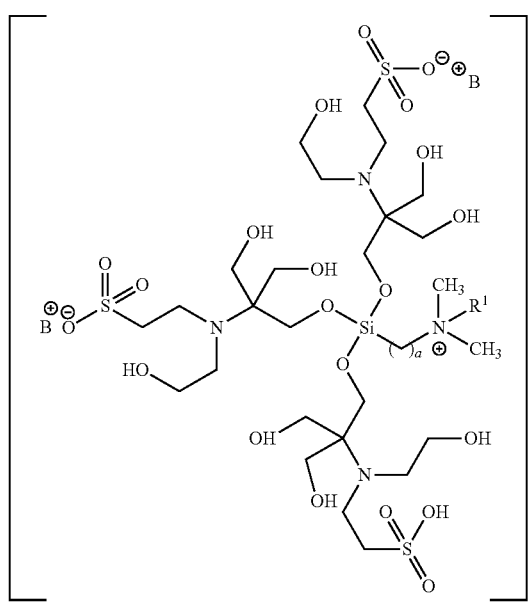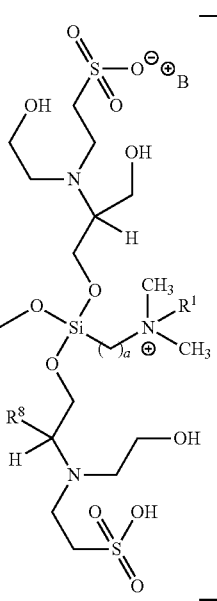

297
-continued
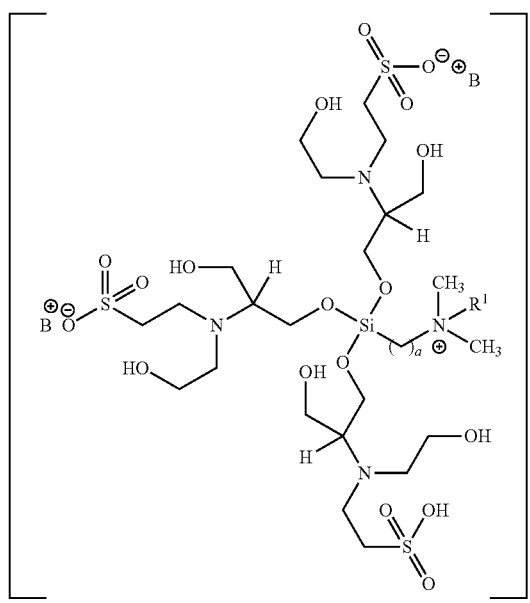
298
-continued
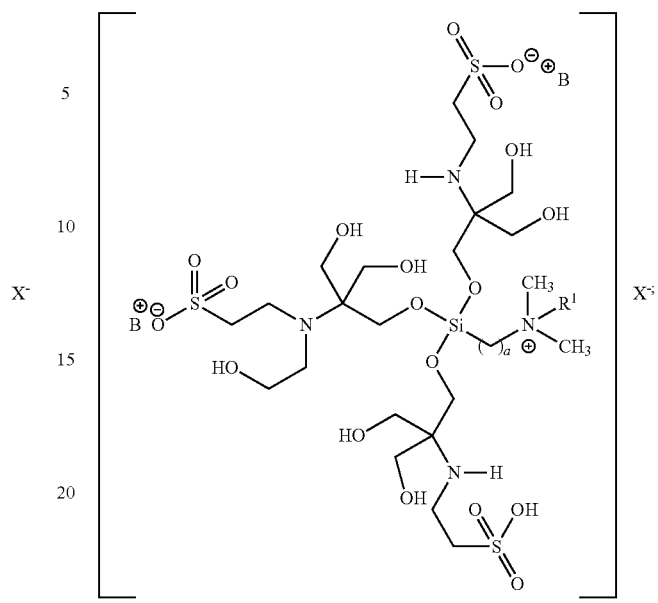
and wherein B⁺ can optionally be replaced with a H⁺ or B⁺ is absent and the moiety is anionic.
In certain embodiments, a quaternary ammonium compound of Formula I is selected from:
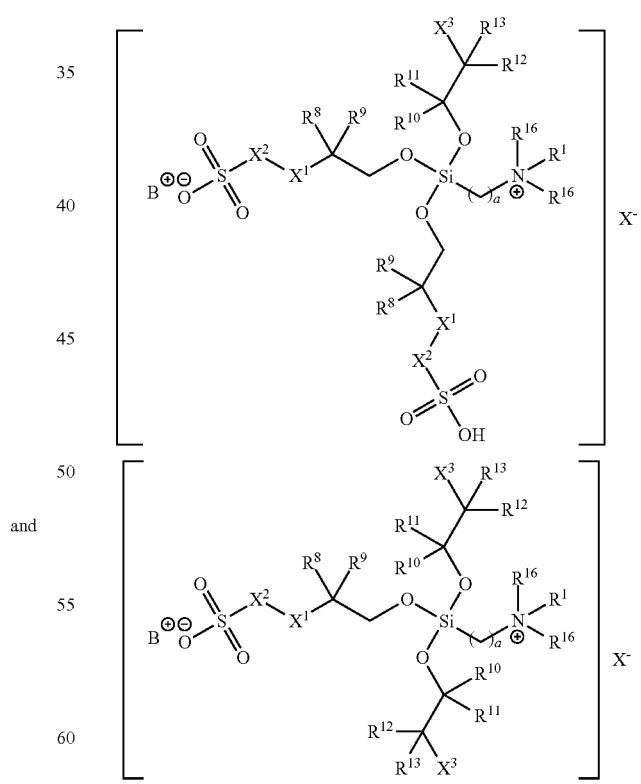
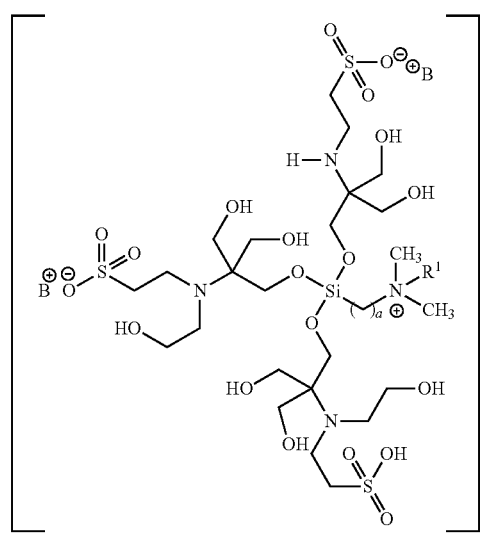
and 299
-continued
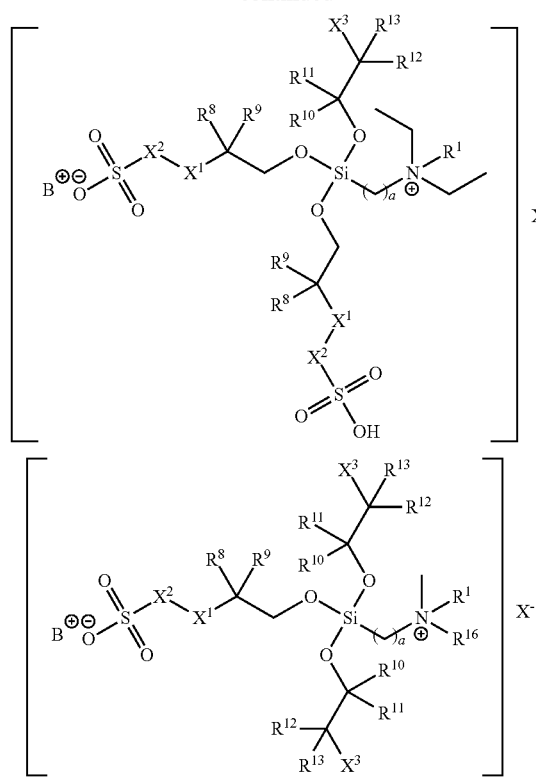
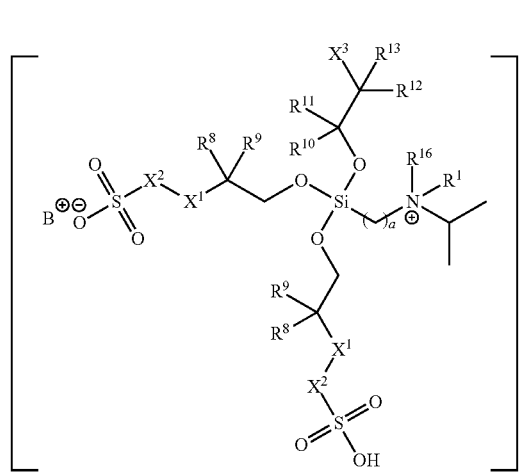
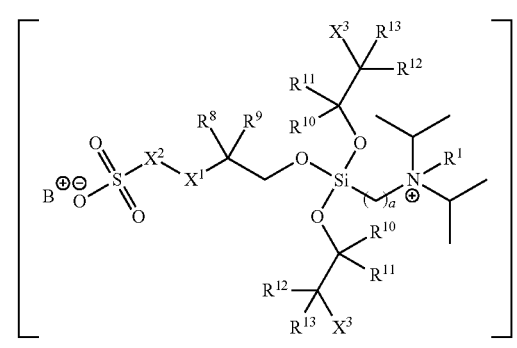
300
-continued
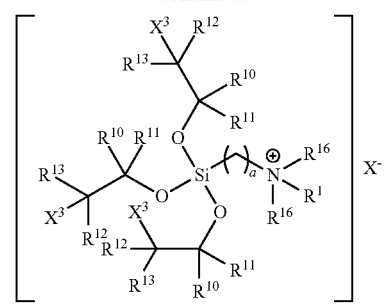
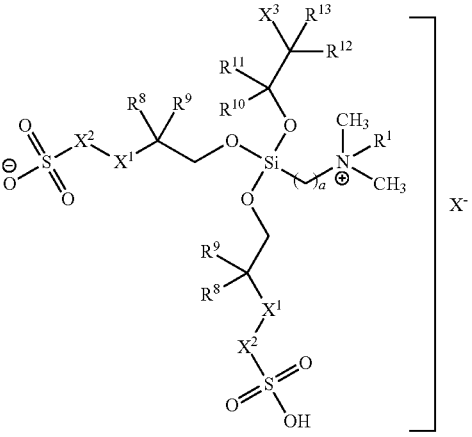
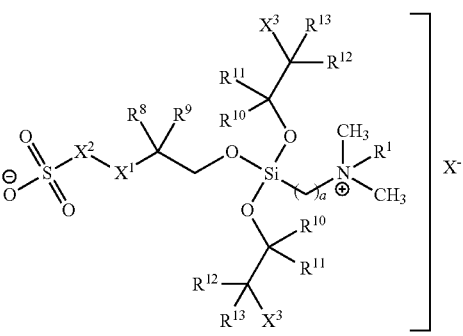
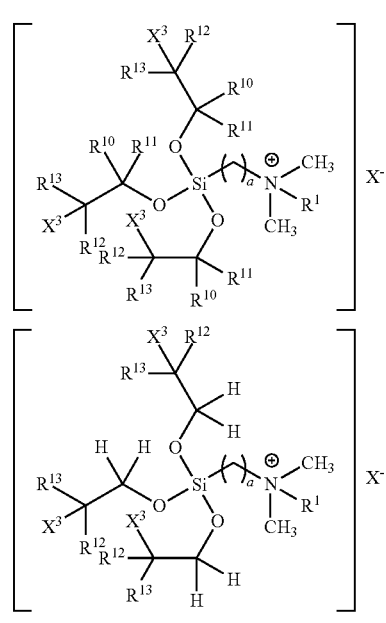

301
-continued
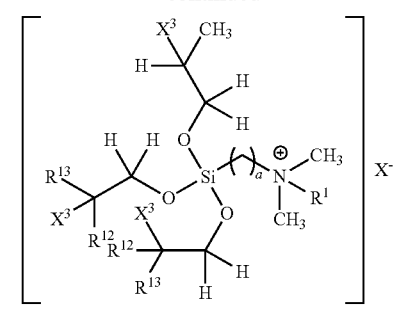
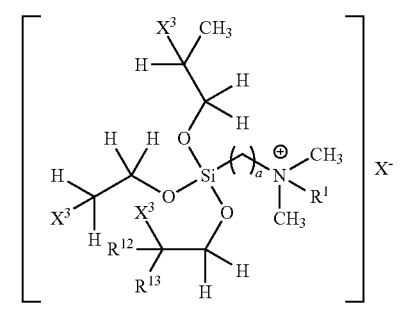
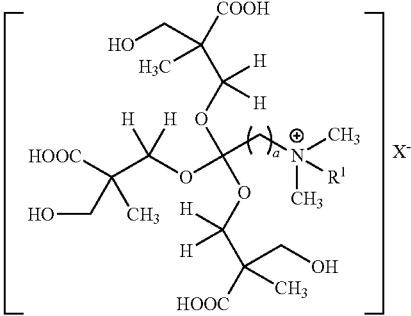
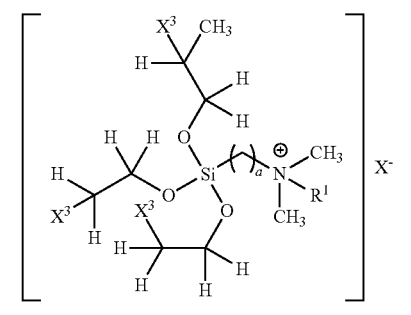
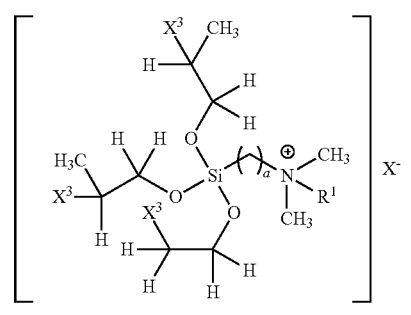
302
-continued
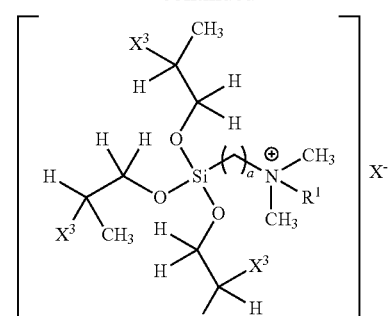
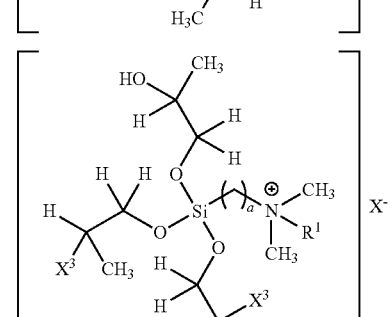
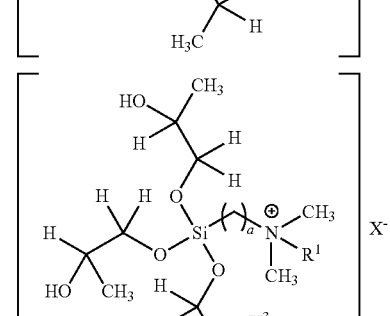
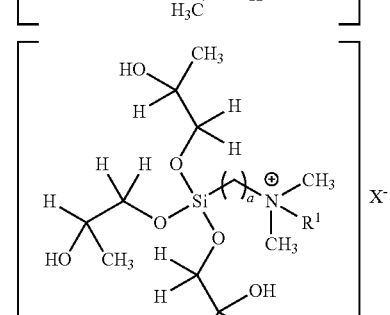
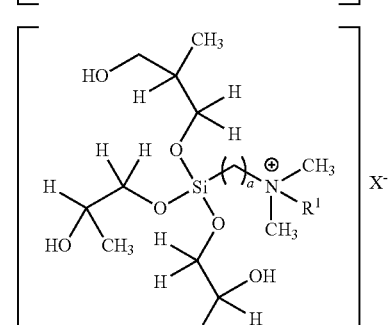

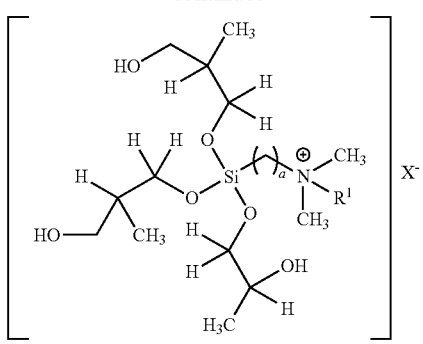
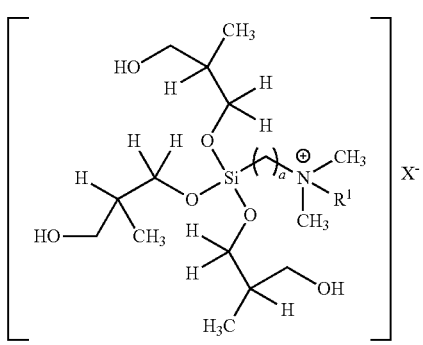
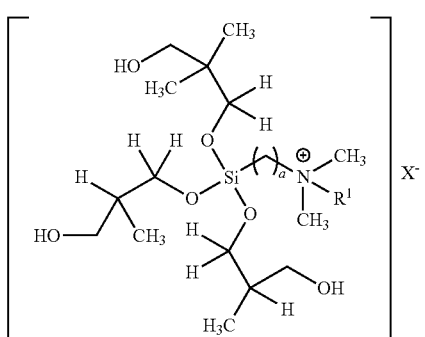
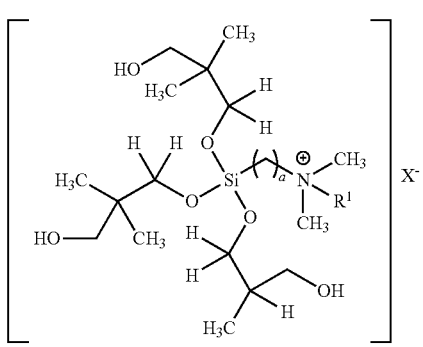
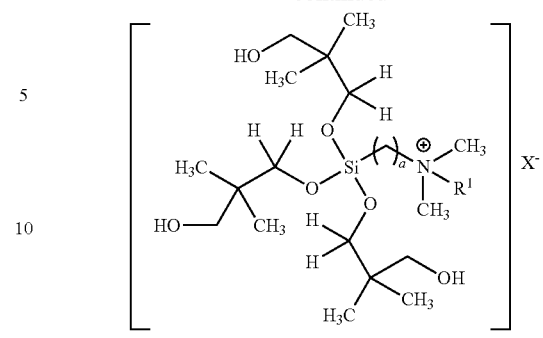
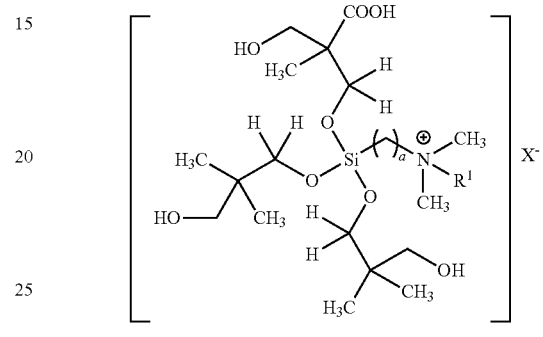
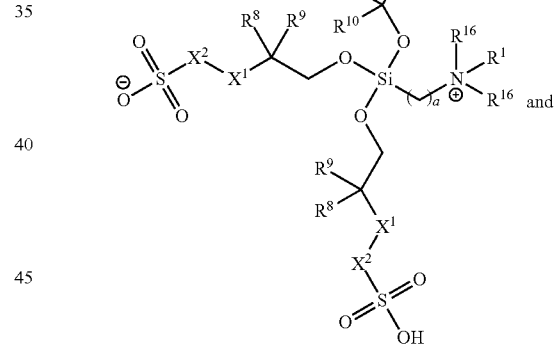
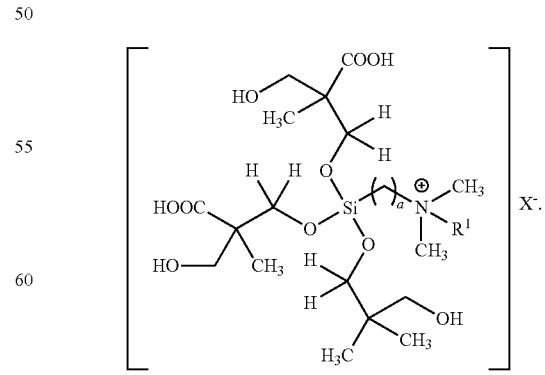
In another aspect of the present invention, a quaternary ammonium compound of Formula I is selected from

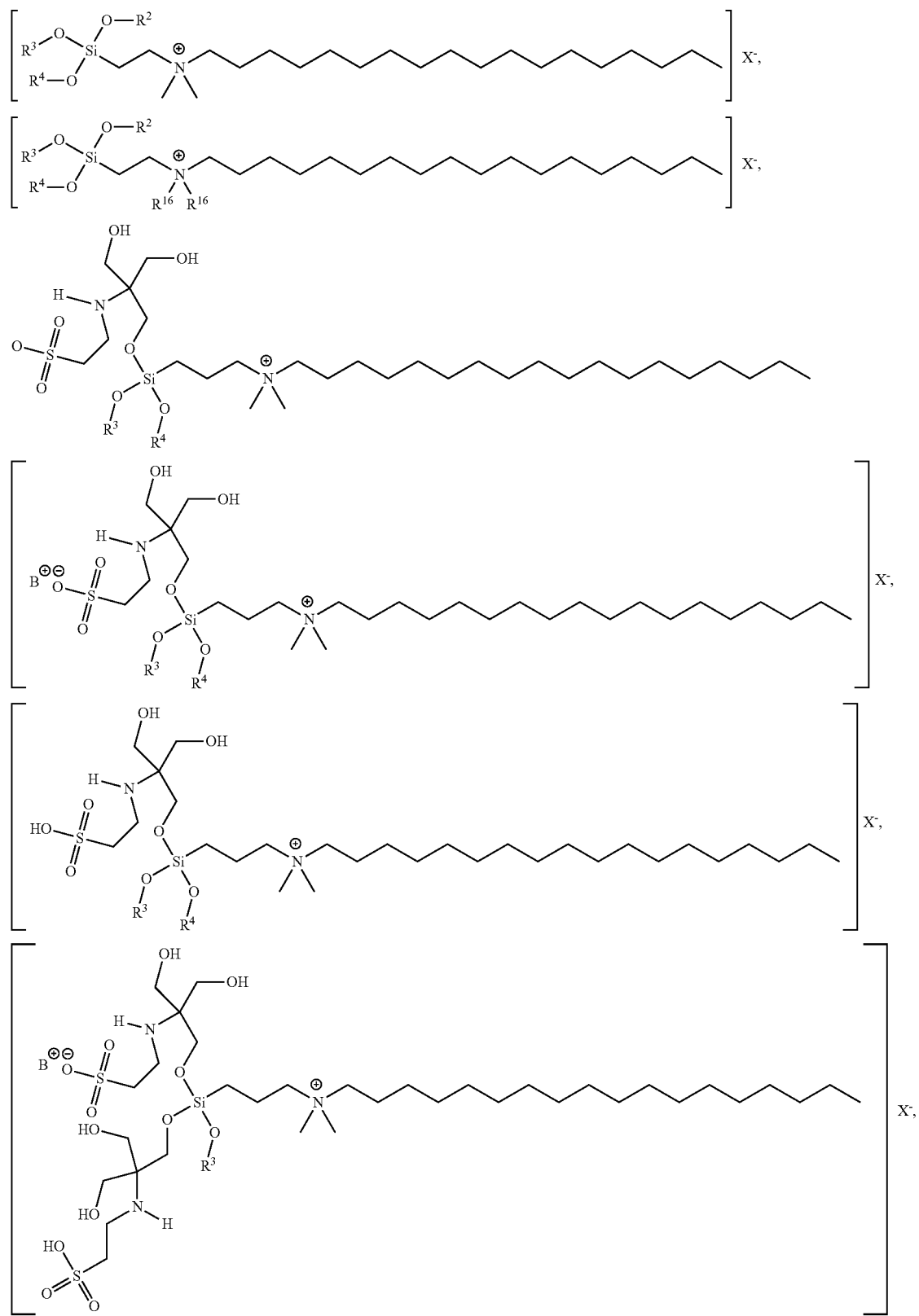

307
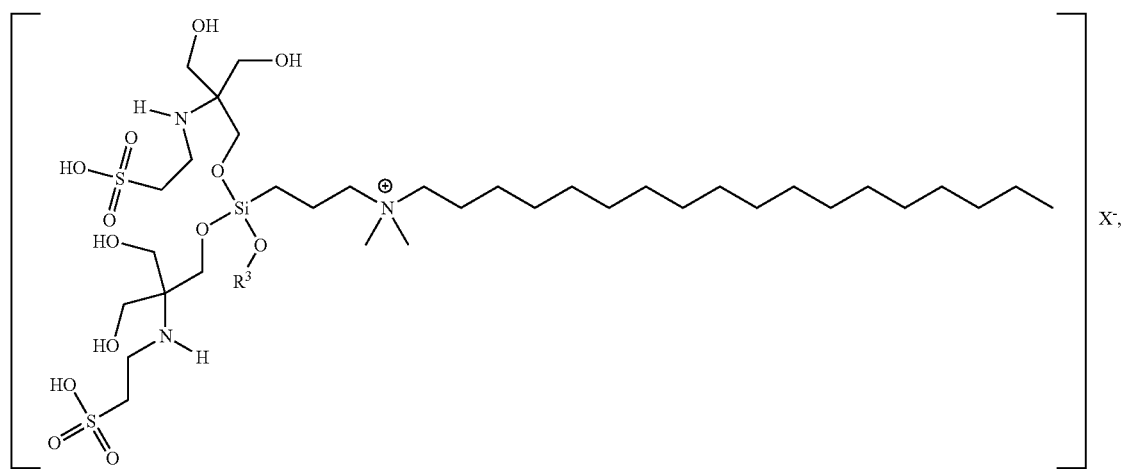
308
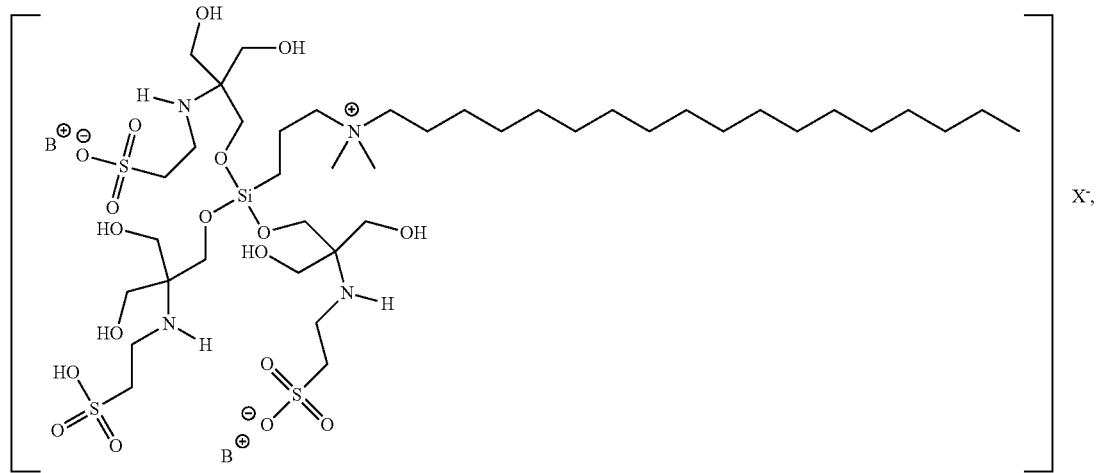
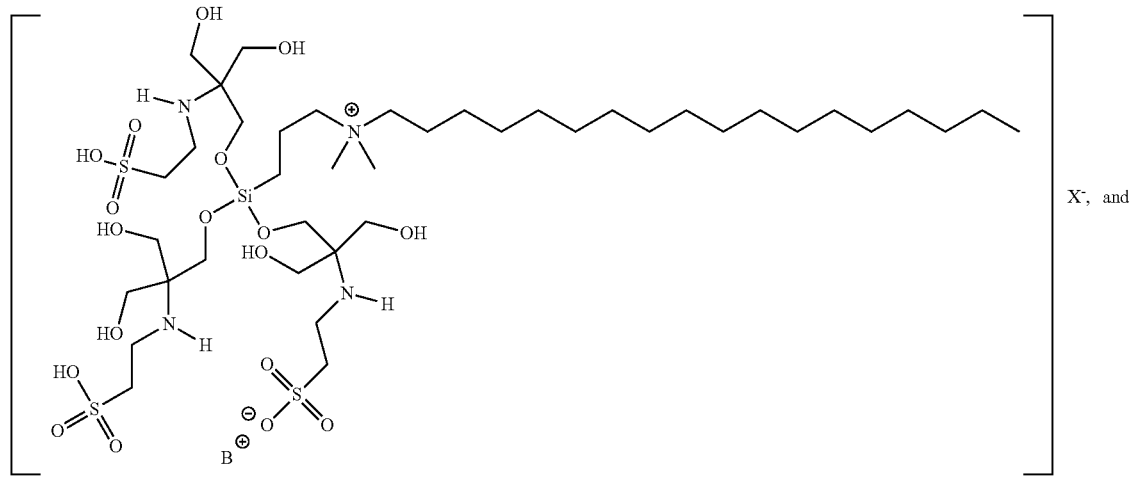

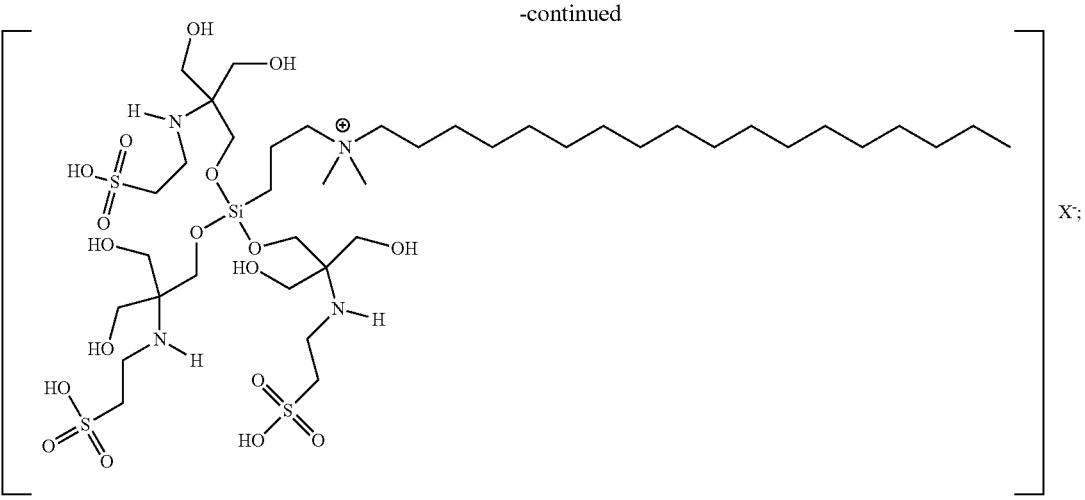
or a salt, or a pharmaceutically acceptable composition thereof.
In another aspect of the present invention, a quaternary ammonium compound of Formula I is selected from
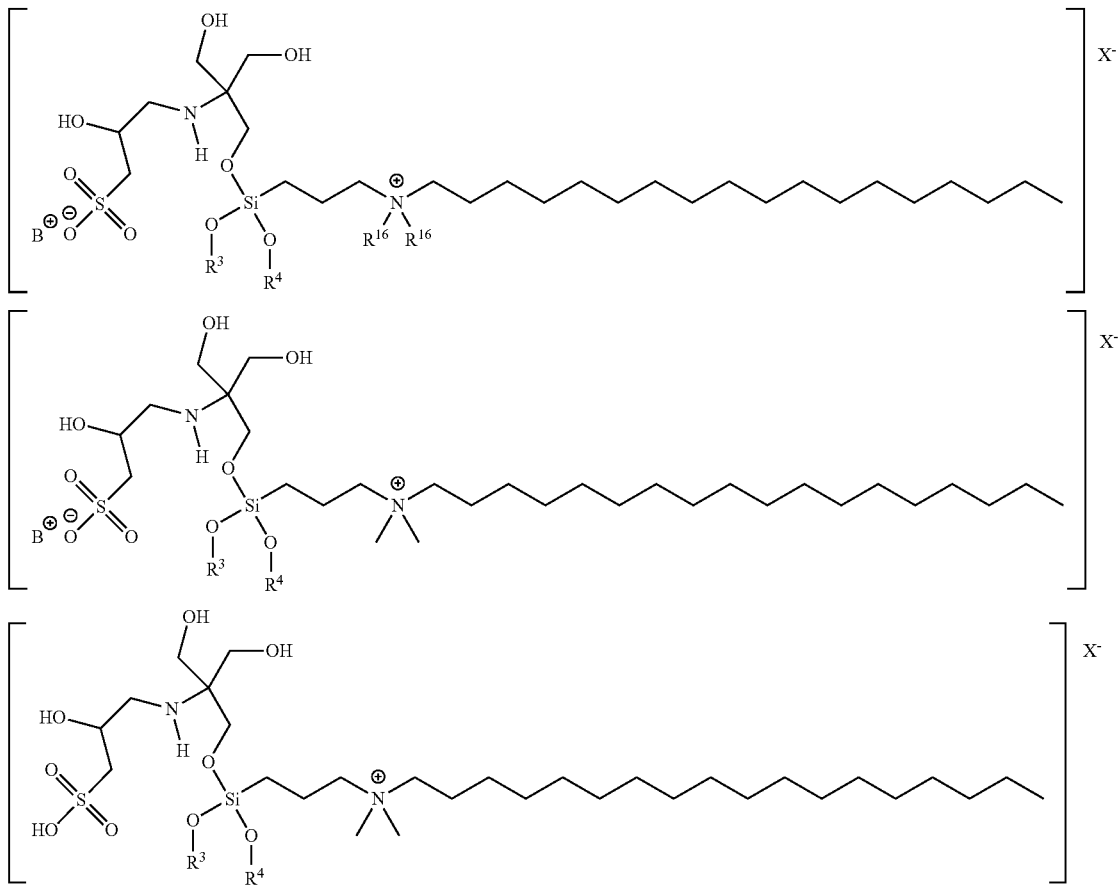

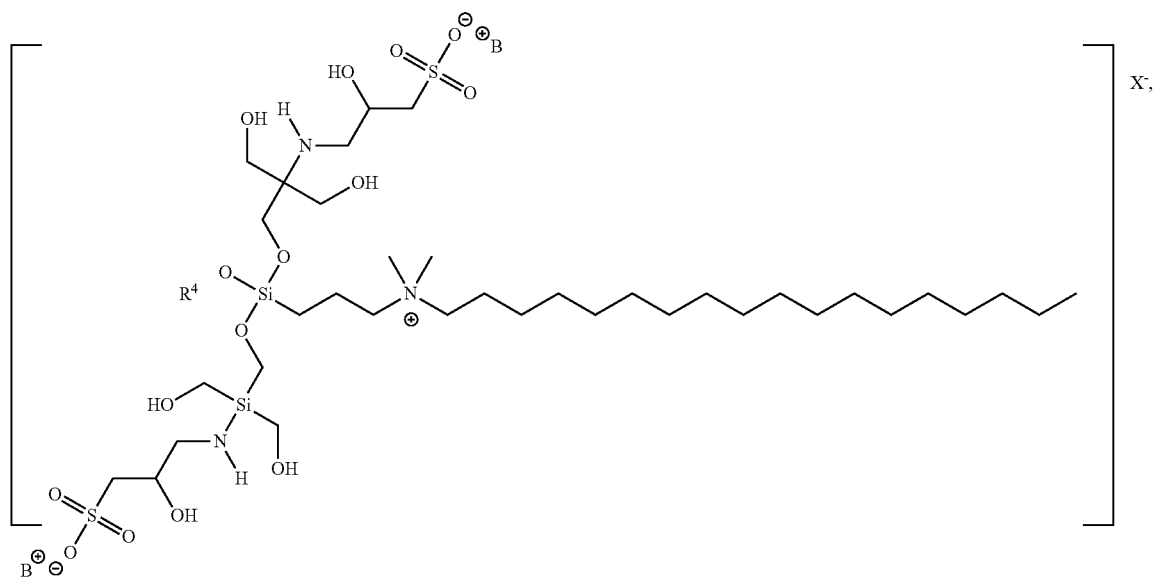
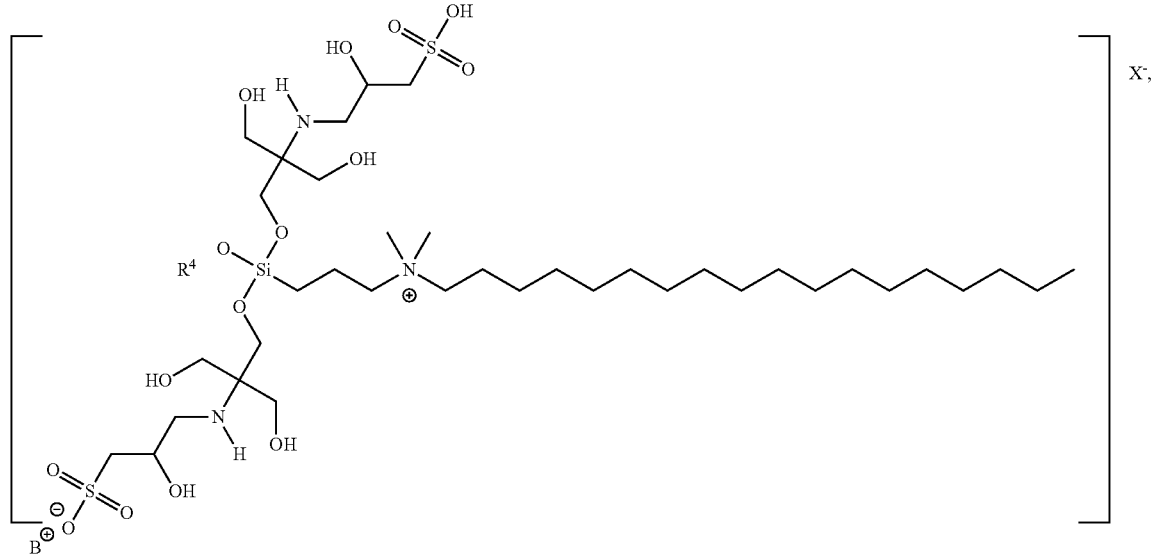
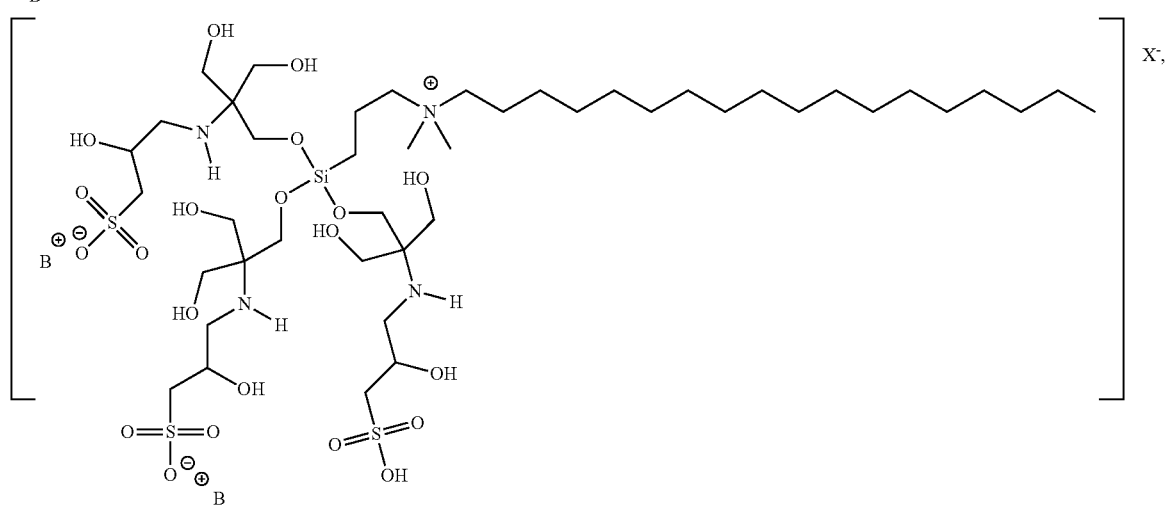

-continued
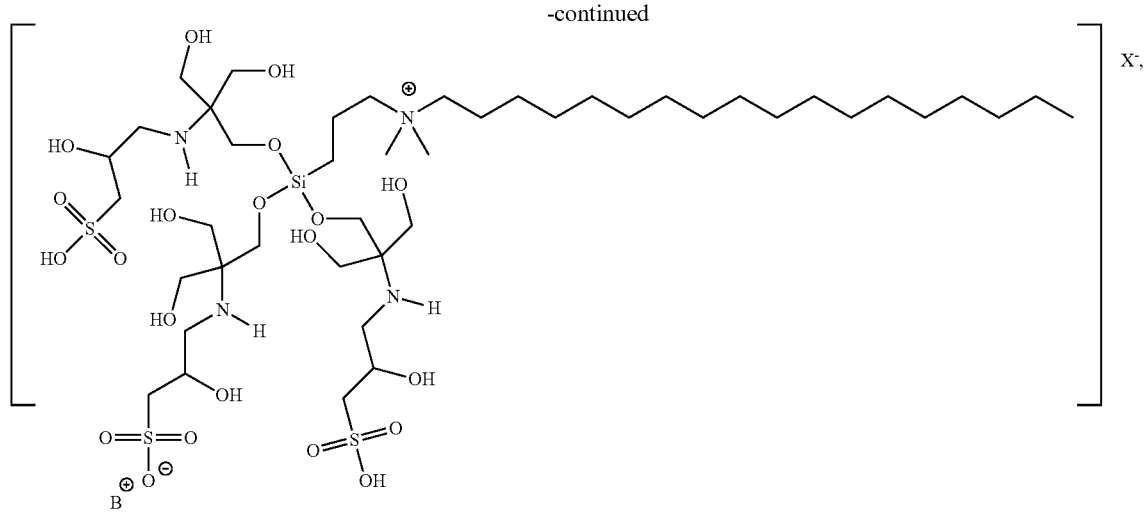
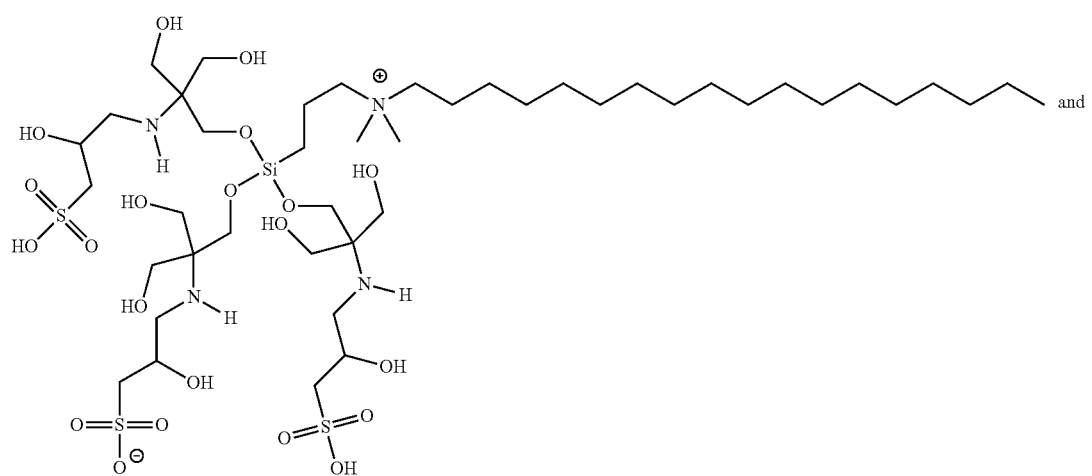
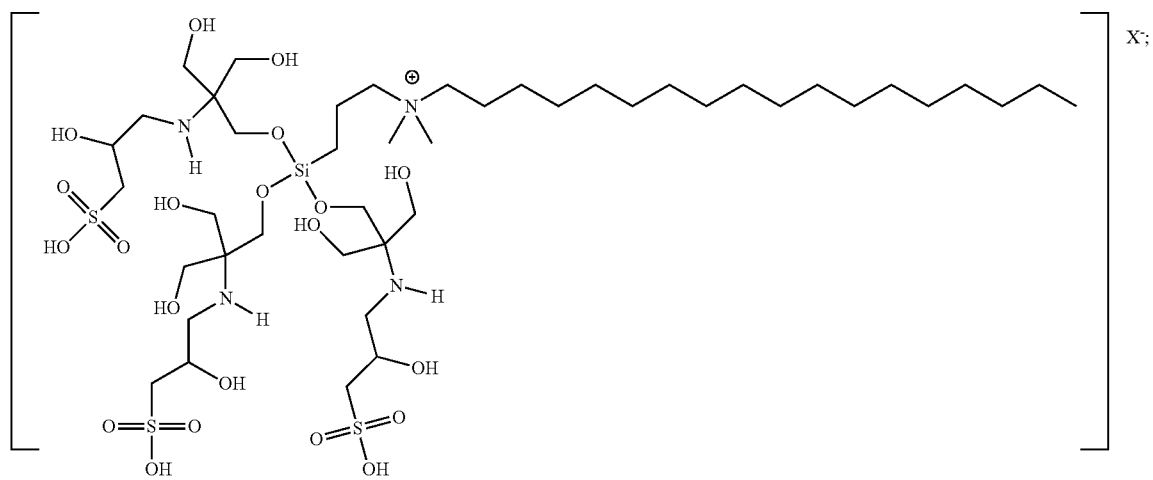
or a salt, or a pharmaceutically acceptable composition thereof.
In another aspect of the present invention, a quaternary ammonium compound of Formula I is selected from:

315
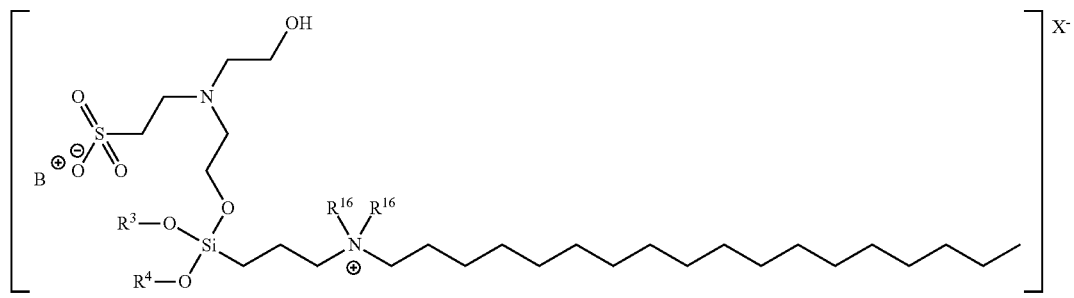
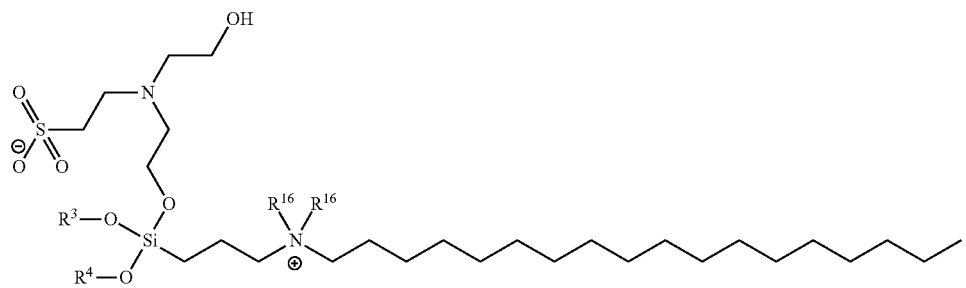
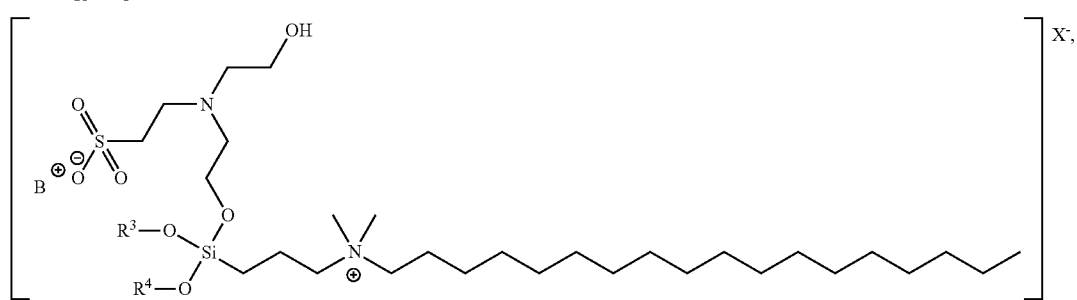
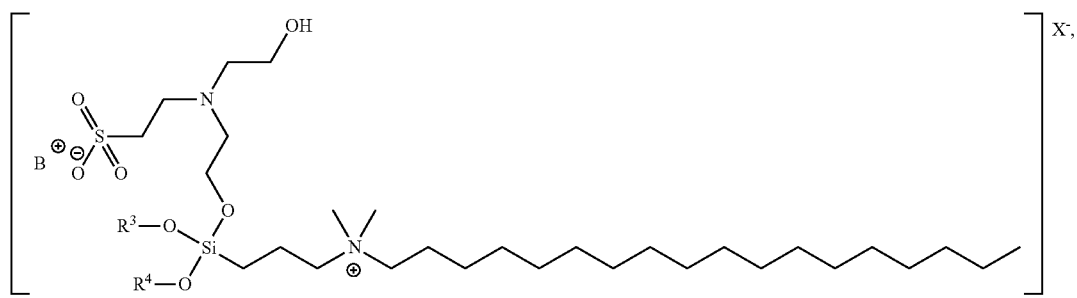
316
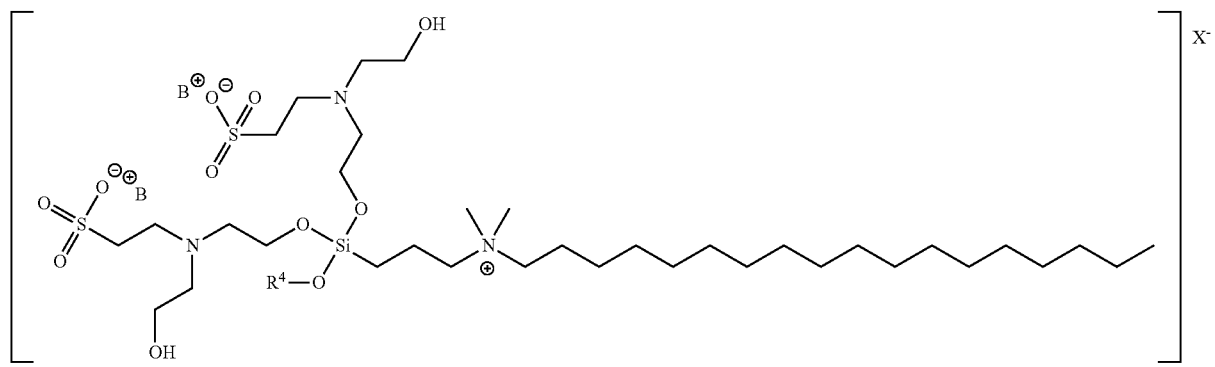

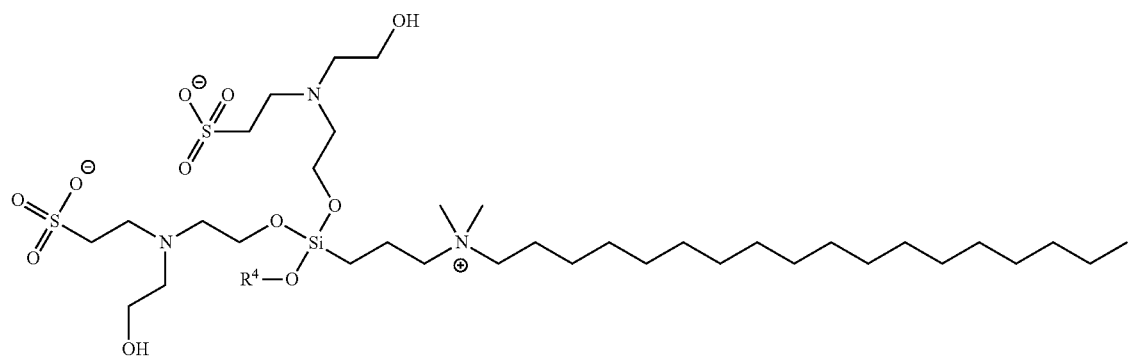
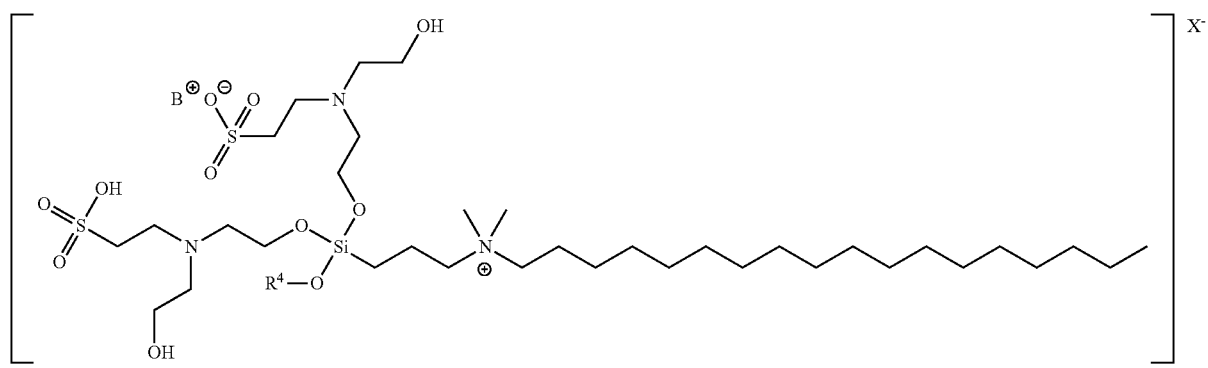
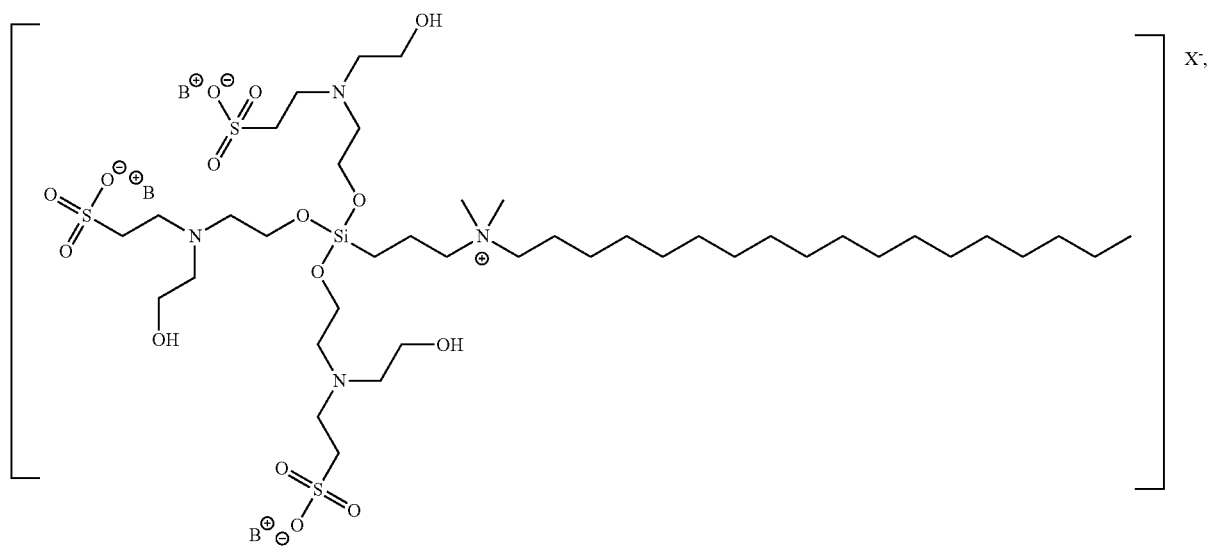

-continued
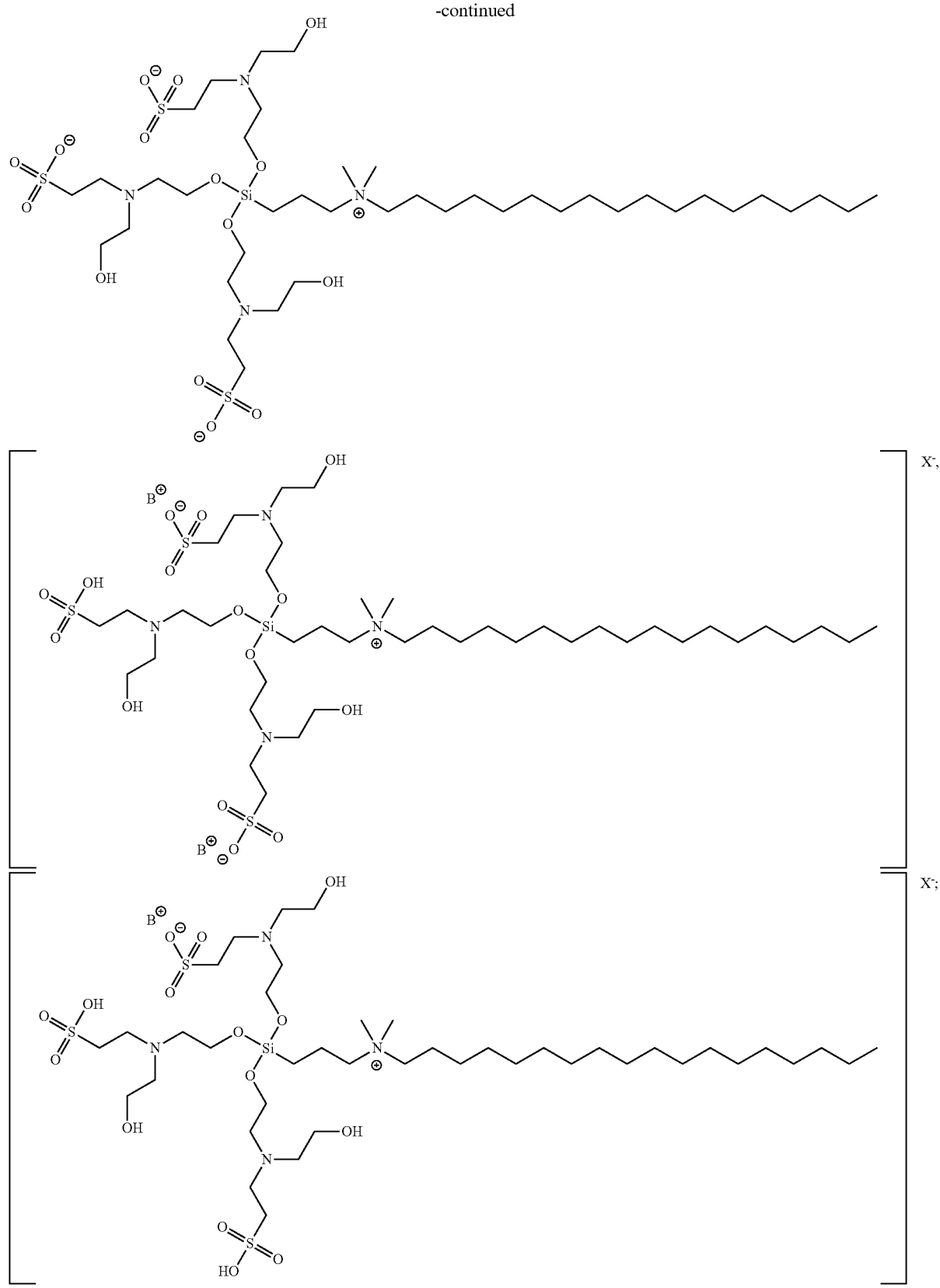
or a salt, or a pharmaceutically acceptable composition thereof.
In another aspect of the present invention, a quaternary ammonium compound of Formula I is selected from:

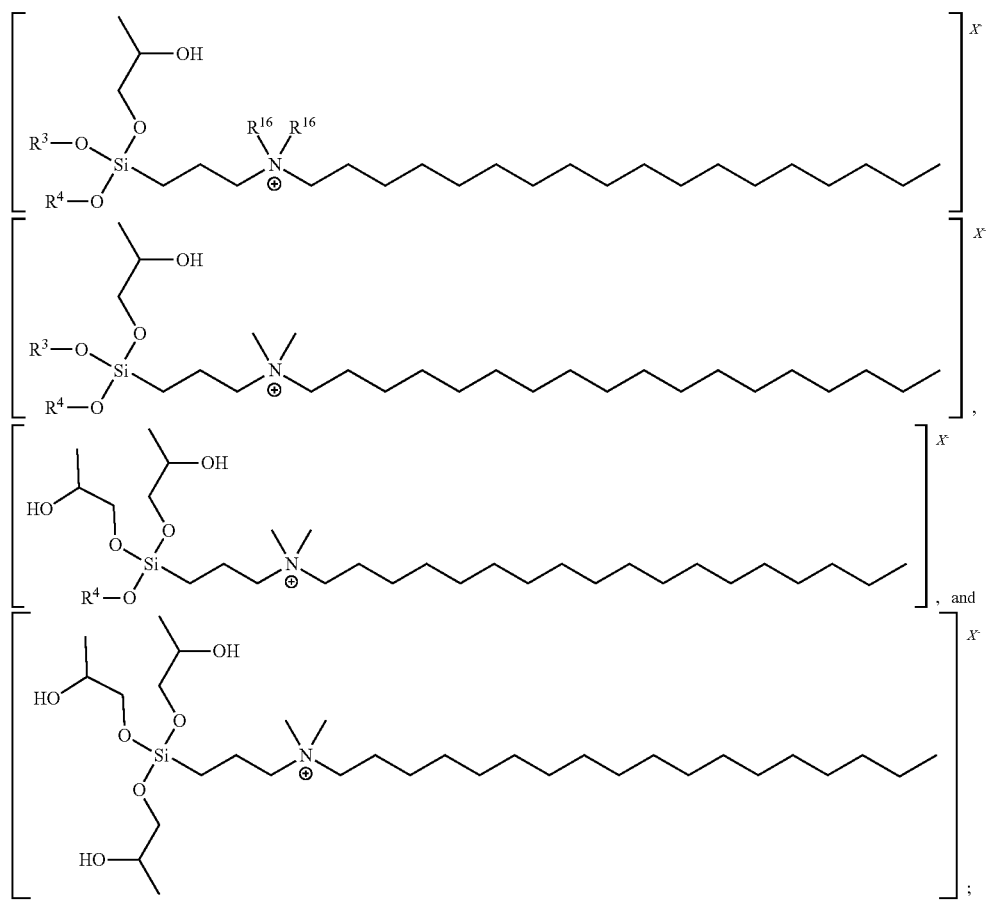
or a salt, or a pharmaceutically acceptable composition thereof.
In another aspect of the present invention a quaternary ammonium compound of Formula I is selected from:
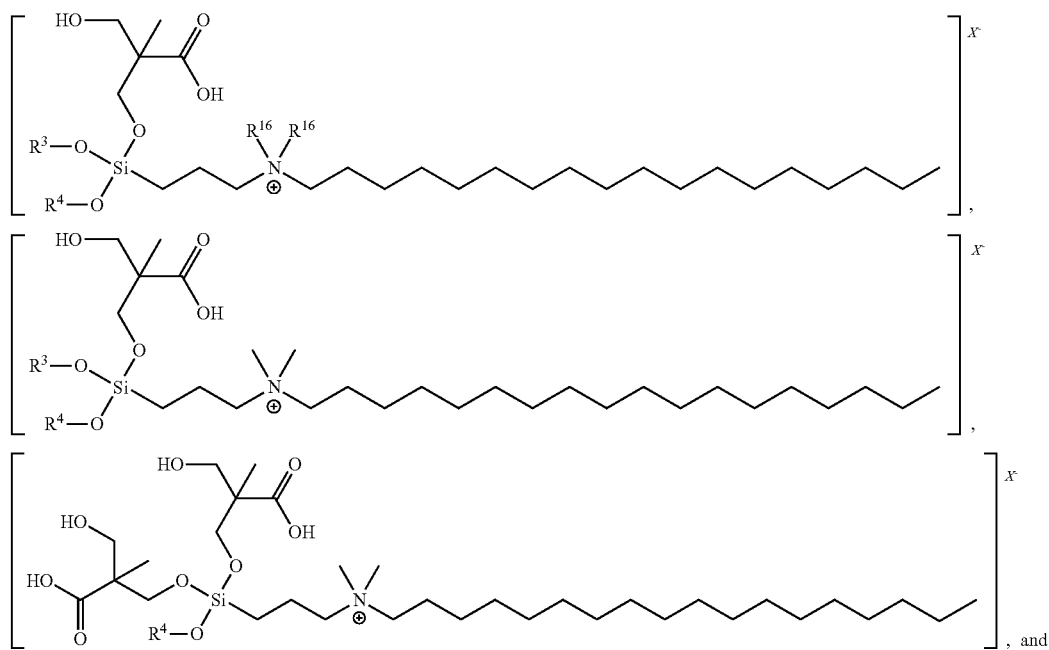

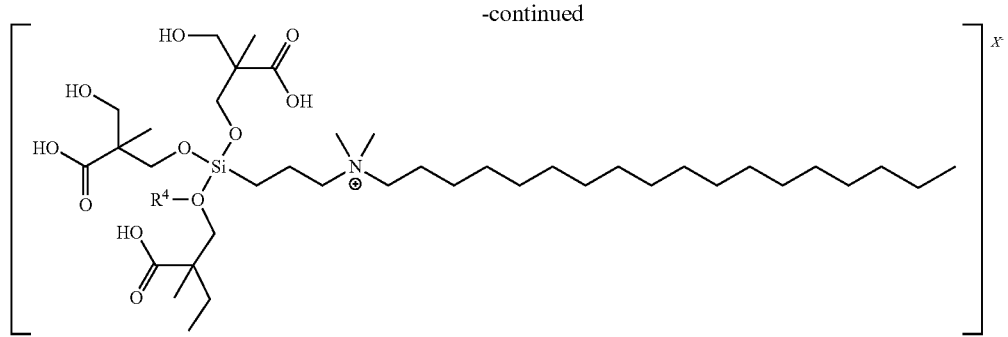
or a salt, or a pharmaceutically acceptable composition thereof.
In another aspect of the present invention, a quaternary ammonium compound of Formula I is selected from:
or a salt, or a pharmaceutically acceptable composition thereof.
In another aspect of the present invention, a quaternary ammonium compound of Formula I is selected from:
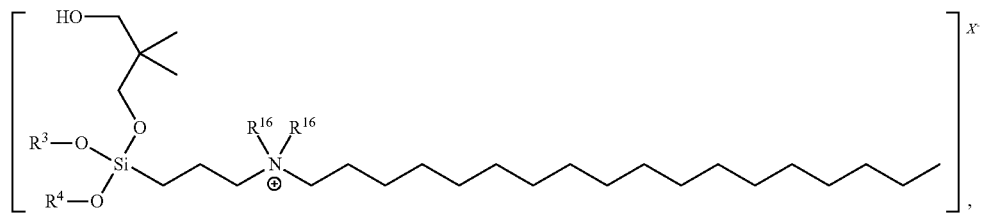
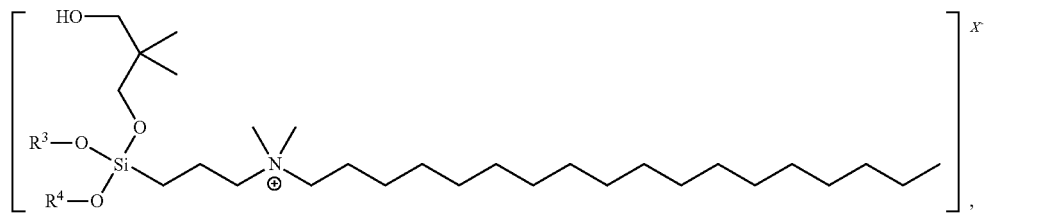
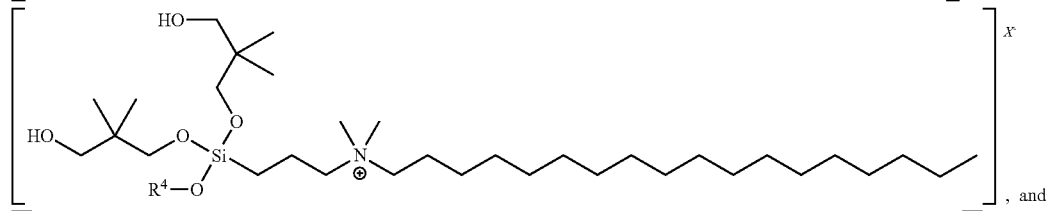
, and
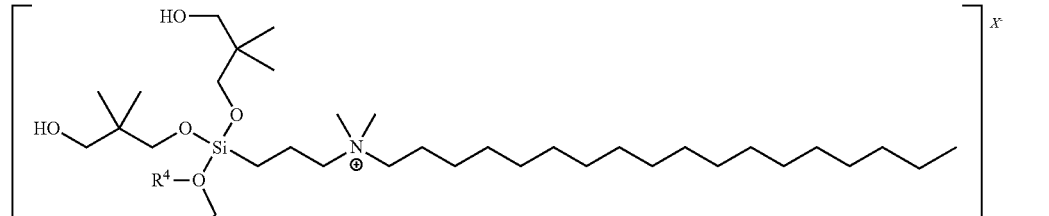

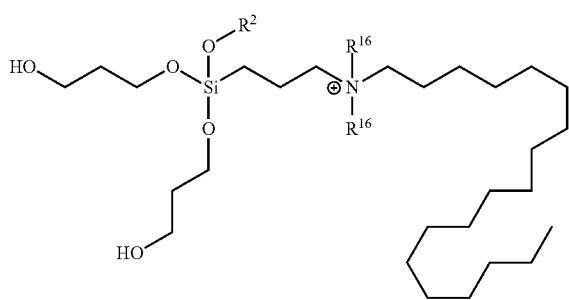
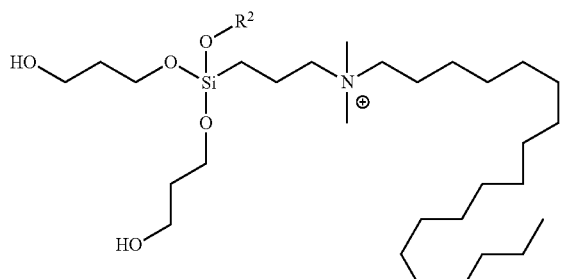
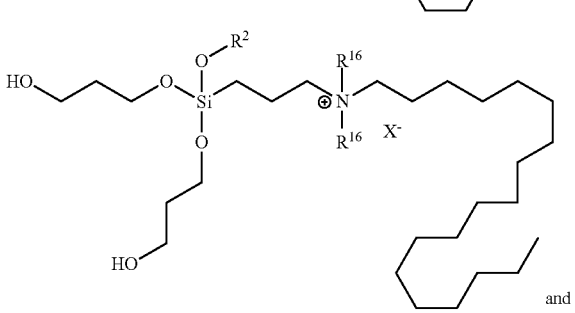
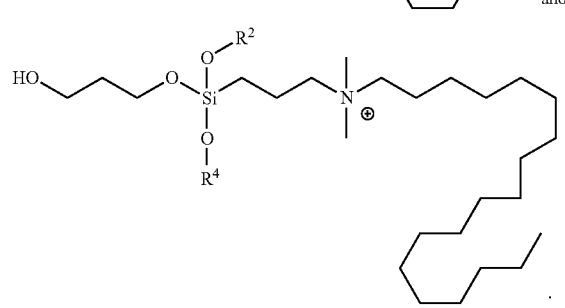
In another aspect of the present invention, a quaternary ammonium compound of Formula I is selected from:
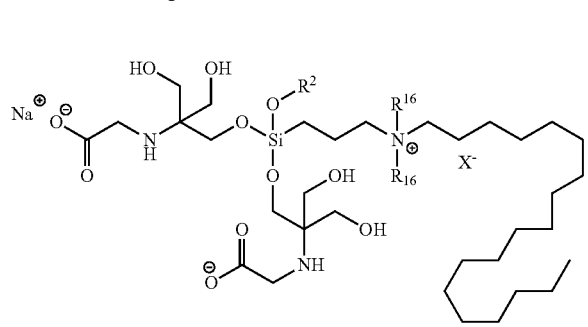
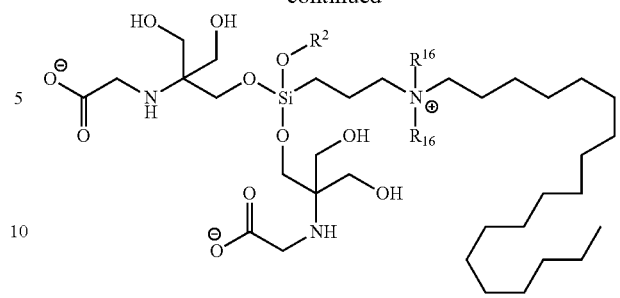
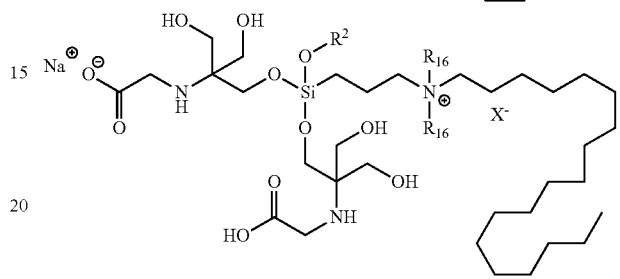
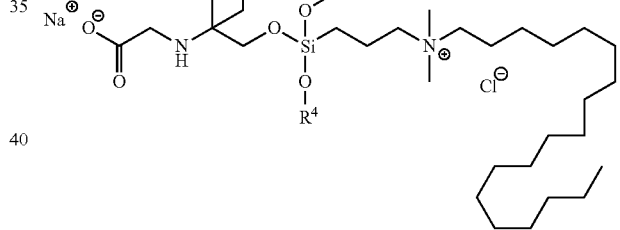
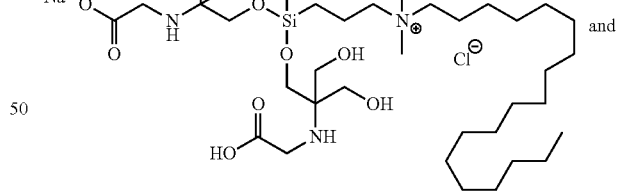
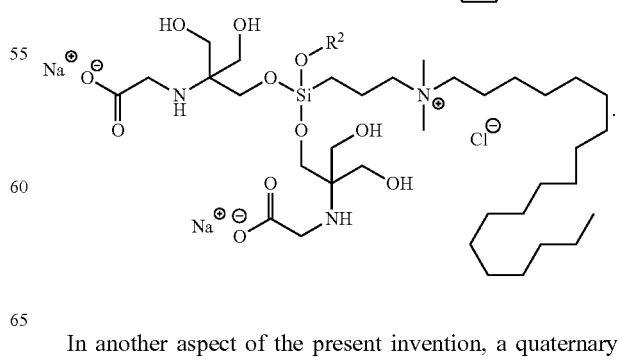
In another aspect of the present invention, a quaternary ammonium compound of Formula I is selected from:

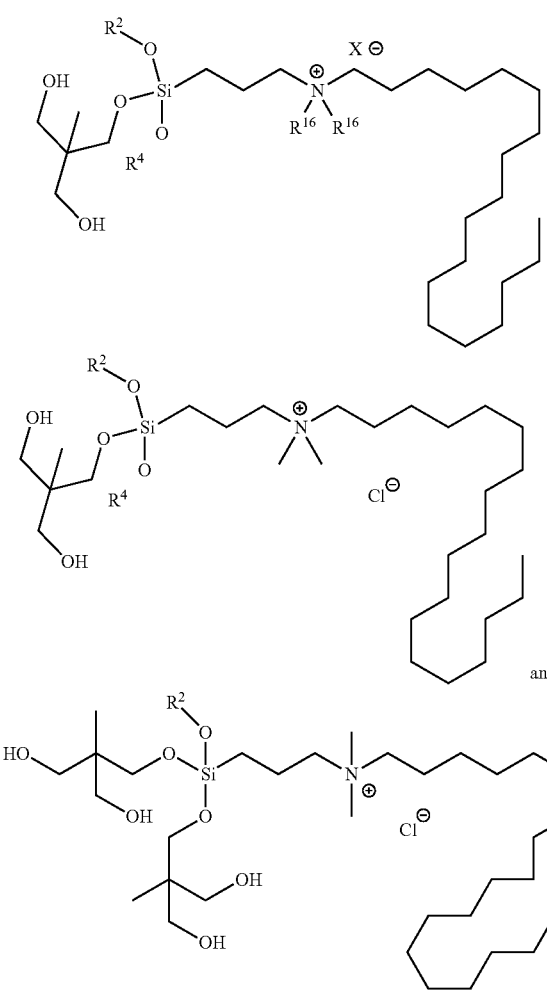
In another aspect of the present invention, a quaternary ammonium compound of Formula I is selected from:
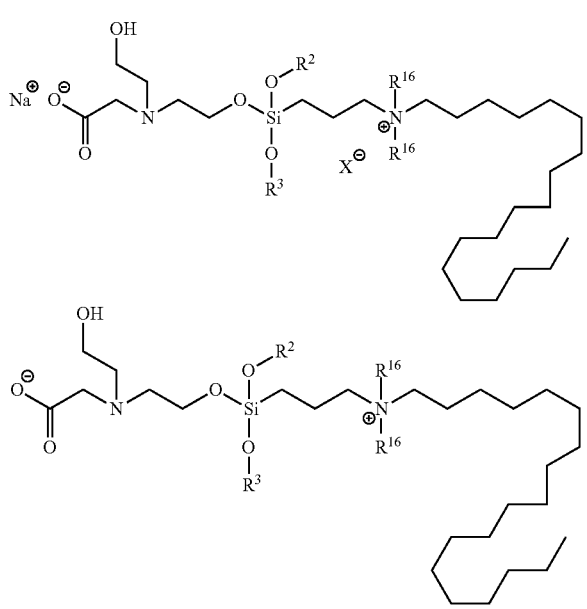
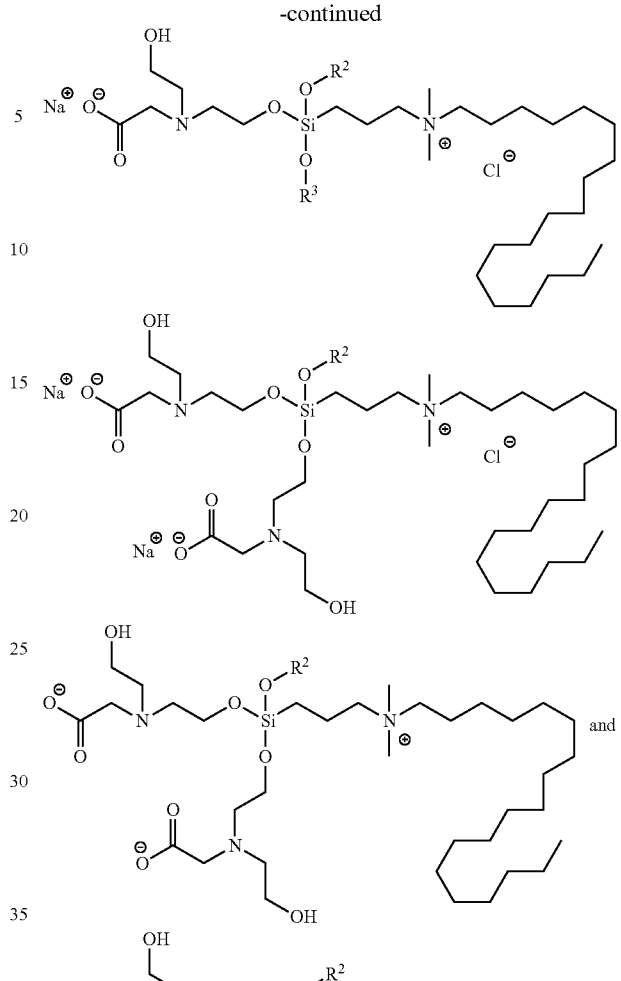
In another aspect of the present invention, a quaternary ammonium compound of Formula I is selected from:
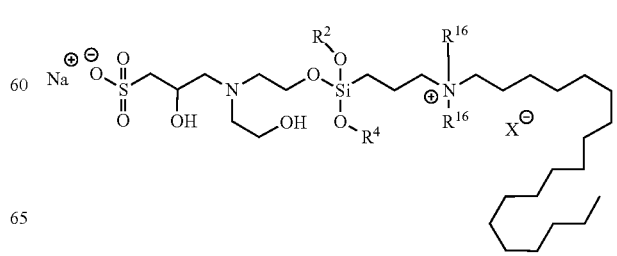

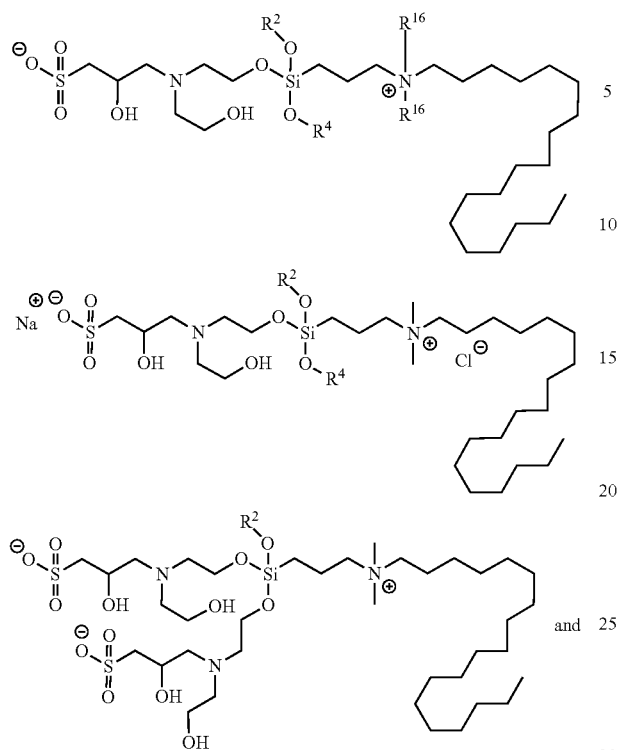
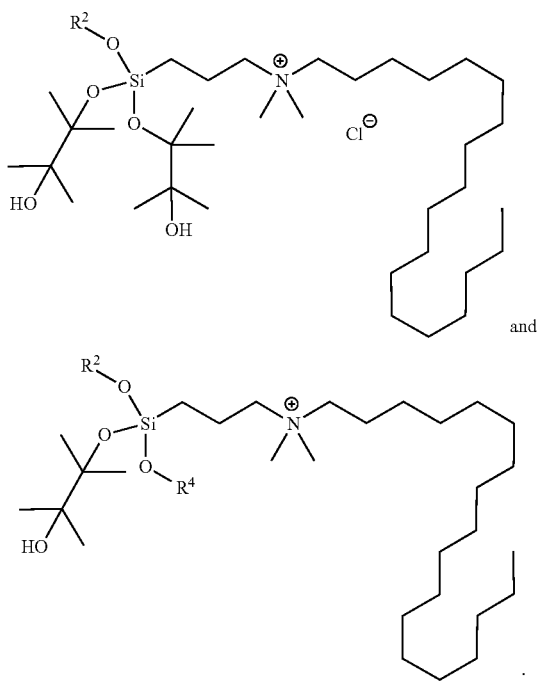
In another aspect of the present invention, a quaternary ammonium compound of Formula I is selected from:
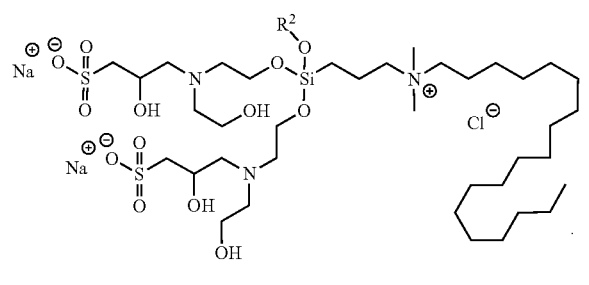
In another aspect of the present invention, a quaternary ammonium compound of Formula I is selected from:
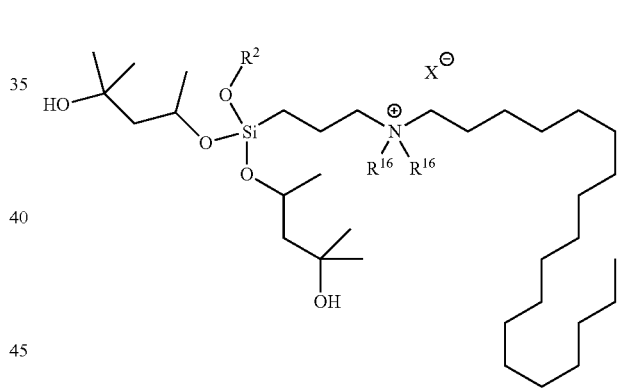
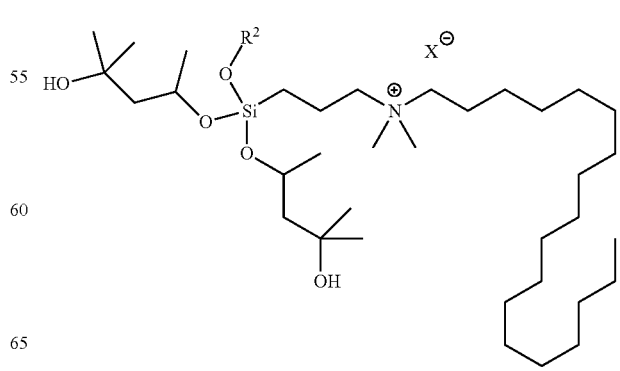

331
-continued
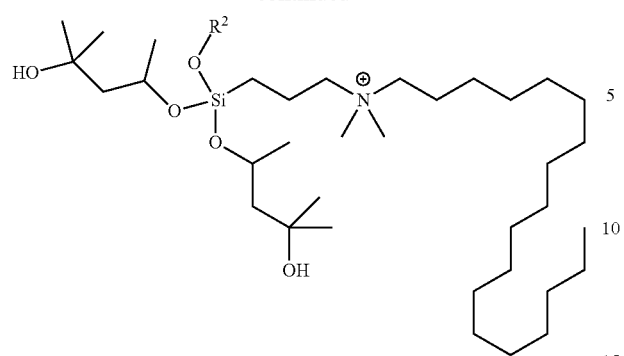
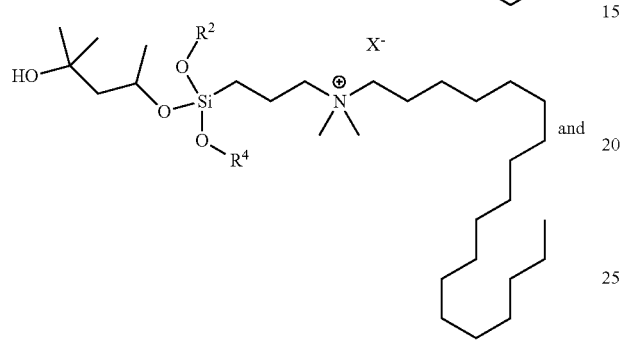
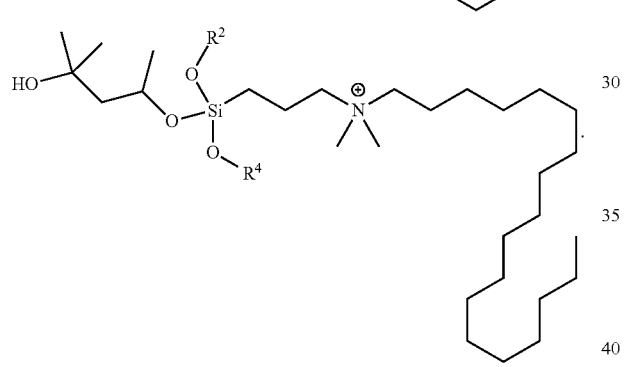
In another aspect of the present invention, a quaternary ammonium compound of Formula I is selected from:
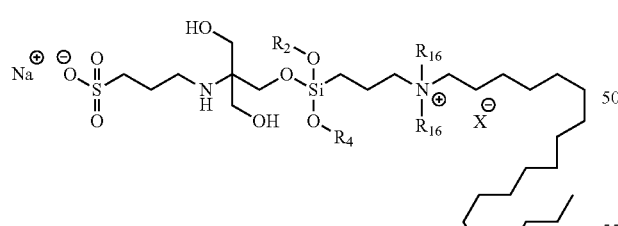
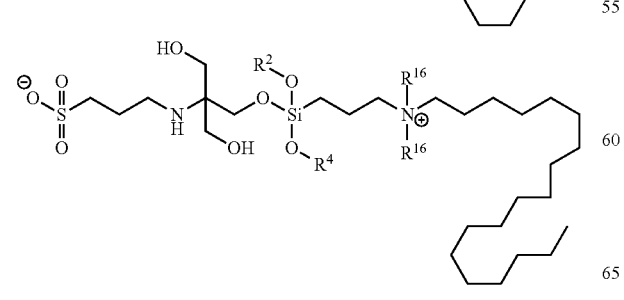
332
-continued
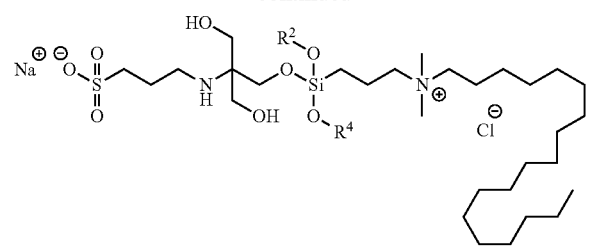
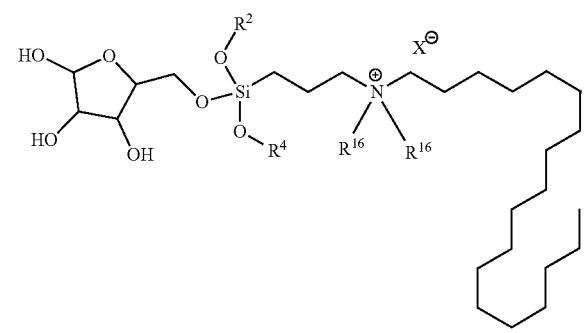
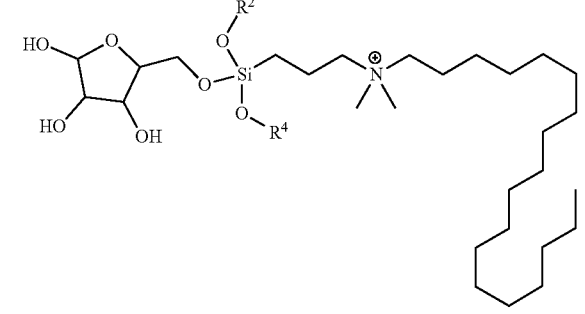
In another aspect of the present invention, a quaternary ammonium compound of Formula I is selected from:
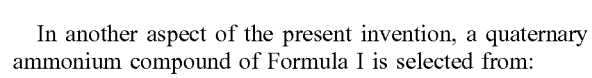

333
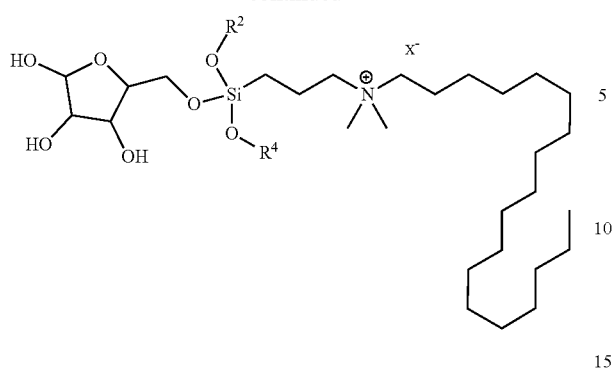
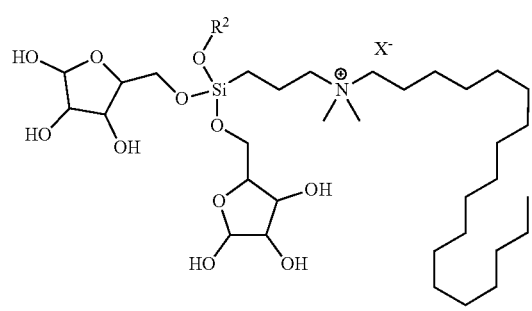
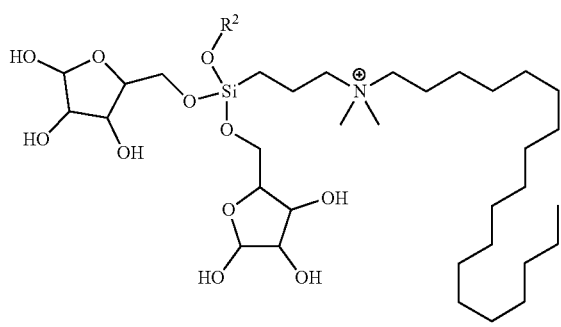
In another aspect of the present invention, a quaternary ammonium compound of Formula I is selected from:
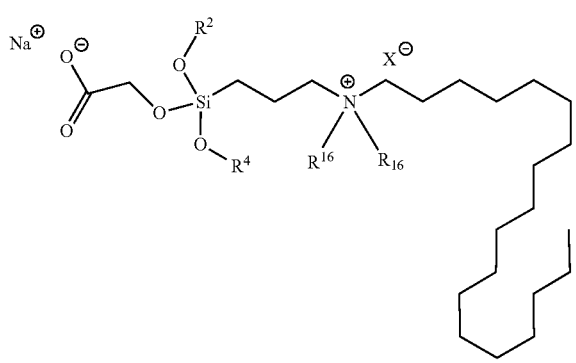
334
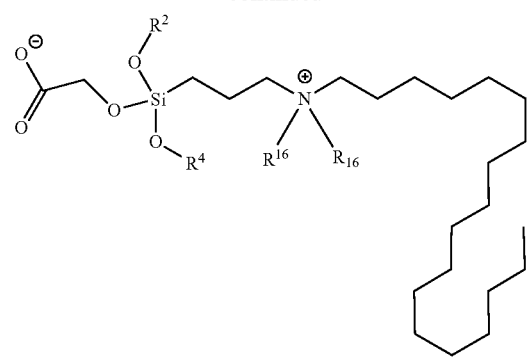
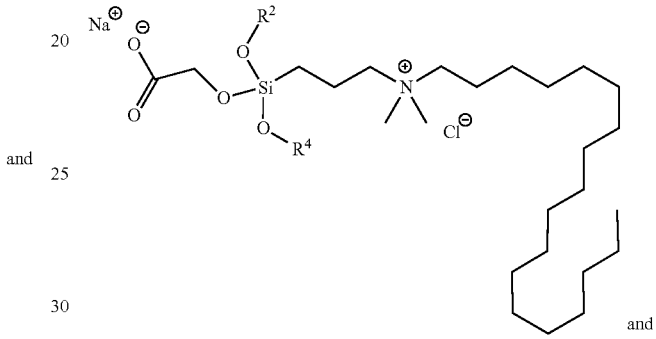
and
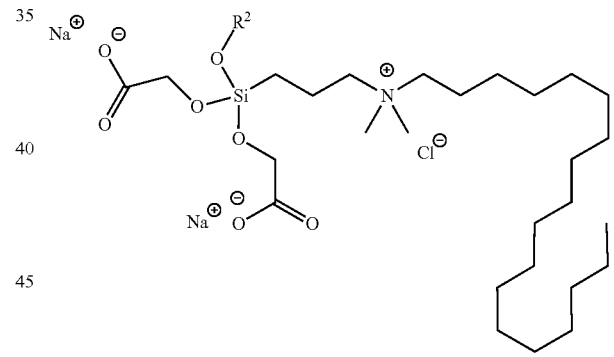
and
In another aspect of the present invention, a quaternary ammonium compound of Formula I is selected from:
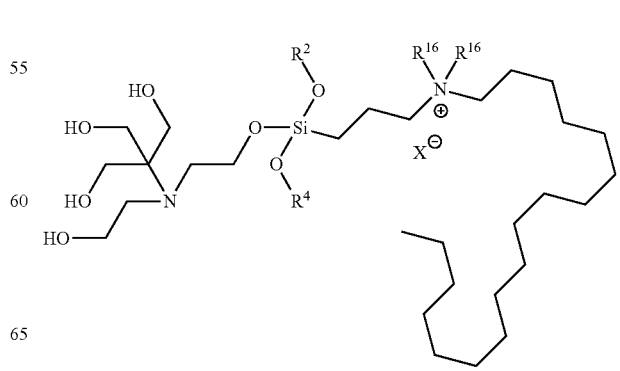

-continued

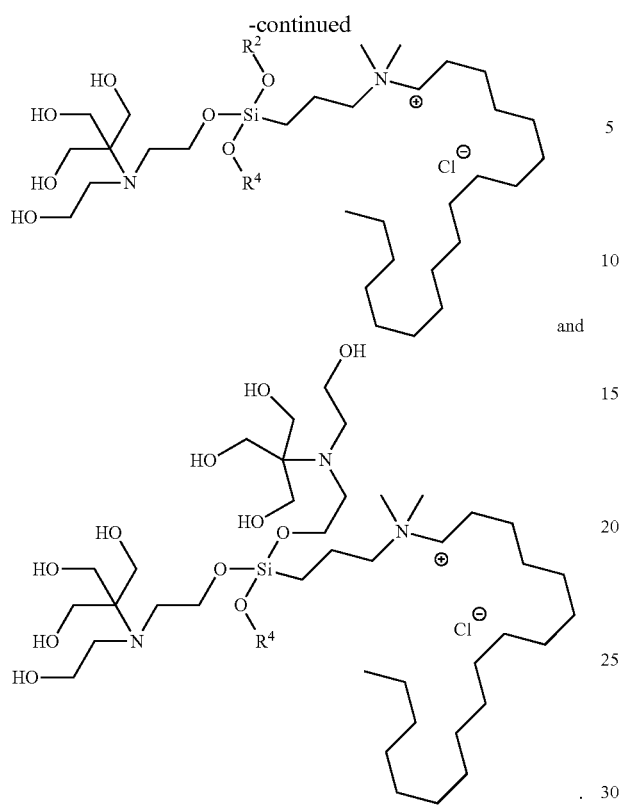

and

In some embodiments, the present invention provides a quaternary ammonium compound having a Formula:

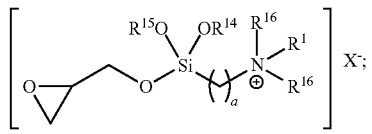

(II)

or a salt, or a pharmaceutically acceptable composition thereof;
wherein
a, $R^1$, $R^{14}$, $R^{15}$, $R^{16}$, and $X^-$ are as defined herein.

In certain embodiments of Formula II, $R^{14}$ and $R^{15}$ are independently at each occurrence selected from:

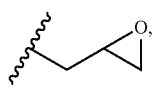

$R^2$, and $R^{17}$.

In certain embodiments of Formula II, $R^{14}$ and $R^{15}$ are independently at each occurrence selected from

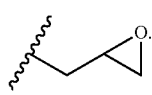

In certain embodiments of Formula II, $R^{14}$ and $R^{15}$ are independently at each occurrence selected from $R^2$.

In certain embodiments of Formula II, $R^{14}$ and $R^{15}$ are independently at each occurrence selected from $R^{17}$.

In certain embodiments, a quaternary ammonium compound of Formula II is selected from:

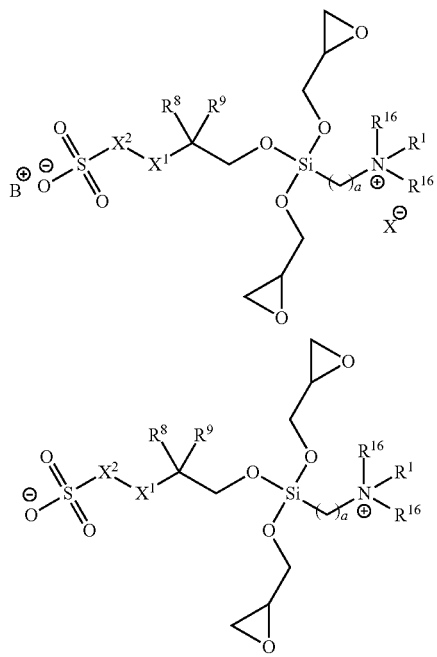

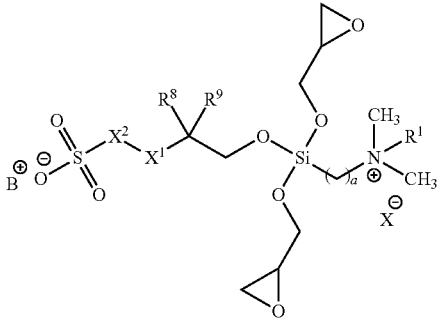

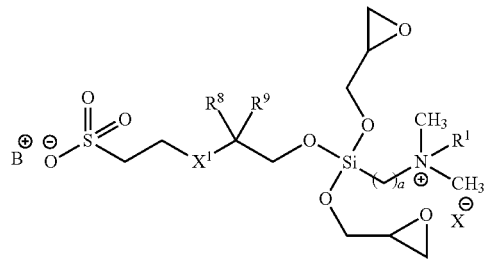

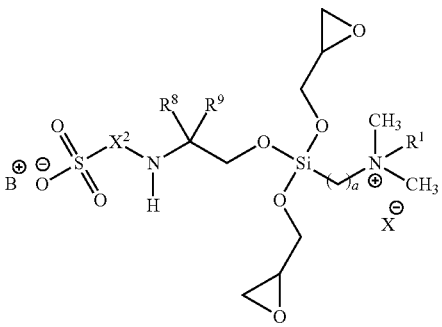

337
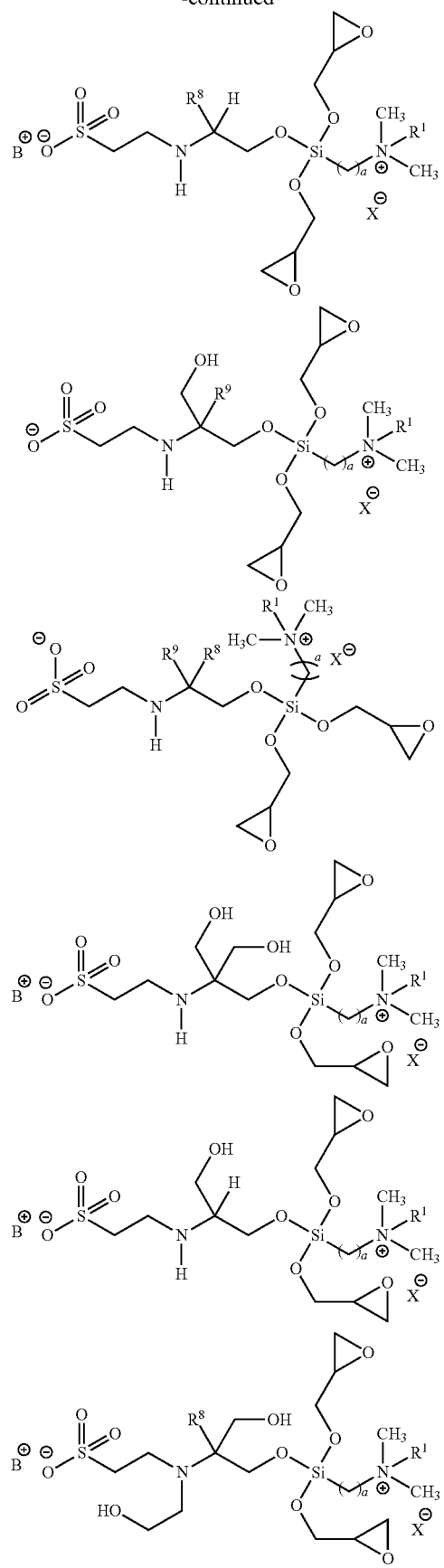
338
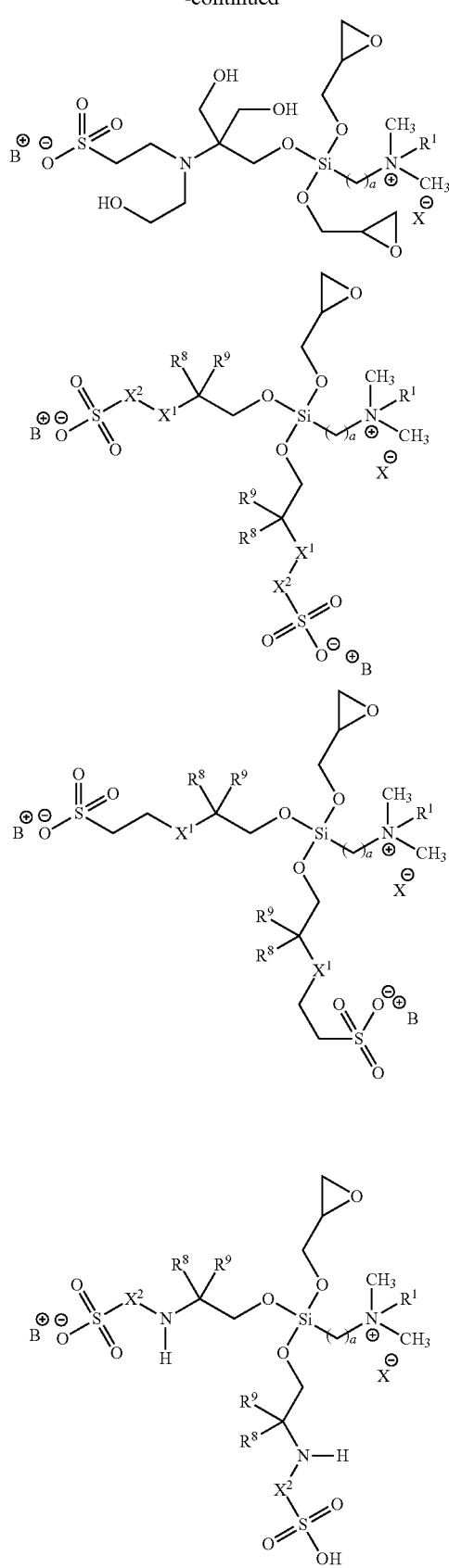

-continued
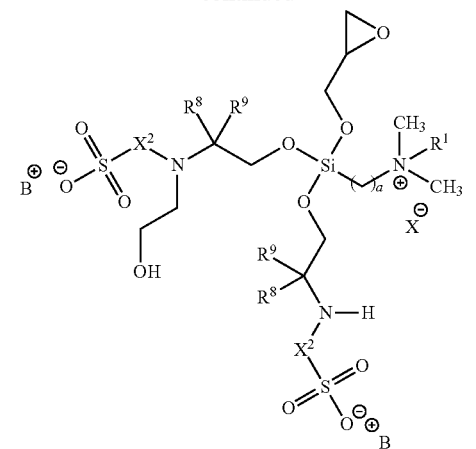
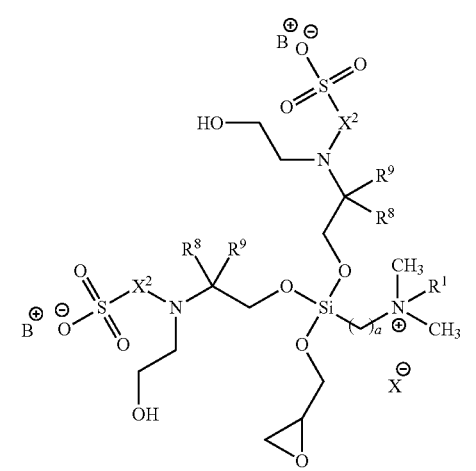
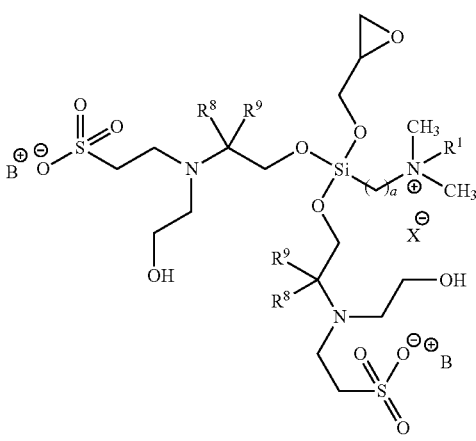
-continued
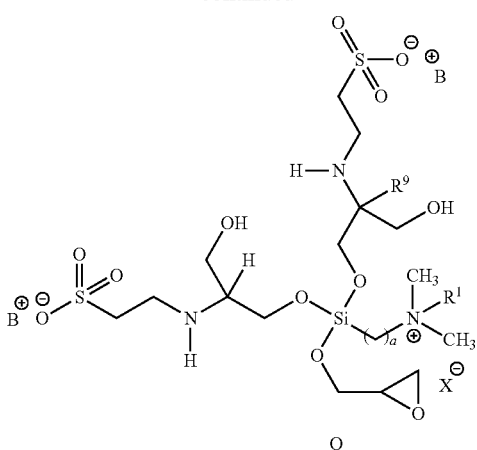
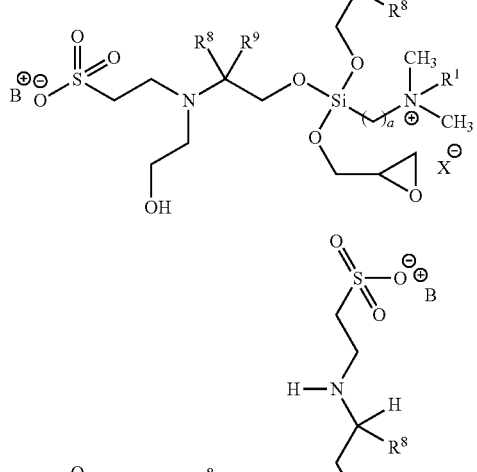
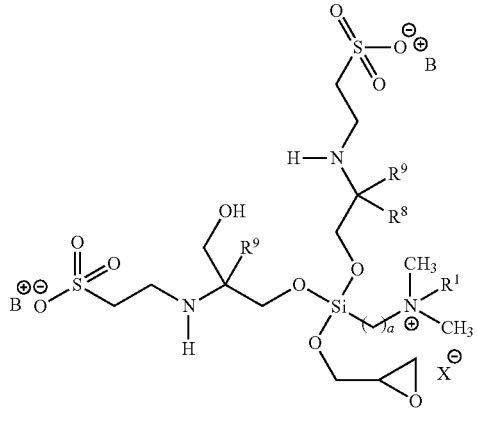

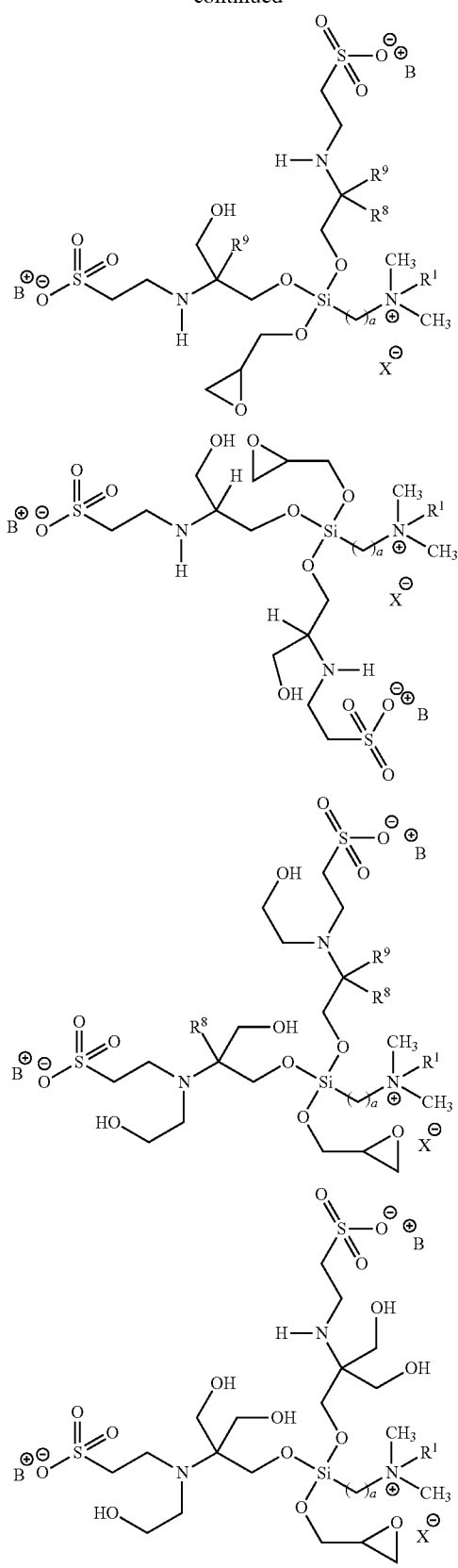
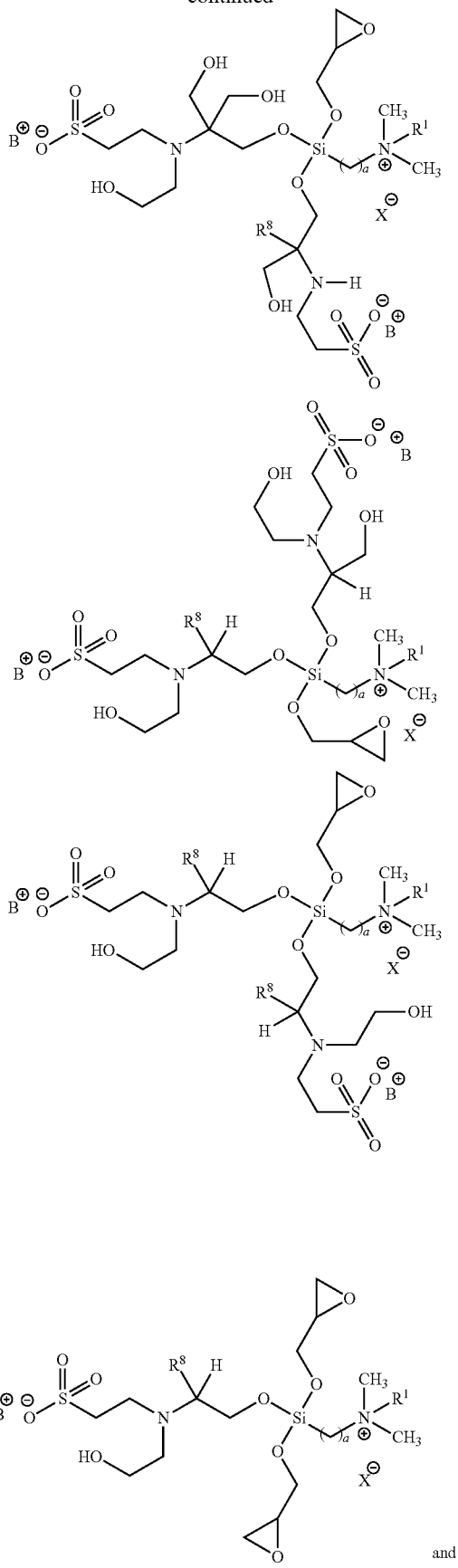
and

-continued

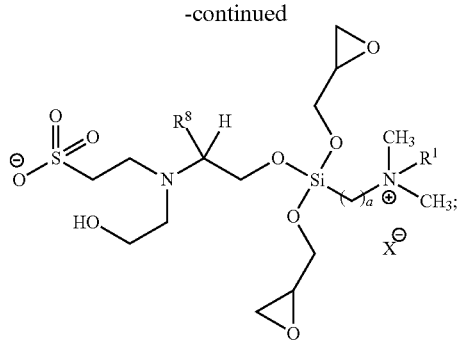

or a salt, or a pharmaceutically acceptable composition thereof.

In another aspect of the present invention, a quaternary ammonium compound of Formula II is selected from

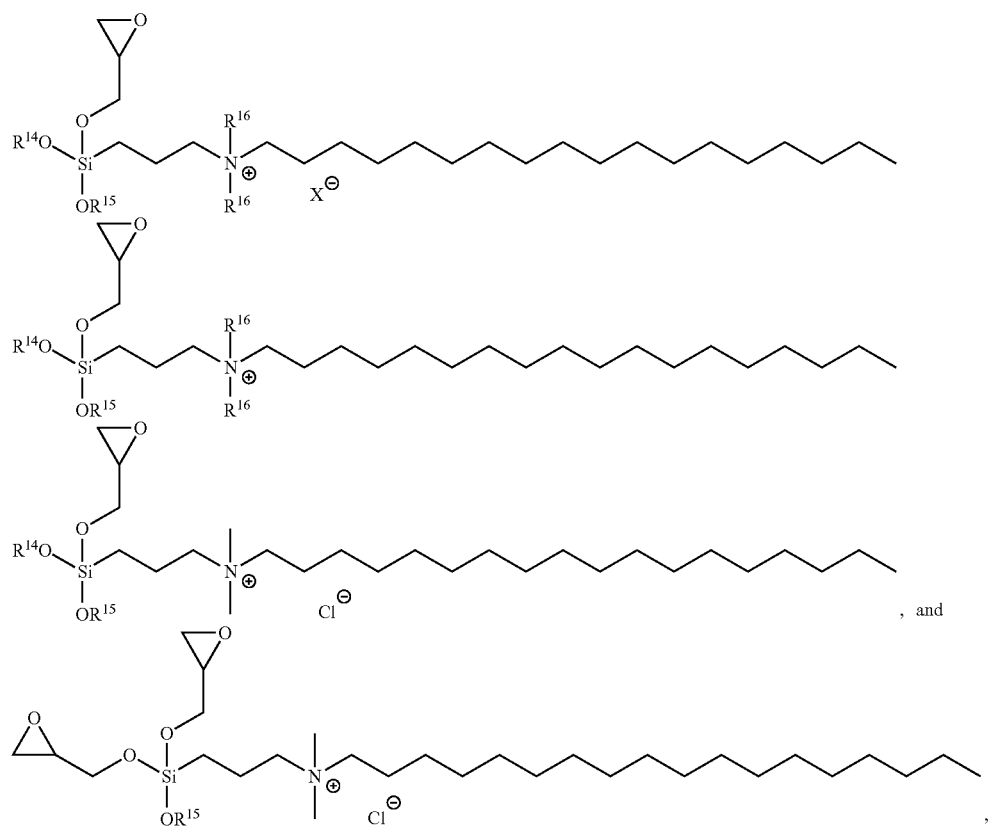

or a salt, or a pharmaceutically acceptable composition thereof.

In another aspect, the present invention provides a quaternary ammonium compound of Formula

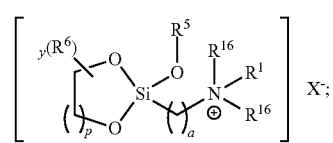

(III)

-continued

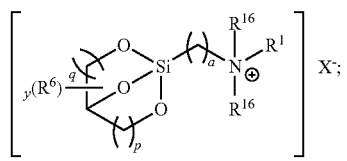

(IV)

or a salt, or a pharmaceutically acceptable composition thereof;

wherein a, p, q, y, $R^1$, $R^5$, $R^6$, $R^{16}$, and $X^-$ are as defined herein.

In certain embodiments of Formula III, $R^5$ is independently selected from

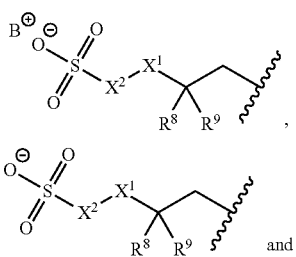

and

-continued

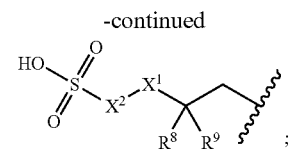

wherein R⁸, R⁹, X¹, X², and B⁺ are as defined herein.

In certain embodiments of Formula III, R⁵ is independently selected from:

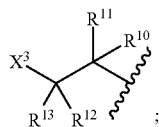

wherein R¹⁰, R¹¹, R¹², R¹³, and X³ are as defined herein.

In certain embodiments of Formula III, R⁵ is independently selected from:

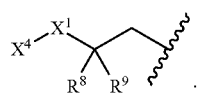

wherein R⁸, R⁹, X¹ and X⁴ are as defined herein.

In certain embodiments of Formula III, R⁵ is independently selected from R¹⁷, wherein R¹⁷ is independently at each occurrence selected from hydrogen, $C_1$-$C_8$ hydroxyalkyl, $C_2$-$C_8$ alkenyl, $C_2$-$C_8$ alkynyl, $C_1$-$C_8$ haloalkyl, $C_1$-$C_8$ alkanoyl, heterocyclyl, heteroaryl, heterocycloalkyl, and aryl.

In certain embodiments of Formula III or Formula IV, R⁶ is independently selected from alkyl, aryl, cycloalkyl and heterocyclyl; wherein each of said alkyl, aryl, cycloalkyl and heterocyclyl, optionally includes a substituent group selected from $C_1$-$C_6$alkyl, hydroxyl, halogen, $NH_2$, $NHR^7$, $N(R^7)_2$, $C(O)OH$, $C(O)R^7$, $C(O)H$, $CH_2OR^7$, $C(O)OR^7$, $CONH_2$, $CONHR^7$, $CON(R^7)_2$ and $NO_2$.

In certain embodiments of Formula III, R⁵ is independently selected from:

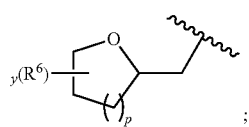

wherein p and $(R^6)_y$ are as defined herein.

In certain embodiments of Formula III,

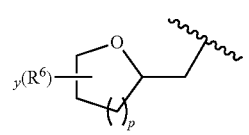

is selected from:

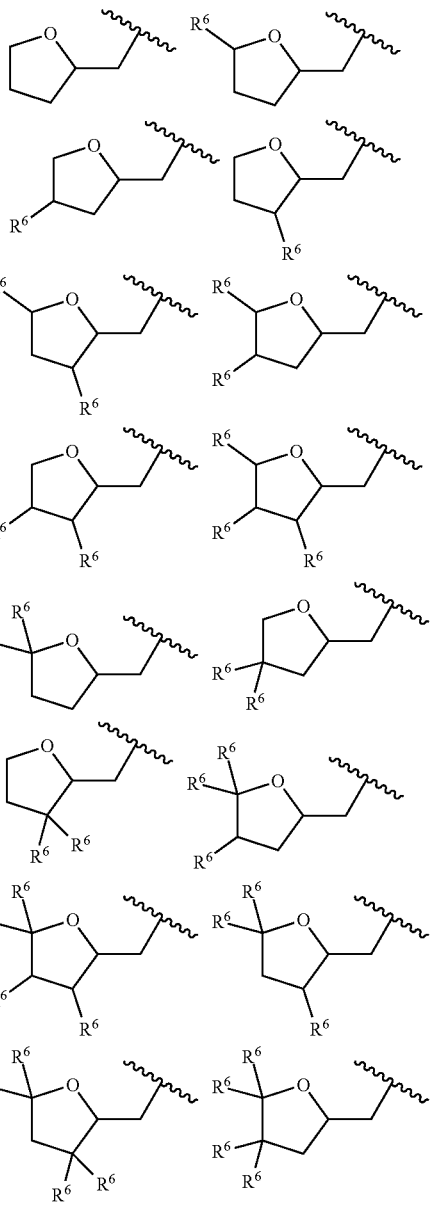

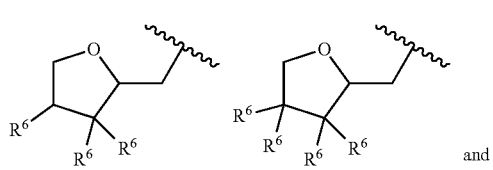

and

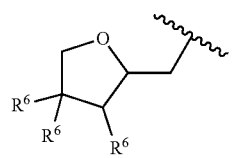

In certain embodiments of Formula III,
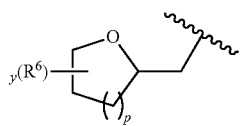
is selected from:
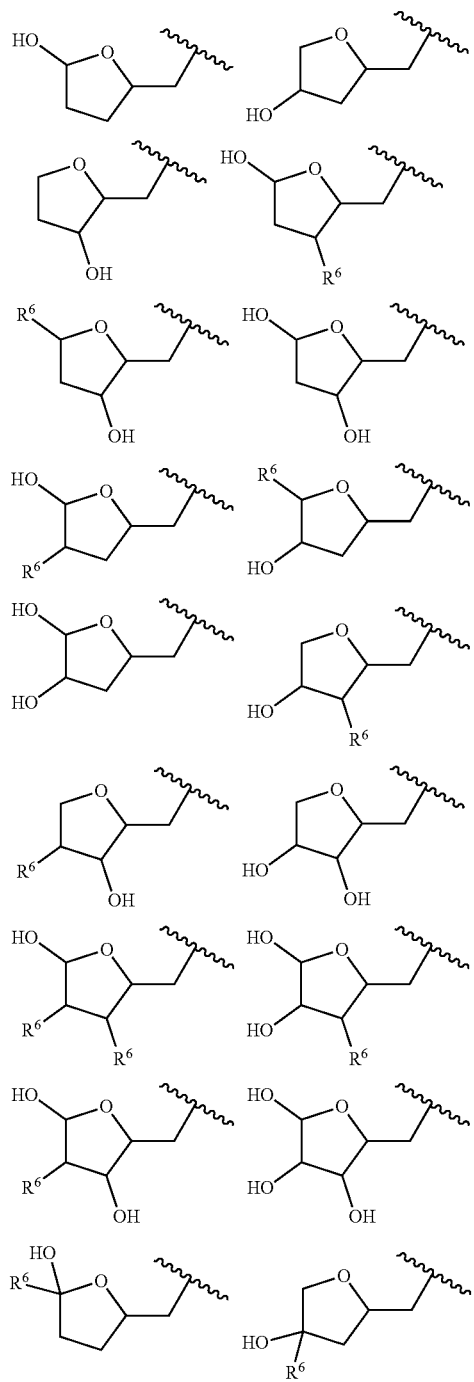
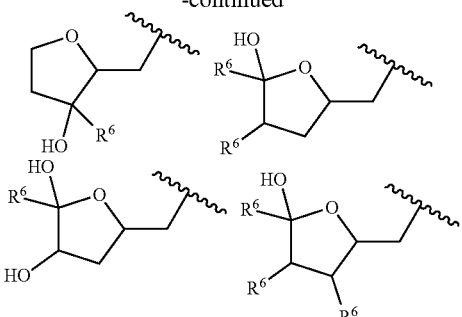
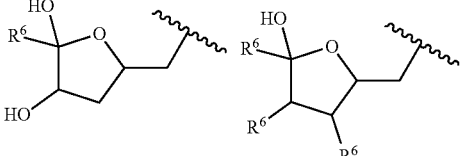
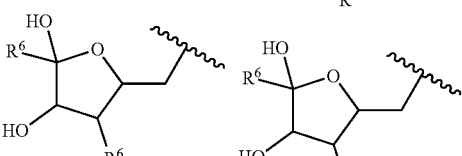
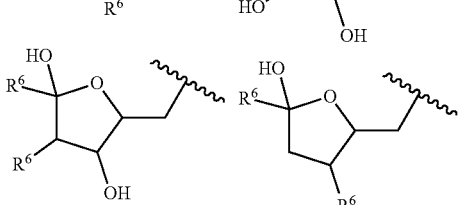
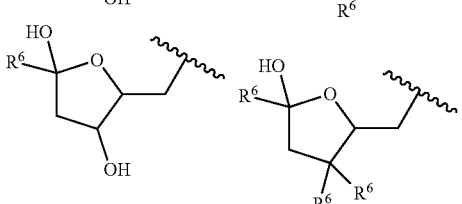
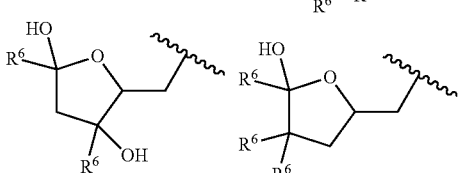
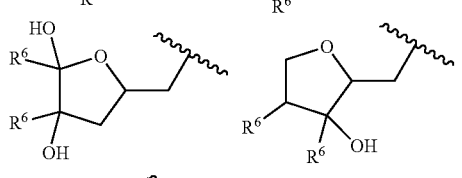
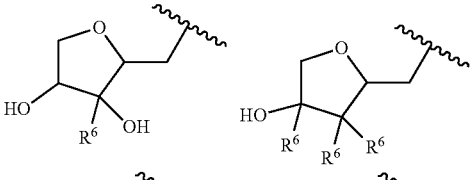
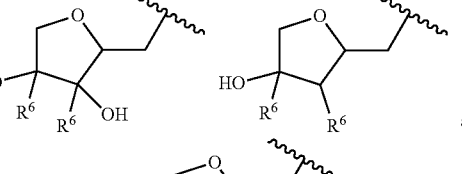
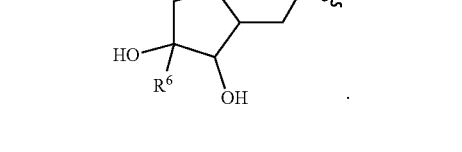
and
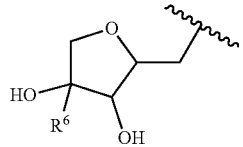
In certain embodiments of Formula III, $R^5$ is independently at each occurrence selected from a $C_1$-$C_{12}$alkanoic acid; or salt thereof; and wherein $R^5$ forms a bond with the alkanoic acid at any carbon atom on the hydrocarbon chain, available to form a C—O bond.

For example, $R^5$ can form a bond at

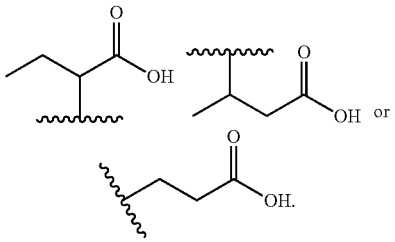

In certain embodiments of Formula III, $R^5$ is a $C_1$-$C_{12}$alkanoic acid; wherein the acid is optionally a diacid; wherein $R^5$ forms a bond with the alkanoic acid at any carbon atom on the hydrocarbon chain, available to form a C—O bond.

For example, wherein the alkanoic acid is a diacid, $R^5$ can form a bond at

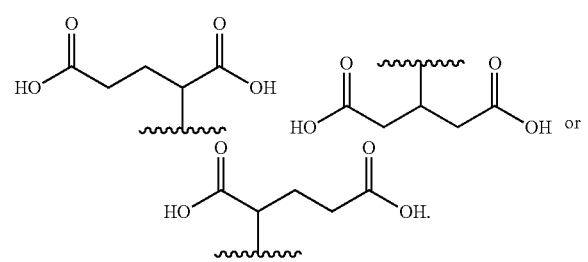

In certain embodiments of Formula III, $R^5$, is a $C_1$-$C_{12}$alkanoic acid; wherein the acid optionally contains one or more substituent groups on the hydrocarbon chain selected from, hydrogen, halogen, hydroxyl, $N(R^7)_2$ among others.

For example, wherein the alkanoic acid contains one or more substituent groups; $R^5$ can form a bond at

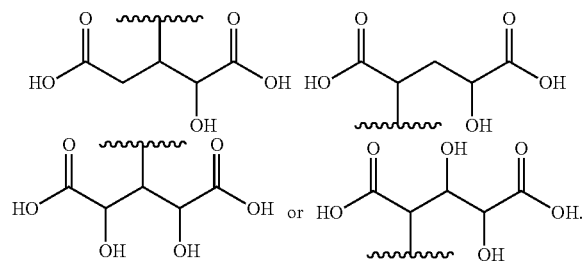

In certain embodiments of Formula III, $R^5$ is a $C_1$-$C_{12}$alkanoic acid selected from:

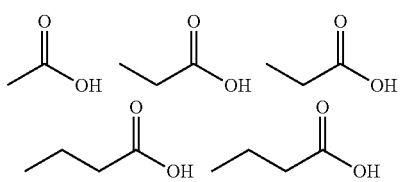

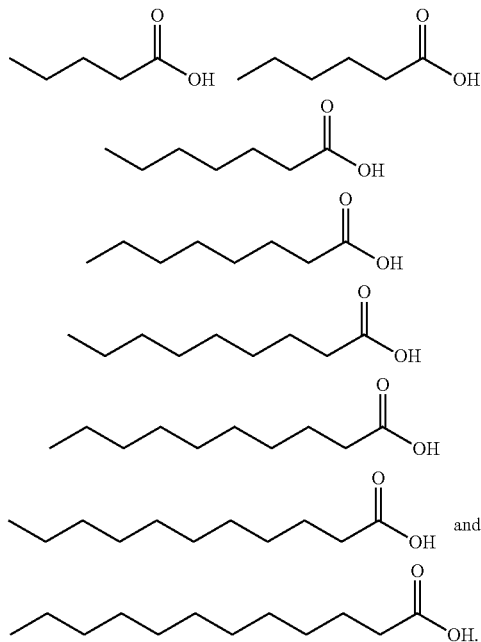

In certain embodiments of Formula III, $R^5$ is a $C_1$-$C_{12}$alkanoic acid selected from:

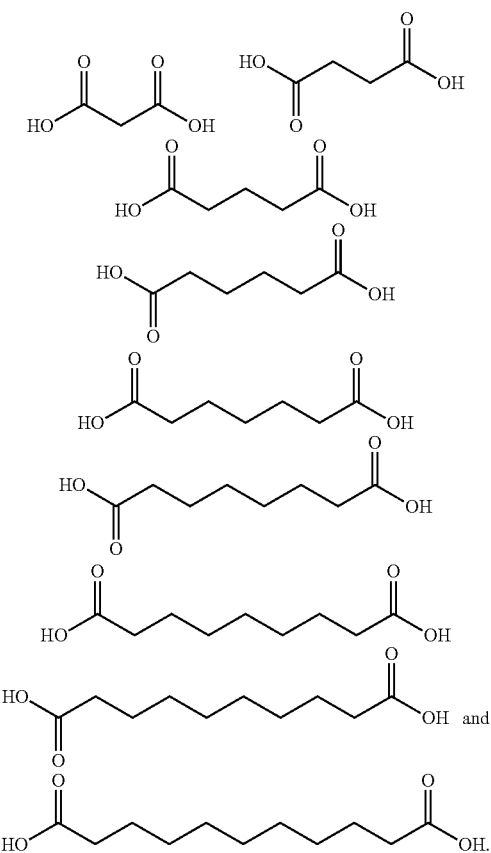

In certain embodiments of Formula III, $R^5$ is a $C_1$-$C_{12}$alkanoic acid selected from:

-continued
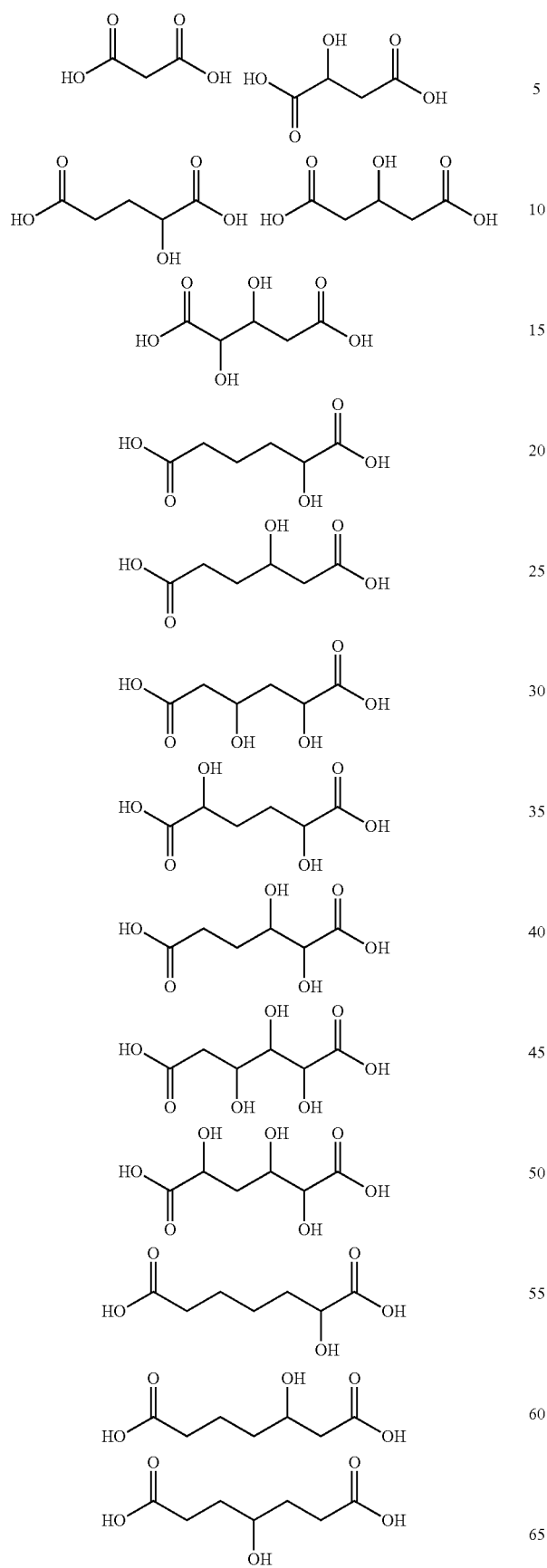
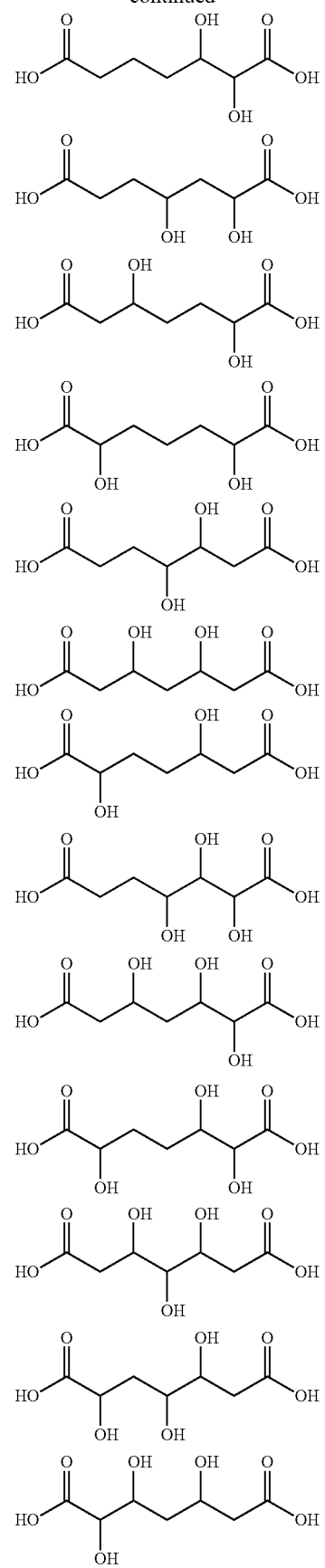

353
-continued
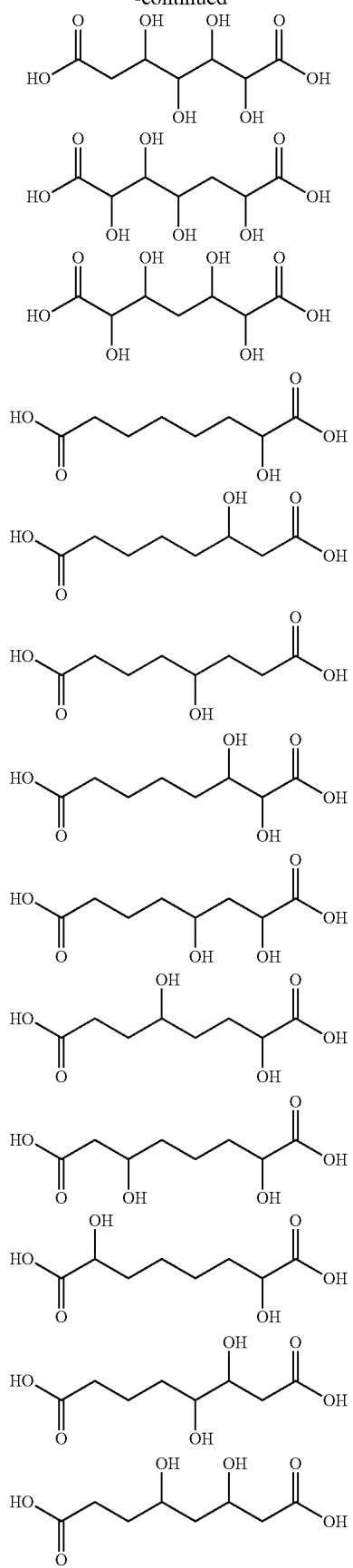
354
-continued
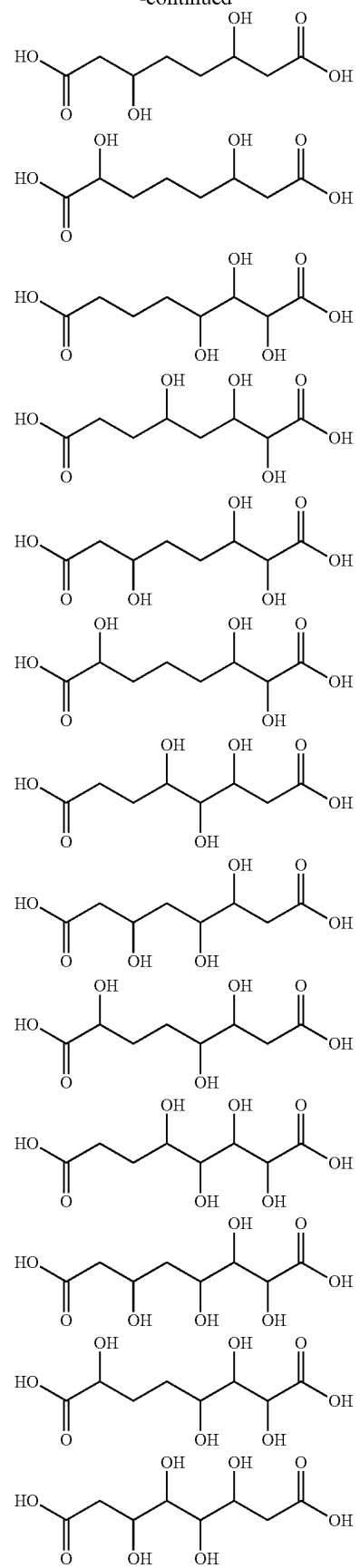

-continued

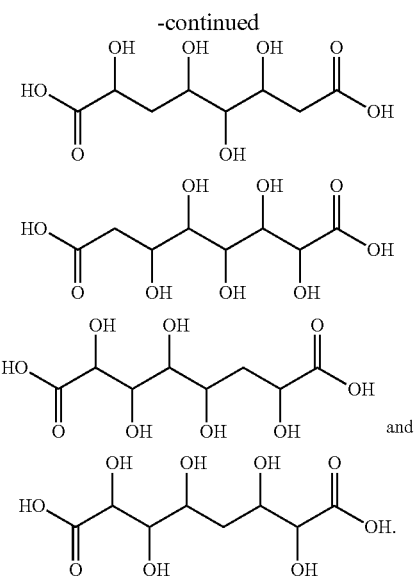

In certain embodiments, y is 0. In certain embodiments, y is 1. In certain embodiments, y is 2. In certain embodiments, y is 3. In certain embodiments, y is 4.

In certain embodiments, p is 0. In certain embodiments, p is 1. In certain embodiments, p is 2. In certain embodiments, p is 3. In certain embodiments, p is 4.

In certain embodiments, q is 0. In certain embodiments, q is 1. In certain embodiments, q is 2. In certain embodiments, q is 3. In certain embodiments, q is 4.

In certain embodiments, a is a 1. In certain embodiments, a 2. In certain embodiments, a is 3. In certain embodiments, a is 4. In certain embodiments, a is 5. In certain embodiments, a is 6. In certain embodiments, a is 7. In certain embodiments, a is 8.

In certain embodiments of Formula III,

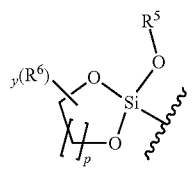

is selected from:

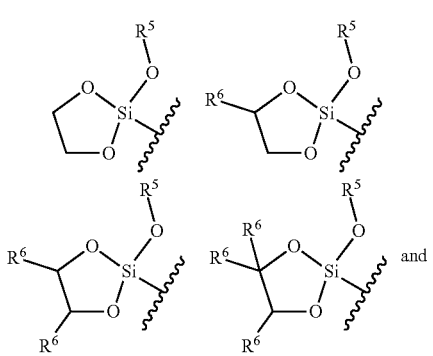

-continued

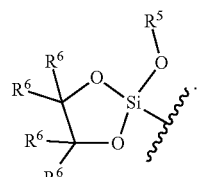

In certain embodiments of Formula III,

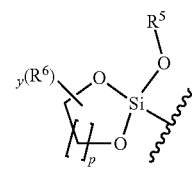

is selected from:

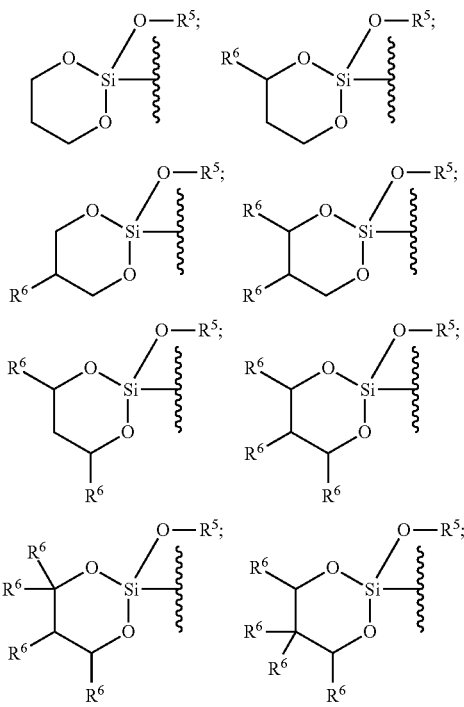

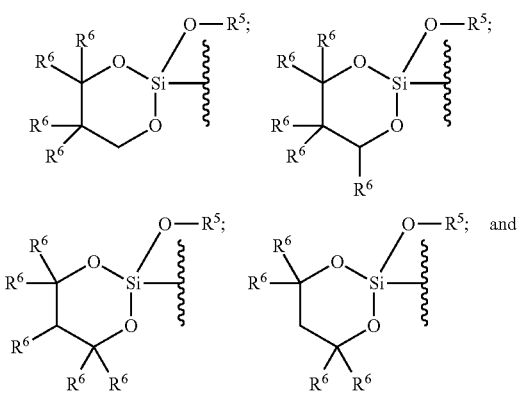

-continued
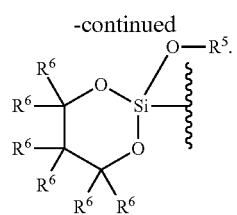
In certain embodiments of Formula III,
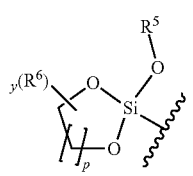
is selected from:
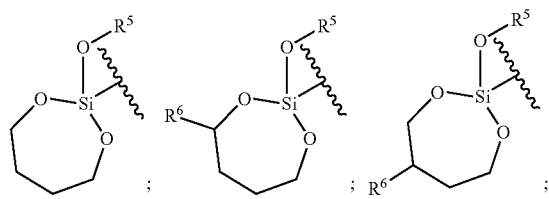
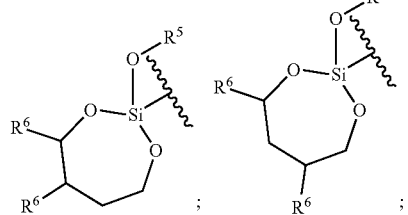
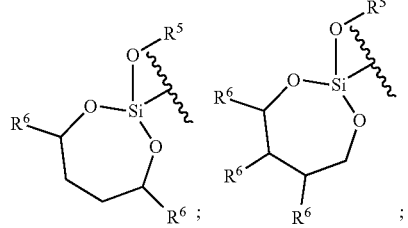
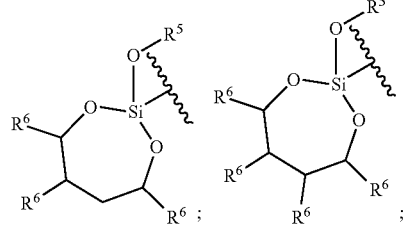
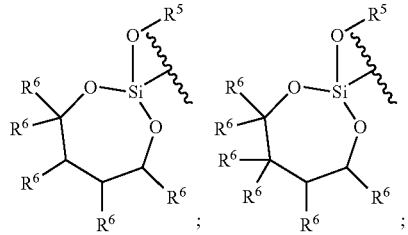
-continued
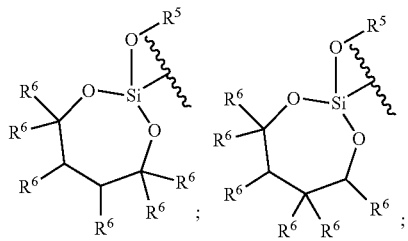
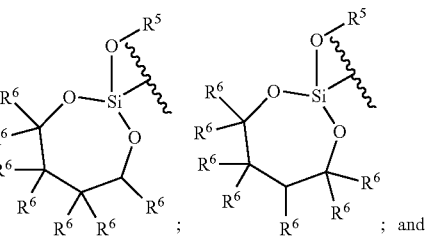
; and
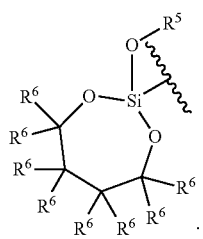
In certain embodiments of Formula III,
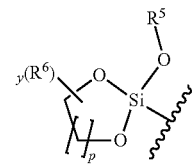
is selected from:
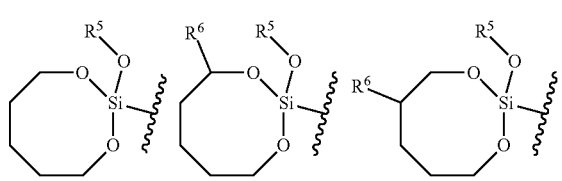
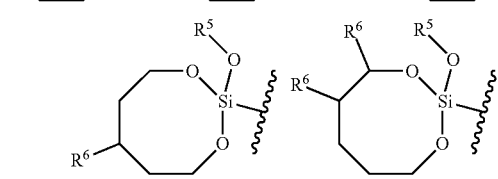
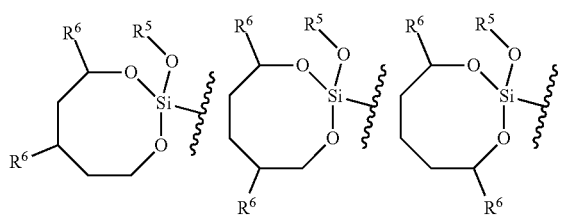

-continued
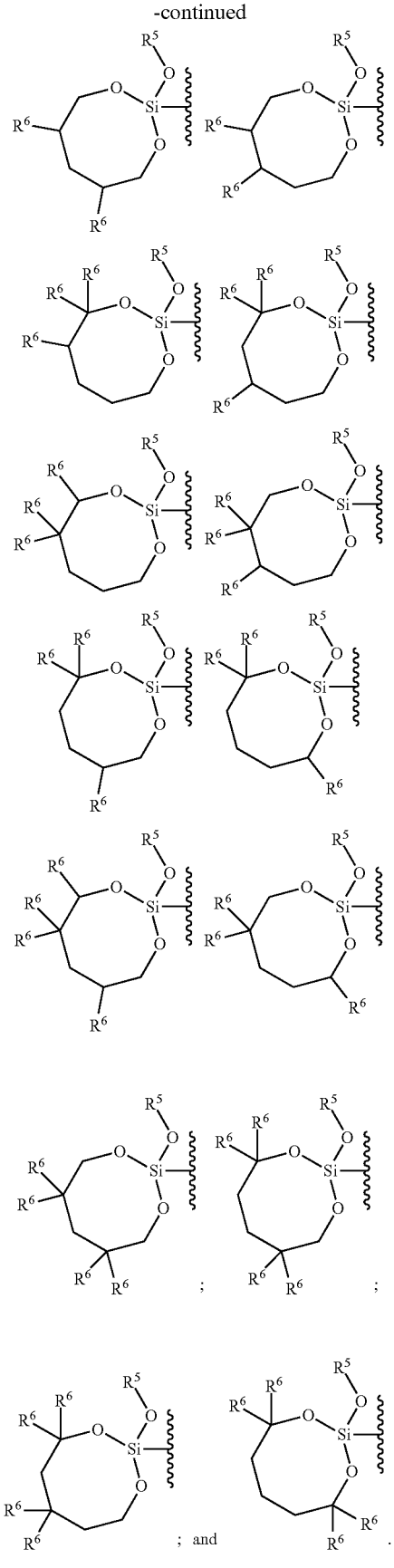
; and
In certain embodiments of Formula III,
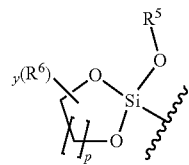
is selected from:
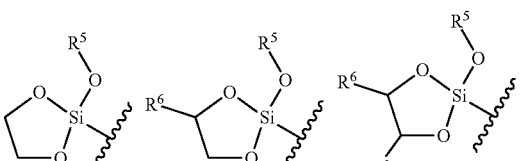
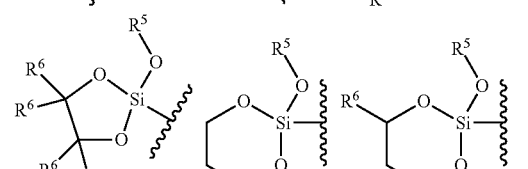
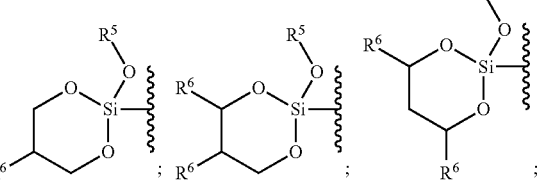
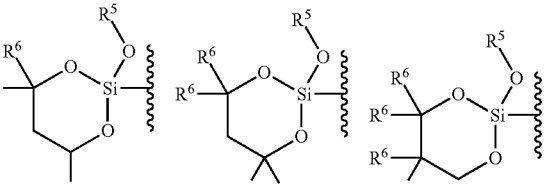
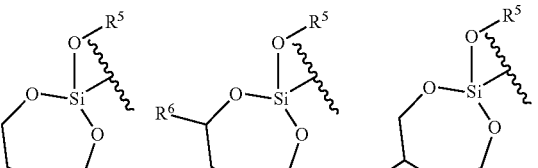
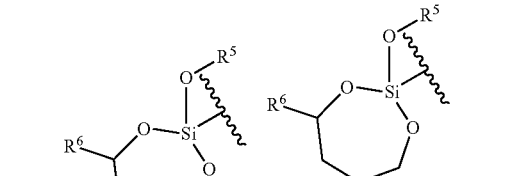
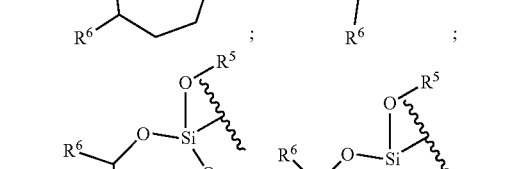
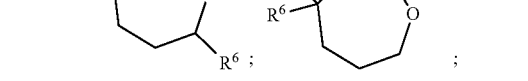

-continued
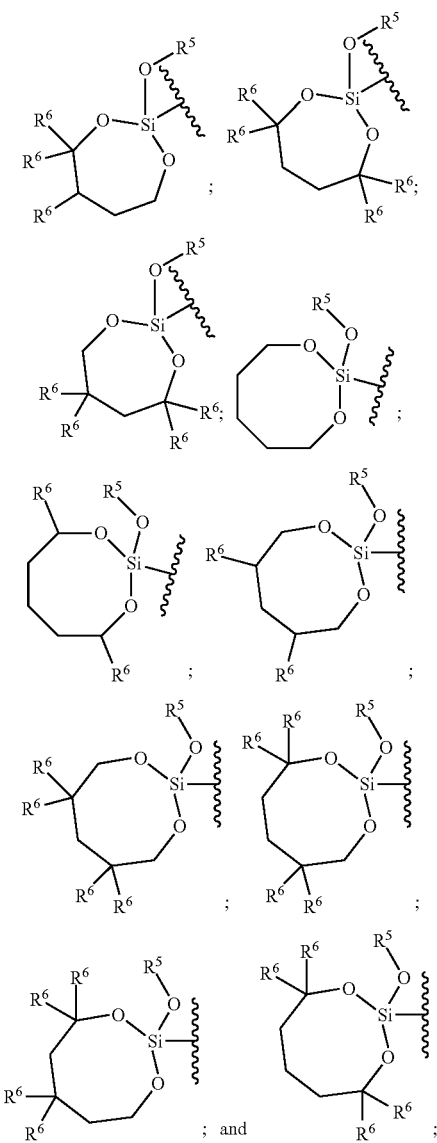
In certain embodiments of Formula III,
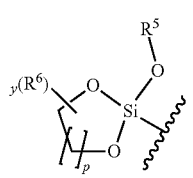
is selected from:
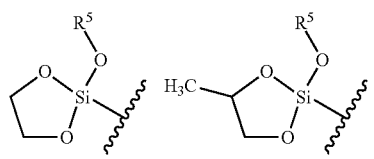
-continued
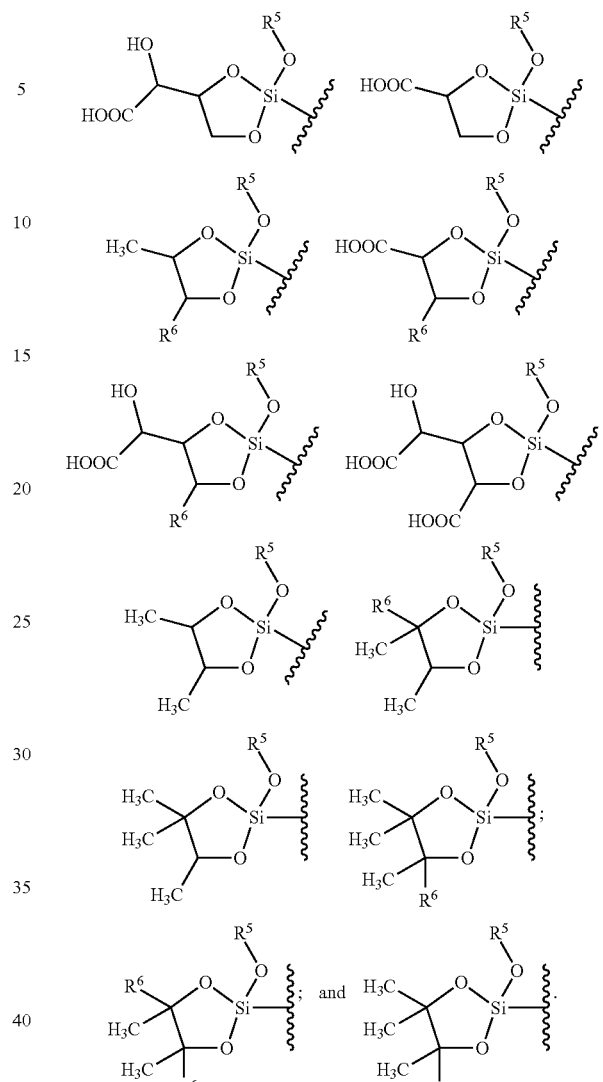
In certain embodiments of Formula III,
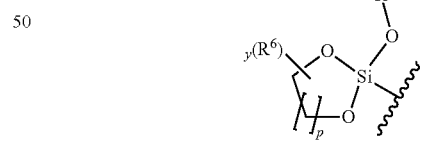
is selected from:
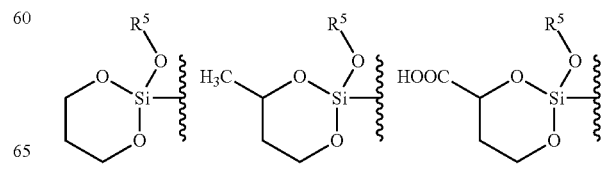

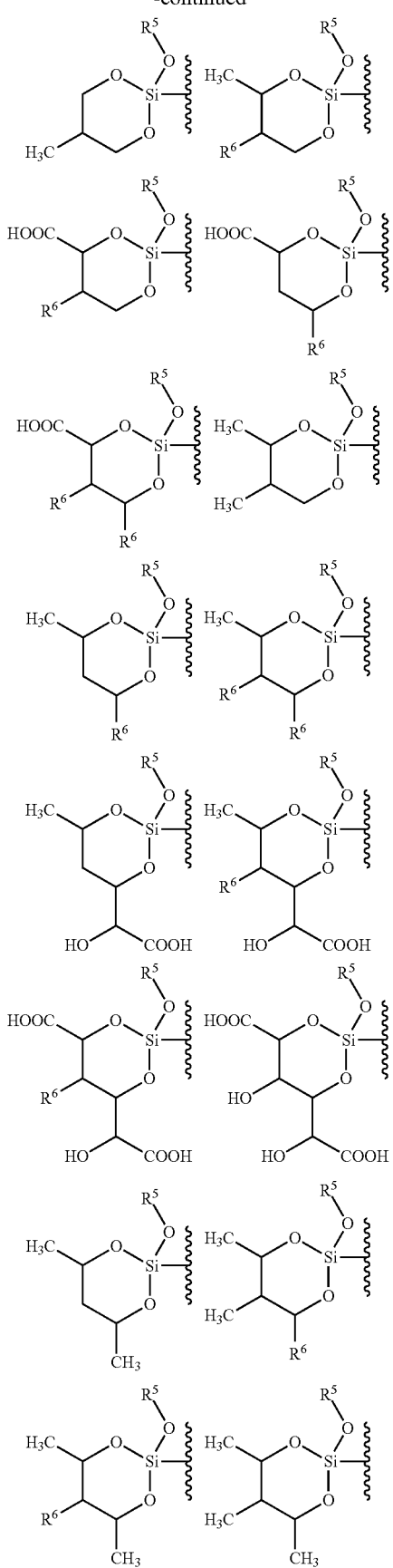
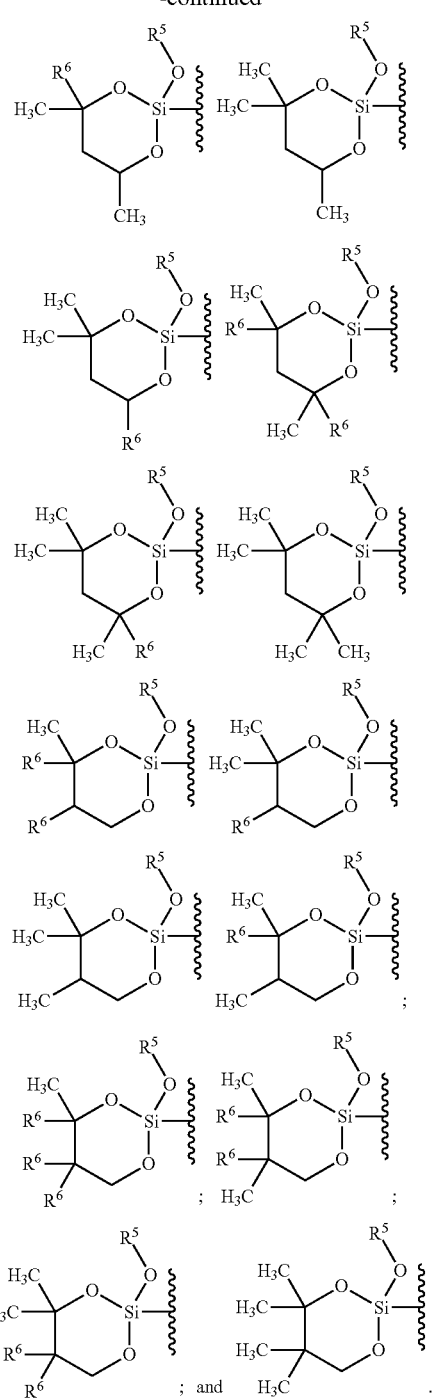
In certain embodiments of Formula III,
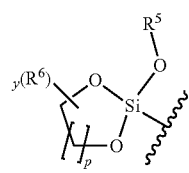

is selected from:
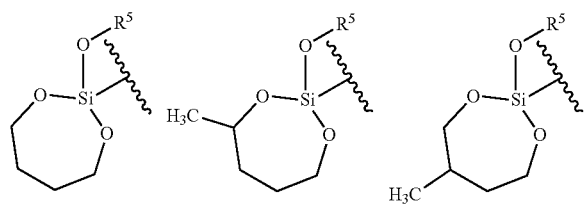
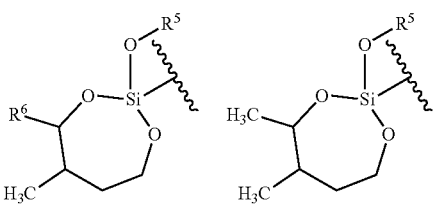
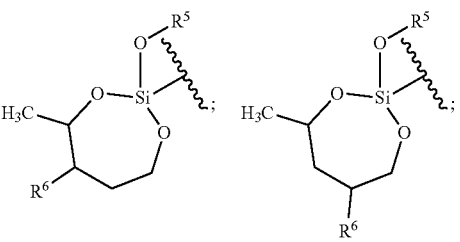
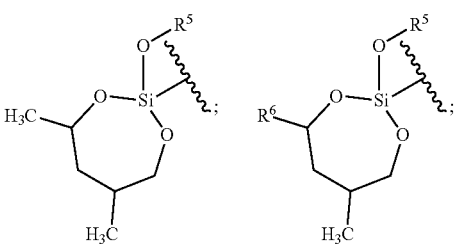
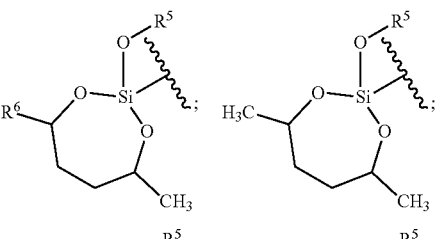
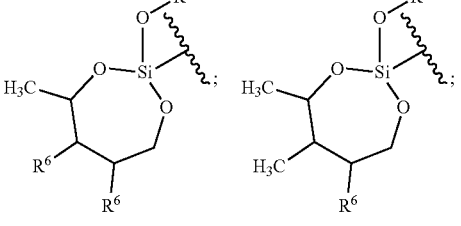
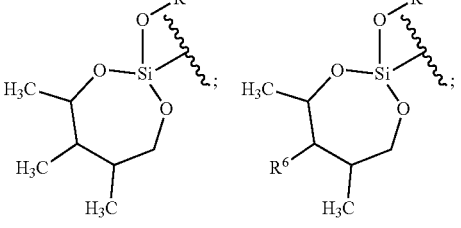
-continued
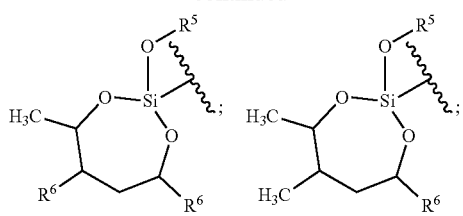
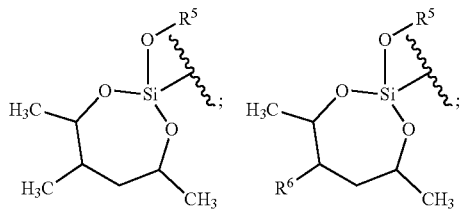
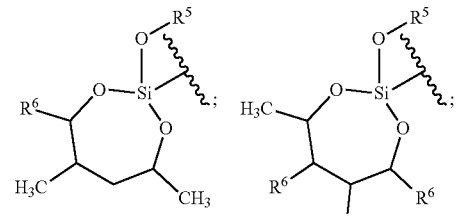
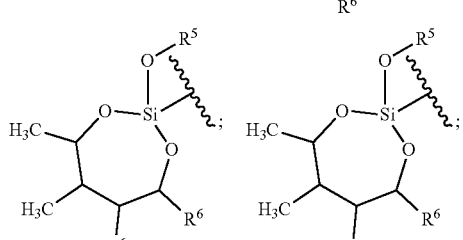
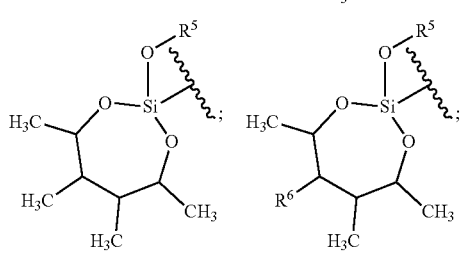
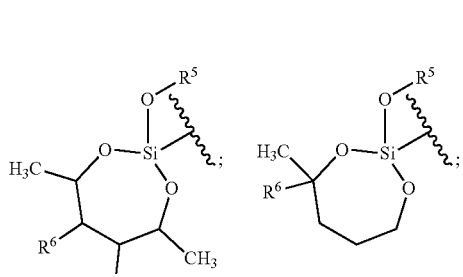
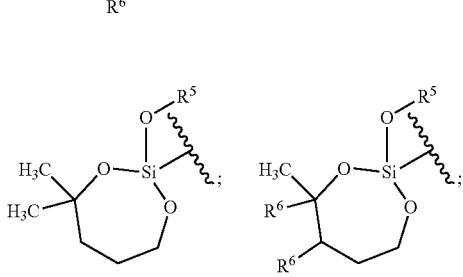

-continued
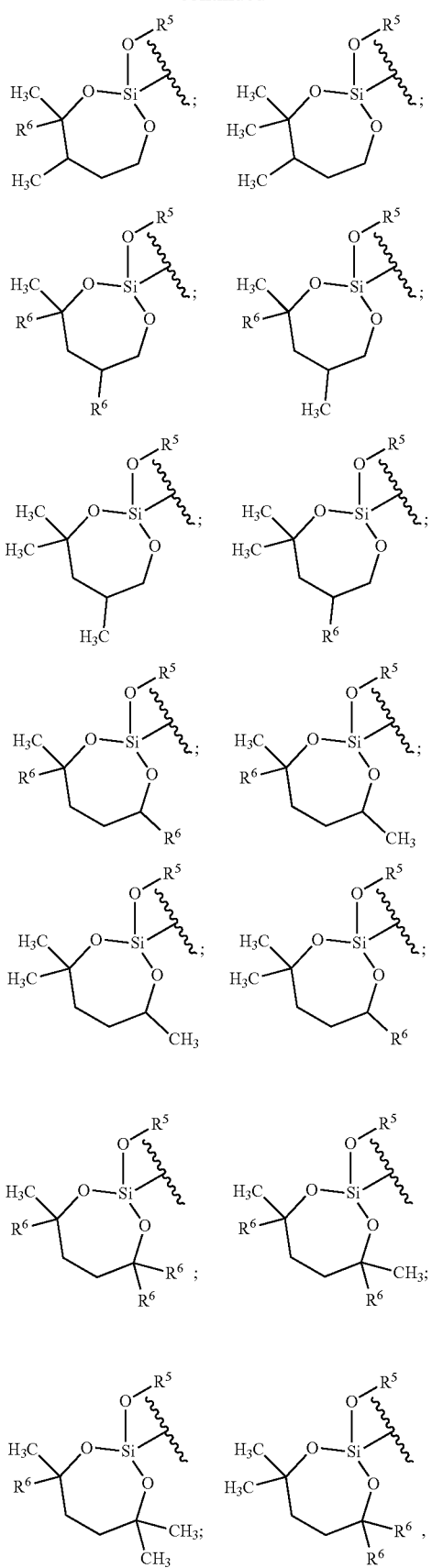
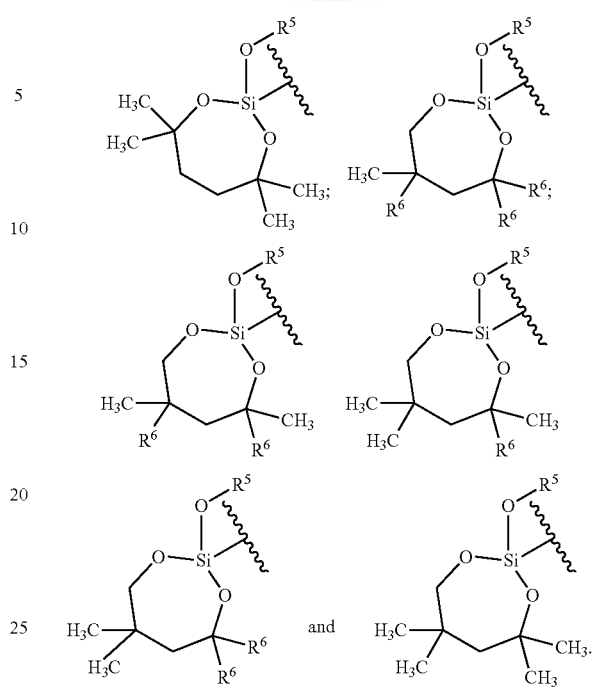
In certain embodiments of Formula III,
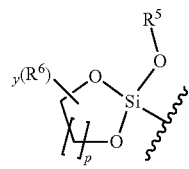
is selected from:
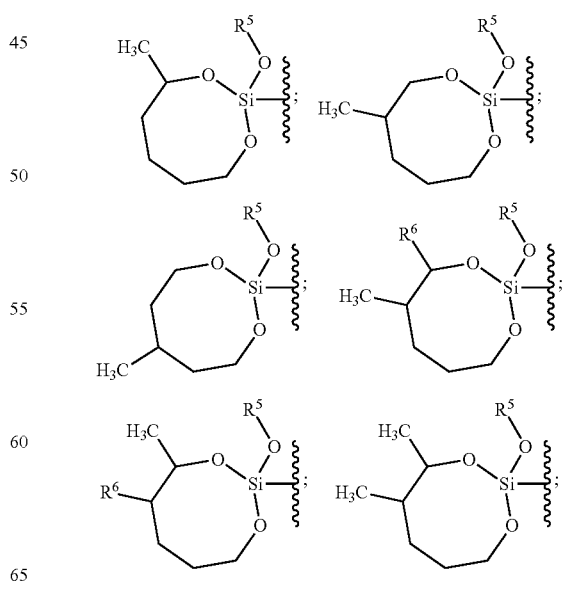

369
-continued
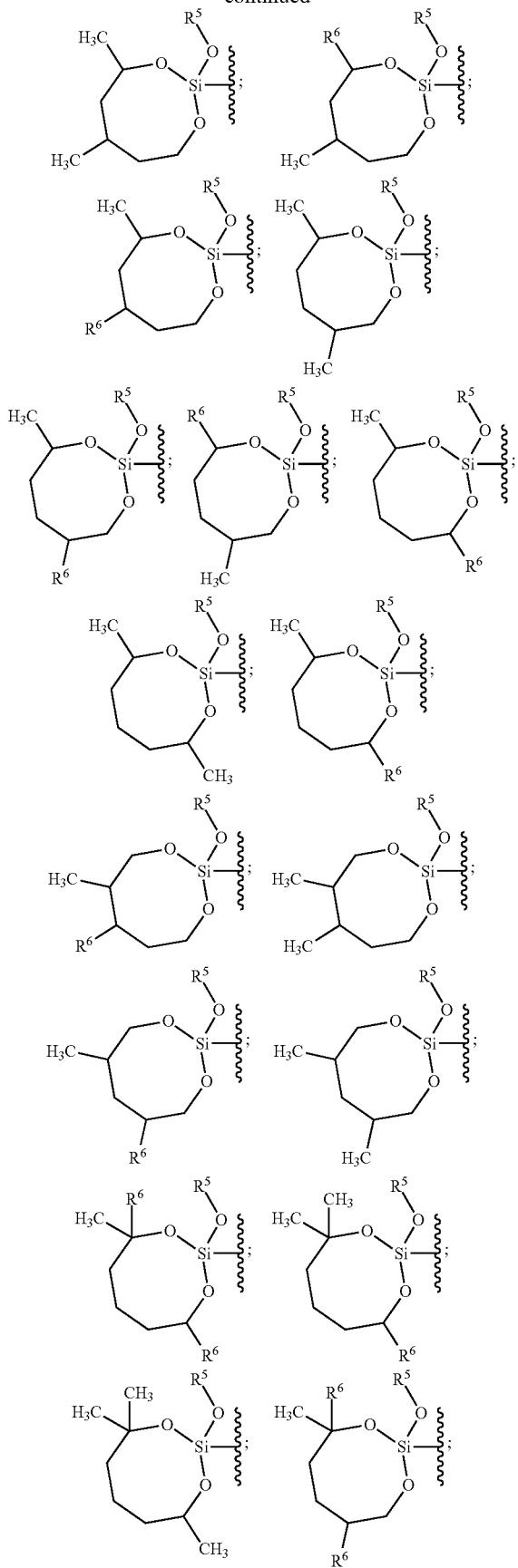
370
-continued
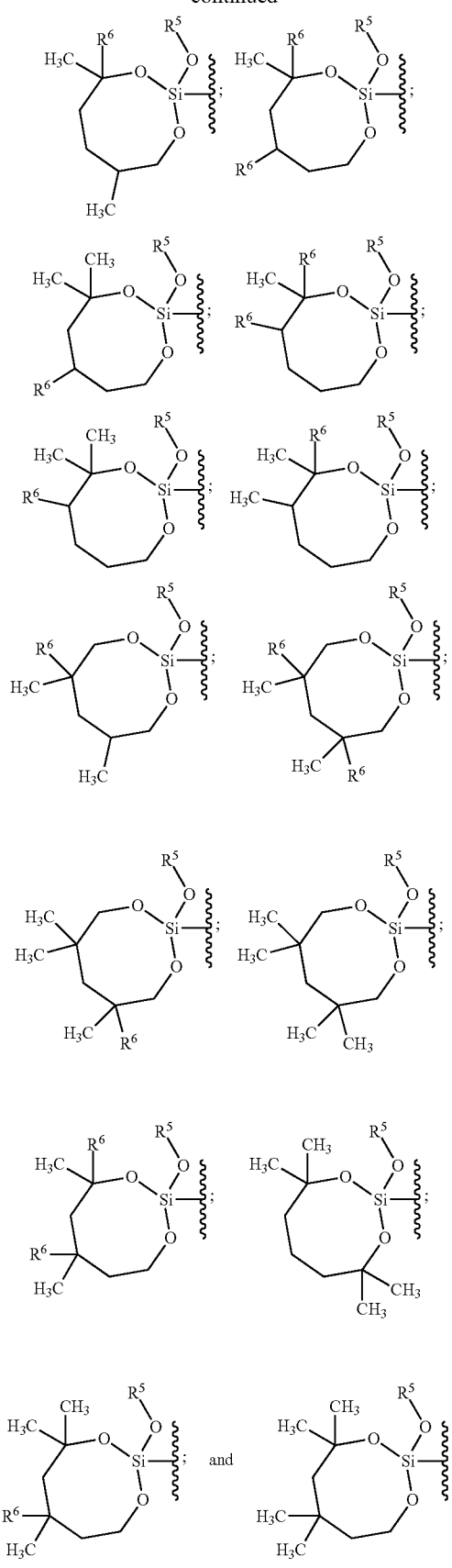

In certain embodiments of Formula III,
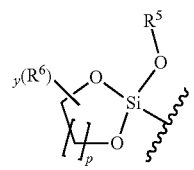
is selected from:
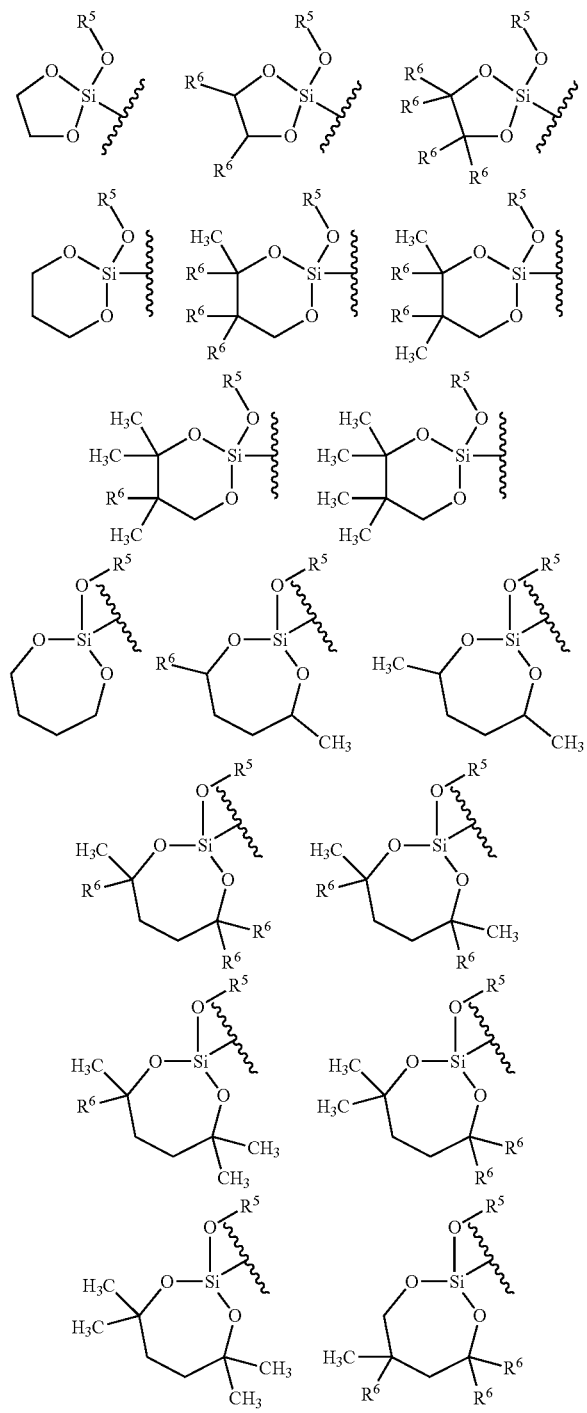
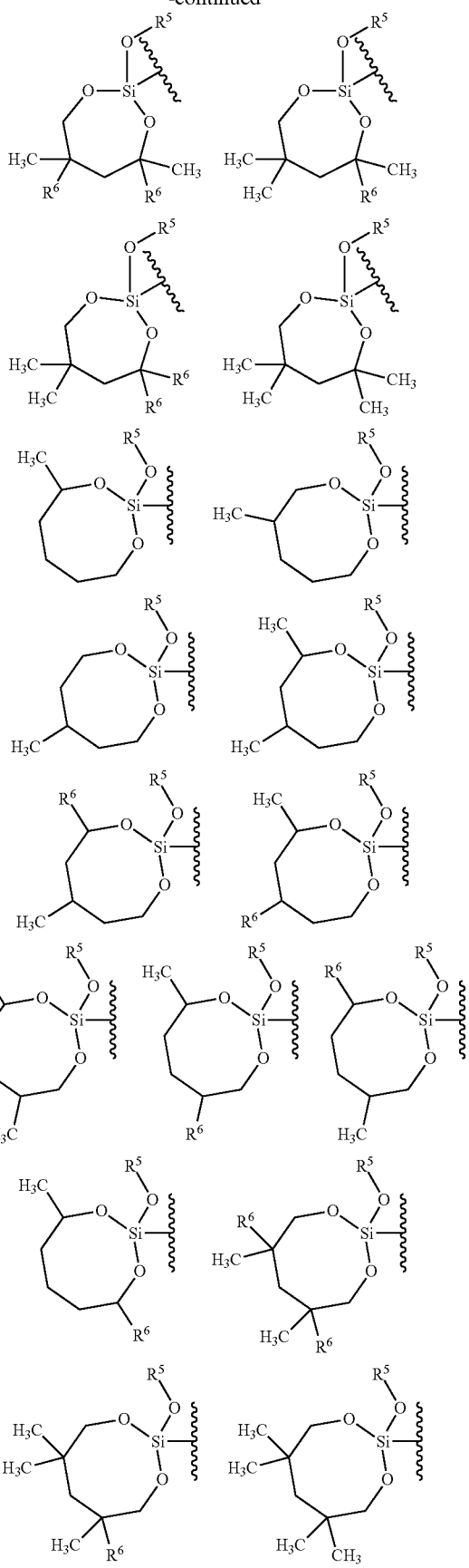

-continued
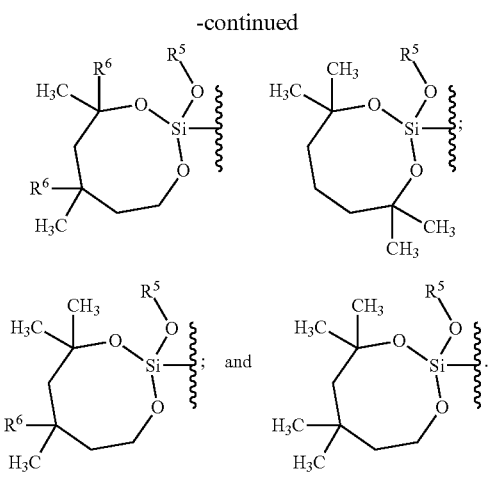
In certain embodiment of Formula IV,
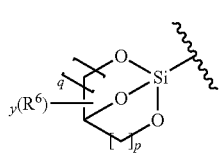
is selected from:
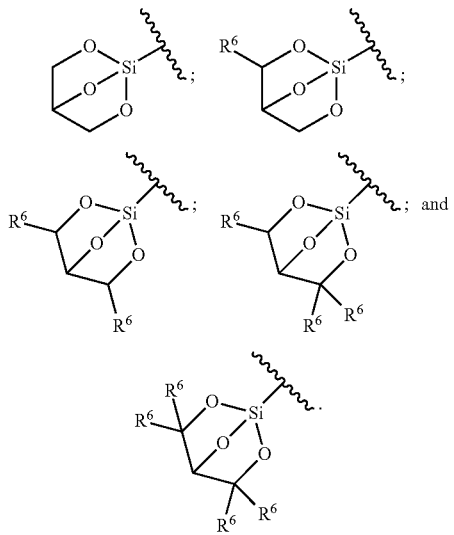
In certain embodiment of Formula IV,
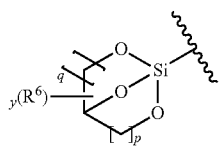
is selected from:
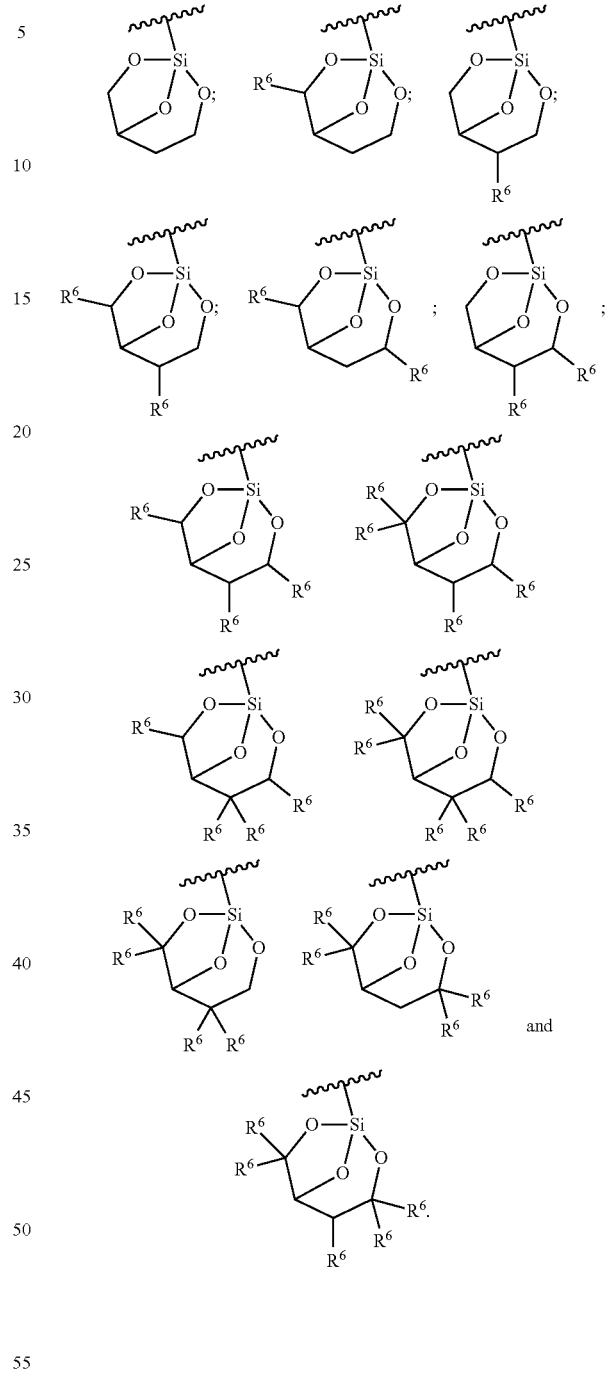
In certain embodiment of Formula IV,
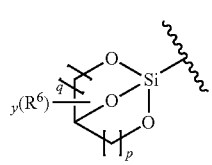

is selected from:
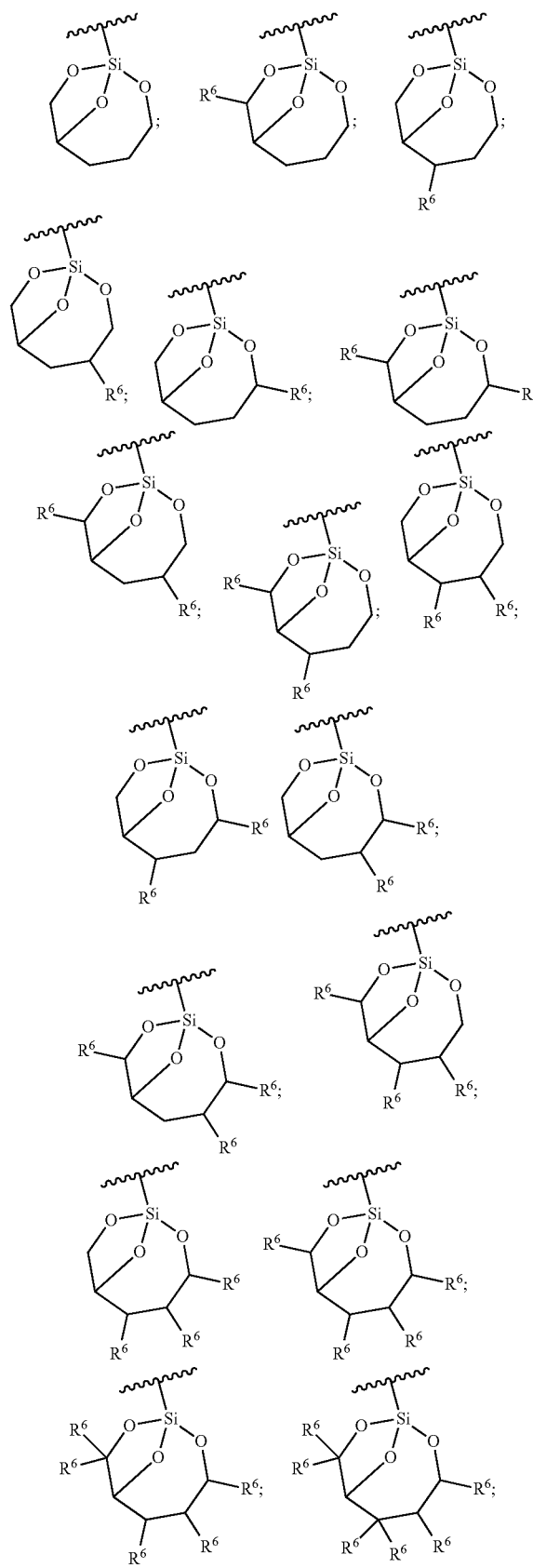
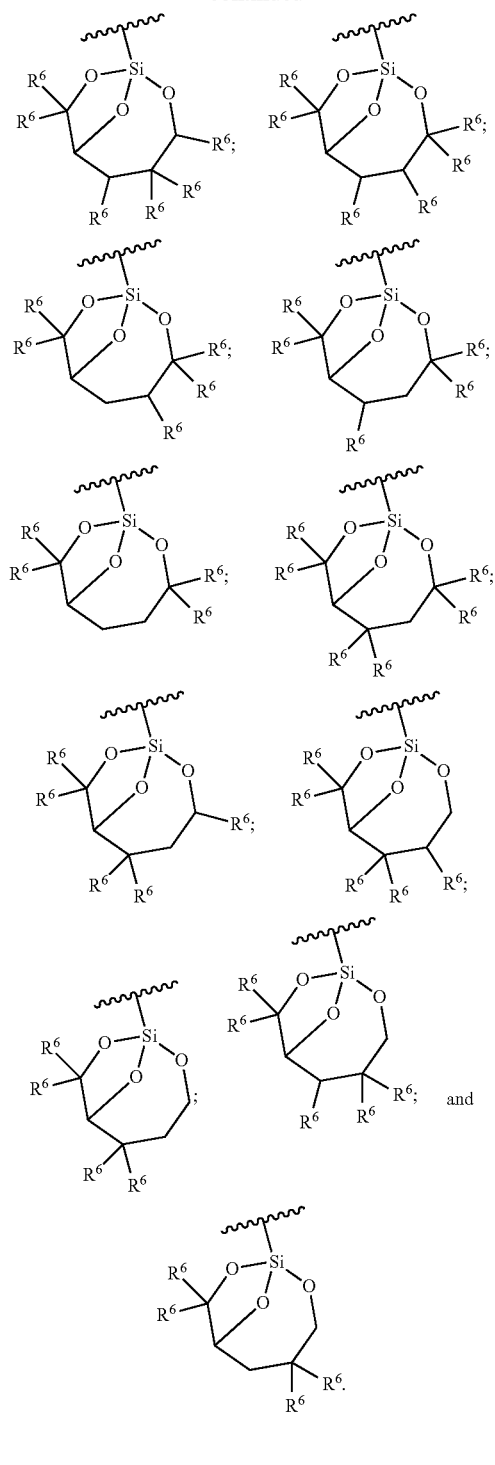
In certain embodiments of Formula IV,
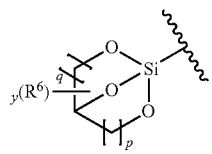

is selected from:
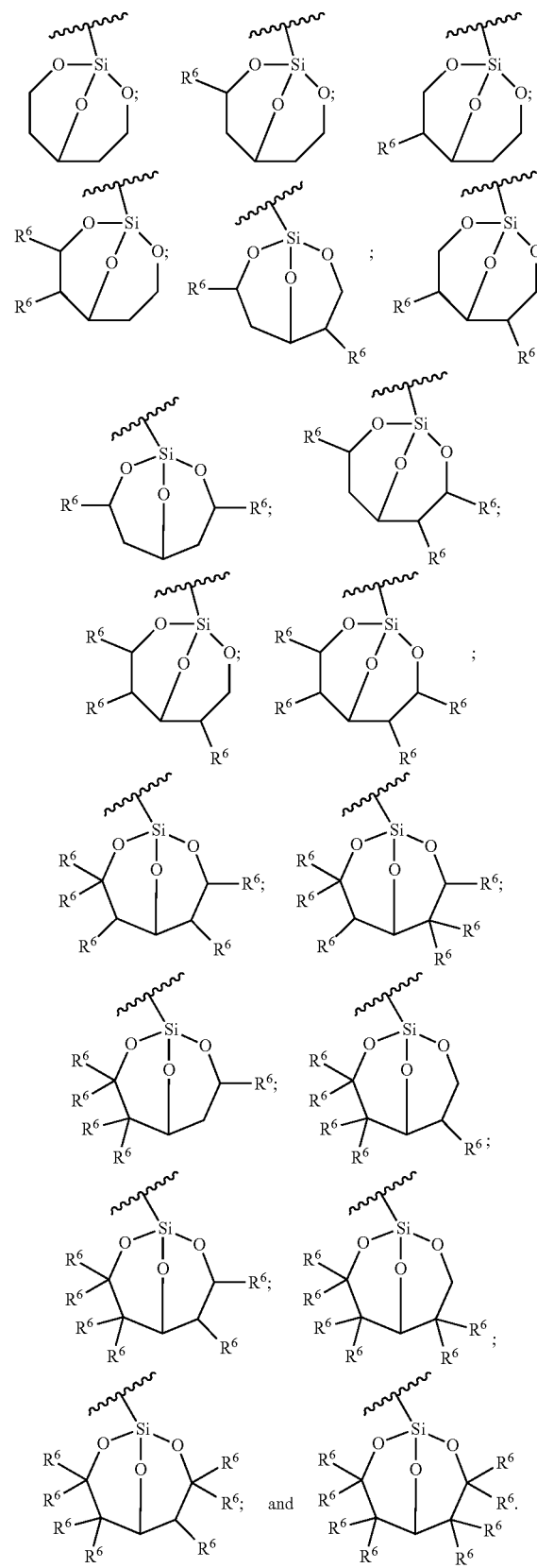
In certain embodiments of Formula IV,
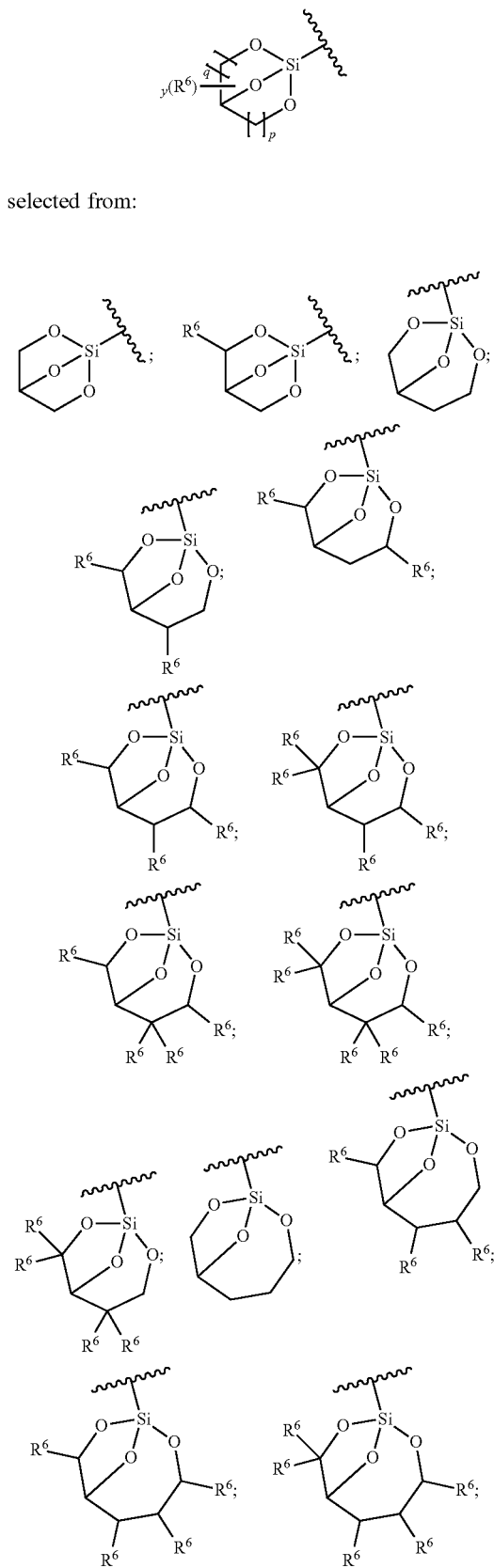
is selected from:

-continued
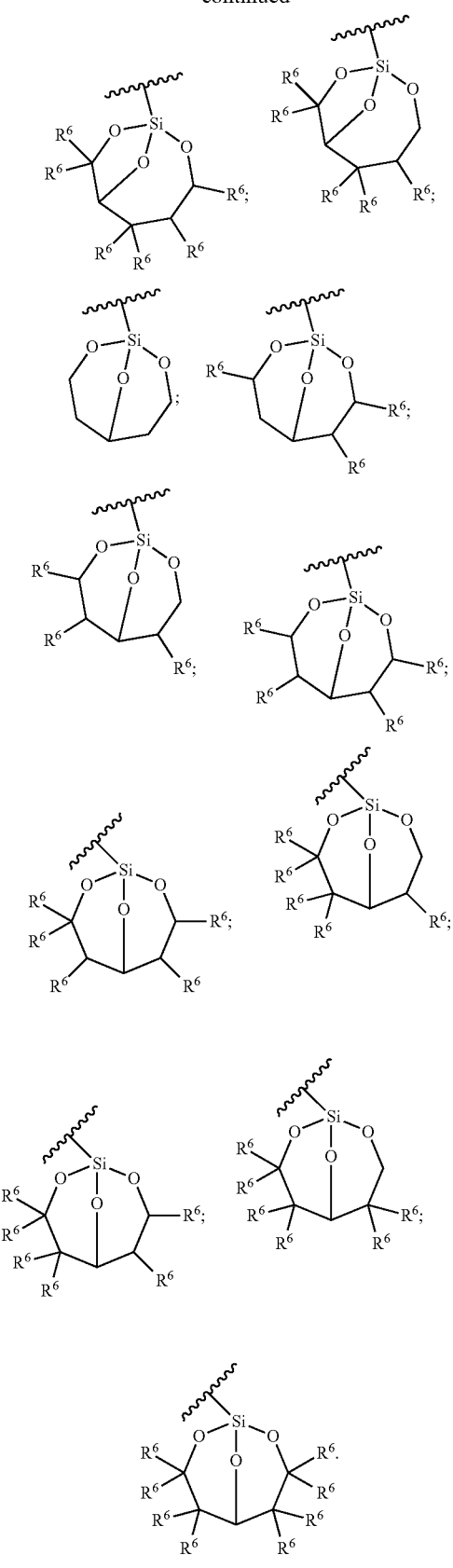
In some embodiments of Formula IV,
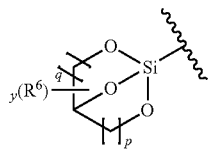
is selected from:
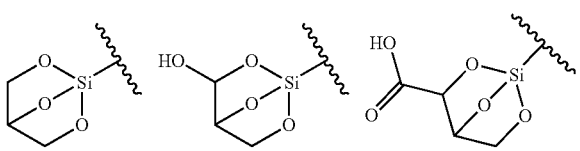
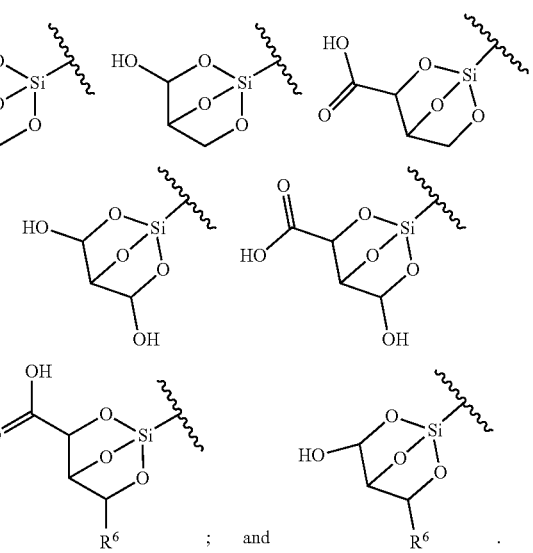
In some embodiments of Formula IV,
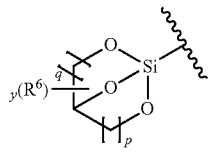
is selected from:
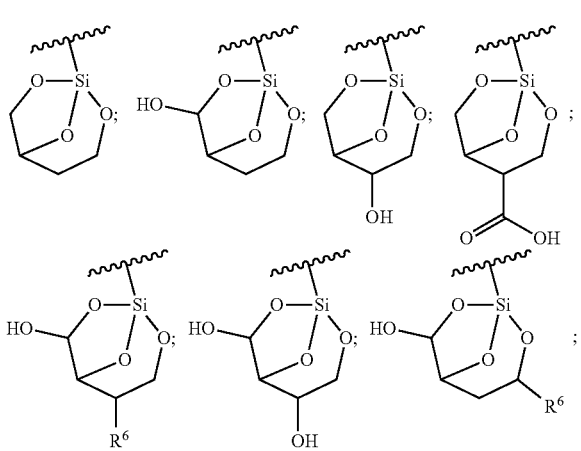

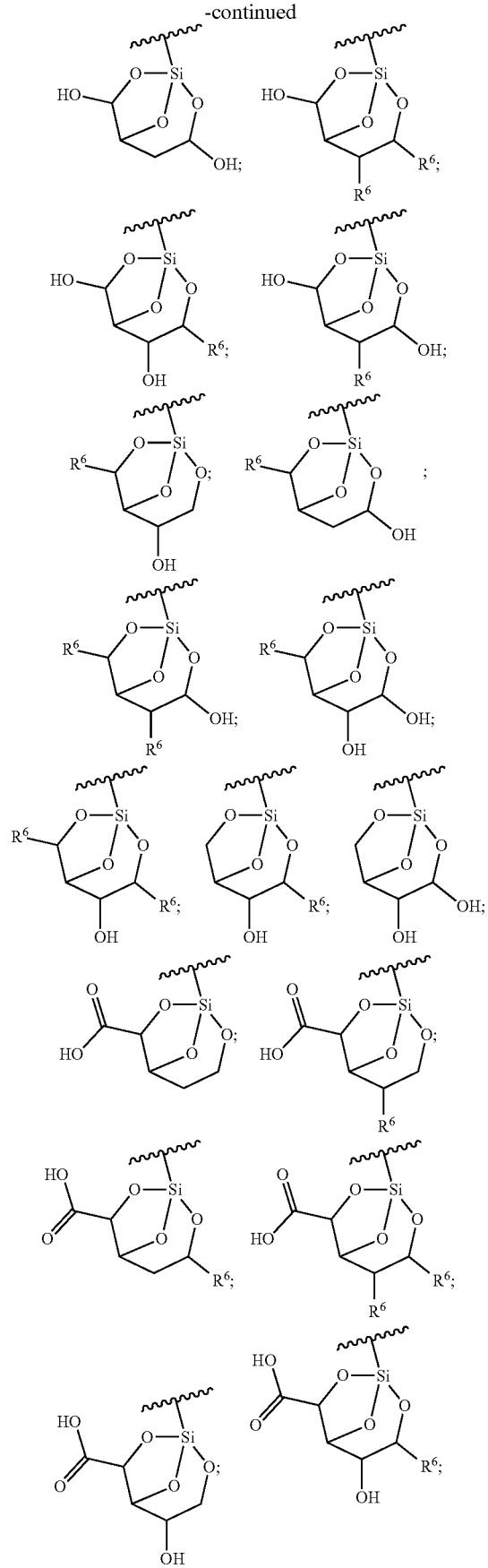
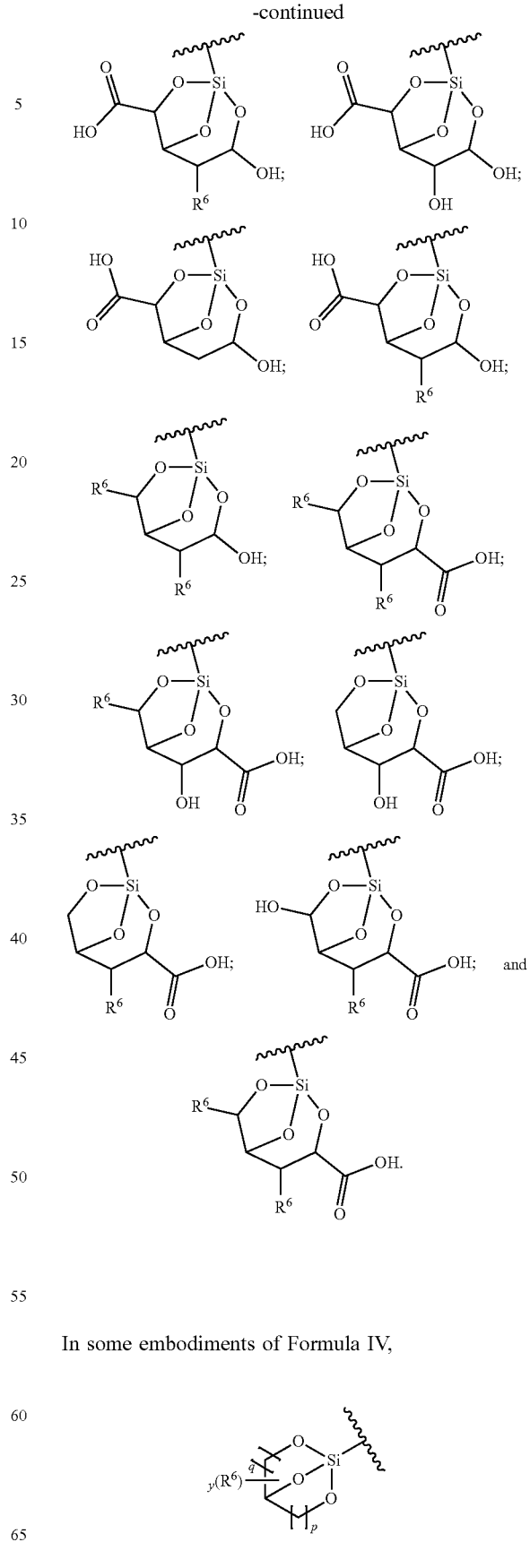
In some embodiments of Formula IV, is selected from:
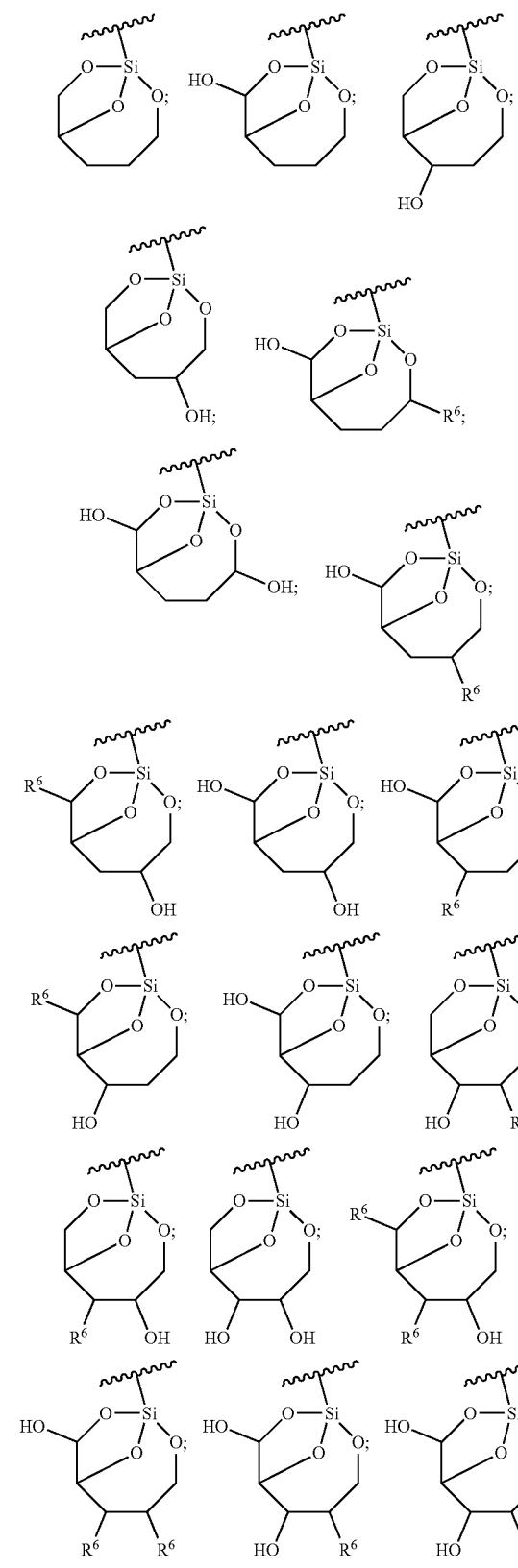
-continued
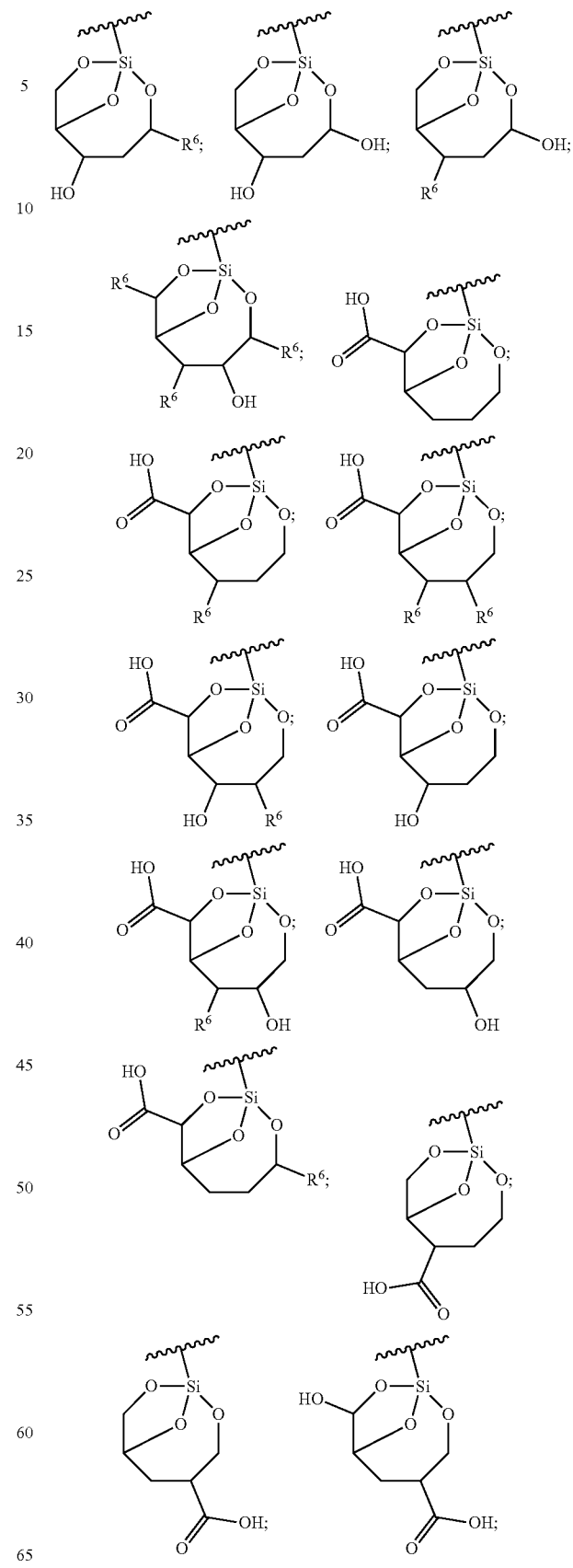

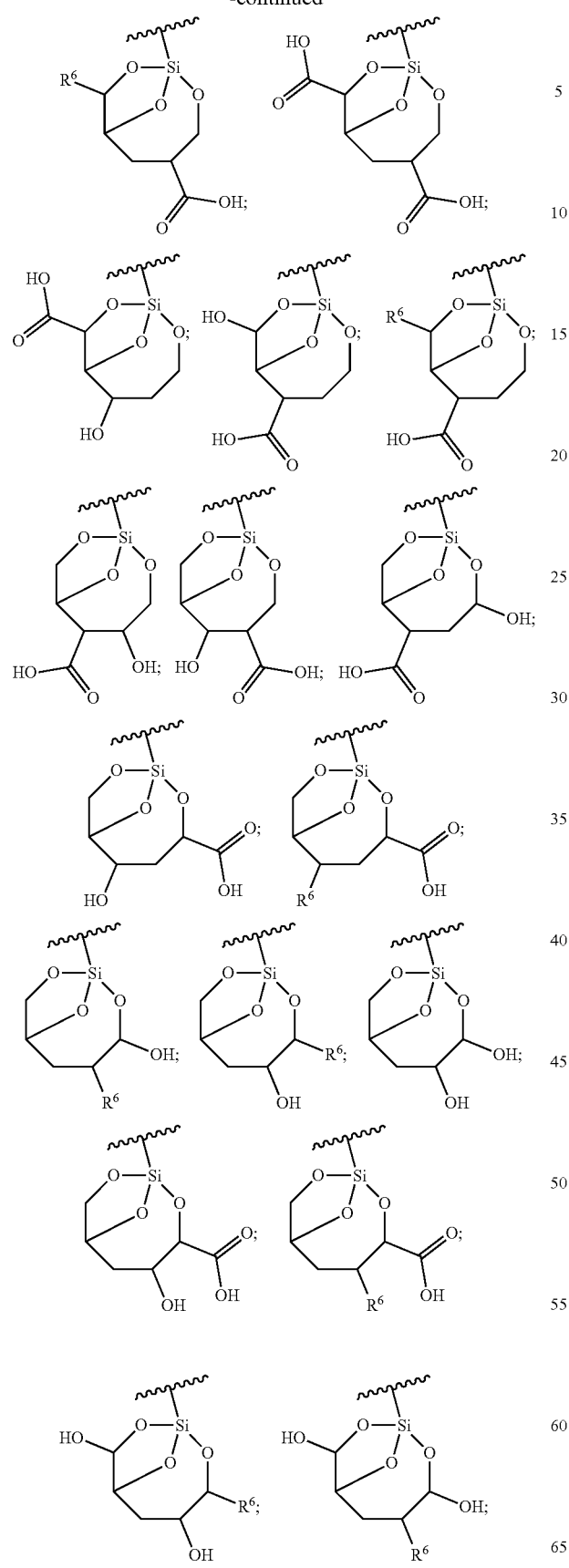
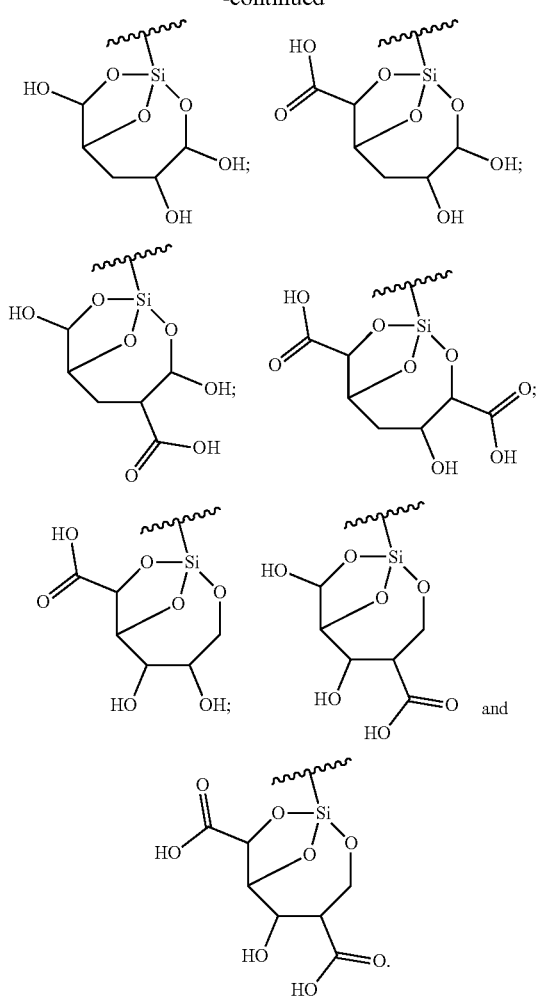
In some embodiments of Formula IV,
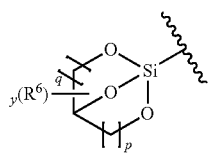
is selected from:
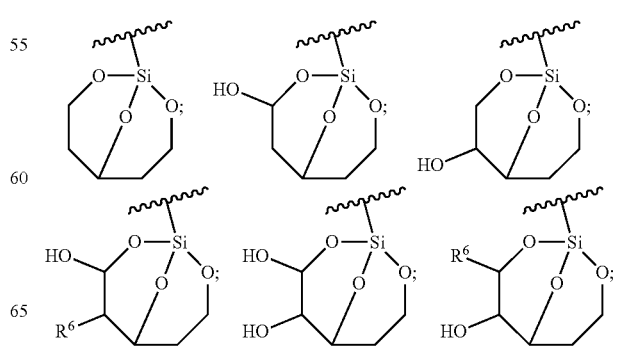

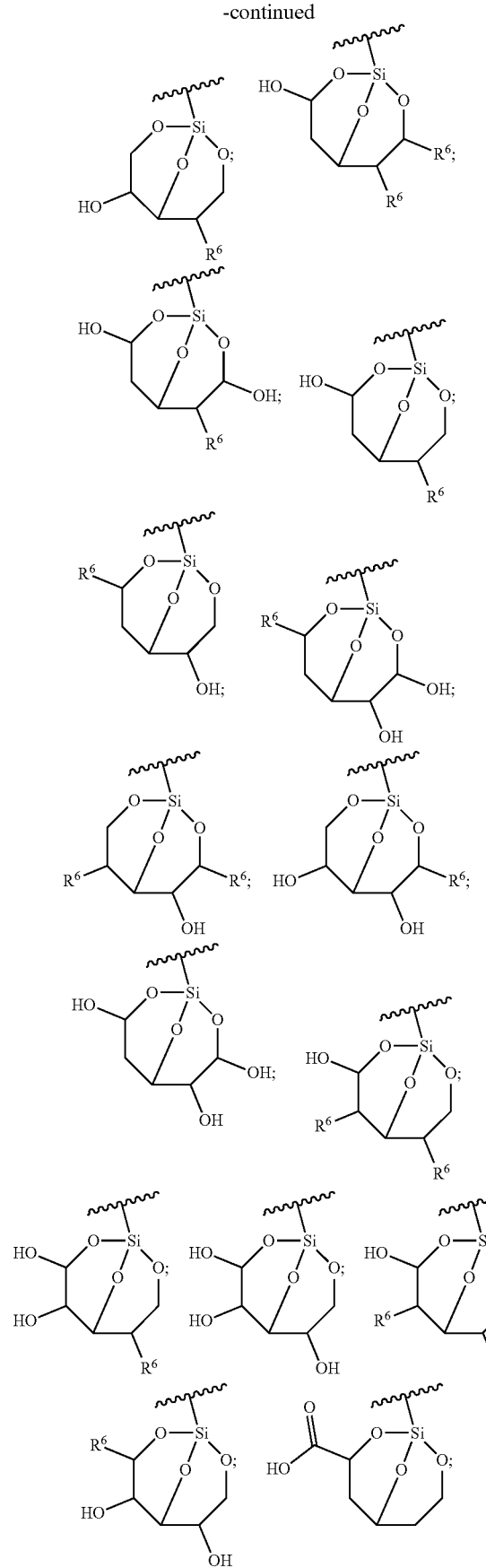
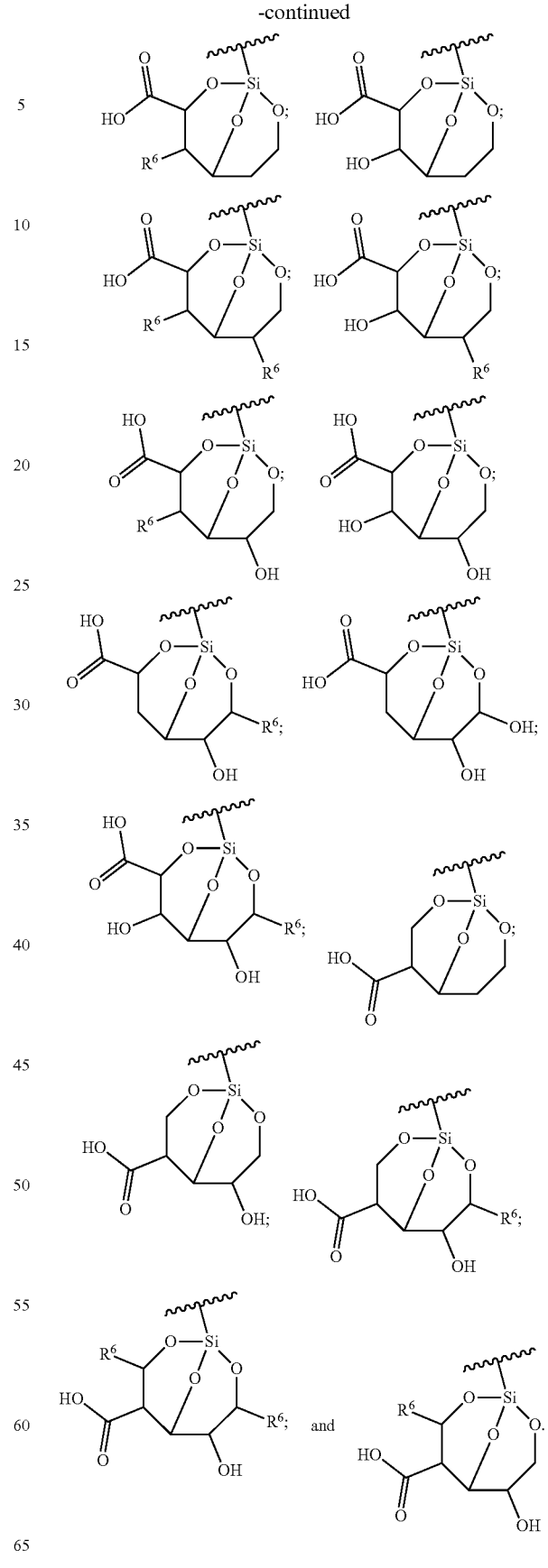

In some embodiments of Formula IV,
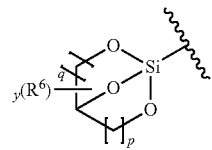
is selected from:
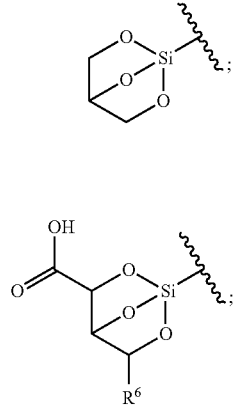
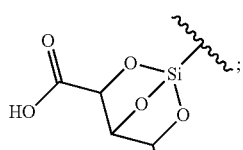
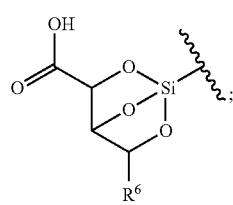
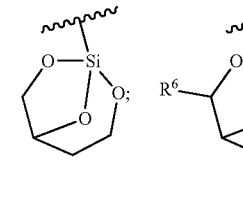
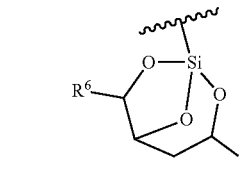
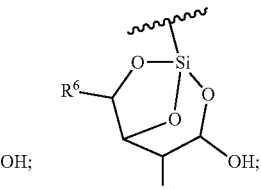
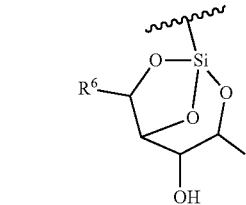
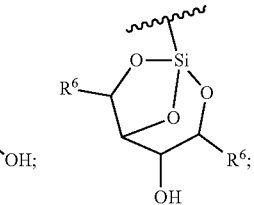
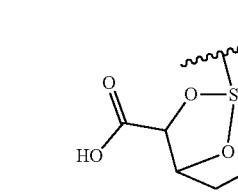
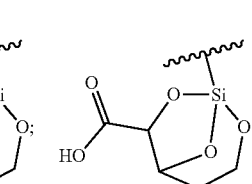
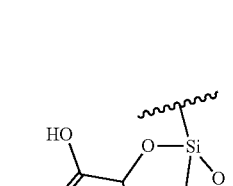
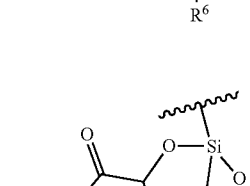
-continued
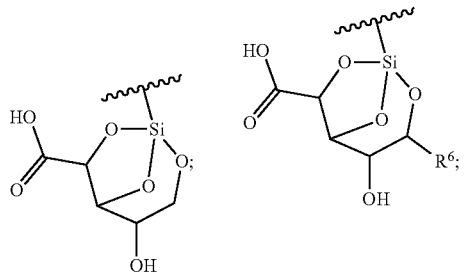
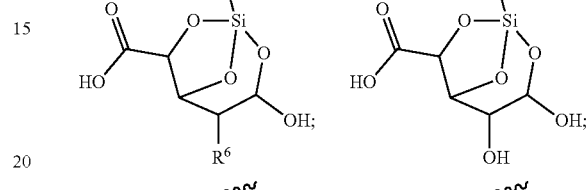
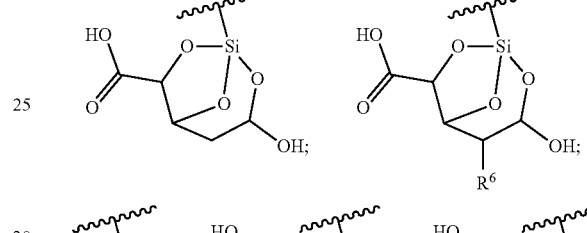
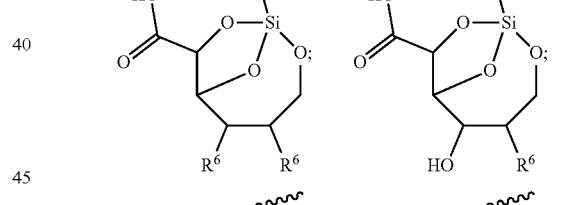
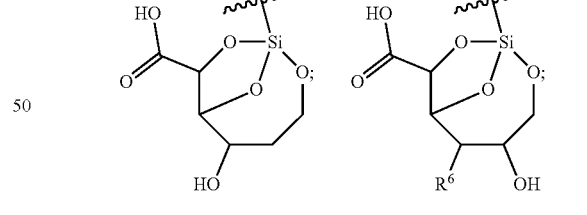
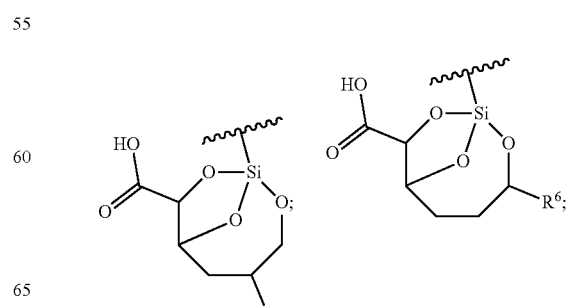

391
-continued
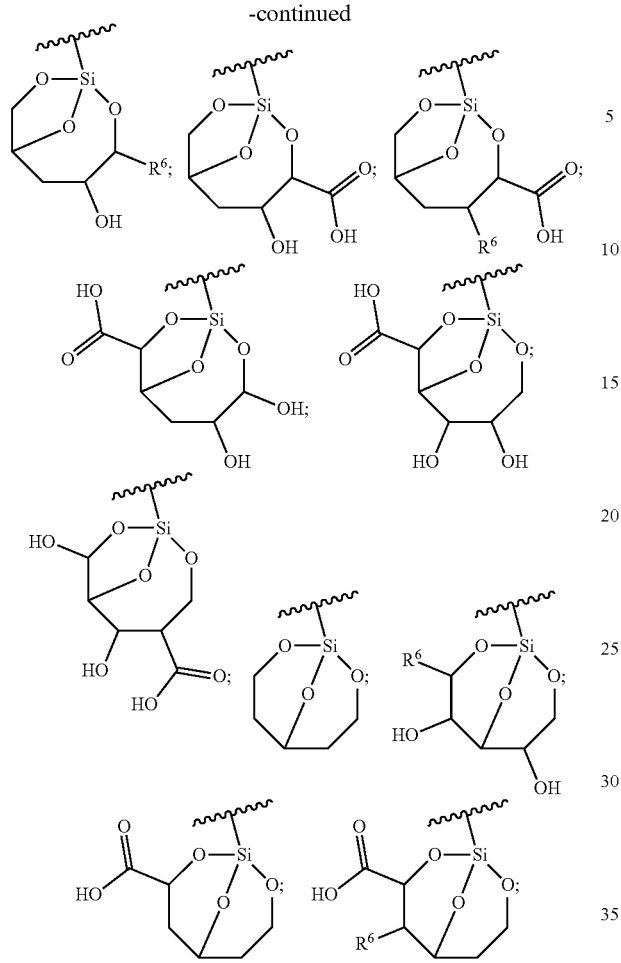
392
-continued
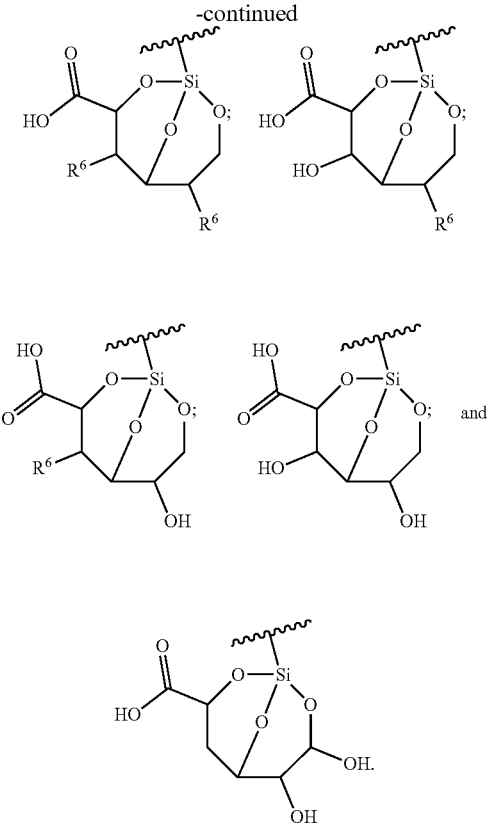
In another aspect of the present invention a quaternary ammonium compound of Formula III is selected from:
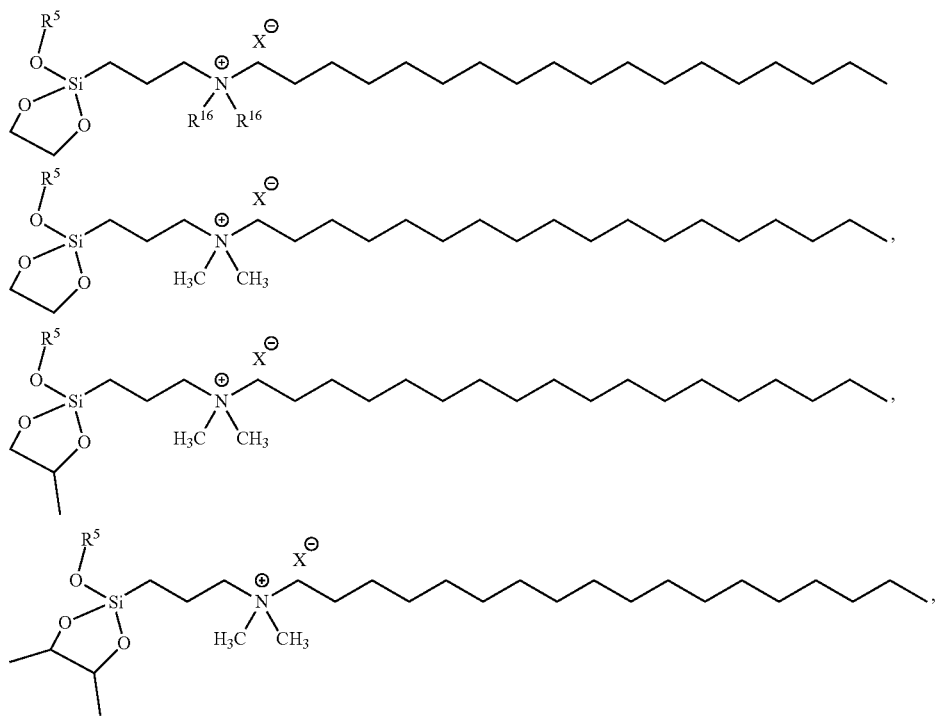

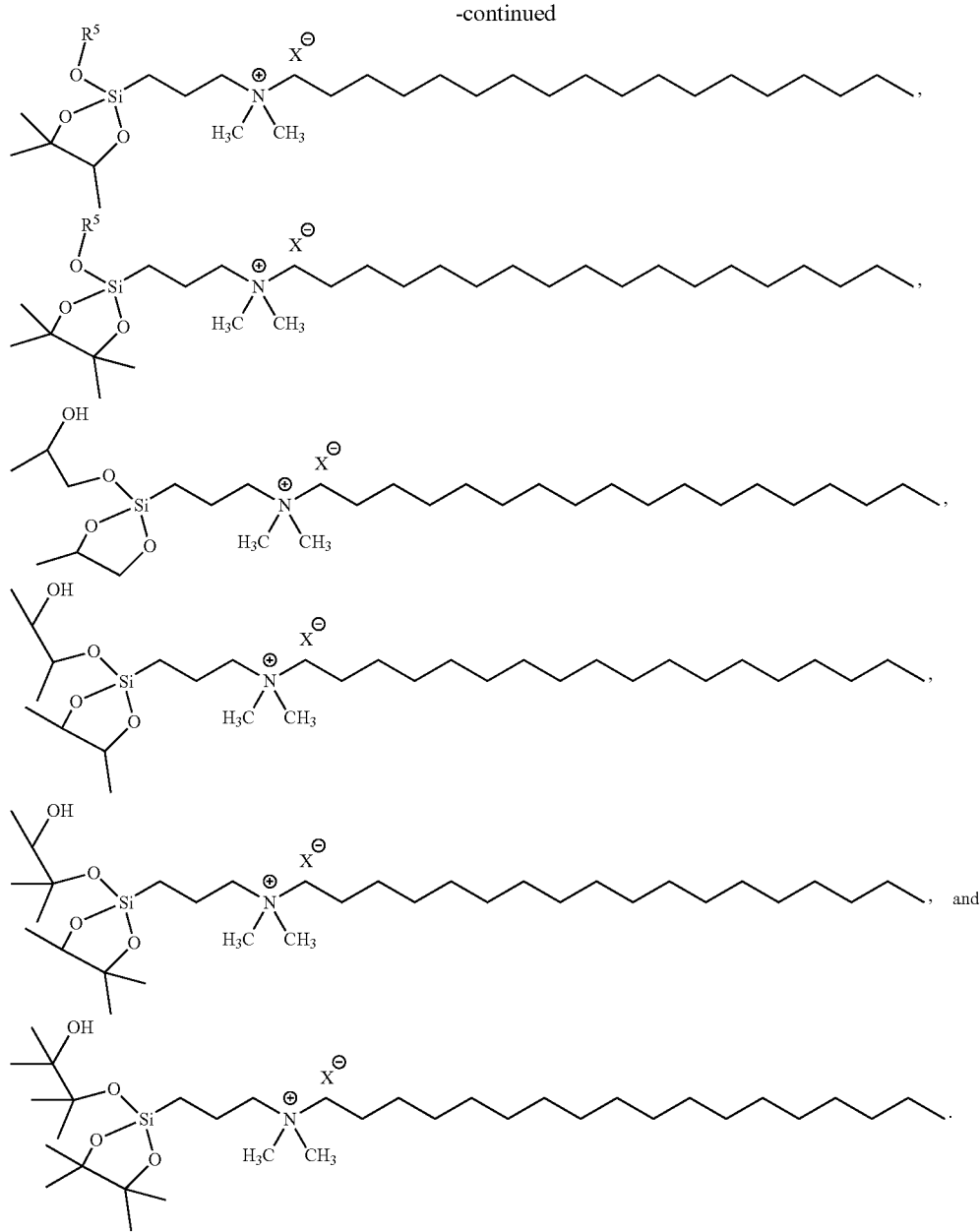
In another aspect of the present invention, a quaternary ammonium compound of Formula III is selected from:
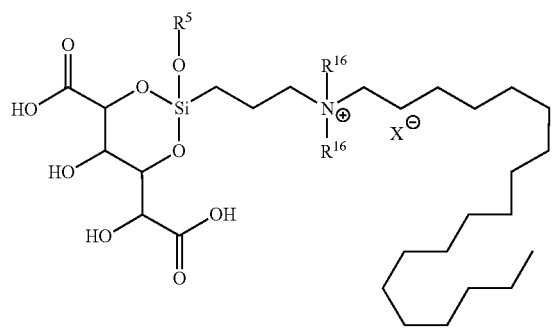
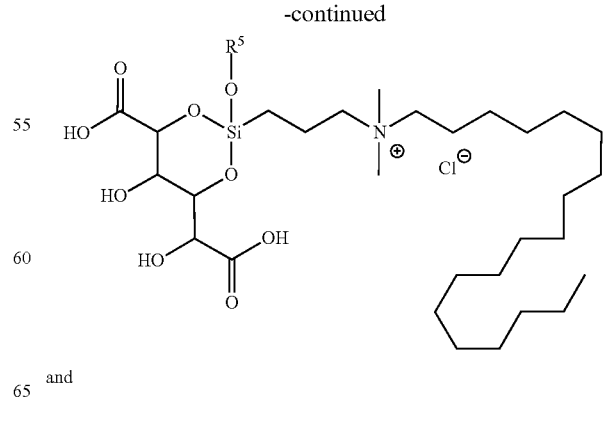
and

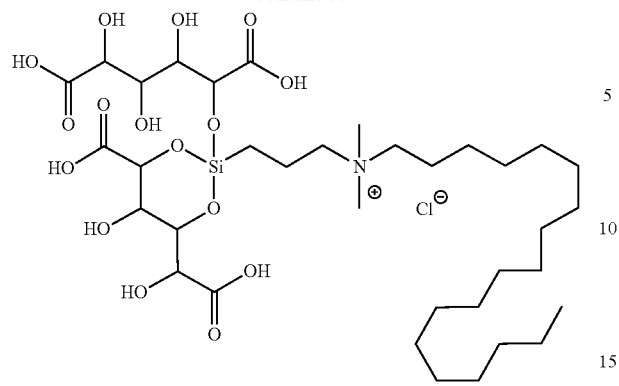
In another aspect of the present invention a quaternary ammonium compound of Formula IV is selected from:
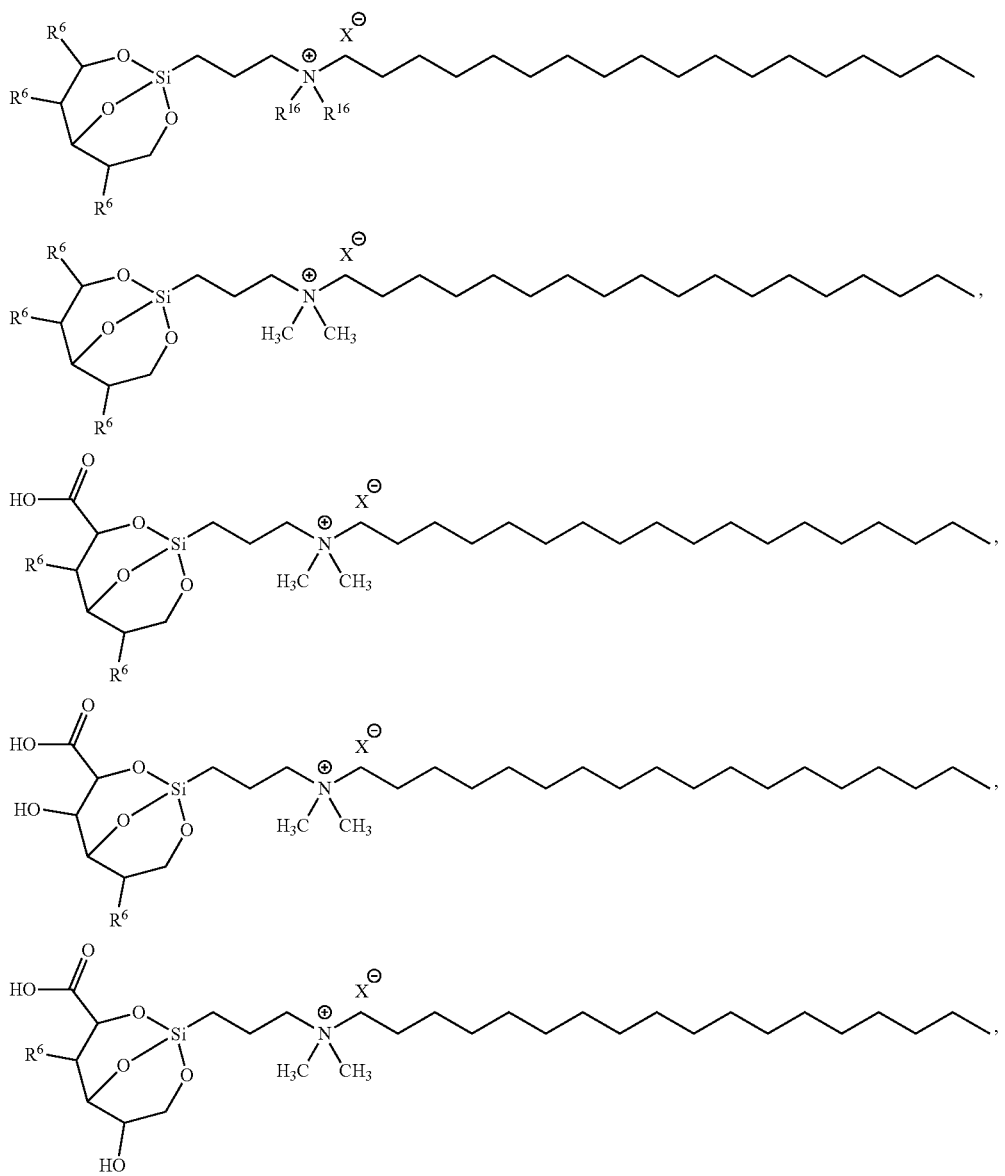

-continued
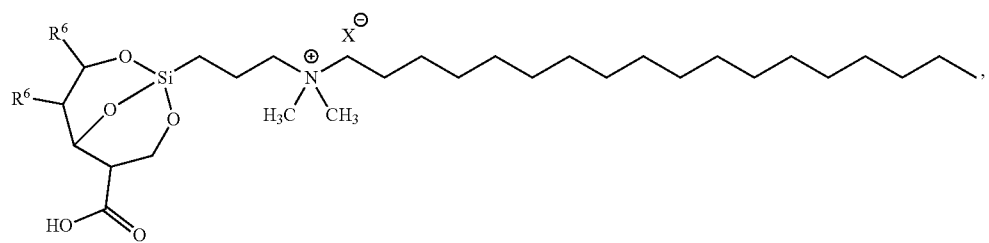
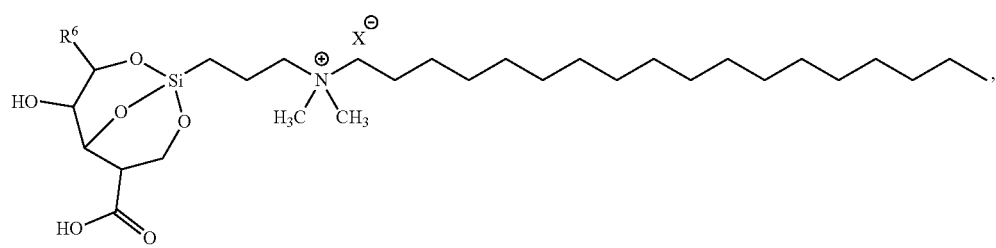
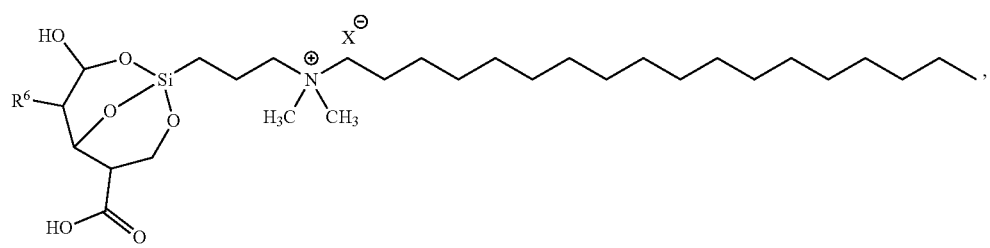
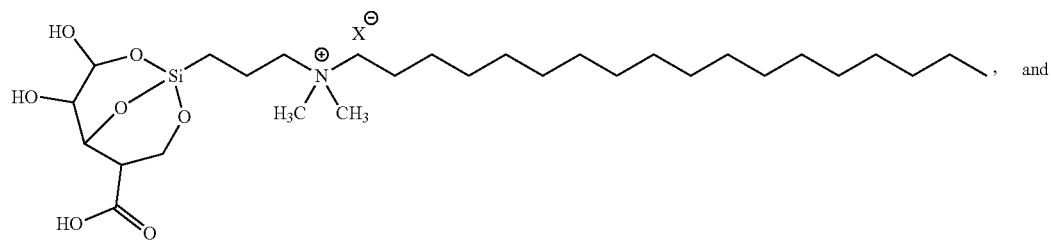, and
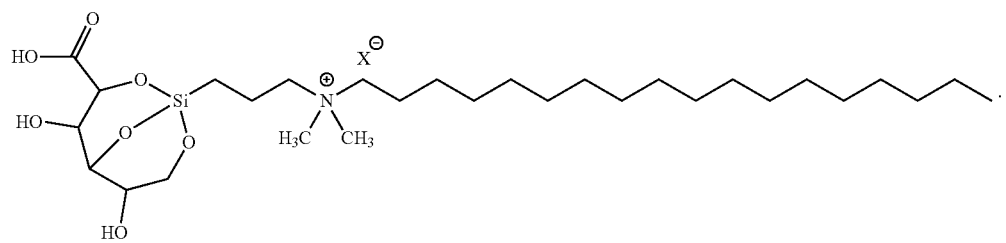

In certain embodiments the quaternary ammonium compound of the present invention is selected from:
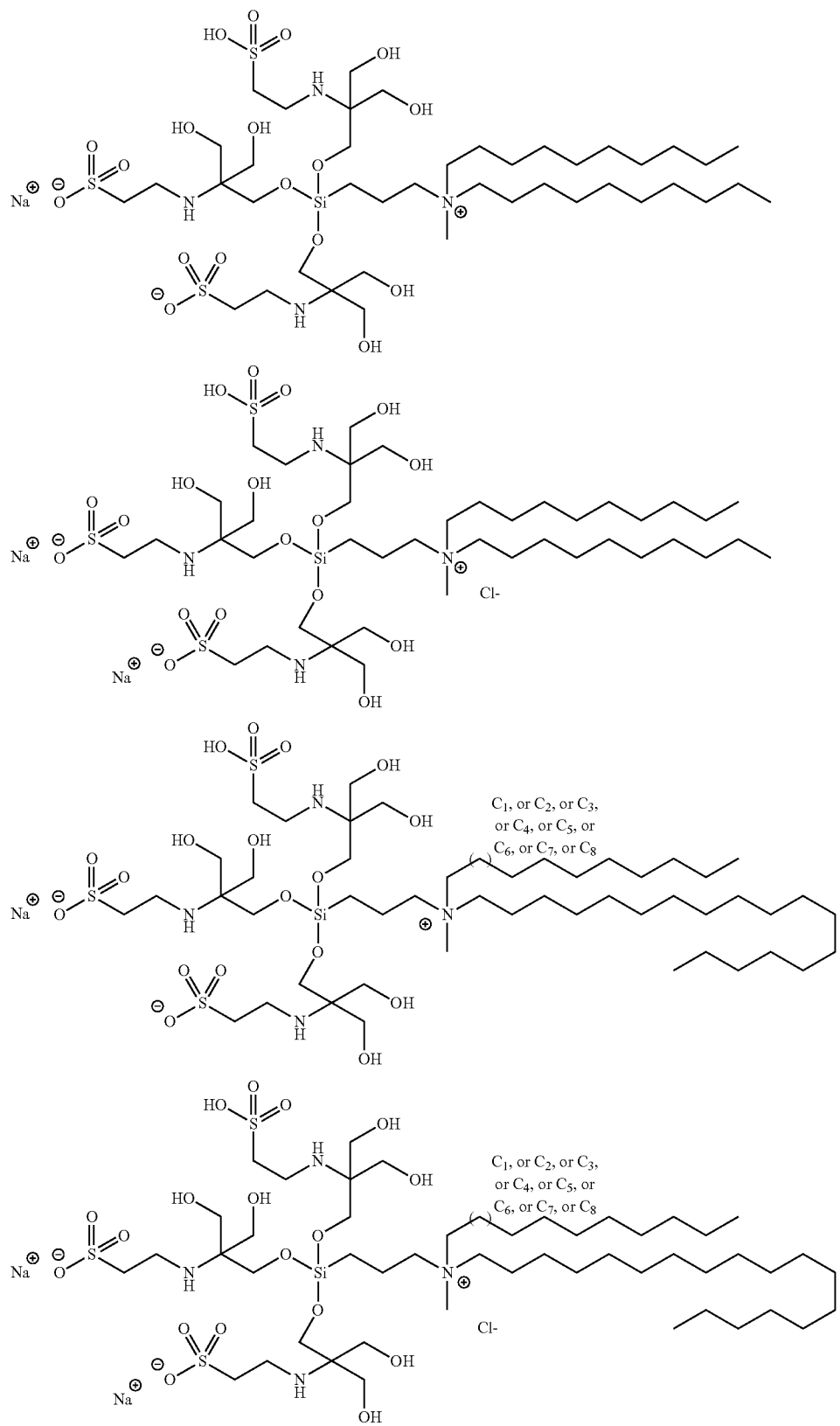

-continued
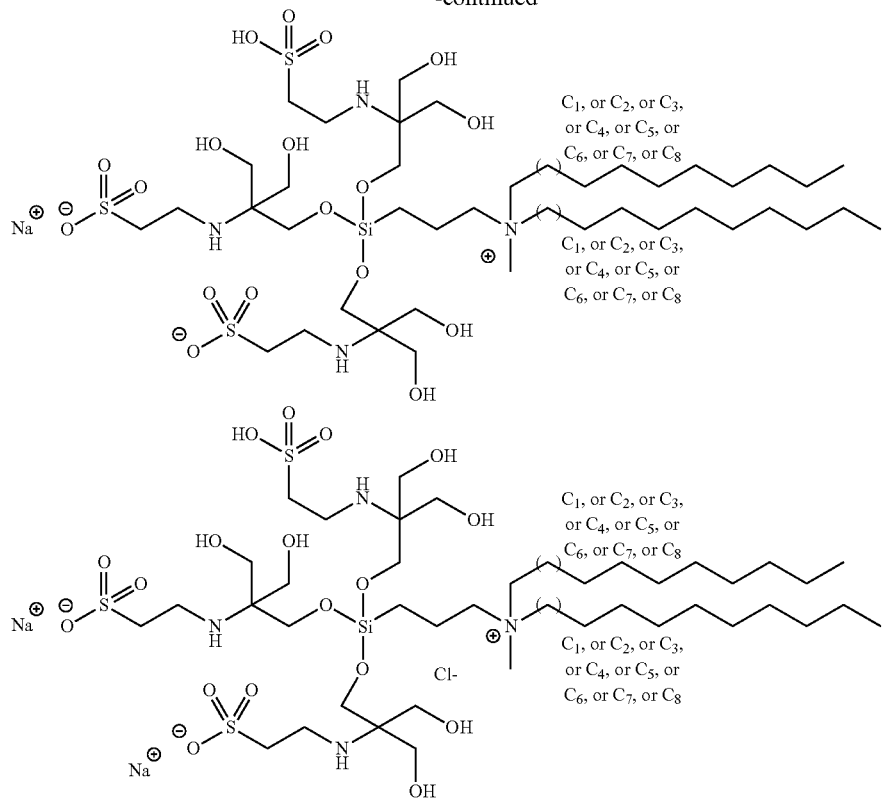
In certain embodiments the quaternary ammonium compound of the present invention is selected from:
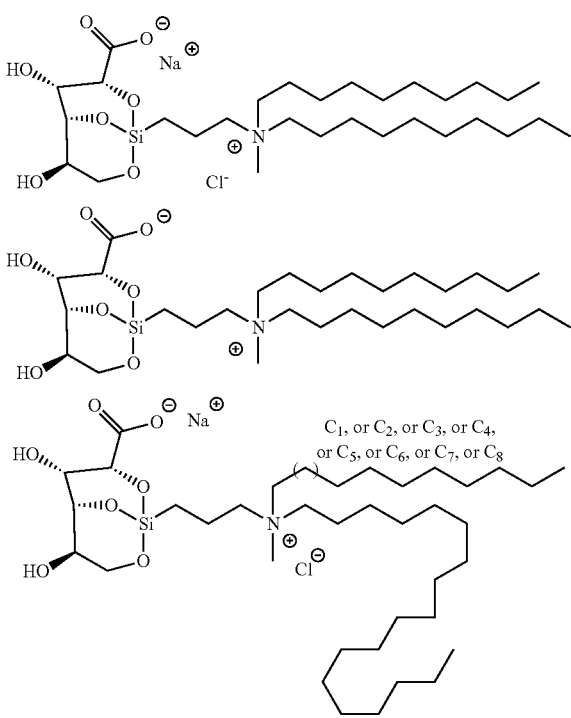
-continued
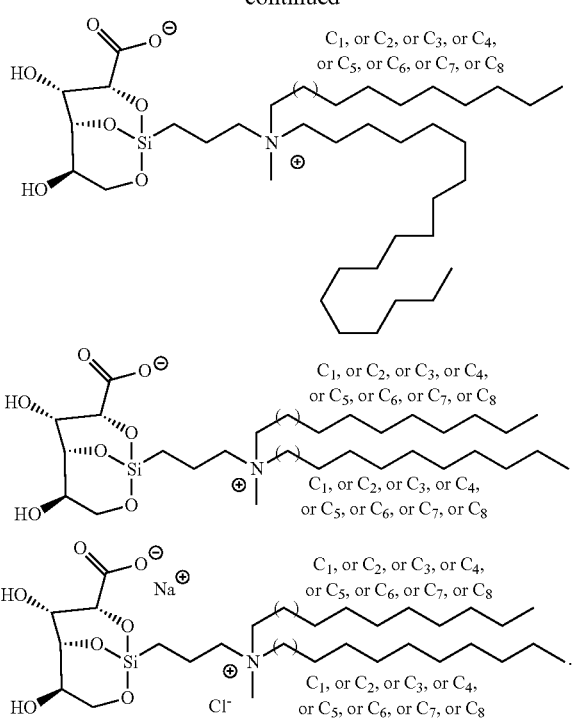
In certain embodiments the quaternary ammonium compound of the present invention is selected from:

403 404
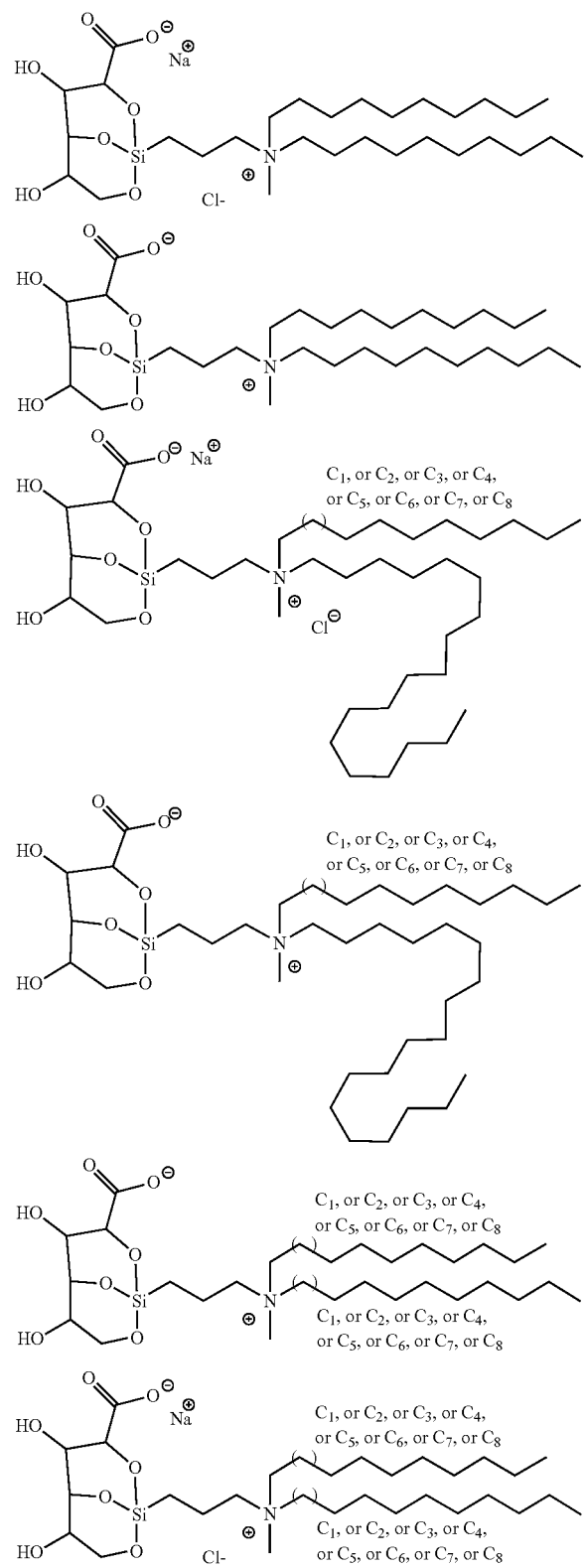
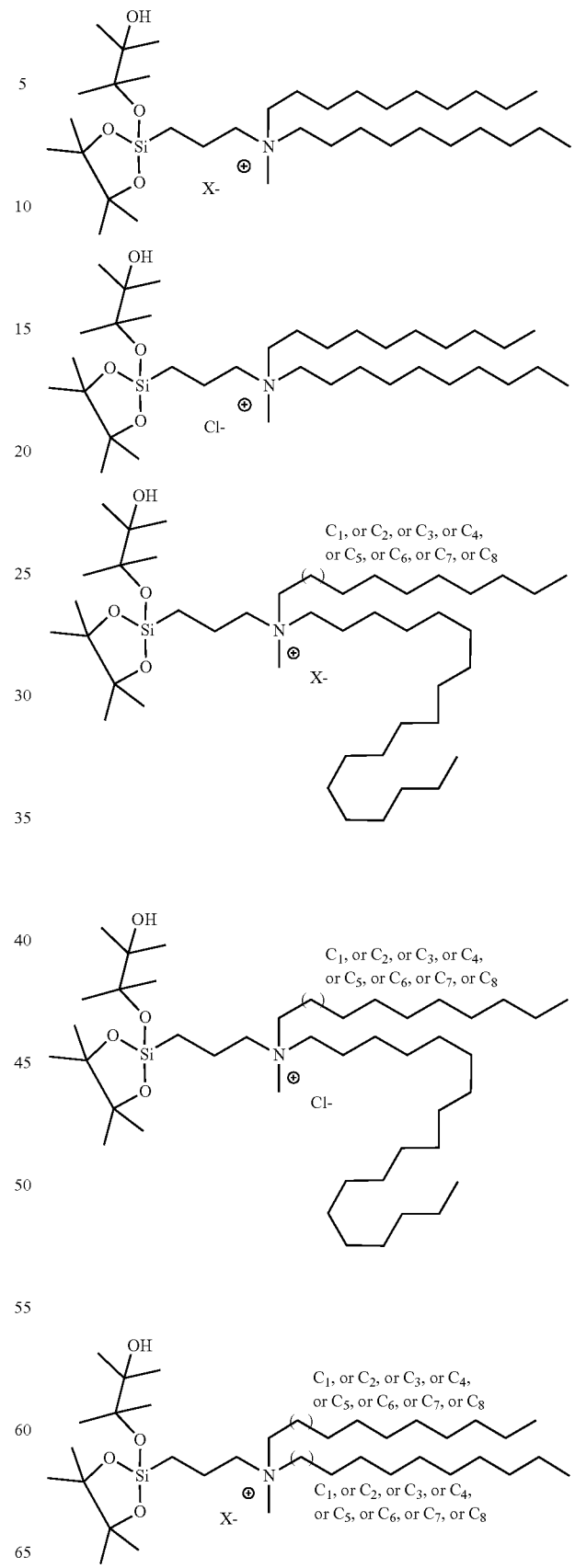
In certain embodiments the quaternary ammonium compound of the present invention is selected from:

405
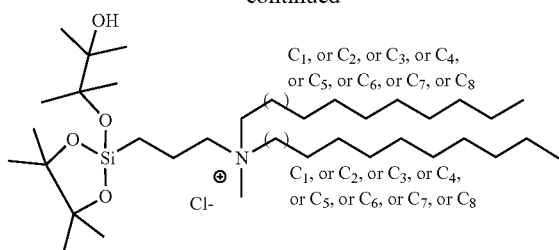
In certain embodiments the quaternary ammonium compound of the present invention is selected from:
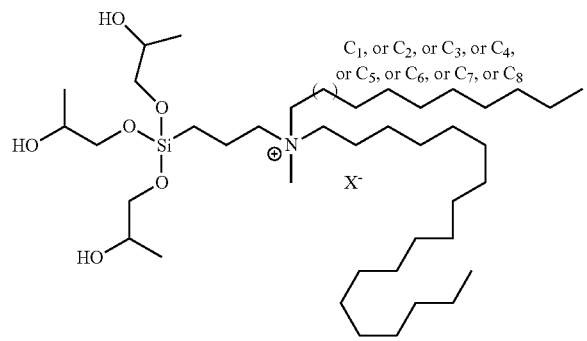
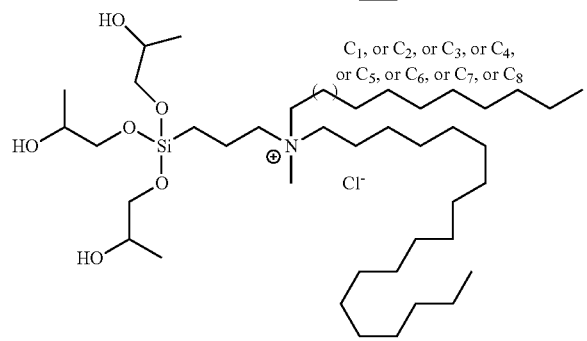
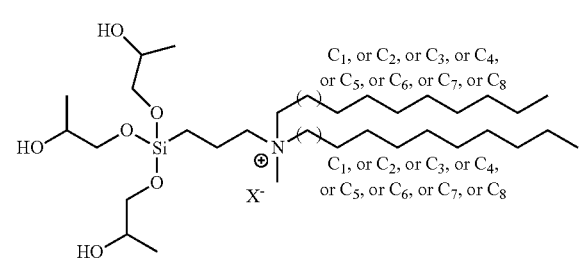
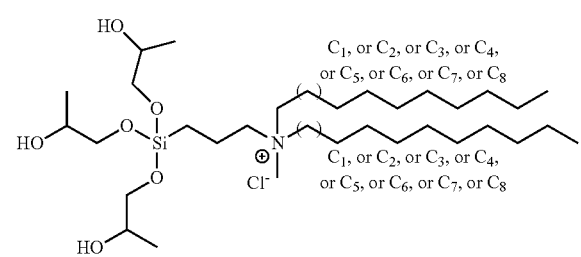
406
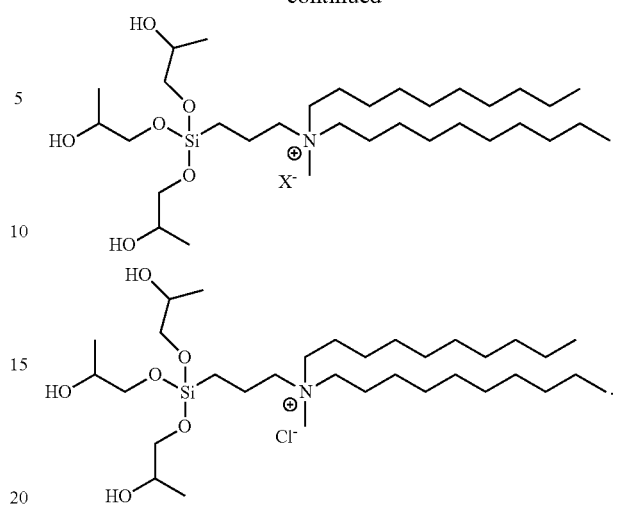
In certain embodiments the quaternary ammonium compound of the present invention is selected from:
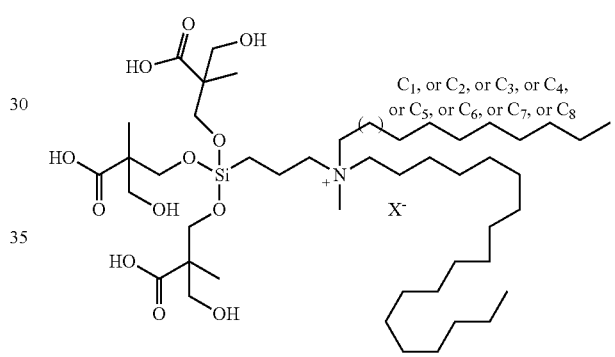
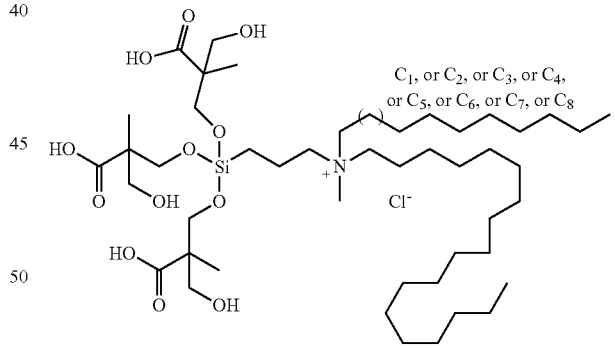
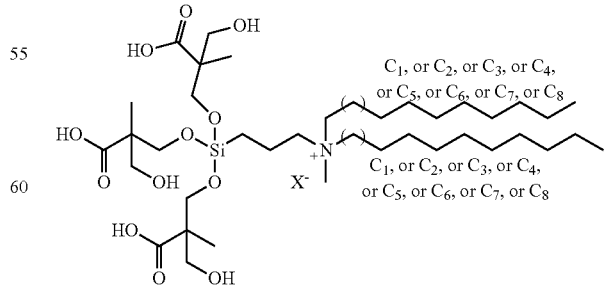

407
-continued
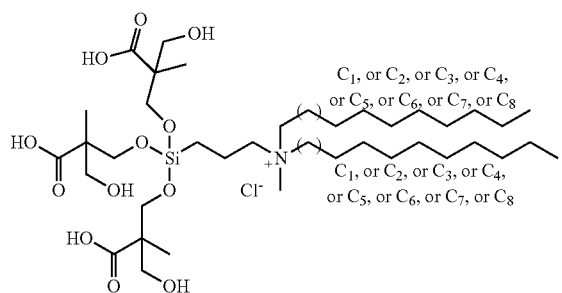
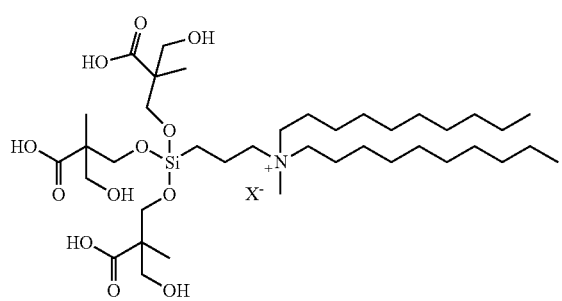
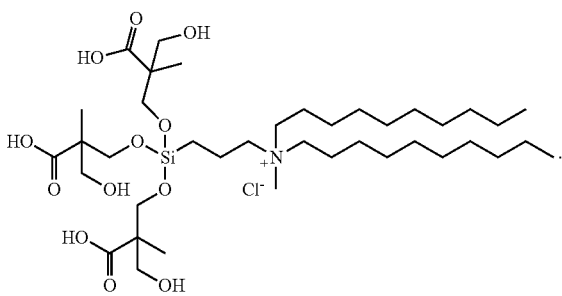
In certain embodiments the quaternary ammonium compound of the present invention is selected from:
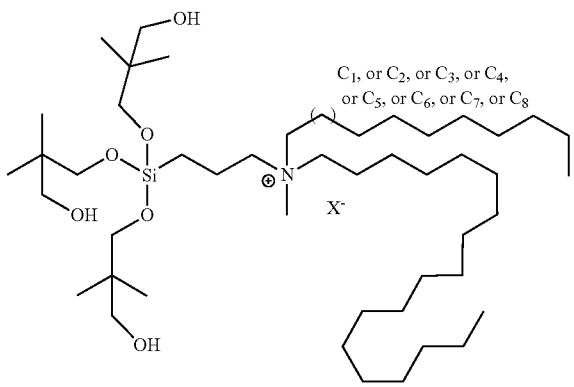
408
-continued
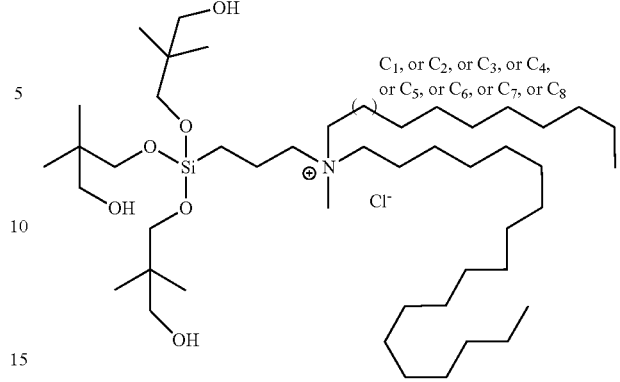
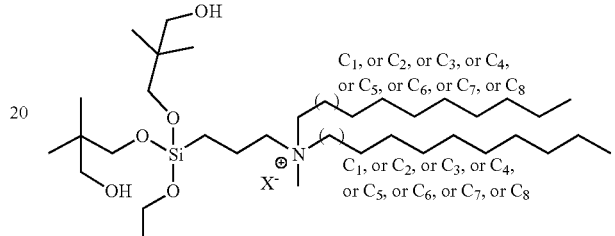
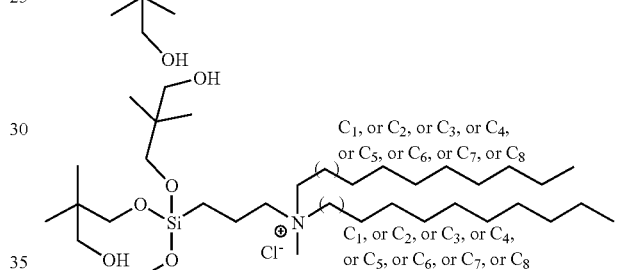
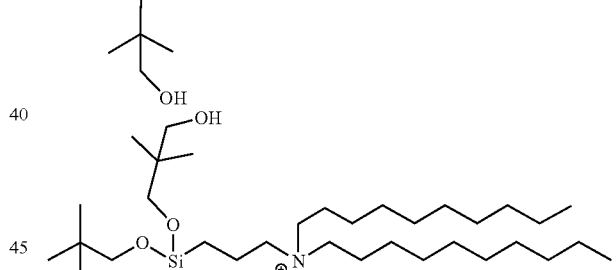
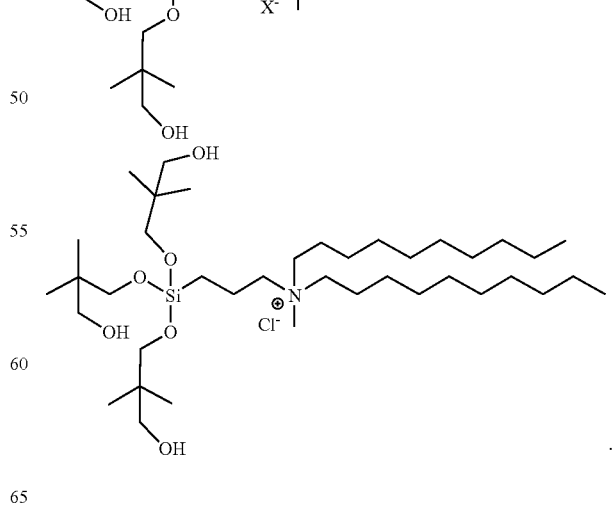
In certain embodiments the quaternary ammonium compound of the present invention is selected from:

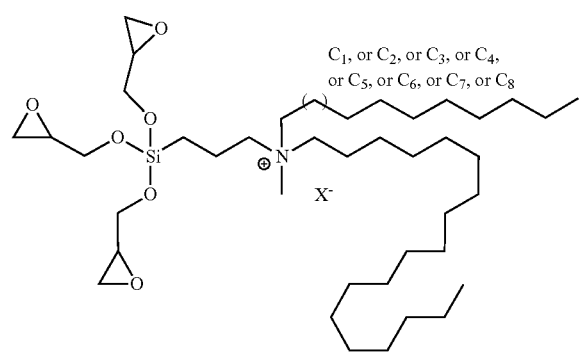
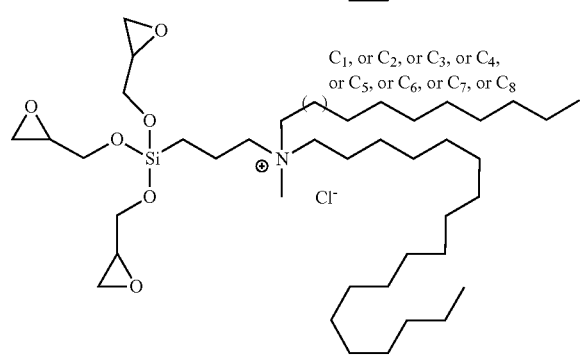
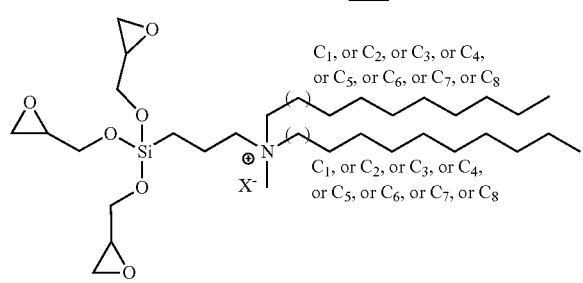
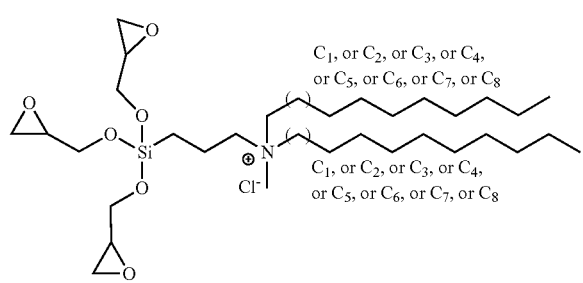
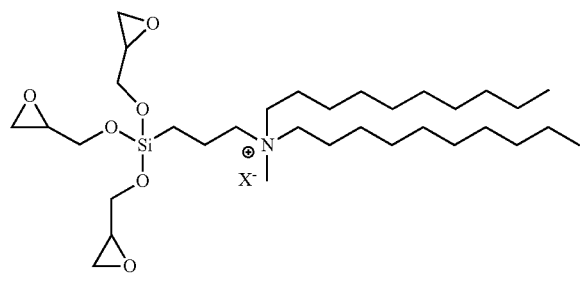
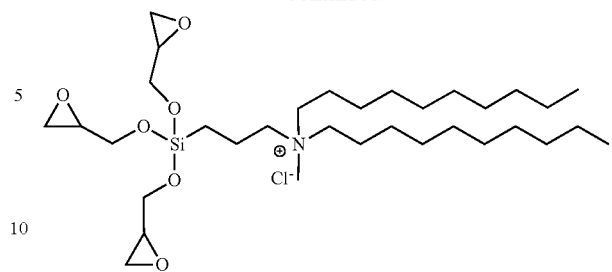
In certain embodiments the quaternary ammonium compound of the present invention is selected from:
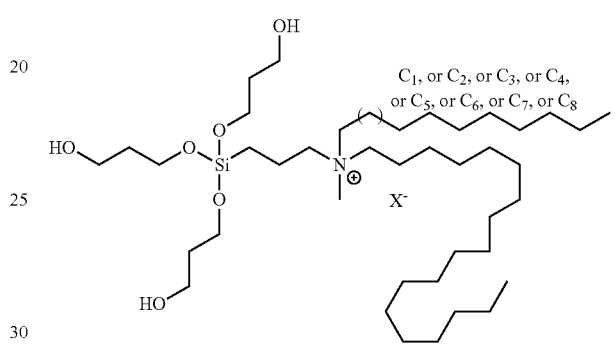
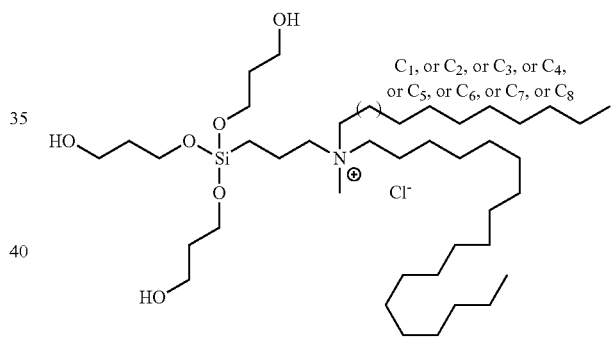
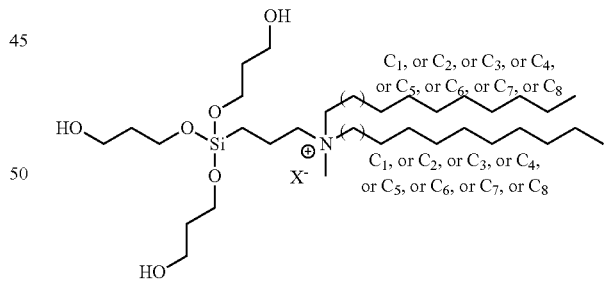
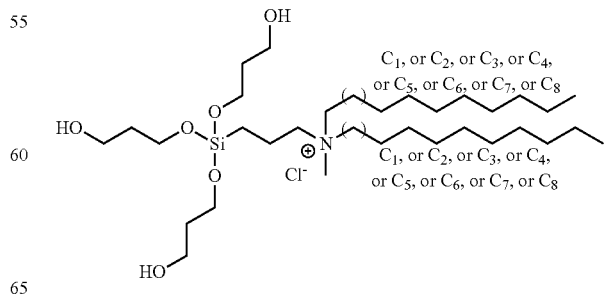

-continued
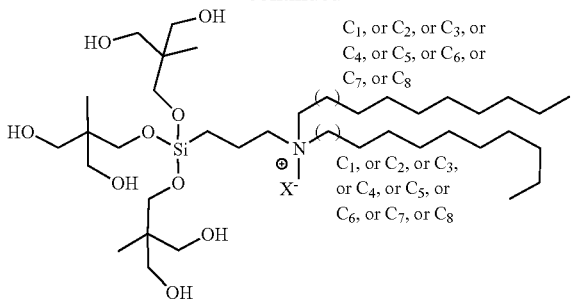
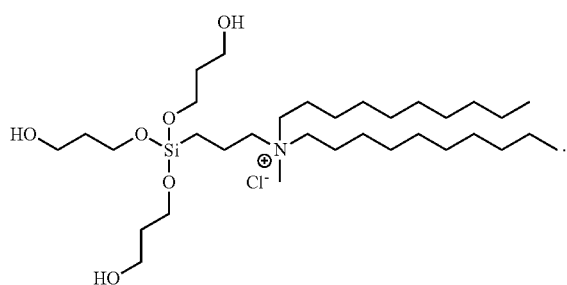
In certain embodiments the quaternary ammonium compound of the present invention is selected from:
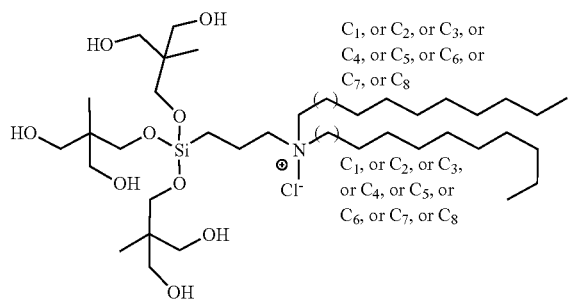
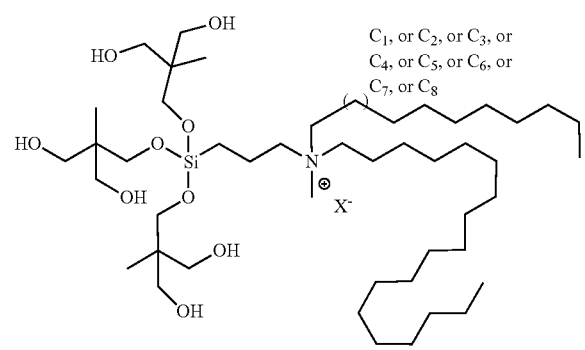
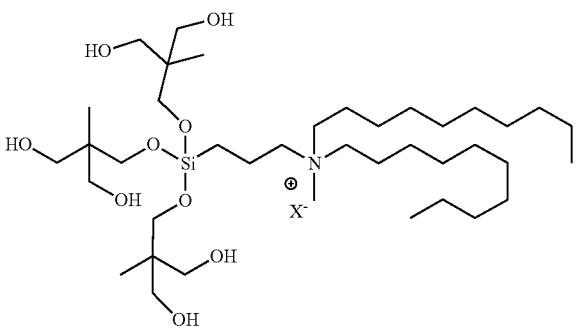
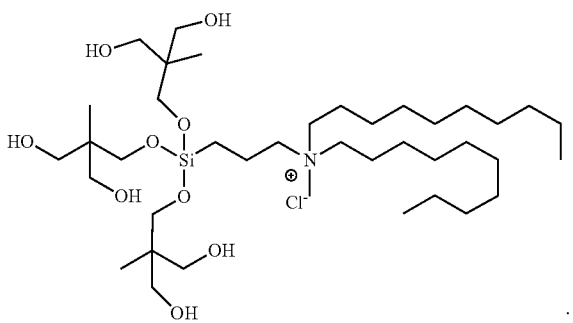
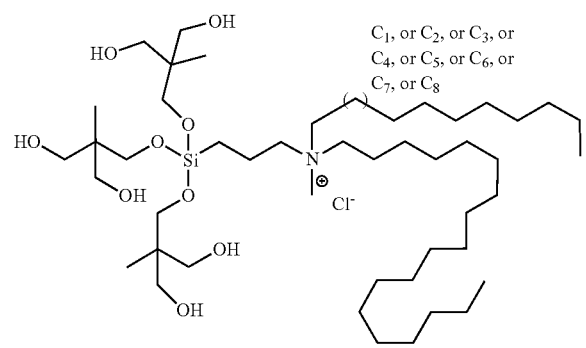
In certain embodiments the quaternary ammonium compound of the present invention is selected from:

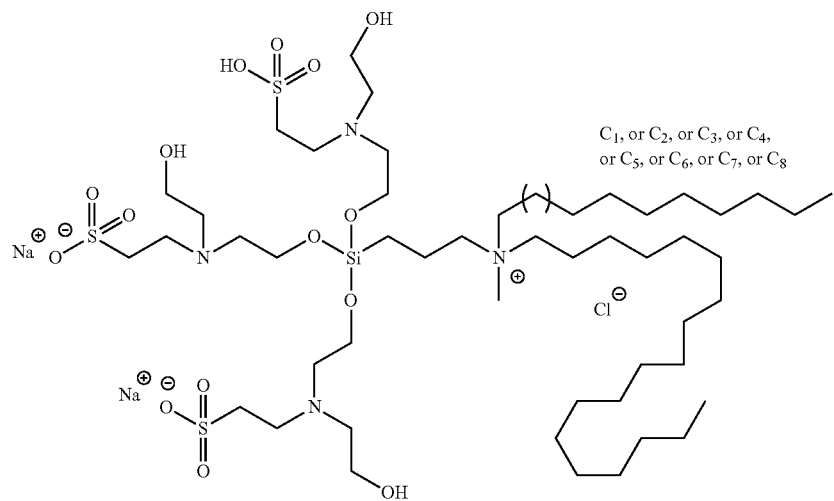
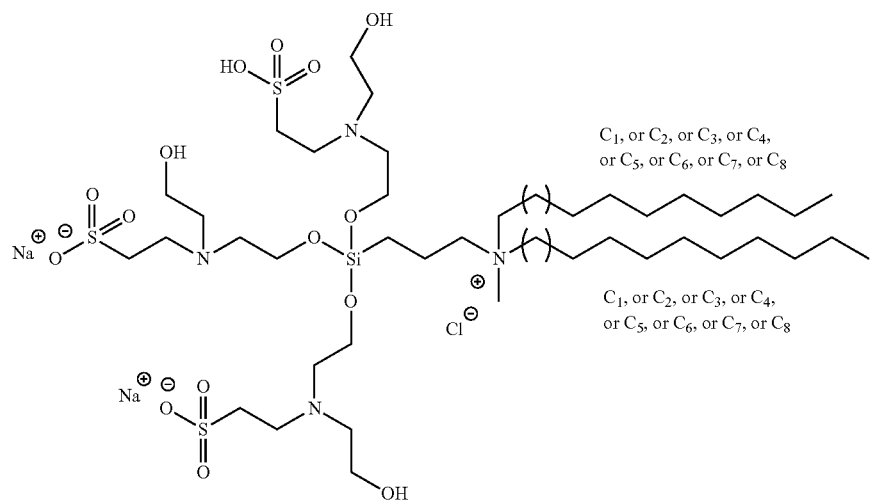
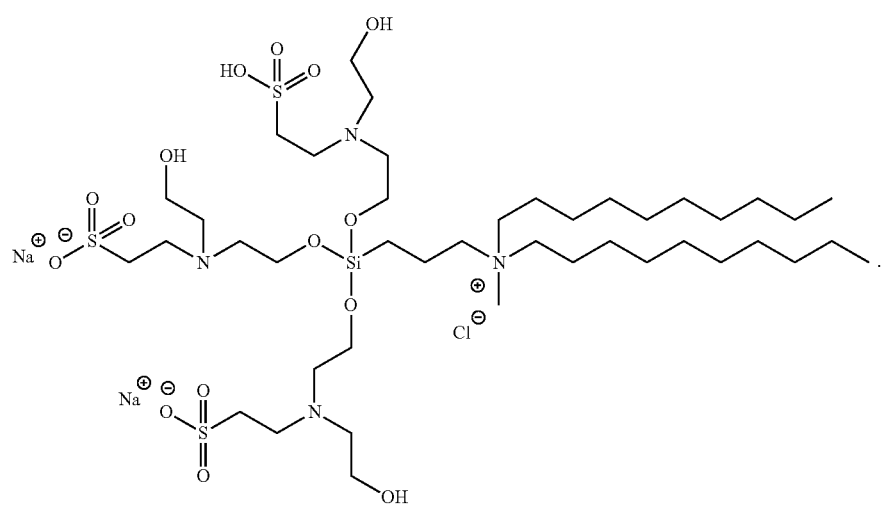
In certain embodiments the quaternary ammonium compound of the present invention is selected from:

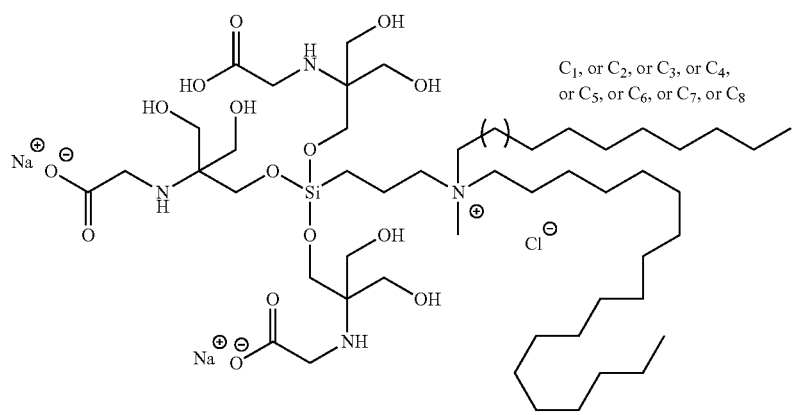
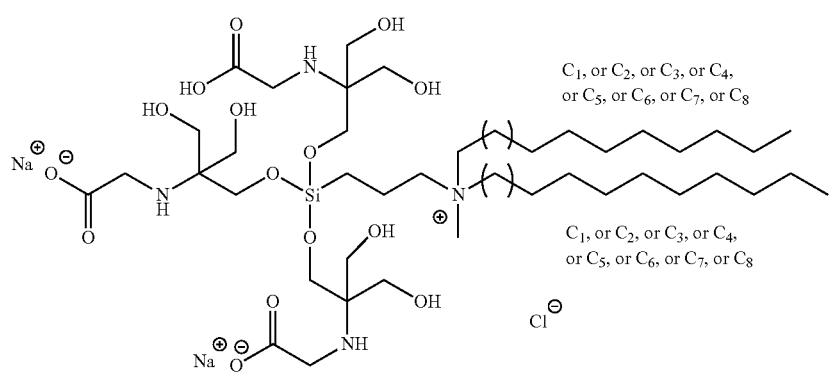
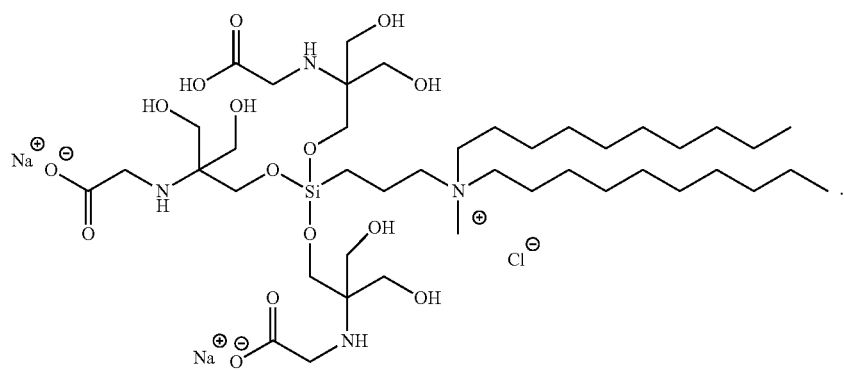
In certain embodiments the quaternary ammonium compound of the present invention is selected from:

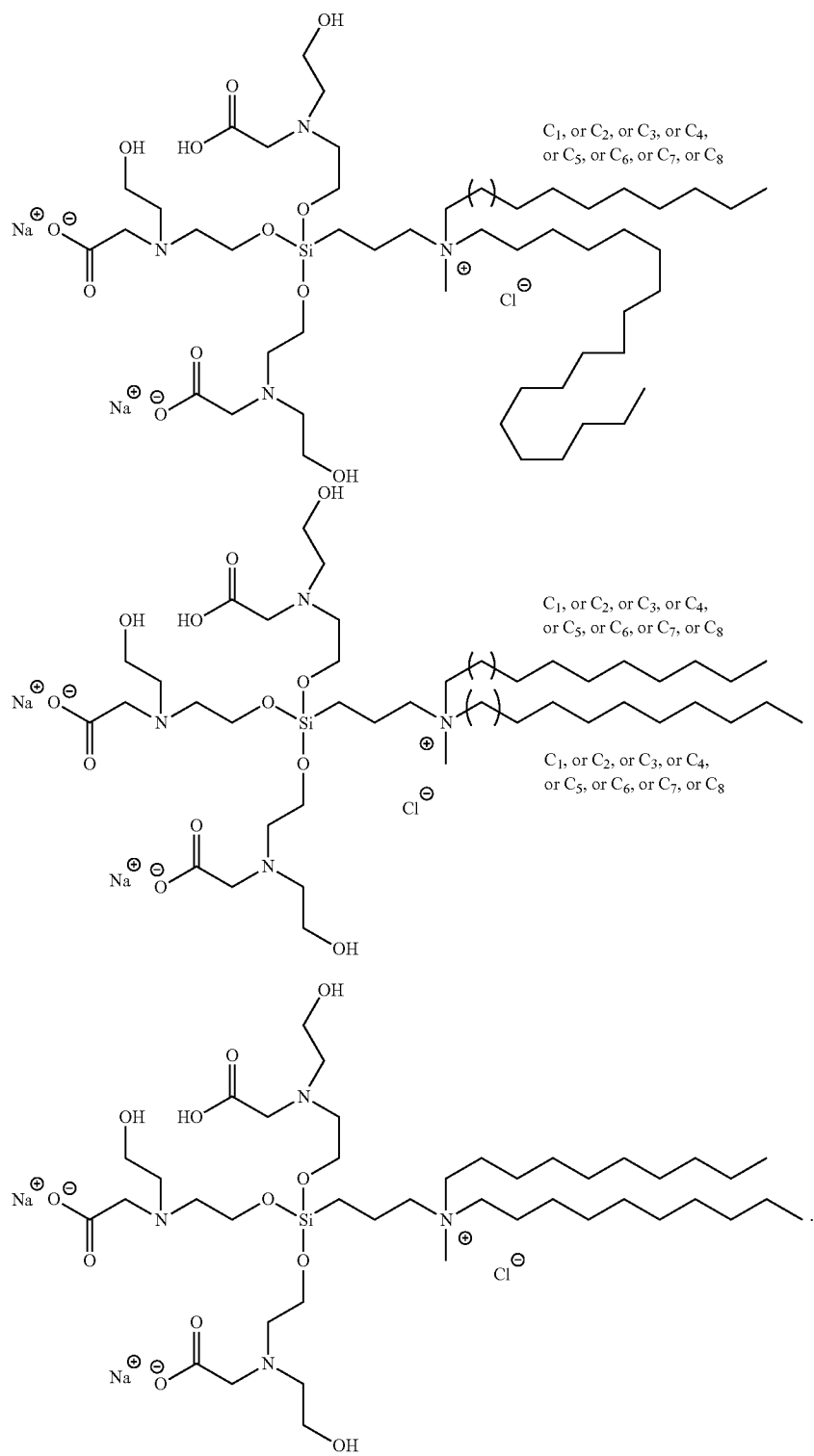
In certain embodiments the quaternary ammonium compound of the present invention is selected from:

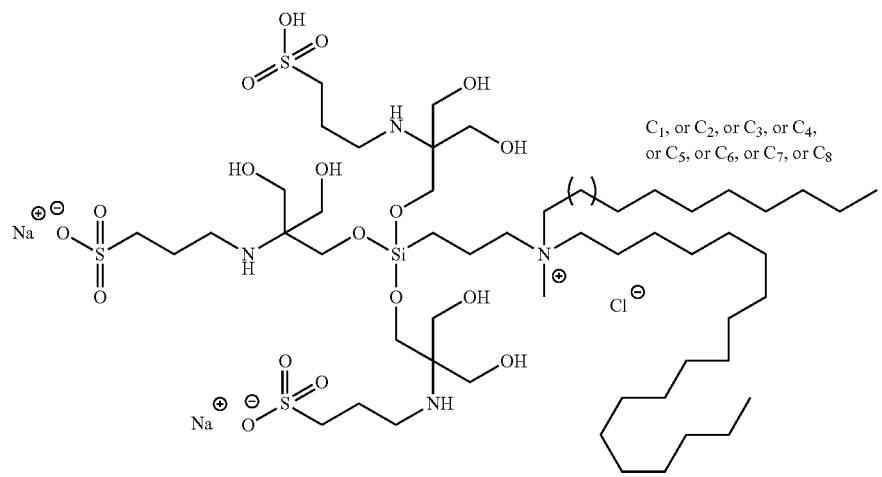
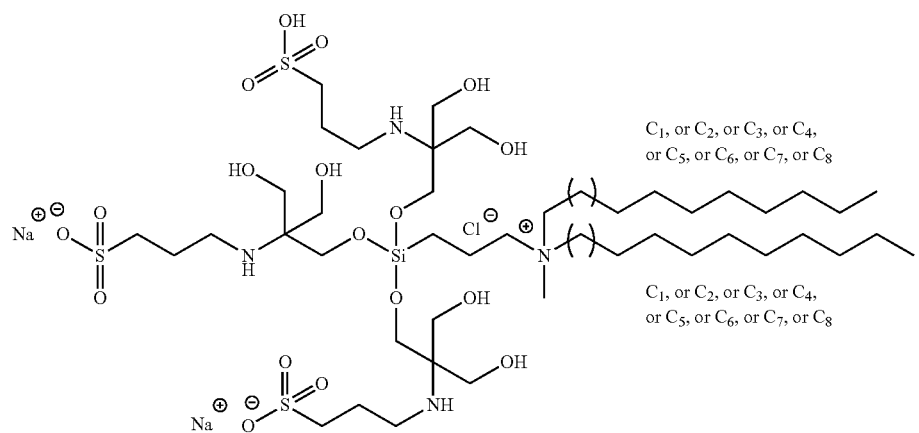
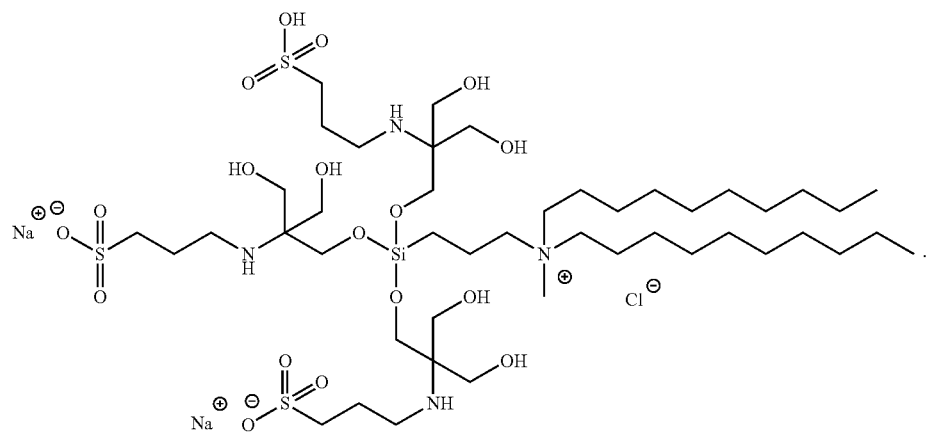
In certain embodiments the quaternary ammonium compound of the present invention is selected from:

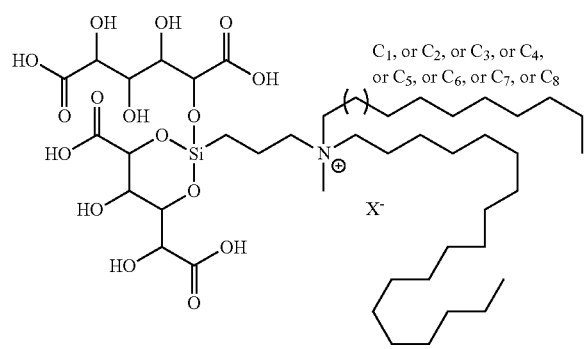
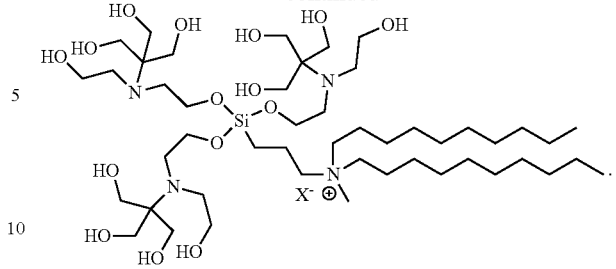
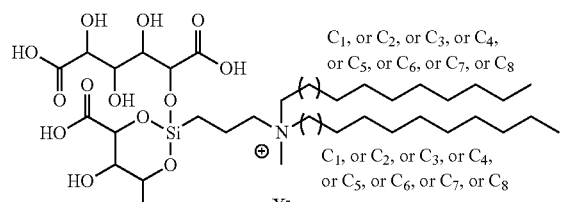
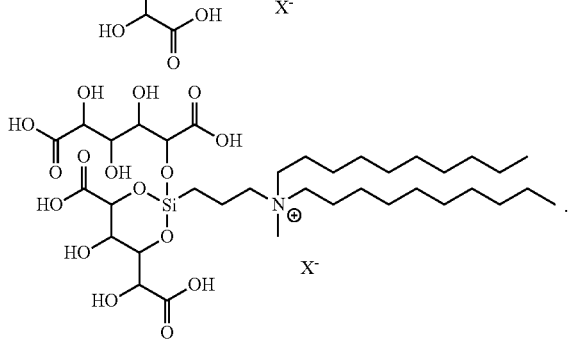
In certain embodiments the quaternary ammonium compound of the present invention is selected from:
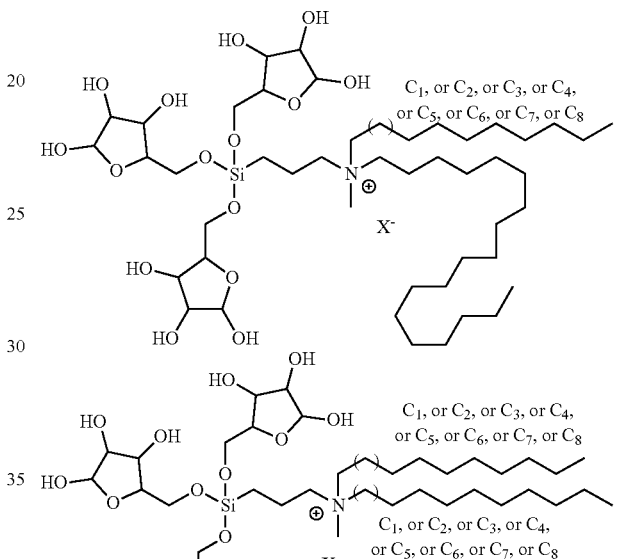
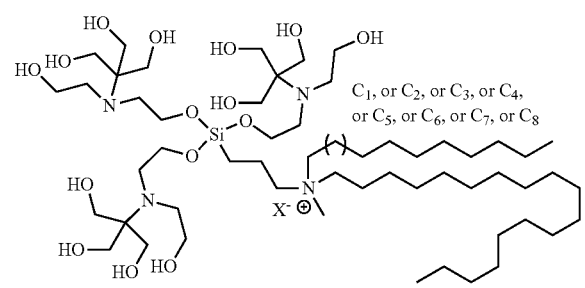
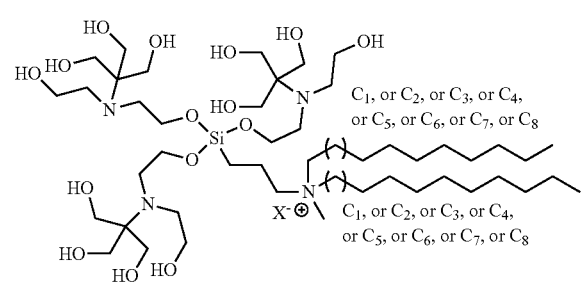
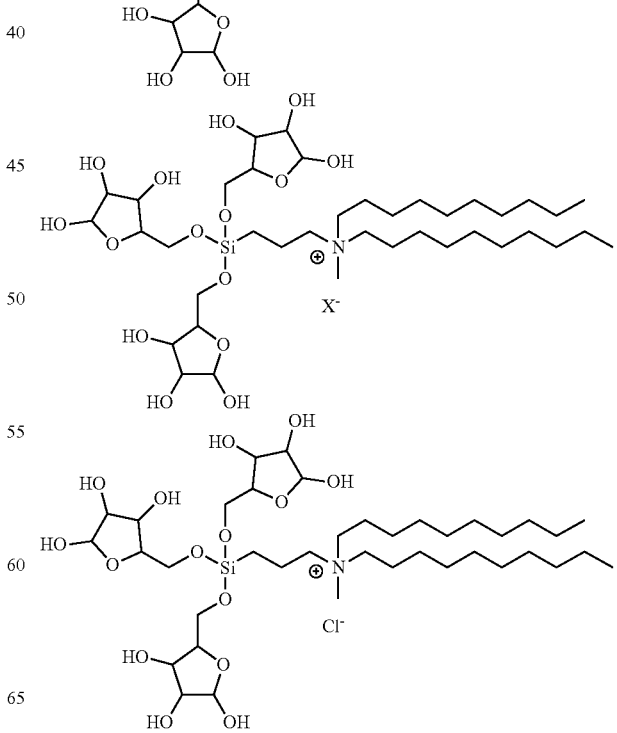

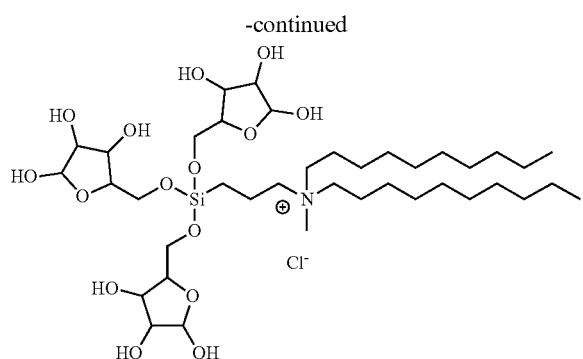
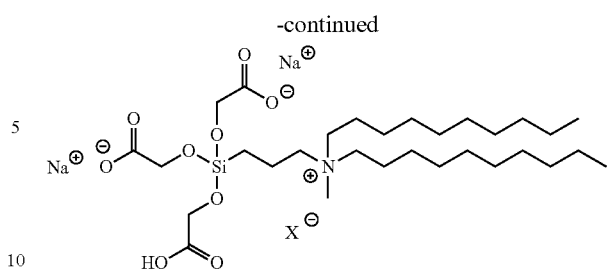
In certain embodiments the quaternary ammonium compound of the present invention is selected from:
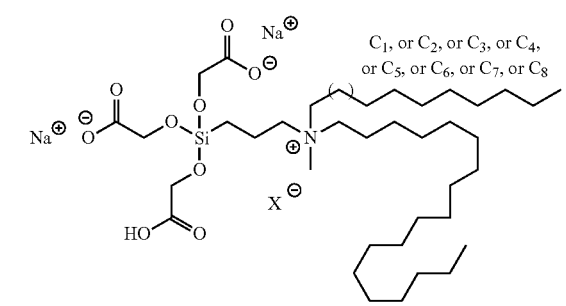
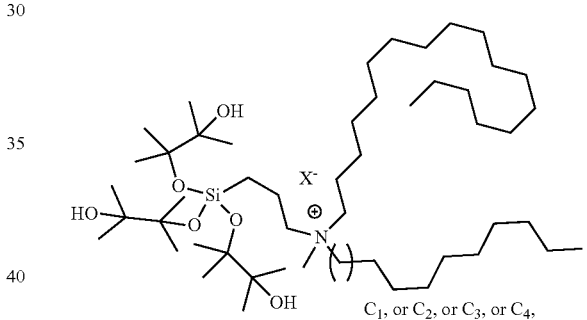
In certain embodiments the quaternary ammonium compound of the present invention is selected from:
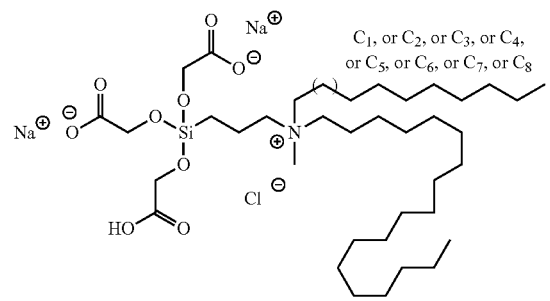
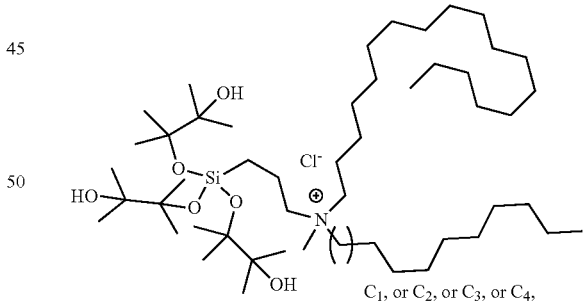
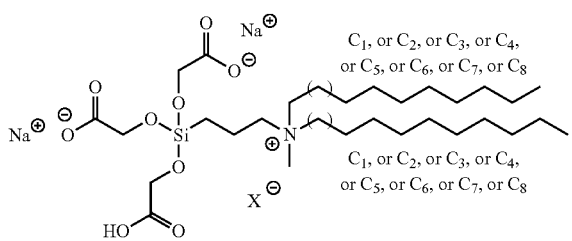
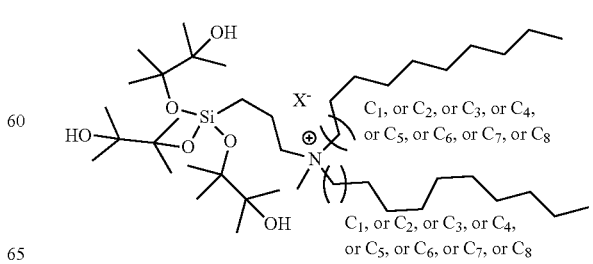
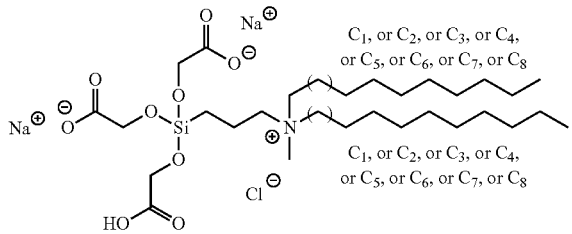

-continued
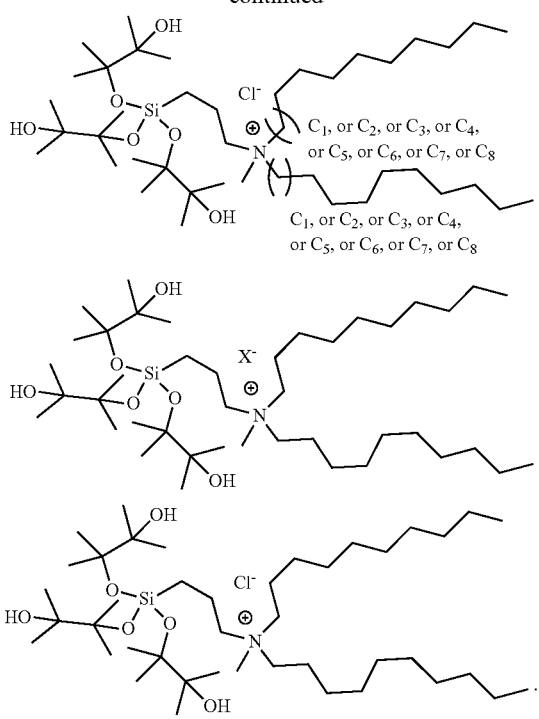
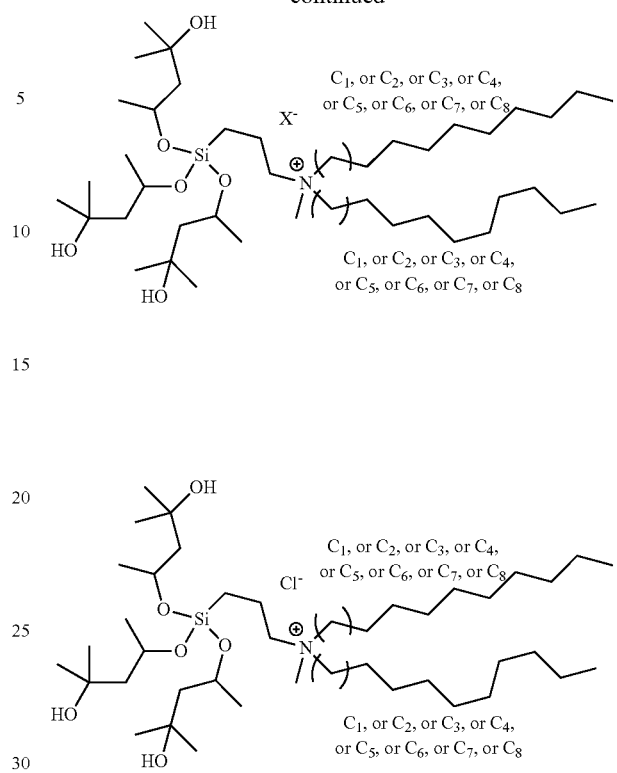
In certain embodiments the quaternary ammonium compound of the present invention is selected from:
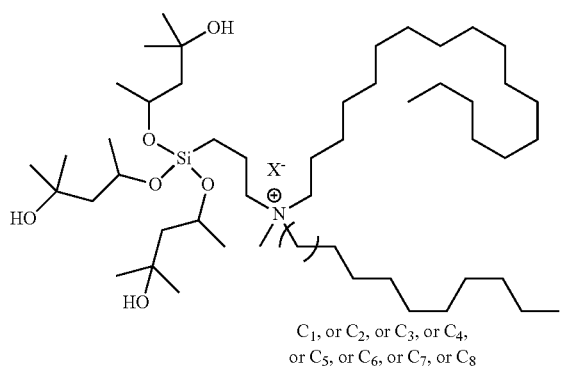
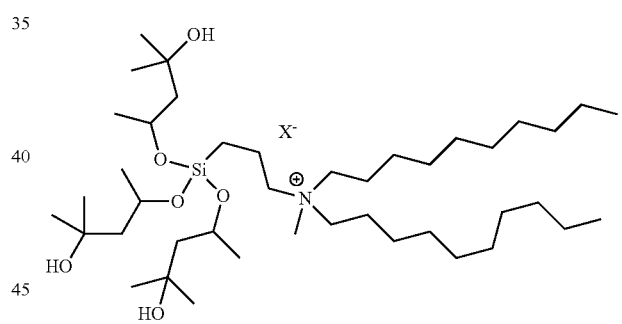
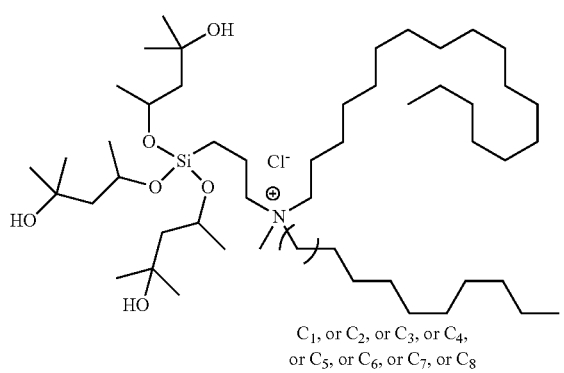
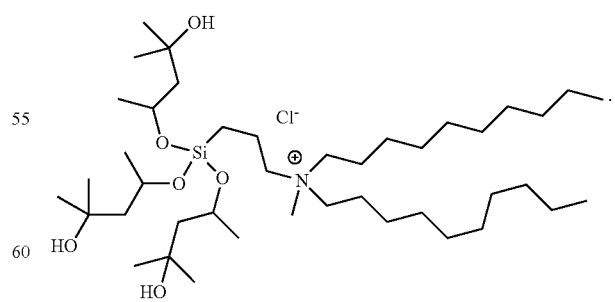
In certain embodiments the quaternary ammonium compound of the present invention is selected from:

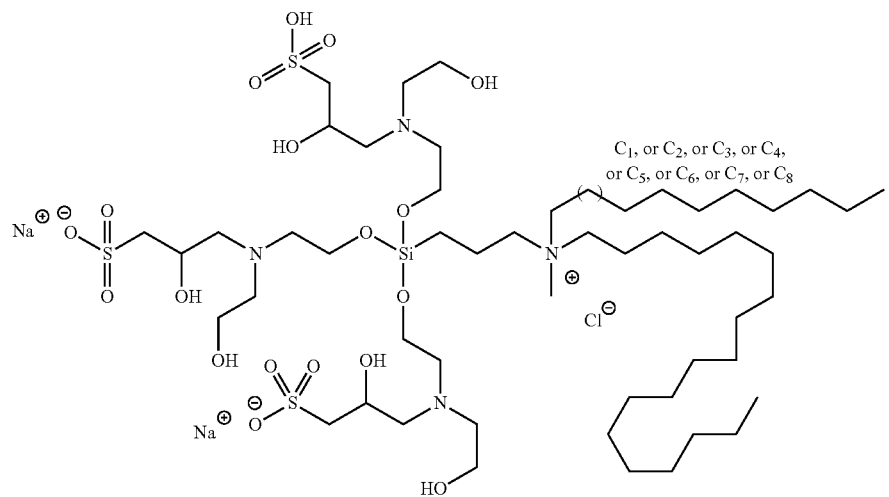
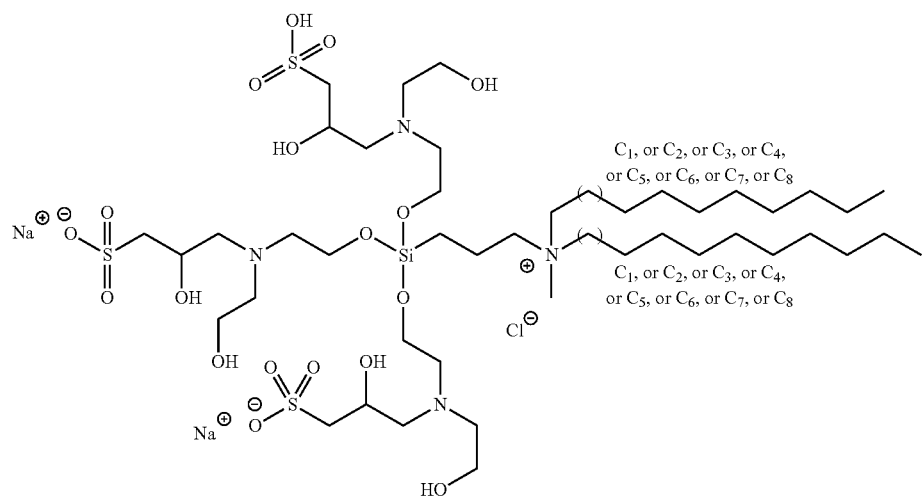
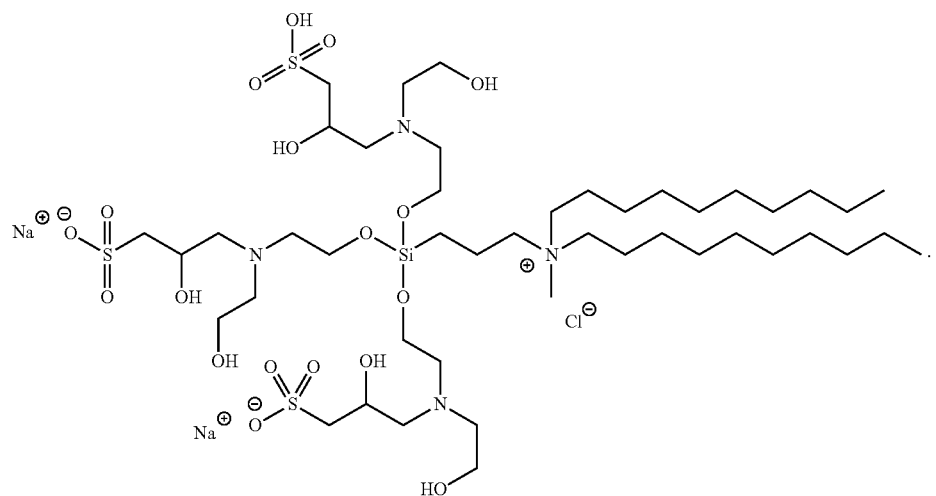
In certain embodiments the quaternary ammonium compound of the present invention is selected from:

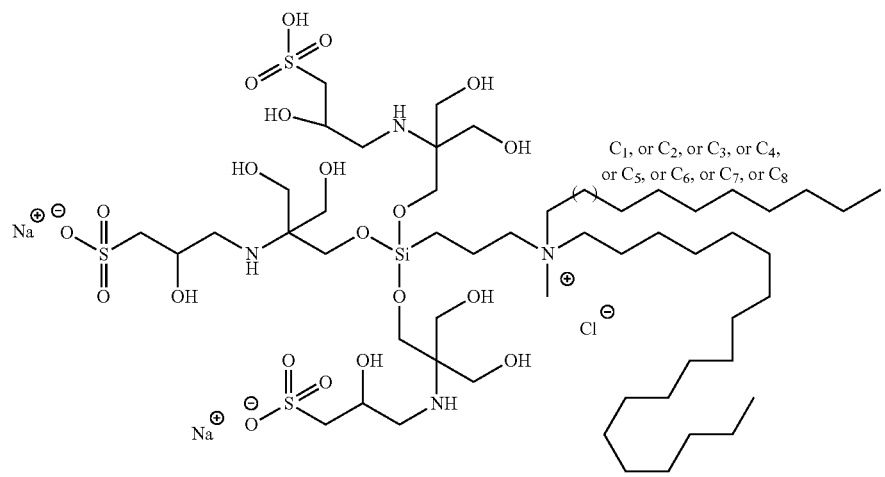
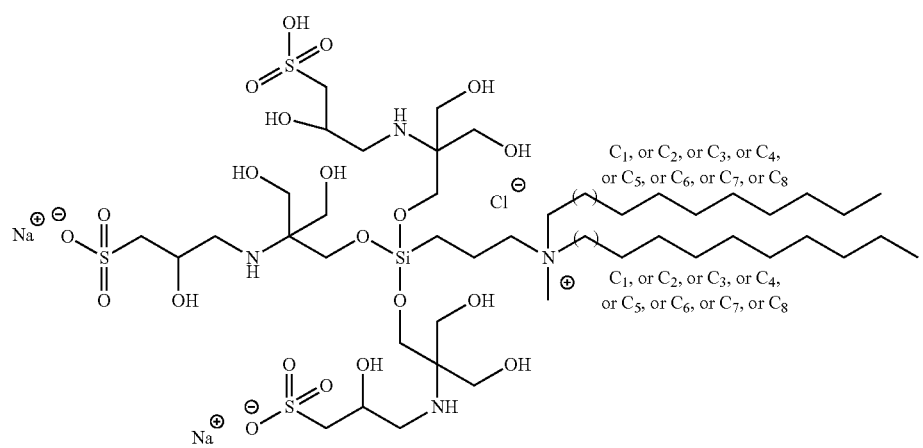
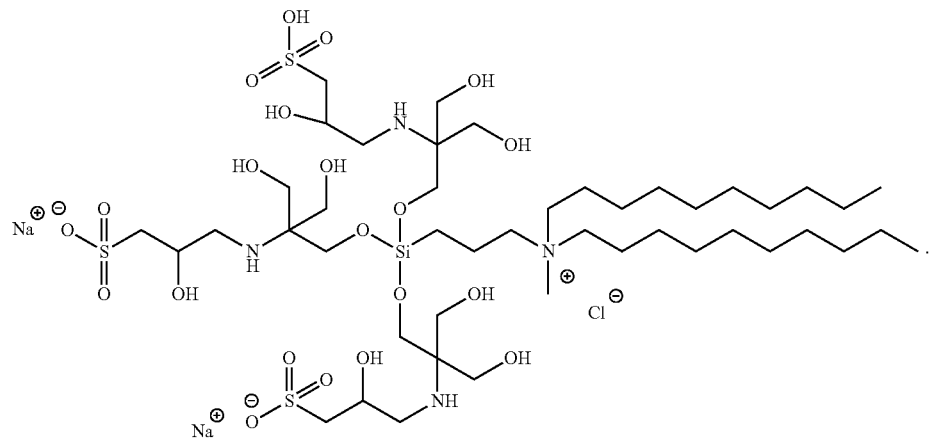
In certain embodiments the quaternary ammonium compound of the present invention is selected from:

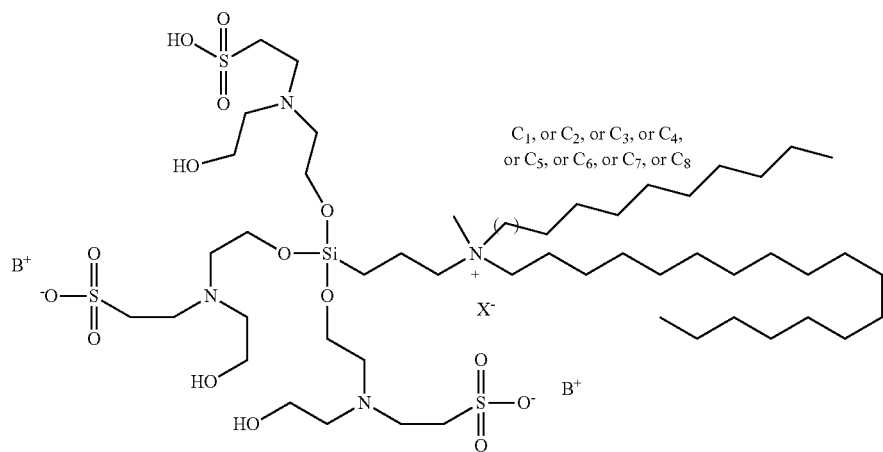
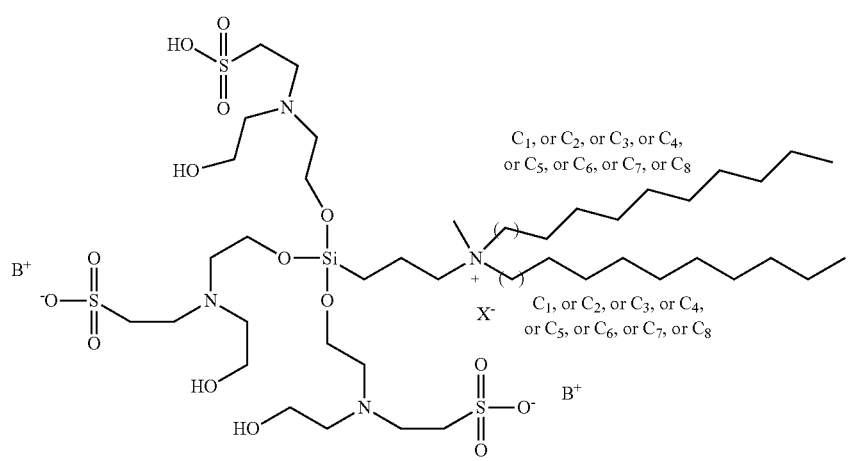
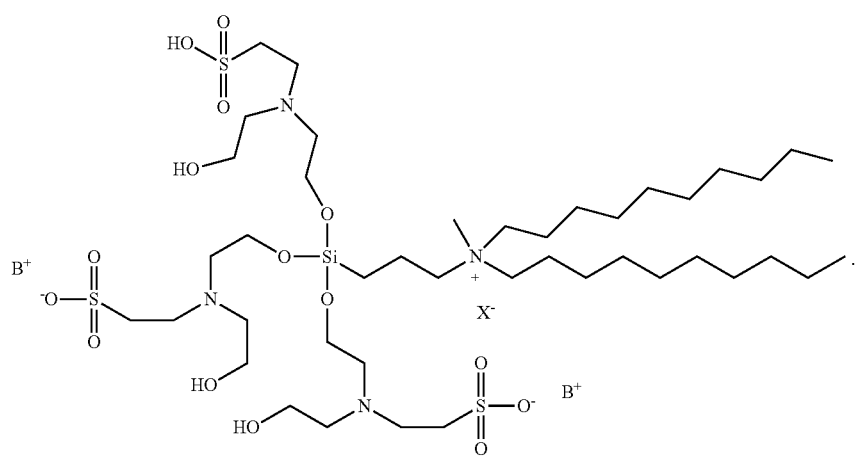
In certain embodiments the quaternary ammonium compound of the present invention is selected from:

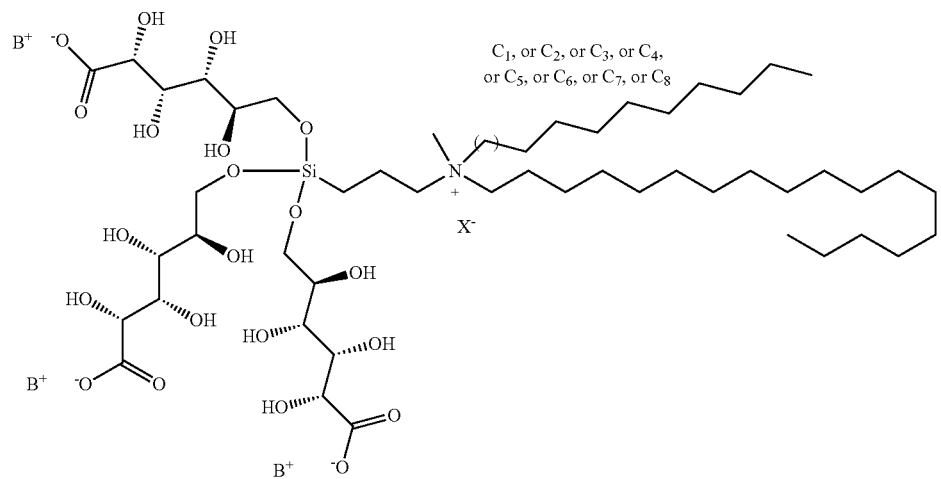
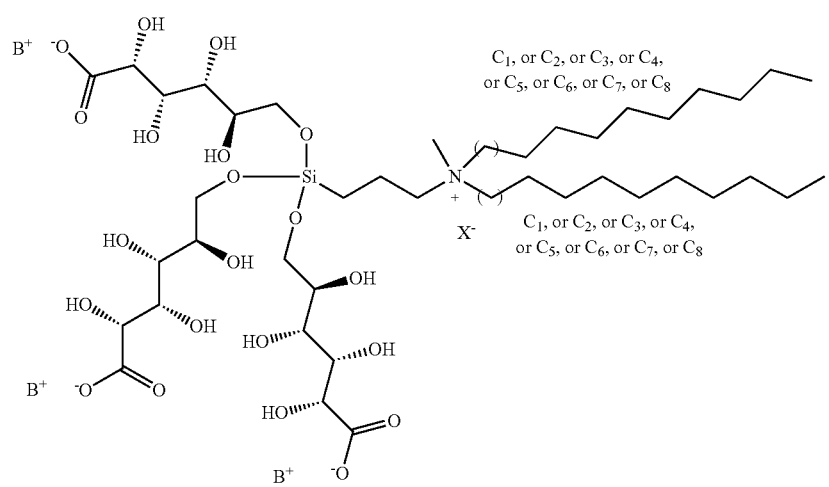
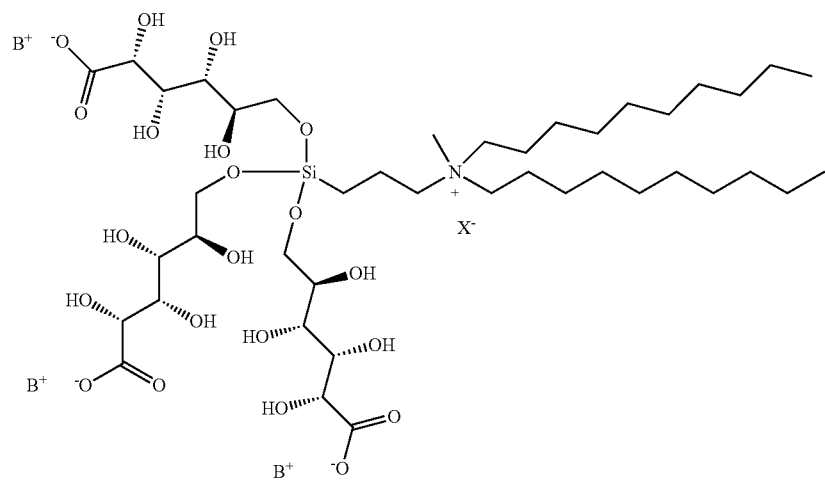

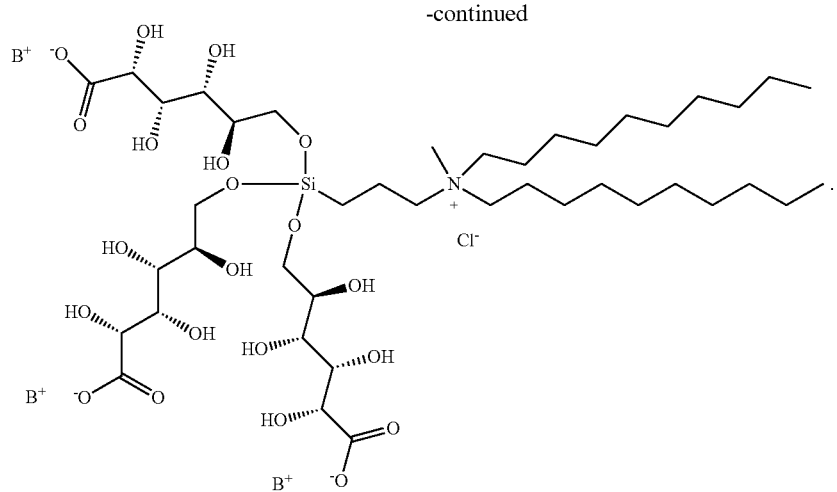

Mixtures

In certain embodiments a mixture of quaternary ammonium compounds is provided wherein the mixture comprises (1) 0.01 to 99.9% of a compound of the present invention; (2) 0.01 to 99.9% of an alkyl(C14, 50%, C12, 40%, C16, 10%) dimethyl benzyl ammonium chloride; and (3) 0.01 to 99.9% of a dioctyl dimethyl ammonium chloride; and any desired mixture of solvents with or without thickening agents (for example, guar gum or PVA).

In certain embodiments a mixture of quaternary ammonium compounds is provided wherein the mixture comprises (1) 0.01 to 99.9% of a compound of the present invention; (2) 0.01 to 99.9% of another compound of the present invention; (3) 0.01 to 99.9% of an alkyl(C14, 50%, C12, 40%, C16, 10%) dimethyl benzyl ammonium chloride; and (4) 0.01 to 99.9% of a dioctyl dimethyl ammonium chloride; and any desired mixture of solvents with or without thickening agents (for example, guar gum or PVA).

In certain embodiments a mixture of quaternary ammonium compounds is provided wherein the mixture comprises (1) 0.01 to 99.9% of a compound of Formula I; (2) 0.01 to 99.9% of a compound of Formula XII; (3) 0.01 to 99.9% of an alkyl(C14, 50%, C12, 40%, C16, 10%) dimethyl benzyl ammonium chloride; and (4) 0.01 to 99.9% of a dioctyl dimethyl ammonium chloride; and any desired mixture of solvents with or without thickening agents (for example, guar gum or PVA).

In certain embodiments a mixture of quaternary ammonium compounds is provided wherein the mixture comprises (1) 0.01 to 99.9% of a compound of the present invention; and (2) 0.01 to 99.9% of another compound of the present invention; and any desired mixture of solvents with or without thickening agents (for example, guar gum or PVA).

In certain embodiments a mixture of quaternary ammonium compounds is provided wherein the mixture comprises (1) 0.01 to 99.9% of a compound of Formula I; and (2) 0.01 to 99.9% of another compound of the present invention; and any desired mixture of solvents with or without thickening agents (for example, guar gum or PVA).

In certain embodiments a mixture of quaternary ammonium compounds is provided wherein the mixture comprises (1) 0.01 to 99.9% of a compound of Formula I; and (2) 0.01 to 99.9% of a compound of Formula XII; and any desired mixture of solvents with or without thickening agents (for example, guar gum or PVA).

In certain embodiments a mixture of quaternary ammonium compounds is provided wherein the mixture comprises (1) 0.01 to 99.9% of a compound of the present invention; and (2) 0.01 to 99.9% of an alkyl(C14, 50%, C12, 40%, C16, 10%) dimethyl benzyl ammonium chloride; and any desired mixture of solvents with or without thickening agents (for example, guar gum or PVA).

In certain embodiments a mixture of quaternary ammonium compounds is provided wherein the mixture comprises (1) 0.01 to 99.9% of a compound of the present invention; and (2) 0.01 to 99.9% of dodecyl dimethyl ammonium chloride; and any desired mixture of solvents with or without thickening agents (for example, guar gum or PVA).

In certain embodiments a mixture of quaternary ammonium compounds is provided wherein the mixture comprises (1) 0.01 to 99.9% of a compound of the present invention; and (2) 0.01 to 99.9% of dioctyl dimethyl ammonium chloride; and any desired mixture of solvents with or without thickening agents (for example, guar gum or PVA).

In certain embodiments one of the mixtures of components above is provided wherein the quaternary ammonium compound (1) is at a concentration between about 5% and 99%.

In certain embodiments one of the mixtures of components above is provided wherein the quaternary ammonium compound (1) is at a concentration between about 10% and 99%.

In certain embodiments one of the mixtures of components above is provided wherein the quaternary ammonium compound (1) is at a concentration between about 20% and 99%.

In certain embodiments one of the mixtures of components above is provided wherein the quaternary ammonium compound (1) is at a concentration between about 30% and 99%.

In certain embodiments one of the mixtures of components above is provided wherein the quaternary ammonium compound (1) is at a concentration between about 5% and 90%.

In certain embodiments one of the mixtures of components above is provided wherein the quaternary ammonium compound (1) is at a concentration between about 10% and 80%.

In certain embodiments one of the mixtures of components above is provided wherein the quaternary ammonium compound (1) is at a concentration between about 20% and 70%.

In certain embodiments one of the mixtures of components above is provided wherein the quaternary ammonium compound (1) is at a concentration between about 30% and 60%.

In certain embodiments one of the mixtures of components above is provided wherein the quaternary ammonium compound (1) is at a concentration between about 40% and 60%.

In certain embodiments one of the mixtures of components above is provided wherein the quaternary ammonium compound (2) is at a concentration between about 5% and 99%.

In certain embodiments one of the mixtures of components above is provided wherein the quaternary ammonium compound (2) is at a concentration between about 10% and 99%.

In certain embodiments one of the mixtures of components above is provided wherein the quaternary ammonium compound (2) is at a concentration between about 20% and 99%.

In certain embodiments one of the mixtures of components above is provided wherein the quaternary ammonium compound (2) is at a concentration between about 30% and 99%.

In certain embodiments one of the mixtures of components above is provided wherein the quaternary ammonium compound (2) is at a concentration between about 5% and 90%.

In certain embodiments one of the mixtures of components above is provided wherein the quaternary ammonium compound (2) is at a concentration between about 10% and 80%.

In certain embodiments one of the mixtures of components above is provided wherein the quaternary ammonium compound (2) is at a concentration between about 20% and 70%.

In certain embodiments one of the mixtures of components above is provided wherein the quaternary ammonium compound (2) is at a concentration between about 30% and 60%.

In certain embodiments one of the mixtures of components above is provided wherein the quaternary ammonium compound (2) is at a concentration between about 40% and 60%.

In certain embodiments one of the mixtures of components above is provided wherein the quaternary ammonium compound (3) is at a concentration between about 5% and 99%.

In certain embodiments one of the mixtures of components above is provided wherein the quaternary ammonium compound (3) is at a concentration between about 10% and 99%.

In certain embodiments one of the mixtures of components above is provided wherein the quaternary ammonium compound (3) is at a concentration between about 20% and 99%.

In certain embodiments one of the mixtures of components above is provided wherein the quaternary ammonium compound (3) is at a concentration between about 30% and 99%.

In certain embodiments one of the mixtures of components above is provided wherein the quaternary ammonium compound (3) is at a concentration between about 5% and 90%.

In certain embodiments one of the mixtures of components above is provided wherein the quaternary ammonium compound (3) is at a concentration between about 10% and 80%.

In certain embodiments one of the mixtures of components above is provided wherein the quaternary ammonium compound (3) is at a concentration between about 20% and 70%.

In certain embodiments one of the mixtures of components above is provided wherein the quaternary ammonium compound (3) is at a concentration between about 30% and 60%.

In certain embodiments one of the mixtures of components above is provided wherein the quaternary ammonium compound (3) is at a concentration between about 40% and 60%.

In certain embodiments one of the mixtures of components above is provided wherein the quaternary ammonium compound (4) is at a concentration between about 5% and 99%.

In certain embodiments one of the mixtures of components above is provided wherein the quaternary ammonium compound (4) is at a concentration between about 10% and 99%.

In certain embodiments one of the mixtures of components above is provided wherein the quaternary ammonium compound (4) is at a concentration between about 20% and 99%.

In certain embodiments one of the mixtures of components above is provided wherein the quaternary ammonium compound (4) is at a concentration between about 30% and 99%.

In certain embodiments one of the mixtures of components above is provided wherein the quaternary ammonium compound (4) is at a concentration between about 5% and 90%.

In certain embodiments one of the mixtures of components above is provided wherein the quaternary ammonium compound (4) is at a concentration between about 10% and 80%.

In certain embodiments one of the mixtures of components above is provided wherein the quaternary ammonium compound (4) is at a concentration between about 20% and 70%.

In certain embodiments one of the mixtures of components above is provided wherein the quaternary ammonium compound (4) is at a concentration between about 30% and 60%.

In certain embodiments one of the mixtures of components above is provided wherein the quaternary ammonium compound (4) is at a concentration between about 40% and 60%.

In certain embodiments the above concentrations are measured as mass of compound (1), (2), (3), or (4) divided by total mass of compound (1), (2), (3), or (4). In other embodiments the concentrations above are measured in mol/L as percent.

In certain embodiments a mixture described above is provided as a blend with another mixture described above.

Non-limiting examples of solvents include water, ethanol, saline, DMSO, glycol (for example propylene glycol).

Non-limiting examples of thickening, wetting, and/or gelling agents include guar gum, PVA, PVP, starch, and xanthan gum.

Methods for the Treatment of an Infection

The present invention includes a method for treating infections in a host with a quaternary ammonium compound or product described herein or a mixture thereof.

In some embodiments, the infection is treated directly with a solution containing one or more quaternary ammonium compounds of the present invention (typically reconstituted from a sterilized powder or solid).

In some embodiments, the infection is treated directly on a biotic surface with a solution containing one or more quaternary ammonium compounds of the present invention. Representative biotic surfaces include, but are not limited to any surface in the oral region, e.g. teeth, gingiva, gingival crevice, periodontal pocket, the otic region, e.g. outer ear, middle ear (tympanic cavity), inner ear (labyrinth), female reproductive tract (e.g. vagina, cervix, uterus, fallopian tubes), male reproductive tract (e.g. penis, scrotum, testicles, epididymis), anus, perineum, rectum, the peritoneum, prostate, urinary tract, vascular intima, conjunctiva, corneal tissue, the respiratory tract, lung tissue (e.g. bronchial and alveolial), heart valves, gastrointestinal tract, skin, scalp, nails and the surfaces of wounds, particularly chronic wounds, which may be topical or internal wounds.

Biofilms

Biofilms can develop in many environments, including on surfaces in healthcare settings, equipment and medical devices, and most importantly, on skin, ears, wounds, and other in vivo topical areas in humans and animals. These sessile microbial communities are profoundly different than that of their planktonic counterparts. While estimates vary, as many as 40% of the genes of a bacterium may undergo up or down regulation in the transition from the planktonic to the biofilm state in order to assume specialized functions (see Davies D. G., Parsek M. R., Pearson J. P., Iglewski B. H., Costerton J. W., Greenberg E. P. "The involvement of cell-to-cell signals in the development of a bacterial biofilm" Science. 1998, 280, 295-298; and Hall-Stoodley L., Costerton J. W., Stoodley P. "Bacterial biofilms: From the natural environment to infectious diseases" Nat. Rev. 2004, 2, 95-108). "What was once defined as the formation of a community of microorganisms attached to a surface has come to be recognized as a complex developmental process that is multifaceted and dynamic in nature." (see Kostakioti M., Hadjifrangiskou M., Hultgren, S. "Bacterial Biofilms: Development, Dispersal, and Therapeutic Strategies in the Dawn of the Postantibiotic Era" Cold Spring Harb Perspect Med 2013, 3:a010306. http://dx.doi.org/10.1101/cshperspect.a010306).

Up to 80% of human bacterial infections are associated with biofilms. Biofilm communities can cause "persistent infections [that are] resistant to conventional antimicrobial treatment and is today a major cause of treatment failure" (see Römling, U. Balsalobre, C. "Biofilm infections, their resilience to therapy and innovative treatment strategies." Journal of Internal Medicine, 2004, 272: 541-561). When microbial organisms form a biofilm in vivo, they can become resistant not only to antimicrobial drugs but also to the host's own immune defenses. Antibiotics designed to combat infections have been traditionally developed to kill planktonic bacteria under the assumption that these drugs would kill the same bacteria in different forms. However, the same bacterium is different in the biofilm state than in the planktonic state due to the dramatic shift in expression of genes. These changes in gene expression have emergent properties that are not predictable based on studies of planktonic cells alone. Bacteria protected within biofilms are up to one thousand times more resistant to antibiotics than they are in the planktonic form (see Rasmussen T B, Givskov M. Int J Med Microbiol. 2006, 296(2-3):149-161).

Clinically, biofilms are responsible for many common persistent and chronic infections in humans and animals due to their acquired and inherent resistance to antimicrobial agents and the selection for phenotypic variants. Such resistance tends to be multi-factorial, and biofilms typically include mixed fungal/bacterial species that may enhance rejection of antimicrobial agents. (see Flemming H.-C., Wingender J., Szewzyk U. Steinberg, P., Rice S. A., Kjelleberg, S. "Biofilms: An emergent form of bacterial life" Nature Reviews Microbiology 2016, 14:563-575; and Al-Fattani M. A and Douglas L. J. "Biofilm matrix of *Candida albicans* and *Candida tropicalis*: chemical composition and role in drug resistance" Journal of Medical Microbiology 2006; 55:999-1008).

Biofilms are often composed of several layers of cells. The layered nature of a biofilm causes uneven exposure to oxygen and nutrients by individual organisms, particularly for organisms present within deeper layers, leading to an environment that may produce altered metabolic activity. Often, the organisms in these deeper layers, known as "persister cells" are present in a quiescent state. These quiescent cells are often buttressed from chemical agents by the layers of cells above them and thus are exposed to lower quantities of treatment than those on the surface of the biofilm. For example, antibiotic efficacy often decreases for deeper layers of a biofilm due to cells in the upper layers consuming most of the antibiotic before it dissipates to lower layers, resulting in ineffective concentrations reaching the deeper layers (Römling and Balsalobre, 551). This phenomenon results in the incomplete elimination of a biofilm during many antimicrobial treatment regimens, resulting in the survival of resistant cells capable of recolonizing, and thus creating a situation of chronic or persistent infection (Musk, Jr. D. and Hergenrother, P. "Chemical Countermeasures for the Control of Bacterial Biofilms: Effective Compounds and Promising Targets" Current Medicinal Chemistry 2006, 13, 2163-2177).

By genetically encoding information identifying the antibiotics encountered, the persister cells enable the new colony to recognize and resist such treatment regimens in the future. This genetic information may be transferred and shared with other bacterium in several ways, such as by electrical signaling, conjugation, mutation and heterologous expression, thus exponentially expanding "antibiotic resistance" against a wide spectrum of available drugs and leading to the development of "superresistant" strains of pathogenic organisms (Davies, J and Davies, D. "Origins and Evolution of Antibiotic Resistance" Microbiology and Molecular Biology Reviews 2010, 417-433; and Humphries, J., Xiong, L., Liu, J., Prindle, A., Yuan, F., Arjes, H. A., Tsimring, L. and Gurol, S. "Species-Independent Attraction to Biofilms through Electrical Signaling" Cell 2017, 168, 200-209).

The formation and maintenance of mature biofilms are intimately linked to the production of an extracellular matrix. The multiple layers of cells and EPS may constitute a complex and compact structure within which biocides find it difficult to penetrate and reach internal layers, thus hampering their efficacy (see Bridier, et. al. "Resistance of bacterial biofilms to disinfectants: a review" Biofouling 2011, Vol. 27). Because biocides are often highly chemically reactive molecules, the presence of organic matter such as proteins, nucleic acids or carbohydrates can profoundly impair their efficacy, and potential interactions between antimicrobials and biofilm components may also contribute to their limited penetration into the biofilm.

"Each year in the US, over five million central venous catheters are placed and biofilm infection occurs in over 50% of these catheters. With about 100,000 deaths and $6.5 billion in excess expenditure annually in the United States alone." Id. Biofilms are also a significant problem with implant devices. "Fungal biofilms are largely resistant to known anti-fungal drugs." Id. "Removal of some of these devices . . . can be costly and, in some cases, dangerous to the patient, and the administration of high dose of anti-fungal agents . . . can result in further complications, including kidney and liver damage. Oftentimes, these treatments are not even possible, as many critically-ill patients are unable to tolerate them, leaving these patients with few available options and underscoring the need to find better therapeutic and diagnostic therapies to combat these biofilms." Id. Gulati, M. and Nobile, C., "*Candida albicans* biofilms: development, regulation, and molecular mechanisms." Microbes Infect 2016, 18(5), 310-321; Doi: 10.101/j.mocomf.2016.01.002). In certain embodiments, the compounds described herein are useful in the treatment, prevention or removal of biofilms.

Eye infections of the greatest frequency include red eyes, bacterial or viral conjunctivitis (pink eye), corneal ulcers, corneal keratitis, bacterial, fungal, herpal infectious keratitis, endophthalmitic, and blepharitis (lid infections). Conjunctivitis is the most common eye infection with viral conjunctivitis being the most common form. The most common causes of bacterial conjunctivitis are *Haemophilus influenza*, *Streptococcus pneumoniae* and *Staphylococcus aureus*. (Antibiotics versus placebo for acute bacterial conjunctivitis. Sheikh A, Hurwitz B., Cochrane Database Syst Rev. 2006 Apr. 19; (2):CD001211;) Both viral and bacterial conjunctivitis present with a red eye and are highly contagious. (https://www.ncbi.nlm.nih.gov/pmc/articles/PMC6003010/) Blepharitis is inflammation of the eyelids. It's a common cause of sore, red eyelids and crusty eyelashes. Lid margins can be infected due to bacterial or fungal infections, with accumulation forming a biofilm. Parasitic eyelash mites called *Demodex* feed on the biofilm, which in turn leads to an overgrowth of these mites that causes a worsening of the eyelid inflammation (https://www.alaboutvision.com/conditions/blepharitis.htm; https://www.reviewofoptometry.com/article/ro1117-could-eyelids-be-the-key-to-ded).

Bacterial infection is the most common cause of infectious keratitis. Common bacteria include *S. aureus*, coagulase-negative staphylococci, *S. pneumoniae* and *Pseudomonas aeruginosa*. (Sharma A, Taniguchi J. Review: Emerging strategies for antimicrobial drug delivery to the ocular surface: Implications for infectious keratitis. Ocul Surf 2017, 15, 670-9.; Green M, Apel A, Stapleton F. Risk factors and causative organisms in microbial keratitis. Cornea 2008, 27, 22-7) *P. aeruginosa* is the most common microorganism implicated in bacterial keratitis among contact lens wearers. *Acanthamoeba* is suspected if a patient has been swimming or in a spa while wearing contact lenses. (Stapleton F, Dart J K, Seal D V, Matheson M. Epidemiology of *Pseudomonas aeruginosa* keratitis in contact lens wearers. Epidemiol Infect 1995, 114, 395-402)

Dry eye syndrome or dry eye disease (DED), is one of the most common eye conditions worldwide. Often, dry eye is accompanied by an inflammation of the lid margins, and that may go relatively unnoticed as a cause rather than a result of dry eye. The blepharitis is often treated with ointment (erythromycin often) and that seems to help. There are suggestive 4 stages of dry eye syndrome. Stage 1 involves the lash follicles, where a biofilm can establish itself. Stage 2 involves both the lash follicles and the meibomian glands and may explain obvious vs. non-obvious meibominan gland dysfunction (MGD). Because the biofilm blocks the large meibomian gland orifices (a combination of biofilm and poor or altered meibum). Stage 2 takes longer to achieve. Stage 3 involves the follicles, meibomian glands and the accessory lacrimal glands of Krause and Wolfring. The distance, narrow ducts and constant tear flushing serve to protect these glands for decades, making them the last glands affected by biofilm formation. Stage 4 occurs when the structural integrity of the eyelid finally breaks down due to the chronic inflammation, which can for example manifest clinically as lid laxity, floppy eyelid syndrome, ectropion and entropion. (Rynerson J M, Perry H D. DEBS—a unification theory for dry eye and blepharitis. Clin Ophthalmol. 2016, 10, 2455-67; Baudouin C. Ocular surface and external filtration surgery: mutual relationships. Dev Ophthalmol. 2012, 50, 64-78; Baudouin C, Messmer E M, Aragona P, et al. Revisiting the vicious circle of dry eye disease: a focus on the pathophysiology of meibomian gland dysfunction. Br J Ophthalmol. 2016, 100(3)300-6).

Ear infections can occur in the outer ear canal (otitis externa), inner ear (otitis interna) or middle ear canal (otitis media). Most ear infections occur in the middle ear, when bacteria or virus grows, causing the accumulation of fluid, swelling, and inflammation. The infections can be chronic and generally due to biofilm accumulation. Recent clinical studies provide evidence that almost all chronic OM cases are accompanied by a bacterial biofilm behind the tympanic membrane (eardrum) and within the middle ear. Biofilms are typically very thin, and cannot be recognized using a regular otoscope. Otitis media (OM) is the most common illness in children in the United States with ¾ of children under the age of 3 having OM at least once. Even though most cases are chronic infections, long-term or permanent damage to the ear can still occur. Acute otitis media may clear in one to two weeks without treatment, or may need to be treated with antibiotics. About 50% of antibiotic prescriptions for children less than 3 years old are given for ear infections. However, in the case of chronic OM, antibiotics may no longer be helpful, surgery is usually required, to place a tympanostomy tube in the tympanic membrane of the middle ear. (https://biophotonics.illinois.edu/sites/default/files/BOE-LCI_Biofilms_0.pdf).

Vulvovaginal candidiasis occurs when *Candida* species superficially penetrate the mucosal lining of the vagina and cause an inflammatory response. The dominant inflammatory cells are typically polymorphonuclear cells and macrophages. Patients may present with discharge, which is typically thick and adherent, or with excoriations, "external" dysuria, vaginal itching, vaginal burning, dyspareunia, or swelling.

Periodontal or gum disease is a pathological inflammatory condition of the gum and bone support (periodontal tissues) surrounding the teeth. The two most common periodontal diseases are gingivitis which is the inflammation of the gum at the necks of the teeth, and periodontitis which is inflammation affecting the bone and tissues of the teeth.

Biofilms formed by pathogenic fungi have gained attention in recent years and several species among filamentous, yeast, and dimorphic fungi have been described as capable of developing into communities. Biofilms are sessile microbial communities that strongly adhere to surfaces and to each other and are protected by a polymeric extracellular matrix (ECM) composed primarily of polysaccharides. Cells here exhibit increased resistance and different phenotypes compared to planktonic or free cells and are associated with the persistence of infections. (Costa-Orlandi et al., "Fungal Biofilms and Polymicrobial Diseases", J. Fungi, 2017, 3, 22; doi:10.3390/jof3020022)

Candida species, including the novel opportunistic pathogen Candida dubliniensis, are now emerging as major agents of nosocomial infections. Many such manifestations of infections associated with the formation of Candida biofilms include those occurring on devices such as indwelling intravascular catheters. Fungal biofilm-associated infections are frequently refractory to conventional therapy because of resistance to antimicrobial agents.

Biofilm-associated Candida show uniform resistance to a wide spectrum of the currently available conventional antifungal agents, which implies that antimicrobial drugs that specifically target biofilm-associated infections are needed. The novel classes of antifungal agents, the lipid formulation of amphotericins, and the echinocandins have demonstrated unique antifungal activity against the resistant Candida biofilms, providing a breakthrough in the treatment of life-threatening invasive systemic mycoses. The use of drugs effective in combating biofilm-associated infections could lead to major developments in the treatment of fungal implant infection (Jabra-Rizk et al., "Fungal biofilm and Drug resistance." (2004). Fungal Biofilms and Drug Resistance, Emerging infectious diseases, 2004, 10, 14-9; 10.3201/eid1001.030119).

Pathogenic fungi can also adhere to abiotic surfaces such as prostheses and catheters; in particular, yeasts take advantage of this condition to gain access to blood circulation, reaching the internal organs of patients. This is alarming, as disseminated fungal infections have a high mortality rate. (Verstrepen K. J., Klis F. M. Flocculation, adhesion and biofilm formation in yeasts. Mol. Microbiol. 2006, 60, 5-15; doi: 10.1111/j.1365-2958.2006.05072.x)

Candida albicans is the most studied model of biofilm formation and shows distinct phases of development that are similar to those of bacterial biofilms. Paracoccidioides brasiliensis is a dimorphic fungus responsible for paracoccidioidomycosis, a systemic mycosis endemic in Latin America. Sardi et al. (Sardi Jde C., Pitangui Nde S., Voltan A. R., Braz J. D., Machado M. P., Fusco Almeida A. M., Mendes Giannini M. J. In vitro Paracoccidioides brasiliensis biofilm and gene expression of adhesins and hydrolytic enzymes. Virulence. 2015, 6, 642-651. doi: 10.1080/21505594.2015.1031437.) Histoplasma capsulatum biofilm was first described by Pitangui et al. This fungus also features thermal dimorphism and is the cause of histoplasmosis, a respiratory and systemic mycosis whose evolution depends on the survival and replication of yeast in alveolar macrophages (Pitangui N. S., Sardi J. C., Silva J. F., Benaducci T., Moraes da Silva R. A., Rodriguez-Arellanes G., Taylor M. L., Mendes-Giannini M. J., Fusco-Almeida A. M. Adhesion of Histoplasma capsulatum to pneumocytes and biofilm formation on an abiotic surface. Biofouling. 2012, 28, 711-718. doi: 10.1080/08927014.2012.703659).

Dermatophytes are fungi that invade keratinized tissues producing dermatophytosis, one of the most common dermatomycoses in human and animals (Weitzman I., Summerbell R. C. The dermatophytes. Clin. Microbiol. Rev. 1995, 8, 240-259. doi: 10.1016/50733-8635(05)70320-X). Among dermatophytosis, onychomycosis often relapses and involves long, sometimes ineffective treatment. Given this context and the hypothesis of Burkhart et al., which states that biofilm formation by dermatophytes can explain dermatophytomas, Costa-Orlandi et al., confirmed in vitro biofilm formation by two of the most prevalent species worldwide: Trichophyton rubrum and T. mentagrophytes (Burkhart C. N., Burkhart C. G., Gupta A. K. Dermatophytoma: Recalcitrance to treatment because of existence of fungal biofilm. J. Am. Acad. Dermatol. 2002, 47, 629-631. doi: 10.1067/mjd.2002.124699; Costa-Orlandi C. B., Sardi J. C., Santos C. T., Fusco-Almeida A. M., Mendes-Giannini M. J. In vitro characterization of Trichophyton rubrum and T. mentagrophytes biofilms. Biofouling. 2014, 30, 719-727. doi: 10.1080/08927014.2014.919282).

Candida auris is an emerging yeast that causes health-care-associated infections. It can be misidentified by laboratories and often is resistant to antifungal medications. We describe an outbreak of C. auris infections in healthcare facilities in New York City, N.Y., USA. (Adams et al., Candida auris in Healthcare Facilities, New York, USA, 2013-2017, Emerg Infect Dis. 2018, 24(10), 1816-1824. https://dx.org/10.3201/eid2410.180649). In another embodiment an infection is treated by applying a dressing comprising one or more quaternary ammonium compounds of the present invention as an antimicrobial composition to the site of infection, wherein the dressing releases one or more quaternary ammonium compounds of the present invention into the site of infection. The infection may involve the presence of bacteria, fungi, viruses, amoebas, or a combination of infectious species thereof.

Topical application also includes treatment of the oral cavity including the teeth and gums. Gingivitis occurs in both chronic and acute forms. Acute gingivitis is usually associated with specific infections, micro-organisms, or trauma. Chronic inflammation of the gum tissue surrounding the teeth is associated with the bacterial biofilm (plaque) that covers the teeth and gums. (https://www.dentalhealth.ie/dentalhealth/causes/periodontaldisease.html). The organosilicon quaternary ammonium compounds of the present invention may be used as oral healthcare agents, for example in the control of dental plaque, e.g. to remove it, or reduce it or to prevent, reduce or delay its development. They may also be used in the treatment and prevention of infections or infectious disease which may occur in the oral cavity, for example gingivitis and periodontitis. The organosilicon quaternary ammonium compounds of this invention may also be formulated as an ingredient in an oral healthcare agent (e.g. toothpaste) to prevent caries (tooth decay) and gingivitis.

Topical application also includes treatment of mouth/lip care, mouth ulcers and cold sores. Cold sores are contagious and strict hygiene measures should be adopted when a person is infected. Primary oral infection with the virus responsible for cold sores herpes simplex virus (HSV). After the primary oral infection, HSV may remain inactive only to be activated later as the more common herpes labialis, or "cold sores". Triggers for reactivation are well known and include sunlight, trauma, tiredness, stress, and menstruation. (https://www.dentalhealth.ie/dentalhealth/causes/cold-sores.html) The most common form of mouth ulcer is called minor aphthous ulceration. Usually one to five small ulcers appear (less than 1 mm in diameter) on the inside of lips or cheeks, floor of the mouth or tongue. The ulcers tend to be concentrated towards the front of the mouth. Other more serious causes of mouth ulcers include herpes infection (https://www.dentalhealth.ie/dentalhealth/causes/mouthulcers.html).

In some embodiments, treatment of an infection comprises placing a dressing comprising an antimicrobial composition as described herein in or on the site of infection.

In another embodiment, treatment of an infection comprises placing an antimicrobial composition containing one or more quaternary ammonium compounds of the present invention at the site of infection. The length of time that the quaternary ammonium compound, or composition is applied is such that antimicrobial treatment is still effective or the infection has resolved. The treatment may be applied continuously, with concurrent successive applications after an appropriate time frame, or in alternation with another treatment for the infection after an appropriate time frame. The quaternary ammonium compounds described herein may be applied at the site of infection in a host at the appropriate interval as determined by a healthcare provider.

In some embodiments, the quaternary ammonium compounds described herein are placed at the site of infection for a day or less. In other embodiments, the quaternary ammonium compounds described herein are placed at a site of infection for a week or more.

An effective amount of the antimicrobial composition as described herein, or the antimicrobial composition described herein in combination or alternation with, or preceded by, concomitant with or followed by another active pharmaceutical agent, can be used in an amount sufficient to inhibit the progression of disorder, for example an infection, caused by the presence of an infectious organism in or on a host; cause a regression of a disorder caused by the presence of an infectious organism in or on a host; cause a cure of a disorder caused by the presence of an infectious organism in or on a host; or inhibit or prevent the development of a disorder caused by the presence of an infectious organism near, in or on a host. The method of treatment can be administered once a day (q.d.), twice a day (b.i.d.), three times a day (t.i.d.), four times a day (q.i.d.), once every other day (Q2d), once every third day (Q3d), as needed, or using any dosing schedule that provides treatment of an infection as described herein.

In some embodiments, the method of treating and/or preventing an infection comprises placing a dressing saturated with the antimicrobial composition in the site of a wound and/or infection. The dressing may be saturated with the antimicrobial composition directly before placement into the site of a wound and/or infection or may be manufactured and packaged presaturated. In other embodiments, the method of treating and/or preventing an infection comprises placing a dressing in the site of a wound and/or infection followed by subsequent saturation of the dressing with the antimicrobial composition. The antimicrobial composition may be added after placement of the dressing by dropper, syringe, or other suitable means.

In some embodiments, one or more of the quaternary ammonium compounds, or pharmaceutical composition as described herein, are used to treat or to prevent a medical disorder which is mediated by the presence of a bacterium, for example a bacterial infection.

In some embodiments, the quaternary ammonium compounds of the present invention may be used to treat a disorder, typically an infection, caused by a pathogenic bacterium.

In some embodiments, a method is provided comprising administering an effective amount of a quaternary ammonium compound, or composition thereof described herein to a subject to treat an infection caused by a bacterium.

In some embodiments, one or more of the quaternary ammonium compounds of the present invention may be used to treat a disorder, typically an infection, caused by a gram-positive bacterium.

In some embodiments, a method is provided comprising administering an effective amount of a quaternary ammonium compound, or composition thereof as described herein to treat an infection caused by a gram-positive bacterium.

Non-limiting example of gram-positive bacteria which may be treated using the quaternary ammonium compounds of the present invention either alone or in combination with another therapeutic include: *Actinomyces* species including *Actinomyces israelii, Actinomyces naeslundii, Actinomyces viscosus, Actinomyces odontolyticus,* and *Actinomyces pyogenes; Bacillus* species including *Bacillus anthracis, Bacillus cereus,* and *Bacillus subtilis; Clostridium* species including *Clostridium botulinum, Clostridium difficile, Clostridium perfringens, Clostridium sordellii,* and *Clostridium tetani; Corynebacterium* species including *Corynebacterium diphtheriae, Corynebacterium jeikeium, Corynebacterium minutissimum, Corynebacterium mucifaciens, Corynebacterium pseudotuberculosis, Corynebacterium striatum, Corynebacterium tenuis,* and *Corynebacterium ulcerans; Enterococcus* species including *Enterococcus casseliflavus, Enterococcus faecalis, Enterococcus faecium, Enterococcus raffinosus,* and *Enterococcus hirae; Leuconostoc* species including *Leuconostoc pseudomesenteroides; Micrococcus* species such as *Micrococcus luteus; Nocardia* species including *Nocardia asteroides; Propionibacterium* species including *Propionibacterium acnes; Staphylococcus* species including *Staphylococcus aureus, Staphylococcus capitis, Staphylococcus epidermidis, Staphylococcus haemolyticus, Staphylococcus hominis, Staphylococcus lugdunensis, Staphylococcus pasteuri,* and *Staphylococcus saprophyticus;* and *Streptococcus* species including *Streptococcus agalactiae, Streptococcus anginosus, Streptococcus bovis, Streptococcus dysgalactiae, Streptococcus mitis, Streptococcus mutans, Streptococcus pneumoniae, Streptococcus pyogenes, Streptococcus sanguinis, Streptococcus suis,* and *Streptococcus viridans.*

In some embodiments, the quaternary ammonium compounds of the present invention may be used to treat a disorder, typically an infection, caused by a gram-negative bacterium.

In some embodiments, a method is provided comprising administering an effective amount of a quaternary ammonium compound, or composition thereof described herein to treat an infection caused by a gram-negative bacterium.

Non-limiting examples of gram-negative bacteria which may be treated using the quaternary ammonium compounds of the present invention either alone or in combination with another therapeutic include: *Acinetobacter* species including *Acinetobacter baumannii* and *Acinetobacter iwoffii; Aeromonas* species including *Aeromonas veronii* biovar *sobria* (previously *Aeromonas sobria*), *Aeromonas caviae,* and *Aeromonas hydrophila; Alcaligenes/Achromobacter* species including *Alcaligenes faecalis* and *Alcaligenes xylosoxidans; Bacteroides* species including *Bacteroides fragilis; Bartonella* species including *Bartonella bacilliformis, Bartonella clarridgeiae, Bartonella elizabethae, Bartonella henselae, Bartonella koehlerae, Bartonalla naantalienis, Bartonella quintana, Bartonella rochalimae, Bartonella vinsonii,* and *Bartonella washoensis; Bordetella* species including *Bordetella bronchispetica, Bordetella pertussis,* and *Bordetella parapertussis; Borrelia* species including *Borrelia afzelii, Borrelia burgdorferi, Borrelia crocidurae, Borrelia duttoni, Borrelia garinii, Borrelia hermsii, Borrelia hispanica, Borellia miyamotoi, Borrelia parkeri, Borrelia persica, Borrelia recurrentis, Borrelia turicatae,* and *Borrelia venezuelensis; Brevundimonas* species including *Brevundimonas diminuta* and *Brevundimonas vesicularis; Brucella* species including *Brucella abortus, Brucella canis,*

*Brucella melitensis*, and *Brucella suis*; *Burkholderia* species including *Burkholderia cepacia*, *Burkholderia mallei*, and *Burkholderia pseudomallei*; *Campylobacter* species including *Campylobacter jejuni*, *Campylobacter coli*, *Campylobacter upsaliensis*, *Campylobacter lari*, and *Campylobacter coli*; *Chlamydia/Chlamidophila* species including *Chlamydophila pneumoniae*, *Chlamydophila psittaci*, *Chlamidophila pecorum*, and *Chlamydia trachomatis*; *Citrobacter* species including *Citrobacter amalonaticus*, *Citrobacter freundii*, *Citrobacter koseri*, and *Citrobacter diversus*; *Coxiella burnetti*; *Ehrlichia* species including *Ehrlichia canis* and *Ehrlichia chaffeensis*; *Enterobacter* species including *Enterobacter aerogenes* and *Enterobacter cloacae*; *Escherichia* species including *Escherichia coli*; *Francisella* species including *Francisella novicida*, *Francisella philomiragia*, and *Francisella tularensis*; *Haemophilus* species including *Haemophilus influenzae* and *Haemophilus ducreyi*; *Helicobacter* species including *Helicobacter pylori*; *Klebsiella* species including *Klebsiella granulomatis*, *Klebsiella oxytoca*, and *Klebsiella pneumoniae*; *Leclercia adecarboxylata*; *Legionella* species including *Legionella pneumophila*; *Leptospira* species including *Leptospira interrogans*, *Leptospira noguchii*, *Leptospira santarosai*, and *Leptospira weilii*; *Listeria* species including *Listeria monocytogenes*; *Moraxella* species including *Moraxella catarrhalis*, *Moraxella lacunata*, and *Moraxella bovis*; *Moraxella bovoculi*; *Morganella* species including *Morganella morganii*; *Mycoplasma* species including *Mycoplasma amphoriforme*, *Mycoplasma buccale*, *Mycoplasma faucium*, *Mycoplasma fermentans*, *Mycoplasma genitalium*, *Mycoplasma hominis*, *Mycoplasma lipophilum*, *Mycoplasma orale*, *Mycoplasma penetrans*, *Mycoplasma pirum*, *Mycoplasma pneumoniae*, *Mycoplasma primatum*, *Mycoplasma salivarium*, and *Mycoplasma spermatophilum*; *Neisseria* species including *Neisseria meningitidis* and *Neisseria gonorrhoeae*; *Orientia* species including *Orientia tsutsugamushi* and *Orientia chuto*; *Pantoea* species including *Pantoea agglomerans*; *Paracoccus* species including *Paracoccus yeei*; *Prevotella* species including *Prevotella intermedia* and *Prevotella melaninogenica*; *Proteus* species including *Proteus mirabilis*, *Proteus penneri*, and *Proteus vulgaris*; *Providencia* species including *Providencia rettgeri* and *Providencia stuartii*; *Pseudomonas* species including *Pseudomonas aeruginosa*, *Pseudomonas oryzihabitans*, *Pseudomonas plecoglossidica*, and *Pseudomonas stutzeri*; *Ralstonia* species including *Ralstonia pickettii* and *Ralstonia insidiosa*; *Rickettsia* species including *Rickettsia africae*, *Rickettsia akari*, *Rickettsia australis*, *Rickettsia conorii*, *Rickettsia felis*, *Rickettsia japonica*, *Rickettsia prowazekii*, *Rickettsia rickettsia*, *Rickettsia sibirica*, and *Rickettsia typhi*; *Roseomonas* species including *Roseomonas gilardii*; *Salmonella* species including *Salmonella bongori*, *Salmonella enterica*, *Salmonella paratyphi*, *Salmonella typhi*, and *Salmonella typhimurium*; *Serratia* species including *Serratia marcescens*, *Serratia liquefaciens*, *Serratia rubidaea*, and *Serratia odoriferae*; *Shigella* species including *Shigella dysenteriae* and *Shigella sonnei*; *Sphingomonas* species including *Sphingomonas mucosissima* and *Sphingomonas paucimobilus*; *Stenotrophomas* species including *Stenotrophomas maltophilia*; *Treponema* species including *Treponema carateum*, *Treponema paraluiscuniculi*, and *Treponema pallidum*; *Ureaplasma* species including *Ureaplasma urealyticum*; *Vibrio* species including *Vibrio cholera*, *Vibrio parahaemolyticus*, and *Vibrio vulrifcus*; and *Yersinia* species including *Yersinia enterocolitica*, *Yersinia pestis*, and *Yersinia pseudotuberculosis*.

In some embodiments, the quaternary ammonium compounds of the present invention may be used to treat a disorder, typically an infection, caused by a *mycobacterium*.

In some embodiments, a method is provided comprising administering an effective amount of a quaternary ammonium compound, or composition thereof described herein to treat an infection caused by a *mycobacterium*.

Non-limiting examples of mycobacteria which may be treated using the quaternary ammonium compounds of the present invention either alone or in combination with another therapeutic include *Mycobacterium abcessus*, *Mycobacterium africanum*, *Mycobacterium agri*, *Mycobacterium aichiense*, *Mycobacterium alvei*, *Mycobacterium arabiense*, *Mycobacterium aromaticivorans*, *Mycobacterium arosiense*, *Mycobacterium arupense*, *Mycobacterium aquaticum*, *Mycobacterium asiaticum*, *Mycobacterium aubagnese*, *Mycobacterium aurum*, *Mycobacterium austroafricanum*, *Mycobacterium avium*, *Mycobacterium avium paratuberculosis*, *Mycobacterium avium silvaticum*, *Mycobacterium avium hominussuis*, *Mycobacterium bacteremicum*, *Mycobacterium barrassiae*, *Mycobacterium boenickei*, *Mycobacterium bohemicum*, *Mycobacterium bolletii*, *Mycobacterium botniense*, *Mycobacterium bovis*, *Mycobacterium branderi*, *Mycobacterium brisbanense*, *Mycobacterium brumae*, *Mycobacterium canariasense*, *Mycobacterium canettii*, *Mycobacterium caprae*, *Mycobacterium chimaera*, *Mycobacterium chelonae*, *Mycobacterium chitae*, *Mycobacterium chubuense*, *Mycobacterium colombiense*, *Mycobacterium conceptionense*, *Mycobacterium confluentis*, *Mycobacterium conspicuum*, *Mycobacterium cookii*, *Mycobacterium cosmeticum*, *Mycobacterium diernhoferi*, *Mycobacterium doricum*, *Mycobacterium duvalii*, *Mycobacterium elephantis*, *Mycobacterium fallax*, *Mycobacterium farcinogenes*, *Mycobacterium flavescens*, *Mycobacterium florentinum*, *Mycobacterium fortuitum*, *Mycobacterium frederikbergense*, *Mycobacterium gadium*, *Mycobacterium gastri*, *Mycobacterium genavense*, *Mycobacterium gilvum*, *Mycobacterium gordonae*, *Mycobacterium haemophilum*, *Mycobacterium hassiacum*, *Mycobacterium heidelbergense*, *Mycobacterium heckshornense*; *Mycobacterium hiberniae*, *Mycobacterium hodleri*, *Mycobacterium holsaticum*, *Mycobacterium houstonense*, *Mycobacterium icosiumassilensis*, *Mycobacterium immunogenum*, *Mycobacterium indicus pranii*, *Mycobacterium intacellulare*, *Mycobacterium intracellulare*, *Mycobacterium interjectum*, *Mycobacterium intermedium*, *Mycobacterium iranicum*, *Mycobacterium kansasii*, *Mycobacterium komossense*, *Mycobacterium kubicae*, *Mycobacterium lentiflavum*, *Mycobacterium leprae*, *Mycobacterium lepraemurium*, *Mycobacterium lepromatosis*, *Mycobacterium liflandii*, *Mycobacterium llatzerense*, *Mycobacterium madagascariense*, *Mycobacterium mageritense*, *Mycobacterium malmoense*, *Mycobacterium marinum*, *Mycobacterium massiliense*, *Mycobacterium massilipolynesiensis*, *Mycobacterium microti*, *Mycobacterium monacense*, *Mycobacterium montoorense*, *Mycobacterium morokaense*, *Mycobacterium mucogenicum*, *Mycobacterium mungi*, *Mycobacterium murale*, *Mycobacterium nebraskense*, *Mycobacterium neoaurum*, *Mycobacterium neworleansense*, *Mycobacterium nonchromogenicum*, *Mycobacterium obuense*, *Mycobacterium orygis*, *Mycobacterium palustre*, *Mycobacterium parascofulaceum*, *Mycobacterium parafortuitum*, *Mycobacterium perigrinum*, *Mycobacterium phlei*, *Mycobacterium phocaicum*, *Mycobacterium pinnipedii*, *Mycobacterium porcinum*, *Mycobacterium pseudoshottsii*, *Mycobacterium psychotolerans*, *Mycobacterium pulveris*, *Mycobacterium pyrenivorans*, *Mycobacterium saskatchewanense*, *Mycobacterium sedimi-* nis, *Mycobacterium senegalense, Mycobacterium septicum, Mycobacterium shimoidei, Mycobacterium shottsii, Mycobacterium simiae, Mycobacterium smegmatis, Mycobacterium sphagni, Mycobacterium stephanolepidis, Mycobacterium suricattae, Mycobacterium szulgai, Mycobacterium talmoniae, Mycobacterium terrae, Mycobacterium thermoresistibile, Mycobacterium triplex, Mycobacterium triviale, Mycobacterium tuberculosis, Mycobacterium tusciae, Mycobacterium ulcerans, Mycobacterium vaccae, Mycobacterium vanbaalenii, Mycobacterium xenopi*, and *Mycobacterium yongonense.*

Non-limiting examples of disorders mediated by a bacterium that may be treated by the quaternary ammonium compounds of the present invention, either alone or in combination with another therapeutic, include actinomycosis, anaplasmosis, anthrax, bacillary angiomatosis, actinomycetoma, bacterial conjunctivitis, bacterial pneumonia, bacterial vaginosis, bacterial endocarditis, bartonellosis, botulism, boutenneuse fever, brucellosis, bejel, brucellosis spondylitis, bubonic plague, Buruli ulcer, Bairnsdale ulcer, bacillary dysentery, campylobacteriosis, Carrion's disease, cat-scratch disease, cellulitis, chancroid, chlamydia, chlamydia conjunctivitis, clostridial myonecrosis, cholera, *Clostridium difficile* colitis, diphtheria, Daintree ulcer, donavanosis, dysentery, erhlichiosis, epidemic typhus, fried rice syndrome, five-day fever, floppy baby syndrome, Far East scarlet-like fever, gas gangrene, glanders, gonorrhea, granuloma inguinale, human necrobacillosis, necrotizing fasciitis, hemolytic-uremic syndrome, human ewingii ehrlichiosis, human monocytic ehrlichiosis, human granulocytic anaplasmosis, infant botulism, Izumi fever, Kawasaki disease, Kumusi ulder, lymphogranuloma venereum, Lemierre's syndrome, Legionellosis, leprosy, leptospirosis, listeriosis, Lyme disease, lymphogranuloma venereum, Malta fever, Mediterranean fever, myonecrosis, mycoburuli ulcer, mucocutaneous lymph node syndrome, meliodosis, meningococcal disease, murine typhus, *Mycoplasma* pneumonia, mycetoma, neonatal conjunctivitis, nocardiosis, Oroya fever, ophthalmia neonatorum, ornithosis, Pontiac fever, peliosis hepatis, pneumonic plague, postanginal shock including sepsis, pasteurellosis, pelvic inflammatory disease, pertussis, plague, pneumococcal infection, pneumonia, psittacosis, parrot fever, pseudotuberculosis, Q fever, quintan fever, rabbit fever, relapsing fever, rickettsialpox, Rocky Mountain spotted fever, rat-bite fever, Reiter syndrome, rheumatic fever, salmonellosis, scarlet fever, sepsis, septicemic plague, Searls ulcer, shigellosis, soft chancre, syphilis, streptobacillary fever, scrub typhus, Taiwan acute respiratory agent, Trench fever, trachoma, tuberculosis, tularemia, typhoid fever, typhus, tetanus, toxic shock syndrome, undulant fever, ulcus molle, *Vibrio parahaemolyticus* enteritis, Whitmore's disease, walking pneumonia, Waterhouse-Friderichsen syndrome, yaws, and yersiniosis.

In some embodiments, one or more of the quaternary ammonium compounds, or pharmaceutical composition as described herein, are used to treat or to prevent a medical disorder which is mediated by the presence of a fungus, for example a fungal infection.

In some embodiments, the quaternary ammonium compounds of the present invention may be used to treat a disorder, typically an infection, caused by a pathogenic fungus.

In some embodiments, a method is provided comprising administering an effective amount of a quaternary ammonium compound, or composition thereof described herein to a subject to treat an infection caused by a fungus.

Non-limiting examples of fungi which may be treated using the quaternary ammonium compounds of the present invention either alone or in combination with another therapeutic include: *Absidia* species including *Absidia corymbifera*; *Alterania* species including *Alterania alternate*; *Aspergillus* species including *Aspergillus clavatus, Aspergullus flavus, Aspergillus fumigatus, Aspergillus niger, Aspergillus sydowii, Aspergillus terreus, Aspergillus versicolor*, and *Aspergillus verrucaria*; *Aureobasidium* species including *Aureobasidium pullans*; *Batrachochytrium* species including *Batrachochytrium dendrobatidis* and *Batrachochytrium salamandrivorans*; *Blastomyces* species including *Blastomyces dermatitidis*; *Candida* species including *Candida albicans, Candida auris, Candida dubliniensis, Candida glabrata, Candida parapsilosis, Candida rugosa*, and *Candida tropicalis*; *Chaetomium* species including *Chaetomium globsum*; *Cladosporium* species including *Cladosporium cladosporoides*; *Coccidioides* species including *Coccidioides immitis* and *Coccidioides posadasii*; *Cryptococcus* species including *Cryptococcus albidus, Cryptococcus gattii, Cryptococcus laurentii, Cryptococcus neoformans*, and *Cryptococcus uniguttulatus*; *Cunninghamella* species; *Curvularia* species including *Curvularia brachyspora, Curvularia clavata, Curvularia geniculata, Curvularia lunata, Curvularia pallescens, Curvularia senegalensis*, and *Curvularia verruculosa*; *Dreschslera* species including *Drechslera australiensis*; *Epidermophyton* species including *Epidermophyton floccosum*; *Fonsecaea* species including *Fonsecaea compacta* and *Fonsecaea pedrosoi*; *Fusarium* species including *Fusarium solani, Fusarium oxysporum*, and *Fusarium chlamydosporum, Geotrichum* species including *Geotrichum capitatum, Geotrichum candidum*, and *Geotricum clavatum*; *Gliomastix* species including *Gliomastix cerealis*; *Gloeophyllum* species including *Gloeophyllum trabeum*; *Histoplasma* species including *Histoplasma capsulatum* and *Histoplasma capsulatum* var. *faciminosum*; *Malassezia* species including *Malassezia furfur* and *Malassezia globosa*; *Microsporum* species; *Monilia* species including *Monilia grisea*; *Mucor* species including *Mucor indicus*; *Paracoccidioides* species including *Paracoccidioides brasiliensis*; *Penicillium* spcies; *Piedraia* species including *Piedraia hortae* and *Piedraia quintanilhae*; *Phialophora* species including *Phialophora verrucosa*; *Phoma* species including *Phoma fimeti*; *Pithomyces* species including *Pithomyces chartarum*; *Pneumocystis* species including *Pneumocystis carinii* and *Pneumocystis jirovecii*; *Poria* species including *Poria placenta*; *Rhizopus* species including *Rhizopus microspores, Rhizopus oryzae*, and *Rhizopus stolonfer*; *Scolecobasidium* species including *Scolecobasidium humicola*; *Sporothrix* species including *Sporothrix brasiliensis, Sporothrix globosa*, and *Sporothrix schenckii*; and *Trichoderma* species including *Trichoderma viride*; and *Trichophyton* species including *Trichosporon beigelii, Trichophyton concentricum, Trichophyton interdigitale, Trichophyton mentagrophytes, Trichophyton rubrum*, and *Trichophyton tonsurans*.

Non-limiting examples of disorders mediated by a fungus that may be treated by the quaternary ammonium compounds of the present invention, either alone or in combination with another therapeutic, include invasive aspergillosis, black piedra, blastomycosis, oropharyngeal candidiasis, vulvovaginal candidiasis, chromoblastomycosis, chytridiomycosis, coccidioimycosis, cryptococcosis, dermatophytosis, fusariosus, geotrichosis, histoplasmosis, mucormycosis, mycetoma, paracoccidioidomycosis, pneumocystis pneumonia, sporotrichosis, *Tinea barbae, Tinea*

*capitis, Tinea corporis, Tinea cruris, Tinea manum, Tinea nigra, Tinea unguium, Tinea versicolor*, white piedra, and zygomycosis.

In some embodiments, the quaternary ammonium compounds of the present invention may be used to treat a disorder, typically an infection, caused by a virus.

In some embodiments, a method is provided comprising administering an effective amount of a quaternary ammonium compound, or composition thereof described herein to treat an infection caused by a virus.

Non-limiting examples of viruses which may be treated using the quaternary ammonium compounds of the present invention either alone or in combination with another therapeutic include: Adeno-associated virus, Astrovirus, BK polyomavirus, Cosavirus A, Coxsackie virus, Echovirus, Epstein-Barr virus, GB virus C, Human adenovirus, Human coronavirus, Human cytomegalovirus, Human herpesvirus (1, 2, 6, 7, and 8), Human papillomavirus (1, 2, 16, and 18), Human parainfluenza, Human parvovirus, Human respiratory syncytial virus, Human rhinovirus, Human SARS coronavirus, Influenza virus (A, B, and C), *Molluscum contagiosum* virus, Norovirus, Rotavirus (A, B, and C), Rubella virus, SARS coronavirus 2, Vaccinia virus, and Varicella-zoster virus.

Non-limiting examples of disorders mediated by a virus that may be treated by the quaternary ammonium compounds of the present invention, either alone or in combination with another therapeutic, include flu, common cold, respiratory syncytial virus infection, adenovirus infection, parainfluenza virus infection, severe acute respiratory syndrome (SARS), norovirus infection, rotavirus infection, astrovirus infection, measles, rubella, chickenpox/shingles, roseola, smallpox, fifth disease, human papillomavirus (HPV), warts, including genital warts, oral herpes, genital herpes, herpes labialis, herpes simplex virus keratitis, and *Molluscum contagiosum*.

In some embodiments, one or more of the quaternary ammonium compounds, or pharmaceutical composition as described herein, are used to treat or to prevent a medical disorder which is mediated by the presence of amoeba, for example an amoebal infection.

In some embodiments, the quaternary ammonium compounds of the present invention may be used to treat a disorder, typically an infection, caused by a pathogenic amoeba.

In some embodiments, a method is provided comprising administering an effective amount of a quaternary ammonium compound, or composition thereof described herein to a subject to treat an infection caused by an amoeba.

Non-limiting examples of amoeba which may be treated using the quaternary ammonium compounds of the present invention either alone or in combination with another therapeutic include: *Acanthamoeba* species; *Balamuthia* species including *Balamuthia mandrillaris; Dientamoeba* species including *Dientamoeba fragilis; Endolimax* species including *Endolimax nana; Entamoeba* species including *Entamoeba* Bangladeshi, *Entamoeba coli, Entamoeba dispar, Entamoeba gingivalis, Entamoeba hartmanni, Entamoeba histolytica, Entamoeba moshkovskii*, and *Entamoeba polecki; Iodamoeba* species including *Iodamoeba butschlii; Naegleria* species including *Naegleria fowleri*; and *Sappinia* species including *Sappinia diploidea* and *Sappinia pedata*.

Non-limiting examples of disorders mediated by an amoeba that may be treated by the quaternary ammonium compounds of the present invention, either alone or in combination with another therapeutic, include amoebiasis, amoebic dysentery, amoebic liver abscess, cutaneous amoebiasis, amoebic brain abscess, amebiasis cutis, *Acanthamoeba keratitis*, cutaneous acanthamoebiasis, granulomatous amoebic encephalitis, *Balamuthia* amoebic encephalitis, and *Sappinia* amoebia encephalitis.

In some embodiments, the infection is caused by *Acinetobacter* species, *Aspergillus* species, *Burkholderia cepacia* complex, *Campylobacter* species, *Candida* species, *Clostridium difficile, Coccidioides species, Cryptococcus* species, Enterobacteriaceae, *Enterococcus* species, *Helicobacter pylori, Mycobacterium tuberculosis* complex, *Neisseria gonorrhoeae, Neisseria meningitidis*, Non-tuberculous mycobacteria species, *Pseudomonas* species, *Staphylococcus aureus, Streptococcus agalactiae, Streptococcus pneumoniae, Streptococcus pyogenes*, and *Vibrio cholerae*.

In certain alternative embodiments, the infection is caused by *Staphylococcus aureus. Pseudomonas aeruginosa, Streptococcus pyogenes, Candida albicans, Candida auris, Cladosporium herbarum, Aspergillus niger, Proteus mirabilis, Klebsiella pneumoniae, Acinetobacter baumanii*, an *Enterobacter* spp. or a *Fusarium* spp.

In some embodiments, the quaternary ammonium compounds of the present invention may be used to treat an inflammatory disorder caused by the presence of an infectious organism, for example a bacterium, a fungus, a virus, or an amoeba as described herein.

Non-limiting examples of such inflammatory disorders include adenoiditis, appendicitis, arteritis, ascending cholangitis, balanitis, blepharitis, bronchitis, bursitis, cellulitis, cerebral vasculitis, cervicitis, chemosis, cholecystitis, chondritis, choroioamnionitis, colitis, conjunctivitis, constrictive pericarditis, cryptitis, dacryoadenitis, dermatitis, diabetic ulcer, duodenal lymphocytosis, encephalitis, endocarditis, endometritis, endotheliitis, enteritis, enterocolitis, eosinophilis fasciitis, epididymitis, esophagitis, folliculitis, gastritis, gingivitis, glomerulonephritis, glossitis, hepatitis, infectious arthritis, ileitis, intertrigo, keratitis, keratoconjunctivitis, labyrithitis, lymphadenitis, mastitis, mastoiditis, myocarditis, myopericarditis, myositis, necrotizing fasciitis, nephritis, omaphalitis, oophoritis, ophthalmitis, orchitis, osteitis, osteomyelitis, pancreatitis, paraproctitis, parotitis, pericarditis, perichondritis, perifolliculitis, periodontitis, peritonitis, pharyngitis, phlebitis, pleurisy, pneumonitis, pulmonitis, proctitis, prostatitis, pulpitis, pyelonephritis, pyomyositis, retinal vasculitis, rheumatic fever, rhinitis, scleritis, salpingitis, sialadenitis, sinusitis, stomatitis, synovitis, septicemia, tenosynovitis, thyroiditis, tonsillitis, tularemia, urethritis, uveitis, vaginitis, vasculitis, and vulvitus.

In some embodiments, the quaternary ammonium compounds of the present invention used to treat a skin infection in a host, for example a human. The infection may be caused by a bacterium, a fungus, an amoeba, or a virus as described herein.

In some embodiments, a method is provided comprising administering an effective amount of a quaternary ammonium compound, or composition thereof described herein to a host, for example a human, to treat a skin infection.

In another embodiment, the method is used to treat a skin infection in another mammal, for example a cat, a dog, a cow, a pig, or a horse.

Examples of bacterial cutaneous infections that may be treated by the quaternary ammonium compounds of the present invention include, but are not limited to: acne vulgaris, African tick bite fever; American tick bite fever (*Rickettsia parkeri* infection); Bacillary angiomatosis; Bejel (endemic syphilis); Blastomycosis-like pyoderma (pyoderma vegetans); Blistering distal dactylitis; Botryomycosis;

Brill-Zinsser disease; Brucellosis (Bang's disease, Malta fever, undulant fever); Bubonic plague; Bullous impetigo; *Campylobacter jejuni*; Cat scratch disease (cat scratch fever, English-Wear infection, inoculation lymphoreticulosis, subacute regional lymphadenitis); Cellulitis; Chancre; Chancroid (soft chancre, ulcus molle); Chronic lymphangitis; Chronic recurrent erysipelas; Chronic undermining burrowing ulcers (Meleney gangrene); Condylomata lata; Cutaneous actinomycosis; Dermatitis gangrenosa (gangrene of the skin); Ecthyma; Ecthyma gangrenosum; Elephantiasis nostras; Endemic typhus (murine typhus); Epidemic typhus (epidemic louse-borne typhus); Erysipelas (ignis sacer, Saint Anthony's fire); Erysipeloid of Rosenbach; *Erythema marginatum*; Erythrasma; Felon; Flea-borne spotted fever; Flinders Island spotted fever; Flying squirrel typhus; Folliculitis; Fournier gangrene (Fournier gangrene of the penis or scrotum); Furunculosis (boil); Gas gangrene (clostridial myonecrosis, myonecrosis); Glanders (equinia, farcy, malleus); Gonococcemia (arthritis-dermatosis syndrome, disseminated gonococcal infection); Gonorrhea (clap); Gram-negative folliculitis; Gram-negative toe web infection; Granuloma inguinale (Donovanosis, granuloma genitoinguinale, granuloma inguinale tropicum, granuloma venereum, granuloma venereum genitoinguinale, lupoid form of groin ulceration, serpiginous ulceration of the groin, ulcerating granuloma of the pudendum, ulcerating sclerosing granuloma); Green nail syndrome; Hospital furunculosis; Hot tub folliculitis (*Pseudomonas aeruginosa* folliculitis); Human granulocytotropic anaplasmosis; Human monocytotropic ehrlichiosis; Impetigo contagiosa; Japanese spotted fever; Leptospirosis (Fort Bragg fever, pretibial fever, Weil's disease); Listeriosis; Ludwig's angina; Lupoid sycosis; Lyme disease (Afzelius' disease, Lyme borreliosis); Lymphogranuloma venereum (climatic bubo, Durand-Nicolas-Favre disease, lymphogranuloma inguinale, poradenitis inguinale, strumous bubo); Malakoplakia (malacoplakia); Mediterranean spotted fever (Boutonneuse fever); Melioidosis (Whitmore's disease); Meningococcemia; Missouri Lyme disease; Necrotizing fasciitis (flesh-eating bacteria syndrome); Neonatal toxic shock-like exanthematous disease; Noma neonatorum; North Asian tick typhus; Ophthalmia neonatorum; Oroya fever (Carrion's disease); Perianal cellulitis (perineal dermatitis, streptococcal perianal disease); Periapical abscess; Pinta; Pitted keratolysis (keratolysis plantare sulcatum, keratoma plantare sulcatum, ringed keratolysis); Plague; Primary gonococcal dermatitis; Pseudomonal Pyoderma; *Pseudomonas* hot-foot syndrome; Pyogenic paronychia; Pyomyositis; Q fever; Queensland tick typhus; Rat-bite fever; Recurrent toxin-mediated perineal erythema; Rhinoscleroma; Rocky Mountain spotted fever; Scarlet fever; Scrub typhus (Tsutsugamushi fever); Shigellosis; Staphylococcal scalded skin syndrome (pemphigus neonatorum, Ritter's disease); Streptococcal intertrigo; Superficial pustular folliculitis (impetigo of Bockhart, superficial folliculitis); Sycosis vulgaris (barber's itch, sycosis barbae); Syphilid; Syphilis (lues); Tick-borne lymphadenopathy; Toxic shock syndrome (streptococcal toxic shock syndrome, streptococcal toxic shock-like syndrome, toxic streptococcal syndrome); Trench fever (five-day fever, quintan fever, urban trench fever); Tropical ulcer (Aden ulcer, jungle rot, Malabar ulcer, tropical phagedena); Tularemia (deer fly fever, Ohara's disease, Pahvant Valley plague, rabbit fever); Verruga peruana; and Yaws (bouba, frambosie, parangi, pian).

Examples of mycobacterial cutaneous infections that may be treated by the quaternary ammonium compounds of the present invention include, but are not limited to: Aquarium granuloma (fish-tank granuloma, swimming-pool granuloma); Borderline lepromatous leprosy; Borderline leprosy; Borderline tuberculoid leprosy; Buruli ulcer (Bairnsdale ulcer, Searl ulcer, Searle's ulcer); *Erythema induratum* (Bazin disease); Histoid leprosy; Lepromatous leprosy; Leprosy (Hansen's disease); Lichen scrofulosorum (tuberculosis cutis lichenoides); *Lupus vulgaris* (tuberculosis luposa); Miliary tuberculosis (disseminated tuberculosis, tuberculosis cutis acuta generalisata, tuberculosis cutis disseminata); Papulonecrotic tuberculid; Primary inoculation tuberculosis (cutaneous primary complex, primary tuberculous complex, tuberculous chancre); Scrofuloderma (tuberculosis cutis colliquativa); *Tuberculosis cutis* orificialis (acute tuberculous ulcer, oriﬁcial tuberculosis); *Tuberculosis verrucosa* cutis (*Lupus verrucosus*, prosector's wart, warty tuberculosis); Tuberculous cellulitis; Tuberculous gumma (metastatic tuberculous abscess, metastatic tuberculous ulcer); and Tuberculoid leprosy.

Examples of fungal cutaneous infections that may be treated by the quaternary ammonium compounds of the present invention include, but are not limited to: African histoplasmosis; Alternariosis; Antibiotic candidiasis (iatrogenic candidiasis); Black piedra; *Candida auris*, Candidal intertrigo; Candidal onychomycosis; Candidal paronychia; Candidal vulvovaginitis; Candidid; Chromoblastomycosis (chromomycosis, cladosporiosis, Fonseca's disease, Pedroso's disease, phaeosporotrichosis, verrucous dermatitis); Chronic mucocutaneous candidiasis; Coccidioidomycosis (California disease, desert rheumatism, San Joaquin Valley fever, valley fever); Congenital cutaneous candidiasis; Cryptococcosis; Dermatophytid; Diaper candidiasis; Disseminated coccidioidomycosis (coccidioidal granuloma); Distal subungual onychomycosis; Entomophthoromycosis; Erosio interdigitalis blastomycetica; Favus; Fungal folliculitis (majocchi granuloma); Fusariosis; Geotrichosis; Granuloma gluteale infantum; Histoplasmosis (cave disease, Darling's disease, Ohio Valley disease, reticuloendotheliosis); Hyalohyphomycosis; Kerion; Lobomycosis (keloidal blastomycosis, lacaziosis, Lobo's disease); Mucormycosis; Mycetoma (Madura foot, maduromycosis); North American blastomycosis (blastomycetic dermatitis, blastomycosis, Gilchrist's disease); Onychomycosis (dermatophytic onychomycosis, ringworm of the nail, *Tinea unguium*); Oral candidiasis (thrush); Otomycosis; Perianal candidiasis; Perleche (angular cheilitis); Phaeohyphomycosis; *Piedra* (trichosporosis); Pityrosporum folliculitis; Primary cutaneous aspergillosis; Primary cutaneous coccidioidomycosis; Primary cutaneous histoplasmosis; Primary pulmonary coccidioidomycosis; Primary pulmonary histoplasmosis; Progressive disseminated histoplasmosis; Proximal subungual onychomycosis; Rhinosporidiosis; South American blastomycosis (Brazilian blastomycosis, paracoccidioidal granuloma, paracoccidioidomycosis); Sporotrichosis (rose-gardener's disease); Systemic candidiasis; *Tinea barbae* (barber's itch, ringworm of the beard, *Tinea sycosis*); *Tinea capitis* (herpes tonsurans, ringworm of the hair, ringworm of the scalp, scalp ringworm, *Tinea tonsurans*); *Tinea corporis* (ringworm, *Tinea circinata*, *Tinea glabrosa*); *Tinea corporis* gladiatorum; *Tinea cruris* (crotch itch, eczema marginatum, gym itch, jock itch, ringworm of the groin); *Tinea faciei; Tinea imbricate* (tokelau); *Tinea incognito; Tinea manuum; Tinea nigra* (superficial phaeohyphomycosis, *Tinea nigra* palmaris et plantaris); *Tinea pedis* (athlete's foot, ringworm of the foot); *Tinea versicolor* (dermatomycosis furfuracea, pityriasis versicolor, *Tinea flava*); White piedra; White superficial onychomycosis; and Zygomycosis (phycomycosis).

In some embodiments, the quaternary ammonium compounds of the present invention may be used to treat an ocular infection in a host, for example a human. Ocular infections that may be treated by the quaternary ammonium compounds of the present invention include, but are not limited to, conjunctivitis, uveitis, styes, blepharitis, chalazion, corneal ulcers and infections, dacryoadenitis, scleritis, keratitis, and iritis. In some embodiments, a method is provided comprising administering an effective amount of a quaternary ammonium compound, or composition thereof, described herein to a subject, for example a human, to treat an ocular infection. In another embodiment, the method is used to treat an ocular infection in another mammal, for example a cat, a dog, a cow, a pig, or a horse.

In some embodiments, the quaternary ammonium compounds of the present invention may be used to treat corneal keratitis in a host, for example a human. Corneal keratitis may be caused by a number of infectious organisms, including: bacteria such as *Staphylococcus aureus* and *Pseudomonas aeruginosa*; fungi such as *Fusarium, Candida, Aspergillus,* and *Curvularia* species; viruses such as Herpes simplex and Herpes zoster; and amoeba such as *Acanthamoeba* species, or combinations thereof. In some embodiments, the quaternary ammonium compounds of the present invention are used to treat bacterial keratitis in a host, for example a human.

In another embodiment, the quaternary ammonium compounds of the present invention are used to treat fungal keratitis in a host, for example a human. In another embodiment, the quaternary ammonium compounds of the present invention are used to treat viral keratitis in a host, for example a human. In another embodiment, the quaternary ammonium compounds of the present invention are used to treat acanthamoebic keratitis in a host, for example a human. In another embodiment, the method is used to treat corneal keratitis in another mammal, for example a cat, a dog, a cow, a pig, or a horse.

In some embodiments, the quaternary ammonium compounds of the present invention may be used to treat conjunctivitis in a host, for example a human. Conjunctivitis may be caused by a number of infectious organisms, including bacteria such as *Staphylococcus aureus, Haemophilus influenzae, Streptococcus pneumoniae* and *Pseudomonas aeruginosa*; and viruses such as adenovirus and enterovirus. In some embodiments, the quaternary ammonium compounds of the present invention are used to treat bacterial conjunctivitis in a host, for example a human. In some embodiments, the quaternary ammonium compounds of the present invention are used to treat viral conjunctivitis in a host, for example a human. In another embodiment, the method is used to treat conjunctivitis in another mammal, for example a cat, a dog, a cow, a pig, or a horse.

In some embodiments, the quaternary ammonium compounds of the present invention may be used to treat an ear infection in a host, for example a human. The ear infection may be present within the outer ear and/or ear canal (otitis externa), the middle ear (otitis media), or the inner ear (otitis interna). In some embodiments, a method is provided comprising administering an effective amount of a quaternary ammonium compound, or composition thereof described herein to a subject to treat an ear infection. In another embodiment, the method is used to treat an ear infection in another animal, for example a cat, a dog, a cow, a pig, or a horse.

In some embodiments, the method of treatment involves application of a dressing comprising an effective amount of a quaternary ammonium compound of the present invention, either alone or as a pharmaceutical composition, to the site of infection in a host in need thereof. The dressing is preferably shaped to fit within the space provided by the external auditory canal. The dressing may be malleable, allowing it to be compressed and shaped to fit within the external auditory canal, or it may be rigid, ensuring it will sit against the walls of the external auditory canal to ensure proper contact and transfer of the antimicrobial composition.

In some embodiments, the dressing is only placed in the external auditory canal for a day or less. In other embodiments, the dressing is placed in the external auditory canal for a week or more.

In some embodiments, the method of treatment of an infection in the ear canal of a host in need thereof involves application of the dressing into the ear canal of the host and subsequent saturation of the dressing with the antimicrobial composition. This method would allow for sequential or continuous application of the antimicrobial composition while the dressing is in place.

In some embodiments, the dressing is composed of a dissolvable material, requiring placement into the ear canal before saturation with the antimicrobial composition. In another embodiment, the dressing is composed of polymeric foam that will expand upon subsequent wetting with the antimicrobial composition.

In some embodiments, a method of treating or preventing an infection in a chronic wound is provided comprising administering an effective amount of a quaternary ammonium compound of the present invention, either alone or in an antimicrobial composition, to the chronic wound in a host in need thereof, for example a human. Types of chronic wounds include venous ulcers, diabetic ulcers, and decubitus ulcers.

In some embodiment, a method of treating or preventing an infection in a chronic wound is provided comprising applying a dressing containing one or more quaternary ammonium compounds of the present invention, either alone or in a composition, to the site of infection in a host in need thereof.

In some embodiments, the quaternary ammonium compounds of the present invention may be used to treat a fungal nail infection, i.e. onychomycosis, in a host, for example a human. Preparations for use in the treatment of nail infections must be able to penetrate deep in the nail bed.

In such embodiments, the antimicrobial composition is formulated using a solvent, for example dimethyl sulfoxide, that is able to penetrate the nail bed of a host.

In some embodiments, a method is provided comprising administering an effective amount of a quaternary ammonium compound, or composition thereof described herein to a subject to treat a fungal nail infection.

In some embodiments, the quaternary ammonium compounds of the present invention may be used to treat a fungal vaginal infection, i.e. vulvovaginal candidiasis, in a host, for example a human.

In some embodiments, the antimicrobial composition is formulated as a vaginal suppository.

In some embodiments, a method is provided comprising administering an effective amount of a quaternary ammonium compound, or composition thereof described herein to a subject to treat a fungal vaginal infection.

Methods of Treatment of a Biofilm on Abiotic Surfaces

The present invention includes a method for treatment of a biofilm on abiotic surfaces with a quaternary ammonium compound or product described herein or a mixture thereof.

In some embodiments, the abiotic surface is treated directly with a solution containing one or more quaternary ammonium compounds of the present invention (typically reconstituted from a sterilized powder or solid).

In some embodiments, the abiotic surface is treated directly with a solution containing one or more quaternary ammonium compounds of the present invention to remove and/or prevent recurrence of a bacterial biofilm.

In some embodiments, the abiotic surface is treated directly with a solution containing one or more quaternary ammonium compounds of the present invention to remove and/or prevent recurrence of a fungal biofilm.

In some embodiments, the abiotic surface is treated directly with a solution containing one or more quaternary ammonium compounds of the present invention to remove and/or prevent recurrence of a viral contamination. In some embodiments, the abiotic surface is treated directly with a solution containing one or more quaternary ammonium compounds of the present invention to prevent transmission of SARS coronavirus 2 from the treated surface to a host.

Abiotic surfaces may harbor both enteric and respiratory human pathogenic viruses or bacteria. High-contact abiotic surfaces can serve as a point of transmission of bacterial, fungal or viral contamination. Biofilms may be present on abiotic surfaces. Viral contamination may be present on abiotic surfaces. The abiotic surface is not limited and includes any surface on which a microorganism may occur or any such surface which may be exposed to microbial or viral contact or contamination. Non-limiting examples of abiotic surfaces include surfaces present in a hospital setting, surgical center, doctor's office, imaging center, dental facilities, nursing homes, assisted-living facilities, athletic locker rooms, mass transit vehicles (e.g. airplanes, trains, buses and commercial vehicles), airports, train stations, bus stations, public restrooms, food or drink processing facilities, manufacturing facilities, schools, dormitories, furniture, tables, desks, walls, stairwells, elevators, surfaces on machinery, surfaces exposed to water such as commercial spas, hot tubs, saunas, bath tubs, or any surface exposed to the external environment. Medical or surgical equipment or devices represent a particular class of surface on which a biofilm may form. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

The surface can be made of any material. Non-limiting examples include metal, e.g. aluminum, copper, nickel-plate, gold-plate, steel, stainless steel, chrome, titanium, iron, and metal alloys. Additional non-limiting surface examples include plastics, for example, polyolefin (e.g., polyethylene, (Ultra-High Molecular Weight) polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), or combinations thereof. Other examples include acetal copolymer, polyphenylsulfone, polysulfone, polythermide, polycarbonate, polyvinylidene fluoride, poly(methyl methacrylate) and poly(tetrafluoroethylene). The surface can also be brick, glass, formica, tile, ceramic, porcelain, wood, vinyl, linoleum, or carpet, or combinations thereof.

Powder Formulations for Use in the Present Invention

In some embodiments, one or more active quaternary ammonium compounds of the present invention can be provided as a powder formulation. Powder formulations can be prepared by a removing any residual solvents, for example by sublimation or boiling. In one embodiment, Lyophilization is used to create the powder for the formulation as it typically maintains the integrity of the product due to the low temperature used in processing. Additionally, lyophilized solids can be reconstituted much more quickly and easily due to the presence of microscopic pores formed by the process. The high vacuum used during lyophilization ensures thorough removal of any undesired volatile components such as methanol, ethanol, or other volatile organic substances. In some embodiments, the powder formulation of the quaternary ammonium compounds and products described herein contains less than about 5%, about 4%, about 3%, about 2%, about 1%, about 0.5%, or about 0.01% of methanol by weight. Methods for the lyophilization of solids, particularly of sensitive materials used in pharmaceutical applications, are known in the art. Lyophilization may be performed using any number of commercially available apparatuses, for example a shelf-cabinet, contact, radiant, or microwave assisted lyophilizer.

Typical lyophilization procedures are composed of four steps. In the first step (Pre-Treatment), the active quaternary ammonium compound is dissolved in an appropriate solvent and additional excipients are optionally added as required to increase stability, preserve appearance, or improve later processing. Additionally, solutions of the active quaternary ammonium compound may be concentrated as appropriate to aid in the freezing and later sublimation processes. Additionally, components may undergo initial individual quick freezing to ensure formation of a free-flowing solid upon completion of the lyophilization.

In the second step (Freezing), the solution of the active quaternary ammonium compound is frozen in a vessel below its triple point to ensure that sublimation rather than melting will occur. Optionally, the material can be cycled up and down in temperature in a process called annealing. If the quaternary ammonium compound to be lyophilized is an amorphous solid, it may not have a triple point and instead has a critical point. Amorphous solids must be maintained below the critical point temperature during the entirety of the lyophilization process to prevent melt-back or collapse of the solid during the subsequent drying steps. For sensitive materials, the freezing step is often performed quickly by lowering the temperature of the material to between about −50 and −80° C. This prevents the formation of large solvent crystals that may diminish the structure integrity of the material being lyophilized and lead to poor texture.

In the third step (Primary Drying), the pressure of the vessel is lowered (typically to the range of a few millibars) and a minimum of heat is applied to the material for the solvent to sublime. Pressure is typically controlled by the application of a partial vacuum. A small amount of heat may be applied to facilitate sublimation of the solvent molecules. Typically, this heat is applied via conduction or radiation due to the low air density within the vessel.

In the final step (Secondary Drying), the temperature is raised higher than in the primary drying phase to remove any residual unfrozen solvent molecules. The rise in temperature is required to break any physio-chemical interactions that may have formed between the solvent molecules and the frozen material. Additionally, the pressure is typically lowered compared to the primary drying step to encourage desorption.

Upon completion of the lyophilization process, the vacuum is typically broken with an inert gas, for example nitrogen, and sealed in an appropriate container. Typical containers include sealed ampoules comprising sealed glass that is broken open at the time of desired application. The active material may be subsequently reconstituted at the time of application by using an appropriate carrier such as those that are described herein, for example sterile water or glycerin.

Antimicrobial Compositions

Active quaternary ammonium compounds described herein can be administered to a host in need thereof as the neat chemical, but are more typically administered as antimicrobial composition that includes an effective amount for a host, typically a human, in need of such treatment of an active quaternary ammonium compound as described herein or combinations thereof.

In some embodiments, the disclosure provides antimicrobial compositions comprising an effective amount of a quaternary ammonium compound together with at least one pharmaceutically acceptable carrier for any of the uses described herein. The pharmaceutical composition may contain a quaternary ammonium compound as the only active agent.

In an alternative embodiment, the quaternary ammonium compound and at least one additional active agent. In a typical formulation, the selected quaternary ammonium compound of the present invention is provided in a sterilized, powder or solid form that is reconstituted on use.

An effective amount of an active quaternary ammonium compound as described herein, or the active quaternary ammonium compound described herein in combination or alternation with, or preceded by, concomitant with or followed by another active agent, can be used in an amount sufficient to (a) inhibit the progression of an infection described herein; (b) cause a regression of an infection described herein; (c) cause a cure of an infection described herein; or inhibit or prevent the development of an infection described herein. Accordingly, an effective amount of an active quaternary ammonium compound, or composition described herein will provide a sufficient amount of the active agent when administered to a patient to provide a clinical benefit.

The exact amount of the active quaternary ammonium compound or antimicrobial composition described herein to be delivered to the host, typically a human, in need thereof, will be determined by the health care provider to achieve the desired clinical benefit.

In certain embodiments the antimicrobial composition is in a dosage form that contains from about 0.1 mg to about 2000 mg, from about 10 mg to about 1000 mg, from about 100 mg to about 800 mg, or from about 200 mg to about 600 mg of the active quaternary ammonium compound and optionally from about 0.1 mg to about 2000 mg, from about 10 mg to about 1000 mg, from about 100 mg to about 800 mg, or from about 200 mg to about 600 mg of an additional active agent in a unit dosage form.

Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active quaternary ammonium compound. In some embodiments, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active quaternary ammonium compound. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The antimicrobial composition may for example include a molar ratio of the active quaternary ammonium compound and an additional active agent that achieves the desired result. For example, the pharmaceutical composition may contain a molar ratio of at least about 0.5:1, at least about 1:1, at least about 2:1, at least about 3:1, or from about 1.5:1 to about 4:1 of an additional active agent in combination with the active quaternary ammonium compound (additional active agent: active compound) described herein.

Quaternary ammonium compounds disclosed herein or used as described herein may be administered topically, by spray, cream, gel, foam, suppository, via implant, including ocular implant, transdermally, dermatological formulation, or as an ophthalmic solution, in dosage unit formulations containing conventional pharmaceutically acceptable carriers. For ocular delivery, the quaternary ammonium compound can be administered, as desired, for example, as a solution, suspension, or other formulation via an immediate or controlled release fashion or via an ocular device, or topically administered formulation, for example a solution or suspension provided as an eye drop.

The antimicrobial composition may be formulated as any pharmaceutically useful form, e.g., as an aerosol, a cream, a gel, foam, a microparticle, a nanoparticle, an injection or infusion solution, a transdermal patch, a subcutaneous patch, a suppository, a dry powder, in a medical device, parenteral formulation, dermatological formulation, or an ophthalmic solution or suspension. Some dosage forms are subdivided into suitably sized unit doses containing appropriate quantities of the active components, e.g., an effective amount to achieve the desired purpose.

Compositions, and methods of manufacturing such compositions, suitable for administration as contemplated herein are known in the art. Examples of known techniques include, for example, U.S. Pat. Nos. 5,723,269 and 9,060,938, incorporated by reference herein.

The antimicrobial compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the quaternary ammonium compound is sufficient to provide a practical quantity of material for administration per unit dose of the compound.

Classes of carriers include, but are not limited to binders, buffering agents, coloring agents, diluents, disintegrants, emulsifiers, fillers, flavorants, glidants, lubricants, pH modifiers, preservatives, stabilizers (for example, xanthan gum, Polyvinylpyrrolidone (PVP), guar gum, polyvinyl alcohols (PVA) and the like), surfactants, solubilizers, tableting agents, thickening agents (for example xanthan gum, Polyvinylpyrrolidone (PVP), guar gum, polyvinyl alcohols (PVA) and the like), gelling agents, and wetting agents (for example, urea and the like).

Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth.

Examples of lubricants include magnesium stearate and calcium stearate.

Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the quaternary ammonium compound of the present invention.

Non-limiting examples of aqueous solutions as can be used in the carrier include distilled water, saline, plasma, bone marrow aspirate, buffers, such as Hank's Buffered Salt Solution (HBSS), HEPES (4-(2-hydroxyethyl)-1-piperazineethanesulfonic acid), Ringers buffer, ProVisc®, diluted ProVisc®, ProVisc® diluted with PBS, Krebs buffer, Dulbecco's PBS, normal PBS, sodium hyaluronate solution, simulated body fluids, plasma platelet concentrate, tissue culture medium, an aqueous solution comprising an organic solvent, and mixtures thereof. The solution in all instances can be sterilized in a suitable manner known to those in the art.

In certain examples the antimicrobial composition contains a polymeric material. The polymeric material should be biocompatible such that it can be administered to a patient without an undesired effect. Polymers are well known in the art and are the subject of extensive literature and patents. In certain embodiments, the polymer is present in an amount effective to provide the desired viscosity and moistening properties as needed for the desired application, for example in the treatment of infected wounds. The specific amount of polymer used depends on a number of factors including, for example and without limitation, the specific chemical composition of the polymer used, the molecular weight of the specific polymer used, the viscosity of the desired antimicrobial composition, and the level of water retainment and release desired for the particular polymer.

In certain embodiments, the antimicrobial composition is used in polymeric material for medical, personal or industrial applications. Examples for medical applications include, but are not limited to, wound care materials, medical devices, proper protective equipment, artificial cartilage, biomaterials, catheters, other implantable devices and non-implant devices (such as surgical sponges, and packaging), medical applications or devices, for example orthopedic or dental applications or devices, ophthalmic solutions or suspensions, short-term wound packing, direct application to eye tissues, hydrophilic coatings for catheters, leads etc., or vascular embolic agents, and the like.

In certain embodiments, the antimicrobial composition is used in polymeric material for medical devices, coverings for medical device infections including pacemakers, contact lenses, dentures, prosthetic devices, heart valves and joints; biomaterials, implantable devices, non-implant devices, wound care material, personal protective material such as gloves, face masks, surgical/hospital gowns, cloth material, sheets, woven or nonwoven materials, sponges; medical devices such as orthopedic or dental devices, ophthalmic solutions or suspensions, ocular inserts, ocular film, targeted ocular delivery, short-term wound packing, direct application to eye tissues, hydrophilic coatings for catheters, leads etc., or vascular embolic agents, and the like.

In certain embodiments the polymeric material comprises polymers thermoplastic polymer, thermosetting polymer, biodegradable polymer, modified polymers, crosslinked polymers, polymers for controlled delivery, hydrogels, hydrocolloids, liquid forming polymer, gel forming polymer, silicone-based polymeric material, film forming polymer, adhesive polymer, polymers for controlled delivery copolymers, polymers for medical uses, copolymers, or mixtures thereof, and the like.

In certain embodiments, the silane quaternary ammonium compound described herein and the polymeric material is in a ratio of at least 1:1000:1000:1; 1:500:500:1, 1:300:300:1, 1:250:250:1; 1:200:200:1; 1:150:150:1; 1:100:100:1; 1:75:75:1; 1:50:50:1; 1:40:40:1; 1:30:30:1, 1:25:25:1; 1:20:20:1; 2:25:15:1; 1:10:10:1; 1:5:5:1; 1:3:3:1; 1:2:2:1; or 1:1.

In certain embodiments, the composition of the silane quaternary ammonium compound and polymer material forms a solid, stable composition.

In certain embodiments, the composition forms a clear stable solution. In certain embodiments, the composition is stable for at least one month. In certain embodiments, the composition is stable for at least 2 months. In certain embodiments, the composition is stable for at least 3 months.

In certain embodiments, a silane quaternary ammonium compound described herein is combined with a polymer described herein to form flexible film. In certain embodiments, the film exists with varying thickness level suitable for a particular application described herein.

In certain embodiments, a silane quaternary ammonium compound described herein is incorporated into polyvinyl alcohol. In certain embodiments, the resultant product is used for medical applications and devices. For example, soft contact lenses, eye drops, embolization particles, tissue adhesion barriers, and as artificial cartilage and meniscus. In certain embodiments, the resultant product is a medical device implant material for cartilage replacement. In certain embodiments, the resultant product is used for transient to short-term wound packing, direct application to eye tissues, hydrophilic coatings for catheters, leads, or vascular embolic agents. See, for example, Baker, M., et al., "A review of polyvinyl alcohol and it uses in cartilage and orthopedic applications", Wiley Online Library. DOI: 10.1002/jbm.b.32694 (2012), incorporated herein.

In certain embodiments, the polymer is a polyvinyl alcohol hydrogel. In certain embodiments, the polyvinyl alcohol hydrogen is useful for drug delivery systems. In certain embodiments, the drug delivery system comprises ocular inserts, ocular films, nanoparticles, microspheres, floating microspheres, mucoadhesive or targeted drug delivery, and the like. In certain embodiments, the drug delivery system is ocular inserts, ocular films, microspheres, floating microspheres, or targeted drug delivery.

Polyvinyl alcohol hydrogels are biocompatible and toxicologically safe polymer used as a matrix for sustained release hydrogel drug delivery systems in solid, liquid and semi-solid formations. Polyvinyl alcohol hydrogels have excellent physical properties like mucoadhesive, swelling make it suitable for the diverse drug delivery applications." See, e.g., Gajra, Balaram & Pandya et al., "Poly vinyl alcohol Hydrogel and its Pharmaceutical and Biomedical Applications: A Review", International Journal of Pharmaceutical Research, 2011, 4. 20-26, incorporated herein by reference.

In some examples, the antimicrobial composition contains a hydrogel. The hydrogel should be biocompatible such that it can be administered to a patient without an undesired effect. Hydrogels are well known in the art and are the subject of extensive literature and patents. The hydrogel is present in an amount effective to provide the desired viscosity and moistening properties as needed for the desired application, for example in the treatment of infected wounds. The specific amount of hydrogel used depends on a number of factors including, for example and without limitation, the specific chemical composition of hydrogel used, the molecular weight of the specific hydrogel used, the viscosity of the desired antimicrobial composition, and the level of water retainment and release desired for the particular hydrogel.

In some embodiments, the hydrogel controls the rate of release of one or more quaternary ammonium compounds of the present invention. In some embodiments, the hydrogel is biodegradable. Examples of useful hydrogel carriers include, but are not limited to, poly(vinyl alcohol), sodium polyacrylate, poly(acrylamide), poly(N-vinyl-2-pyrrolidone), poly(N-isopropylacrylamide), cross-linked carboxymethylcellulose, cross-linked polyethylene glycol, poly (lactic acid), hyaluronic acid, sodium alginate, agarose, starch, chitosan, methylcellulose, polyethylene oxide, amorphous hydrogel, crosslinked polymer gels with high water content, copolymers thereof, derivatives thereof, mixtures thereof, and the like.

In some examples, the antimicrobial composition contains a hydrocolloid. In some embodiments, the hydrocolloid may interact with the site of infection by forming a gel. A hydrocolloid may be present to provide combined moisture and absorptivity in sites where it is deemed necessary. The hydrocolloid may include, but is not limited to, natural gums such as Arabic gum, ghatti gum, karaya gum, tragacanth gum, guar gum, locust bean gum, acacia gum; seaweed extracts such as agar, algin, alginate salts and carrageenan, cereal gums, starches, microbial gums such as dextran gum and xanthan gum, pectins, gelatins, casein, collagens, polyvinylpyrrolidone, low methoxyl pectin, propyleneglycol alginates, carboxymethyl locust bean gum, carboxymethyl guar gum, and modified forms that have been oxidized, acetylated, carboxylated, esterified, methylated, aminated, etherated, sulfated, borated, or phosphated, absorbent colloidal material with elastomers covered with polyurethane; and the like.

In certain embodiments, the antimicrobial composition for administration further includes a quaternary ammonium compound as described herein and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span® 85) glycocholate; sorbitan monolaurate (Span® 20); polysorbate (Tween® 20); polysorbate 60 (Tween® 60); polysorbate 65 (Tween® 65); polysorbate 80 (Tween® 80); polysorbate 85 (Tween® 85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the antimicrobial composition may include polymers for controlled delivery of the described compounds, including, but not limited to pluronic polymers, polyesters (e.g., polylactic acid, poly(lactic-co-glycolic acid, polyethylene terephthalate (PET), glycol-modified polyethylene terephthalate (PETG), polybutylene terephthalate (PBT), polycyclohexylenedimethylene terephthalate (PCT), polycyclohexylendimethylene terephthalate glycol (PCTG), acid-modified polycyclohexylenedimethylene terephthalate (PCTA), polytrimethylene terephthalate (PTT), woven and non-woven polyethylene terephthalate (PET), spun-bonded, spun-laced, embossed polyethylene terephthalate, LDPE non-woven polyethylene terephthalate, glycol-modified polyethylene terephthalate (PETG), or another kind of polyester which can include monomers or co-monomers that have other carboxylic acid or alcohol functions), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

In certain embodiments, additional polymers include but are not limited to, polyolefin (including cyclic polyolefin), including polypropylene and polyethylene; polyvinyl chloride; polystyrenes; polyvinylidene chlorides; polynorbornene; polyimide; polyamide; polyurethane; polystyrene; polyvinylidene chloride; polyvinyl chloride; polylactic acid; or a combination or combinations thereof.

In some embodiments, the antimicrobial composition contains a biodegradable polymer. The biodegradable polymer should be biocompatible such that it can be administered to a patient without an undesired effect. Biodegradable polymers are well known in the art and are the subject of extensive literature and patents. The biodegradable polymers or combination of polymers can be selected to provide the desired characteristics for the chosen application including, but not limited to, the appropriate mix of hydrophobic and hydrophilic qualities, half-life and degradation kinetics, compatibility with one or more quaternary ammonium compounds of the present invention to be delivered, and the appropriate behavior at the site of application.

In some embodiments, the biodegradable polymer gelates in the presence of an aqueous solution such as is present in the site of a wound or infection.

In some embodiments, the biodegradable polymer carrier provides release of one or more quaternary ammonium compounds of the present invention into the site of infection at a desired rate. Examples of useful biodegradable polymers include, but are not limited to, poly(lactic acid), polyglycolic acid, poly(D,L-lactide-co-glycolide), poly(D,L-lactic acid), polyesters, poly(caprolactone), poly(3-hydroxybutyrate), poly(s-caproic acid), poly(p-dioxanone), poly(propylene fumarate), poly(orther esters), polyol/diketene acetals, poly(sebacic anhydride), poly(maleic anhydride), poly(carboxybis-carboxyphenoxyphosphazene), poly[bis(p-carboxyphenoxy)methane], poly(amino acids), or copolymers thereof.

Optional active ingredients may be included in the antimicrobial composition which do not substantially interfere with the activity of one or more quaternary ammonium compounds of the present invention used in the present invention. In certain embodiments, two or more of the carrier components may be combined as deemed necessary for the particular application.

In some embodiments, the antimicrobial composition further comprises one or more additional additives, for example, urea and/or DMSO. These quaternary ammonium compounds may be included to increase the efficacy of the desired antimicrobial composition in penetrating the site of infection being treated, to aid in tissue healing or symptom abatement at the site of infection if it is deemed necessary, or to increase the effective shelf life of the antimicrobial composition either alone or in combination with other active agents.

In some embodiments, the antimicrobial composition further comprises a surfactant. The surfactant can be added to help facilitate penetration of one or more quaternary ammonium compounds of the present invention into subsurface layers of a biofilm present at the site of infection by disrupting the complex hydrophobic/hydrophilic interactions between biofilm layers if one or more quaternary ammonium compounds of the present invention alone prove insufficient for this purpose. The surfactant additive selected can be chosen to provide desired characteristics to the antimicrobial composition, such as stability of the surfactant and one or more quaternary ammonium compounds of the present invention in the appropriate carrier, level of desired penetration into the biofilm, and level of reactivity with other components in the composition. An appropriate surfactant would be able to be chosen by one skilled in the art. In some embodiments, the surfactant can facilitate leaching of one or more quaternary ammonium compounds of the present invention from the selected carrier.

In some embodiments, the surfactant can facilitate leaching of one or more quaternary ammonium compounds of the present invention from either a formulated microparticle or polymeric nanoparticle. Examples of appropriate surfactants include, but are not limited to, octenidine dihydrochloride, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), cocamidopropyl hydroxysultaine (CAHS), cocamidopropyl betaine (CAPB), cocamide MEA, sodium oxychlorosene, and combinations thereof.

In some embodiments, the antimicrobial composition further comprises a buffer. Some of the other potential additives (for example, urea and/or DMSO) to the antimicrobial composition may require very narrow pH ranges to optimally function. A buffer can be provided at appropriate concentrations to maintain an optimized pH range. The optimized buffer for the particularly desired application would be known to known to those skilled in the art. Examples of appropriate buffers include, but are not limited to, salts of citrates, sulfonates, carbonates, acetate, borates, gluconates, phosphates, or combinations thereof.

In some embodiments, the antimicrobial composition further comprises appropriate enzymes. The enzymes can be added to assist in disrupting the established biofilm by either decomposition of the extracellular polymeric substances (EPS) or by suppressing cell to cell communications, sent via ion channels in the form of electrical signals, to coordinate their behavior. In some embodiments, the enzymes may be proteolytic enzymes. Proteolytic enzymes may be able to act upon some of the polymeric materials present in the EPS, allowing increased penetration of the antimicrobial composition. Examples of proteolytic enzymes include, but are not limited to, collagenase, cellulase, keratinase, papain, bromelain, trypsin, thermolysin, and combinations thereof.

In some embodiments, the antimicrobial composition further comprises an appropriate tissue growth promoter. In some applications, the biofilm-induced infection that is being treated is present within a wound. Inclusion of an appropriate tissue growth promoter may help facilitate regrowth of tissue within the present wound during the time of infection treatment with the dressing. Examples of appropriate tissue growth promoters include, but are not limited to, endothelial cell growth factors (ECGF), epidermal growth factors (EGF), fibroblast growth factors (FGF), hepatocyte growth factors (HGF), nerve growth factors (NGF), platelet-derived growth factors (PDGF), transforming growth factors (TGF), or combinations thereof.

In some embodiments, the antimicrobial composition further comprises a preservative. While one or more quaternary ammonium compounds of the present invention antimicrobial in nature, an additional preservative may be optionally included dependent on the desired shelf life of the antimicrobial composition. Examples of appropriate preservatives include, but are not limited to, methylparaben, propylparaben, benzyl alcohol, benzalkonium chloride, sorbic acid, phenol, phenylethyl alcohol, BHA, BHT, or combinations thereof.

In some embodiments, the antimicrobial composition further comprises an antioxidant. An antioxidant may be necessary to stabilize any other additive present within the antimicrobial composition from air oxidation over a suitable shelf life. Examples of appropriate antioxidants include, but are not limited to ascorbic acid, BHA, BHT, sodium bisulfite, vitamin E, sodium metabisulfite, propyl gallate, or combinations thereof.

In some embodiments, the antimicrobial composition further comprises an astringent. Addition of an astringent to the antimicrobial composition may be desirable by causing surface tissues that contain an infection to shrink, allowing ready penetration of the antimicrobial composition into the infected space. Examples of appropriate astringents include, but are not limited to, zinc oxide, ferric oxide, zinc sulfate, silver nitrate, potassium permanganate, aluminum chloride, aluminum acetate, formaldehyde, Burow's solution, tincture of benzoin, or combinations thereof.

Antimicrobial compositions suitable for topical application to the skin preferably take the form of an ointment, cream, lotion, foam, paste, gel, spray, aerosol, or oil. Carriers which may be used include petroleum jelly, lanoline, polyethylene glycols, alcohols, transdermal enhancers, and combinations of two or more thereof.

Antimicrobial compositions suitable for transdermal administration may be presented as discrete patches adapted to remain in intimate contact with the epidermis of the recipient for a prolonged period of time. Antimicrobial compositions suitable for transdermal administration may also be delivered by iontophoresis (see, for example, *Pharmaceutical Research* 3 (6):318 (1986)) and typically take the form of an optionally buffered aqueous solution of the active quaternary ammonium compound. In some embodiments, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen O Y); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active quaternary ammonium compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nano-particles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

In another aspect, an ocular formulation is provided comprising one or more quaternary ammonium compounds described herein, in a carrier that is suitable to the eye. The appropriate carrier must avoid quaternary ammonium compounds that are toxic or irritating to the eye to prevent unwanted side effects or damage to the eye. Examples of components that are not suitable for use in an ocular formulation include corrosives such as strongly alkaline or acidic substances such as urea or ammonia, strong surfactants, and substances with known ocular toxicity such as methanol and hydrogen peroxide.

In another aspect, a formulation for the treatment of onychomycosis is also provided comprising one or more quaternary ammonium compounds described herein, in a carrier that is capable or penetrating the nail bed to deliver the active quaternary ammonium compounds therein. One representative example of a carrier able to penetrate the nail bed is dimethyl sulfoxide.

Additional non-limiting examples of drug delivery devices and methods include, for example, US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic/hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Dressings and the Like

In some embodiments, the antimicrobial composition containing one or more quaternary ammonium compounds of the present invention is dispersed in a suitable dressing. The dressing that is chosen should allow release of the desired antimicrobial composition over a period of time dependent upon the desired application. The dressing can be wetted before placement at the site of infection by saturation with the antimicrobial composition, even though it may be additionally moistened due to exudate at the site of infection. Alternatively, the dressing can be placed at the site of a wound and/or infection and subsequently saturated with the antimicrobial composition, for example by application of the antimicrobial composition by dropper or syringe, or other suitable means.

In another embodiment an infection is treated by applying a dressing comprising one or more quaternary ammonium compounds of the present invention as an antimicrobial composition to the site of infection, wherein the dressing releases one or more quaternary ammonium compounds of the present invention into the site of infection. The infection may involve the presence of bacteria, fungi, viruses, amoebas, or a combination of infectious species thereof.

In some embodiments, treatment of an infection comprises placing a dressing comprising an antimicrobial composition as described herein in or on the site of infection.

In certain embodiments, one or more of the quaternary ammonium compounds of the present invention may be used to treat a disorder, typically an infection, caused by gram-positive bacterium, gram-negative bacterium, mycobacterium, fungal species or viral species described herein.

In certain embodiments, a method is provided comprising administering an effective amount of a quaternary ammonium compound, or composition thereof described herein to treat an infection caused by gram-positive, gram-negative bacterium, mycobacterium, fungal species or viral species described herein.

In an additional embodiment, a dry powder formulation containing the quaternary ammonium compound of the present invention is impregnated within the dressing and subsequently wetted upon interaction with exudate or other bodily fluids at the site of infection. The dressing may be placed in or on the location of an infection involving a biofilm. The dressing may adhere to the location of a wound and/or infection to provide suitable localization, or may not adhere to the location of the infection in order to prevent undesired tissue damage upon removal. The dressing may be rigid, to allow for it to be held in place during treatment, or may be malleable to allow for placement and adherence in the desired location.

Additionally, the dressing may comprise additional additives (for example, urea and/or DMSO) that ensure the maintenance of a moist environment at the site of infection. The dressing must be composed of a material that is hypoallergenic and non-toxic in order to be acceptably applied to a living host. In some embodiments, the dressing would absorb the antimicrobial composition and would then subsequently release the antimicrobial composition once placed in the site of infection involving a biofilm.

In certain embodiments, the dressing has a bulk density that is low enough to allow the antimicrobial composition to be incorporated within, but high enough to provide sufficient structural integrity. The dressing should be porous to provide sufficient intercalation of the antimicrobial composition among the material, allowing space for sufficient wetting with the antimicrobial composition along with efflux into the site of treatment. The level of porosity of the dressing should be high enough to allow sufficient wetting with the antimicrobial composition, but should still allow for the dressing to have sufficient material strength.

In certain embodiments, the dressing is fashioned from a flexible polymeric material that provides sufficient porosity but still provides structural integrity in the desired application. In certain embodiments, two or more of the dressing components may be combined, as deemed necessary for the particular application, into a composite material. In some cases, the two or more components may be present in layers. In other cases, the two or more components may be impregnated or intercalated into each other. The combination of dressing components may be necessary for structural integrity to ensure placement, positioning, and functioning at the site of infection.

In some embodiments, the dressing comprises a polymer foam, for example a conformable foam. The polymer foam may allow release of the desired antimicrobial composition by either diffusion, ionic interactions, or by degradation of the material composition of the dressing.

In some embodiments, the polymer foam can absorb exudate that may occur due to infection involving the presence of a biofilm. In some embodiments, the polymer foam is biodegradable or non-degradable, depending upon the intended use within the patient.

Examples of materials suitable for the formation of a polymer foam include, but are not limited to, cellulose and cellulose derivatives, microcrystalline cellulose, calcium alginate, polyacrylic acid, polyethylene glycol, polypropylene glycol, divinyl glycol, polyethylene oxide, polypropylene oxide, carboxymethyl cellulose, hydroxyethyl cellulose, polylactide, polyglycolide, polymethacrylic acid, poly-γ-benzyl-L-glutamate, polypropylene fumarate, poly-F-caprolactone, poly-butylene terephthalate, polyvinyl alcohol, polyvinyl ether, poly-1-vinyl-2-pyrrolidinone, 2,5 dimethyl-1,5-hexadiene, divinyl benzene, polystyrene-divinyl benzene, polyanhydrides such as polybis(p-carboxy-phenoxy) propane-co-sebacic acid, polyhydroxyalkanoates such as poly-β hydroxybutyrate or poly-β-butyrolactone, and alkyl-substituted silica gel formed from reagents such as tetraethylorthosilicate and dimethyldiethoxysilane. In preferred embodiments, the polymer foam is composed of polyurethane.

In another embodiment, the polymer foam is composed of cellulose. In yet another embodiment, the polymer foam is composed of calcium alginate.

In some embodiments, the dressing comprises a fabric composition. The fabric composition may be composed of fibers including natural fibers, synthetic fibers, cellulose, woven or nonwoven fabric material, gauze material, or mixtures thereof. Examples of acceptable fibers include, but are not limited to, cotton, polyester, wool, silk, and rayon. The fabric composition may have varying levels of absorbency depending on the desired application. The fabric composition may additionally be coated with an appropriate polymer composition that effects absorbance and dispersion of the active quaternary ammonium compound or additional additives (for example, urea and/or DMSO).

In some embodiments, the dressing additionally comprises a polymeric film. A polymeric film may be desirable to ensure proper sealing of the dressing to maintain moisture at the treatment site. In preferred embodiments, the polymeric film comprises an adhesive side that adheres to the edges of the site of the infection to provide a seal and a non-adhesive side. In some embodiments, the polymeric film is composed of polyurethane.

In certain embodiments, the dressing is self-adhesive.

In some embodiments, the dressing additionally comprises a collagen matrix. A collagen matrix may be included in applications where it would be deemed desirable, such as providing a template in wound healing. The collagen matrix may be present as a gel, pad, paste, or sheet. The collagen matrix may be derived from a bovine, porcine, equine, or avian source. The collagen matrix may be composed of type I, II, III, IV, or V collagen.

In some embodiments, the collagen matrix may interact with the site of infection caused by a biofilm by forming a gel. Additional macromolecular structures, such as hyaluronic acid or hyaluronan, fibronectin, laminin, proteoglycans and mixtures thereof, may be incorporated into the collagen matrix. In some embodiments, the collagen matrix is chemically cross-linked.

In some embodiments, the dressing is composed of a dissolvable material. A dressing composed of a dissolvable material can allow for the dressing to be placed in the site of a wound and/or infection without the need for retrieval upon completion of the treatment. In certain embodiments, the dressing comprises a polymeric material comprises thermoplastic polymer, thermosetting polymer, biodegradable polymer, modified polymers, crosslinked polymers, polymers for controlled delivery), hydrogels, hydrocolloids, liquid forming polymer, gel forming polymer, silicone-based polymeric material, film forming polymer, adhesive polymer, polymers for controlled delivery copolymers, polymers for medical uses, or mixtures thereof; fabric material, nonadherent dressing material or hydrofibers.

In certain embodiments, the dressing is hydrofiber. Hydrofibers are soft, sterile, non-woven pad or ribbon dressing composed of sodium carboxymethylcellulose, which is incorporated in the form of a fleece held together by a needle-bonding process. This conformable material can absorb a large amount of wound fluid, such as exudate with bacteria. This is then transformed into a soft gel, which creates a moist environment to support the body's healing process. The gel also aids the removal of non-viable tissue from the wound (autolytic debridement), without damaging newly formed tissue. Hydrofibers are neither hydrocolloids nor alginates, but a separate category incorporating the benefits of both. (Thomas S. Sodium Carboxymethylcellulose Primary Wound Dressing, Aquacel. Available accessed 22 Oct. 2010)

In certain embodiments, the nonadherent dressing material comprises a nonadherent fabric material, for example, nonadherent gauze, petroleum impregnated gauze, petroleum blend impregnated gauze, oil emulsion dressing, and the like.

In certain embodiments, the dressing comprises polymeric gel (gel forming polymer), silicone, or copolymer thereof, and optionally additional ingredient for the use in topical applications. A polymeric gel may be desirable to ensure proper sealing of the dressing to maintain moisture at the treatment site. In preferred embodiments, the polymeric film comprises an adhesive side that adheres to the edges of the site of the infection to provide a seal and a non-adhesive side.

In some embodiments, the polymeric film is composed of polyurethane. In certain embodiments, the polymeric gel comprises a biodegradable polymer.

In certain embodiments, the polymeric film has a glue-like consistency.

In certain embodiments, the dressing comprises a compound described herein, polymeric gel, silicone, or copolymer thereof, and a pharmaceutically acceptable carrier.

In certain embodiments, the dressing additionally comprises a polymer wherein the polymer can form various shapes, sizes and thicknesses levels suitable for specific applications.

In certain embodiments, the polymer is silicone-based or silicone gel, or silicone-based polymer.

In certain embodiments the polymer is hydrogel, hydrocolloid, or organogel.

In certain embodiments, the polymer is polymeric biomaterial.

In certain embodiments, the polymer is guar gum.

In certain embodiments, the polymer is polyvinyl alcohol.

In certain embodiments, the polymer is hydrogel or cross-linked hydrogel.

In certain embodiments, the polymer is hydrocolloid.

In certain embodiments, the dressing is in the form of a gel, film, foam, liquid, or hydrocolloid.

In certain embodiments, the polymer is a polyvinyl alcohol; wherein the polymer is a dissolvable polyvinyl alcohol film.

In certain embodiments, the dissolvable polyvinyl alcohol film comprises a silane quaternary compound described herein for the treatment of an infection described herein.

In certain embodiments, the dissolvable polyvinyl alcohol film comprises a silane quaternary compound described herein for the treatment of an ocular infection.

In certain embodiments, the dissolvable polyvinyl film is in the form of an ophthalmic solution or suspension.

In certain embodiments, the dissolvable polyvinyl film is used to coat medical devices for example, catheters and leads and coverings for medical device infections including pacemakers, contact lenses, dentures, prosthetic devices, heart valves or joints, and the like.

In certain embodiments, the dissolvable polyvinyl film is used to treat biofilm; wherein the biofilm is bacterial or fungal. Fungal biofilms on implanted medical devices are highly resistant to drugs and the host immune system and have the potential to seed disseminated blood stream infections. Desai, J., et al., "Fungal Biofilms, Drug Resistance, and Recurrent Infection", Cold Spring Harb Perspect Med., 2014 4(10), a019729.

In certain embodiments, the gel, film or hydrocolloid forms a clear stable solution. In certain embodiments, the gel, film or hydrocolloid is stable for at least one month. In certain embodiments, the gel, film or hydrocolloid is stable for at least 2 months. In certain embodiments, the gel, film or hydrocolloid is stable for at least 3 months. In certain embodiments, the gel, film or hydrocolloid is stable for at least 4 months. In certain embodiments, the gel, film or hydrocolloid is stable for at least 5 months. In certain embodiments, the gel, film or hydrocolloid is stable for at least 6 months.

Examples of polymeric gels, include but are not limited to, polyvinyl alcohol, polyvinyl acetate, sodium polyacrylate, acrylate polymers, agarose, galactoarabinan, Poly acrylic acid, polyvinyl chloride, guar gum, xanthan gum, Poly acrylonitrile, polyurethane, Poly(lactide-co-glycolide) (PLGA), Polyethylene glycol (PEG), polyethyleneglycol/dopa, Polycaprolactone (PCL), (poly(vinyl pyrrolidone), poly(ethylene glycol), poly(methyl methacrylate), Poly(N-isopropylacrylamide, polyaniline (PANI), polypyrrole (PPy), polythiophene (PTh), poly(3,4-ethylenedioxythiophene) (PEDOT), polyesters, sulphated polysaccharides (such as heparin, chondroitin, dermatan, keratan sulphates), proplasts or alloplastics, glucan, dextran, derivatives or copolymers thereof.

Examples of polymeric gels include, but are not limited to, Silk sericin, spider silk protein, keratin, hyaluronic acid, pectin, Homoglycans, pallulan, yeast, cellulose, chitin, engineered skin substitutes (single or multilayers), bioengineered skin substitutes (single or multilayers), tissue engineered skin substitutes, dermal substitutes (such as Transcyte, Dermagraft, Composite graft, Orcel, Apligraf, and the like), epidermal substitutes, cultured epidermal autografts (such as Epicel and the like), or acellular xenografts (such as EZ-Derm, Integra, AlloDerm, Derma Martix, and the like) (Mir et al., "Synthetic polymeric biomaterial for wound healing: a review", Prog Biomater., 2018, 1-21; doi: 10.1007/s40204-018-0083-4; Murray et al., "Development and use of biomaterials as wound healing therapies", Burns & Trauma, 2019, 7(2), DOI: https://doi.org/10.1186/s41038-018-0139-7)

In certain embodiments, the dressing is used for covering wounds or wound care applications, infection or exposed skin. The wound for example, can be due to an infection, burn, exposed skin, open wound, skin lacerations, abrasions, punctures, avulsions, scabs, surgical wounds, abscesses, skin tears, skin ulcers or lesions, damaged tissue, bites, moisture associated skin damage, foot ulcers, necrosis, non-healing wounds, compromised skin grafts or flaps, acute wounds, chronic wounds, trauma, and other skin exposure related injuries.

Examples include but not limited to, fiber mats gauze (cotton, yarn, natural or synthetic fibers, nonwoven, blends thereof, and the like), cotton balls, tulle, bandages (liquid bandage), adhesive, tissue adhesive, bioadhesives, tapes, sheets, labels, liners, rolls of film and sheets, tear-apart sheets, rolls, fabric materials described herein, and the like.

In certain applications, the dressing comprises a composite material; wherein the backing materials comprises polyethylene or polypropylene (which can be spun-bonded, spun-laced, or embossed), or a combination thereof. The backing material may for example include one or more materials such as paper, cloth, including medical grade cloth and coated cloth, such as vinyl coated cloth, vinyl, including embossed vinyl, polypropylene, including oriented polypropylene such a MOPP and BOPP, polyesterurethane, polyethylene, including LDPE, LLDPE, MDPE, HMWPE, and HDPE, more generally polyolefin, acrylonitrile butadiene styrene, polycarbonate, polyvinyl chloride, cellophane, cellulose, cellulose acetate, films comprised of block co-polymers such as styreneisoprene, butadiene or thylene-butylene/styrene (SIS, SBS, or SEBS), polyurethane, ethylene copolymers such as ethylene vinyl acetates, including embossed ethylene vinyl acetate, ethylene/propylene copolymer elastomers or ethylene/propylene/diene terpolymer, nylon, crepe, flat back, a foil, rayon, a polyvinyl derivative, polyamides, cuproammonium cellulose, wool, silk, jute, hemp, cotton, linen, sisal, ramie, polystyrene, polyurethane, polyvinylidene chloride, saponified ethylene-vinyl acetate copolymer, linoleum, acrylics, natural rubber, reclaimed rubber, synthetic rubber, thermoplastic resin films, biodegradable resins such as polylactic acid and polyhydroxyalkanoates, polyamide, polyimide, paper, foil, metallized films, such as copper film, other resin based films, polylactic acid films, other thin-films, or combinations thereof. Other backing materials may include a fabric material such as one or more woven or non-woven fabric layers, such as non-woven, polyester fabric with a strengthening mesh therein, or a combination thereof. One example is a fabric produced by DuPont E. I. de Nemours & Co., Inc. under the trademark Sontara®.

In certain embodiments, the dressing comprises a composite backing material; wherein the backing material comprises a medical grade cloth material, a polyethylene film material, a vinyl material, an ethylene vinyl acetate material, a polyurethane material, a polyesterurethane material, a polyester material, including a polyethylene terephthalate material, a glycol-modified polyethylene terephthalate (PETG) material, a spun-laced polyethylene terephthalate material, a spun-laced polyethylene terephthalate non-woven material, an embossed non-woven polyethylene terephthalate material, an LDPE non-woven polyethylene terephthalate fabric material, or a coated cloth material, such as a vinyl coated cloth. Non-limiting examples of suitable dissolvable materials for the dressing include poly(lactic acid), polyglycolic acid, poly(caprolactone), poly(3-hydroxybutyrate), poly(s-caproic acid), poly(propylene fumarate), poly (sebaic anhydride), poly(maleic anhydride), poly(ethenol), poly(dioxanone), polyglactin 910, starch or starch derivatives, collagen, chitosan, or mixtures thereof. In some embodiments, the dressing is composed of starch foam that slowly dissolves upon contact with the antimicrobial composition.

In some embodiments, the dressing further comprises one or more additives (for example, urea and/or DMSO). The addition of an additive may be necessary to aid in binding of the antimicrobial composition to the dressing or to aid in release of the antimicrobial composition from the dressing into the site of a wound and/or infection. The addition of an additive may also be necessary to favorably change the material properties of the dressing or to enhance binding of the dressing to the site of a wound and/or infection to ensure sufficient delivery of the antimicrobial composition.

In some embodiments, a permeation enhancer is added to the dressing. Permeation enhancers are compounds that increase the level of permeation of the antimicrobial composition provided from the dressing into the layers of the biofilm and any under- or overlaying tissues. Examples of appropriate permeation enhancers include, but are not limited to, ethanol, polyethylene glycol, isopropyl myristate, glycerol trioleate, linolenic acid, glycerol monooleate, glycerol monolaurate, n-decyl alcohol, capric acid, and fatty acid esters, fatty acid alcohols, fatty acid monoglycerides, fatty acid acetates, fatty acid diethanolamides, fatty acid N,N-dimethylamides, and combinations thereof.

In some embodiments, a tissue adhesion agent is added to the dressing. In some applications, adhesion of the dressing would be desirable to ensure sufficient delivery of one or more compounds of the present invention contained in the antimicrobial composition to the biofilm. In many cases, the components of the dressing when impregnated with the antimicrobial composition will have enough adhesion properties to provide sufficient adherence to the tissue containing the infectious biofilm. Such adhesion may not be enough to provide proper support of the dressing on the infected tissue, necessitating the addition of additional tissue adhesion agents. Examples of appropriate adhesion agents include, but are not limited to, hydroxypropylmethylcellulose, carboxymethylcellulose, polylactide-co-glycolide, chitosan, chitosan ester or trimethylenechloride chitosan, sodium alginate, poloxamer, Carbopol, pectin, polyacrylic acid, hyaluronic acid, polyvinyl alcohol, polyvinylpyrrolidone, polycarbophil, and mixtures thereof.

In some embodiments, a plasticizer is added to the dressing. Addition of a plasticizer may be appropriate in order to soften and increase the flexibility of the components of the dressing in certain applications. The improved softness and flexibility increases the number of locations the dressing can be placed within the living host. Some examples of appropriate plasticizers include, but are not limited to, glycerin, water, polyethylene glycol, propylene glycol, sorbitol, and triacetin. Plasticizers are typically added in an amount from about 5% to about 25% by weight.

In certain embodiments, the dressing is designed for placement in a body cavity, for example the external auditory canal so that it might treat infections therein.

In some embodiments, the dressing is of such a size and shape as to fit within the external auditory canal.

In another embodiment, the dressing is malleable such that it can be compressed before placement in the ear, followed by subsequent re-expansion once properly placed.

In another embodiment, the dressing for placement in the external auditory canal is composed of a polymer foam of sufficient porosity to allow intercalation and efflux of the antimicrobial composition described herein.

The compounds of the present invention may be incorporated in liquid or solid carriers to yield products with antimicrobial properties. The liquid products may be in the form of a lotion.

Compounds of this invention may be added uniformly to thermoplastic polymer products which are extruded (including fibers and tubes) or molded (e.g., supports and scaffolds), or the products may only be protected by coatings containing a organosilicon quaternary ammonium compound described herein. These thermoplastic products may be rigid or flexible; hydrophobic or hydrophilic depending on the dressing required for a given wound. Fibers made using the above process may be converted to yarns, fabrics, scaffolds, etc.; and the organosilicon quaternary ammonium compound-containing product (e.g., fibers) can be combined with other non-antimicrobial-containing product (e.g., fibers) to obtain a final product with a desired level of antimicrobial activity at reduced cost. The materials may also be biocompatible polymers which may remain in the body or decompose to harmless products as healing progresses.

For thermoset polymers the organosilicon quaternary ammonium compound containing materials of the present invention may be combined with monomeric formulations and then these may be used for molding, casting or coating, etc. The monomers or a part of the monomeric composition may also provide biodegradability to the thermosetting polymer. Curing of any of the thermoset materials/products may be done thermally or by radiation (UV, microwaves, etc).

An organosilicon quaternary ammonium compound of this invention may be added to a variety of solvent (including water)-borne coating formulations, and articles of manufacture coated with these, where the coating is solidified by removing the solvent and/or by curing. One may also fabricate sutures and wound dressings (including burn dressings) using the compounds of the present invention. Sutures, dressings, or other antimicrobial products and materials used to make final dressings, may consist of fibers, yarns, fabrics, foams, etc. These may be made by incorporating particles containing compounds of this invention into them. One way of such incorporation is to mix a compound of this invention in the polymer and then extrude fibers containing the organosilicon quaternary ammonium compound. These fibers could then be used to make yarns which may be sued as antimicrobial sutures or converted to antimicrobial fabrics for wound dressings or other uses. The antimicrobial fibers may even be converted directly into non-woven fabrics. Antimicrobial fibers may even be mixed with non-antimicrobial fibers to still give an overall antimicrobial character to the products by using these blends. Antimicrobial dressings may also be formed by soaking fibers, yarns, gauze, fabrics and flexible open cell foams in aqueous solutions containing an organosilicon quaternary ammonium compound, removing excess liquids and drying these so that antimicrobial coatings are formed on them. When rigid foams or closed cell foams are used, it is preferred that the antimicrobial material is incorporated into the resin. Products containing antimicrobial materials made by the earlier process may be coated further with additional antimicrobial agents. One may also coat objects using powder coating a well-known technique, where a solid polymeric powder (with a organosilicon quaternary ammonium compound of the present invention incorporated in this polymeric powder) is applied on an object. The object is then heated to melt the powder to form a coating which is then solidified by curing (due to continued heating or a radiation treatment-such as UV) or by cooling of this coating.

Another area of application is antimicrobial adhesives (including pressure sensitive adhesives). These adhesives may also be biodegradable. These adhesives may be used as a component in the wound dressing or they may be used directly on the wounds. The antimicrobial additives (for example, urea and/or DMSO) of this invention are preferably added to these when they are in the liquid state.

The organosilicon quaternary ammonium compound of this invention may also be used for dental work. These include applications such as dental adhesives, sutures, primers, sealants and composite fillings and products such as dentures (including antimicrobial solutions to treat dentures), crowns, bridges and coatings including coatings on implants. The methods of incorporating organosilicon quaternary ammonium compounds of this invention in solutions, sealants/adhesives and coatings for dental applications are very similar to those employed for other applications discussed throughout this patent application.

In another example, antimicrobial foams are used in wound dressings so that they would absorb any fluids exuding from the wounds and also ensure that these fluids do not promote colonization of microbes both to prevent infection from spreading and also to act as a deodorant. These antimicrobial foams may be formed by adding an organosilicon quaternary ammonium compound described herein to the monomers or materials which are used to produce this foam, or by first forming the foam, then treating (e.g., soaking and squeezing) the foam with a liquid composition comprising these particles so that they are trapped in the pores or attach to their surfaces.

Other embodiments of products formed from the organosilicon quaternary ammonium compounds of the present invention include topical creams and liquid suspensions/solutions for both pharmaceutical (e.g., wound care, skin infection care, etc) and consumer product use (e.g., personal care products). They can impart one or both of antimicrobial and/or preservative properties. Preservative property typically means to preserve the product from spoiling under storage conditions-which may go bad due to bacterial and/or fungal growth. The organosilicon quaternary ammonium compounds of this invention may be added to either hydrophilic or hydrophobic cream compositions. As an example, materials compatible with petroleum jelly (a hydrophobic material), may be an appropriate surfactant or a polymer.

The wound dressings may be formed by laminating or combining various layers where each layer provides different functions. A few or all of these layers contain an organosilicon quaternary ammonium compound described herein. The feel or the drape of the dressings and their adhesion properties to the wounds may be modified by adding non-toxic surfactants, glycols, fatty acids and oils, etc. to the compositions containing antimicrobial particles. These dressings may have other medications or additives also incorporated in them (e.g., analgesics) in a post treatment or by adding them to the same solution which contains the organosilicon quaternary ammonium compound. The additives may further include materials which provide enhanced transport of the organosilicon quaternary ammonium compound through the mucus membranes, since the mucus agents form biofilms to protect the bacteria and spores within them. Examples of some materials which penetrate mucus effectively include glucose and xylitol.

A lotion composition for wound management, comprising conventional Povidone-iodine (i.e., PVP-Iodine) could be enhanced by adding an organosilicon quaternary ammonium compound of this invention. As a specific example, aqueous topical solutions of PVP and iodine (where iodine is about 8 to 12% by weight of the PVP) are commonly used as disinfectants for wounds and for disinfecting skin prior to surgery. As an example, BETADINE® is a commercially available PVP-iodine solution. Povidone-iodine (PVP-I) is a stable chemical complex of PVP and elemental iodine. 10% solutions in water are commonly used as a topical antiseptic. Such a metal halide-enhanced PVP-I solution would be formulated having about 88-99% PVP, 2 to 10% Iodine, and 0.005-5% organosilicon quaternary ammonium compound on a wt/wt basis.

The organosilicon quaternary ammonium compounds of this invention may also be used as co-additives (for example, urea and/or DMSO) to other drug/topical formulations including other antibiotic creams or liquid formulations (lotions) for curing or preventing dermal/hair infection control, wound care or related purposes. Some of the typical skin/topical/hair problems caused by microbial infection relate to acne, athlete's foot, nail infections, dandruff, etc., to just name a few. The antimicrobial materials of this invention may be added in a burn cream, which while assisting the repair of burnt tissue, will also keep infection away, or it may be mixed with other antibiotics, infection reducing/prevention analgesic and wound healing materials such as bacitracin, neomycin, polymyxin, silver sulfadiazine, polyenes, selenium sulfide, zinc pyrithione and paramoxine. Many of these compositions listed above are available in commercial products, and the antimicrobial materials of this invention can be added to them to result in a concentration that is most effective.

Published US patent application 20060269485, incorporated herein by reference, teaches the uses of antibiotic kits which deliver wound care topical materials through aerosol spray and forms a coating (a wound dressing) on the sprayed area.

The organosilicon quaternary ammonium compounds may also contain an additional medicinal compounds and formulations for inclusion in a wound care product. Some examples of medicinal compounds that may be added include, but are not limited to, other antimicrobials, antibiotics, other antifungal agents, other antiviral agents, nutrients (e.g., proteins, carbohydrates, amino acids (such as glutamine, arginine), vitamins (such as A, C and E) and trace elements (such as zinc, iron and magnesium and their compounds)), anti thrombogenic agents, anesthetics, anti-inflammatory agents, analgesics, anticancer agents, vasodilation substances, other wound healing agents, angiogenic control agents, anti-pruritic agents (anti-itch agents), angiostatic agents, immune boosting agents, growth factors, epithelialization promoting materials (e.g., gentamicin sulfate) and other biological agents. Examples of suitable antimicrobial agents and antibiotics include, but are not limited to, silver preparations (silver and silver compounds (e.g. silver sulfadiazine), in solution or as nanoparticles, silver containing zeolites), elemental iodine, povidone-iodine, biguanide compounds (e.g., polyhexamethylene biguanide), such as chlorhexidine and its salts; triclosan; penicillins; tetracyclines, aminoglycosides, such as gentamicin and Tobramycin™; polymyxins; rifampicins; bacitracins; erythromycins; vancomycins; neomycins; chloramphenicols; neomycin; polyenes; selenium sulfide; zinc pyrithione; paramoxine, maltodextrin; azoles including miconazoles; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds may provide for enhanced antimicrobial activity. Some natural wound healing materials are acemannan, chitosan, collagen, honey (e.g., medical honey, Manuka honey), sugar, etc. Depending on the formulation and the delivery method used, some of these products may be produced to treat humans or animals as a whole (e.g., by oral administration, injection, etc).

Antimicrobial Hand Sanitizer

In some embodiments, the quaternary ammonium compounds of the present invention may be formulated as an antimicrobial hand sanitizer.

In some embodiments, a method is provided comprising administering an effective amount of a quaternary ammonium compound, or composition thereof described herein to provide enhanced antimicrobial activity to the surface of the skin. An effective amount is the amount of antimicrobial hand sanitizer that kills at least about 90 percent of the bacteria or virus on the surface of the skin where the hand sanitizer is applied.

The antimicrobial hand sanitizer may optionally include several other components in various embodiments.

In some embodiments, the antimicrobial hand sanitizer optionally includes a thickener at from about 0.01 to about 2 weight percent. In some embodiments, a thickener may be present at from about 0.01 to about 1 weight percent or from about 0.01 to about 0.5 weight. The thickener is used to increase the viscosity of the hand sanitizer to produce a gel or a gel-type hand sanitizer. Thickeners can be organic or inorganic. Non-limiting examples of organic thickeners include: (1) cellulosic thickeners and their derivatives, including but not limited to carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, and sodium cellulose sulfate; (2) natural gums, including but not limited to the gums of acacia, calcium carrageenan, guar, gelatin, hydroxypropyl guar, karaya, kelp, locust bean, pectin, sodium carrageenan, tragacanth, and xanthan; (3) acrylates, including but not limited to polyacrylic acid copolymer, potassium aluminum polyacrylate, sodium acrylate/vinyl alcohol copolymer, and sodium polymethacrylate; (4) starches, including but not limited to oat flour, potato starch, wheat flour, and wheat starch; (5) stearates, including but not limited to methoxy polyethylene glycol (PEG)-22/dodecyl glycol copolymer, PEG-2M, and PEG-5M; and (6) fatty acid alcohols, including but not limited to caprylic alcohol, cetearyl alcohol, lauryl alcohol, stearyl alcohol, oleyl alcohol, cetyl alcohol, and palm kernel alcohol. Non-limiting examples of inorganic thickeners include: (1) clays, including but not limited to bentonite, magnesium aluminum silicate, magnesium trisilicate, stearalkonium bentonite, and tromethamine magnesium aluminum silicate; and (2) salts, including but not limited to calcium chloride, sodium chloride, sodium sulfate, and ammonium chloride. In some embodiments, waxes and oils can also be used as thickeners. Non-limiting examples of waxes include candelilla wax, carnauba wax, and beeswax, and non-limiting examples of oils include vegetable oils and animal oils.

In some embodiments, the antimicrobial hand sanitizer optionally includes an alcohol at from about 50 weight percent to about 95 weight percent. Alcohols can serve as an antimicrobial agent when present at concentrations of about 50 weight percent, or about 60 weight percent, or about 75 weight percent or more. Alcohols kill many bacteria that are resistant to various antibiotics, and alcohols can also kill many types of viruses and fungi. However, alcohols are not effective against all bacteria and virus. In some embodiments, the antimicrobial hand sanitizer may optionally include water at from about 5 to about 40 weight percent, based on the total weight of the hand sanitizer. In some embodiments, water may be present at from about 5 to about 30 weight percent or from about 10 to about 30 weight percent or from about 15 to about weight percent, based on the total weight of the hand sanitizer. In some embodiments, the antimicrobial hand sanitizer may optionally include one or more skin conditioners. In some embodiments, the skin conditioner may be present at from about 0.1 to about 5 weight percent. In some embodiments, the skin conditioner may be present at from about 0.1 to about 2 weight percent, or from about 0.5 to about 2 weight percent, based on the total weight of the hand sanitizer. Several different compounds may serve as skin conditioners, wherein the skin conditioner is a moisturizer that helps to soften skin or to treat dry skin. A skin conditioner increases the ability of the skin to hold water, and this provides the skin with a layer of oil to prevent water loss and to lubricate the skin. Non-limiting examples of skin conditioners include: octyl isononanoate; cetyl myristate; glyceryl dioleate; methyl laurate; PPG-9 laurate; soy stearyl; octyl palmitate; PPG-5 lanoate; lanolin; propylene glycol; glycerine; fatty acids; natural oils such as almond, mineral, canola, sesame, avocado, balm mint, cod liver, soybean, wheat germ, corn, peanut, vegetable, and olive; isopropyl myristate; myristyl alcohol; aloe vera; hydrolyzed silk protein; vitamin E; stearyl alcohol; isopropyl palmitate; sorbitol; amino acid complexes; polyethylene glycol; agarose; arginine PCA; fructose; glucose; glutamic acid; honey; lactose; maltose; methicone; phenyl trimethicone; trimyristin; stearyl stearate; synthetic wax; cholesterol; cystine; keratin; lecithin; egg yolk; glycine; PPG-12; retinol; salicylic acid; orotic acid; vegetable oil; and others.

In some embodiments, the antimicrobial hand sanitizer may optionally include one or more fragrances. As used herein, "fragrance" is a chemical compound that humans can detect by smell, where the fragrance is added to the hand sanitizer to impart a pleasant smell. In some embodiments, the fragrance may be present in the antimicrobial hand sanitizer at from about 0 to about 5 weight percent. In some embodiments, the fragrance may be present in the antimicrobial hand sanitizer at from about 0.01 to about 5 weight percent, or from about 0.01 to about 3 weight percent, or from about 0.01 to about 0.5 weight percent, based on the total weight of the hand sanitizer. Non-limiting examples of compounds that impart a fragrance include: natural extracts, oils, resinoids, resins, and/or essences which may include one or more of many different constituents, such as orange, lemon, rose, nutmeg, lavender, musk, patchouli, balsam, sandalwood, pine, cedar, and cassia; 7-acetyl-1, 2, 3, 4, 5, 6, 7, 8-octahydro-1, 1, 6, 7-tetramethylnaphthalene, -ionone, β-ionone, γ-ionone, a-isomethylionone; methyl cedryl ketone; methyl dihydrojasmonate; methyl 1, 6, 10-trimethyl-2, 5, 9-cyclododecatrien-1-yl ketone; 4-acetyl-6-tert-butyl-1, 1-dimethylindane; hydroxyphenylbutanone; benzophenone; methyl 0-naphthyl ketone; 6-acetyl-1, 1, 2, 3, 3, 5-hexamethylindane; 5-acetyl-3-isopropyl-1, 1, 2, 6-tetramethylindane; 1-dodecanal; 4-(4-hydroxy-4-methylpentyl)-3-cyclohexene-1-carboxaldehyde; 7-dimethyloctanal; 10-undecen-1-al; isohexenylcyclohexylcarboxaldehyde; formyl tricyclodecane; condensation products of hydroxycitronellal and methyl anthranilate; condensation products of hydroxycitronellal and indole; condensation products of phenylacetaldehyde and indole; 2-methyl-3-(para-tert-butylphenyl) propionaldehyde; ethylvanillin; heliotropin; hexylcinnamaldehyde; amylcinnamaldehyde; 2-methyl-2-(isopropylphenyl) propionaldehyde; coumarin; decalactone-γ; cyclopentadecanolide; 16-hydroxy-9-hexadecenolactone; 1, 3, 4, 6, 7, 8-hexahydro-4, 6, 6, 7, 8, 8-hexamethylcyclopenta-Y-2-benzopyran; β-naphthol methyl ether; ambroxan; 5-(2,2,3-trimethylcyclopent-3-enyl)-3-methylpentan-2-ol; 2-ethyl-4-(2, 2, 3-trimethyl-3-cyclopenten-1-yl)-2-buten-1-ol; caryophyllene alcohol; tricyclodecenyl propionate; tricyclodecenyl acetate; benzyl salicylate; cedryl acetate; tert-butyleyelohexyl acetate; and many other compounds.

Wounds

A particular aspect provided herein is the use of the compounds described herein for the treatment of a wound or burn. A compound described herein can be contained in a lotion, ointment, liquid, gel, film or other type of carrier for direct application to the wound. In an alternative aspect, a compound described herein can be contained in a dressing, foam, wrap, bandage, gauze, film, packing, or other material as described above, wherein the material is applied to or used to cover the wound or burn. In some embodiments, a compound described herein is contained in a material applied to or used to cover the wound or burn and is released into the wound, for example, in a controlled release manner.

Types of wounds that can be treated include a chronic wound, for example but not limited to, a pressure ulcer, venous ulcer, arterial wound, neuropathic ulcer, diabetic ulcer, for example a lower limbic ulcer or foot ulcer, skin tear, or moisture-associated skin damage (MASD), for example incontinence-associated dermatitis. In some embodiments, the compounds described herein are used to treat a wound caused by a burn.

Pressure ulcers (also known as pressure injuries) are defined by the National Pressure Ulcer Advisory Panel (NPUAP) as localized damage to the skin and/or underlying soft tissue, usually over a bony prominence or related to a medical or other device. The injury can present as intact skin or an open ulcer and may be painful. The injury results from intense and/or prolonged pressure or pressure combined with shear. The tolerance of soft tissue for pressure and shear may also be affected by microclimate, nutrition, perfusion, comorbidities, and condition of the soft tissue. Pressure ulcers are described according to the NPUAP staging system based on damage that is clinically observed.

Venous ulcers are related to incompetence of the valves of the lower extremities, allowing blood to reflux into the superficial venous system and causing edema. Incomplete emptying of the deep veins can result in higher-than-normal pressure in the peripheral venous system of the lower extremities, which can eventually result in ulcerations.

Arterial wounds result from severe tissue ischemia. One of the most common causes of lower extremity arterial disease and ulceration is atherosclerosis of peripheral arterial vessels. Diabetic foot wounds are also called neuropathic ulcers. Peripheral neuropathy is present in over 80% of patients with foot ulcers. Neuropathy promotes ulcer formation by altering both pain sensation and pressure perception in the foot. Neuropathy can also alter the microcirculation and impair skin integrity. Once wounds occur, healing may be difficult to achieve, especially in patients with deep tissue or bone infections and in those with diminished blood flow to the foot.

A skin tear is defined by the International Skin Tear Advisory Panel (ISTAP) as a traumatic wound caused by mechanical forces (shear, friction, or blunt force), such as the mechanical force required to remove adhesives. Severity may vary by depth but does not extend through the subcutaneous layer. Skin tears are classified based on the degree of skin damage: Type 1: no skin loss; a skin flap can be positioned to cover the exposed wound base; Type 2: partial loss of the skin flap; Type 3: total loss of the skin flap; entire wound bed is exposed.

Moisture-associated skin damage (MASD) is defined as the inflammation and erosion of the skin that accompanies exposure to many different types of moisture, such as urine, perspiration, and wound drainage.15,16 Chronic exposure to moisture macerates the skin, impairing its protective mechanisms and disrupting normal skin flora, which can predispose the patient to cutaneous infections such as candidiasis. Incontinence-associated dermatitis (IAD), a subtype of MASD, is caused by chronic exposure to urine and/or liquid stool.

Acne Vulgaris

Acne is a common skin disease that occurs when hair follicles become clogged with dead skin cells and oil from the skin. Acne vulgaris severity may be classified as mild, moderate, or severe. Mild acne is classically defined by the presence of clogged skin follicle (known as comedones) limited to the face with occasional inflammatory lesions. Moderate acne occurs when a higher number of inflammatory papules and pustules occur on the face, with some being found on the trunk of the body. Severe acne occurs when nodules are the characteristic facial lesions and involvement of the trunk is extensive.

Mild acne is classically defined by the presence of clogged skin follicle (known as comedones) limited to the face with occasional inflammatory lesions. Moderate acne occurs when a higher number of inflammatory papules and pustules occur on the face, with some being found on the trunk of the body. Severe acne occurs when nodules are the characteristic facial lesions and involvement of the trunk is extensive.

Typically, acne is caused by colonization of the follicle and excessive outgrowth of *Propionibacterium acnes* bacteria and inflammation induced in response to the *P. acnes* bacteria. While less common, *Staphylococcus epidermidis* can also cause acne. The earliest pathological change involves the formation of a microcomedone due to the accumulation of skin cells in the hair follicle, which mix with oily sebum to block the follicle, a process further exacerbated by the presence of the *P. acnes* biofilm. If the microcomedone is superficial, melanin within the plug oxidizes upon exposure to air, forming a blackhead or open comedo. If the microcomedone is deeper within the hair follicle, a whitehead or closed comedo forms.

*Propionibacterium acnes* (reclassified as Cutibacterium acnes in 2016) is a Gram-positive bacterium (rod) linked to acne that belongs to the Cutibacterium Genus and the Propionibacteriaceae Family. Typically, slow-growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately lives deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris.

The presence of *P. acnes* induces skin inflammation due to the bacteria's ability to bind to toll-like receptors (TLRs), especially TLR2 and TLR4 and by altering the fatty composition of the oily sebum by oxidizing squalene. The subsequent inflammatory cascades lead to the formation of inflammatory acne lesions such as papules, pustules, or nodules. If the inflammatory reaction is very severe, the follicle will break into the dermis and subcutaneous tissue as a deep nodule, leading to local tissue destruction and scarring.

*Staphylococcus epidermidis* is a Gram-positive bacterium belonging to the *Staphylococcus* Genus and the Staphylococcaceae Family that is part of the normal human flora and typically skin flora or mucosal flora. It is a facultative anaerobic bacterium and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

Traditionally, acne is classified as either non-inflammatory (open/closed comedones) or inflammatory (papules, pustules, or nodules). Mounting evidence indicates that inflammation exists throughout the entire duration of the acne lesion lifecycle, establishing the critical role of inflammation in the pathology of acne. In the earliest stages of acne lesion development, CD3+ T cell, CD4+ T cell, and macrophage populations are elevated, while the levels of the pro-inflammatory cytokine interleukin-1 are also upregulated. Initiation of inflammatory events have been documented even before clinical detection of acne lesions.

In certain embodiments, one or more of the quaternary ammonium compounds of the present invention may be used to treat a dermatological disorder, caused by gram-positive bacterium, gram-negative bacterium, described herein.

In certain embodiments, a method is provided comprising administering an effective amount of a quaternary ammonium compound, or composition thereof described herein to treat aa dermatological disorder caused by gram-positive, gram-negative bacterium, described herein.

In certain embodiments, the dermatological disorder is acne vulgaris or cystic acne.

In certain embodiments, the compounds described herein may be used in the topical compositions and methods provided herein, having anti-microbial effects that help alleviate the symptoms of acne vulgaris and treats the underlying overgrowth of bacterial that cause acne, for example, the bacterium *Propionibacterium acnes* or *Staphylococcus epidermidis*. In certain embodiments, the compounds provided herein, may be applied in topical formulation in any amount that achieves the desired effect. In certain non-limiting examples, the weight percentage of the active compound in the topical formulation is from about 0.1% to about 50%, or from about 0.1% to about 40%, or about 1% to about 30%, or from about 2, 3, 4 or 5% to about 20%, or between about 5% to about 10%. Examples include at least about 0.5, 1, 2, 3, 4, 5, 10 or 15% by weight.

In certain embodiments, treatment of an infection comprises placing the topical composition containing one or more quaternary ammonium compounds of the present invention at the site of infection. The length of time that the quaternary ammonium compound, or composition is applied is such that antimicrobial treatment is still effective or the infection has resolved. The treatment may be applied continuously, with concurrent successive applications after an appropriate time frame, or in alternation with another treatment for the infection after an appropriate time frame. The quaternary ammonium compounds described herein may be applied at the site of infection in a host at the appropriate interval as determined by a healthcare provider.

In some embodiments, the quaternary ammonium compounds described herein are placed at the site of infection for a day or less. In other embodiments, the quaternary ammonium compounds described herein are placed at a site of infection for a week or more.

In certain embodiments, the method of treatment can be administered once a day (q.d.), twice a day (b.i.d.), three times a day (t.i.d.), four times a day (q.i.d.), once every other day (Q2d), once every third day (Q3d), as needed, or using any dosing schedule that provides treatment of an infection as described herein.

In certain embodiments, a method is provided for the treatment of acne vulgaris in a human comprising administering a topical formulation containing, either alone or in combination with an effective amount of an antibiotic.

In certain embodiments, a topical formulation is also provided for the treatment of acne vulgaris comprising administering an effective amount of a compound described herein, or its pharmaceutically acceptable salt and a topically acceptable carrier.

In certain embodiments, an antimicrobial composition is also provided for the treatment of acne vulgaris comprising administering an effective amount of a compound described herein, or its pharmaceutically acceptable salt and a topically acceptable carrier.

In certain embodiments, the compounds described herein can be administered to a human in need thereof as a neat chemical, but are more commonly administered as a topical formulation that includes an effective amount of a compound described herein, or its pharmaceutically acceptable salt, for a human in need of treatment of acne vulgaris.

In certain embodiments, the disclosure provides topical formulations comprising an effective amount of a compound described herein, or its pharmaceutically acceptable salt, together with at least one topically acceptable carrier for any of the uses described herein. The topical formulation may contain a compound or salt as the only active ingredient, or, in an alternative embodiment, the compound and at least one additional active agent.

In certain embodiments, an effective amount of a compound as described herein, or the compound described herein in combination or alternation with, or preceded by, concomitant with or followed by another active agent, can be used in an amount sufficient to (a) inhibit the progression of acne vulgaris; (b) cause a regression of acne vulgaris; (c) cause a cure of acne vulgaris; or inhibit or prevent the development of acne vulgaris. Accordingly, an effective amount of a compound or its salt or composition described herein will provide a sufficient amount of the agent when administered to a human to provide a desired benefit.

Topical formulations are classified into three major categories: solid forms (such as dusting powders); liquid forms (such as lotions and liniments); and semi-liquid forms (such as ointments, pastes, creams, and gels). Additives or excipients (for example, urea and/or DMSO) are used as inactive ingredients in topical formulations for structuring. The main use of topical formulation additives are to control the extent of absorption of the active compound, maintaining the viscosity, improving the stability and organoleptic properties, and increasing the bulk of the formulation. The main goal of topical formulations is to confine the desired effect to the skin or within the skin. Such formulations are preferred because they are protective, emollient, and deliver the active agent to exert local activity when applied to the skin or mucous membranes.

In certain embodiments, the topical formulation is a solid formulation such as a dusting powder. A dusting powder is a finely divided insoluble powder containing ingredients used on skin especially for allaying irritation or absorbing moisture, discouraging bacterial growth and providing lubricant properties. Easy powder flow ability and spreadability are important parameters that are considered in the manufacture and evaluation of a dusting powder formulation. The dusting powder should adhere to the skin, provide good coverage and skin adsorption, should be free of irritant properties, and should protect the skin from drying and irritation. Representative examples of excipients that can be used in dusting powder formulations include, but are not limited to, talc, starch (such as corn starch, wheat starch, or potato starch), kaolin, zinc stearate, zinc oxide, aluminum chlorohydrate, aluminum zirconium chlorhydrex, micronized wax, and chlorhexidine (as the acetate, gluconate, or hydrochloride salt).

In certain embodiments, the topical formulation is a cream formulation. Creams are semisolid emulsion formulation for application to the skin or mucous membranes. Creams may be formulated as water in oil (w/o) emulsions or as oil in water (o/w) emulsions. Water in oil emulsion creams are less greasy and provide good spreadability compared to ointments. Oil in water emulsion creams, often called vanishing creams, readily rub into the skin and are easily removed by water.

Water in oil emulsion formulations typically consist of a hydrophilic component, e.g. water or other hydrophilic diluent, and a hydrophobic component, e.g. a lipid, oil, or oily material. The hydrophilic component is typically dispersed, i.e. exists as small particles and droplets, within the hydrophobic component. Water in oil emulsions typically comprise from about 1% to about 98% of the dispersed hydrophilic phase and from about 1% to about 50% of the hydrophobic phase. Additives commonly used in water in oil emulsion formulations include wool fat (containing sterols, cholesterol, oxycholesterol, triterpene, or aliphatic alcohols), waxes, bivalent soaps, sorbitan esters, borax, and oleic acid. In some embodiments, the water in oil emulsion refers to a water in silicone emulsion.

Oil in water emulsion formulations typically consist of a hydrophilic component, e.g. water or other hydrophilic diluent, and a hydrophobic component, e.g. a lipid, oil, or oily material. The hydrophobic component is typically dispersed, i.e. exists as small particles and droplets, within the hydrophilic component. Water in oil emulsions typically comprise from about 1% to about 98% of the hydrophilic phase and from about 1% to about 50% of the dispersed hydrophobic phase. Additives commonly used in oil in water emulsion formulations include polysorbates (such as Tween 80, Tween 21, and Tween 40), methylcellulose, acacia, tragacanth, triethanolamine oleate, arachis oil, and cetostearyl alcohol.

In certain embodiments, the topical formulation is an ointment formulation. Ointments are greasy semisolid preparations of a dissolved or dispersed active compound. Ointment bases often influence topical drug bioavailability due to their occlusive properties of the stratum corneum, which enhances the flux of drug across the skin and affects drug dissolution or partitioning within and from the ointment to the skin. Ointments usually are moisturizing and are good for dry skin, as well as having a low risk of sensitization or irritation due to having few ingredients beyond the base oil or fat. The vehicle for an ointment formulation, known as an ointment base, may be an oleaginous base, an absorption base, or a water-soluble base.

Oleaginous bases are composed entirely of lipophilic materials. They are anhydrous, insoluble in water, and not easily removable with water. Oleaginous bases are inexpensive, non-reactive, nonirritating, are good emollients, have protective and occlusive properties, and are not water washable. Representative examples of oleaginous bases include hydrocarbons (such as petrolatum, paraffin wax, liquid paraffin, microcrystalline wax, plastibase, or Ceresi), vegetable oils and animal fat (such as coconut oil, bees wax, olive oil, lanolin, peanut oil, spermaceti wax, sesame oil, or almond oil), hydrogenated and sulfated oils (such as hydrogenated castor oil, hydrogenated cotton seed oil, hydrogenated soya bean oil, hydrogenated corn oil, or hydrogenated sulfated castor oils), alcohols/acids/esters (such as cetyl alcohol, stearic acid, stearyl alcohol, oleic acid, olelyl alcohol, palmitic acid, lauryl alcohol, lauraic acid, myristyl alcohol, ethyl oleate, isopropyl myristicate, or ethylene glycol), and silicones (such as dimethylpropylsiloxanes, methyl phenyl polysiloxanes, and steryl esters of dimethyl polysiloxanes).

Absorption bases are known to take up several times their own weights in water but not permit absorption of medicament form the base. The advantages of absorption bases are their protective, occlusive, and emollient properties, their ability to absorb liquids, and that they do not wash off easily so they hold the incorporated compound with sufficient contact with the skin. Representative examples of absorption bases include hydrophilic petrolatum and anhydrous lanolin.

Water-soluble bases, also known as greaseless ointment bases, consists of water-soluble ingredients such as polyethylene glycol polymer (carbowax). Polyethylene glycol is water soluble, nonvolatile, and inert. Other water-soluble bases include glyceryl monostearate, cellulose derivatives, sodium alginate, bentonite, and carbopol 934.

In certain embodiments, the topical formulation is a gel formulation. Gels are transparent or translucent semisolid preparations of one or more active ingredients in suitable hydrophilic or hydrophobic bases. Gels may be clear or opaque, and polar hydroalcoholic or nonpolar. Gels are prepared by either a fusion process or a special procedure necessitated by the gelling agents, humectants, and preservatives. Gelling agents exhibit pseudoplastic properties that give the formulation a thixotropic consistency. Gelling agents are typically used in concentrations of 0.5-10% to allow for easy addition of the active drug before the gel is formed. Representative examples of agents used in gel formulations include tragacanth, fenugreek mucilage, methyl cellulose, hydroxy ethyl cellulose, hydroxy propyl cellulose, hydroxy propyl methyl cellulose, carboxy methylcellulose, carbopol, pectin, poloxamers, alginates (such as sodium, potassium, or ammonium alginates), gelatin, starch, polyvinyl alcohol, povidone, propylene glycol, and ethyldiamine tetraacetic acid.

In some embodiments, the topical formulation is a paste formulation. Pastes are stiff preparations containing a high proportion of a finely powdered solid such as starch, zinc oxide, calcium carbonate, or talc. Pastes are often less greasy than ointment formulations.

In some embodiments, the topical formulation is a lotion formulation. Lotions are low- to medium-viscosity preparations intended for application to unbroken skin. Lotions are applied to external skin with bare hands, a clean cloth, cotton wool or gauze. Lotions provide cooling effects to the skin by the evaporation of solvents formulated therein. Typical additives in lotion formulations include bentonite, sodium carboxymethylcellulose, alcohols, and glycerin.

In some embodiments, the topical formulation is a liniment formulation. Liniments are liquid or semiliquid preparations meant for application to the skin with friction or rubbing. They act as a rubefacient, soother, or stimulant. Typical vehicles for liniment formulations are alcohol, oil, or soap based. Typical additives in a liniment formulation include castor oil, cotton seed oil, peanut oil, sesame oil, and oleic acid.

A wide variety of optional components/ingredients may be included in the topical formulations including, but not limited to, absorbents, abrasives, anticaking agents, antifoaming agents, antimicrobial agents, binders, biological actives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-inflammatory agents, anti-androgens, depilation agents, desquamation agents/exfoliants, organic hydroxy acids, vitamins and derivatives thereof, and natural extracts.

The present method includes identifying a target portion of skin affected with acne vulgaris and in need of treatment and applying a compound or its salt or composition as described herein to the target portion of skin. In certain embodiments, the target portion of skin may not appear to be suffering from acne vulgaris, i.e. the compound or its salt or composition as described herein may be used as a preventative therapy for acne vulgaris. The compound or its salt or composition may be applied to the target skin portion and, if desired, to the surrounding skin at least once a day, twice a day, or on a more frequent daily basis during the treatment period. Typically, the compound or its salt or composition is applied in the morning and/or in the evening before bed.

The treatment period is ideally sufficient time for the active compound to reduce or eliminate the appearance of acne vulgaris on the target portion of skin. The treatment period may last for at least 1 week, about two weeks, about 4 weeks, about 8 weeks, or about 12 weeks. The treatment period may extend over multiple months (about 3-12 months) or multiple years. The step of applying the compound or its salt or composition may be accomplished by localized application, i.e. by applying to the targeted area while minimizing delivery to skin surfaces where treatment is not desired, or by applying more generally or broadly to one or more skin surfaces.

Eczema

Atopic dermatitis (AD) also known as eczema, is the most common allergic skin disease in the general population. It is a chronic inflammatory skin disease complicated by recurrent bacterial and viral infections that, when left untreated, can lead to significant complications. The current article will review immunologic and molecular mechanisms underlying the propensity of AD patients to microbial infections. These infections include *Staphylococcus aureus* (*S. aureus*) skin infections, eczema herpeticum, eczema vaccinatum, and eczema coxsackium.

More recent studies suggest that skin microbiome including *Staphylococcus epidermidis* or other coagulase-negative staphylococci may play an important role in controlling *S. aureus* skin infections in AD. Other studies also suggest that genetic variants in the innate immune response may predispose AD patients to increased risk of viral skin infections. (Ong P Y et al., "Bacterial and Viral Infections in Atopic Dermatitis: a Comprehensive Review.", Clin Rev Allergy Immunol., 2016, 51(3), 329-337; DOI: 10.1007/s12016-016-8548-5; InformedHealth.org [Internet]. Cologne, Germany: Institute for Quality and Efficiency in Health Care (IQWiG); 2006. Eczema: Overview. 2013 Sep. 26 [Updated 2017 Feb. 23]. Available from: https://www.ncbi.nlm.nih.gov/books/NBK279399/) In certain embodiments, treatment of an infection comprises placing the topical composition containing one or more quaternary ammonium compounds of the present invention at the site of infection. The length of time that the quaternary ammonium compound, or composition is applied is such that antimicrobial treatment is still effective or the infection has resolved. The treatment may be applied continuously, with concurrent successive applications after an appropriate time frame, or in alternation with another treatment for the infection after an appropriate time frame. The quaternary ammonium compounds described herein may be applied at the site of infection in a host at the appropriate interval as determined by a healthcare provider.

In some embodiments, the quaternary ammonium compounds described herein are placed at the site of infection for a day or less. In other embodiments, the quaternary ammonium compounds described herein are placed at a site of infection for a week or more.

In certain embodiments, the method of treatment can be administered once a day (q.d.), twice a day (b.i.d.), three times a day (t.i.d.), four times a day (q.i.d.), once every other day (Q2d), once every third day (Q3d), as needed, or using any dosing schedule that provides treatment of an infection as described herein.

In certain embodiments, one or more of the quaternary ammonium compounds of the present invention may be used to treat a dermatological disorder, caused by gram-positive bacterium, gram-negative bacterium, or virus described herein.

In certain embodiments, a method is provided comprising administering an effective amount of a quaternary ammonium compound, or composition thereof described herein to treat a dermatological disorder caused by gram-positive, gram-negative bacterium, or virus described herein.

In certain embodiments, the dermatological disorder is eczema.

In certain embodiments, a topical formulation is also provided for the treatment of eczema comprising administering an effective amount of a compound described herein, or its pharmaceutically acceptable salt and a topically acceptable carrier.

In certain embodiments, an antimicrobial composition is also provided for the treatment of eczema comprising administering an effective amount of a compound described herein, or its pharmaceutically acceptable salt and a topically acceptable carrier.

In certain embodiments, the compounds described herein can be administered to a human in need thereof as a neat chemical, but are more commonly administered as a topical formulation that includes an effective amount of a compound described herein, or its pharmaceutically acceptable salt, for a human in need of treatment of eczema.

In certain embodiments, the disclosure provides topical formulations comprising an effective amount of a compound described herein, or its pharmaceutically acceptable salt, together with at least one topically acceptable carrier for any of the uses described herein. The topical formulation may contain a compound or salt as the only active ingredient, or, in an alternative embodiment, the compound and at least one additional active agent.

In certain embodiments, an effective amount of a compound as described herein, or the compound described herein in combination or alternation with, or preceded by, concomitant with or followed by another active agent, can be used in an amount sufficient to (a) inhibit the progression of eczema; (b) cause a regression of eczema; (c) cause a cure of eczema; or inhibit or prevent the development of eczema. Accordingly, an effective amount of a compound or its salt or composition described herein will provide a sufficient amount of the agent when administered to a human to provide a desired benefit.

Topical formulations are classified into three major categories: solid forms (such as dusting powders); liquid forms (such as lotions and liniments); and semi-liquid forms (such as ointments, pastes, creams, and gels). Additives or excipients are used as inactive ingredients in topical formulations for structuring. The main use of topical formulation additives are to control the extent of absorption of the active compound, maintaining the viscosity, improving the stability and organoleptic properties, and increasing the bulk of the formulation. The main goal of topical formulations is to confine the desired effect to the skin or within the skin. Such formulations are preferred because they are protective, emollient, and deliver the active agent to exert local activity when applied to the skin or mucous membranes.

In certain embodiments, the topical formulation is a solid formulation such as a dusting powder. A dusting powder is a finely divided insoluble powder containing ingredients used on skin especially for allaying irritation or absorbing moisture, discouraging bacterial growth and providing lubricant properties. Easy powder flow ability and spreadability are important parameters that are considered in the manufacture and evaluation of a dusting powder formulation. The dusting powder should adhere to the skin, provide good coverage and skin adsorption, should be free of irritant properties, and should protect the skin from drying and irritation. Representative examples of excipients that can be used in dusting powder formulations include, but are not limited to, talc, starch (such as corn starch, wheat starch, or potato starch), kaolin, zinc stearate, zinc oxide, aluminum chlorhydrate, aluminum zirconium chlorhydrex, micronized wax, and chlorhexidine (as the acetate, gluconate, or hydrochloride salt).

In certain embodiments, the topical formulation is a cream formulation. Creams are semisolid emulsion formulation for application to the skin or mucous membranes. Creams may be formulated as water in oil (w/o) emulsions or as oil in water (o/w) emulsions. Water in oil emulsion creams are less greasy and provide good spreadability compared to ointments. Oil in water emulsion creams, often called vanishing creams, readily rub into the skin and are easily removed by water.

Water in oil emulsion formulations typically consist of a hydrophilic component, e.g. water or other hydrophilic diluent, and a hydrophobic component, e.g. a lipid, oil, or oily material. The hydrophilic component is typically dispersed, i.e. exists as small particles and droplets, within the hydrophobic component. Water in oil emulsions typically comprise from about 1% to about 98% of the dispersed hydrophilic phase and from about 1% to about 50% of the hydrophobic phase. Additives commonly used in water in oil emulsion formulations include wool fat (containing sterols, cholesterol, oxycholesterol, triterpene, or aliphatic alcohols), waxes, bivalent soaps, sorbitan esters, borax, and oleic acid. In certain embodiments, the water in oil emulsion refers to a water in silicone emulsion.

Oil in water emulsion formulations typically consist of a hydrophilic component, e.g. water or other hydrophilic diluent, and a hydrophobic component, e.g. a lipid, oil, or oily material. The hydrophobic component is typically dispersed, i.e. exists as small particles and droplets, within the hydrophilic component. Water in oil emulsions typically comprise from about 1% to about 98% of the hydrophilic phase and from about 1% to about 50% of the dispersed hydrophobic phase. Additives commonly used in oil in water emulsion formulations include polysorbates (such as Tween 80, Tween 21, and Tween 40), methylcellulose, acacia, tragacanth, triethanolamine oleate, arachis oil, and cetostearyl alcohol.

In certain embodiments, the topical formulation is an ointment formulation. Ointments are greasy semisolid preparations of a dissolved or dispersed active compound. Ointment bases often influence topical drug bioavailability due to their occlusive properties of the stratum corneum, which enhances the flux of drug across the skin and affects drug dissolution or partitioning within and from the ointment to the skin. Ointments usually are moisturizing and are good for dry skin, as well as having a low risk of sensitization or irritation due to having few ingredients beyond the base oil or fat. The vehicle for an ointment formulation, known as an ointment base, may be an oleaginous base, an absorption base, or a water-soluble base.

Oleaginous bases are composed entirely of lipophilic materials. They are anhydrous, insoluble in water, and not easily removable with water. Oleaginous bases are inexpensive, non-reactive, nonirritating, are good emollients, have protective and occlusive properties, and are not water washable. Representative examples of oleaginous bases include hydrocarbons (such as petrolatum, paraffin wax, liquid paraffin, microcrystalline wax, plastibase, or Ceresi), vegetable oils and animal fat (such as coconut oil, bees wax, olive oil, lanolin, peanut oil, spermacetic wax, sesame oil, or almond oil), hydrogenated and sulfated oils (such as hydrogenated castor oil, hydrogenated cotton seed oil, hydrogenated soya bean oil, hydrogenated corn oil, or hydrogenated sulfated castor oils), alcohols/acids/esters (such as cetyl alcohol, stearic acid, stearyl alcohol, oleic acid, olelyl alcohol, palmitic acid, lauryl alcohol, lauraic acid, myristyl alcohol, ethyl oleate, isopropyl myristicate, or ethylene glycol), and silicones (such as dimethylpropylsiloxanes, methyl phenyl polysiloxanes, and steryl esters of dimethyl polysiloxanes).

Absorption bases are known to take up several times their own weights in water but not permit absorption of medicament form the base. The advantages of absorption bases are their protective, occlusive, and emollient properties, their ability to absorb liquids, and that they do not wash off easily so they hold the incorporated compound with sufficient contact with the skin. Representative examples of absorption bases include hydrophilic petrolatum and anhydrous lanolin.

Water-soluble bases, also known as greaseless ointment bases, consists of water-soluble ingredients such as polyethylene glycol polymer (carbowax). Polyethylene glycol is water soluble, nonvolatile, and inert. Other water-soluble bases include glyceryl monostearate, cellulose derivatives, sodium alginate, bentonite, and carbopol 934.

In certain embodiments, the topical formulation is a gel formulation. Gels are transparent or translucent semisolid preparations of one or more active ingredients in suitable hydrophilic or hydrophobic bases. Gels may be clear or opaque, and polar hydroalcoholic or nonpolar. Gels are prepared by either a fusion process or a special procedure necessitated by the gelling agents, humectants, and preservatives. Gelling agents exhibit pseudoplastic properties that give the formulation a thixotropic consistency. Gelling agents are typically used in concentrations of 0.5-10% to allow for easy addition of the active drug before the gel is formed. Representative examples of agents used in gel formulations include tragacanth, fenugreek mucilage, methyl cellulose, hydroxy ethyl cellulose, hydroxy propyl cellulose, hydroxy propyl methyl cellulose, carboxy methylcellulose, carbopol, pectin, poloxamers, alginates (such as sodium, potassium, or ammonium alginates), gelatin, starch, polyvinyl alcohol, povidone, propylene glycol, and ethyldiamine tetraacetic acid.

In certain embodiments, the topical formulation is a paste formulation. Pastes are stiff preparations containing a high proportion of a finely powdered solid such as starch, zinc oxide, calcium carbonate, or talc. Pastes are often less greasy than ointment formulations.

In certain embodiments, the topical formulation is a lotion formulation. Lotions are low- to medium-viscosity preparations intended for application to unbroken skin. Lotions are applied to external skin with bare hands, a clean cloth, cotton wool or gauze. Lotions provide cooling effects to the skin by the evaporation of solvents formulated therein. Typical additives in lotion formulations include bentonite, sodium carboxymethylcellulose, alcohols, and glycerin.

In certain embodiments, the topical formulation is a liniment formulation. Liniments are liquid or semiliquid preparations meant for application to the skin with friction or rubbing. They act as a rubefacient, soother, or stimulant. Typical vehicles for liniment formulations are alcohol, oil, or soap based. Typical additives in a liniment formulation include castor oil, cotton seed oil, peanut oil, sesame oil, and oleic acid.

A wide variety of optional components/ingredients may be included in the topical formulations including, but not limited to, absorbents, abrasives, anticaking agents, antifoaming agents, antimicrobial agents, binders, biological actives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-inflammatory agents, anti-androgens, depilation agents, desquamation agents/exfoliants, organic hydroxy acids, vitamins and derivatives thereof, and natural extracts.

The present method includes identifying a target portion of skin affected with eczema and in need of treatment and applying a compound or its salt or composition as described herein to the target portion of skin. In certain embodiments, the target portion of skin may not appear to be suffering from eczema, i.e. the compound or its salt or composition as described herein may be used as a preventative therapy for eczema. The compound or its salt or composition may be applied to the target skin portion and, if desired, to the surrounding skin at least once a day, twice a day, or on a more frequent daily basis during the treatment period. Typically, the compound or its salt or composition is applied in the morning and/or in the evening before bed.

The treatment period is ideally sufficient time for the active compound to reduce or eliminate the appearance of eczema on the target portion of skin. The treatment period may last for at least 1 week, about two weeks, about 4 weeks, about 8 weeks, or about 12 weeks. The treatment period may extend over multiple months (about 3-12 months) or multiple years. The step of applying the compound or its salt or composition may be accomplished by localized application, i.e. by applying to the targeted area while minimizing delivery to skin surfaces where treatment is not desired, or by applying more generally or broadly to one or more skin surfaces.

Microparticles and Nanoparticles for Use in the Present Invention

In some embodiments, a quaternary ammonium compound or product described herein is provided in the form of a microparticle or nanoparticle. The desired microparticles or nanoparticles can be formed using a method to provide pharmaceutically suitable microparticles.

In some embodiments, the microparticles or nanoparticles are dispersed in water or other pharmaceutically appropriate carrier.

In some embodiments, the microparticles or nanoparticles allow controlled release of the desired antimicrobial agent by slow dissolution of one or more quaternary ammonium compounds of the present invention in the chosen carrier or in the moisture present at the site of infection.

In some embodiments, the microparticles or nanoparticles are combined with an appropriate polymer matrix for use during processing. The appropriate polymer matrix is chosen such that the rate of dissolution of one or more quaternary ammonium compounds of the present invention into the carrier is controlled at the site of infection.

In another embodiment, the microparticles or nanoparticles are intercalated within a dressing as described herein.

Microparticles and nanoparticles can be formed using any suitable method for the formation of microparticles known in the art. Microparticles assembled with two-dimensional nanostructures, such as CNT's, can be equipped with improved mechanical and electrical properties without sacrificing permeability at the molecular level to assist in the desired placement of the compound (Kim, M., Choi, M. G., Ra, H. W., Park, S. B., Kim, Y.-J., & Lee, K. (2018). Encapsulation of Multiple Microalgal Cells via a Combination of Biomimetic Mineralization and LbL Coating. *Materials,* 11(2), 296. http://doi.org/10.3390/ma11020296).

The method employed for particle formation will depend on a variety of factors, including the characteristics of one or more quaternary ammonium compounds of the present invention, as well as the desired particle size and size distribution. The type of compound being incorporated into the microparticles may also be a factor as some compositions are unstable in the presence of certain solvents, in certain temperature ranges, or in certain pH ranges.

Particles having an average particle size of between about 1 micron and 100 microns are useful as microparticles in the compositions described herein. In typical embodiments, the particles have an average particle size of between about 1 micron and 40 microns, more typically between about 10 microns and about 40 microns, more typically between about 20 microns and about 40 microns. The particles can have any shape but are generally spherical in shape.

Particles having an average particle size of between about 1 and 100 nanometers (nm) are useful as nanoparticles in the compositions described herein. In typical embodiments, the particles have an average particle size of between about 1 nm and 75 nm, more typically between about 10 microns and about 40 microns, more typically between about 20 microns and about 40 microns. The particles can have any shape but are also generally spherical in shape.

Nanoparticles are useful for delivery through mucosal barriers where very small particles have an advantage of easier travel through the mucus than larger particles. This is useful for ocular delivery, as the eye is covered with a mucosal barrier.

In circumstances where a monodispersed population of particles is desired, the particles may be formed using a method which produces a monodisperse population of microparticles. Alternatively, methods producing polydispersed microparticle distributions can be used, and the particles can be separated using methods known in the art, such as sieving, following particle formation to provide a population of particles having the desired average particle size and particle distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formation are briefly described below. Pharmaceutically acceptable excipients, including pH modifying agents, disintegrants, preservatives, and antioxidants, can optionally be incorporated into the particles during particle formation.

In some embodiments, the desired microparticles and nanoparticles are obtained through a solvent evaporation method. In one aspect, a method is provided whereby one or more quaternary ammonium compounds of the present invention or polymer matrix and one or more compounds of the present invention, is dissolved or dispersed in a volatile organic solvent, such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. The organic solution containing one or more quaternary ammonium compounds of the present invention is then suspended in an aqueous solution that contains a surfactant, such as poly (vinyl alcohol). The resulting emulsion is stirred until most of the organic solvent is evaporated, leaving solid microparticles. The resulting microparticles are rinsed with water and dried in a lyophilizer overnight. Microparticles with different sizes and morphologies can be obtained with this method.

Solvent removal can be used to prepare particles from quaternary ammonium compounds of the present invention that are deemed hydrolytically unstable. In one aspect, a method is provided whereby one or more quaternary ammonium compounds of the present invention are dissolved or dispersed in a volatile organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. This mixture is then suspended by stirring in an organic oil (such as silicon oil, castor oil, paraffin oil, or mineral oil) to form an emulsion. Solid particles form from the emulsion, which can subsequently be isolated from the supernatant. The external morphology of spheres produced with this technique is highly dependent upon the identity of one or more quaternary ammonium compounds of the present invention.

In some embodiments, the microparticles are formed by using an oil-in-water emulsion. In one aspect, a method is provided whereby, one or more quaternary ammonium compounds of the present invention are dissolved or dispersed in a volatile organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. This mixture is then suspended by stirring in an aqueous solution of a surfactant to form an emulsion. Solid particles form from the emulsion, which can subsequently be isolated from the supernatant. The external morphology of the spheres produced with this technique is highly dependent upon the identity of one or more quaternary ammonium compounds of the present invention.

In some embodiments, the microparticles are derived by spray drying. In one aspect, a method is provided whereby, one or more quaternary ammonium compounds of the present invention are dissolved in an organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. The mixture is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

Particles can be formed from one or more quaternary ammonium compounds of the present invention using a phase inversion method. In one aspect a method is provided whereby one or more quaternary ammonium compounds of the present invention are dissolved in a solvent, and the solution is poured into a strong non-solvent for the substrate to spontaneously produce, under favorable conditions, microparticles. The method can be used to produce particles in a wide range of sizes, including, for example, from about 100 nanometers to about 10 microns, typically possessing a narrow particle size distribution.

In some embodiments, the particles can be formed from one or more quaternary ammonium compounds of the present invention using coacervation. Techniques for particle formation using coacervation are known in the art, for example, in GB-B-929 406; GB-B-929 50 1; and U.S. Pat. Nos. 3,266,987, 4,794,000, and 4,460,563.

In some embodiments, the particles can be formed from one or more quaternary ammonium compounds of the present invention by low temperature casting. Methods for very low temperature casting of microspheres are described in U.S. Pat. No. 5,019,400 to Gombotz et al. In one aspect, a method is provided whereby one or more quaternary ammonium compounds of the present invention is dissolved in an appropriate solvent. The mixture is then atomized into a vessel containing a liquid non-solvent at a temperature below the freezing point of the organosilicon QAC solution which freezes the droplets. As the droplets and the non-solvent for the organosilicon QAC are warmed, the solvent in the droplets thaws and is extracted into the non-solvent, hardening the microspheres.

In certain embodiments, one or more quaternary ammonium compounds of the present invention can be incorporated into a polymeric nanoparticle, e.g. for convenience of delivery, targeted delivery or extended release delivery. The use of materials in nanoscale provides one the ability to modify fundamental physical properties such as solubility, diffusivity, blood circulation half-life, release characteristics of one or more quaternary ammonium compounds of the present invention, or immunogenicity. A number of nanoparticle-based therapeutic and diagnostic agents have been developed for the treatment of cancer, diabetes, pain, asthma, allergy, and infections. These nanoscale agents may provide more effective or more convenient routes of administration, lower therapeutic toxicity, extend the product life cycle, and ultimately reduce health-care costs. As therapeutic delivery systems, nanoparticles can provide targeted delivery and controlled release.

In addition, nanoparticle-based delivery can be used to release one or more quaternary ammonium compounds of the present invention at a sustained rate and thus lower the frequency of administration, deliver one or more quaternary ammonium compounds of the present invention in a targeted manner to minimize side effects, or to deliver one or more quaternary ammonium compounds of the present invention and an additional pharmaceutical active simultaneously for combination therapy to generate a synergistic effect and suppress drug resistance. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et 84 al., 2001, J. Am. Chem. Soc., 123:2460; Langer, 2000, Acc. Chem. Res., 33:94;

Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390: 386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010); U.S. Pat. No. 6,632,671 to Unger Oct. 14, 2003, all incorporated herein by reference.

Combination Therapy

In some embodiments, an active compound, or composition as described herein may be provided in combination or alternation with or preceded by, concomitant with or followed by, an effective amount of at least one additional therapeutic agent, for example, for treatment of a disorder listed herein.

Non-limiting examples of additional active agents for such combination therapy are provided below. In the described below and herein generally, whenever any of the terms referring to an active quaternary ammonium compound, or composition as described herein are used, it should be understood that salts, prodrugs, or compositions are considered included, unless otherwise stated or inconsistent with the text.

In some embodiments, an active quaternary ammonium compound, or composition as described herein may be used in combination or alternation with an antibiotic.

In some embodiments, the antibiotic is an aminoglycoside. In some embodiments, the antibiotic is selected from amikacin, gentamicin, kanamycin, neomycin, netilmicin, tobramycin, paromomycin, streptomycin, and spectinomycin.

In some embodiments, the antibiotic is an ansamycin. In some embodiments, the antibiotic is selected from geldanamycin, herbimycin, and rifaximin.

In some embodiments, the antibiotic is a carbapenem. In some embodiments, the antibiotic is selected from ertapenem, doripenem, imipenem, panipenem, biapenem, tebipenem, and meropenem.

In some embodiments, the antibiotic is a cephalosporin. In some embodiments, the antibiotic is selected from cefacetrile, cefadroxil, cephalexin, cefaloglycin, cefalonium, cefaloridine, cefalotin, cefapirin, cefatrizine, cefazaflur, cefazedone, cefazolin, cefradrine, cefroxadine, and ceftezole. In some embodiments, the antibiotic is selected from cefaclor, cefonicid, cefprozil, cefuroxime, cefuzonam, cefmetazole, cefotetan, cefoxitin, loracarbef, cefbuperazone, cefminox, cefoxitin, and cefotiam. In some embodiments, the antibiotic is selected from cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, and latamoxef. In some embodiments, the antibiotic is selected from cefclidine, cefepime, cefluprenam, cefoselis, cefozopran, cefpirome, cefquinome, and flomoxef. In some embodiments, the antibiotic is selected from ceftobiprole, ceftaroline, and ceftolozane.

In some embodiments, the antibiotic is a glycopeptide. In some embodiments, the antibiotic is selected from teicoplanin, vancomycin, telavancin, dalbavancin, ramoplanin, decaplanin, and oritavancin.

In some embodiments, the antibiotic is a lincosamide. In some embodiments, the antibiotic is selected from lincomycin, clindamycin, and pirlimycin.

In some embodiments, the antibiotic is daptomycin. In some embodiments, the antibiotic is a macrolide. In some embodiments, the antibiotic is selected from azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin.

In some embodiments, the antibiotic is a ketolide. In some embodiments, the antibiotic is selected from telithromycin, cethromycin, and solithromycin. In some embodiments, the antibiotic is a monobactam.

In some embodiments, the antibiotic is selected from aztreonam. In some embodiments, the antibiotic is a nitrofuran. In some embodiments, the antibiotic is selected from diruazone, furazolidone, nifurfoline, nifuroxazide, nifurquinazol, nifurtoinol, nifurzide, nitrofural, and nitrofurantoin.

In some embodiments, the antibiotic is an oxazolidinone. In some embodiments, the antibiotic is selected from linezolid, posizolid, tedizolid, radezolid, torezolid, and cycloserine.

In some embodiments, the antibiotic is a penicillin. In some embodiments, the antibiotic is selected from penicillin G, penicillin K, penicillin N, penicillin O, and penicillin V. In some embodiments, the antibiotic is selected from meticillin, nafcillin, oxacillin, cloxacillin, dicloxacillin, and flucoxacillin. In some embodiments, the antibiotic is selected from ampicillin, amoxicillin, pivampicillin, hetacillin, bacampicillin, metampicillin, talampicillin, and epicillin. In some embodiments, the antibiotic is selected from carbenicilin, ticarcillin, and temocillin. In some embodiments, the antibiotic is selected from mezlocillin and piperacillin. In some embodiments, the antibiotic is selected from clavulanic acid, sulbactam, and tazobactam.

In some embodiments, the antibiotic is a polypeptide antibiotic. In some embodiments, the antibiotic is selected from bacitracin, colistin, and polymyxin B.

In some embodiments, the antibiotic is a quinolone or fluoroquinolone antibiotic. In some embodiments, the antibiotic is selected from flumequine, oxolinic acid, rosoxacin, cinoxacin, nalidixic acid, and piromidic acid. In some embodiments, the antibiotic is selected from ciprofloxacin, fleroxacin, lomefloxacin, nadifloxacin, norfloxacin, ofloxacin, pefloxacin, rufloxacin, and enoxacin. In some embodiments, the antibiotic is selected from balofloxacin, grepafloxacin, levofloxacin, pazufloxacin, sparfloxacin, temafloxacin, and tosufloxacin. In some embodiments, the antibiotic is selected from clinafloxacin, gatifloxacin, moxifloxacin, sitafloxacin, prulifloxacin, besifloxacin, gemifloxacin, trovafloxacin, delafloxacin, and ozenoxacin.

In some embodiments, the antibiotic is a sulfonamide. In some embodiments, the antibiotic is selected from sulfacetamide, sulfadiazine, sulfadimidine, sulfafurazole, sulfisomidine, sulfadoxine, sulfamethoxazole, sulfamoxole, sulfanitran, sulfadimethoxine, sulfamethoxypyridazine, sulfametoxydiazine, sulfadoxine, sulfametopyrazine, terephtyl, mafenide, sulfanilamide, sulfasalazine, sulfisoxazole, and sulfonamicochrysoidine.

In some embodiments, the antibiotic is a tetracycline. In some embodiments, the antibiotic is selected from tetracycline, chlortetracycline, oxytetracycline, demeclocycline, lymecycline, meclocycline, metacycline, minocycline, and rolitetracycline.

In some embodiments, the antibiotic is selected from clofazimine, dapsone, capreomycin, cycloserine, ethambutol, ethionamide, isoniazid, pyrazinamide, rifampicin, rifabutin, rifapentine, and streptomycin. In another embodiment, the antibiotic is selected from arsphenamide, chloramphenicol, fosfomycin, fusidic acid, metronidazole, mupirocin, platensimycin, quinupristin, dalfopristin, thiamphenicol, tigecycline, and trimethoprim.

In some embodiments, an active quaternary ammonium compound, or composition as described herein may be used in combination or alternation with an antifungal drug.

In some embodiments, the antifungal drug is an azole antifungal. In some embodiments, the antifungal drug is selected from bifonazole, butoconazole, clotrimazole, econazole, fenticonazole, isoconazole, ketoconazole, luliconazole, miconazole, omoconazole, oxiconazole, sertaconazole, sulconazole, and tioconazole. In some embodiments, the antifungal drug is selected from albaconazole, efinaconazole, epoxiconazole, fluconazole, isavuconazole, itraconazole, posaconazole, propiconazole, ravuconazole, terconazole, and voriconazole.

In some embodiments, the antifungal drug is abafungin. In some embodiments, the antifungal drug is an echinocandin. In some embodiments, the antifungal drug is selected from anidulafungin, caspofungin, and micafungin.

In some embodiments, the antifungal drug is a polyene antifungal. In some embodiments, the antifungal drug is selected from amphotericin B, candicidin, filipin, hamycin, natamycin, nystatin, and rimocidin. In some embodiments, the antifungal drug is selected from griseofulvin, terbinafine, and flucytosine.

In certain embodiments, the compound, its salt or composition as described herein may be used in combination or alternation with benzoyl peroxide. In the skin follicle, benzoyl peroxide kills *P. acnes* by oxidizing its proteins through the formation of oxygen free radicals and benzoic acid. These radicals are believed to interfere with the bacterium's metabolism and ability to make proteins. Additionally, benzoyl peroxide is mildly effective at breaking down comedones and inhibiting inflammation. In some embodiments, an active compound or its salt is formulated in combination with benzoyl peroxide in a topical formulation as described herein.

In certain embodiments, the compound, its salt or composition as described herein may be used in combination or alternation with a retinoid. Retinoids are medications which reduce inflammation, normalize the follicle cell life cycle, and reduce sebum production. They are structurally related to vitamin A. The retinoids appear to influence the cell life cycle in the follicle lining; this helps prevent the accumulation of skin cells within the hair follicle that can create a blockage. Frequently used topical retinoids include adapalene, isotretinoin, retinol, tazarotene, and tretinoin. In some embodiments, an active compound or its salt is formulated in combination with a retinoid in a topical formulation as described herein.

In certain embodiments, the compound, or its salt or composition as described herein may be used in combination or alternation with an antibiotic. Antibiotics are frequently applied to the skin or taken orally to treat acne and are thought to work due to their antimicrobial activity against *P. acnes* and their ability to reduce inflammation. Commonly used antibiotics, either applied to the skin or taken orally, include clindamycin, erythromycin, metronidazole, sulfacetamide, and tetracyclines such as doxycycline and minocycline. Other representative topical antibiotics include bacitracin, polymycin b, neomycin, retapamulin, mupirocin, pramoxine, gentamicin, mafenide, and ozenoxacin. The compounds described herein are particularly effective in combination with antibiotics due to their potentiation of the antimicrobial effect of the antibiotic. In some embodiments, an active compound or its salt is formulated in combination with an antibiotic in a topical formulation as described herein.

In certain embodiments, the compound, its salt or composition as described herein may be used in combination or alternation with azelaic acid. Azelaic acid is thought to be an effective acne treatment due to its ability to reduce skin cell accumulation in the follicle, along with its antibacterial and anti-inflammatory properties. In some embodiments, an active compound or its salt is formulated in combination with an antibiotic in a topical formulation as described herein.

In certain embodiments, the compounds, its salt or composition as described herein may be used in combination or alternation with salicyclic acid. Salicyclic acid is a topically applied beta-hydroxy acid that has keratolytic properties in addition to stopping bacterial reproduction. In some embodiments, an active compound or its salt is formulated in combination with salicyclic acid in a topical formulation as described herein.

In certain embodiments, the compound, its salt or composition as described herein may be used in combination or alternation with niacinamide. Niacinamide can improve acne by decreasing inflammation, suppressing sebum production, and promoting wound healing. In some embodiments, an active compound or its salt is formulated in combination with salicyclic acid in a topical formulation as described herein.

PRESENTATIVE EXAMPLES OF THE PRESENT INVENTION

Abbreviations in the examples below are defined as follows: DMF is dimethylformamide, MeOH is methanol, and NMR is nuclear magnetic resonance spectroscopy. In the examples below, a skill artisan can remove and substitute compounds with Na+ and Cl− charges with other salts.

In one non-limiting embodiment of the invention a compound in the examples below can be prepared with dimethyloctadecyl[3-(triethoxysilyl)propyl]ammonium chloride instead of dimethyloctadecyl[3-(trimethoxysilyl)propyl]ammonium chloride.

Example 1. Synthesis of Disodium; 2-[[1-[[3-[dimethyl(octadecyl)ammonio]propyl-[3-hydroxy-2-(hydroxymethyl)-2-(2-sulfoethylamino)propoxy]-[3-hydroxy-2-(hydroxymethyl)-2-(2-sulfonatoethylamino)propoxy]silyl]oxymethyl]-2-hydroxy-1-(hydroxymethyl)ethyl]amino] ethanesulfonate chloride

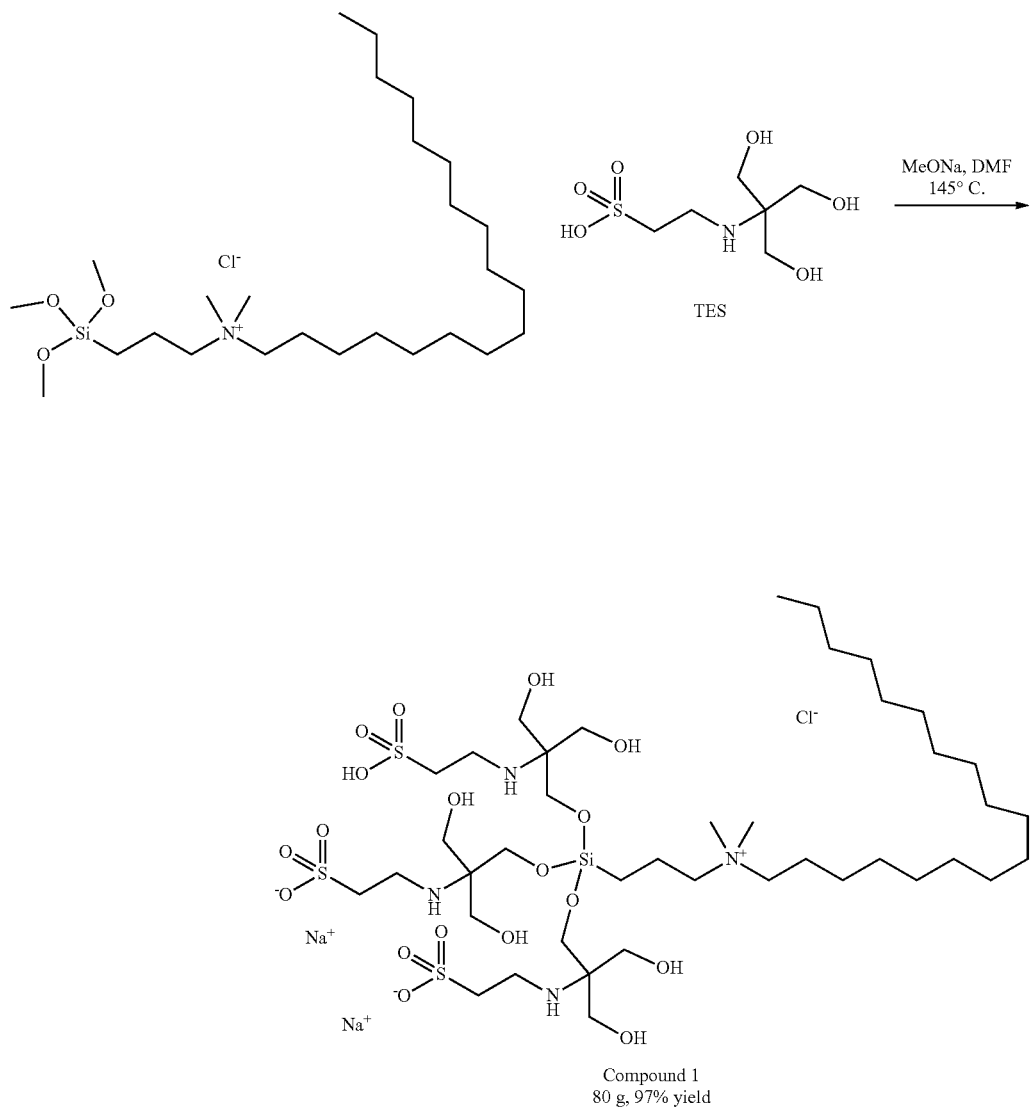

Compound 1
80 g, 97% yield

A 1-liter round bottom reaction vessel was outfitted with a heating mantle, magnetic stirring bar, downward condenser, receiving flask, oil bubbler, an immersion thermoprobe for the pot, and a thermoprobe for the head. The reactor was charged with 54 mL of a 67% solution of dimethyloctadecyl[3-(trimethoxysilyl)propyl]ammonium chloride, 50 g of TES, and 300 mL DMF. The mixture was heated to 145° C. (pot temp) and the methanol was collected until the head temp drops and no more MeOH evolved. The reaction was then cooled and 7.83 g (2 mol eq) of sodium methoxide was added with stirring. The DMF was evaporated and reduced pressure to yield a semi-solid. Toluene (250 ml) was added, the mixture stirred at room temp for 1 hour, and then evaporated. Acetonitrile (250 ml) was added, the suspension stirred at room temp for 1 hour, and then evaporated. This process was repeated until DMF no long was evident by NMR. The resultant product was placed under high vac overnight to yield an off-white solid. This solid was ground in a blender to yield a fine hygroscopic powder that dissolves in water. 1H NMR: δ 0.86 (3H, t, J=7.0 Hz), 1.05 (2H, t, J=7.6 Hz), 1.19-1.39 (30H), 1.98-2.14 (4H), 2.88 (6H, s), 2.90-3.01 (6H), 3.06-3.11 (4H), 3.25-3.32 (4H), 3.47 (2H, t, J=6.3 Hz), 3.52-3.55 (18H).

Example 2. Synthesis of Disodium; 3-[[1-[[3-[dim-ethyl(octadecyl)ammonio]propyl-[3-hydroxy-2-(hydroxymethyl)-2-[(2-hydroxy-3-sulfonato-propyl)amino]propoxy]-[3-hydroxy-2-(hydroxymethyl)-2-[(2-hydroxy-3-sulfo-propyl)amino]propoxy]silyl]oxymethyl]-2-hydroxy-1-(hydroxymethyl)ethyl]amino]-2-hydroxy-propane-1-sulfonate; chloride

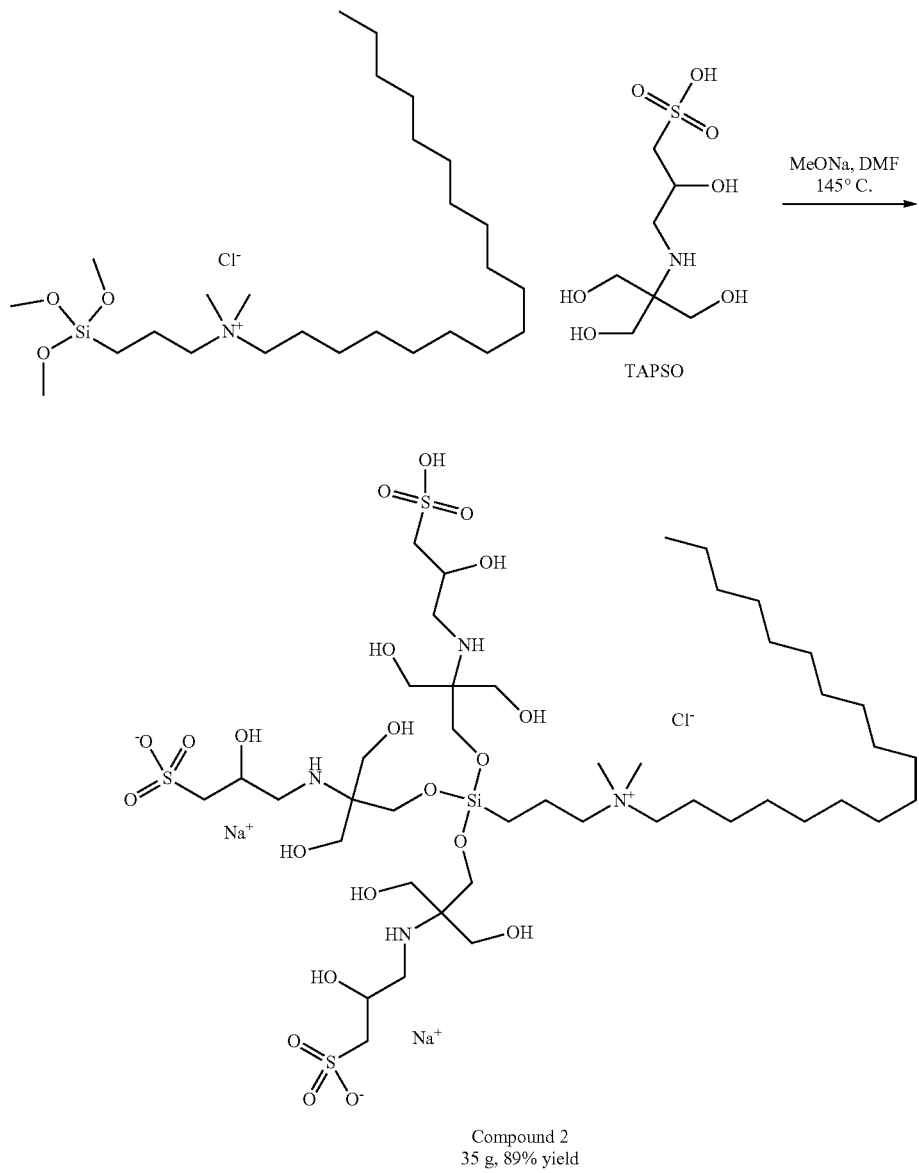

A 1-liter round bottom reaction vessel was outfitted with a heating mantle, stir bar, downward condenser, receiving flask, oil bubbler, an immersion thermoprobe for the pot, and a thermoprobe for the head. The reactor was charged with 24 mL of a 67% solution of dimethyloctadecyl[3-(trimethoxysilyl)propyl]ammonium chloride, 25 g of TAPSO, and 300 mL DMF. The mixture was heated to 145° C. (pot temp) and the methanol was collected until the head temp drops and no more MeOH evolved. The reaction was then cooled and 3.5 g (2 mol eq) of sodium methoxide was added with stirring. The DMF was evaporated at reduced pressure to yield a semi-solid. Toluene (250 ml) was added, the mixture stirred at room temp for 1 hour, and then evaporated. Acetonitrile (250 ml) was added, the suspension stirred at room temp for 1 hour, and then evaporated. This process was repeated until DMF no long was evident by NMR. The resultant product was placed under high vac overnight to yield an off-white solid. This solid was ground in a blender to yield a fine hygroscopic powder that dissolves in water. 1H NMR: δ 0.86 (3H, t, J=7.0 Hz), 1.05 (2H, t, J=7.6 Hz), 1.19-1.39 (30H), 1.98-2.14 (4H), 2.88 (6H, s), 2.90-3.01 (6H), 3.06-3.11 (4H), 3.25-3.32 (4H, 3.29 (t, J=6.2 Hz), 3.29 (t, J=6.2 Hz)), 3.47 (2H, t, J=6.3 Hz), 3.52-3.55 (18H).

Example 3. Synthesis of Disodium 2-[2-[3-[heptadecyl(dimethyl)ammonio]propyl-[2-[2-hydroxyethyl(2-sulfoethyl)amino]ethoxy]-[2-[2-hydroxyethyl(2-sulfonatoethyl)amino]ethoxy]silyl]oxyethyl-(2-hydroxyethyl)amino]ethanesulfonate chloride

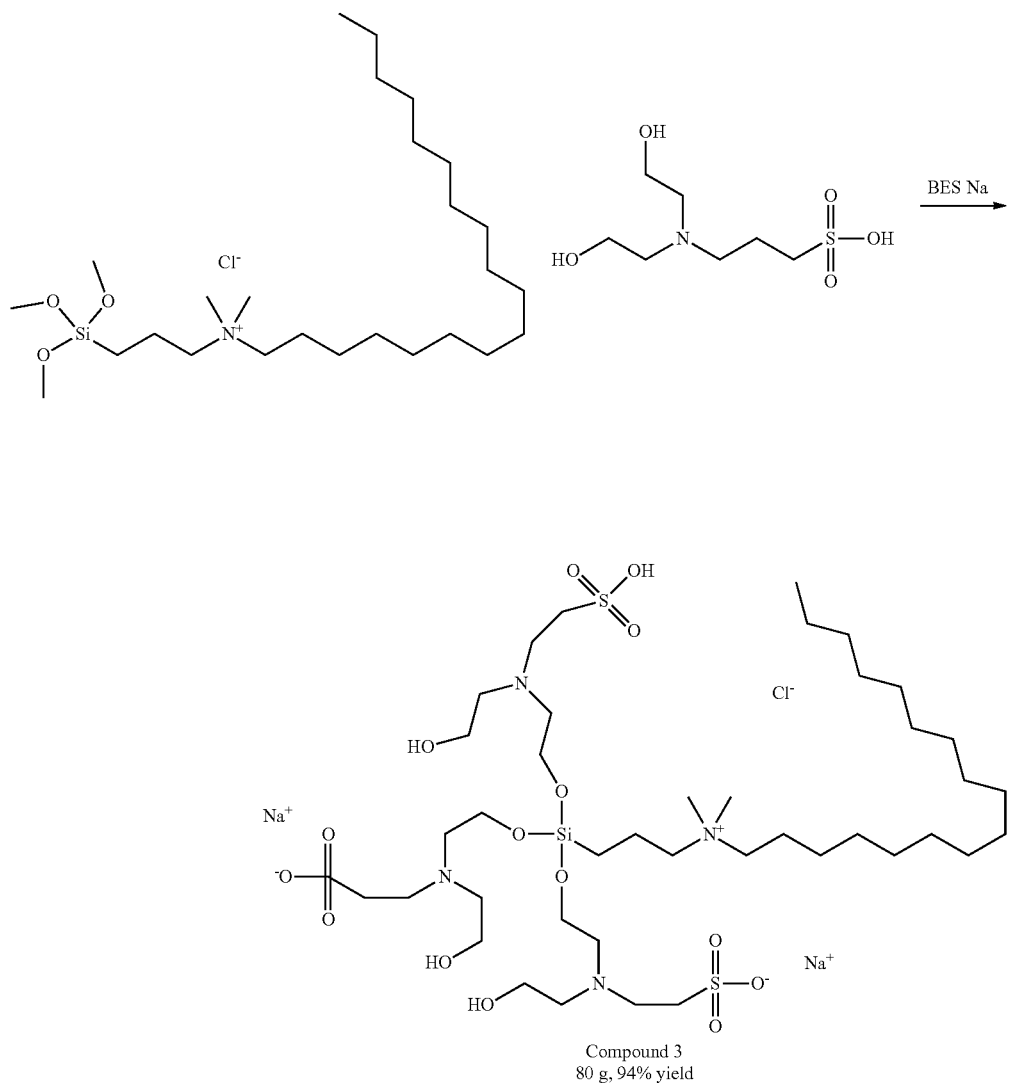

Compound 3
80 g, 94% yield

To 58.2 g of a 67% (w/w) solution of dimethyloctadecyl [3-(trimethoxysilyl)propyl]ammonium chloride in methanol was added 16.7 g (1 eq) of BES, 37.1 g (2 eq) of BES sodium and 200 mL DMF. The mixture was heated to 145° C. The DMF was evaporated and reduced pressure to yield a semi-solid. Toluene (250 ml) was added, the mixture stirred at room temp for 1 hour, and then evaporated. Acetonitrile (250 ml) was added, the suspension stirred at room temp for 1 hour, and then evaporated. This process was repeated until DMF no long was evident by NMR. The resultant product was placed under high vac overnight to yield an off-white semi-solid. 1H NMR: δ 0.86 (3H, t, J=7.0 Hz), 1.03 (2H, t, J=7.7 Hz), 1.19-1.39 (28H), 2.01 (2H, tt, J=7.8, 7.7 Hz), 2.10 (2H, tt, J=7.7, 7.4 Hz), 2.75-2.83 (4H), 2.86-2.92 (14H), 2.95-2.98 (6H), 3.05-3.11 (4H), 3.26-3.33 (4H, 3.29 (t, J=6.0 Hz), 3.29 (t, J=6.0 Hz)), 3.43 (2H, t, J=6.6 Hz), 3.48-3.51 (6H), 3.55-3.59 (6H).

Example 4. Synthesis of Sodium; 7,7-bis(3-hydroxy-2-(hydroxymethyl)-2-((2-sulfoethyl)amino)propoxy)-4,4-bis(hydroxymethyl)-11,11-dimethyl-6-oxa-3,11-diaza-7-silanonacosan-11-ium-1-sulfonate; chloride

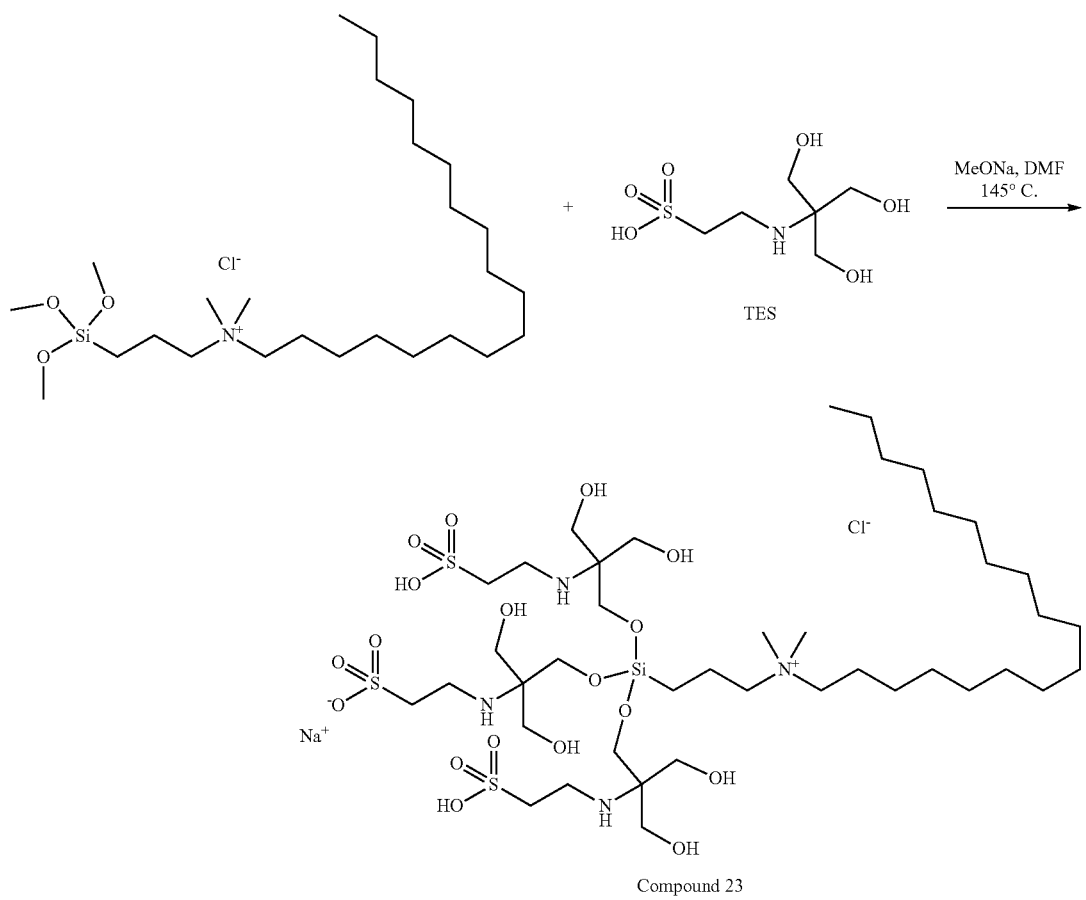

Compound 23

A 2-liter round bottom reaction vessel was outfitted with a heating mantle, magnetic stirring bar, downward condenser, receiving flask, oil bubbler, an immersion thermoprobe for the pot, and a thermoprobe for the head. The reactor was charged with 95 mL of a 42% solution of dimethyloctadecyl[3-(trimethoxysilyl)propyl]ammonium chloride, 36.9 g of TES, and 20.2 g of TES sodium, and 400 mL DMF. The mixture is heated to 145° C. (pot temp) and the methanol was collected by distillation. As the reaction was heated a homogenous solution forms and as the methanol was distilled off, a white precipitate begins to form. The reaction was heated until the head temperature drops and no more methanal evolved. The reaction was then cooled and the sodium chloride precipitate was removed by filtration through a glass fiber filter and the DMF was evaporated at reduced pressure to yield a semi-solid. Toluene (200 ml) was added, the mixture stirred at room temp for 1 hour, and then evaporated. Acetonitrile (200 ml) was added, the suspension stirred at room temp for 1 hour, and then evaporated. The colorless solid was collected on a glass frit and rapidly washed with acetonitrile and ether, taking care to minimize exposure to air as the product is very hygroscopic. The solid was then transferred to a vacuum flask and dried under vacuum. Fine powder dissolved quickly in water, initially hazy but slowly forms clear.

Example 5. Synthesis of Dimethyl-octadecyl-[3-[tris(2-hydroxypropoxy)silyl]propyl]ammonium; chloride

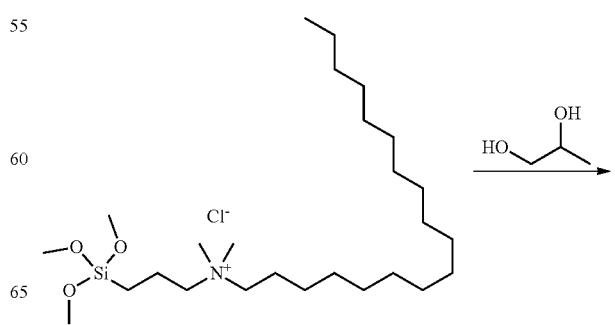

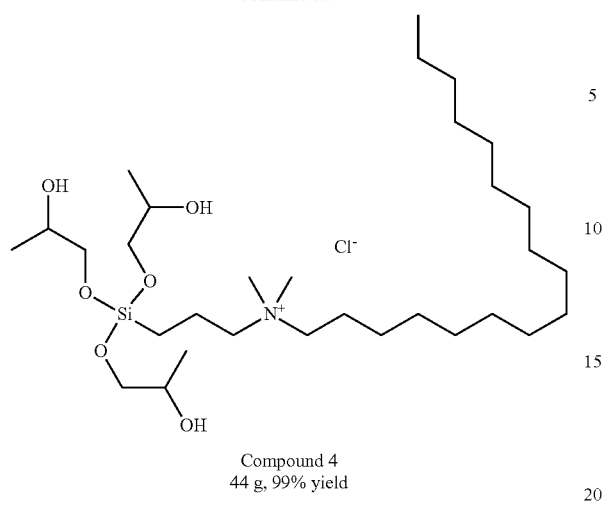

Compound 4
44 g, 99% yield

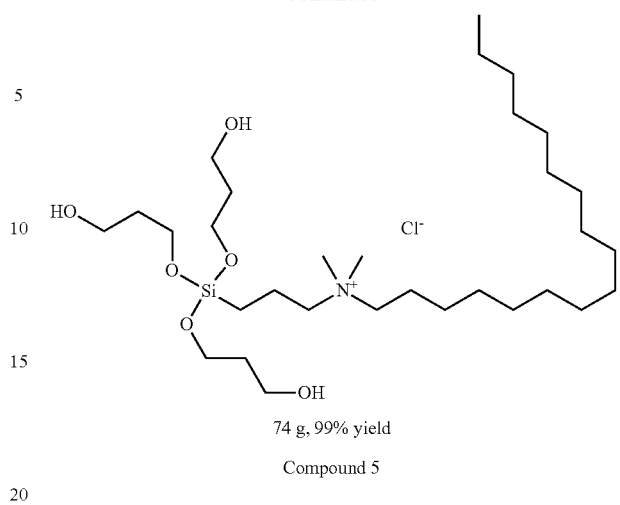

74 g, 99% yield
Compound 5

A 1 L round bottom reaction vessel was outfitted with a heating mantle, stir bar, downward condenser, receiving flask, oil bubbler, a thermoprobe for the pot, and a thermoprobe for the head. The reactor was charged with 36 g of dimethyloctadecyl[3-(trimethoxysilyl)propyl]ammonium chloride, 16.4 g of 1,2-propanediol and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid. The NMR was consistent with the proposed structure. The product dissolved readily in water and was stable for weeks.

Example 6. Synthesis of Dimethyl-octadecyl-[3-[tris(3-hydroxypropoxy)silyl]propyl]ammonium; chloride A 1 L round bottom reaction vessel was outfitted with a heating mantle, stir bar, downward condenser, receiving flask, oil bubbler, a thermoprobe for the pot, and a thermoprobe for the head. The reactor was charged with 60 g of dimethyloctadecyl[3-(trimethoxysilyl)propyl]ammonium chloride, 28 g of 1,3-propanediol and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid. The NMR was consistent with the proposed structure. The product dissolved readily in water and was stable for weeks.

Example 7. Synthesis of Dimethyl-octadecyl-[3-tris (2-carboxy-3-hydroxy-2-methyl-propoxy)silylpropyl]ammonium; chloride

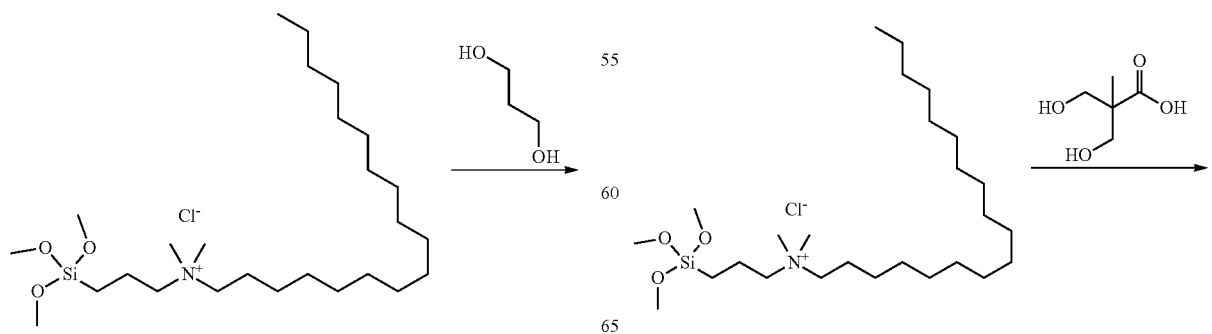

-continued

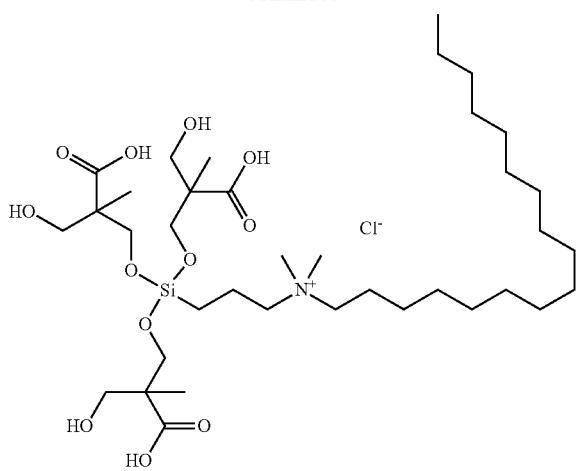

Compound 6
62 g, 96% yield

A 1 L round bottom reaction vessel was outfitted with a heating mantle, stir bar, downward condenser, receiving flask, oil bubbler, a thermoprobe for the pot, and a thermoprobe for the head. The reactor was charged with 59.7 mL of a 67% solution of dimethyloctadecyl[3-(trimethoxysilyl)propyl]ammonium chloride (A), 32.4 g of Bis(hydroxymethane)propanoic acid and ~300 mL of DMF. The mixture was heated to 145° C. (pot temp) and the methanol was collected until the head temp drops and no more MeOH evolved. The reaction was then cooled and DMF was then evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous semi-solid. The NMR was consistent with the proposed structure. The product dissolved readily in water and was stable for weeks.

Example 8. Synthesis of Disodium; 3-[2-[3-[heptadecyl(dimethyl)ammonio]propyl-[2-[2-hydroxyethyl-(2-hydroxy-3-sulfonato-propyl)amino]ethoxy]-[2-[2-hydroxyethyl-(2-hydroxy-3-sulfo-propyl)amino]ethoxy]silyl]oxyethyl-(2-hydroxyethyl)amino]-2-hydroxy-propane-1-sulfonate; chloride

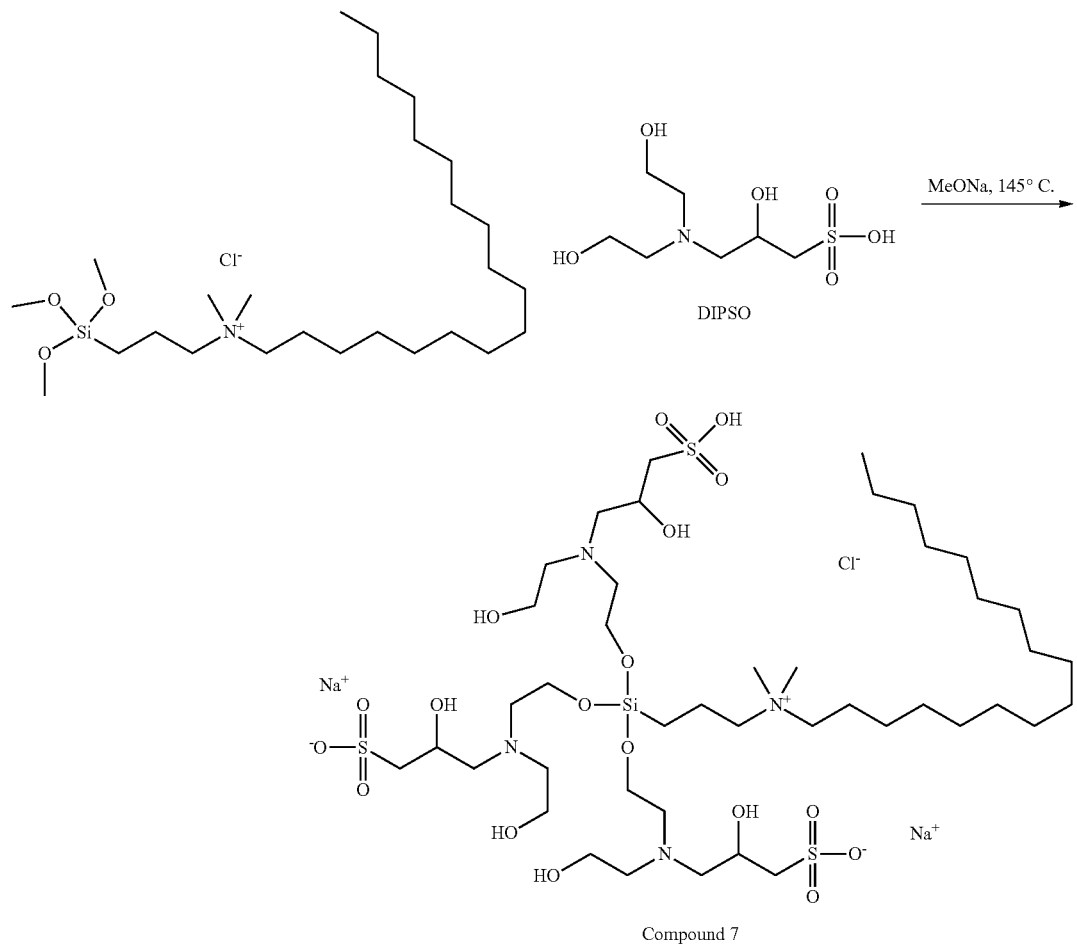

Compound 7
32 g, 84% yield

A 1 L round bottom reaction vessel was outfitted with a heating mantle, stir bar, downward condenser, receiving flask, oil bubbler, an immersion thermoprobe for the pot, and a thermoprobe for the head. The reactor was charged with 17 grams of dimethyloctadecyl[3-(trimethoxysilyl)propyl]ammonium chloride, 25 g of DIPSO, and 300 mL DMF. The mixture was heated to 145° C. (pot temp) and the methanol is collected until the head temp drops and no more MeOH evolved. The reaction was then cooled and 3.7 g (2 eq) NaOMe was added with stirring. The DMF was evaporated at reduced pressure to yield a semi-solid. Toluene (250 ml) was added, the mixture stirred at room temp for 1 hour, and then evaporated at reduced pressure. Acetonitrile (250 ml) was added, the suspension stirred at room temp for 1 hour, and then evaporated at reduced pressure. This process was repeated until DMF no long was evident by NMR. The resultant product was placed under high vacuum overnight to yield an off-white semi-solid. The solid dissolved in water but forms a precipitate after 5 hours. The NMR spectrum conformed to the expected product.

Example 9. Synthesis of Dimethyl(octadecyl)(3-(tris(oxiran-2-ylmethoxy)silyl)propyl)ammonium Chloride

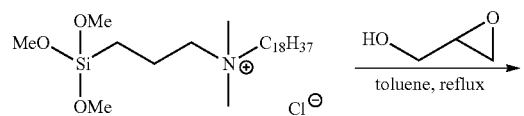

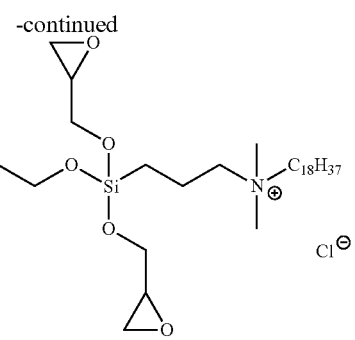

Compound 8

To a mixture, 100 g of dimethyloctadecyl[3-(trimethoxysilyl)propyl]ammonium chloride (42% solution by weight in methanol, 85 mmol) was subject to vacuum distillation until no further volatiles distilled. Glycidol (62.6 g, 850 mmol) was then added and the mixture stirred overnight under nitrogen. 1H NMR show that transesterification took place as indicated by a shift in glycidol signals and formation of free methanol. The glycidol/methanol was then distilled: 5 torr, oil bath 60-70 C, over @35 C. Collected ~40 g of glycidol which roughly corresponds to 6 eq unreacted glycidol as expected. The residue (pot) became extremely viscous as the glycidol was removed. 1H NMR indicated depletion of free methanol and glycidol. A second transesterification/distillation was performed in a similar manner. Distillation of volatiles provided a viscous liquid. The NMR spectrum conformed to the expected product.

Example 10. Synthesis of Disodium, 7-(2-((carboxymethyl)amino)-3-hydroxy-2-(hydroxymethyl)propoxy)-7-(3-(dimethyl(octadecyl)ammonio)propyl)-4,4,10,10-tetrakis(hydroxymethyl)-6,8-dioxa-3,11-diaza-7-silatridecanedioate; chloride

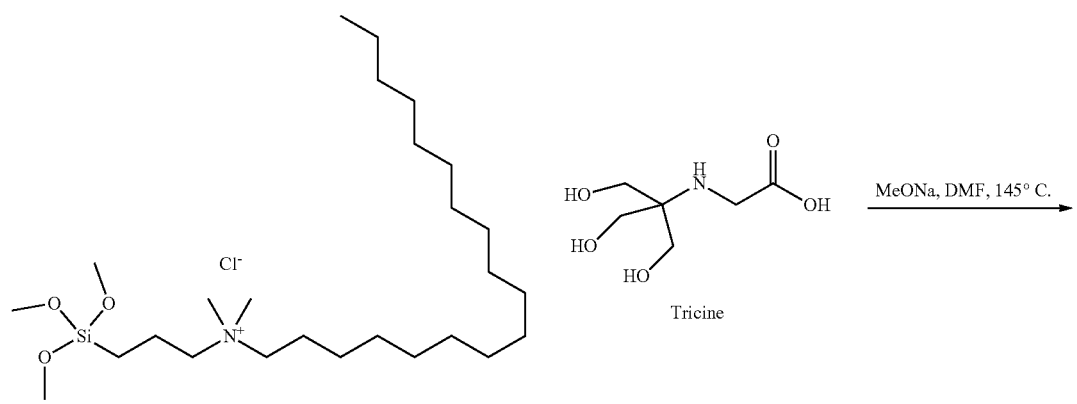

-continued

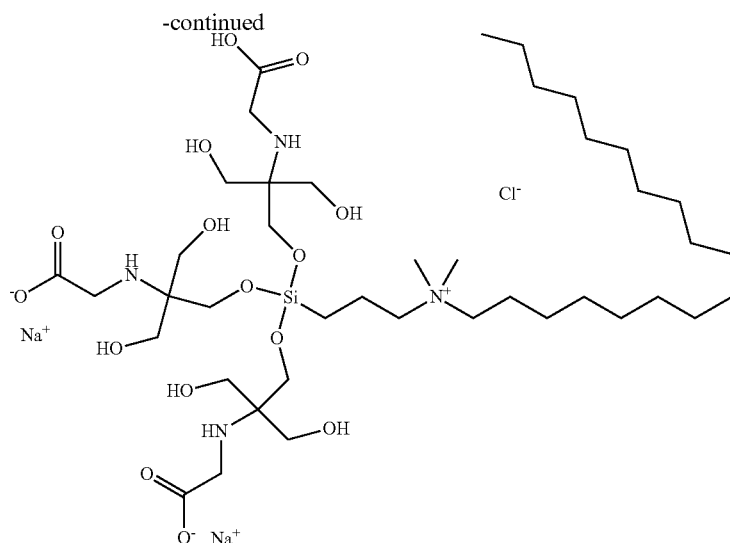

Compound 9
65 g, 89% yield

A 1 L round bottom reaction vessel was outfitted with a heating mantle, stir bar, downward condenser, receiving flask, oil bubbler, a thermoprobe for the pot, and a thermoprobe for the head. The reactor was charged with 55.2 mL of a 67% solution of dimethyloctadecyl[3-(trimethoxysilyl)propyl]ammonium chloride, 40 g of tricine, and 300 mL DMF. The mixture was heated to 145° C. (pot temp) and the methanol was collected until the head temp drops and no more MeOH evolved. The reaction was then cooled and 8.05 g (2 mol eq) of sodium methoxide was added with stirring. The DMF was evaporated at reduced pressure to yield a semi-solid. Toluene (250 ml) was added, the mixture stirred at room temp for 1 hour, and then evaporated at reduced pressure. Acetonitrile (250 ml) was added, the suspension stirred at room temp for 1 hour, and then evaporated at reduced pressure. This process was repeated until DMF no long was evident by NMR. The resultant product was placed under high vac overnight to yield an off-white solid which readily dissolved in water but soon formed a suspension.

Example 11. Synthesis of 3-[2-(2-hydroxy-1,1,2-trimethyl-propoxy)-4,4,5,5-tetramethyl-1,3,2-dioxasilolane-2-yl]propyl-dimethyl-octadecyl-ammonium; chloride

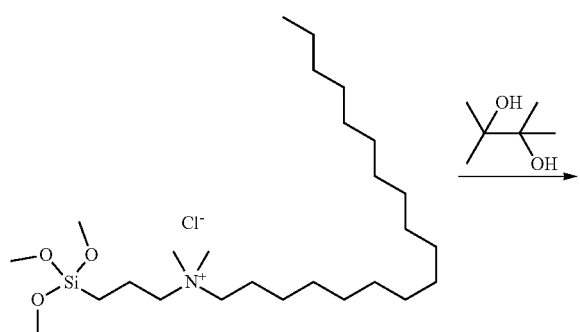

-continued

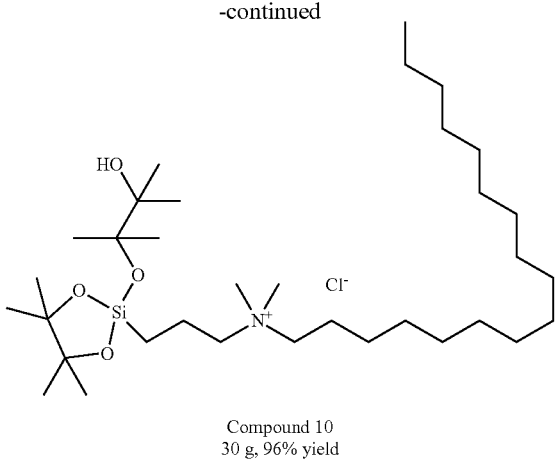

Compound 10
30 g, 96% yield

A 1 L round bottom reaction vessel was outfitted with a heating mantle, stir bar, downward condenser, receiving flask, oil bubbler, a thermoprobe for the pot, and a thermoprobe for the head. The reactor was charged with 52 g of dimethyloctadecyl[3-(trimethoxysilyl)propyl]ammonium chloride (A), 21 g of pinacol and ~300 mL of DMF. The mixture was heated to 145° C. (pot temp) and the methanol is collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid. The NMR spectrum conformed to the expected product.

Example 12. Synthesis of Compound 11

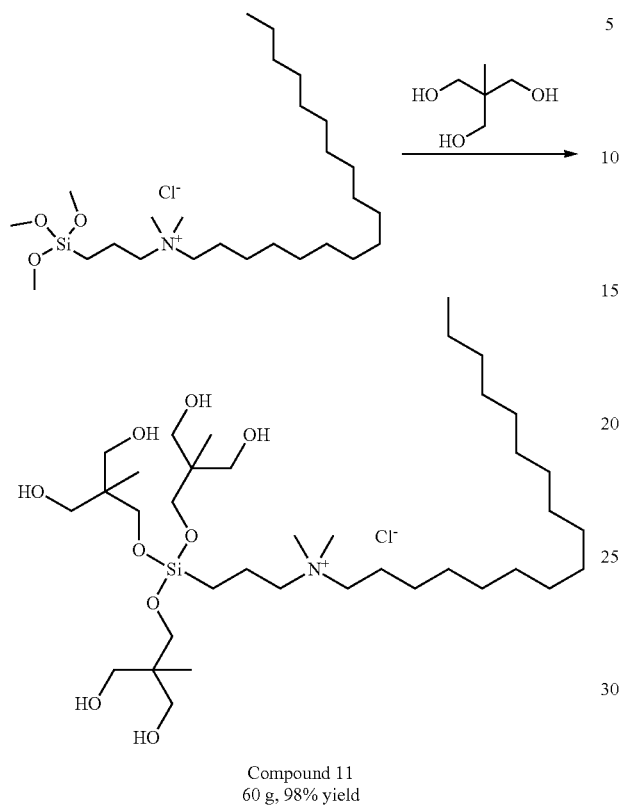

Compound 11
60 g, 98% yield

A 1 L round bottom reaction vessel was outfitted with a heating mantle, stir bar, downward condenser, receiving flask, oil bubbler, a thermoprobe for the pot, and a thermoprobe for the head. The reactor was charged with 59.7 mL of a 67% solution of dimethyloctadecyl[3-(trimethoxysilyl)propyl]ammonium chloride (A), 30 g of tris(hydroxymethyl)ethane and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid. The NMR spectrum conformed to the expected product.

Example 13. Synthesis of Disodium, 7-(2-((carboxymethyl)(2-hydroxyethyl)amino)ethoxy)-7-(3-(heptadecyldimethylammonio)propyl)-3,11-bis(2-hydroxyethyl)-6,8-dioxa-3,11-diaza-7-silatridecanedioate; chloride

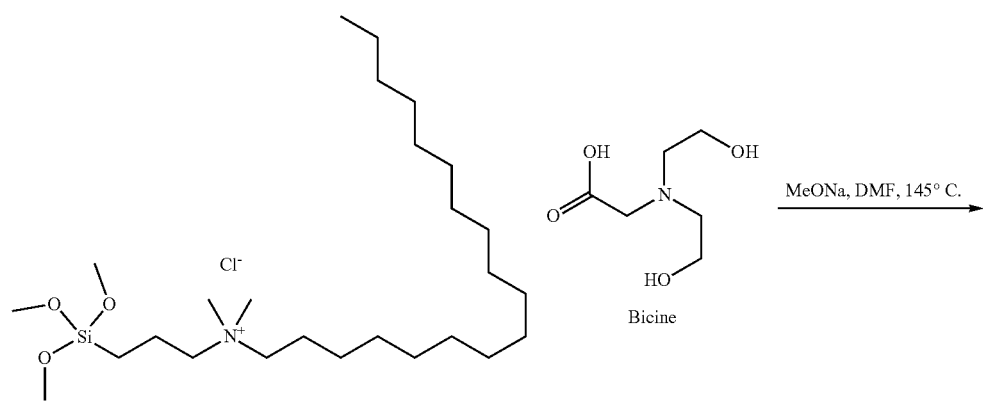

-continued

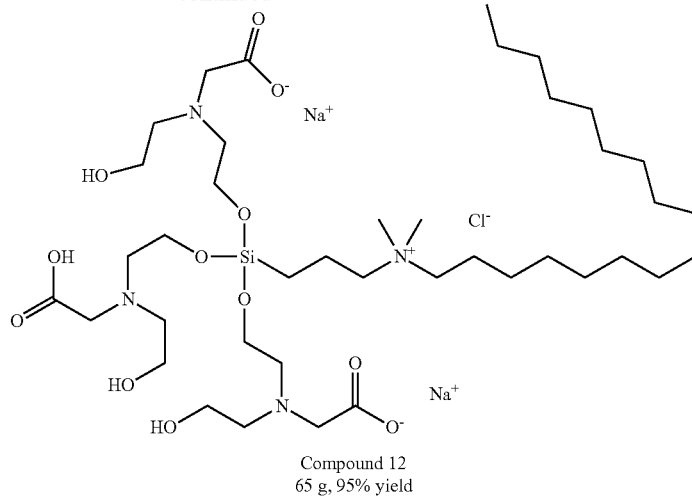

Compound 12
65 g, 95% yield

A 1 L round bottom reaction vessel was outfitted with a heating mantle, stir bar, downward condenser, receiving flask, oil bubbler, a thermoprobe for the pot, and a thermoprobe for the head. The reactor was charged with 55.2 mL of a 67% solution of dimethyloctadecyl[3-(trimethoxysilyl)propyl]ammonium chloride, 36.5 g of bicine, and 300 mL DMF. The mixture was heated to 145° C. (pot temp) and the methanol was collected until the head temp drops and no more MeOH evolved. The reaction was then cooled and 8.05 g (2 mol eq) of sodium methoxide was added with stirring. The DMF was evaporated at reduced pressure to yield a semi-solid. Toluene (250 ml) was added, the mixture stirred at room temp for 1 hour, and then evaporated at reduced pressure. Acetonitrile (250 ml) was added, the suspension stirred at room temp for 1 hour, and then evaporated at reduced pressure. This process was repeated until DMF no long was evident by NMR. The resultant product was placed under high vac overnight to yield an off-white solid which readily dissolved in water but soon formed a suspension.

Example 14. Synthesis of Compound 13

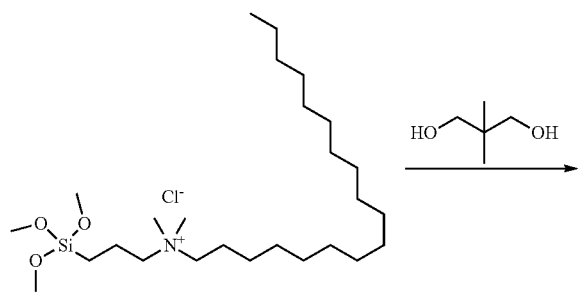

-continued

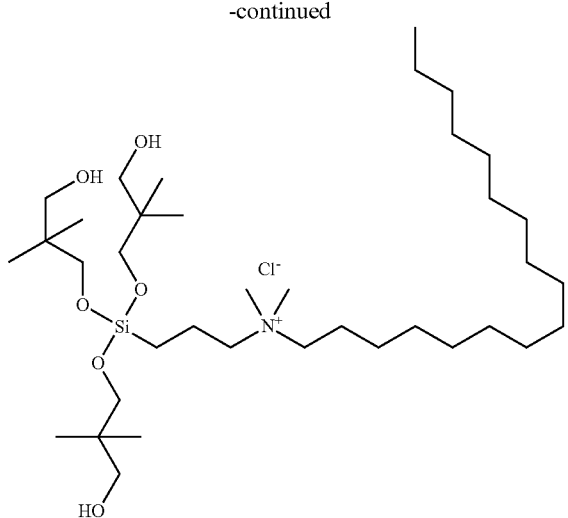

Compound 13
55g, 96% yield

A 1 L round bottom reaction vessel was outfitted with a heating mantle, stir bar, downward condenser, receiving flask, oil bubbler, a thermoprobe for the pot, and a thermoprobe for the head. The reactor was charged with 59.7 mL of a 67% solution of dimethyloctadecyl[3-(trimethoxysilyl)propyl]ammonium chloride (A), 28.8 g of neopentylglycol and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The NMR spectrum conformed to the expected product.

Example 15. Synthesis of N,N-dimethyl-N-(3-(tris((3-hydroxy-2,3-dimethylbutan-2-yl)oxy)silyl)propyl)heptadecan-1-aminium chloride

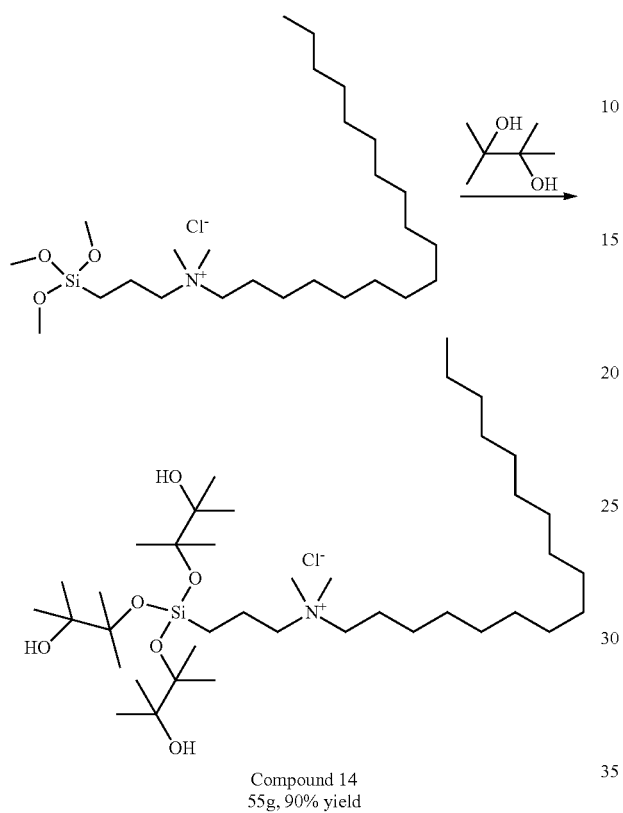

Compound 14
55g, 90% yield

A 1 L round bottom reaction vessel was outfitted with a heating mantle, stir bar, downward condenser, receiving flask, oil bubbler, a thermoprobe for the pot, and a thermoprobe for the head. The reactor was charged with 59.7 mL of a 67% solution of dimethyloctadecyl[3-(trimethoxysilyl)propyl]ammonium chloride (A), 28.5 g of pinacol and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid. The NMR spectrum conformed to the expected product.

Example 16. Synthesis of Sodium (3R,4S,5S,6R)-1-(3-(heptadecyldimethylammonio)propyl)-4,6-dihydroxy-2,8,9-trioxa-1-silabicyclo[3.3.1]nonane-3-carboxylate; chloride

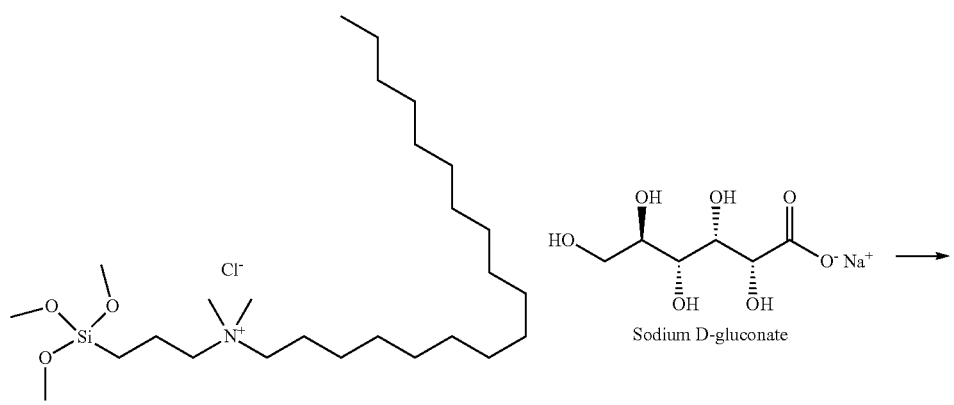

Sodium D-gluconate

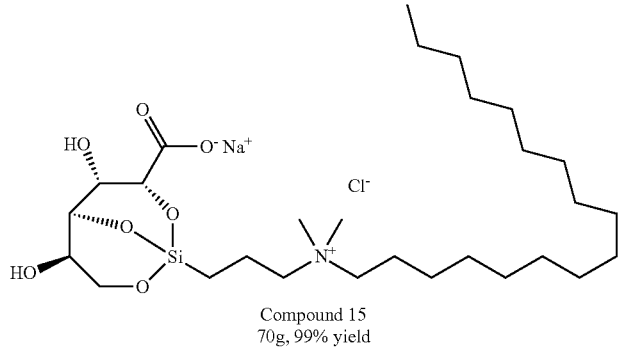

Compound 15
70g, 99% yield

A 1 L round bottom reaction vessel was outfitted with a heating mantle, stir bar, downward condenser, receiving flask, oil bubbler, an immersion thermoprobe for the pot, and a thermoprobe for the head. The reactor was charged with 57 grams of dimethyloctadecyl[3-(trimethoxysilyl)propyl]ammonium chloride, 25 g of sodium D-gluconate, and 300 mL DMF. The mixture was heated to 145° C. (pot temp) and the methanol was collected until the head temp drops and no more MeOH evolved. The reaction was then cooled. The DMF was evaporated at reduced pressure to yield a semisolid. Toluene (250 ml) was added, the mixture stirred at room temp for 1 hour, and then evaporated at reduced pressure. Acetonitrile (250 ml) was added, the suspension stirred at room temp for 1 hour, and then evaporated at reduced pressure. This process was repeated until DMF no long was evident by NMR. The resultant product was placed under high vac overnight to yield an off-white solid. The solid poorly dissolved in water and quickly decomposed to for a biphasic mixture.

Example 17. Synthesis of N-(3-((4R,5S,6R)-4-carboxy-6-((S)-carboxy(hydroxy)methyl)-2-((1S,2R,3S,4R)-1,4-dicarboxy-2,3,4-trihydroxybutoxy)-5-hydroxy-1,3,2-dioxasilinane-2-yl)propyl)-N,N-dimethylheptadecan-1-aminium chloride

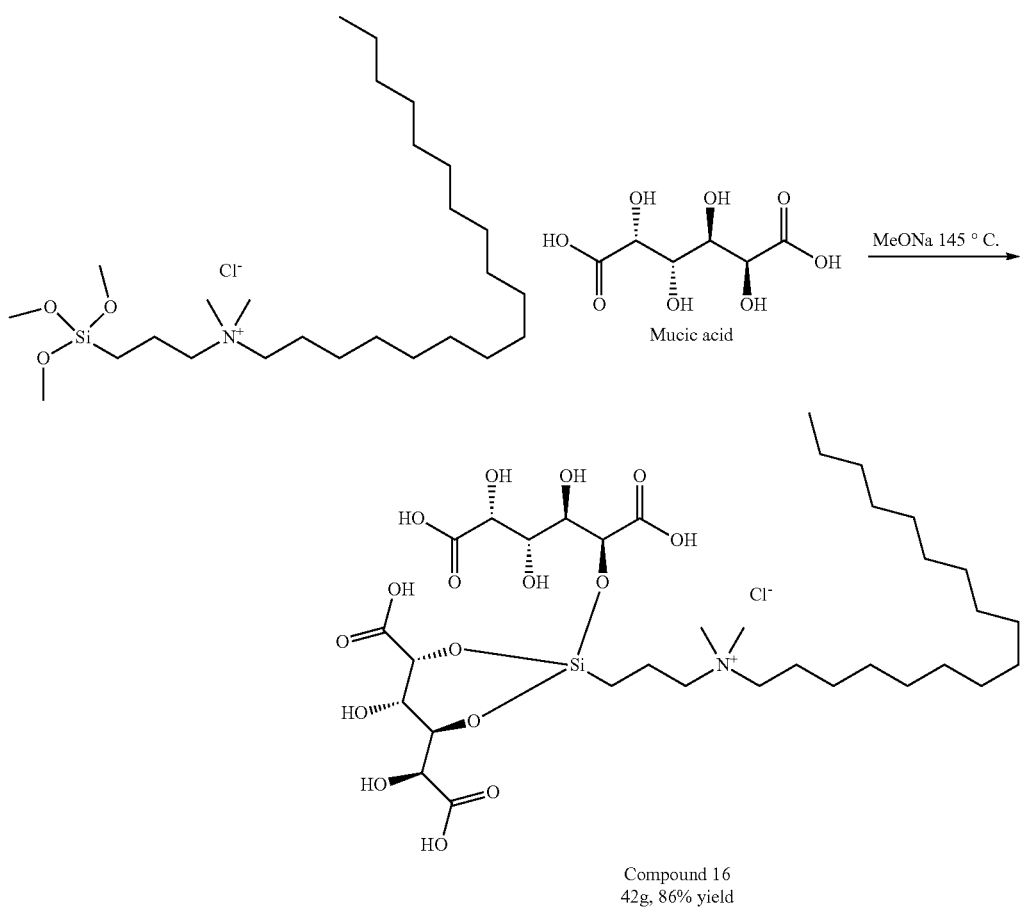

Compound 16
42g, 86% yield

A 1 L round bottom reaction vessel was outfitted with a heating mantle, stir bar, downward condenser, receiving flask, oil bubbler, an immersion thermoprobe for the pot, and a thermoprobe for the head. The reactor was charged with 30 grams of dimethyloctadecyl[3-(trimethoxysilyl)propyl] ammonium chloride, 28 g of mucic acid, and 300 mL DMF. The mixture was heated to 145° C. (pot temp) and the methanol was collected until the head temp drops and no more MeOH evolved. The reaction was then cooled. The DMF was evaporated at reduced pressure to yield a semi-solid goo. Converted to the disodium salt by dissolving in DMF and adding 2 eq NaOMe, then removing DMF at reduced pressure. Toluene (250 ml) was added, the mixture stirred at room temp for 1 hour, and then evaporated at reduced pressure. Acetonitrile (250 ml) was added, the suspension stirred at room temp for 1 hour, and then evaporated at reduced pressure. This process was repeated until DMF no long was evident by NMR. The resultant product was placed under high vac overnight to yield an off-white solid. The solid poorly dissolved in water and quickly decomposed to for a biphasic mixture.

Example 18. Synthesis of N-(3-(7-(2-((1,3-dihydroxy-2-(hydroxymethyl)propan-2-yl)(2-hydroxyethyl)amino)ethoxy)-1,13-dihydroxy-3,11-bis(2-hydroxyethyl)-2,2,12,12-tetrakis(hydroxymethyl)-6,8-dioxa-3,11-diaza-7-silatridecan-7-yl)propyl)-N,N-dimethylheptadecan-1-aminium; chloride

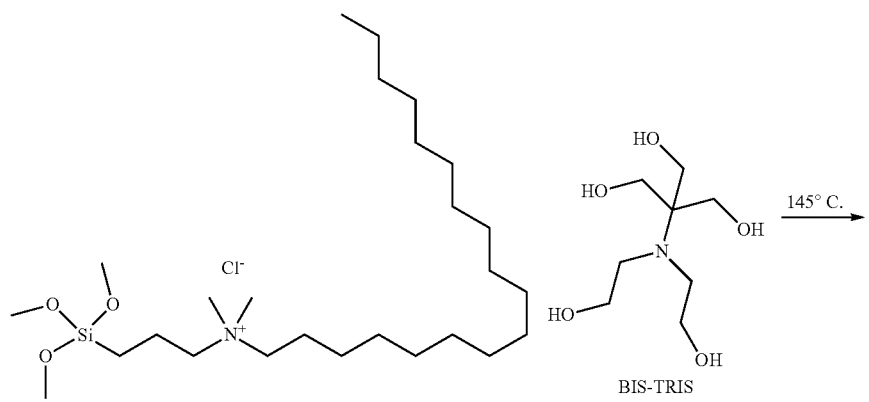

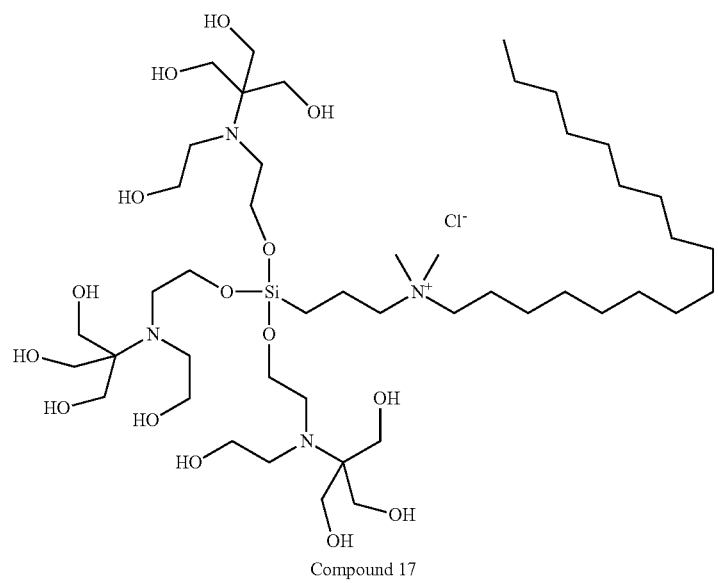

Compound 17

A 1 L round bottom reaction vessel was outfitted with a heating mantle, stir bar, downward condenser, receiving flask, oil bubbler, a thermoprobe for the pot, and a thermoprobe for the head. The reactor was charged with 59.7 mL of a 67% solution of dimethyloctadecyl[3-(trimethoxysilyl)propyl]ammonium chloride (A), 50 g of BIS-TRIS and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid.

Example 19. Synthesis of N,N-dimethyl-N-(3-(tris((3,4,5-trihydroxytetrahydrofuran-2-yl)methoxy)silyl)propyl)octadecan-1-aminium chloride

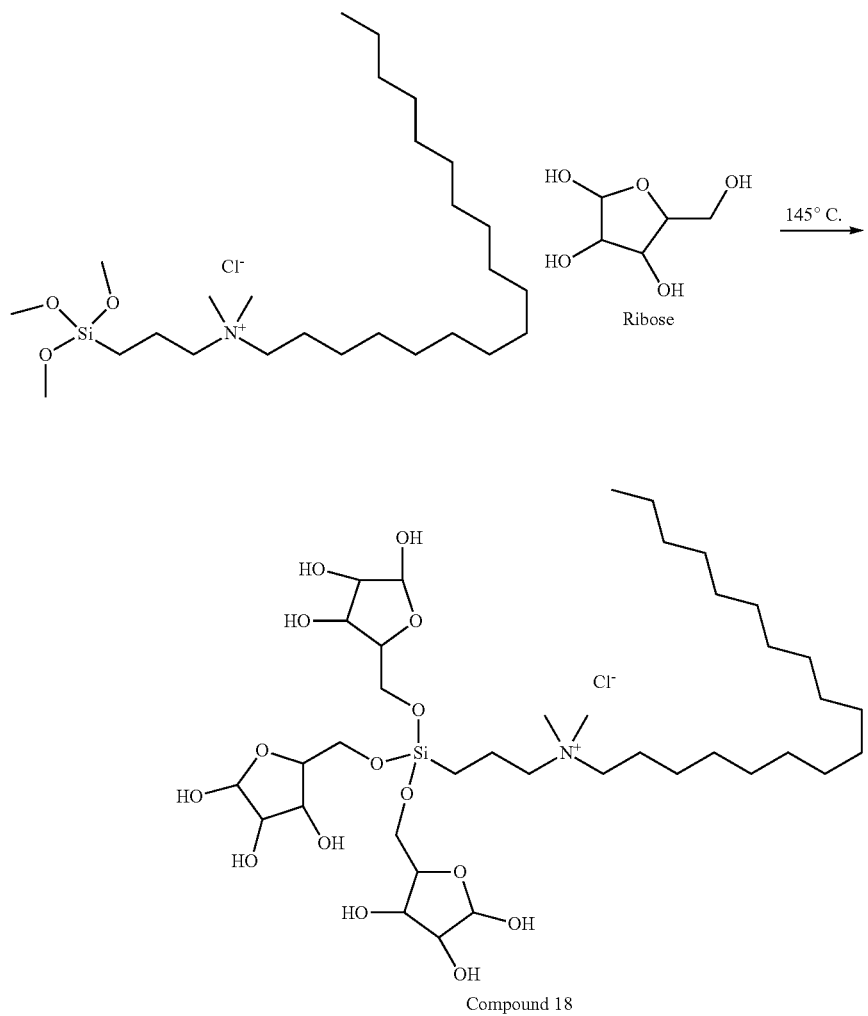

Compound 18

A 1 L round bottom reaction vessel was outfitted with a heating mantle, stir bar, downward condenser, receiving flask, oil bubbler, a thermoprobe for the pot, and a thermoprobe for the head. The reactor was charged with 30 mL of a 67% solution of dimethyloctadecyl[3-(trimethoxysilyl)propyl]ammonium chloride, 18.1 g of ribose, and ~300 mL of DMF. The mixture was heated to 145° C. (pot temp) and the methanol was collected until the head temp drops and no more MeOH evolved. The reaction was then cooled and DMF evaporated at reduced pressure. Toluene (250 ml) was added, stirred at room temp for 1 hour, and then evaporated at reduced pressure. Acetonitrile (250 ml) was added, stirred at room temp for 1 hour, and then evaporated at reduced pressure. The resultant product was placed under high vac overnight to yield an off-white viscous liquid.

Example 20. Synthesis of Trisodium (2R,2'R,2"R, 3S,3'S,3"S,4R,4'R,4"R,5R,5'R,5"R)-6,6',6"-(((3-(heptadecyldimethylammonio)propyl)silanetriyl)tris(oxy))tris(2,3,4,5-tetrahydroxyhexanoate); chloride

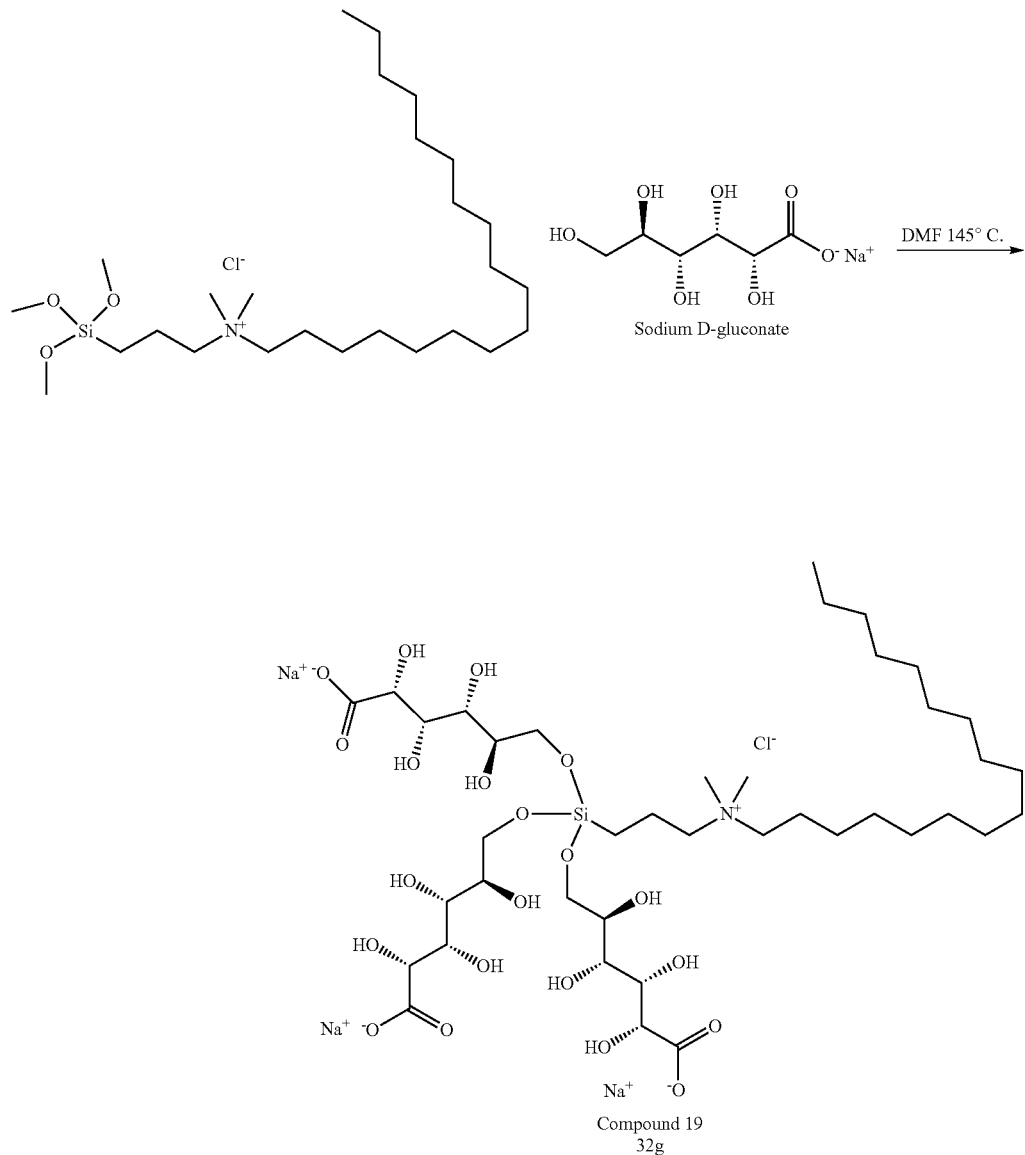

Compound 19
32g

A 1 L round bottom reaction vessel was outfitted with a heating mantle, stir bar, downward condenser, receiving flask, oil bubbler, an immersion thermoprobe for the pot, and a thermoprobe for the head. The reactor was charged with 20 grams of dimethyloctadecyl[3-(trimethoxysilyl)propyl]ammonium chloride, 26.3 g of sodium D-gluconate, and 300 mL DMF. The mixture was heated to 145° C. (pot temp) and the methanol was collected until the head temp drops and no more MeOH evolved. The reaction was then cooled. The DMF was evaporated at reduced pressure to yield a semi-solid. Toluene (250 ml) was added, the mixture stirred at room temp for 1 hour, and then evaporated. Acetonitrile (250 ml) was added, the suspension stirred at room temp for 1 hour, and then evaporated. This process was repeated until DMF no long was evident by NMR. The resultant product was placed under high vac overnight to yield an off-white solid. The solid poorly dissolved in water and quickly decomposed to form a biphasic mixture.

Example 21. Synthesis of Monosodium; 2-[[1-[[3-[dimethyl(octadecyl)ammonio]propyl-[3-hydroxy-2-(hydroxymethyl)-2-(2-sulfoethylamino)propoxy]-[3-hydroxy-2-(hydroxymethyl)-2-(2-sulfonatoethylamino)propoxy]silyl]oxymethyl]-2-hydroxy-1-(hydroxymethyl)ethyl]amino] ethanesulfonate chloride

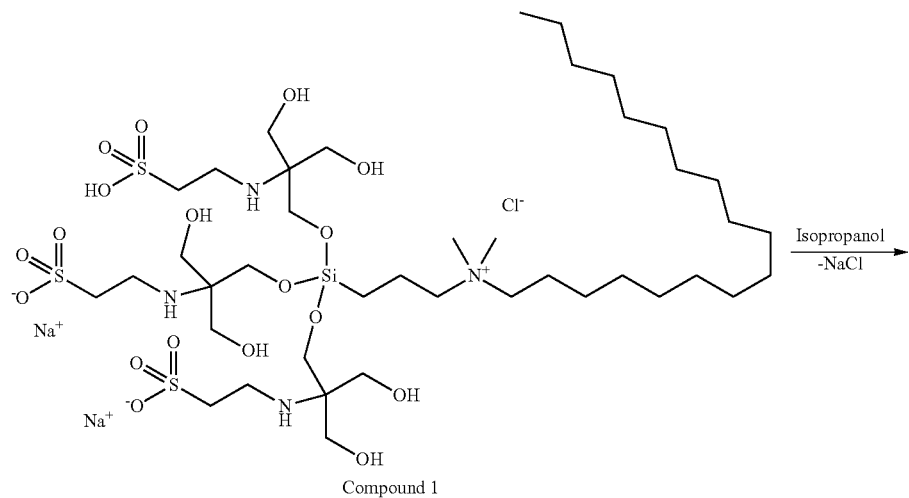

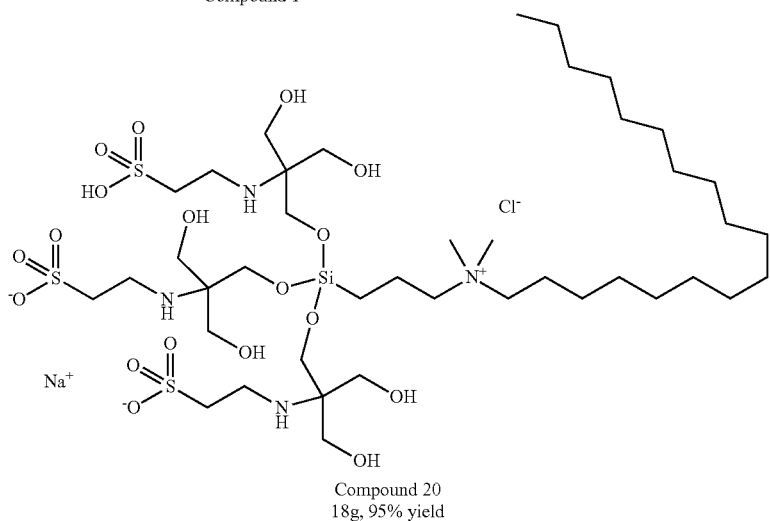

A 20 g of Compound 1 was dissolved in anhydrous isopropanol with heating. The resulting milky suspension was filtered through a glass filter and the solvent removed in vacuo to yield a translucent solid. This product was dried under high vacuum and then ground in a mortar and pestle to provide a white powder which dissolves readily in water.

Example 22. Synthesis of Dimethyl(octadecyl)(3-(tris(oxiran-2-ylmethoxy)silyl)propyl)ammonium Chloride

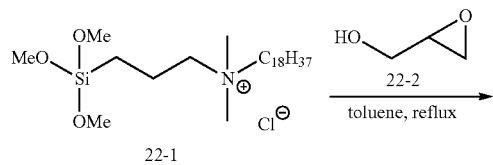

-continued

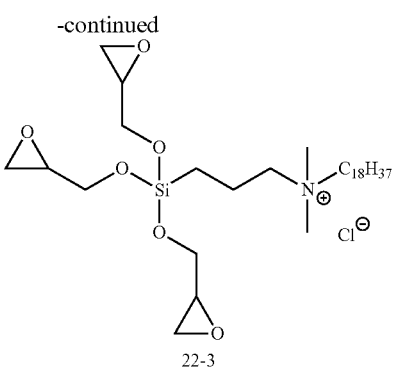

To a solution of glycidol 22-2 (3 equivalents) in toluene was added a 50% solution of 3-(trimethoxysilyl)-N-propyl-N,N-dimethyloctadecyl ammonium chloride 22-1 in methanol, and the reaction mixture was heated up to reflux for 24 hours. Upon cooling, a crude solid precipitated from the reaction mixture. The crude solid was filtered using a Buchner funnel, washed three times with pentane, and dried under vacuum. Recrystallization of the crude solid provides dimethyl(octadecyl)(3-(tris(oxiran-2-ylmethoxy)silyl)propyl)ammonium chloride 22-3. A 100 g of dimethyloctadecyl[3-(trimethoxysilyl)propyl]ammonium chloride (42% solution by weight in methanol, 85 mmol) was subject to vacuum distillation until no further volatiles distilled. Glycidol (62.6 g, 850 mmol) was then added and the mixture stirred overnight under nitrogen. 1H NMR show that transesterification took place as indicated by a shift in glycidol signals and formation of free methanol. The glycidol/methanol was then distilled: 5 torr, oil bath 60-70 C, over @35 C. Collected ~40 g of glycidol which roughly corresponds to 6 eq unreacted glycidol as expected. The residue (pot) became extremely viscous as the glycidol was removed. 1H NMR indicated depletion of free methanol and glycidol. A second transesterification/distillation was performed in a similar manner. Distillation of volatiles provided a viscous liquid. The NMR spectrum conformed to the expected product.

Example 23. Synthesis of Sodium; 2-hydroxy-8,8-bis(3-hydroxy-2-((2-hydroxy-3-sulfopropyl)amino)-2-(hydroxymethyl)propoxy)-5,5-bis(hydroxymethyl)-12,12-dimethyl-7-oxa-4,12-diaza-8-silatriacontan-12-ium-1-sulfonate, chloride salt; chloride

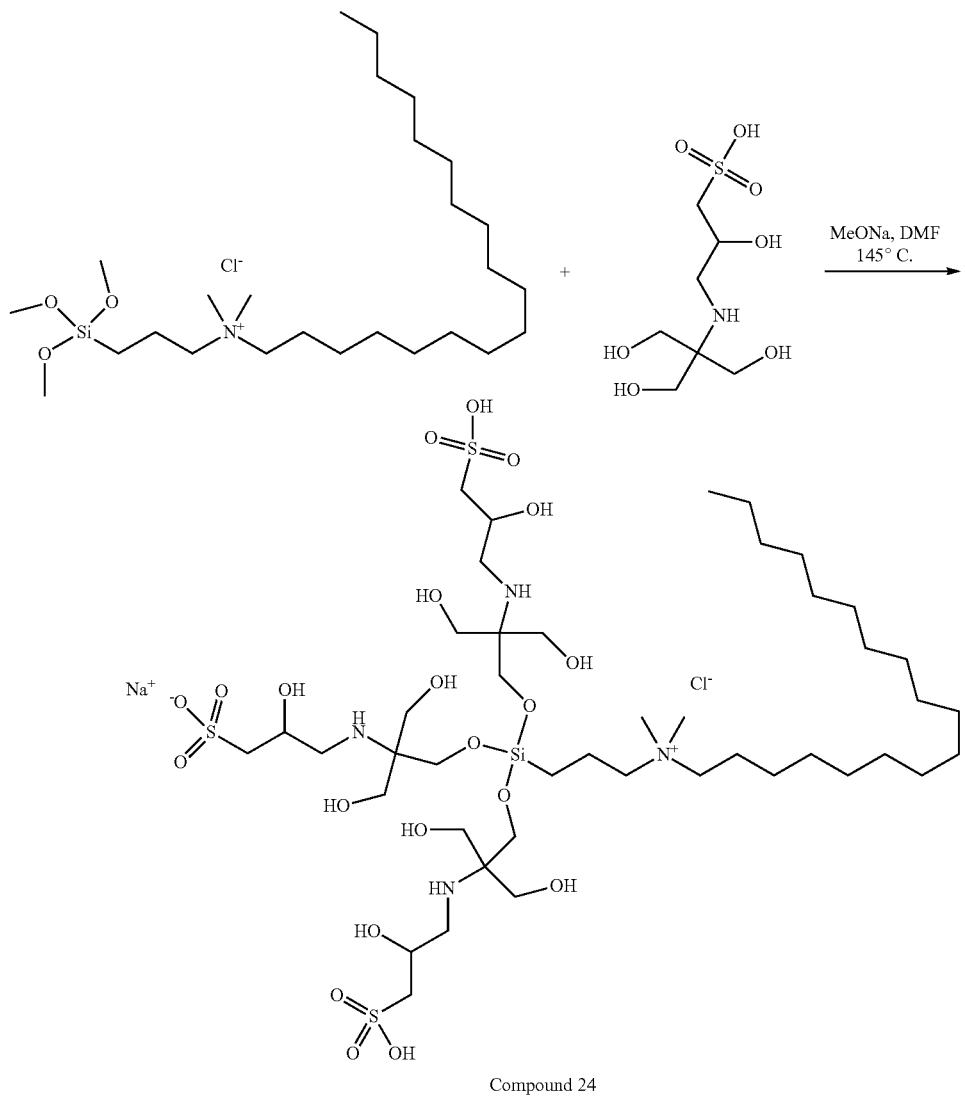

Compound 24

A 1-liter round bottom reaction vessel was outfitted with a heating mantle, stir bar, downward condenser, receiving flask, oil bubbler, an immersion thermoprobe for the pot, and a thermoprobe for the head. The reactor was charged with 60 mL of a 42% solution of dimethyloctadecyl[3-(trimethoxysilyl)propyl]ammonium chloride, 62.6 g of TAPSO, and 200 mL DMF. The mixture was heated to 145° C. (pot temp) and the methanol was collected until the head temp drops and no more MeOH evolved. The reaction was then cooled and 17.4 ml of a 25% solution of sodium methoxide was added with stirring. As the methanol was distilled off, a white precipitate begins to form. The reaction was heated until the head temperature drops and no more methanol evolved. The reaction was then cooled to room temperature and the sodium chloride precipitate was removed by filtration through a glass fiber filter and the DMF was evaporated at reduced pressure to yield a semi-solid. Toluene (200 ml) was added, the mixture stirred at room temp for 1 hour, and then evaporated. Acetonitrile (200 ml) was added, the suspension stirred at room temp for 1 hour, and then evaporated. The colorless solid was collected on a glass frit and rapidly washed with acetonitrile and then ether, taking care to avoid long exposure to air as the product is hygroscopic. The solid was then transferred to a flask and dried under vacuum.

Example 24. Synthesis of monosodium mono(8-(3-(dimethyl(octadecyl)ammonio)propyl)-2,14-dihydroxy-8-(3-hydroxy-2-((2-hydroxy-3-sulfopropyl)amino)-2-(hydroxymethyl)propoxy)-5,5,11,11-tetrakis(hydroxymethyl)-7,9-dioxa-4,12-diaza-8-silapentadecane-1,15-disulfonate); chloride flask, oil bubbler, an immersion thermoprobe for the pot, and a thermoprobe for the head. The reactor was charged with 50 ml of a 42% solution of dimethyloctadecyl[3-(trimethoxysilyl)propyl]ammonium chloride (Aldrich), 32.9 g of TAPSO, and 200 ml of DMF; 18.3 g of 25% sodium methoxide was then added in small portions. The mixture was heated to 145° C. (pot temp) and the methanol was collected by distillation as the reaction was heated a homogenous solution quickly forms. As the methanol was distilled off, a white precipitate begins to form. The reaction was heated until the head temp drops and no more MeOH evolved. The reaction was then cooled to room temperature and the precipitate (NaCl) is removed by filtration through a glass fiber filter and the DMF was evaporated at reduced pressure to concentrate to near dryness. Acetonitrile (200 ml) was added and the suspension stirred at room temperature overnight to yield a fine suspension. The colorless solid was collected on

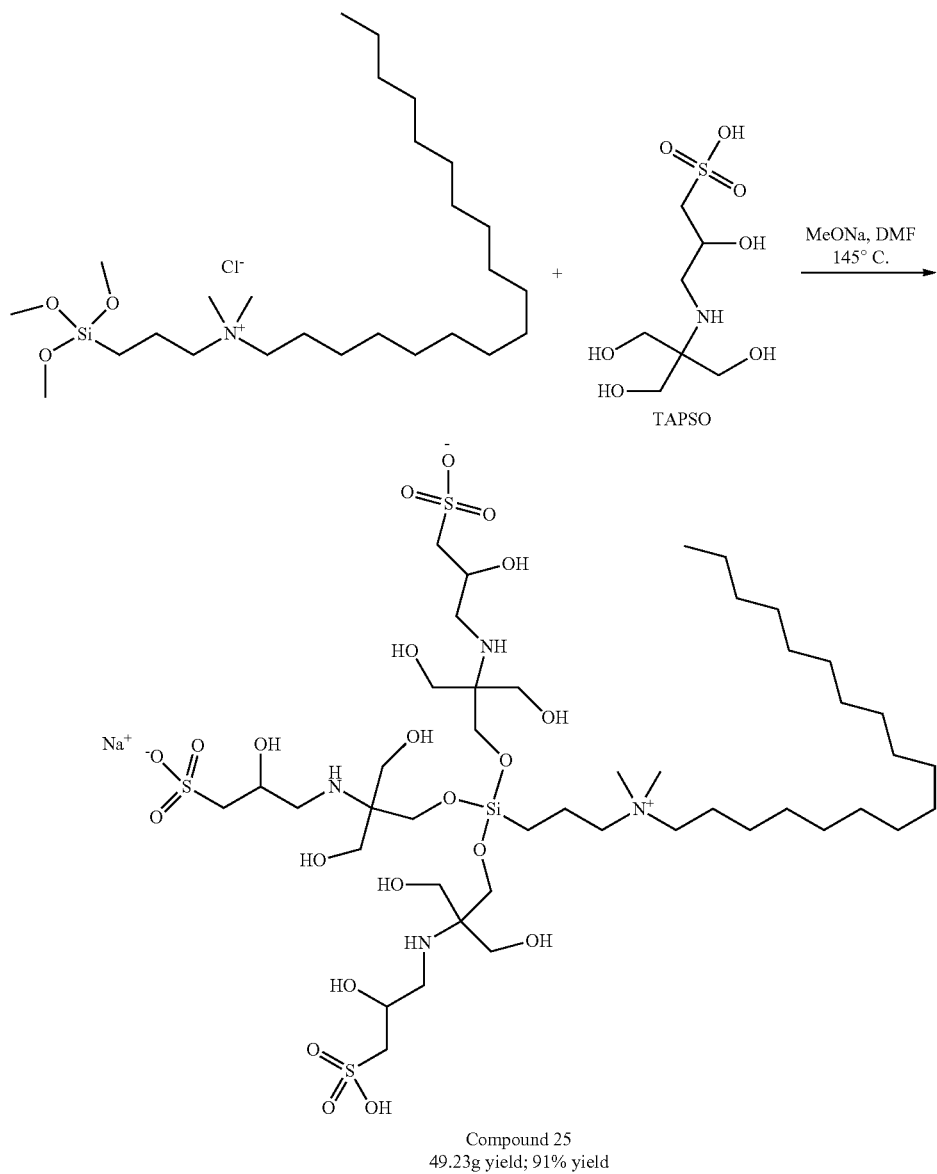

Compound 25
49.23g yield; 91% yield

A 1-Liter round bottom reaction vessel was outfitted with a heating mantle, stir bar, downward condenser, receiving a glass frit and rapidly washed with acetonitrile and then ether. The solid was then transferred to a flask and died under vacuum. Product was a fine colorless solid that readily dissolved in water, 2% solution was pH 7.65.

Example 25. Synthesis of N-(1,3-dihydroxy-2-(hydroxymethyl)propan-2-yl)palmitamide

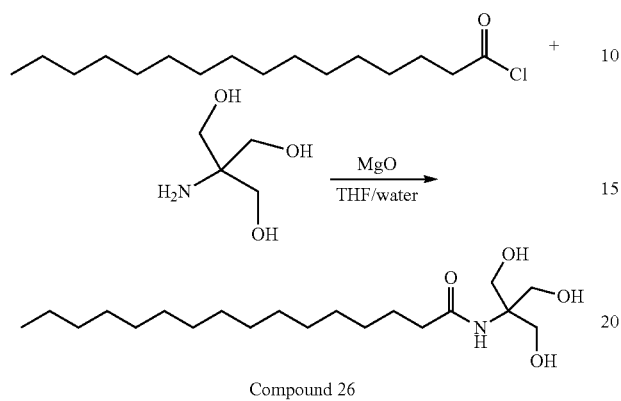

Compound 26

A 1 L round-bottom flask is charged with 2-amino-2-(hydroxymethyl)propane-1,3-diol, H₂O, and magnesium oxide. Under rapid stirring, THE is added followed by the slow addition of a solution of hexadecanoyl chloride in THE at room temperature. An ice bath is used to maintain the reaction temperature below 30° C. The reaction stirring continues for 1 hr after completion of the addition, resulting in a white suspension. The reaction mixture is then filtered and concentrated to dryness. Hot EtOAc is used to dissolve the crude mixture and the hot EtOAc solution is again filtered. The filtrate is placed in a refrigerator at approximately 5° C., with white precipitate forming rapidly on cooling. After 2 hr of cooling, the resulting slurry is filtered through a glass frit and air dried to obtain Compound 26.

Example 26. Synthesis of N-decyl-N-(3-(21-(3-hydroxy-2-(hydroxymethyl)-2-palmitamidopropoxy)-18,18,24,24-tetrakis(hydroxymethyl)-16,26-dioxo-20,22-dioxa-17,25-diaza-21-silahentetracontan-21-yl)propyl)-N-methyldecan-1-aminium chloride

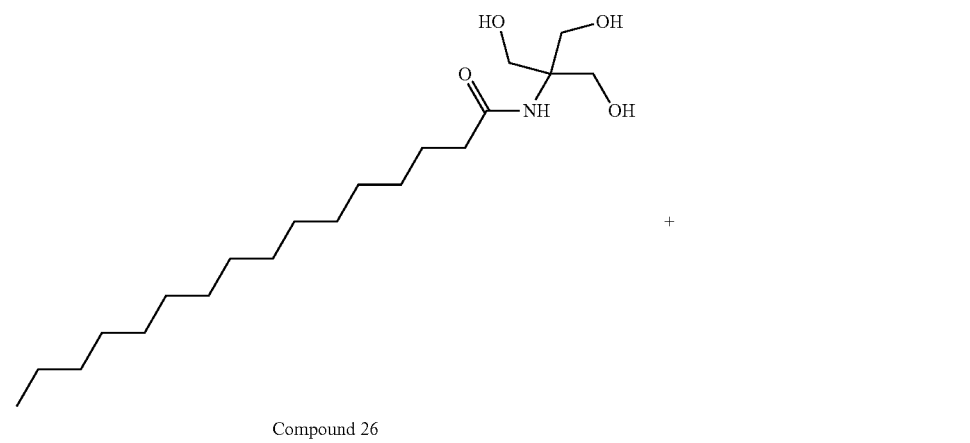

Compound 26

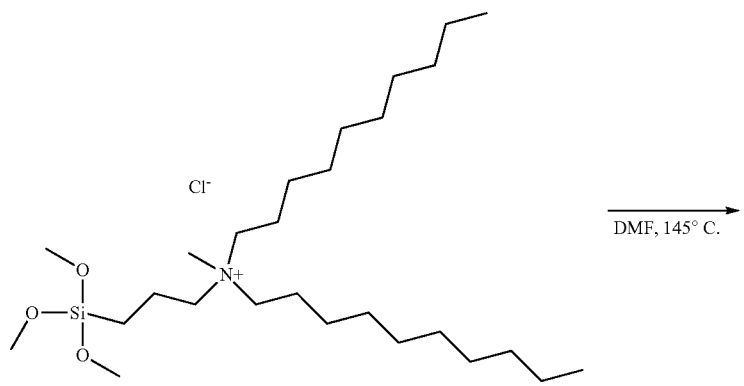

DMF, 145° C.

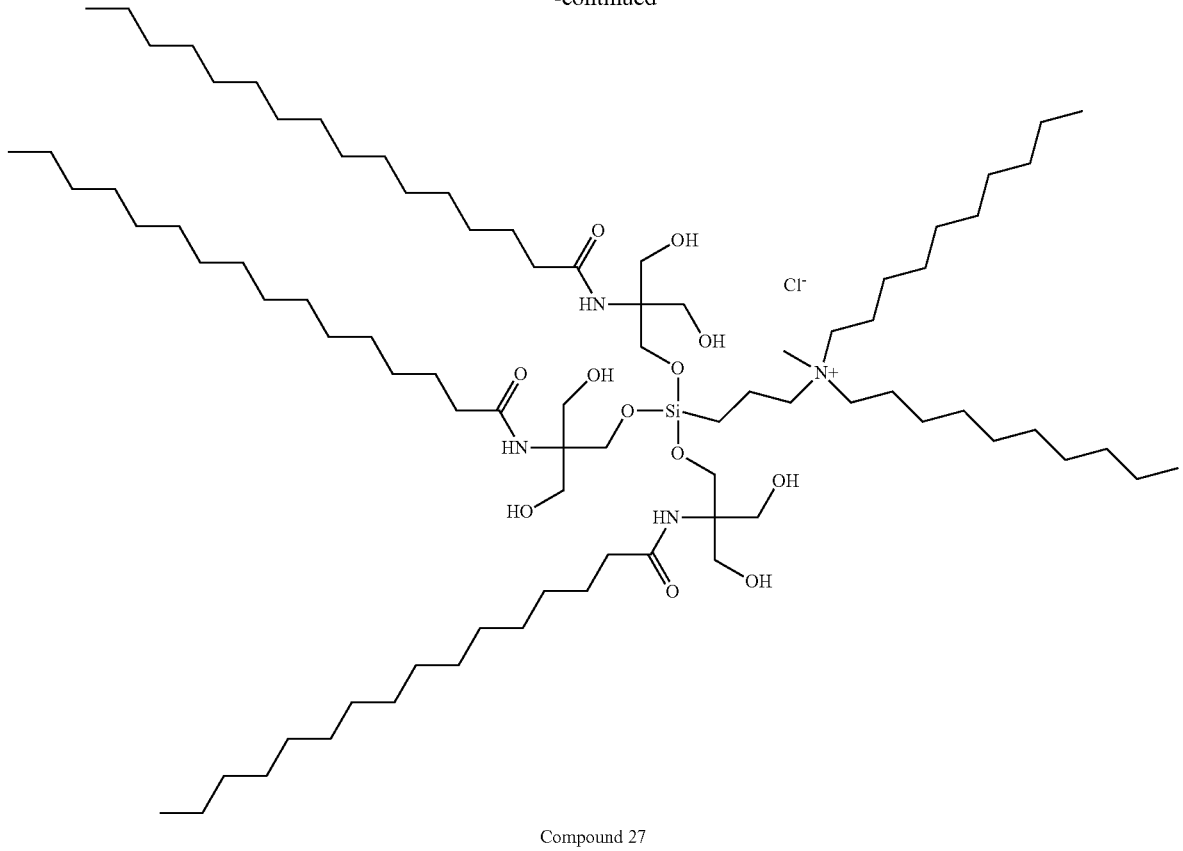

Compound 27

A round bottom reaction vessel is outfitted with a heating mantle, stir bar, downward condenser, receiving flask, oil bubbler, a thermoprobe for the pot, and a thermoprobe for the head. The reactor is charged with a solution of didecyl-methyl[3-(trimethoxysilyl)propyl]ammonium chloride, Compound 26 and DMF. The mixture is heated to 145° C. (pot temp) and the methanol is collected until the head temp drops and no more MeOH evolves. The reaction is then cooled and DMF evaporated at reduced pressure. Toluene is added, stirred at room temp for 1 hr, and then evaporated at reduced pressure. Acetonitrile is added, stirred at room temp for 1 hr, and then evaporated at reduced pressure. The resultant product is placed under high vac overnight to yield the expected product Compound 27.

Example 27. Synthesis of N-(3-(21-(3-hydroxy-2-(hydroxymethyl)-2-palmitamidopropoxy)-18,18,24,24-tetrakis(hydroxymethyl)-16,26-dioxo-20,22-di-oxa-17,25-diaza-21-silahentetracontan-21-yl)propyl)-N,N-dimethyloctadecan-1-aminium chloride

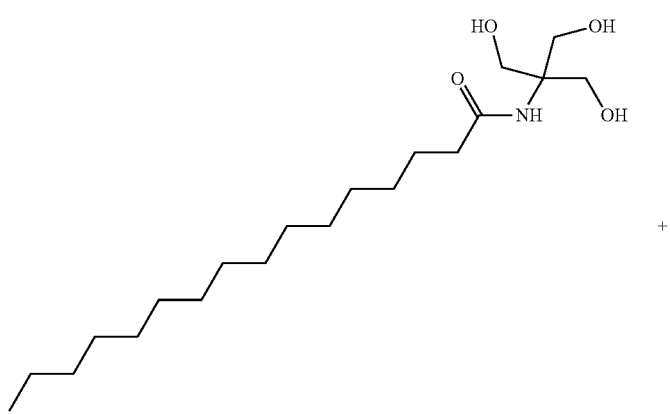

+

Compound 26

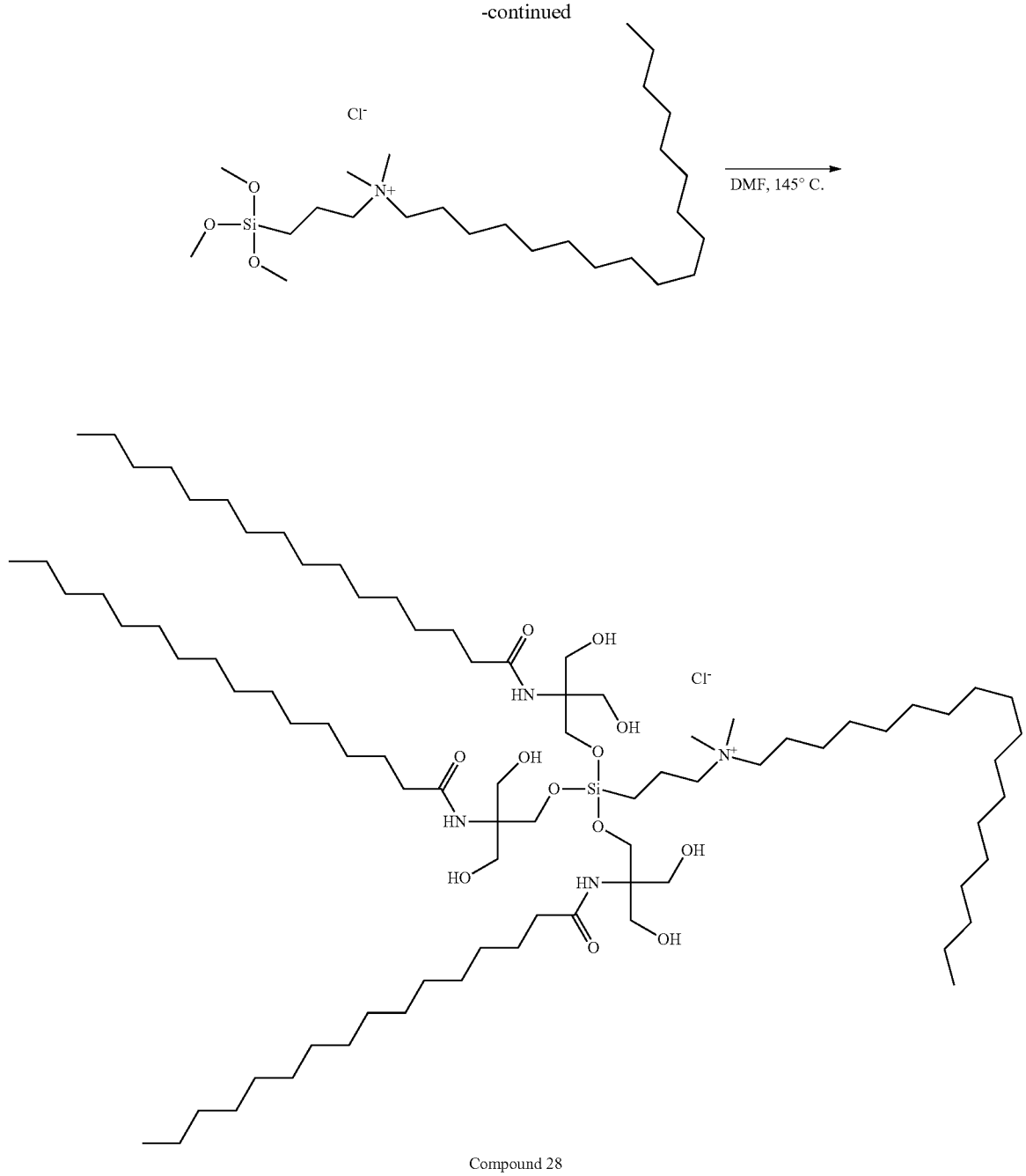

Compound 28

A round bottom reaction vessel is outfitted with a heating mantle, stir bar, downward condenser, receiving flask, oil bubbler, a thermoprobe for the pot, and a thermoprobe for the head. The reactor is charged with a solution of dimethyloctadecyl[3-(trimethoxysilyl)propyl]ammonium chloride, Compound 26 and DMF. The mixture is heated to 145° C. (pot temp) and the methanol is collected until the head temp drops and no more MeOH evolves. The reaction is then cooled and DMF evaporated at reduced pressure. Toluene is added, stirred at room temp for 1 hr, and then evaporated at reduced pressure. Acetonitrile is added, stirred at room temp for 1 hr, and then evaporated at reduced pressure. The resultant product is placed under high vac overnight to yield the expected product Compound 28.-

Example 28. Synthesis of N-decyl-N-(3-(7-(3-hydroxy-2-(hydroxymethyl)-2-((2-sulfoethyl)amino)propoxy)-4,4,10,10-tetrakis(hydroxymethyl)-1,14-disulfo-6,8-dioxa-3,11-diaza-7-silatetradecan-7-yl)propyl)-N-methyldecan-1-aminium chloride

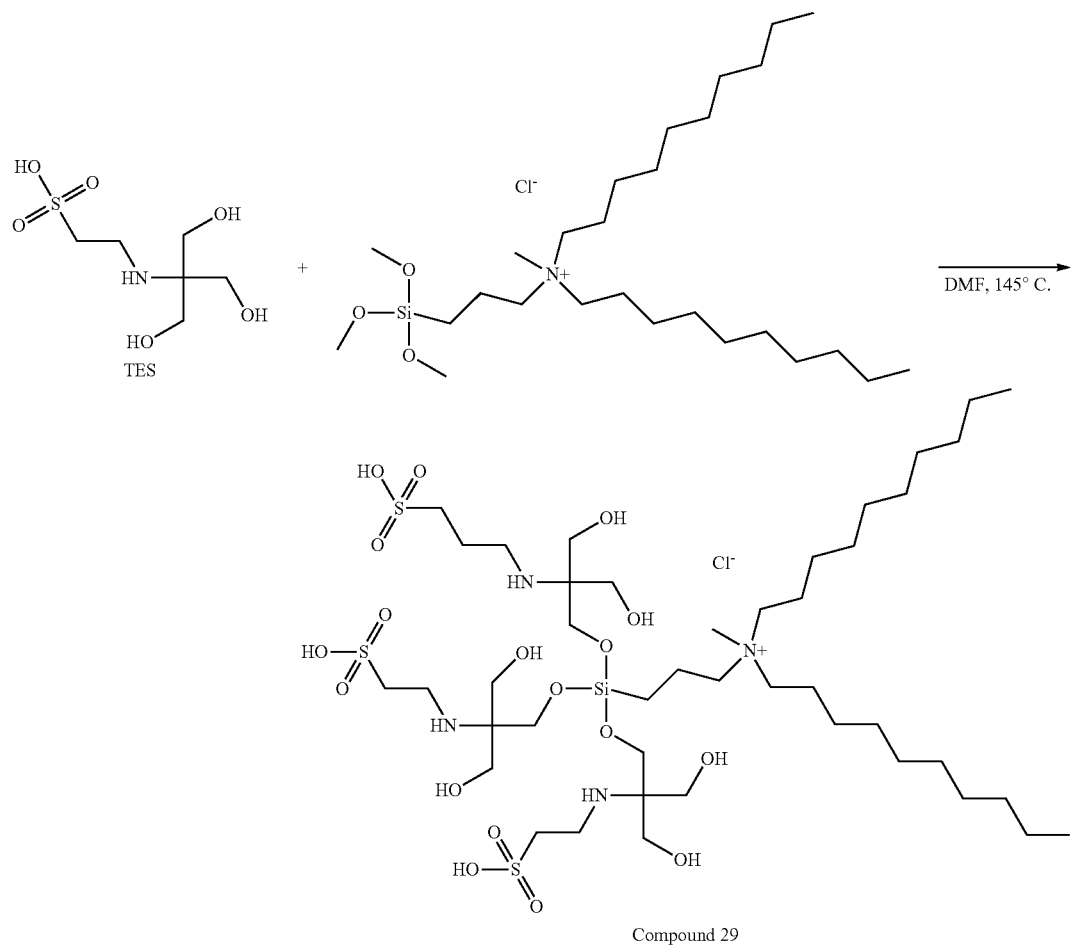 [SMILES: O=S(=O)(O)CCNC(CO)(CO)CO ; CCCCCCCCCC[N+](C)(CCCCCCCCCC)CCC[Si](OC)(OC)OC ; [Cl-] ; CCCCCCCCCC[N+](C)(CCCCCCCCCC)CCC[Si](OCC(CO)(CO)NCCCS(=O)(=O)O)(OCC(CO)(CO)NCCS(=O)(=O)O)OCC(CO)(CO)NCCS(=O)(=O)O ; [Cl-]]

Compound 29

A round bottom reaction vessel is outfitted with a heating mantle, magnetic stirring bar, downward condenser, receiving flask, oil bubbler, an immersion thermoprobe for the pot, and a thermoprobe for the head. The reactor is charged with a solution of didecylmethyl[3-(trimethoxysilyl)propyl]ammonium chloride, TES, TES sodium, and DMF. The mixture is heated to 145° C. (pot temp) and the methanol is collected by distillation. As the reaction is heated, a homogenous solution forms and the methanol is distilled off, as a white precipitate begins to form. The reaction is heated until the head temperature drops and no more methanol evolves. The reaction is then cooled and the sodium chloride precipitate is removed by filtration through a glass fiber filter and the DMF evaporated at reduced pressure to yield a semi-solid. Toluene is added, the mixture stirred at room temp for 1 hour, and then evaporated. Acetonitrile is added, the suspension stirred at room temp for 1 hour, and then evaporated. The colorless solid is collected on a glass frit and rapidly washed with acetonitrile and ether, taking care to minimize exposure to air as the product is very hygroscopic. The solid is then transferred to a vacuum flask and dried under vacuum to afford Compound 29.

Example 29 Antimicrobial Screening Assays

The antimicrobial activity of the compounds described herein can be determined using any number of standard in vitro or in vivo assays known in the art. For example, the minimum inhibitory concentration (MIC) activity of the compounds described herein can be determined using the disk diffusion susceptible test (also known as the Kirby-Bauer test) or the broth dilution test, or any other suitable in vitro assay known in the art to determine the susceptibility of a microorganism to an antimicrobial. In addition, in vivo assays, for example in vivo methods for evaluating topical antimicrobial agents such as occlusion assays or rabbit eye efficacy testing may be used to characterize the antimicrobial activity of the compounds described herein.

Disk Diffusion Susceptibility Test

One particularly suitable test is the disk diffusion susceptibility test (see Jan Hudzicki, Kirby-bauer disk diffusion susceptibility test protocol, December 2009, American Society for Microbiology, incorporated herein by reference). In the disk diffusion susceptibility test, a known concentration of a compound described herein is absorbed on a disk of filter paper (generally 6-mm) and placed on a Mueller-Hinton (MH) agar plate or other suitable agar plate used for testing the particular antimicrobial. Water is immediately absorbed into the disk from the agar and the compound begins to diffuse into the surrounding agar. The rate of diffusion through the agar is not as rapid as the rate of extraction of the compound out of the disk, therefore the concentration of the compound is highest closest to the disk and a logarithmic reduction in concentration occurs as the distance from the disk increases (see, e.g., Jorgensen, J. H., and J. D. Turnidge. 2007. Susceptibility test methods: dilution and disk diffusion methods, p. 1152-1172. In P. R. Murray, E. J. Baron, J. H. Jorgensen, M. L. Landry, and M. A. Pfaller (ed.), Manual of clinical microbiology, 9th ed. ASM Press, Washington, D.C., incorporated herein by reference). The rate of diffusion of the compound through the agar is dependent on the diffusion and solubility properties of the drug in MH agar and the molecular weight of the compound (see, e.g., Bauer, A. W., W. M. M. Kirby, J. C. Sherris, and M. Turck. 1966. Antibiotic susceptibility testing by a standardized single disk method. Am. J. Clin. Pathol. 36:493-496, incorporated herein in its entirety). Larger molecules will diffuse at a slower rate than lower molecular weight compounds. These factors, in combination, result in the compound having a unique breakpoint zone size indicating susceptibility to that compound. The disk diffusion method can also be used to test antifungals (see, for example, CLSI M44; Clinical and Laboratory Standards Institute Method for Antifungal Disk Diffusion Susceptibility Testing of Yeasts; Approved Guideline 2ndWayne: Clinical and Laboratory Standards Institute; 2009, incorporated herein). To test antifungal activity, the use of Mueller-Hinton agar supplemented with 2% glucose is recommended, providing a suitable growth for most yeasts, and 0.5 mg/L methylene blue dye medium (enhances the zone edge definition) minimizing the trailing effect. The pH of the medium should be between 7.2 and 7.4 after gelling and the agar should be 4 cm high. The inoculum is standardized to 0.5 McFarland using a densitometer and plates should be incubated at 35° C. for between 24 hours and 48 hours.

If the agar plate has been inoculated with a suspension of the pathogen to be tested prior to the placing of disks on the agar surface, simultaneous growth of the bacteria and diffusion of the compound occurs. Growth occurs in the presence of the compound when the bacteria reach a critical mass and can overpower the inhibitory effects of the compound. The estimated time of a bacterial suspension to reach critical mass is 4 to 10 hours for most commonly recovered pathogens, but is characteristic of each species, and influenced by the media and incubation temperature. The size of the zone of inhibition of growth is influenced by the depth of the agar, since the antimicrobial diffuses in three dimensions, thus a shallow layer of agar will produce a larger zone of inhibition than a deeper layer. The point at which critical mass of the antimicrobial is reached is demonstrated by a sharply marginated circle of microbial growth around the disk. The concentration of compound at this margin is called the critical concentration and is approximately equal to the minimum inhibitory concentration obtained in broth dilution susceptibility tests. Although not all fastidious or slow growing bacteria can be accurately tested by this method, the disk test has been standardized for testing streptococci, *Haemophilus influenzae*, and *N. meningitidis* through use of specialized media, incubation conditions, and specific zone size interpretive criteria (see, e.g., Clinical and Laboratory Standards Institute, Performance standards for antimicrobial disk susceptibility tests. Approved standard M2-A10, 2009, Wayne, PA Clinical and Laboratory Standards Institute, incorporated herein by reference).

Antimicrobial Gradient Diffusion Method

Additional assays may also be used. For example, the antimicrobial gradient diffusion method uses the principle of establishment of an antimicrobial concentration gradient in an agar medium as a means of determining susceptibility (see, e.g., Reller et al., Antimicrobial Susceptibility Testing: A Review of General Principles and Contemporary Practices, Clinical Infectious Diseases, Volume 49, Issue 11, 1 Dec. 2009, Pages 1749-1755, https://doi.org/10.1086/647952). The Etest (bioMerieux AB BIODISK) is a commercial version available in the United States. It employs thin plastic test strips that are impregnated on the underside with a dried antibiotic concentration gradient and are marked on the upper surface with a concentration scale. As many as 5 or 6 strips may be placed in a radial fashion on the surface of an appropriate 150-mm agar plate that has been inoculated with a standardized organism suspension like that used for a disk diffusion test. After overnight incubation, the tests are read by viewing the strips from the top of the plate. The MIC is determined by the intersection of the lower part of the ellipse shaped growth inhibition area with the test strip.

Broth Dilution Susceptibility Test

In addition to or in alternative, the antimicrobial activity of a compound described herein can be determined through the use of a broth dilution susceptibility test (see, e.g., Reller et al., Antimicrobial Susceptibility Testing: A Review of General Principles and Contemporary Practices, Clinical Infectious Diseases, Volume 49, Issue 11, 1 Dec. 2009, Pages 1749-1755, https://doi.org/10.1086/647952). This procedure uses serial dilutions (usually 2×) of a compound of interest (eg, 0.25, 0.5, 1, 2, 4, 8, and 16 µg/mL) in a liquid growth medium dispensed in, e.g., test tubes or standard trays containing 96 wells. The compound-containing tubes are inoculated with a standardized suspension of the microbe, for e.g., $1-5 \times 10^5$ CFU/mL for bacterial cultures). Following overnight incubation at, e.g., 35° C., the tubes are examined for visible microbial growth as evidenced by turbidity. The lowest concentration of antibiotic that prevents growth generally represents the minimal inhibitory concentration (MIC). The advantage of this technique is the generation of a quantitative result (i.e., the MIC).

Currently, phenotypic assays to perform in vitro antifungal broth dilution susceptibility tests for either yeasts or filamentous fungi (also termed molds) include two universally recognized standard methods, Clinical and Laboratory Standards Institute (CLSI) (Clinical and Laboratory Standards Institute. M27-A3: Reference Method for Broth Dilution Antifungal Susceptibility Testing of Yeasts; Approved Standard—3rd ed.; CLSI: Wayne, PA, USA, 2008; Clinical and Laboratory Standards Institute. M38-A2: Reference Method for Broth Dilution Antifungal Susceptibility Testing of Filamentous Fungi; Approved Standard—2nd ed.; CLSI: Wayne, PA, USA, 2008, incorporated herein by reference) and the European Committee on Antimicrobial Susceptibility Testing (EUCAST) (Arendrup et al., EUCAST-AFST. EUCAST technical note on the EUCAST definitive document EDef 7.2: Method for the determination of broth dilution minimum inhibitory concentrations of antifungal agents for yeasts EDef 7.2 (EUCAST-AFST). Clin. Microbiol. Infect. 2012, 18, E246-E247; Arendrup et al., Subcommittee on Antifungal Susceptibility Testing (AFST) of the ESCMID European Committee for Antimicrobial Susceptibility Testing (EUCAST). In EUCAST Method for the Determination of Broth Dilution Minimum Inhibitory Concentrations of Antifungal Agents for Conidia Forming Moulds Version 9.3; EUCAST: Växjö, Sweden, 2015, incorporated herein by reference), which apply the broth microdilution method (BMD). Both measure antifungal activity, expressed as the minimum inhibitory concentration (MIC) of an antifungal drug, which indicates the minimal drug concentration that inhibits fungal growth. Despite some methodological differences (e.g., glucose concentration, inoculum size, reading endpoint, etc.) between the two, CLSI and EUCAST have been proven to yield, upon completion of testing, comparable MIC data for all classes of antifungal agents (see, e.g., Posteraro et al., The future of fungal susceptibility testing. Future Microbiol. 2014, 9, 947-967; Pfaller et al., Comparison of the broth microdilution (BMD) method of the European Committee on Antimicrobial Susceptibility Testing with the 24-hour CLSI BMD method for testing susceptibility of Candida species to fluconazole, posaconazole, and voriconazole by use of epidemiological cutoff values. J. Clin. Microbiol. 2011, 49, 845-850; Pfaller et al., Progress in antifungal susceptibility testing of Candida spp. by use of Clinical and Laboratory Standards Institute broth microdilution methods, 2010 to 2012. J. Clin. Microbiol. 2012, 50, 2846-2856, incorporated herein by reference).

Minimum Bactericidal Concentration (MBC) Assay

Additional assays may be performed to further characterize the antimicrobial activity of the compounds described herein. For example, the minimum bactericidal concentration (MBC) or minimum lethal concentration (MLC) may be determined following the M26-A guidelines of the Clinical and Laboratory Standards Institute (Barry et el., A-26: Methods for determining Bactericidal Activity of Antimicrobial Agents; Approved Guidelines, September 1999, Vol. 19(18), incorporated herein by reference. The minimum bactericidal concentration (MBC) is the lowest concentration of an antibacterial agent required to kill a particular bacterium. It can be determined from broth dilution minimum inhibitory concentration (MIC) tests by sub-culturing to agar plates that do not contain the test agent. The MBC is identified by determining the lowest concentration of antibacterial agent that reduces the viability of the initial bacterial inoculum by ≥99.9%. The MBC is complementary to the MIC; whereas the MIC test demonstrates the lowest level of antimicrobial agent that inhibits growth, the MBC demonstrates the lowest level of antimicrobial agent that results in microbial death.

Additional Useful In Vitro Assays

Additional assays well-known in the art that may be used to test the antimicrobial activity, including antibacterial and antifungal activity, include the agar well diffusion methods, the agar plug diffusion method, the cross streak method, the poisoned food method, thin-layer chromatography bioautography, agar dilution methods, the time-kill test (time-kill curve), ATP bioluminescence test, and the flow cytofluorometric method (see Balouiri et al., Methods for in vitro evaluating antimicrobial activity: A review. Journal of Pharmaceutical Analysis, Vol. 6, No. 2, April 2016; pg. 71-79, incorporated herein by reference). Assays well-known in the art that may be used to test the anti-viral activity of the compounds described herein include cytopathic effect (CPE) inhibitory assays (see, e.g., Schmidtke et al., A rapid assay for evaluation of antiviral activity against coxsackie virus B3, influenza virus A, and herpes simplex virus type 1. J Virol Methods. 2001 June; 95(1-2):133-43; Cotarelo et al., Cytopathic effect inhibition assay for determining the in-vitro susceptibility of herpes simplex virus to antiviral agents, Journal of Antimicrobial Chemotherapy, Volume 44, Issue 5, November 1999, Pages 705-708, https://doi.org/10.1093/jac/44.5.705 incorporated herein by reference).

In Vivo Topical Assays

In addition to the in vitro assays described above, the antimicrobial efficacy activity of the compounds described herein can be characterized using suitable in vivo assays. For example, an occlusion test measures the ability of an agent to prevent the expansion of the resident microflora which occurs when an impermeable dressing is applied to the forearm (see, e.g., Leyden et al. Updated in vivo Methods for Evaluating Topical Antimicrobial Agents on Human Skin, Journal of Investigative Dermatology, 72: 165-170 (1979), incorporated herein by reference). The principle of this test is that the micro flora of the forearm skin is sparse (101 to 102 organisms per square cm). An impermeable dressing will increase surface moisture by preventing diffusional water loss and thus enhance bacterial growth. The density of resident organisms increases significantly, with counts frequently reaching millions per sq cm by 48 hr. The organisms involved in this expansion are primarily gram-positive cocci and diphtheroids. The procedure is as follows: on each arm 0.1 ml of a compound is delivered to each of two 5-cm squares (25 sq cm), by a plastic tuberculin syringe (0.1 ml). Each site is immediately covered with a 5-em square of impermeable plastic, e.g., Saran Wrap. The site is occlusively sealed by encircling the limb with plastic tape (Dermiclear). A strip of wide white-backed adhesive tape (Zonas, Johnson & Johnson) is placed between each test site to prevent the possibility of translocation of test agents and organisms from one site to another. A third site on each arm is treated with 0.1 ml of the vehicle. The control site is always prepared first to prevent its potential contamination by the test substances. After 24 hr of occlusion, the 3 sites on one arm are quantitatively sampled. The opposite arm is sampled after 48 hr.

Additional or alternative tests include the expanded flora test, persistence test, ecological shift test, and serum inactivation test, which are known in the art (see, e.g., Leyden et al. Updated in vivo Methods for Evaluating Topical Antimicrobial Agents on Human Skin, Journal of Investigative Dermatology, 72: 165-170 (1979), incorporated herein by reference).

In vivo testing to determine the efficacy of a compound described herein for use in the eye to treat an infection are also well known. For example, the compound described herein can be tested against targeted microbial infections by induced infections in rabbit eyes, and treating the rabbit (see, generally, Deren et al., Comparison of antifungal efficacies of moxifloxacin, liposomal amphotericin B, and combination treatment in experimental Candida albicans endophthalmitis in rabbits. Can J Microbiol. 2010 January; 56(1):1-7. doi: 10.1139/w09-112, incorporated herein by reference).

Exemplary Disk Diffusion Susceptibility Test

An exemplary disk diffusion susceptibility test for testing the antibacterial activity of a compound described herein is provided below.

Mueller-Hinton Agar

Mueller-Hinton agar (MH agar) is the standard medium for use in routine susceptibility testing of, for example, nonfastidious bacteria, including, for example, aerobic or facultative bacteria. MH agar may be purchased as prepared agar plates from Remel (Lenexa, KS), BD BBL (Franklin Lakes, NJ), or any other supplier of prepared agar plates. Follow the manufacturer's recommendation for storage of prepared plates. MH agar can also be prepared from dehydrated media available from companies such as Remel, BD BBL, or any other supplier of dehydrated media. Prepare the media according to the manufacturer's directions.

Formula for Mueller-Hinton agar per liter of purified water:

| | |
|---|---|
| Beef, Infusion from | 300.0 g |
| Casamino acid, technical | 17.5 g |
| Starch | 1.5 g |
| Agar | 17.0 g |

Suspend the components listed above in 1 liter of purified water. Mix thoroughly. Heat with frequent agitation and boil for 1 minute to completely dissolve the components. Autoclave at 121° C. for 15 minutes. Dispense as desired. Allow to solidify at room temperature, then store at 4 to 8° C. Mueller-Hinton agar is stable for approximately 70 days (per Remel Technical Services, 1 Sep. 2009) from the date of preparation. If MH agar plates are prepared from dehydrated media, the plates should be poured to a depth of 4 mm (approximately 25 ml of liquid agar for 100-mm plates and 60 ml of liquid agar for 150-mm plates, but in any case to a measured depth of 4 mm. pH of the MH agar should fall between 7.2 and 7.4 at room temperature after solidification and should be tested when the media is first prepared.

Antimicrobial Susceptibility Disks

Impregnate a disk of standard filter paper (approximately 6-mm) with a known concentration (e.g., 1 µg/ml) of a compound, for example a compound of Formula I, described herein in a suitable growth medium and allow to dry at 4° C.

McFarland Standard

McFarland standards are suspensions of either barium sulfate or latex particles that allow visual comparison of bacterial density. Commercially prepared standards are available for purchase from companies such as Remel or BD BBL. These often include a Wickerham card, which is a small card containing parallel black lines. A 0.5 McFarland standard is equivalent to a bacterial suspension containing between $1\times10^8$ and $2\times10^8$ CFU/ml of *E. coli*. McFarland standard may be prepared as describe below:

1. Add a 0.5-ml aliquot of a 0.048 mol/liter $BaCl_2$ (1.175% wt/vol $BaCl_2.2H_2O$) to 99.5 ml of 0.18 mol/liter $H_2SO_4$ (1% vol/vol) with constant stirring to maintain a suspension.
2. Verify the correct density of the turbidity standard by measuring absorbance using a spectrophotometer with a 1-cm light path and matched cuvette. The absorbance at 625 nm should be 0.08 to 0.13 for the 0.5 McFarland standard.
3. Transfer the barium sulfate suspension in 4- to 6-ml aliquots into screw-cap tubes of the same size as those used in standardizing the bacterial inoculums.
4. Tightly seal the tubes and store in the dark at room temperature.
5. Prior to use, vigorously agitate the barium sulfate standard on a mechanical vortex mixer and inspect for a uniformly turbid appearance. Replace the standard if large particles appear. If using a standard composed of latex particles, mix by inverting gently, not on a vortex mixer.
6. As the bacterial colonies are added to the saline in the "preparation of the inoculum" step of the procedure, compare the resulting suspension to the McFarland standard. This is done by holding both the standard and the inoculum tube side by side and no more than 1 inch from the face of the Wickerham card (with adequate light present) and comparing the appearance of the lines through both suspensions. Do not hold the tubes flush against the card. If the bacterial suspension appears lighter than the 0.5 McFarland standard, more organisms should be added to the tube from the culture plate. If the suspension appears denser than the 0.5 McFarland standard, additional saline should be added to the inoculum tube in order to dilute the suspension to the appropriate density.

Preparation of Mueller-Hinton Plate

1. Allow a MH agar plate (one for each organism to be tested) to come to room temperature. It is preferable to allow the plates to remain in the plastic sleeve while they warm to minimize condensation.
2. If the surface of the agar has visible liquid present, set the plate inverted, ajar on its lid to allow the excess liquid to drain from the agar surface and evaporate. Plates may be placed in a 35° C. incubator or in a laminar flow hood at room temperature until dry (usually 10 to 30 minutes).
3. Appropriately label each MH agar plate for each organism to be tested.

Preparation of Inoculum

1. Using a sterile inoculating loop or needle, touch four or five isolated colonies of the organism to be tested, for example, an organism selected from *Pseudomonas* (Gram-negative), *Proteus* (genus of Gram-negative Proteobacteria), *Staphylococcus* (Gram-positive), MRSA (methicillin resistant *S. aureus*), *Escherichia coli* (Gram-negative), *Klebsiella* (Gram-negative), *Enterococcus* (Gram-positive), or *Haemophilus influenzae*,
2. Suspend the organism in 2 ml of sterile saline.
3. Vortex the saline tube to create a smooth suspension.
4. Adjust the turbidity of this suspension to a 0.5McFarland standard by adding more organism if the suspension is too light or diluting with sterile saline if the suspension is too heavy.
5. Use this suspension within 15 minutes of preparation.

Inoculation of the MH Plate

1. Dip a sterile swab into the inoculum tube.
2. Rotate the swab against the side of the tube (above the fluid level) using firm pressure, to remove excess fluid. The swab should not be dripping wet.
3. Inoculate the dried surface of a MH agar plate by streaking the swab three times over the entire agar surface; rotate the plate approximately 60 degrees each time to ensure an even distribution of the inoculum.
4. Rim the plate with the swab to pick up any excess liquid.
5. Discard the swab into an appropriate container.
6. Leaving the lid slightly ajar, allow the plate to sit at room temperature at least 3 to 5 minutes, but no more than 15 minutes, for the surface of the agar plate to dry before proceeding to the next step arrow indicates the path of the swab.

Placement of the Antimicrobial Disks

Place the appropriate antimicrobial-impregnated disks on the surface of the agar. Disks should not be placed closer than 24 mm (center to center) on the NM agar plate. Ordinarily, no more than 12 disks should be placed on a 150-mm plate or more than 5 disks on a 100-mm plate. Avoid placing disks close to the edge of the plate as the zones will not be fully round and can be difficult to measure.

Each disk must be pressed down with forceps to ensure complete contact with the agar surface or irregular zone shapes may occur. If the surface of the agar is disrupted in any way (a disk penetrating the surface, visible lines present due to excessive pressure of the swab against the plate during inoculation, etc.) the shape of the zone may be affected.

Incubation of the Plates

Incubate the inoculated plates at a temperature range of 35° C.±2° C. Results are read after about 18 hours of incubation.

Example 30. Disk Diffusion Susceptibility Test of Compound 1

Figure 2:
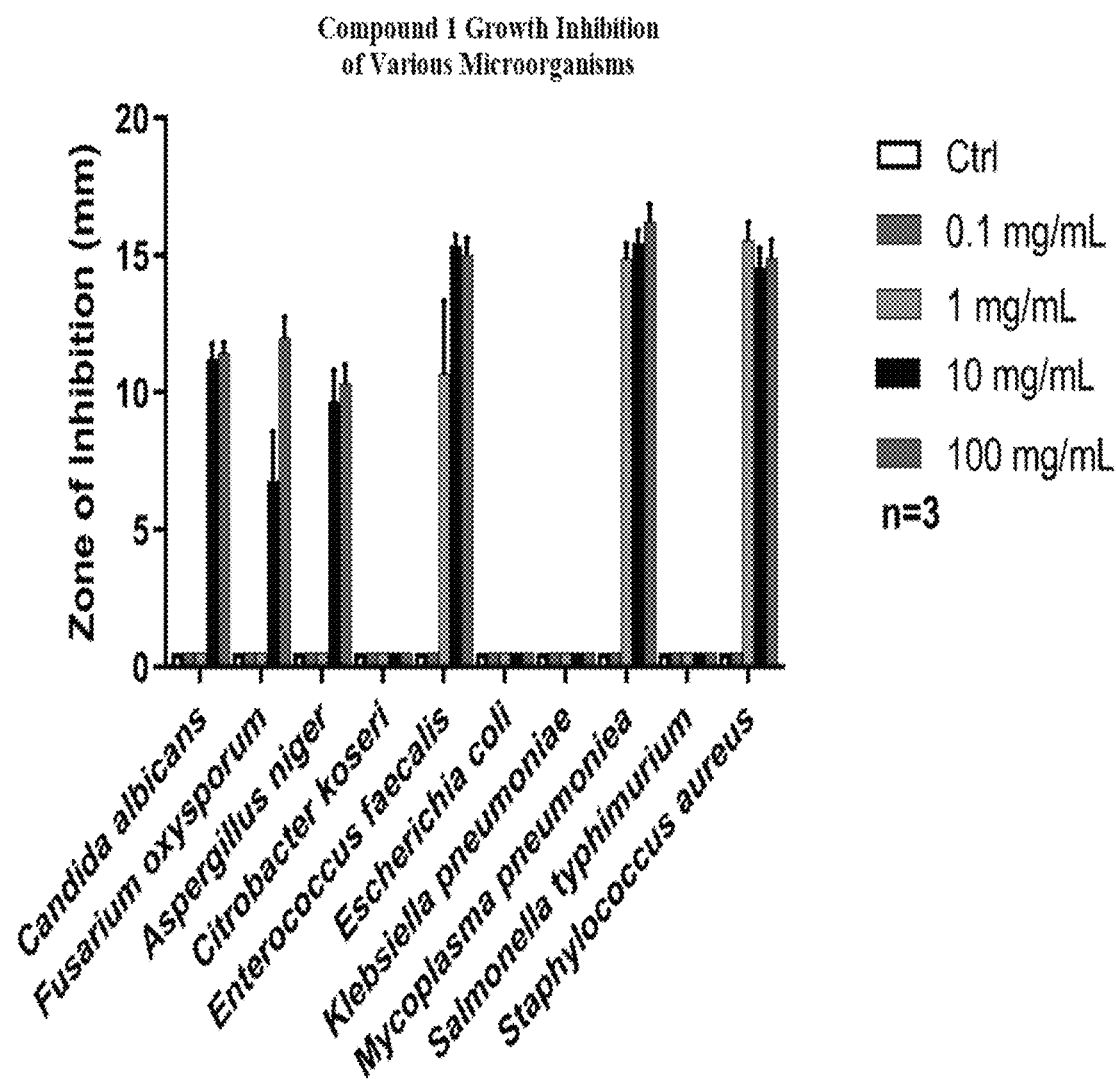
FIG. 2 is a bar graph showing the results of a disk diffusion susceptibility test of a range of increasing concentrations of Compound 1 against a range of microorganisms. The x-axis shows the strains being tested under five reaction conditions, which include four increasing concentrations of Compound 1 and a control. The y-axis is the zone of inhibition, which is measured in millimeters.

An initial disk diffusion susceptibility screening test was performed similarly to as described above using a 1% and 2% aqueous solution (powder reconstituted in water), respectively, of Compound 1. The experiment was repeated with a broader range of concentrations (0.1 mg/mL, 1.0 mg/mL, 10 mg/mL and 100 mg/mL) tested as well as some additional microbes. As seen in FIG. 1, complete inhibition was seen at both the 1% and 2% solutions of Compound 1 for the fungal strains of *Aspergillus niger, Candida albicans*, and *Fusarium oxysporum*. In addition, complete inhibition at both the 1% and 2% solution of Compound 1 was seen for *Enterococcus faecalis*. In the repeated experiment shown in FIG. 2, complete inhibition was seen at 1 mg/mL, 10 mg/mL and 100 mg/mL for *Enterococcus faecalis, Mycoplasma pneumoniae*, and *Staphylococcus aureus*. Additionally, complete inhibition was seen for at 10 mg/mL and 100 mg/mL for the fungal strains of *Aspergillus niger, Candida albicans*, and *Fusarium oxysporum*.

Example 31. Determination of Minimum Inhibitory Concentration and Minimum Bactericidal or Fungal Concentration of Compounds 2 and 23

Compounds 2 and 23 were tested to determine the Minimum Inhibitory Concentration (MIC) and Minimum Bactericidal Concentration (MBC) or Minimum Fungicidal Concentration (MFC) against six test strains listed below in Table 2.

TABLE 1

Strains used in study

| Number | Species | Strain ID | Characteristic |
|---|---|---|---|
| 1 | *Staphylococcus aureus* | ATCC 33591 | Clinical isolate |
| 2 | *Pseudomonas aeruginosa* | ATCC 27583 | Clinical isolate |
| 3 | *Steptococcus pyogenes* | ATCC 51339 | Clinical isolate |
| 4 | *Candida albicans* | ATCC 90028 | Clinical isolate |
| 5 | *Candida auris* | CDC 0381 | Clinical isolate |
| 6 | *Cladosporium herbarum* | ATCC MYA-4682 | Clinical isolate |

Materials and Methods

Microorganisms and Media.

Strain numbers starting with "ATCC" were acquired from the American Type Culture Collection (Manassas, VA), while strain numbers starting with "CDC" were acquired from the Centers for Disease Control and Prevention (Atlanta, GA). All strains were maintained as −80° C. frozen glycerol stocks. *S. aureus* and *P. aeruginosa* were grown overnight on Tryptic Soy Agar (TSA) plates at 35±2° C., ambient atmosphere, while *S. pyogenes* was grown overnight on TSA+5% defibrinated sheep blood at 35±2° C., 5% $CO_2$. All fungal species (i.e. *C. albicans, C. auris* and *C. herbarum*) were grown on Sabouraud Dextrose Agar (SDA) plates. *C. herbarum* was grown at 25±2° C. for 5 to 7 days, while all other fungal strains were grown at 35±2° C. overnight.

Test Articles and Control Antimicrobials.

Test articles Compound 2 (batch #2G13A0.368) and Compound 23 (batch #2G17A0.372) were received and stored at 4° C. The antibiotic Tobramycin and antifungal Amphotericin B were used as quality control (QC) compounds for the MIC assay. Stock solutions of 3.2 mg/mL Tobramycin (Sigma-Aldrich, cat #T1783-500MG) and 3.2 mg/mL Amphotericin B (CP Lab Chemicals, cat #TOK-A007-1G) were prepared in sterile ultrapure water.

MIC Microdilution Assay.

All test articles were diluted to 6.4 mg/mL in sterile ultrapure water, then ten 2-fold serial dilutions were made in sterile ultrapure water in a 96-well master plate to generate 10× starting concentrations for MIC testing. For bacteria strains, a few colonies of each strain were collected with a sterile swab and used to make a McFarland 0.5 standard solution (approximately 1×108 CFU/mL) in sterile PBS. The McFarland was then diluted 1:180 in Cation Adjusted Muller-Hinton Broth (CAVHB) for *S. aureus* and *P. aeruginosa*, and in CAMHB+5% defibrinated sheep blood for *S. pyogenes*. 90 µL of this inoculum was combined with 10 µL of the 10× test article in a 96-well plate for a final concentration of 1×.

For the yeasts *C. albicans* and *C. auris*, a McFarland 0.5 standard solution in sterile PBS was similarly prepared (approximately $1 \times 10^6$ CFU/mL) and was subsequently diluted 1:180 in RPMI 1640 media buffered with 0.165 M MOPS at pH 7.0 (herein referred to as "RPMI media"). 90 µL of the *Candida* inoculum was combined with 10 µL of the 10× test article in a 96-well plate for a final concentration of 1×.

For the filamentous fungi *C. herbarum*, the fungal culture was harvested from SDA plate with a sterile swab into RPMI media after 5 to 7 days of growth. This suspension was allowed to stand for 5-10 minutes before the spores in suspension were collected and adjusted to McFarland 0.5 (approximately 2×106 CFU/mL) in sterile PBS. The *C. herbarum* inoculum was diluted 1:50 in RPMI media, and 180 µL of the *C. herbarum* inoculum was combined with 20 µL of the 10× test article in a 96-well plate for a final concentration of 1×.

All bacterial-strain MIC 96-well plates were incubated at 35±2° C. for 18 to 20 hours, while all *Candida* MIC 96-well plates were incubated at 35±2° C. for 24 to 48 hours. *C. herbarum* MIC 96-well plates were incubated at 25±2° C. for 3 to 5 days, until growth was visible in the growth control wells. After incubation, the 96-well plates were examined visually and on a spectrophotometer at absorbance $OD_{650}$. MIC is defined as the lowest concentration of a compound in which no visible growth is observed.

MBC/MFC Determination

10 µL of liquid from each test condition was plated on the appropriate agar media for each test strain. For bacteria strains, plating for MBC occurred after 18 to 20 hours incubation. For the *Candida* species, plating for MFC occurred after 48 hours incubation, while *C. herbarum* plating for MFC occurred 3 days after incubation when growth in growth control wells was visually observed. Once the liquid from the 96-well plate has been allowed to air dry in a biosafety cabinet, the agar plates were incubated under the appropriate conditions and colony formation was assessed. MBC/MFC is defined as the lowest concentration of a compound in which no colonies were recovered.
Results and Discussion The MIC/MBC/MFC values for the strains assayed, as well as the expected CLSI QC values, are listed below in Table 2. Compound 2 and Compound 23 were active against *S. aureus* ATCC 33591, as well as all three strains of fungi, with MIC values between 0.5 to 2 µg/mL. However, neither compound was active against *P. aeruginosa* ATCC 27853, which was able to grow at the highest concentration tested i.e. 64 µg/mL. Both compounds also had limited activity against *S. pyogenes* ATCC 51339, with MIC values ranging between 32 to >64 µg/mL. The MIC values of Tobramycin and Amphotericin B for the QC strains ATCC 27853 and ATCC 90028 fell within their expected CLSI QC ranges, thereby validating the MIC assay method.

frozen glycerol stocks. *S. aureus* and *P. aeruginosa* were grown overnight on Tryptic Soy Agar (TSA) plates at 35±2° C., ambient atmosphere, while *S. pyogenes* was grown overnight on TSA+5% defibrinated sheep blood at 35±2° C., 5% $CO_2$. *C. jejuni* was grown for 48 hours on TSA+5% defibrinated sheep blood at 35±2° C., in a microaerophilic environment generated by CampyGen sachet. All fungal species (i.e. *C. albicans* and *C. auris*) were grown overnight on Sabouraud Dextrose Agar (SDA) plates at 35±2° C., ambient atmosphere.

Test Article and Control Antimicrobials

Test article Compound 1 (batch #7G30A9.203) was stored at 4° C. The antibiotic Tobramycin and antifungal Amphotericin B were used as quality control (QC) compounds for the MIC assay. Stock solutions of 3.2 mg/mL Tobramycin (Sigma-Aldrich, cat #T1783-500MG) and 3.2

TABLE 2

MIC/MBC/MFC Values of strains tested

| | | MIC/MBC/MFC (µg/mL) | | | | | | | | | | |
|---|---|---|---|---|---|---|---|---|---|---|---|---|
| | | Compound 23 | | | | Compound 2 | | | | Tobramycin | | Amphotericin B |
| Species | Strain ID | MIC | | MBC/MFC | | MIC | | MBC/MFC | | MIC | | MIC |
| *S. aureus* | ATCC 33591 | 0.5 | 0.5 | 0.5 | 0.5 | 1 | 1 | 2 | 8 | >32 | >32 | >32 | >32 |
| *P. aeruginosa* | ATCC 27853 | >64 | >64 | >64 | >64 | >64 | >64 | >64 | >64 | 0.25 | 0.25 | >32 | >32 |
| *S. pyogenes* | ATCC 51339 | 64 | 32 | 64 | 32 | >64 | >64 | >64 | 64 | 16 | 32 | >32 | >32 |
| *C. albicans* | ATCC 90028 | 1 | 1 | 1 | 1 | 2 | 1 | 2 | 1 | >32 | >32 | 2 | 2 |
| *C. auris* | CDC 0381 | 0.5 | 0.5 | 0.5 | 0.5 | 1 | 1 | 1 | 1 | >32 | >32 | 1 | |
| *C. herbarum* | ATCCMYA-4682 | 0.5 | 0.5 | 1 | 1 | 2 | 2 | 2 | 2 | >32 | >32 | ≤0.03 | ≤0.03 |

Example 32. Determination of Minimum Inhibitory Concentration and Minimum Bactericidal or Fungal Concentration of Compound 1

Compound 1 was tested to determine the Minimum Inhibitory Concentration (MIC) and Minimum Bactericidal Concentration (MBC) or Minimum Fungicidal Concentration (MFC) against six test strains listed below in Table 3.

TABLE 3

Strains used in study

| Number | Species | Strain ID | Characteristic |
|---|---|---|---|
| 1 | *Pseudomonas aeruginosa* | Eurofins 1674623 | Clinical isolate |
| 2 | *Pseudomonas aeruginosa* | CDC 0248 | Clinical isolate |
| 3 | *Candida auris* | CDC 0385 | Clinical isolate |
| 4 | *Acinetobacter baumannii* | Eurofins 1674627 | Clinical isolate |
| 5 | *Streptococcus pyogenes* | Eurofins 2065755 | Clinical isolate |
| 6 | *Campylobacter jejuni* | CDC 0413 | Clinical isolate |
| 7 | *Pseudomonas aeruginosa* | ATCC 27853 | Quality control |
| 8 | *Candida albicans* | ATCC 90028 | Quality control |

Materials and Methods

Microorganisms and Media

Strain IDs starting with "ATCC" were acquired from the American Type Culture Collection (Manassas, VA), strain IDs starting with "Eurofins" were acquired from Eurofins (Herndon, VA), while strain IDs starting with "CDC" were acquired from the Centers for Disease Control and Prevention (Atlanta, GA). All strains were maintained as −80° C.

mg/mL Amphotericin B (CP Lab Chemicals, cat #TOK-A007-1G) were prepared in sterile ultrapure water.

MIC Microdilution Assay

The test article was diluted to 6.4 mg/mL in sterile ultrapure water, then ten 2-fold serial dilutions were made in sterile ultrapure water in a 96-well master plate to generate 10× starting concentrations for MIC testing. For bacteria strains, a few colonies of each strain were collected with a sterile swab and used to make a McFarland 0.5 standard solution (approximately 1×108 CFU/mL) in sterile PBS. The McFarland was then diluted 1:180 in Cation Adjusted Muller-Hinton Broth (CAMHB) for *S. aureus* and *P. aeruginosa*. *S. pyogenes* McFarland was diluted 1:180 in CAMHB+5% defibrinated sheep blood, while *C. jejuni* McFarland was diluted 1:180 in CAMHB+5% leaked horse blood. 90 µL of this inoculum was combined with 10 µL of the 10× test article in a 96-well plate for a final concentration of 1×.

For the yeasts *C. albicans* and *C. auris*, a McFarland 0.5 standard solution in sterile PBS was similarly prepared (approximately 1×10⁶ CFU/mL) and was subsequently diluted 1:180 in RPMI 1640 media buffered with 0.165 M MOPS at pH 7.0 (herein referred to as "RPMI media"). 90 µL of the *Candida* inoculum was combined with 10 µL of the 10× test article in a 96-well plate for a final concentration of 1×.

Except for *C. jejuni*, all bacterial-strain MIC 96-well plates were incubated at 35±2° C. for 18 to 20 hours, ambient atmosphere. *C. jejuni* was incubated at 35±2° C. for 48 hours, under microaerophilic condition. All *Candida* MIC 96-well plates were incubated at 35±2° C. for 24 to 48 hours, ambient atmosphere, until growth in control wells were observed. After incubation, the 96-well plates were examined visually and on a spectrophotometer at absorbance $OD_{650}$. MIC is defined as the lowest concentration of a compound in which no visible growth is observed.

MBC/MFC Determination

10 µL of liquid from each test condition was plated on the appropriate agar media for each test strain. Except for *C. jejuni*, all other strains were plated for MBC/MFC after 18 to 20 hours incubation, or until growth in growth control wells were visually observed. MBC for *C. jejuni* was plated 48 hours after incubation of the 96-well plate. Once the liquid from the 96-well plate has been allowed to air dry in a biosafety cabinet, the agar plates were incubated under the appropriate conditions and colony formation was assessed. MBC/MFC is defined as the lowest concentration of a compound in which no colonies were recovered.

Results and Discussion

The MIC/MBC/MFC values for the strains assayed, as well as the expected CLSI QC values, are listed below in Table 3. Compound 1 was active against both *C. auris* and *C. albicans*, with MIC values at 1 µg/mL. However, the compound was inactive against clinical isolates of *P. aeruginosa*, as all three strains were able to grow at the highest concentration tested i.e. 64 g/mL. Comparatively, the compound had limited activity against *S. pyogenes* Eurofins 2065755, *A. baumannii* Eurofins 1674627, and *C. jejuni* CDC 0413, with MIC values ranging between 8 to 64 µg/mL. The MIC values of Tobramycin and Amphotericin B for the QC strains ATCC 27853 and ATCC 90028 fell within their expected CLSI QC ranges, thereby validating the MIC assay method.

Example 34. Antimicrobial Dressing

The compounds described herein can used in any number of antimicrobial applications. For example, the compounds described herein can be used for the application of wound dressings, films, bandages, plastics for various medical applications such as wound care and the like; and personal care applications such as acne, eczema and the like. For example, the compounds described herein can be incorporated into various gels and polymers for medicinal applications.

An antimicrobial gel for wound dressing was formed by adding 2 g of Compound 1 with 1 g of guar gum. The mixture was stirred until a homogenous solution was formed. The homogenous solution formed was a stable, viscous gel applicable for use in wound care applications.

Example 35. Antimicrobial Bandages

An microbial bandage was formed by adding 2.50 g of Compound 1 with 15.70 g of polyvinyl alcohol (Elvanol 70-30). The polyvinyl alcohol was first mixed under heat with 200 mL of water. Once the homogenous solution formed, and the solution cooled, Compound 1 was added, resulting in a slightly hazy and stable solution. The stable solution was formed into a stable resilient, solid film, suitable as a bandage or other would healing material.

This specification has been described with reference to embodiments of the invention. However, one of ordinary skill in the art appreciates that various modifications and changes can be made without departing from the scope of the invention as set forth in the claims below. Accordingly,

TABLE 4

| | | MIC/MBC/MFC values of strains tested | | | | | | | |
|---|---|---|---|---|---|---|---|---|---|
| | | MIC (µg/mL) | | | | | | MBC (µg/mL) | |
| Species | Strain ID | Compound 1 | | Tobramycin | | Amphotericin B | | Compound 1 | |
| *P. aeruginosa* | Eurofins 1674623 | >64 | >64 | >32 | >32 | >32 | >32 | >64 | >64 |
| *P. aeruginosa* | CDC 0248 | >64 | >64 | >32 | >32 | >32 | >32 | >64 | >64 |
| *C. auris* | CDC 0385 | 1 | 1 | >32 | >32 | 4 | 4 | 2 | 2 |
| *A. baumannii* | Eurofins 1674627 | 64 | 64 | 1 | 1 | >32 | >32 | 64 | 64 |
| *S. pyogenes* | Eurofins 2065755 | 8 | 8 | 16 | 16 | >32 | >32 | 8 | 8 |
| *C. jejuni* | CDC 0413 | 32 | 32 | >32 | >32 | >32 | >32 | 32 | 32 |
| *P. aeruginosa* | ATCC 27853 | >64 | >64 | 0.25 | 0.25 | >32 | >32 | >64 | >64 |
| *C. albicans* | ATCC 90028 | 1 | 1 | >32 | >32 | 1 | 1 | 1 | 1 |

Example 33. Administration of Compound 1 to Treat Ocular Infection

A male bull dog presented with an infection in both eyes which was cultured and tested positive for *Proteus mirabilis* and *Pseudomonas aeruginosa*. The dog was administered a 2% aqueous solution of Compound 1 at a rate of 3 times per day for 7 days. On day 2, the dog was examined and the eyes showed signs of reduced infection. On day 6, the dog was reexamined. Both eyes showed no sign of infection. To verify, a swab of the eye was taken and cultured. The culture was negative for both *Proteus mirabilis* and *Pseudomonas aeruginosa*.

the specification is to be regarded in an illustrative rather than a restrictive sense, and all such modifications are intended to be included with the scope of invention.

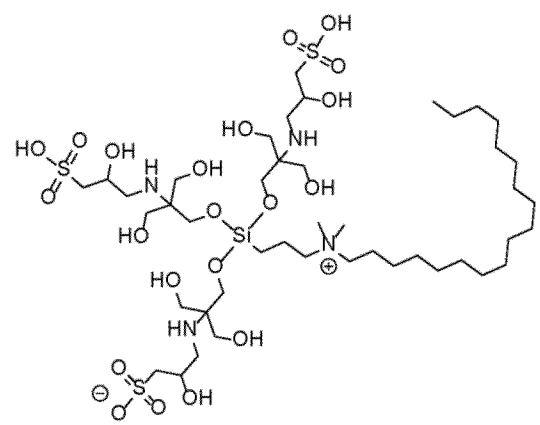

We claim:

1. A quaternary ammonium compound of Formula:

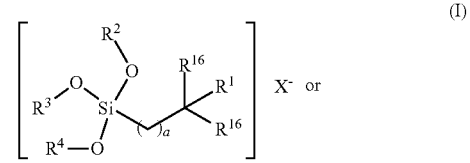

-continued

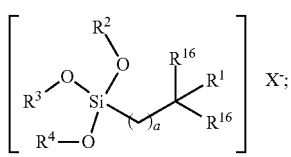
(V)

wherein
a is 1, 2, 3, 4, 5, 6, 7 or 8;
$R^1$ is independently at each occurrence selected from the group consisting of $C_6$-$C_{22}$alkyl and $C_6$-$C_{22}$alkanoyl;
$R^2$, $R^3$, $R^4$, $R^{22}$, $R^{23}$, and $R^{24}$ are independently at each occurrence selected from the group consisting of:

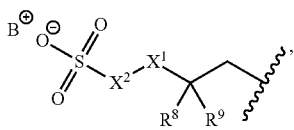

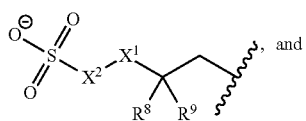

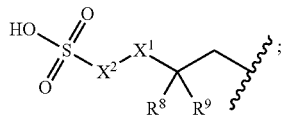

each $R^{21}$ is independently selected from the group consisting of $C_1$-$C_{22}$alkyl and $C_2$-$C_{22}$alkanoyl;

$R^7$ is independently at each occurrence selected from the group consisting of hydrogen, $C_1$-$C_8$alkyl, $C_1$-$C_8$hydroxyalkyl, and $C_1$-$C_8$ alkanoyl;
$R^8$ and $R^9$ are independently at each occurrence selected from the group consisting of hydrogen, halogen, hydroxyl, $N(R^7)_2$, $CH_2OR^7$, $CON(R^7)_2$, $COOR^7$, $C(O)R^7$, $C_1$-$C_8$alkyl, $C_1$-$C_8$hydroxyalkyl, and $C_1$-$C_8$alkanoyl;
$X^1$ is $NR^{17}$, $CH_2$, CHOH, or C(O);
$X^2$ is $C_1$-$C_3$alkyl or $C_1$-$C_3$hydroxyalkyl;
$R^{16}$ is $C_1$-$C_4$alkyl;
$R^{17}$ is hydrogen, $C_1$-$C_8$hydroxyalkyl, or $C_1$-$C_8$alkanoyl;
$X^-$ is an anion or is absent if the quaternary amine is balanced with an internal anion; and
$B^+$ is a cation.

2. The quaternary ammonium compound of claim 1, wherein $X^-$ is selected from the group consisting of chloride, fluoride, iodide, bromide, hydroxide, chlorite, chlorate, hydroxide, formate, acetate, lactate, benzoate, methane sulfonate, and salicylate anion.

3. The quaternary ammonium compound of claim 1, wherein $B^+$ is selected from the group consisting of $Na^+$, $K^+$, $Li^+$, $Mg^{2+}$, and $Ca^{2+}$.

4. The quaternary ammonium compound of claim 1, wherein the compound is a zwitterion and X is absent.

5. The quaternary ammonium compound of claim 1, wherein $X^1$ is NH or $N(CH_2CH_2OH)$.

6. The quaternary ammonium compound of claim 1, wherein $X^2$ is $CH_2CH_2$ or $CH_2CH(OH)CH_2$.

7. The quaternary ammonium compound of claim 6, wherein $R^{16}$ is $CH_3$.

8. The quaternary ammonium compound of claim 7, wherein $R^1$ is octadecyl.

9. The quaternary ammonium compound of claim 8, wherein $R^8$ and $R^9$ are each $CH_2OH$.

10. The quaternary ammonium compound of claim 9, wherein a is 3.

11. The quaternary ammonium compound of claim 10, wherein $X^1$ is NH or $N(CH_2CH_2OH)$.

12. The quaternary ammonium compound of claim 1 selected from the group consisting of:

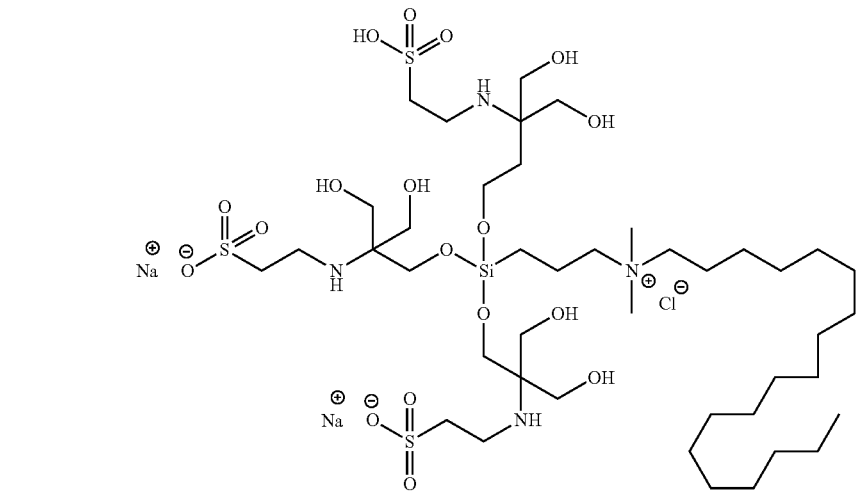

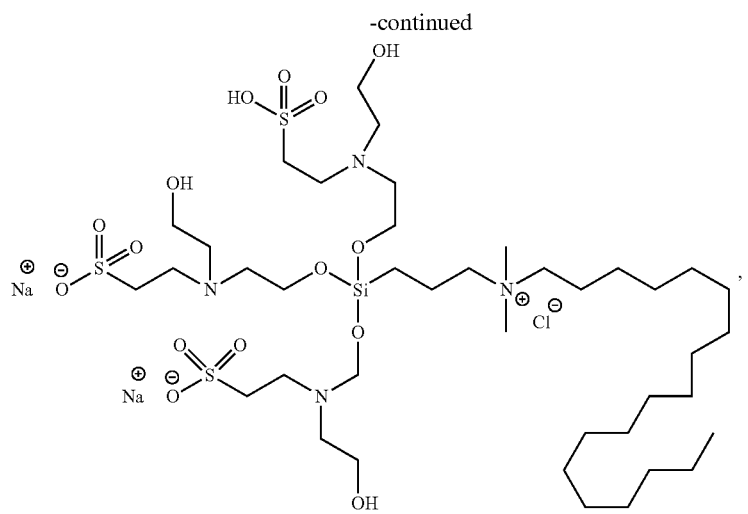
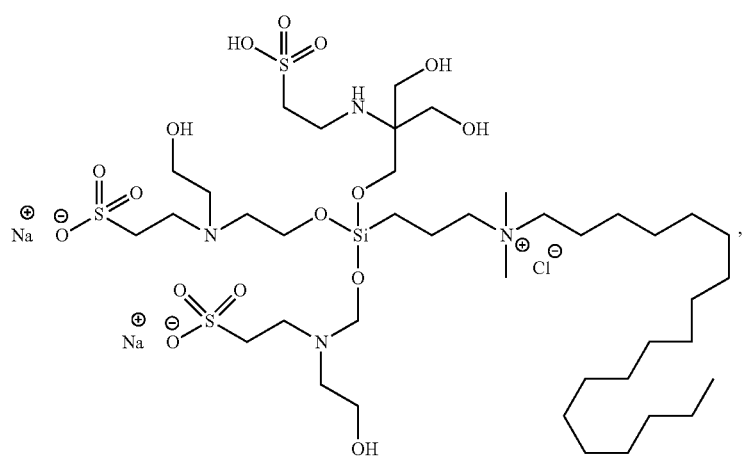
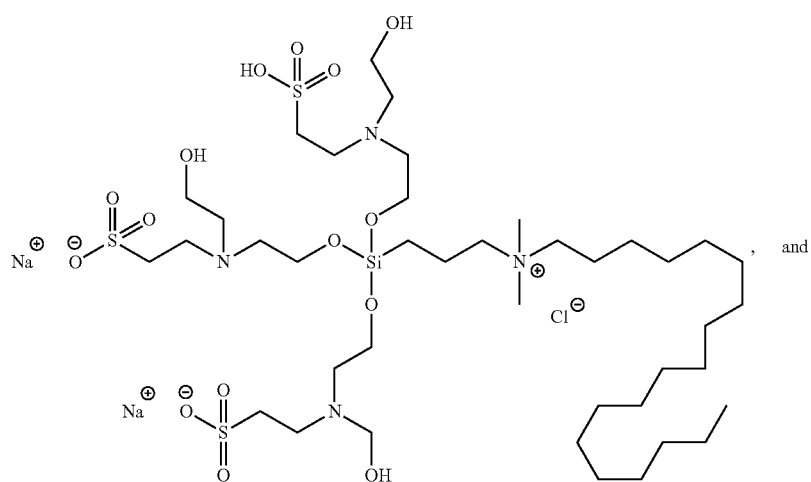

-continued
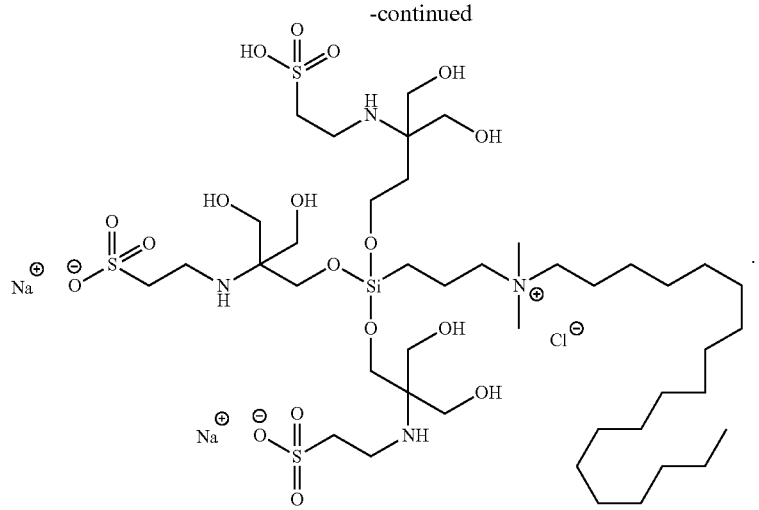
13. The quaternary ammonium compound of claim 1 of structure:
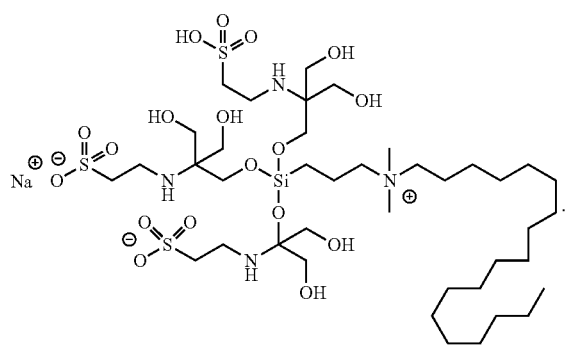 [SMILES: [Na+] ; CCCCCCCCCCCCCCCCCC[N+](C)(C)CCC[Si](OCC(CO)(CO)NCCS(=O)(=O)[O-])(OCC(CO)(CO)NCCS(=O)(=O)O)OC(CO)(CO)NCCS(=O)(=O)[O-]]
14. The quaternary ammonium compound of claim 1 of structure:
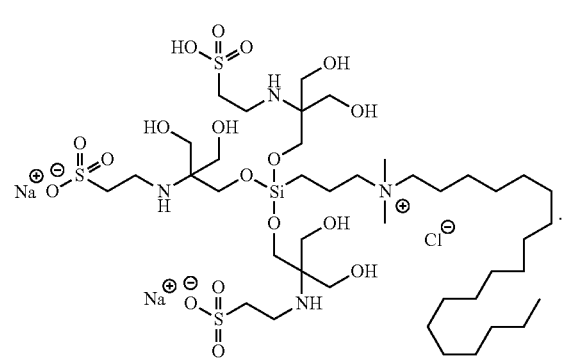 [SMILES: [Na+] ; CCCCCCCCCCCCCCCCCC[N+](C)(C)CCC[Si](OCC(CO)(CO)NCCS(=O)(=O)[O-])(OCC(CO)(CO)NCCS(=O)(=O)[O-])OCC(CO)(CO)NCCS(=O)(=O)O ; [Na+] ; [Cl-]]
15. The quaternary ammonium compound of claim 1 of structure:
16. The quaternary ammonium compound of claim 1 of structure:
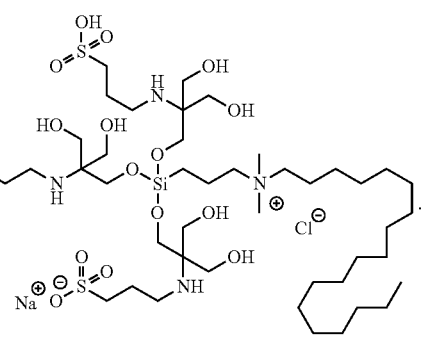
17. The quaternary ammonium compound of claim 1 of structure:
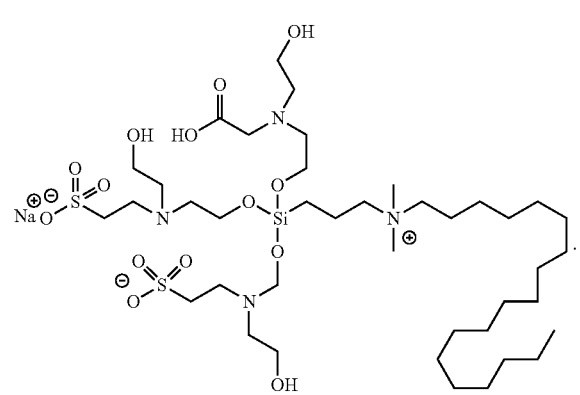 [SMILES: [Na+] ; CCCCCCCCCCCCCCCCCC[N+](C)(C)CCC[Si](OCCN(CCO)CCS(=O)(=O)[O-])(OCCN(CCO)CC(=O)O)OCN(CCO)CCS(=O)(=O)[O-]]

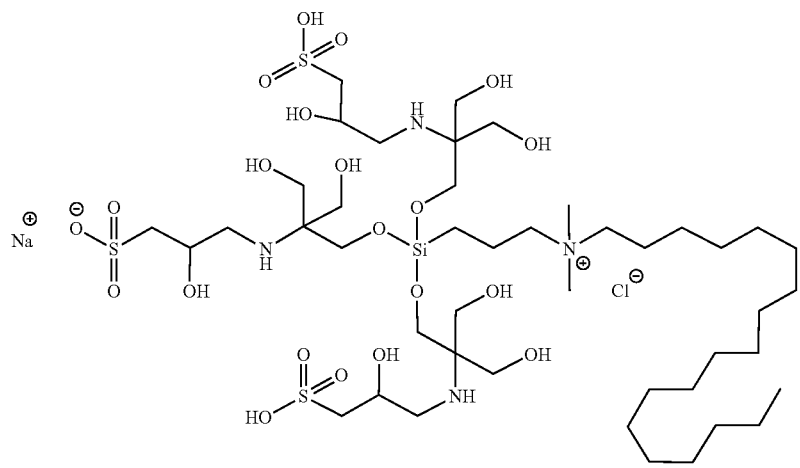
18. The quaternary ammonium compound of claim 1 of structure:
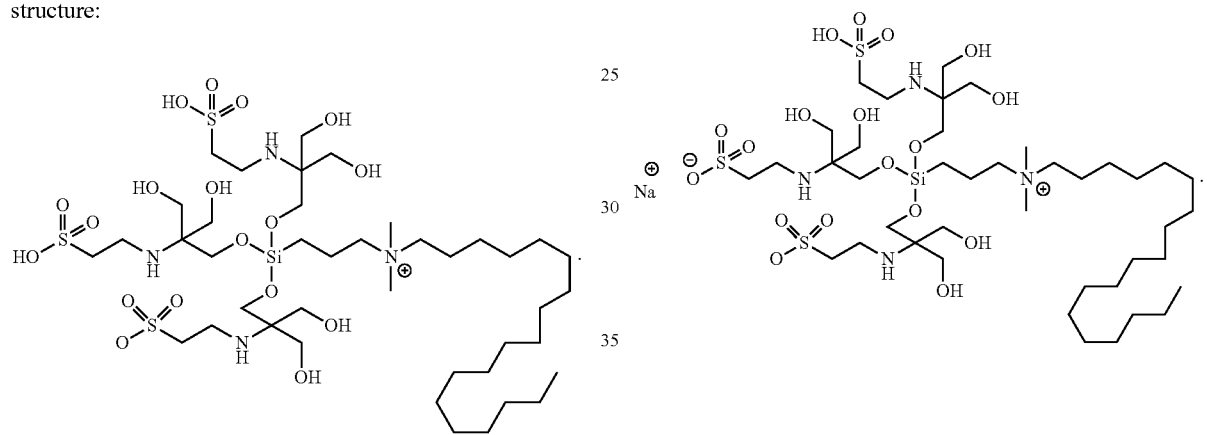
19. The quaternary ammonium compound of claim 1 of structure:
20. The quaternary ammonium compound of claim 1 of structure:
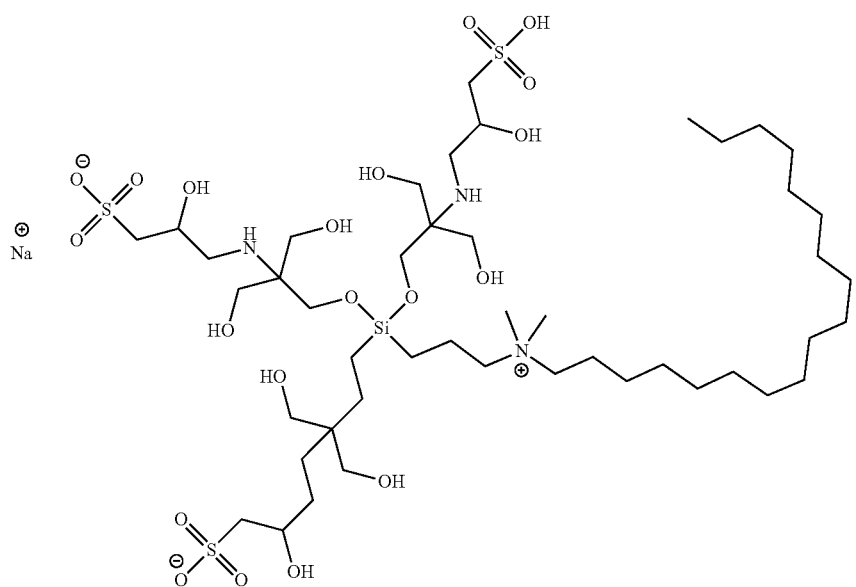

21. The quaternary ammonium compound of claim 1 of structure:
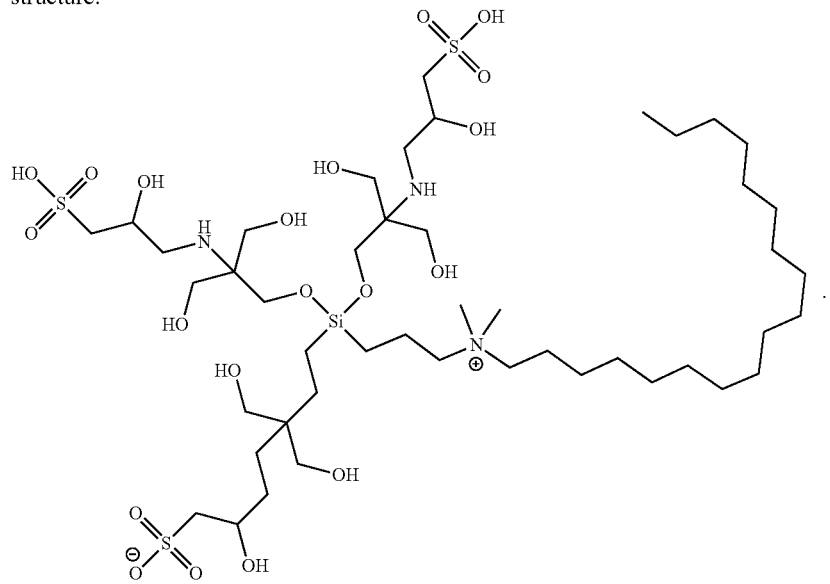
22. The quaternary ammonium compound of claim 1 of structure:
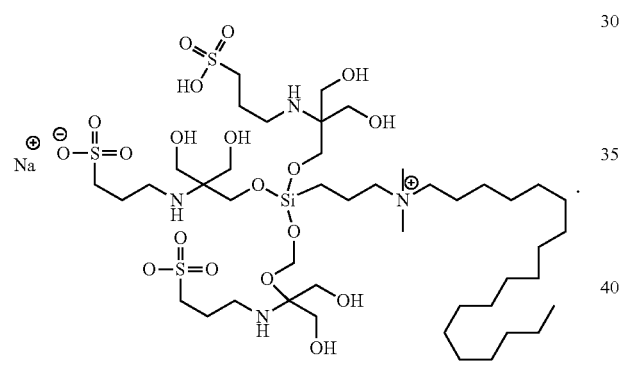
23. The quaternary ammonium compound of claim 1 of structure:
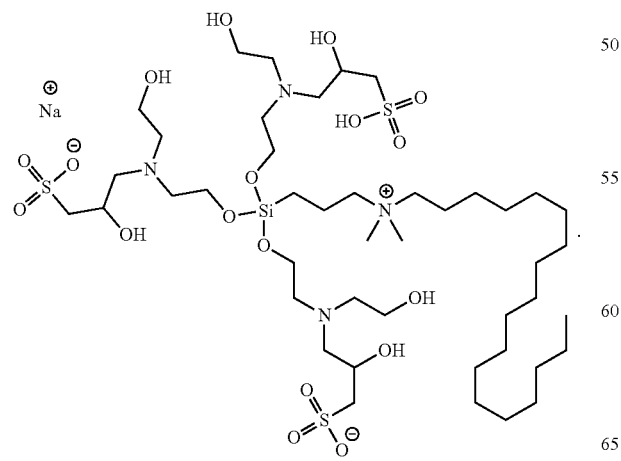

24. The quaternary ammonium compound of claim 1 of structure:

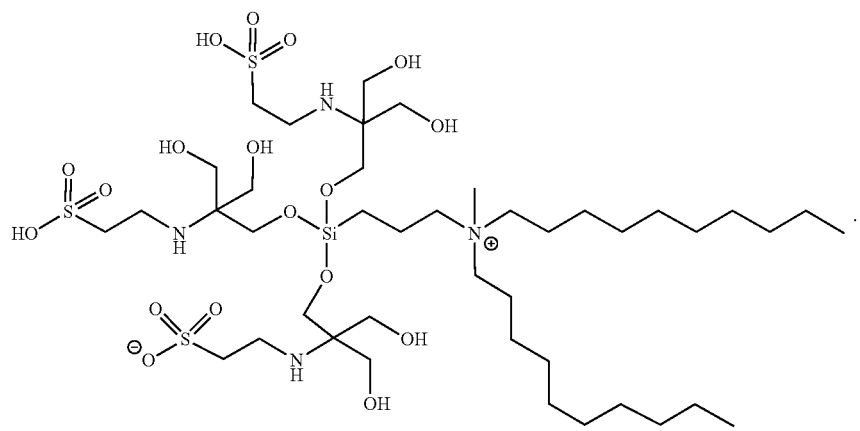 [SMILES: CCCCCCCCCC[N+](C)(CCCCCCCCCC)CCC[Si](OCC(CO)(CO)NCCS(=O)(=O)[O-])(OCC(CO)(CO)NCCS(=O)(=O)O)OCC(CO)(CO)NCCS(=O)(=O)O ; "."]

25. An antimicrobial composition comprising a quaternary ammonium compound of claim 1 and a pharmaceutically acceptable carrier.

26. The antimicrobial according to claim 25, wherein the pharmaceutically acceptable carrier is selected from the group consisting of alcohol, aqueous solution, and glycerin solution.

27. The antimicrobial composition of claim 26, wherein the composition is suitable for topical delivery.

28. The antimicrobial composition of claim 25, wherein the quaternary ammonium compound is

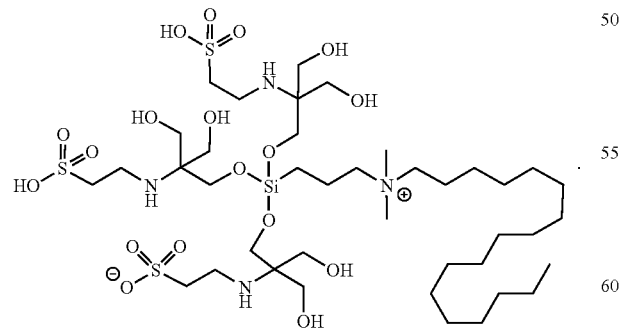

29. The antimicrobial composition of claim 25, wherein the quaternary ammonium compound is

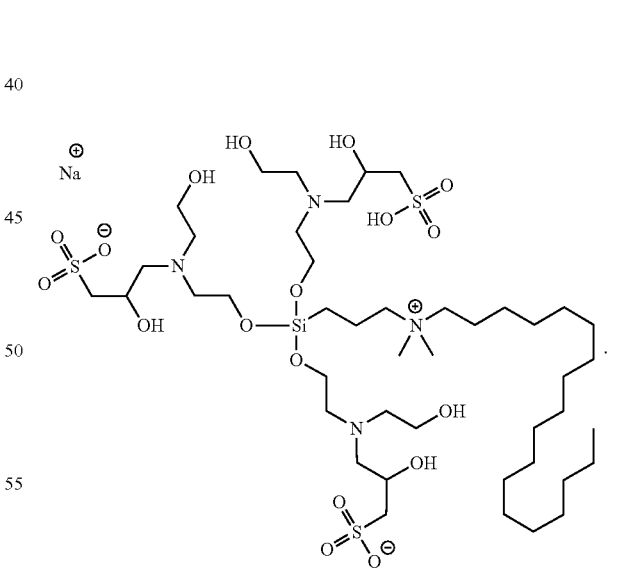

30. The antimicrobial composition of claim 25, wherein the quaternary ammonium compound is

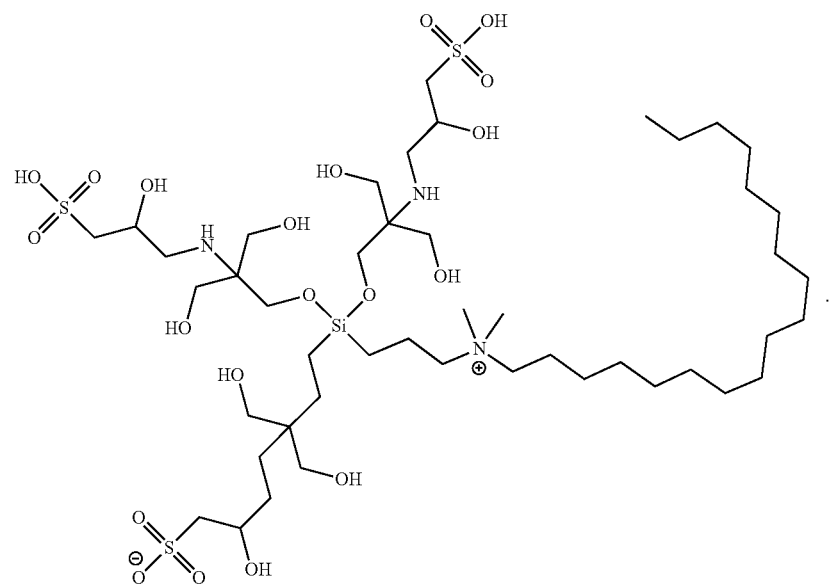 [SMILES: CCCCCCCCCCCCCCCCCC[N+](C)(C)CCC[Si](CCC(CO)(CO)CCC(O)CS(=O)(=O)[O-])(OCC(CO)(CO)NCC(O)CS(=O)(=O)O)OCC(CO)(CO)NCC(O)CS(=O)(=O)O ; "."]
\* \* \* \* \*

UNITED STATES PATENT AND TRADEMARK OFFICE
CERTIFICATE OF CORRECTION

PATENT NO. : 12,024,533 B2
APPLICATION NO. : 18/087587
DATED : July 2, 2024
INVENTOR(S) : Gary Allred et al.

It is certified that error appears in the above-identified patent and that said Letters Patent is hereby corrected as shown below:

In the Claims

In Claim 1, Column 556, Lines 60-65:

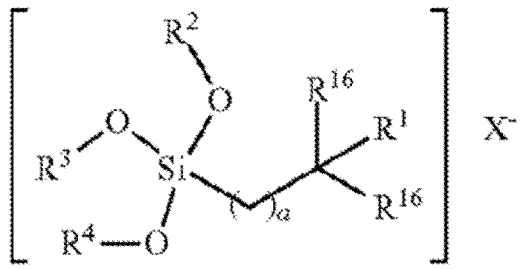

Should read:

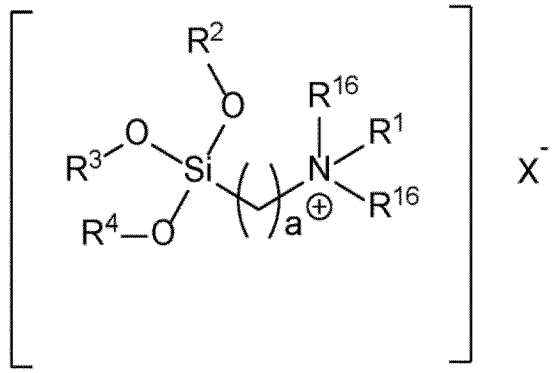

Signed and Sealed this
Twenty-ninth Day of April, 2025

Coke Morgan Stewart
*Acting Director of the United States Patent and Trademark Office*

In Claim 1, Column 557, Lines 1-9:
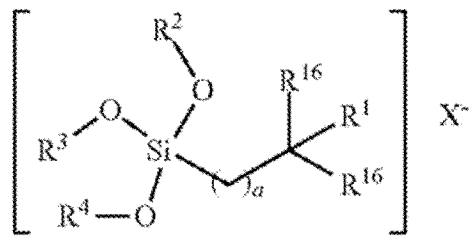
Should read:
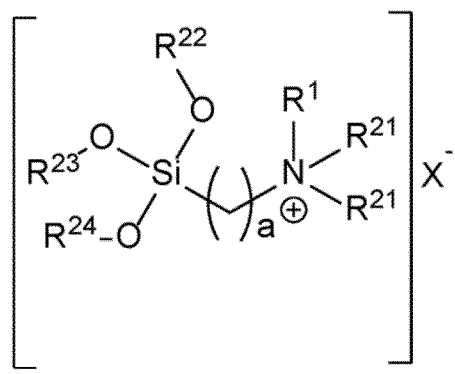
In Claim 4, Column 558, Lines 25:
X is absent
Should read:
X⁻ is absent
In Claim 12, Column 558, structure at the bottom of the page:
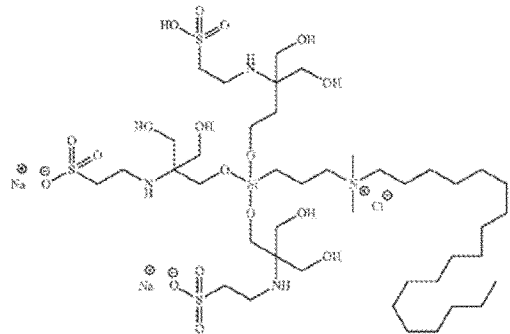
Should read:
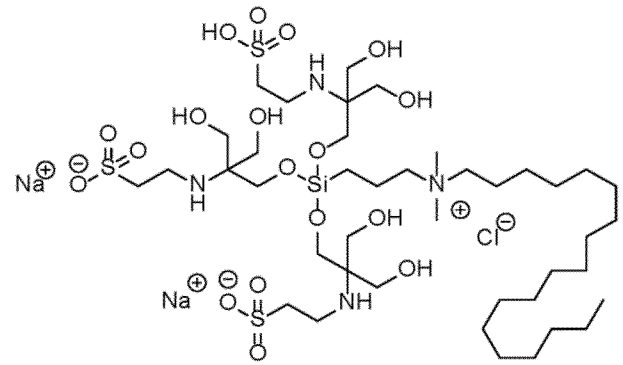

In Claim 12, Column 559, the first structure on the page:
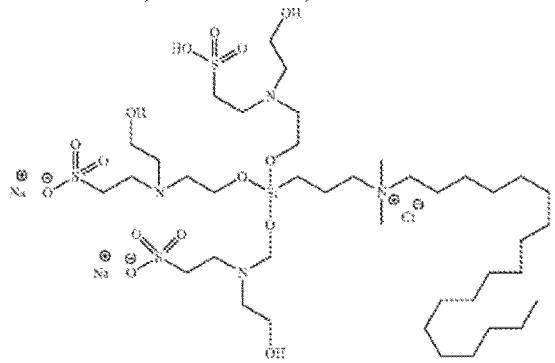
Should read:
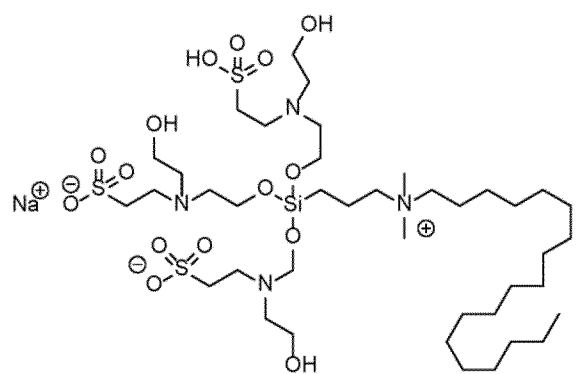
In Claim 12, Column 559, the second structure on the page:
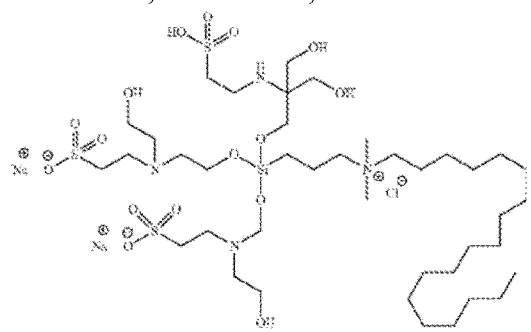
Should read:
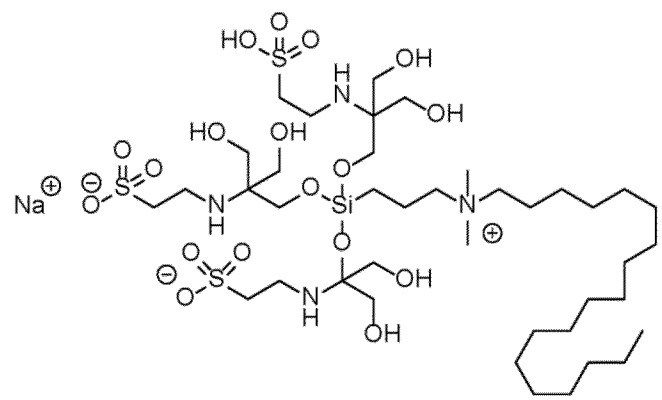

In Claim 12, Column 559, the third structure on the page:
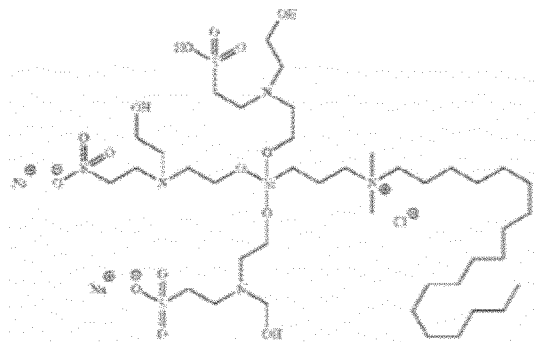
Should read:
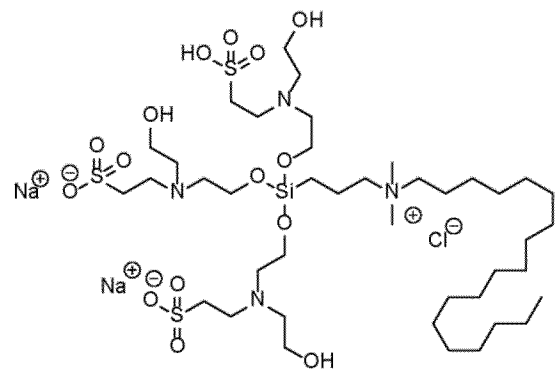
In Claim 12, Column 561, the first structure on the page:
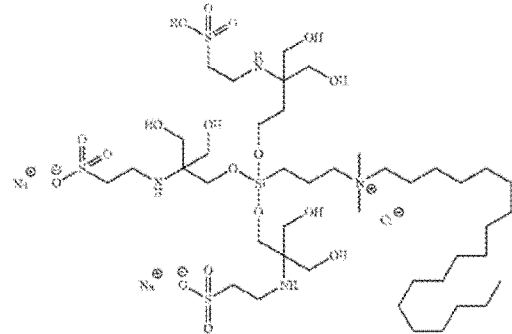
Should read:
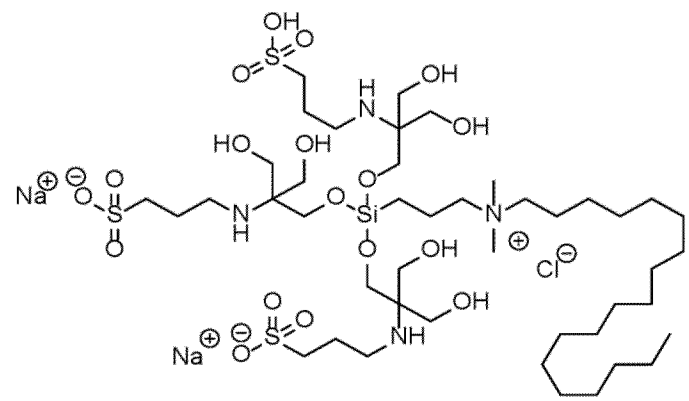

CERTIFICATE OF CORRECTION (continued)
U.S. Pat. No. 12,024,533 B2

Page 5 of 8

In Claim 16, Column 562, Lines 50-65:

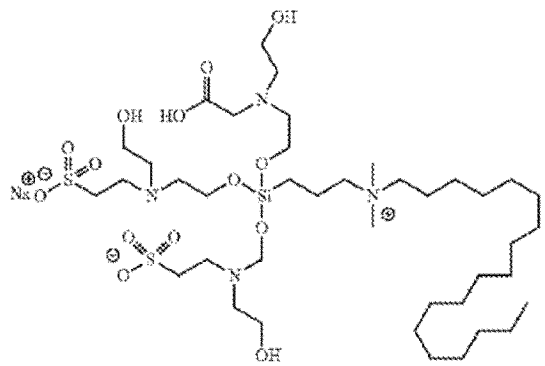

Should read:

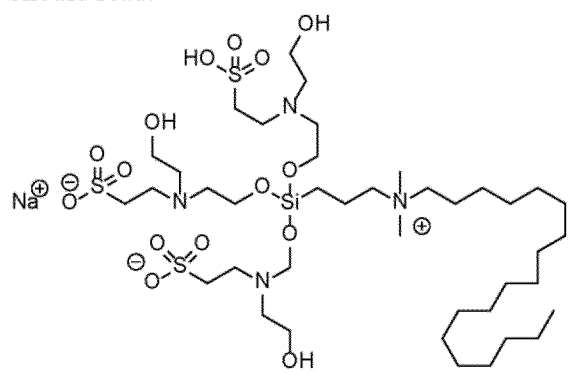

In Claim 18, Column 563, Lines 25-40:

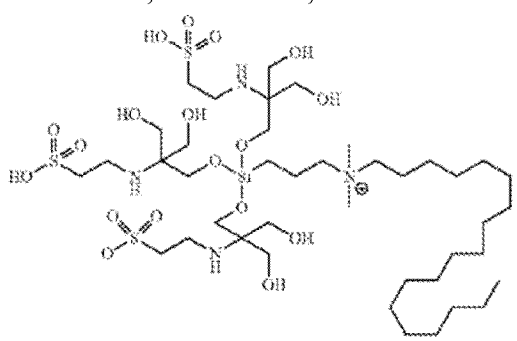

Should read:

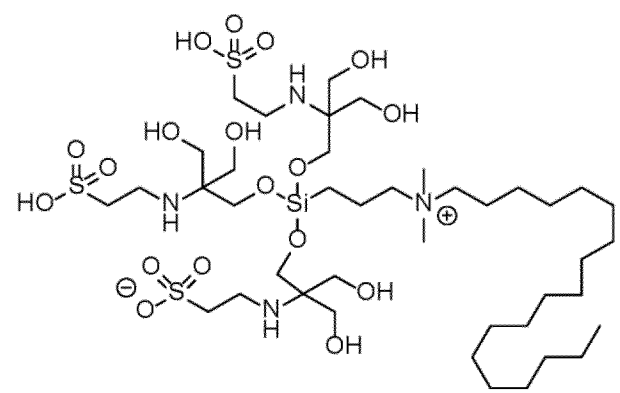

CERTIFICATE OF CORRECTION (continued)
U.S. Pat. No. 12,024,533 B2

In Claim 19, Column 564, Lines 20-35:

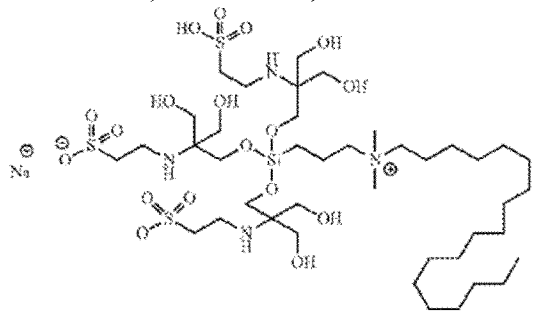

Should read:

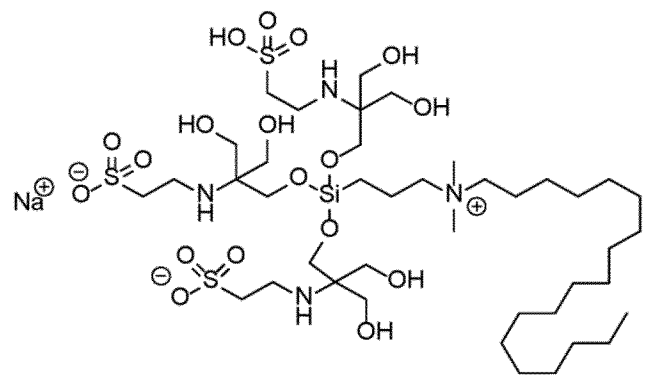

In Claim 20, Column 564, structure at the bottom of the page:

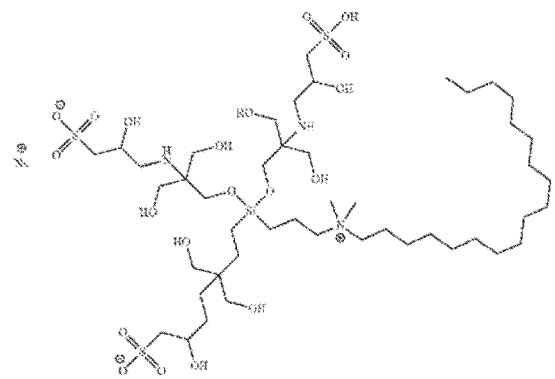

Should read:

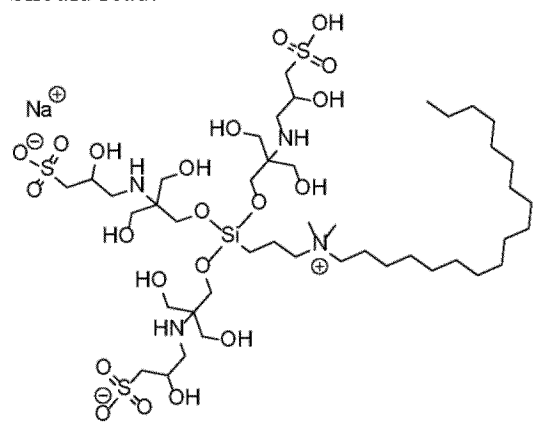

In Claim 21, Column 556, Lines 1-24:
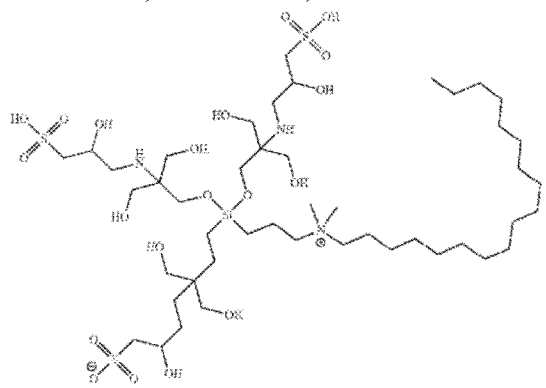
Should read:
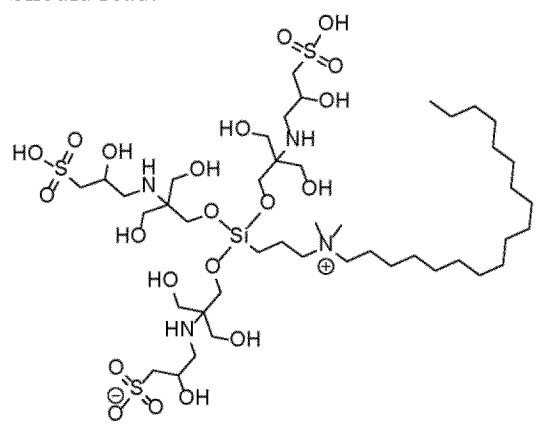
In Claim 22, Column 565, Lines 30-44:
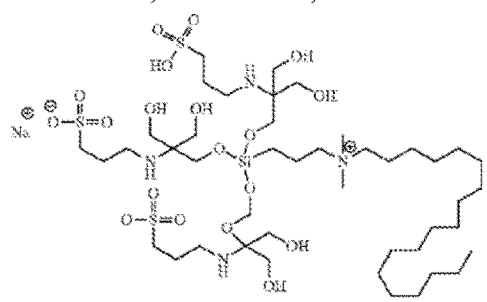
Should read:
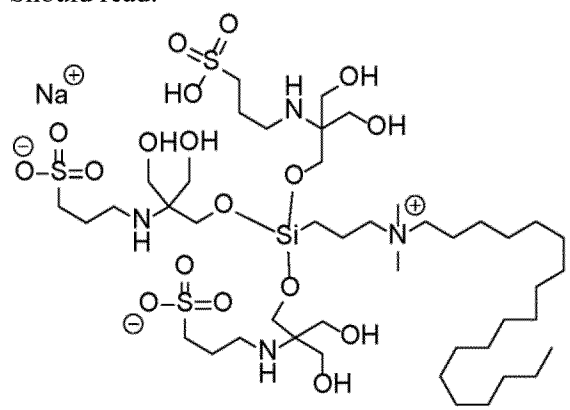

CERTIFICATE OF CORRECTION (continued)

In Claim 30, Column 569:

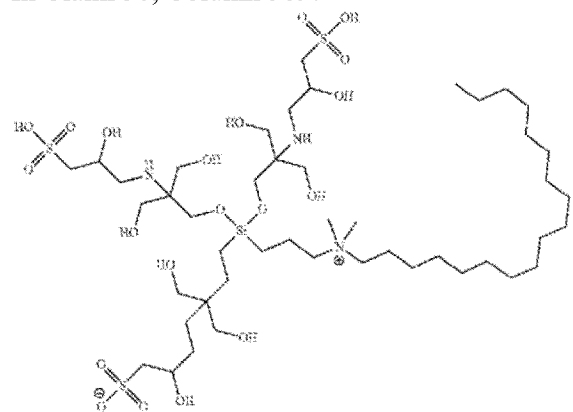

Should read: